(12) United States Patent
Weinshilboum et al.

(10) Patent No.: US 7,485,711 B2
(45) Date of Patent: Feb. 3, 2009

(54) CYP19A1 POLYMORPHISMS

(75) Inventors: Richard M. Weinshilboum, Rochester, MN (US); Eric O. Wieben, Rochester, MN (US); Oreste Salavaggione, St. Louis, MO (US); Araba A. Adjei, Rochester, MN (US); Linda Pelleymounter, Rochester, MN (US); Josefa Coronel, Union City, CA (US); Liewei Wang, Rochester, MN (US); Bruce Eckloff, Oronoco, MN (US); Daniel Schaid, Rochester, MN (US); Cynthia X. Ma, Ladue, MO (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 217 days.

(21) Appl. No.: 11/206,251

(22) Filed: Aug. 16, 2005

(65) Prior Publication Data

US 2007/0037177 A1  Feb. 15, 2007

Related U.S. Application Data

(63) Continuation-in-part of application No. 11/203,569, filed on Aug. 12, 2005, now abandoned.

(51) Int. Cl.
*C07H 21/04* (2006.01)
*C12P 19/34* (2006.01)
*C12Q 1/68* (2006.01)

(52) U.S. Cl. .................... 536/23.1; 435/6; 435/91.1

(58) Field of Classification Search .................. None
See application file for complete search history.

(56) References Cited

U.S. PATENT DOCUMENTS

| | | | |
|---|---|---|---|
| 5,451,683 | A | 9/1995 | Barrett et al. |
| 5,733,729 | A | 3/1998 | Lipshutz et al. |
| 5,770,722 | A | 6/1998 | Lockhart et al. |
| 2001/0053519 | A1* | 12/2001 | Fodor et al. .................... 435/6 |
| 2005/0228172 | A9* | 10/2005 | Wang ........................ 536/24.3 |

FOREIGN PATENT DOCUMENTS

WO  WO 98/20019  5/1998

OTHER PUBLICATIONS

GenBank Accession No. NM_000103.2 dated Jul. 23, 2006, 23 pages.
GenBank Accession No. NM_001785 dated May 7, 2006, 5 pages.
GenBank Accession No. NT_010194.16 dated Mar. 2, 2006, 5 pages.
GenBank Accession No. S52794 dated May 8, 1993, 1 page.
Ausubel et al. (eds.), *Short Protocols in Molecular Biology*, 1992, Second Edition, Chapters 8 and 11, Green Publishing Associates and John Wiley & Sons.
Brueggemeier et al., "Molecular pharmacology of aromatase and its regulation by endogenous and exogenous agents," *J. Steroid Biochem. Mol. Biol.*, 2001, 79:75-84.
Bulun et al., "The human *CYP19* (aromatase P450) gene: update on physiologic roles and genomic organization of promoters," *J. Steroid Biochem. Mol. Biol.*, 2003, 86:219-224.
Caine et al., "Recombinant Human Phenylethanolamine N-Methyltransferase: Overproduction in *Escherichia coli*, Purification, and Characterization," *Protein Expr. Purif.*, 1996, 8:160-166.
Carlson et al., "Selecting a Maximally Informative Set of Single-Nucleotide Polymorphisms for Association Analyses Using Linkage Disequilibrium," *Am. J. Hum. Genet.*, 2004, 74:106-120.
Chadwick et al., "Heterozygote and Mutation Detection by Direct Automated Fluorescent DNA Sequencing Using a Mutant *Taq* DNA Polymerase," *BioTechniques*, 1996, 20(4):676-683.
Chin, "On the Preparation and Utilization of Isolated and Purified Oligonucleotides," (CD-ROM and paper copy of first 2 pages and letter from Chin), Mar. 9, 2002.
Cibelli et al., "Cloned Transgenic Calves Produced from Nonquiescent Fetal Fibroblasts," *Science*, 1998, 280:1256-1258.
Cleland, "Computer Programmes for Processing Enzyme Kinetic Data," *Nature*, 1963, 198:463-465.
Cole et al., "The EBV-Hybridoma Technique and Its Application To Human Lung Cancer," *Monoclonal Antibodies and Cancer Therapy*, 1985, Alan R. Liss, Inc., pp. 77-96.
Cote et al., "Generation of human monoclonal antibodies reactive with cellular antigens," *Proc. Natl. Acad. Sci. USA*, 1983, 80:2026-2030.
Excoffier and Slatkin, "Maximum-Likelihood Estimation of Molecular Haplotype Frequencies in a Diploid Population," *Mol. Biol. Evol.*, 1995, 12(5):921-927.
Fullerton et al., "Apolipoprotein E Variation at the Sequence Haplotype Level: Implications for the Origin and Maintenance of a Major Human Polymorphism," *Am. J. Hum. Genet.*, 2000, 67:881-900.
Gordon et al., "*Consed*: A Graphical Tool for Sequence Finishing," *Genome Res.*, 1998, 8:195-202.
Guatelli et al., "Isothermal, in vitro amplification of nucleic acids by a multienzyme reaction modeled after retroviral replication," *Proc. Natl. Acad. Sci. USA*, 1990, 87:1874-1878.
Hacia et al., "Detection of heterozygous mutations in *BRCA1* using high density oligonucleotide arrays and two-colour fluorescence analysis," *Nat. Genet.*, 1996, 14:441-447.
Hahn and Fishman, "Immunological Probe of Estrogen Biosynthesis. Evidence for the 2β-Hydroxylative Pathway in Aromatization of Androgens," *J. Biol. Chem.*, 1984, 259(3):1689-1694.
Hartl and Clark, "Chromosomes and Heredity," *Principles of Population Genetics*, 3rd Edition, 1997, Sinauer Associates, Inc., (Sunderland, MA), pp. 96-106.

(Continued)

*Primary Examiner*—Sarae Bausch
(74) *Attorney, Agent, or Firm*—Fish & Richardson P.C.

(57) ABSTRACT

Isolated CYP19A1 nucleic acid molecules that include a nucleotide sequence variant and nucleotides flanking the sequence variant are described, as well as CYP19A1 allozymes. Methods for determining the aromatase status of an individual also are provided, as are methods for determining if a subject is predisposed to certain clinical conditions.

7 Claims, 47 Drawing Sheets

OTHER PUBLICATIONS

Haugen et al., "Amino-Terminal Sequence of Phenobarbital-Inducible Cytochrome P-450 from Rabbit Liver Microsomes: Similarity to Hydrophobic Amino-Terminal Segments of Preproteins," *Biochem. Biophys. Res. Comm.*, 1977, 77(3):967-973.

Hedrick, "An Introduction to Gametic Disequilibrium," *Genetics of Populations*, 2nd edition, 2000, Jones and Bartlett (Sudbury, MA), pp. 396-405.

Huse et al., "Generation of a Large Combinatorial Library of the Immunoglobulin Repertoire in Phage Lambda," *Science*, 1989, 246:1275-1281.

Hyrup and Nielsen, "Peptide Nucleic Acids (PNA): Synthesis, Properties and Potential Applications," *Bioorgan. Med. Chem.*, 1996, 4(1):5-23.

Köhler and Milstein, "Continuous cultures of fused cells secreting antibody of predefined specificity," *Nature*, 1975, 256:495-497.

Kozbor and Roder, "The production of monoclonal antibodies from human lymphocytes," *Immunology Today*, 1983, 4(3):72-79.

Lewis, "PCR's Competitors Are Alive and Well and Moving Rapidly Towards Commercialization," *Genetic Engineering News*, 1992, 12(9):1-3.

Long et al., "An E-M Algorithm and Testing Strategy for Multiple-Locus Haplotypes," *Am. J. Hum. Genet.*, 1995, 56:799-810.

Myakishev et al., "High-Throughput SNP Genotyping by Allele-Specific PCR with Universal Energy-Transfer-Labeled Primers," *Genome Res.*, 2001, 11(1):163-169.

Nelson et al., "P450 superfamily: update on new sequences, gene mapping, accession numbers and nomenclature," *Pharmacogenetics*, 1996, 6:1-42.

Nickerson et al., "PolyPhred: automating the detection and genotyping of single nucleotide substitutions using fluorescence-based resequencing," *Nucl. Acids Res.*, 1997, 25(14):2745-2751.

Prince et al., "Robust and Accurate Single Nucleotide Polymorphism Genotyping by Dynamic Allele-Specific Hybridization (DASH): Design Criteria and Assay Validation," *Genome Res.*, 2001, 11(1):152-162.

Sambrook et al., *Molecular Cloning, A Laboratory Manual*, 1989, second edition, Sections 9.37-9.52,Cold Spring Harbor Press, Plainview, NY.

Schafer and Hawkins, "DNA variation and the future of human genetics," *Nat. Biotechnol.*, 1998, 16:33-39.

Schaid et al., "Score Tests for Association between Traits and Haplotypes when Linkage Phase Is Ambiguous," *Am. J. Hum. Genet.*, 2002, 70:425-434.

Sebastian and Bulun, "Genetics of Endocrine Disease. A Highly Complex Organization of the Regulatory Region of the Human CYP19 (Aromatase) Gene Revealed by the Human Genome Project," *J. Clin. Endocrin. Metab.*, 2001, 86(10):4600-4602.

Shastry, "Gene disruption in mice: Models of development and disease," *Mol. Cell. Biochem.*, 1998, 181:163-179.

Simpson et al., "Aromatase—A Brief Overview," *Annu. Rev. Physiol.*, 2002, 64:93-127.

Simpson et al., "Aromatase Cytochrome P450, The Enzyme Responsible for Estrogen Biosynthesis," *Endocr. Rev.*, 1994, 15(3):342-355.

Stoneking et al., "Population Variation of Human mtDNA Control Region Sequences Detected by Enzymatic Amplification and Sequence-specific Oligonucleotide Probes," *Am. J. Hum. Genet.*, 1991, 48:370-382.

Summerton and Weller, "Morpholino Antisense Oligomers: Design, Preparation, and Properties," *Antisense Nucleic Acid Drug Dev.*, 1997, 7:187-195.

Tajima, "Statistical Method for Testing the Neutral Mutation Hypothesis by DNA Polymorphism," *Genetics*, 1989, 123:585-595.

Terwilliger and Ott, "Linkage Disequilibrium between Alleles at Marker Loci," *Handbook of Human Genetic Linkage*, 1994, The Johns Hopkins University Press, Baltimore, pp. 188-193.

Underhill et al., "Detection of Numerous Y Chromosome Biallelic Polymorphisms by Denaturing High-Performance Liquid Chromatography," *Genome Res.*, 1997, 7:996-1005.

Wakayama et al., "Full-term development of mice from enucleated oocytes injected with cumulus cell nuclei," *Nature*, 1998, 394(6691):369-374.

Weinshilboum and Wang, "Pharmacogenetics: Inherited variation in amino acid sequence and altered protein quantity," *Clin. Pharmocol. Ther.*, 2004, 75(4):253-258.

Weiss, "Hot Prospect for New Gene Amplifier," *Science*, 1991, 254:1292-1293.

Wilkinson, "Statistical Estimation in Enzyme Kinetics," *Biochem. J.*, 1961, 80:324-332.

Wilmut et al., "Viable offspring derived from fetal and adult mammalian cells," *Nature*, 1997, 385(6619):810-813.

Wong et al., "Human GM-CSF: Molecular Cloning of the Complementary DNA and Purification of the Natural and Recombinant Proteins," *Science*, 1985, 228:810-815.

\* cited by examiner

Figure 1 - page 1

```
   1    AACGTAGACA GCAATCTTCA AGCCCCATGT TAAGAACCTC GGGTTTGACA TTGTTTAAGA    60
  61    AAAAAAAAAA ATCACTCTGT TTGGATGTCT CCCATTTGGG AGACCCAACC AGAAGGCAGG   120
 121    ATTGCTGTTT CCATAGCCCA ATAACTCAAG GAAGAGGTGC CTCCCCGCCA ATGAGCCAGC   180
 181    TGGAGCAGTT ATAGAGAAAG GACTTCCTCT ATCAGAGACC ACACTGTTTC AGCACCTGAG   240
 241    GGAGACCAGT AAAATGATCA GAGAGCAAGC TCCTTTTGAC TTAATGGTAG GAGCTCTGTA   300
 301    ACCATCTACT CCCCAAAGAT TCACATTCTG ATGTGGTTTG GATCTGTGTC CCCACCCAAA   360
 361    TCTCATGTTG AATTGCGATT CCCAGTATTG GTGGTGGAGC CCAGTGGGAG GTGACTGGAT   420
 421    CATGGGAGTG GTCCTTCATG AATGGTTTAG CACCATCCCC TCAGTGCTGT TCTCATGATA   480
 481    GTGAGTTATC ATGAGATCTG GTTGTTTAAA AGTGTGTAGC ATCTCTCCTG GCCCCTCTTC   540
 541    CTCCTGCTCC CACCATGTGA GATGTTCCTG CTCCTGCTTT GCCTTCCTCC ATGAGTAAAA   600
 601    GCTCCCTGAG GCCTCCCCAG ATGCAGGTGC TGCCATGCTT CCTGTTCAGC CTGTGGAACC   660
 661    ATGAGCCAAT TAAACTTCTT TTCTTGTAAG TTACCCAGTC TCGGGCTTTT CTTTATAGCA   720
 721    AGGCAAGAAT GGACTAATAC ACATACCAAT TCTTGCAGGT AGGATTTTTT GGCACAGGAG   780
 781    AGAAAGCTGA GTAGTATCAG ACTTCTTGCC CCCTACTCTC CAGGGTGAGC CAGGGTAGAG   840
 841    CCTCTGAGAA TGCACAAGGA AACTGAAGTG ACATCTCAAT CAGAAATTCT GAGTCAAAGT   900
 901    TTAGATTCCT GAGTTTTAAT AGGAACATTG ACCAACTTCA GTATTCTTAG AAGAGCATAC   960
 961    AGGATAAGAA GAAATTAGGA AAGCATGAAG GTCCAAGTGT TTCATAAAGT ACCCCCACTG  1020
1021    TGGGGATATG ATGACTGGGA GGGGATGGCA GTGATGTAAA AAGCTTTGTC CATTTCCTCC  1080
1081    CAACTCAAAC GTTCTGTGAC CTACTTGAAG AACTGTCATG TATCCTTATC TCTTTTCATC  1140
1141    CAGGTATCAG GTTTAGGGCC AATGGGGAGG AGCCACTGAG AGGGAGGGTT GACACTCAGC  1200
1201    ATCATTCAGA TCTTCATTTA ATTCAGTAAA CACTTAACTG AGCACTTCCT GTGCCTGGTA  1260
1261    TGATAATGGG CATTGGAGAT ACGGAAGTAA AAAAGACAGG CAGATTACCC TGTGAGCAGC  1320
1321    TGGAACACCG TGGAGCCTTC TGGGCTTCTC TTTATCCTAA CATTCATTGC AGTTACTGTT  1380
1381    GACTGATCAT CTCTCAGCAA TACCCACCAT TAACCATGGA ATAGAAGCCT CCTGAGGCTA  1440
1441    GGGGCCATGT CACCCCCAAC ACATAGCACA GTTCCTGATT TGGAATTCAC TATTACCCGT  1500
1501    TGAATAAATG AGTGAATGAA CGAATGAATA AAGGAAAAGC TGTATAGTGA AGGCACTTCT  1560
1561    ATGTAGAACA ATGTGGTGTG TGGTGGGGGG TGTGATCTTA TGATTACATG TATATAGATT  1620
1621    TTTGTCCATG GTTCTTGTCC ATAACTCCCA TGACACTTGC TGAGGTCTTT TGCTATAATG  1680
1681    TAGAGGTGCT TTAGGCCTCA GGAAACAGAA TATTTCTCTG GCCTTCTTTG CCCTCCTTTC  1740
1741    ATCCACCCAA GGCGGGACTC TATAATCTGA TTGTGGGTCA TAAGACCCTC ATTCCAGAGG  1800
1801    AGGTCATGCC CCATACCCTG GAGGAAGGAA TGCTGCACAA AGAGAGGAAG AAGAATCTGG  1860
1861    ACAGACAGAC CTTGCTGAGA TTAGATCATA CCCTTTTTGT CCAATACAT  TTTGTTCAAT  1920
1921    CACATGCTTC AGTCATGGAC AACAAATGAA ATCTCCATAA AAGCCCAAA  GGACAGGGTT  1980
        (Placenta-Major)I.1
1981    CAGGGAGTTT CTGGAGGGCT GAACACGTGG AGGCAAACAG GAAGGTGAAG AAGAACTTAT  2040
2041    CCTATCAGGA CGGAAGGTCC TGTGCTCGGG ATCTTCCAGA CGTCCCGTAT GTATCTCTTA  2100
2101    ATCTGACTGA GCCCTCAACC TGTGGGATCA GACACTCTTT CCAGGTAGAT AGTGTTGGAA  2160
2161    CTGAGTTGGA GGACACCCAG CTGGTGCCCG CTGCTTGGTG TGTGGGGGAA AATCCCCTAC  2220
2221    ATTTGGTCGC AGAAGTCTTC TGTGTTGATG ACTGTTGTCG TGGTGTGAGA GCAGAGGGAA  2280
2281    AACACTGCTT GAGTGTTTTT CTGAAATAGG AGGGCCTAAG AACTATACTG TTCTATGCCA  2340
2341    CAGAACTGGC CCCCTACTTT CCTTGAAAGG CTGGCTATCC AATGGTGAGG AGAGGAAGTG  2400
2401    GTAGCCTGAA CCAGCCTCCC CATTTCCCCA CCTCCCACCC CAGTTCAGAG CCCAGATCCA  2460
2461    GTAGACAGAG CAGAGATGAG GCCTGCTTGG AGCCAGGCAG GCTCTATTAG ACAACTTCAG  2520
2521    GCCAAGAAGC TGCCCCTCTT GGGATGCAGG ACTCAAAAGG CTTGTAGCAT GGCCACCCCG  2580
2581    TGGGCTGGGT TGGTGGAAAG CCTGGGATAT TGCTCTGGGG CAAGAGGGGC AGAAGGAAGC  2640
2641    GCAAATGAAA AGCCAGACTC CTTTCCTACC AGACTCCACT GTCAGATCCC TCTCCAACTC  2700
2701    TTCCTGTGTG GGATGATGGC ATTTTTCACA GAAGAAGGGG GACATGTTGA TATGGCCTAC  2760
2761    AAGGTAGACA TCTTCACTCA TCTCTCACCC TAAAGTGGCT GTGCCAAGC  AGCTGCCATG  2820
2821    CTCTGCCCTC TTTCCTCTTC TCCTCTATCT TCTCTCTCCA ACCCTCTTTC CACCGCAGTG  2880
2881    CCACACAGTG ACCTATCTCC ATCACTGGCC TATTTCAGTG TTGCCCACTT TAAGGCCTAA  2940
2941    CTCCGAGTAC CCTTCCTCAT CTAGCCTTGA CTTCCTAGGC CAGTCCCAAG CACTGTGAGC  3000
```

Figure 1 - page 2

```
3001  TCTACAAGCT GCAGGGGCTC TGTGGTTATG CACCTGGGCT TTGGAATCAG ACCTGACCTT  3060
3061  GAAACTGTTT TTTAACTGCA TGACTTTAGA TATGCTACTC AAGTTCTTTA AAGAGACTGT  3120
3121  AATTGTATCT ATTTCATAGG GTTGTGAAGC TTTAATAAGA AATACTTGT AAAGCACTTG   3180
3181  TATAATAAAT GTTCAACACG GGTTGGTATT GTTGGATATG GGCCATATGA ACTGGCTGAG  3240
3241  ACTTACACTG TGTGTGCCTT GTGCTGTTAG TTGACACTTT AGTTCTTCTG TGCCTTGTGC  3300
3301  TGTTAATCGA CATCTTAGTT CTTCCACATC CTATTTCTTC AGTTGGGTTA CAATATTCTT  3360
3361  AAGGCAGGGA CCTATCTTAA CTGTCCTCTC ACAGCAGGGA CTTGTGCCAA GTAGGAATAT  3420
3421  TTGATTAATG GATTCATTAG CTAATCACAC TTTGTAATG CTTTTTGAGG AACAGAACTT    3480
3481  TTGAATGCAC GATAAACTTG GGTTCTCGTC TGAATACCAT GGCTTTGAGG TTGGTTATAT  3540
3541  GGAGCCTTTC AGTGTGAATC CCTAAGCCTC TTGAGATTTC TTGAGAGGCA GATATGCCTG  3600
3601  CATAGCCTGC CCTGCCTGAT ACTTCACAGA ATGGGCTGCT ACTTTTTACT TATTATTAAA  3660
3661  AAAAAAAAAA AGCTATCAAT CTGGCCTGTT TTGTTGACAC AGGAGGCTCA GGATATAATG  3720
3721  CGGACACAGG GAGATATCTC AATTCCCTTT TTTTGGAGAC CAAAGCAGCC AAGAACATTG  3780
3781  TGTGCTATCT TTACAATGAG AAGTAGTTTT TCCATTAAAA GGCAGATGCT TCATTTCCAA  3840
3841  AAGTTAAATA GAATGGTCCT TAAAAATGAT TCCAGCTGGT TAACTTTAGG GCTCTGGAGA  3900
3901  ATAAAATCAA ATTCAAGAAT ATACCCCAAC TTTAGTTCCA CAGCATTTCT TCCTGATTGT  3960
3961  GAAGTAAATA ATTTTCCTGG CCTGGCACTT GGGTATTCTT GTCTTCAGTG ATGAGATTGA  4020
4021  CAGCTACACT GTGACTTTTG ATGGTTTTAC TGCCCCACCA CCCTTCCACC ACACTGGTGA  4080
4081  TTAGGGAGAG AGCCACCCTA AAAGTTGTCA CCACATGCAT CTTCCACTCA GCCTCTTATG  4140
4141  GTTTTAACTC CCCATTCCTA CTGTTAAACC CCAAGAAACT TCACACCATC CAACCAAAGT  4200
4201  CAGCAATTCT CCCTTTTTTC TTTCTTTTAT TCTTTCATGT ATTCATTTAC TCAGCAAATG  4260
4261  GTAATTGGGT GCCTACTATC TGCCAGGAAC TGTGCCAGGA GCCAGGAATA GCATGGAGAG  4320
4321  CAAAGCCAGG CATCATTCCT GAAGCCTGGA GTGGGGAGAC AGATTTACCA AACAATATTA  4380
4381  GACATGAGGG TGCAATTCTA AATGCGGCCA CGAGACAAAT GCTCTGGAAG AAAGGAATGC  4440
4441  AGTTCCTTGA GATCATATCA CTGAAGAGCC TGTCCTGTAG TTGGATGTGT GGTTCAGGGA  4500
4501  AGGCTTCCCT GAGAAAAGGA TGCTTGTGTT GGCACCTGAA GCTGAGTTGT AAACTAGGCG  4560
4561  AAGATAGGGG TGAGGAGAAT TGCAGAGAGG AGGAACAACA CGTTCAAGGC CCTATGGCAG  4620
4621  GAGATGGCAT GGCTTATTTG AGGAACCGTA AGAAGCCAAT GCGGTGCCAC ATGGAGCGTC  4680
4681  AGGAGCAAGG AGGAGGGAGT GAAATGAGGC TGTAACCAAG GCAGGGACCA GACTCTGTGG  4740
4741  GTGGGACCTT CCTTGTAGGG CTGAGGCCTT TACTGTAAAA GCAATGGGAA ACAAATGAGG  4800
4801  AGTTTTACGT GTGTGTGGGA TGGGGAGGAG TCGGTAGATG GATGACAGAT TTTCATTTTA  4860
4861  AAAGATTACC TTTTACTGCC AAGACTTGCA GTGGCTTCTG TCACTATGGA AACCATGTAT  4920
4921  GATCTCTGAC CTCCACCAGG GCCAACTTCA GCCTTTAAAA CCACCTGGAA ATAAGGAAGT  4980
4981  GCTGAGTTCT AGAAAATGTA ACTTTCTCTT TCATCTGTAT GTAAAAGGT AGTTGAAAAA    5040
5041  CAGAACCGTG ACTAAATTTA GATCATTTAG CCAATCTTGA TACTAGTAGG GGTTTTGTA    5100
5101  TAAAACACAG TGTGTTGTTA GCATTTTCTT GGAAGTTAGC CTTTGGTGCT TCCAGGTAAG  5160
5161  AGCACCAAAT CTGCTTATCT CTAGGGTTGG GAATAAGAAT AGATGATATT GCTTCCGTTG  5220
5221  TGAGATTTTG GTCCAAGTCG GGCTGGTAAC AACAGATTTC CGCCTATCGT AGTAGCAGTG  5280
5281  TCTTAGACCT TTGAGTTGCC CACTCATTGT TTGACGTGGA GCTGTCTGTG GTTGTGAAGG  5340
5341  TGATGCCATT TCAAATCCCC ACTTCCCATT GTTTTCTCTC CTTCTTTGCA ACAAACATGC  5400
5401  CCTCCCACCC CACCCCACTC CACCTTTCTA GTGTAGTGTA CCCAATTGTC ACAGATCAGA  5460
5461  TTCTCTGGAA ACAAGTGCTG AGATGGAATT TGGAGTACAA AATGGTTATT AGGGATCAGC  5520
5521  ACCTATGAAG GAAAGAAGGA GAAGCAGGAT TGGGCAGAGG GAGAAATCCA GCACAGTCCA  5580
5581  ACCCTGCAAA GCCTCAGCCA ACCCACTGGG AAGCTCTGGA TTGTGTATTG CTCATCAGAG  5640
5641  TGTCCTGTGT CAGGCCAGAG TGACTGGGCT TTTACCTACC TCACTCAGTC ACAGGACAGA  5700
5701  TGTGGGATGC CCTGGGAAGG TATGACCTGG GCCAGGTGG CTCTCTGCAG CTGAAGCATG    5760
5761  CTTTAATCTT AATCTCTGCA GCCAGGCAGT CAGTCCTTTC TTGAAGGGGG ACCCTCAGGT  5820
5821  CCCCACATCT CCACATCTAC CACATCAACC ACCTGAATCT GCCATTCCAA CATTAGTAGG  5880
5881  CTTTAAATTG TAACCGTGAC AGGCTGTAGA AAGAAATCTT TTCCTTTTTC ACCTGGAGTG  5940
5941  ATGGCCTTTC AATAAATGAA AAAGTGATTG TTTTCAGAAA CAATGAAAAT GTAAAGGAAG  6000
6001  CTCTAAGAGT GGATTCTGTG CAATCATGAG AATGGCTCAT GAATTTGAAA CTGCAAAATC  6060
6061  CACAGAAGTA AGTTAATACT GCAAAGCTCC ACTTATGGAA CTCGAGCCAC TGTTTTTGAA  6120
```

Figure 1 - page 3

```
6121    AGATAAAACA AAGCCTTACA TGTGTAGAGC ACTTCAGTTT TCAAAGTGCT TTCTCATGTC    6180
6181    ATTTGAGTTC CATAATAAGC CTGTGAACGG GGCAGGGCAG GTTTTATAAG CATTTCACAG    6240
6241    ATGAGGAAGT CAGGGCTCAG GAGGTTTAAG TGATCTGCCC AAGGTCACAT TGTTGAAACC    6300
6301    TCATCAACGT TCACCCATGC CCTGTTTATC AAAAGTAGGA AATTTTTGGC CCCCATCTTG    6360
6361    GGCCACTGAG GAATGCTCAA AATGATGGAC AGGAAGTGAA ACAATAGAGC AGGGAAATGA    6420
6421    TTCAAAGTGA TGGAGTGGAA AACAGCTCAG ACTGGCACTT GGCTCCAAGG CTTAAAAACA    6480
6481    AACCTGGAGC AGACACTGAA TGCTAGAATG TGTAAGCTAG TCAGGAAAGA AAGCCAAGCC    6540
6541    TGGTCTAGCA GATTAAGGAG GATTTTAAGA GATCAATGAT GTAAGAACAT GATTTCCTAA    6600
6601    AAACCATGTA GGGGAACTGT CATCTCTGCA GTGAATAGGT GCATATAGGT CCTAAAAAAA    6660
6661    AAGTGAATTT GGGGCCTGAT AGCCTAAGAC CTTTCATTCC TGGGTTGCAA AGGCAGAGTA    6720
6721    ACAAGCTAGA ATAGATATGC CTCACCTCTC CAGAGAGACT GGTTGGGAGT GACCAAAAGG    6780
6781    GATTCCTGCC AATATTAAGC CTGGAGAAGA TGACACCCCA TCTGCTGAGC CTGGAGACTC    6840
6841    AAGCCAGGGA CCAGAGGAGT GGCCCCGGCT AAGAGAAGCT TACCTTTTAT TGCCAAGACT    6900
6901    TGCACTGGCT TCTGTCACTA TGGAAACCAC GTATGATCTC TGACCTCCAC CAGGGCCAAC    6960
6961    TTCAGCCTTT AAAACCACCT TTCCAATGA AACAAGAAAG TGCTGAGTTC TAGAAAATGT    7020
7021    GACTTTTTAG GTCAAACTGT GGACCCTAAA CATGTGCTAC TTTCTTAAAG CTGTATGAGT    7080
7081    AAACACATGG TCTCCAAACC ACCCCGATT CTGTAATCAT AAGAGGGCAC CAGTATCTGG    7140
7141    GCATCAGTGA GTATCCTGGC AGATGGATCT GGCTGGATGA GGTAAGGGAG TTGTACAGGT    7200
7201    GTGCTGAGTC TATCTCTACT CCTGAGCCTG GGAGATGTGA GAAAACAGGA AAATGAGAGT    7260
7261    CTCCCCGCCA GTGACTTGAT AGGGGATTGA GAACCACCAT TTTTGTCCCT TCTGAGAAGG    7320
7321    CACCTCAGCT GCTGGCCCTG AGCCCAGAGA GCAGACAAAA GAAAACATTA CCCTTATACT    7380
7381    TAGGGGCAC AGCAATGCTC TTAGAAGAGG CTCACATGAA ACCAAGCCAC TAGGGAACAG    7440
7441    TAATACATTT AAAATATTAA CGTTAGGACA TAAACATTCC AGTAGAGCAC AAAAAGACTT    7500
7501    TCTGGAACCA AATGACAAGA TCTGCAGACA AATTCAGTAG CTGAAGGAAA GAAAAGTAGT    7560
7561    AGTTAATAGG AAGTAAATTT CCCAAGTTAA GAAAGGGCCT GAGTCTGCCT ATTGGAAGGT    7620
7621    TTTGGCAAGT TATGGGCAAG ACAAATGATT CATAGGTTGA GAAATTCAG AAGTCTAAGG    7680
7681    ATGAAAAGAA AATCTTACAG TCTTCCAGAA AGAAAGTACA AGTGACTTAT AGGGGAAGAA    7740
7741    GGATCATGGG GGCATCAACT TTCTCTTCTA TGACACCTGA AGTAGGGATG ATTGAGGCCA    7800
7801    ATCGTGTGAA GATTACTGAG AGAAAAACAC TGCACACCAA GAATCCTGTA GCAAGACCCC    7860
7861    ACTCCTCTGT CAGGGTCAAG GAAACATAGT TGAGAATATG CAAGGAAAAG ACCTGTCACC    7920
7921    CATATCTTCC ACCAGATAAA AGGGTGTTAA GATCTAACCA AACAATAGAT GAATCAGCTT    7980
7981    AAAGGCTACA GGATGGAAAG AGGAGGAAAA GGGAGAAAAA AATTAGTGGT GAGCAAGGAG    8040
8041    CCTTACAACA CATCGTCAGT TAAATTCAGA CAGATAATAA TAGACAGTTC AGGAATGTGT    8100
8101    AATATAATTG CTGAAAATAG AAGAGACATA TTTCAAGGGA AATGTTAACA ATAGCCTGGA    8160
8161    ACAAAAAGTT CTAAAGGAGA AAGAGGGGAA GTGAAGTTTC CACAGGTCTC ACATTGGTGT    8220
8221    GTGAGAGTGG GAAGTGAAAG CGTCCTAAAG GCCTCATGCT GGGGGAGGAG GAACAGCAGG    8280
8281    AGAGGAGAGA ATCTGGGGAA ATAGTTGGAC TCTTATGTTG GTATAATGGA ATAAAGAAT    8340
8341    GAGTTTGACT ACCAGTGACA AAAAGGAGAA GGACCTGGTA GAATGAAAAA CTAGACTAGA    8400
8401    GCTCCCAAAT TAAGAAGAGA AAGAAAATAA TTGAACAGAA ACTTGATAAC TAATTAATAT    8460
8461    AAAGAACATC AAGGGGCTT AAATAAGTAA TAAATATTAA GTAAATAGA AGCAATAAAA    8520
8521    TTCAATGTAT TATTAAATGT GAATAGAATT ATTCTTAAAA GAGACTATTA GATTTGGTAA    8580
8581    AATAAAAGC AGACAGTTAT ATGCTTTCTT GTATATATAT ATGTATGTGT GTGTGTGTAT    8640
8641    GTGTGTATAT ATATATATAT ACACACACAT ACAAGAAATA AACACATTTA ACAAATGTGA    8700
8701    TAAAAATTGA GAATAAAAAG TCAAGAAAAA ATACCAGGCA AATGCAAATA ACAAAGCAGG    8760
8761    AAAGAATTAC TCTGTTAATA CCCAGCAAAA TGAAATGTAA AGAGCACTGA ATAAGATAGA    8820
8821    GTTGCTATGT AATGATAATA ATTTGCAAAA AGTCACTAAC CAGTATGTGT TAAAAATCAA    8880
8881    ATGTGAAAAA TAGTAAAGCC ATGTGTGATT TCAGTACCTT TCTTCTTTAC AGAGAGCAAG    8940
8941    AAGTCGCGCC CCCTGAACT CGCCCCCATT CTATCCAGTC CTACCACATA AATAACCATT    9000
9001    CTGGGTCATA CAAATACATA TGCTCTTGCA AAGATGCAAA AAAAGATGCT AACTATACTT    9060
9061    ATCTCCTTCT GGGTCAGTAT TTACAGGTTT GCCCCATTC CTTATTTCCA TGAGGAGAGA    9120
9121    TTTCCCTAAA ATGCCCCTTG TCCTCTTTCC GCTTCTCCTT TCTTCTCCC CAGAGAGGAG    9180
9181    GAATGTCTTG GCTGACTCAT CTTCTTCACC TCTCCTCTTT CCTTTTCGTA GCCAGCCTTA    9240
```

Figure 1 - page 4

```
 9241   TCAGCAAGCT CTCATTCTAG TCTACTCTCA CGTGGCTCCA GCTCTCCAGG GGCAGCCTCT    9300
 9301   CTGCAGGAAG GCCTCGGGTG TTCAGTGCTG CCTGTGATGA GTGGGTCTGT CTTTCTCATT    9360
 9361   TGGAAAAAAT GTTGCTGAAC ATTTAATGTT ACCATTTCCA ATGTCAGCTT TATCCCTAAT    9420
 9421   AAAGCTGACG TTTTGATCTC CATCTGCCTT GCTCTCATCC TACCACCCGA TTGGTTTAGA    9480
 9481   ATTGTGGTGG AGAAAACAGG AACTCAATTC TGGGGGTCTC CTTACAACTC CAAAACAACC    9540
 9541   TTATTCTTCC CAAAGTCAAC CAGCCATCTT TAATGTGGCT ATACTCCTCA TCTGCGCTTC    9600
 9601   CTCATCCCTC ATTCATTCGC CACGTCACGG CCATGTAGCT TCTTCTCCCA CCAAACATTG    9660
 9661   AACCCATCCT GCCAAGGTCG CTGATGACTT ATTTGCAAAA TACAATGAAA ACTTTTCAGT    9720
 9721   CTAAAGGTCA ATCTTACTTG AAGTCTCTGC AACTTTCAAA GCTCTTCATC ACTTCCTCCT    9780
 9781   CCTTGACATT CCTTCCTCTC TGAGCTTCCA TGACACTACT TTCTCTTGGT TTTCCTCCTA    9840
 9841   CTTCTCCGAC TGTTCCTTCT CAGCCTCCTT GAACTGTTCT TCAACTTCTG TGCACCCAAC    9900
 9901   TGCTAGTGTT CTCCAGGGTT GTGCCCTACA TCCTCACTCT GTTGACTCTT CCTTGGTGAT    9960
 9961   TTTATCCACT GCCGAGGCCT CTGACCACCA CATACCCAAA CCCTGCCTGT TGCCCAGGGC   10020
10021   TCTCTTTGGA GCTCTAGACT CAAAGGGCCA AGTACCAGTG GTGTAACTCC ATGTACGACA   10080
10081   GAAGAAGGTA CCATATCATT TTATTTTTTA TCACTTTATT AATGATAGCA AGATTTTTTC   10140
10141   ATATTTTACT GATCAGTTGT GCATGTTTAC AGGTGTATGT GTATAAATCC TTTCCTCACT   10200
10201   TGACATTTCT TATGCCCCTT CTCTCCTCCT CTTCCTTTCT GTCCTGCACC TTAGTTTGGG   10260
10261   TCCACAACAC ACCTCAACGA TGTCGCTGTG CCACTTCTCC AAGTGCACCT TCTACTCCCA   10320
10321   GTCTGCTAGT TTGTGAGCCC AGACTCGATT CTTCGGTCCA TGTGATATGT TCATACACAG   10380
10381   GGCTCTCCAC AACCCCACCC CTGCCTACTC TCTCTCTGCC CTGTTTCTCA CCATTCCGCC   10440
10441   CTTGTGCCTC ACGTTCCTTC TTCCAGCTTC CGGGAGGTGC CTGCTCCCTC CCTGCTCCTT   10500
10501   GCCACTATCA TGCTCATTTC TCTGCCTGTT TTCCTCTTCT CCCCTTCTCT GACTGGCTGA   10560
10561   CTTTATTCTT TAAAACACAC ATCTGATGTC CCTTCTGGGG AGCCCTCCAG CCCCACATCC   10620
10621   CAGGGAGGGC TAGCTGCTCC GACTGTGTGC TCCCACTGTA ATTGTATTTA CCCATCCTGG   10680
10681   TGTATATCTG GTCATTTCAC AATGGCCTGT CGCTCCCTGT CTGTCTCCCT GTTAGGCTGT   10740
10741   GAACTCCTTG GGAATACTCC TGTATCTTGC TCATCTAATA CTCCCAGAAC CTCATGCATA   10800
10801   CCTGGCATGT AGTAGATGTT CAATACATTT TTGAATGAGT GAAAGTGTGA TAGAGGGCAG   10860
10861   TGCCCTTACA ATTTCTTTCT GAGATCTTGC TTCCTGACCA CAGGATTCAC TCGCTGAAGA   10920
10921   GGAGTGATCA GTTTCATACC AGCAGCACCC TCTGCCCACT GACAGATGGT TCTCCACTGG   10980
10981   GAAACTTTCT TCATCCCCGG TGGTATTTGA AGGGAGTTCT CTATACATGT TTACCTTGTA   11040
11041   AAATTTCCCT CCATCAGTGG CCCTGGCCTT GCTGGCCTTC CCATTATACC TCTTGGGGGG   11100
11101   CACTACTAAT ACCCATGTCT TCTGCTGTTT CTCAAAAGGC CCCTAGCCTT ACTATCCAAA   11160
11161   TAGACACTGA AAAGGGGTGG AAATCCTGGG GGCAGTCAGC TCTCAGAGGG TGCCTTTTTA   11220
11221   GTGTCTCCTG CCCCTCTGGT TTGCCATTGC CTGGCTCCTG CTGAGTCTGG AGTGGGCCC    11280
11281   TATGTGTGAA GCAGTAGCCT CCTGTTAGAG TGCTCCAGAC CATCTCAGTG TGAACCAAGG   11340
11341   GCTGTTGTGG CCAAGAGCTC GGCATCCCAG AGTCAGTGAC GAGAAGGGAG GAGGCAGGCC   11400
11401   AGGGCAAGAA CATGGCTCAG ACTTGTGTGG GAGTGTATTA GTCGGGGTTT TCAGAGAAG    11460
11461   CAGAACCAAT AGGTTGTATA CAGAAAGAGA TTTATTATAA GGAATTGGCT CATGCAATTA   11520
11521   TGTAGGCTGA CAAATCCCAA AGTCTGCAGG GTAAGTTGGC AAGCTGGAGA CCTACGAGAG   11580
11581   TGTAGGCCTG GTCTGAGGAC CAGCAAGCTC ACAACCCAGG AAGAGCCAAT GTTTCAGTTT   11640
11641   GTATCTGAAG GCAGGAAGAA GCCAGCATCC TAGCTTGAAG CCAGTCAGGC AGCAGCAATT   11700
11701   CTCTTACTTG TGGGACAGTA AACTTTTTGC TCTATTCAGG CCTTCAGCTG ATTTTTTGAG   11760
11761   GCCACTTGCA TTGGTGAGGG CAATCTGCTT TACTCCAACT CATTCCATTT AGATGTGAAT   11820
11821   CACATCCAGA AACACCCTCC CCAACACACC CAGAAAATG TTTGACCAAA TATCTGGGCA    11880
11881   CCCTATGACC CAGTCAAGTT GACACATAAA ATTAACCATC ACAGGGAGCA ATAGGGGAT    11940
11941   CAGATGACTC TCAACTCCAG CTGTTGGAAG TCACACTTAA CGTACACACA CATGTACACA   12000
12001   CACACACACA CACACACACA CACACACACC CACCCCTGCC CTGTAACTCA GGATTCCCAG   12060
12061   TGAGGGTGGT TCCACCCATT AGAGCTATCT TTGGAAATTT GTGGAGGCAT TTGTTACTAT   12120
12121   CACAGTTTGT TACGACGGTG AATGTGGGAT GCCATTGACA TTTAGTGGAT GGGTAGGGGG   12180
12181   GGATGTCAGA TGCTCTGCAG TGGTCAGGAC CATCCACATC ACAAGTGACT GTCCCTCATC   12240
12241   ACTTTCAAAT GTCCTGCTCA ATGTTTATGT CCATGAAAAC TTGTTTATAC ATAGGTGGAT   12300
12301   CTAGCATCCA ACCCCATTTT ATATATAAAC ACACAGGATT TATTTTTTGC AGTTTTAAAA   12360
```

Figure 1 - page 5

```
12361  TACACTGAAT TTTTCAGGAA TGCAGCATAG AGTGAAGATG GTACATATTT GTTCAGGACT  12420
12421  TTATGAAGAT TGTTCACCAT TTTGGAAAAT CATGTTACAA ATGGCAATGG TAATCACAGT  12480
12481  GTTTGAGCCA TACTAAAAAC ACATGTGACT CTGTGTGCAT TTAAATCTAT TGCATTCATG  12540
12541  GCGACTCTAC ACATAGGTGC AGACATCTAA CTACTTAGTA GGATTTCCAG TGTAGTCATG  12600
12601  TACAAGATTT TTTAGATACT GAAATACTTA TTTTTCTATA AAATTGCTTT TCTTTCTTTC  12660
12661  TTGATTATAA CCCAGTGAGT GTATTCCATT TTTTTTTTAT ATTATGAATT TTGGGAGGAA  12720
12721  ATTTTATGTG TAGGTAGATA TATTATCTAT GGGTTTCATT TGAGCATAAC AAAAGGAGAG  12780
12781  TTACAAGTTA TGTGTTGTTG GTTTGTTTTC ATTTGTTTGT TTTTTCTGAG ACGGAGTCTT  12840
12841  GTGTTATAAG AAGGGACACT GAGTCTGATG TGGCAGAGAG CCACTATTTC AACTGAACTA  12900
12901  GTGCCTGTGA AGAACACGCA TCTGTCTGTT GGGCTGAGCC TGGCCCCAAG GGACCTGTGG  12960
12961  ACCCTGGATC CTGAAGACAC TGGATCCTTG AGAATCGCTT GAACCCCGGA GGCAGAGGTT  13020
13021  GCAGTGAGCT GAGATCATGC CACTATATGA CAGAGCAAGA TTCTGCCTCA AGGAAAAAA   13080
13081  AAAAAAAAGA ACAATGTCAA ATGAATTAGT GAATGGATGG ATGAGTGAAT GCATGCATGC  13140
13141  ATGATTTGGG GGGTGAGAAC ATTAGATGGC TCTACTCATT TAATCCCAGT GTCTGTGGAA  13200
13201  ATCAAACACA GGAGACTGCT TTGTGTTTTC TACCAGCCAG CTCACCAACT GAGCCCCTAA  13260
13261  TGGTGCCTTG GCTTTACTCA GGAGTTTAAT TAGCCCTGGC GCTTGATTCT GAAAGAAATG  13320
13321  GAGAGCAGTG ATGAACACAA ACAGGAGAGA TCTGGGCAGT AACAAGCCTG GCATATGGCA  13380
13381  CCATGGATCA CCCATTGGCC TTAGGGCTGG ACTAAGTCCT AGGTGACTTT ACTTCTAAAT  13440
13441  GTTACTCATG TTTATTCTTT CAAGATGCTA GATAATTAAG ACCTGACTAC CCGAAACCAA  13500
13501  AAATACGAGC TGCTTTTGGA TGATTAGTGG TGCATGCAGA GTCATTGGAA ATGTAGTGGG  13560
13561  AGTAGGGAAA ACAGTTCTGG GTTTGGATTC AAAAGACTGA GCTTGACCCC AGACTTTCCC  13620
13621  CACAACTACC TGTATGGTCA TGGGCAAGCT AGTTCATATT TCCAGGTTTA AAAGCCTATG  13680
13681  GTTCAATGAA ATGCAGTAAA CAACGATTCA GAGGAATTAC ACAGTGATGT GTTTATAGTA  13740
13741  GATACACCAC GAAGTTAAAA ACACTTGTAC TTTCAGGTCT CTCATTGCTC TGGCCCCTTC  13800
13801  CAAAGCCCTG TGTCTCATTT TGTTAGATGG TATCATTATC CTAAACCTGG GTCTCATATT  13860
13861  AAGGTTTCTT CCAGGTTCAA AATTCTATGT TACTGGCCAA TGAATTTAAA AAAGAACATT  13920
13921  TTCTGTTATA CAACTCCATT CTATTCCATA ACTTGTAATT TTTTAGTTTC AAGGACACCA  13980
13981  CTATGTCATA TACACATTGT TCTTTTCTTT AGGTACTTAG CATGATTTTG GACAAATCTG  14040
14041  ATAAAGAAAA TTGAAAGTCT AGATCCCTGG GATTTACTAC TATAATGCTT AAAGTTGAGC  14100
14101  CACATTCTCA ACTTTATCGT AGTTGAAAAT TCTACAGCAA GAATTCTTTA ACTGTAAGAT  14160
14161  CTGTGTTGGG TTACTGTGAG TTTCATTTCA GTCTCATTTT CATTGTTCTG GAGTTCTGGA  14220
14221  CATCTGAGGC AGCCCATGCA ATTTTCTTCC TTTCTTTTTC TAGAAGAGCT TCGCCTCTGG  14280
14281  CCACTTGGAA GCTGGGCCTT GGGAGGTCCA GGGGTAAACT GTGCATTAAG CTGACAGTGC  14340
14341  TCAGTAAGAA AAATCTTTAC TCTGTGGCAA TCTGGTTTGG ACACCTACCC TAATCAAACT  14400
14401  GGGAACATTT GGGGAGGACT CAGGAATTAT CTTAATTATA GACACCTCTG ACTTATAATG  14460
14461  ATTCAACTTA TGATTTTCA GTTTATAAT GGTGTGAAGT TCACTTTCAG TAGAAACTGT  14520
14521  ACTTCAAGTA CCCATACAAC CATTCTGTTT CTCACTTTCA GTACAATATT CAATAAATAA  14580
14581  CAAGAGCTAT TCAACACTTT ATTATAAAAT GGGCTTTGAT TTGCCTAAT TGTACGCTAA   14640
14641  TGTAAGTGTT CTGAGCACAT TTAAGGTAGG CTGGGCTAAG CTATGATATT TGGTAGGTTA  14700
14701  GGTGGACTCA ATGCCCTTTT TTTTTTTTTT TTTTTTTTTT TTTTGAGACG GAGTCTCACT  14760
14761  CTGTCACCAG GCTGGAGTGC AGTGGCGCCA TCTTGGCTCA CTGCAACCTC TGACTCCTGG  14820
14821  GTTCAAGCGA TTCTCTTGCC TCAGTCTCCC AAGTAGCTGG GATTACAGGC ATGTGCCACC  14880
14881  ACGCCCAGCT AATTTTTGTA TTTTTAGTAG AGACGGGGTT TCACCGTGTT AGCCAGGATG  14940
14941  GTCTTGATCT ACTGACCTCG TGATCCGCCC ACCTCGGCCT CCCAAAGTGC TGGGATTACA  15000
15001  GGCATGAGCC ATGGCGCCTG GCCTGCACTT TCAACTTTTC AATATTTCCA GCGTACAATG  15060
15061  GGCATATAGA GATGTAGCAC CATGGTAAGT TGAGGAGCAT CTGTACTTGT TGGATAAGTA  15120
15121  TGAAGCTCAA TCCTCATGGT TAGTGTCATA CTCTGCTAGC CAAGAGGCT AGAGCAGAAA   15180
15181  AAGTGGGTGG CAGGGAGGC GAATATCTAT GGGCTGCAAG TCCTTACAAT GGGATCTTTC   15240
15241  TTCCCAGACT CCTCAGTCCT CACCACTCCT ACACCCTGCC AGTGAAGAAC ACCCACAGGA  15300
15301  CATCTGTCTT CAGCTTGCCA TTCAGATCCA CTATAAGGGC TTCACCCTGT AGCAACTTGG  15360
15361  CTTGGACACT GACCCTAGGC AAACAGGGAA TGTTTTTTGA GATAGGGTCT CTTGCTTCTT  15420
15421  GCCCAAGCTG GCCTCAGCCT CCTGGGCTCA AGCAATCTTC TGGCCTCCCA AGCAGCTGGG  15480
15481  ACTACAGGCA CATAACCGTG TGCCCTAAAC TTGGAAATTT TACCTGGTTC AGGAATTCTC  15540
```

Figure 1 - page 6

```
15541  TTAATTATTT TGTTTTTCTT GTAACTGGTA TTTTGTTCCC TTTGTGAGGA GGGGAAAGGA  15600
15601  AGTATTTTCT TTATTTATCC TGCTTTCTCA TTTTCACCAA AAATGAGGTT ACAGATCTAC  15660
15661  TTCTGACTTT AATTTGTAAC ACACCCCAGA ATTTTGTTAT TGTTTTGCCT CTGACTTTTG  15720
15721  TTTTCCCAAC ATAAAATCAC TTCCACCTCA GAATTATAAC CCCTAGGGTC CCTAGAACTG  15780
15781  ATAATAAAAA TTCTAGATCA GTGGACAACT TAAAGGATTT CCTGTTAACA TTTACTCTAC  15840
15841  CTGTCTAAAA TTTGCATCTT CCATTGCTTT TTCTCAATTT TAATTTCTAT GTGTTTGTTT  15900
15901  GCTAGTTGGA TTTAAGTAGA CATTTCGTTT TTAACCAGTT TTAAAGTTGC CTTTTATTTT  15960
15961  TGGCTAATAA TTATGTTTTA GTTTATATTA TTTTATTGCC ATTTCATTCT CAACCAGCCA  16020
16021  GGAGCTGGCC TGGATTAGAA GAACTGGTTC TAACCTCATT GGTCTGTTAT GTTGTCACAC  16080
16081  AGGGTACATT ACTTAATTCA TCAGAGTGGG GCTAATCAG TGTGATGGCC CCTGTCTTTA  16140
16141  CAATGTTCTG GTAGCCTATA AATCGGCTTT GTTTTATTCA CTCTTATTTC TATGTTAGCA  16200
16201  TCTTTGGAAA AATTCCTAAA CTTATTTGGG AACAAATTGT TATTATATGA GGCTAATGGT  16260
16261  ACCTAGAAAT AACTAGAATA ATTCCCAAGA AGTTATGGCT TTATAAAATA TTCATCTTTG  16320
16321  GCAATGACCA GAAATGGCTA CCTTTACATA AATTAGTGTG TCCACTCTTT TTGGGGCTGG  16380
16381  TGGGGTGTCT TCTGACTGGC CTTCATGTGT GGGAATAGCC CCATTCCAAG TGCTGCTTGA  16440
16441  TTGTAAAATT GGACCAAGCC TGTCATCACA CTGCCCAGTC TTTGGGTAGG GGGAGCTGAG  16500
16501  AGATTCTGTG AATATTGTCA GAAGGGACAT GTTTTGGAT AGGGAGGGAA AAAAGCAAG   16560
16561  ATCCCCAGGT CCCCTGATTT TAACCATGAC GTAGAAAACT CCACACAGAC CCTCCTGCCT  16620
                                                        (Placenta-Minor)2a
16621  TCCGCCCTGG CACAGAGTCC GGTTGTCCTT TCATAGGCGG TGTCAGAAAC CCTGTGGTGA  16680
16681  AATTCAGCCT GTGGATTCCA GAAATTTGGA GTGTTCTTGG GGGGAAAGAT CCGCACACAC  16740
16741  AAAGGAACAT TTGGAAATCC CTGTGGTGAG TTGGGAGGTG GGGAGGGGAT GCAGTATGGG  16800
16801  AAGGCTGGAA GGGAAAGCGC CGGTGTACAT CCCTCCCTCT TCTTTCCAGG GCTCTGAGTG  16860
16861  TCAGGGCTGA GATGAAGATG ACACCCTGGC AGAGGAGGAG GCAGGGTGCT GGGGGCAGGG  16920
16921  CATGGACATT GAGGTCTGTG CTGAGCTTTA CAGTTTGCAA GCACTTTCAT GTTATCTTGT  16980
16981  GGGGGTAGAT CAGTGACTCC ATAGCCATTT TATAGGCATA GACACTGAAT TCACAGTGG   17040
17041  TTAAATAAAT TTCCCAAGAC CACATGGTTG GAAAAAAAAA AAAAAGTAGA GACACATCCA  17100
17101  AATCCAAAAA TTTTGTGCTG GAAGGTTTTC ATGCCATAAA ACAGTTCCAT CTCCGTTTAT  17160
17161  CATTGATCCC ACAAGTTCTA CTATTTACTT TACTTCTTC GGAAGCTTAG TTGATTTTTT   17220
17221  CCTTCTATAG GACATCTGCA CTTAAATTCT TTAGGAAGTA TTATGCCTGA GTGTGGCTAC  17280
17281  TCCCTACCTG AGAGCAGCTT CCTATAAGAA GGAGCTTCTC AGCAGGCAAG GAGAGAGAGG  17340
17341  GCTGGAGAAA GGCCAGGCAT GGTGACAAT TGTGGGCCAC CCAAGGGCCT GGACTCTCAG   17400
17401  GGTGGTGATA ACATAGTGGT AGGGGTTTGG GGAGAGGCCC AGAGACAGTG GCCCTGGAGG  17460
17461  CCACTGCAAG GGAAACAGG AAGAAGGCAG TAGGTCAAGT TCCTTCTTTA AACCAAGCCA    17520
17521  ACTAAGGCTT GTCCAGGGCC CTTCCTGTAG CTCCAGCATT CATTTGGTGC AGAAGAAAAC  17580
17581  ACTGAATTCC TTGGAGCCAT TATTGAGGCT TGAAAGTTTG GAAGCTCTGT GTTAGCAGCA  17640
17641  TTTTAGGGAC AGTTCAGCCA GAAGTGGATG TGTTCCCTAC AGACATGAAA TTCTAGCAAC  17700
17701  TGCATTGTTT CCTAATGGGA TCACAGGTTA TGGACTCATG GAGCTGAAAA AGTCTCCACA  17760
17761  ATGGGAGAGA AACTGAGAGG TGCTGAATCC AGCTGGTGAG ACCCAGCACA GTAGAGGCTG  17820
17821  GCCCAATGCC ACCCAGTGAG TTAGTGTTCC CTCAAGATTG TTACAGTTAA ATGCACTTGC  17880
17881  AAAATCCTAG TGGGGAAGCG GGGGTGGGGG TGATGCAAGG ATGGAAAACA TTTTGTCAAG  17940
17941  CATCAGATTA TGACAAGGGC TCTTCCTAAA AGTTAAGAAT GTGATGACTG AAAGGGGCCT  18000
18001  AGGATATATT TTATATATTG GAGGTGGTAC TGGCATTTGA GTATTTCTAG TTTGCTTTTA  18060
18061  TTATCTGGAT GATGAACAGT AACAACAGCA GAAGCAGCAA TAAACTCTTA CATAAAATTT  18120
18121  ATCTCTAAAT GCCAAAGCAG TTTGTTTCTC TAAATATAGT GTACAAAAAG AGAGGTATTT  18180
18181  ACATAAAGTG ACTCGCTATT AATTTATTAA TTGTCACTTG CACTTCCCAA TCAGGTAAGG  18240
18241  ATTGCACAGT TCAGGCGAAA GCCTCCACTG GCTGCTTGTT CTCTGCTCAG CTCTTGGGCA  18300
18301  CAGACACCTG CCCTGCCTTG TGATGAGGAA GCCTTCCTCT GACAAGGGCA GAGATCTCCA  18360
18361  TACTCACCAA CAGCTCCTTT CCATGCACAG GGAAGCAGCC AGGGGCTCGC AGGTTTTCAC  18420
18421  TCAGCCTATT TCAAGCCCAC CCTAAGCAGC CCCTTTGTCT GTGGAGCCAG GTCCGACCCA  18480
18481  TGGCCCGTGG CGGGAAGGCC ACACCAGATG CTGATGTGGG ACGGGAGCTG TAGCTCCATC  18540
18541  TTCTCATTCT CTTGCAGAAG GGGATGAGTG TGGTGCTCCC TGACTTAGCA GCTTCTCTCA  18600
```

Figure 1 - page 7

```
18601 GGAATTTTAT TTATTATGTT TTTTTTTTTT TCCCCTAAAC AGCATTTCTC TCCGTTTAGT 18660
18661 TAACAGGATG TTGATGGGTT TCTCTTCCTT TTGGGGTCCT TCCCTTTCGA TGAGGGCCCA 18720
18721 GGCCTTCCCC CTTCCCAGCA TAGTCCAGCC TGCCTGGATA CTCTTTCATG GGCCTCTGGG 18780
18781 GCCAGAGGAC AAGTCCCTAG TGCTGTCCAT CTGCTCTGTG CATGTCTGTT CAATTCAGTA 18840
18841 GATGTTCACT GAAGAGCCAC TCTGGGAGGA TGCAGATTAG GCCTGGAGAA TGTAGCAATG 18900
18901 GAAATGTTTG ATATCTGACT TCATGAGCC TGTAGATGAG TGAGGGACAT AAGTGGGACC 18960
18961 TTAAAAAATC ATCTACAAGA CAGAGAGAGA TATGATCAAG TTAGAAGGTC TTTTCTTAAA 19020
19021 GATCCCAGAG ATAATCTACC CCTAGATGTG CAGACGAAAT TAGGGCCAGA GGGGGTGGAT 19080
19081 GAACTGGTTT GAGGACTCTA AGGATGGCGT AAGTGATTTC GAATCGAAAG ATGGGGAAGG 19140
19141 AGCTCCTGGA GAAGGTGGCC ACTGGGCAGG GCATCATGAG GGAAATTGGA TTGTGGCAGA 19200
19201 GGGAGCAGGG TGAGCACAGG CTGGGAAGGA AAGTGTGGTG GGCTCCCCCA ACAGTAGGCA 19260
19261 GTCATGGGGG ATCTAGGGGC ATGGTGGGTG GATGGGGAGG GGTGCTCACA GGGTCCATCA 19320
19321 GTGATGATTG TGAAGGGCCT GAATTATGTG TGCAATGGAG AGGCACTGGT GGGTCACAGA 19380
19381 TGACTTCTAT GTGGGGCTTG GCCAGCAGTG TGCAGGGTGG TTGGGAAGTT CAAAGGCTGT 19440
19441 AGCTTGGGTG TGGGCAAGAG ACAGCAAGGC CCTGGATGAA GTAAGCAGGC TGGAGTGGGG 19500
19501 AGACAGGAAT GGGTTGAAGG CACAGGGTGG AGAGAACCCA CCCATTGGGT TCCAGCTGCA 19560
19561 CTGTCCAGTA CAGGCCGTGA GCCACAGGTG GCTGTCGAGC ACTGGAGTGT GGCTGGTCTG 19620
19621 AATTGAGATG TGCTGTAAGG ATAAAACACA CACCAGATTT TGAAAGCTTG ATGTGAAGAA 19680
19681 TGTACAATTC TCAATCATTT TTAAAATATT GATTACATGA TGAAATAATT TCATTTAGAA 19740
19741 TATGCTGGGT TGAATTAAAT ATATTAAGAT TAATTTCACC TGTTTCTCTT TTTAATATGT 19800
19801 GTGTTACACA ATTTAAGATT ACTTACATGG CTCACATTCT ATCTCCATTG GACAGCACTG 19860
19861 GGTTAGAGGG GAAGAGGATA AGGCAGAGCT TTGGGGACAG GAAGGAACAG GGCTGAGAGG 19920
19921 AGGACCTGAG AAGTGGGGTT AAGGAAAAAG GAGAGATACT ACAGATTTGG TGTCTTCCCA 19980
19981 GATTGAGACA GCTTTTGGGC CTCTTGGGGC CACAAGGAGC TTCAGAAATT GCCAGTGTCT 20040
20041 TTACATGGAG TACCTGAAAT GTCCATCTGG TCTCCTCACT CACCTGGCAC CTAACCATGT 20100
20101 GCTGTTTTGT ACTTGACTGT TGCTTACCTG TGTCTCTAAG TCCTTGCCTC AGCCAGATAA 20160
20161 AAAGCCTTCT CAGGGCAATG CCATTGTATC CTGTCTGTTC TCTCCAGTGC TTACTTCACC 20220
20221 CAGGGCTGGG GGTAGCAGGT GCTCCCTGGA ACTTGGCAAA CATCCTCATA TTGGGAGGAG 20280
20281 CTTGGCTGGT TTTCCTTGAT CTCCCTCTTC CCAGTGTGTG GCTCTTGACA ACTGATTGGA 20340
20341 CCCCAGACTT AAGGTAAGAC TATACAATGT GATGCTCACA GTATGCACAT GATGCAGCTG 20400
20401 TGAGCAGGGA TGGGAGCCGA GGATGGTGCC TGAGCACAGA GGGGAAGAGC ATTGGATGGG 20460
20461 GAGATTTGAG TTGGAAGGTC AGATCCTCAA AGGTCTACTC ATTGGAGTCT CCACATCTGT 20520
20521 GAAAGGAGGG GATGATATCT ATCTCCTAGT GTTGTAGAAA GTAAGAGTTA ATATACGTGA 20580
20581 ACAAATGATG GCTGGCATTC AAGTGTCGCT CTGTGACCCT CAGAAGGTGT TCACATCCAT 20640
20641 GAGCTCATCT GAACTTCACA GCAGGGCAGG CATTATTATA ATTTCCATTG GCAGACAAGA 20700
20701 AACCTGAGGT TCAGAGAATA CAAATGACCT GATAGAGATC ACCTGACTAT TAAGGTAGAG 20760
20761 CTGGATCTGG AGCCCAGCCT GACGTCTGCC ACTGTCTTTT GCTGTCCACT TAAAAGAGCA 20820
20821 GCTTGCACAC GTGCAGGGCT ACATAGGGTT CAAAGGCCTT TCATGCCCAT TAACTGCTTA 20880
20881 TTCTTCCTAG AAGGATGCAT AAGCCCAAAG TTTTGCTATA TATGAAGACA TGATTTTCAT 20940
20941 GAGATTCCTG CAGCCAATGA AGAAACAAGC CTTCAGTAAT CATGTGGATC CATGGTTTAG 21000
21001 TTGTCCCTTA TGGGTGACAG GTGATGGGTT ATGAGGATTA GATAAGAGCT GTTTGTAAGA 21060
21061 ATGTCTACAA GGTGCAGTGA CAGGCTCTGG TCAGATATTT TGATCATGCT ACAGTGCATG 21120
21121 AAATTGTTCA TAAGAATTGT ATGTGCATCT GTATCTAACA GGATCTGCTT ATATCTTCAG 21180
21181 AAAACTTTGT CATAAATTTA AATTACTTAA AGTGTCTGAT CTTCAGATAC TTTAAGTAGT 21240
21241 GCATTTGAGA ATGGGAATGT TGATTACAGT GCGTATAGGG AAATAGATGA ATATTCCATT 21300
21301 AATAACTATT AAAATCTGCT AAAGCTTAGG CTAAGCTGAA TATATTTAGT TGTAATAAAA 21360
21361 TTGGGTGAAC ACATTCCAAC TTCAGCCTGA TTAAGGGAAA GGGTGTAGGG GTGAGACACT 21420
21421 TAGGCGGAGC TTGAAAGGA ATGGTGAGAG TTTGGCCAAT GGGAAGGAAG GCTGTGCCAG 21480
21481 ACAGGAATAG TGTGGGCTGA CGACAACTGA GGGCAAAGTG CTTGTCCCCT CATAGTTGCG 21540
21541 CAATGAATGC AGAGGGGCTG AGGTTCATCT GTCGTCTTCA GCTCTGGAGG CTACATCTCA 21600
21601 GGGTGTTTCC TGTGAAAGTT CCAGAAGAAA GCTGTATGGT CAGCTTGGGG AAATATGTGG 21660
21661 TTCATGCTGG AATGCTGGAC ATACCACATT ATTGGAAAGA TGCACATTGA ATGACCGACA 21720
21721 AAATGAAACT CAACTTTCCA AATGCTGGTA ATGAGAGAAG ATTCTGTTCT AATGACCAGT 21780
```

Figure 1 - page 8

(Skin/Adipose)I.4

```
21781  TGTTTCCTGA AAGAATGTCA GCTCGATTCA TAATGAATGC ATTCTAACCA TGACAGCCAC  21840
21841  AGTCAGGACA CAAAAAACAA AGTGTCCTTG ATCCCAGGAA ACAGCCCTCT GGAATCTGTG  21900
21901  AAATCTAGAA ACTAGATTGG GAAAACTCTG ACACCCCTGC CCCATGACCA ACCAAGACTA  21960
21961  AGAGTCCCAG GAAGATTGAG GTCACAGAAG GCAGAGGCCT GCCCCCTCTC CAGGAGATCC  22020
22021  CTGACCCATG TGGGGTCATG GGCGGGGCAT GAGTGATGTG ATGGGAAACT GGCTCCTGGC  22080
22081  TCCAAGTAGA ACGTGACCAA CTGGAGCCTG ACAGGAGGTC CCTGGCACTG GTCAGCCCAT  22140
22141  CAAACCAGGT AAGTCCTTGG AGTCTGAGTA GGGACAAGAG ACTGTTCTGT GCTTTGGCAG  22200
22201  GGATCAGGAA GATGTTAGAA TGTGGTTGTT GGAACTTATC TTTGGAGCTG AACAAACATG  22260
22261  GCTTTGCATC TCCACTTTGC TATCAACTGA GTGGCTTTAA TTAAGTGGCT TCATTTCTTA  22320
22321  GATCCTCAGT TTCTTCATAT TCACCTGTAA ATTTTTTTTT TTACATTTTT AGACTGTTGA  22380
22381  GGGCAGTAAA TTAGATCATG TACATAAAGC ACCGAGCACT GTGCTAGACA CATTGGTACT  22440
22441  TACTACACAG TGGGATAGCA CCCCAGCTGT GACAGCCTTG TGAGGGGAGC TACACAGGAG  22500
22501  GCCCAGGGAG AGTGCTCTGA GTTAAGGATA GGTCCAGATC CTACACTTCT AGCAACACCC  22560
22561  AAAGCCCCCT CTTGAACATG TTGGGGTGTG ATGGGGGTGG GGAGATACAG TCGTGTTCCC  22620
22621  TGGCTGTGTC AAAGTGTGAA ATCTTTATAC TCCGTCTGCC CCAGATTCTC TCAAAGAGCA  22680
22681  CAGAATTGAA GGATAGCACT GGACCAAGTG TCAGGAGAAT TGAGATGGGC TCTGCCACTC  22740
22741  CCTGGCTGGG TGACCTTGGA CAAGTCCTTC AACCTATTGA GGTCTGGGCT TCTTCATTTG  22800
22801  TACATTGGAA CAAGATTATC TGCTCTGTCA CAGGATGAAC TCCAGCCTCA TTAGCCTGGC  22860
22861  ATTCAAGAAC CTTCCATCAT ATTCCCTCAC CACAGCTCCC ATGAGTCCTC TTCATGCCCA  22920
22921  CATGGTTCTG CCATATCAAA CTCTTCTGGG CCTTTCTTTC ACCCCTAGAC AGAATGTTCT  22980
22981  TGCATTCTGT GTGGGGGTGA ATGTTCTTGC CCAAATCTCT GTGTATCTAA AGCCCATATA  23040
23041  CCTTTGCATC CCCTGCAGCA TCTTGCACAG GGCTTGCAT AAAGCAGATC ATTGTTTTCT  23100
23101  CAGTTAGGAT TAGGTTTGGG GCAGGAAAAC AAAAATAATA TTTATTTAGC AAGTTAGAAG  23160
23161  TGATTTTTCT CTTGCCGGGC GCAGTGGCTC ACGCCTGTAA TCCCAGCACT TTGGGAGGCC  23220
23221  AAGGCAGGCC GATCACGAGG TCAGGAGATC AAGACCATCC TGGCTAACAT GGTGAAACCC  23280
23281  TGTCTCTACT AAAAATACAA AAAAATAAT AATTAGCCAG GCATGGTGGT GGAGGCCTGT  23340
23341  AGTCCCAGCT ACTCGGGAGG CTGAGACAGG AGAATGGCGT GAACCTGGGA GGCAGAGCTT  23400
23401  GCAGTGAGCT GAGAATGTGC TATTGCACTC TAGCCTGGGC GATAGAGTGA GACTCTGTCA  23460
23461  AAAAAAAAAA AAAAAGAAG TGATTTTTCC CTTATGCCAA AGAATCCTA AAAGGAGGGT  23520
23521  AGCCCAGGAC TGGGAAGGTG GCTCCTTGTG TTGGGGACCC ATGCTCCCTC TGTCTTGCCA  23580
23581  CACCAGCACT CTTGGCACCC TACCTCATAG TCCCATATGG CTGCCTGGGT TTCAGACATC  23640
23641  TTATTCTCAT TTAGCCAGCA AAGGATGAAA AGGGCAAAGC ATGCATTCTC TTCCTTAAGG  23700
23701  GAGGCTTCCT AAATGCTGCA CATGACACTT TGCTTATAG CTTTTGGCT AGAACTTAGT  23760
23761  CACATGGTCA TATCCAGCTG AAGAGAGGC TGGGGAATAT AGTTTTTAAC TGCACATATT  23820
23821  GCCATTCCTT CTTTCTTTCT TTTCTTTCTT CCTTTTTTTT TTTTTAAGAG ACAGAGGTCT  23880
23881  CCCCATGTTG CCCAGGCTGC TCTCCAACTC CTGGGCTCAA GCAATGCACC CACTTCGGCC  23940
23941  TTCCAAAGAG TTGGGATTAC AGGGGTGAGC CACCATACCT GGCCATATTG CCATTTCTAA  24000
24001  TAAAATTGAT AGGGGAGACT GGGAGAACAG ATATTCACAA CCCATACAGT GCCTCTGCCA  24060
24061  CAGCTACTGA AAGAACCAAA AATATAAAA CTCACTAAGA AGTTTAAAGC CTATCTAAT  24120
24121  ATATGAGATT ATTATTACAA AACACTTAAC TCATTTTAGA TAAGTTAATT GTCCTGACTT  24180
24181  TTAGGTTGAA AACAGCCCAA TTTTTCTTCA CCTCTAGTGG AAATATGATG ACATGTTTTT  24240
24241  TCTTTTTTTAT TTTTTGTAGA GACAGGATCT CGCTATGTTG CCCAGGCTGG TCTTGAACTC  24300
24301  CTGGCTCAAG CAATCCTCCT GTCTCAAACT CCCAAAGTGC TGGGATTAGA GACATGAGCC  24360
24361  AACATGCCCA GCCAACATAT TTTTTTCATA GAATAATAAC TCAGAGTTGT AAGTGAAGAT  24420
24421  AAATTATTAG TCCTTCCCCT TACCTTACCA CATTTTACTA CTGAGGAAAC TGAACTCCAG  24480
24481  TGAGGCTAAG TGATGTGCCC ATGATGGCAC AGCTGAATGG CGAAGGAACC AGAACTGGGA  24540
24541  CTTGAGTTCC TGGACTCCAT CAGGGCTTTT TCCTTGATGA GCAGCCCATT CAGGTTCTGC  24600
24601  TAACTGTCAC TCGGAAGCCT TGAATTCTGT GCATCTCCTA ACCCTGCGTG AGAGCCCTGC  24660
24661  TCTGCCAGCA CCCCTGGAGG CAGATCCAGG TCACCGTGTT GTCAGCCACA TCTTGCCAG  24720
24721  CACGTAGTTC AAGTTTCCAT CTGAAGAGAG GGAAACATGA AGAAATAGAG GAGCGTGCTA  24780
24781  TTAAAATAAC GAGGCCTTTT TGCTAAGAGC AAACAATCAC TTCCTTTCCT TGGCACCCAG  24840
24841  AATCTGCAGG GCCCTGAATT AGGCACTGAA GGGAGATCCA GGAAGCATG AGGAATAGTC  24900
```

Figure 1 - page 9

```
24901  ACTGCCCTTG AGGGCCTGGA TGTATAGGTT CATTCTACTT TTCATTCATT TATTCAAGAA  24960
24961  TTATTTCTTG AGCCTCTACC AACAGCAGAC ACTGAGCCTG GCACTGGGTT TAGAGCAAGA  25020
25021  ACCATATAAC TGGGTATACA ACAGTAAACT GTGCAGATAT GGTTCTTGCT CTAAAATTGC  25080
25081  TTGTAGTCTA GTGAAGGACA GAGGCAAGTA AACAAGCAAC TACAAAATGA AATGAAGATT  25140
25141  GCAGTGATGG GGAGGGGAGG GGGTACTCTG GGTGTAGACT GGGGTAGGGT GGGCAAGGCT  25200
25201  GAGTGGGTGA GATATCATTA CAGTGGAAAC CCGAAGACTG AGTATGTGTG AGCTAAGCAT  25260
25261  GCACCATGAG GGGTCTGGCA GTTGGGACGG AAGTGTACTC CCCATGGAGA GAATGTGCAG  25320
25321  AAGCACGCAT AACCTTCTGA CCGGACTGCA GCAGGCCTGG GTGACGGTGG TGGTGAAGGT  25380
25381  GGGGAGTGTT GAGAAACACA ACCAGCAAGG TAGGCAGGGG CCCGTAAGTG AAGGACTTTG  25440
25441  AAAGGCCTGT TGGAGAGTTT CTGTGTTATC TCAAGGCCAG TGAGATAAAG GGCTTGAAGC  25500
25501  AGCAGATTTG TATGTTAGAG TCCTCTGGCC TCGGGGTAGA GAGTGGATGA AAGCAAGCAG  25560
25561  GATCGGATTC AGAGAGGTCA ATTAGGAGCT GTTGCCAGGG ACAGTGGCTT GAACCAGGAA  25620
25621  ACAGCCCAGA GAGGTGCAGA GAGGTTGAGG AATTTGAGAC ATCTTTAAGA GGTACAACCA  25680
25681  ACAGGTTTGG AGACTGGGTC GGAAGTAGGA AATGAGGAAA ATGGAGGAAA CCAACACTTA  25740
25741  TGAAGAAACA AAGACAGAGG CTGACAAACA AAAGCAATAG CCATTCTCCA GGAAGAAAAT  25800
25801  GGTGGCATGA CCATGTGTTT TGAGCAAGGA AAAATTGCAA TGGGCTAGAG AGATTTTGAA  25860
25861  GGACTTTCTA GAAGAGTTAG AATTGGAGCT GGGTCTCCGA CATGGGTAGG ATTTTGGTGG  25920
25921  GTAGAGAGGA CATTCCAGGC TAAACAATGA TGCAAGTTAG AGTTCTAAGG CAGAACAGTG  25980
25981  TGTGATTTGT TTAGCATGAT TTGGTCATGG TTTTCTTGGG AGAGTCCCAA AGAACTGATT  26040
26041  CTCCAGGGGG TGTTACTAAA ACTCTTATTG AAAGGAGGGA CTACAGAGAT GAATCTCATC  26100
26101  ACTCTCCCAG AATGGCACAG AGCTTTTCAT GGACCCCCGG GCCACCTATG TAGGAACCTC  26160
26161  AGGGGGTCTG TGGACCACTA AAAGCCCAAC ATGCCTGAGA CTCCACAGAT ACTGGCTTCC  26220
26221  ACCATGATAA AGGCAAAAAG TCCCTCTTTC CCAAAATCAA TACTTTTATT CTCATAGGCC  26280
26281  TCCTGCTGTG GTCTAGTCCC CATGTTGAAA GCTGCTGTCC CAGGGTGTTG CTTCACTACT  26340
26341  TCTAGGCTCC TGCAGAGTCC TGCCTCATAG GCCGCACTGG TGAGTGAGGC CAGCAAACCC  26400
26401  ATCAGGGAGA CTACATGAAT CCAAGGCCGT GGAAGACTTA GGTTTGGATA TTCCCTCTGC  26460
26461  TCCCTCCTGG CTGTGTGACC CTAGAATAAT TACTCACCCT CTCAAAACCG AGACTCAGAG  26520
26521  ACGTTGGGTA ATTATTCTAG GGTCACACAG CGAGGAAGGA GGAGAGGGAG TATCCAAACC  26580
26581  TAAGTCTGTC TGACAGCAAA GCCTGTTCTC TCCATCTCTC CAGGTTCCTA AGCCAGGTGA  26640
26641  GCGTTGAACC TTTCTTGAAT CAAGGTTCCA ATTCCAAGGT AGGAAAGCAC AGTCAGTCAG  26700
26701  GGAAATATTT ACACTGAGAC CACGCACCCC AGCCCTTTCC CAACCTGCTC TTGTGTGATC  26760
26761  CTTTTGAGGT TTTTTGTTTG TTTTGAGATA GAGTCTCACT CTGTCGCCCA GGCTGGACTG  26820
26821  CAGTGGTATG ATCTCAGCTC ACTGCAACCT CCGCCTCCCA GGTTCAAGTG ATTCTCCTGC  26880
26881  CTCAGCCTCC TGAGTAGCTG GGATTATAGA TGCCCGCCAC CATGCCCAGC TAATTTTTGT  26940
26941  ATTTTTAGTA GAGATGGGAT TTCACCATGT TGGCCAGGCT GGTCTTGAAC TCCTGACCTC  27000
27001  AAGTGATCCC CCCACCTCAG CCTCCCAAAG TGCTGGGATT ACAGGCATGA GCCACTGTGC  27060
27061  CTGGCCTTAA GTTTTTTATA GATGGGAAAA CCGAGGTCCA AACGTGAGCA GGGCTCTGC   27120
27121  ATGCTACCTC TCTATTTTCT CAGCCCCTTC TGCAGGCTCC ATGCCATAAG AACATGGCTC  27180
27181  CTAAGGTTCA GGCCTATGGC CCCAGTTTAG GTGGTGCCTC TGCTCTGCTC CCCACCACCC  27240
27241  CAGCCTCCTA TTTGAAGGCC AAGACTACTC AGCTTTGATT CAGGTTGAAT GAGTCATCAA  27300
27301  GGGTAAAACA AAGAAGAGAA TAAAACAAAG AAGAGAAGGC CTATTCCCTT GCAGATGAAA  27360
27361  TCAATCCACT CACCTTTGA CATCTTTTTG TTCTAGAATG ATGACAGTAT GCAATGACTC   27420
27421  AGAATCATCA CACTCACAGA GACTACTTTG TATTTTTCT TGCAAATGAA GAGACAATAT   27480
27481  GCCCAAAAAA TGAGCTGAAA ATGGCTCATG AAGGGAGGGA AGATGACCTC CAGCACACCA  27540
27541  GGGCAGAGTG GGGGCCACAT GAAGGTGCAA GAGTGGGAGG GAACCACAAC GCCTTGGCAG  27600
27601  AGAGGAGAGC AAGTGGGGGC CAAGCCACAA AGCTCTTCAA GGCCAGTCAA CAGTGAAACC  27660
27661  TGAAGGAGTC CCATCCATCC CCAAGTCTGC TTGAGTTAAA GCCCTGCACC CTCACAAGCA  27720
27721  GCTGGAGGGA GGGAGGAAA GATATTTCA AAAGAGCCAT CATATATGGG GTGTGGGAAA    27780
27781  GAAAACTTG CTGCGTCTAA CACCAGAGAG CCTCTCCAAG CCAAGCCATC TGCCTCAGGG   27840
27841  CAAAGGAGGG AATGGAAGCG GGAGAGAAGG GTTTGAGCC AGCTCTCAGC AACATGTTTC   27900
27901  TATCTGGAGA AATGAGCTGA GAAGATCTGA ATCTTCTCCA GCCTGTTCTG CAAATGTGGG  27960
27961  ATAATCGGCC CCTGGCCCAA AGGCTGGTGC TCACAGCGTG GCTCCGGCAT TACCCAGGAC  28020
28021  TTTGGTTCTT GGTGATGGGA AAGAGGACAA ATTTGGAAGC CAGAGAAGCT AGGGCTGGAT  28080
```

Figure 1 - page 10

```
28081  GGTCTGGAGG AAAACCTCCA CTTCTCTCAG ACTGTTTTTT CTGAGGAAAC AGATGATTGC  28140
28141  AACCTCAGAG GTTGGGAGGA TGAAATGATG TAATGCATCT GGAGCTGCTC TGTAAACTGT  28200
28201  AAAATGCTAT GCAAACGGTG CTTGTTAATG TGTTTACATA TATGGGTGAG TTAACATAGT  28260
28261  CTGACAGACT GGACGCCAAA CTCAGAGTCC AAGGCAATGG GGCATTATAT TCTGTGCCTT  28320
28321  AGCATCTGGA AAACATGATG AAATTGGAAA TGCATTTATT GAAAATGAAA AGTTTTCTAC  28380
28381  AGAGCTTCCT GTCCTTTCCA ATGAATTCCA GGCTTCCCAT GGTGCTTGCA GGGCTCTGCC  28440
28441  GGAAGCTGCT GGGAAAGCTG ACTTCCATTC TGGTTGCTAT GAACTCCATT TTTGGTTCTG  28500
28501  TTCTGTGACC ATCTTCATTT CAGTCACTTG CACCATTATA AGGATTGAAA AGACTCTTGG  28560
28561  CAGAAAAGCA GTTTTTTGTT TCATAGCATT AGGGTTTGAT ATATAATATT ATTTTTGAAC  28620
28621  AGAAAAATTT CACATAAGAG TTCATAAAGG GTGTATTTT AGACGTGAAG GGGCTTAGAA  28680
28681  GACTGTCTAG TTCAACCCTG AGATTTTTTT CAGGTGAGGA ACTGAGGCCC AGGCAGAAAG  28740
28741  ACTGGTTTTC TCCAGCCCTC ACACATGTCA GTGAGCCAGG GTTAAAATCC CCAGAGGTCT  28800
28801  GACTCCTATT CATGTGCTAC TTCCCTTACC CCAGGGTCAA AAGCTCAGAT GCTTTCAGAG  28860
28861  TCCAGATAAG TGAGGAGGAG GGCATTGGCG GGTAGGAAGG TAGGGAGTTG TGGGACATTC  28920
28921  AGTTTTGTTT ACATTTATCC TGTTAGAGGT TTAACGAGCT ACTTGAATCT TAAATTTATG  28980
28981  TCAGTCATCA AATCTGGGAA GTTTTCAGCC ATTGTTTTTT CAAATATTTT GTTCTATAAC  29040
29041  AATCTCTTTC TCCTTGCCTT TAAGGATTCC AATGACATGA ACATTAGACC ATTTGGTATT  29100
29101  GTCCCACAGA TCCTCGAGGC TTTATTCATT ATTTTTCAAA CACTTTTCTA TCTTTCACAT  29160
29161  TGGATAATTT CTGATGATCT ACCTTCTAGT CTACTGACAT TACCTCTGTC ATTTGCATTC  29220
29221  TGCTATTGGG CCCATCCAGT GAATTTATTT CAGATATTGT GTTTCTCAGT TCTAATATAT  29280
29281  TGCCATTTGG TTCTTCTTTT ATATAATTTC TATTGCTTGA CTGAGAATTT CTATTTTTCC  29340
29341  ATTCATTGTA AGAGCATTCA CCTTTATGTC ACGCAGGATG ATTATAATAG ATGCTTCGGA  29400
29401  GTTTTTTTTT TCCAGTTCCA ACATTGTCTT ATCTTTTCCC TTGAGAACTG GTCATGTTTT  29460
29461  CCTGGTCCTT ATCACTTTGG GTAGTTTTAA ATTGTTTCCT GGACATTTCA TATAGTATAC  29520
29521  TATGAGACTC TGGGTCCTGT TAAAATCATA AAGCATGTTG AGTTTTGTTT TGTTTTAGCA  29580
29581  GGTAATCAAC CCCGTTAAGT TCAACAGCAA GCTCTGTCTC ATCTTGTGTA GGCAGTGGTC  29640
29641  TCAACGTCAG CTCAGTTTTC AAAGCCTTTG TTAATGCTGT TTGTGTTCCA CACATGCACA  29700
29701  TCTTGGAGGT GAGGTCAGGA CTTGTGCTGG CTCCTACATG GAATCCCTTT CTCCCCCTCT  29760
29761  TTCCTCTGCA AGAGTTCCGT CTTGCCGGAA AAGGACCAGC TCCTTTTCCT GGTCCTCTGG  29820
29821  CTAGAAGGAT GGATTTCTCT CAGAGCTGGA GCCGCTGATG ATGTCACAAA GTTTCATGCC  29880
29881  ACTTGGCCAG ACCTTAGAGC AAAGTGCAAG GGGAAAAAAG TGAGGACTCC CCTGATACTT  29940
29941  TTGACATAAC AGGGACCCCT TTTCTGAATT TCTGTACCCA AAGGGACAGG TTTTCTCTTG  30000
30001  AGATTTTAGT GCTCAAGCTG CTGCCAAGGT GATGGCGATA CAGTTTGGGG GCTGCATCTG  30060
30061  ACTGTGTGTC CAAGCTGAGA GAGAAAAAAA GACAAAGATT TCCCCACAC TTTTTGTCTT  30120
30121  GCAGAGGCCC CTTTTCCAGA TTATCTATCC AGAAAGATGG GCCATTTCTT GGGGTTGTTG  30180
30181  CTGTCTATGA CTGCTGGGAG GTCTCATGAT TCAGCTCACC CTTGGGCCAA AGCCAGGAGA  30240
30241  AAACAAATTC CAGGAAATTC ACCATCACCA TATTGGTCAT TCAGCAAATT TTGACTTCTT  30300
30301  TTCGCAATCT AGCTGCTTTT AGAGGACTTT TCAGAGACCT CAGTTAATTG TTTTTTTTGT  30360
30361  ATTTTGTTAA GAGTGTTTGG TTGTAATCAG TGAGGAGAT AGTGTGCAAT GCATGCCTTC  30420
30421  CATTTGGTTG GAACTAGAAG TTGAGCAACA CAGTTGGAAT TCATCTTTTT TGGTTAGTGC  30480
30481  TTCCCCAGGA CTTTCACGGA CAGAATCCCA AAATAGAACC TGTATTTGGG AATCCTATAT  30540
30541  TCCCTGGCCT GGTGGTGGCA GGTCCCAGGA GTCTATGGCT CCAAGTTTTC TACCTTATTT  30600
30601  GGGTAGACAC TTAAAACAAT GCTCATTCAA CAAAGACGTA GTGGGTGCCC ACCATATGCT  30660
30661  ATATCCTGGA GACACAAAAA TGACTAAGAC ATAGTGCCCA CCCTCAAGTA GCTCATGGGC  30720
30721  GAGTGGAATA AAGGGATTTT CAGTAAAAAT TTAAGATCCA AGCTTGAAAG CTTCTTTCCC  30780
30781  AAGACATCTT GTGGATCTGA GAACCACAAC ACCTTGTCAG AGAGCAATTT CTAGCCTGAT  30840
30841  TCTGGAGCTT TGCCCTTCTA GAAACTTCTA TCATTGTTTC TCTCCTCTGA GCGGAACCAA  30900
30901  CAGTAAAGCA CTATATATTA AAAACAGTA TATAAATTC TCCTTTTGTT TTGTGAACTC  30960
30961  TACAAATGCC TAGATTACCT GTTTTTAACA GTCTTCTTGC CTACTAAACA TAGACTTAGA  31020
31021  GAACACAGTC TGTTTTGGGG CTCCAGAACT CAAAAGGGAA GTGAAGACAA TGGAGAGTGT  31080
31081  TCAGATAGCA CTTTTAGTAG ATAGAATCTG ATATTTAAAA ATAAAGAGTG GGGGAGTTGG  31140
31141  GGGCCATCTG CCAAGGAGAT AATCCTTCAT AAAGCAGATT AACCATATCT TTGTCTTAGT  31200
31201  TCAAATCACT ATAACAAATT ACCATAGACC GGGTAGCTTA ACCAACAAAC ATTTATTTCT  31260
```

Figure 1 - page 11

```
31261  CATTGTTCTG GAGGCTAGAA ATCTGAGATC AGGGTGCTAG CAGAGACAGG TTCTGGCAAG  31320
31321  GGTCTTTGCC AACTTTTGCT GTATTCTCAC ATAGCAGAAA GAGAGCTAAA AAGCCGTCTG  31380
31381  GTACCTCTTC TTACAGAGGC ACCAATCCAA TTCATGTGGG CTCCACCCTC ATGACCTAAT  31440
31441  CACCTCAAAA GGTCCCACCA CATAATACCA TCACACTGGG GATTCAATTT CAACATGTGA  31500
31501  ATTTTGGGGG AACACAAACA CTCAGTCCAT AACACTCCCC CAGCCCACCT CTGCTGCCTT  31560
31561  TTCTCTTTGA AAGCACTTAC CTTCTCTTTC TGCATTGATG TAATGCCAGA GGATTGGATC  31620
31621  TGGGAAAGGA AGTAAATGTG GGAGGGAAGA ATCAGGGTTC AGCCATTTAG CGAGCACAAG  31680
31681  TAGGTGCCGT GTGTCAGCAA GGGTACCCTG TGCATGAGTT ATTTTACCAC CCTTACAGCA  31740
31741  ATCCAGCAGG CCTGTGTGAT AAGTGTTGTG TTTCCTGTGT GGTAGACGAG GAGACCGAGA  31800
31801  CTCAGAAGTG ACGTGATTTT TCTCAAGGTA TTAGCTGGCA AATTGTAGAC TAGAATCCAG  31860
31861  GTCTCCTGAG TGTGGGTTCT GTTTATCTAG TTTACCTACT GCGCCGGCCT CTAAGACTTT  31920
31921  GGGGTCTGAA TATGTACCTC TTCATACCAC TAGAGCCCCA GCAGTCTTCT AAGTGACATG  31980
31981  TGAGCCATAC TGGGGAGGAG TTTGGGGAAA GGAGACCTTA CCACTGACAG CAGAGTCTGG  32040
32041  GGGCTCACAA GAGAGGAAGA TGCCCACTGG GAAGCCAGAT CTCAGGTTCT TCAGACCTAT  32100
32101  ACCTCCCTGG GATATAATTC AATCAAGTGC TTATTCCCCT CTTTAAAAAA AACTAAAATG  32160
32161  ATGCAGAAAC TAACTATGAA ACAAAGGAAG AAAAAACAAG AGAAGGCAGG GATTATTTCC  32220
32221  CAGGACATTT TCCTCTGACC AGGAGGGTAA GTTGGGGACA GAGGACCGAC TTGGTGGGGA  32280
32281  TCAGAGGCAG CCCAAGGGAG AAGAGTCATT CCTTCTACTC TCCCACCTGT CCTCATTGCT  32340
32341  GGCTCTGACC CAGATGAGAG CTGGGGGCGT TGACATGGGA AGCTTCTCTC CTTCCTGAGT  32400
32401  GGTCAGTGAG GGGCAGCTTC TCCTCCTACT CCAGGAGGGT TGCGGGAACC TGCATGTTGC  32460
32461  ATCCCAGAGC AGCCAGAGCT TCTTCTTGCC AGTCTCCTAC CTTCCCTTTC TGGCTCCTTT  32520
32521  ACTCCCACCT CCTCATGCCC TCTTTCTCAT TTAATAGCAG GGAGAAAGGA AATGAAACTT  32580
32581  GATGGAGCCT GACTGTGCCA GGCACTGTGC CAAGAACTTT GTGTTCATTT GTTTCTAGAA  32640
32641  GAGGGCTTGG TATACTGTAG ATGCTCAATA AACGTTAACT CTTAGCTTTA GTGTCTCCGG  32700
32701  TCCTTCACTT CAGTGATCTC TAGGCACAGT TGATGGCTCA GTTCACAAC TGCTGCAGAG  32760
32761  AGGATGAAAG AACAATGTCA AGTGGTTGGG TGGGGAAAA TGAAACTGGC ATTAGGGCTA  32820
32821  ATCACATACA TTTCTCAGGG TGCTCCTCTT TTGAGGCCCT ATTTCCATGA GAAGGAAATT  32880
32881  GAGGCAAACC CAGAAGTTGA CAGCTTAGCT GGGAACCAAA GATGATGATA TACGGGAGCC  32940
32941  CATGGAATCT CATAGCTCGA GCAGCACTTT TGGCACCAAC CTGCACCCAA AGAGCATCTT  33000
33001  TAAAAGTTGT CACATACTTG CTCCGGGCAG CTCTTTCACA CCACTACCAT GCTCTGTGCC  33060
33061  AGACATGACT AATTTTTTAA ATCTCTGACA CTCTTAATTA GTCATGAGCT AATTCTGTAA  33120
33121  GAATGTTAGA GTAAGCACAC TAAAATTATA TTCTTCTGCA AAGAGAAAGA AGATTACCTG  33180
33181  AGACCACTTG TCCCCCCTCA AAGAAGCAAG GTCTCAGCCA AAATCTTTGA AGCCTTGTGA  33240
33241  CATCAATAGA TTTTCTAGGG TGGCATCATG TCCTTTTGAT TTTTCTGTAT ATAGTAGTTC  33300
33301  AAATGCCACC TTCTCCTCTC CTTTCCATTG CCACTGCCCT GGCTAGGTCC TCATCAGTGC  33360
33361  CATCAACTCT CACCAGGCTC CCTGCCACCA ATCCAAACAA AACCAAACAC TACTAATCAT  33420
33421  GGATCTTCAT GGCACGTTTG CTTTCGTTGG CTCCAAAAGC CTCCAGTGGC TTTCCATTGC  33480
33481  AGATTGGAAA GGTCTAGACT CAGCGATCAA AACTTCCACC ACTGATTGCT TTTCCAAACA  33540
33541  TCTCCCCTAC TTCCTGTTGT GAATACCACC TGGTTTACTT ATTATCTCTG GCTTGCCATT  33600
33601  ATCTGGTTTA CTTATTATCA TCAATATGTC TAGACCCTTC TGATCTTCCC AACTTTACCC  33660
33661  GTGCCTTTTC AGTTCTCTTC TTCTCATTCC TCACCACTGA TGGACAGTCA TCCTTCCTTC  33720
33721  CAAGAAGGGC TTAAGTCTGG TTGCCTGGAC TCTAGATAAT TTCCCTCCTC CTTAGCAATT  33780
33781  CCACCTTTGA TTGTCTGGAC TCCTTGTGCC ATGTACAATT ATCCTGTATT GTTAATTGTC  33840
33841  TTTCTATGTC TGTAACTTGC TTCTGTGTTA TAGACATCAT CATGGCACAG TGCCGTGCTT  33900
33901  TTTCACAGAA TAGGTACTTA ATATTCTATT ATTTAATTTA CTAGAACTTT GCAATTTCAT  33960
33961  AAAGATAACT TTGTCATTAA AAATGTTTCC AGTGGGGATT TAGGGCCCTT GAGATGGTGC  34020
34021  AAGAAAAGGA GATAAAGGGT TTTTTTTAAG CTATTTGTTC TTTCTGTGCA AATTACATAA  34080
34081  CTTCCAATTA TTTCCAACGT TAAAGAAATA GTCCCTCTGA ATCCTTTATG ATTTAAACAT  34140
34141  TAAAATGATT CACTAGTTTT TAGAAAAAAA ACAAAAAACA AAAAACAAA AACTGCTGTC  34200
34201  ACCCTTCCAA AAATGTAAAA AAGAAGAAAG AAAACCCAAA TATTGGCTCT TTTGGAGGAA  34260
34261  AAATAAACTG GCTGTGCTTT TATTTCTCCA ATATTCTGAA AGAACTGGGA ATGCACCACA  34320
34321  AAATGGCAGT GCTTGTGTGT ACCCGAGTGT GTACACCTCA CCTCTGTCTT GAGTCCACTC  34380
34381  TCCCTACCAA GCTTTTCTTG GGTAGAAGTC ATGGAGCCAT ATCCAGCACC AGTCACCTGA  34440
```

Figure 1 - page 12

```
34441   GCACTCCTCT CATAAAGGAG ACTTTGGGTT TAATCCCTGC CAGGGGGATT CAAGTGCTGC   34500
34501   TCTCCTAAGG AGGAGAGCAG GTTTTCTTTG CTTGACTATA TTTCAACACC TCTGACAGAA   34560
34561   TGACTCCAGC CAGCCAGGGT GCTTTTTTGC TTCCCAGCTT CTCATAGCGC CCAGATGTA    34620
34621   GCATCCTTTC GGTCCTCAAC ATTTACTTCC CTCTTTACTC ACTGTATTAG TTTTCTGTTG   34680
34681   CTATGTAATT ACCAAAGCTT ATTAATTTAA AGCAATACAA GGTGGCGCGC AGTGGCTCAT   34740
34741   GCTTGTAACC CCAACACTTT GGGAGACCAA GGAGGGCGGA TCACCTGAGG TCAGGAGTTC   34800
34801   GAGACCAGCC TGGCCAACAT AGTGAAACCC CGTTTCTACT AAAAATACAA AAATTAGCCC   34860
34861   AGTGTGGTGA TGCATGCCTG TAGTTCCAGC TACTCAGGAG GCTGAGGCAG GAGAATTGCT   34920
34921   TGAACCCAGG AGGCAGAGGT TGCAGTAAGC CAAGATTGCA CCATTGCACT CCATCCTGGG   34980
34981   CGACAGAGTG AGACTCTGTC TCAAAACAAA CAAACGAAAA CACACACACA AATTTATTAT   35040
35041   CTCATGGTAC CAGCTGGCTC CTCTGCTCAG GGTCTCACTA GGCCCAAAGC CCTTTTCATC   35100
35101   CTGTGTCCCT GTCTATCACT GCCATCATCC CACATCCCTG TCTCTGTGGC ATCTTGTGCT   35160
35161   TCACAGCTCA AGGTCATATT ATCTGCATTT AGTTTTGAGA CAATCATAAC GTTATGACCA   35220
35221   CTTTCTCCAT TCTTCTCTGC TAGCTGAGTT TCTCCAAGGC CTAAGACATA GGCCACACCC   35280
35281   TCACAATTCT ATACTCAGGC ACTTTCTAAA ATCACACATT CCTTAATGCA GTGAAGAATT   35340
35341   GATGCTCATG AGTGACATCC TACATTGAAA GGAAGAGACG TGGCCGGGCG CGATGGATCA   35400
35401   CGCCTGTGAT CCCAGCACTT TGGGAGGCCA AGGTGGGCGG ATAACTTGAG GTCAGGAGTT   35460
35461   TGAGACTAGC CTGGCCAATA TGGTGAAACC CTGTCTCTAC TAAAAATACA AAAATTAGCT   35520
35521   GGGCGTGGTG GCAGGCGCCT GTAATGCCAG CTGCTCGGGA GGCTGAGGCA GGAGAATCGC   35580
35581   TTGAACCTGG AAGGCGGAGG TTCCAGTAAG CCAAGATCGT GCCACTGCAC TCCAGCCTGG   35640
35641   GTGACAAGAG TGAAACCCTG TCTCAAAAAA AAAAAAAAAA AAAAAAAAAA GGAAGAGACA   35700
35701   CAATTACCTG AGGGATGAAT GGCAAATGTT CTATTTAGAA ACGCATTTTT AAAGCTCACC   35760
35761   TTGTAGGGTT TCTTGTCATG CATCATTTAA AAAAATAAAT TAAAAACCTT GAATATTAGG   35820
35821   CTGAGGATTT TCTCTTGAAA GAGACAAAGA GACATGGTCA AGTCACTGGG AATTTCATGA   35880
35881   CTTAGGAGGA TTCTCTCAGA AGACTTTCTA AGAATAACTT CAATAATCTC CAATAATCTG   35940
35941   CAACCTACTT TTCTTTCATT GAAACAAACA AAGTTAGCTA TGGAATTAAT ATTTGGAAAA   36000
36001   TGAAGAAAGC TTAAAGGAGA TAAACATTTC CCATAATCTT ACCATCCACT GAAAACCATG   36060
36061   GTTAACTTGA CATGGGAGTG GGCTTGGGTT GGAAAAAAAT AGGGAGAGAG TTTTATCTCT   36120
36121   GGAAAGCATT GCTGGCTCCC TTCCACACTT TACAGCATGT ATTAGCTTAG TGACACTGTA   36180
36181   GGGAGAAGCA CAAGCCATGT AAAGAGGACT TAATTTGTCA AGATTTACTG ACTAGCTAAG   36240
36241   GGCTAAAAAG AGATGAGTGG GGTGGAAGCA ATGGTTTCCA CAACACCCCC AAGATAAGGG   36300
36301   GTATCACTTG TGCAAATTTA GCACCAGGGA GTGGGGCCAG CCCAGAACTT CAACTCAACA   36360
36361   TTTGTCAAGC CCTCAGTATA CCTTCCAACC CAGAAAAACA ATAAAAATGT TAATTTTTGA   36420
36421   AATCACTAGC AAAATACTAA ATACAAGGTC AATATTTTAA ACCAAAGTGC CTGAGAGCA    36480
36481   CCGTTGTTTC TAATGACTTC CTCCTCCCTG ATCGTCTATT TTTCTCCCTG GTCTTATCTT   36540
36541   TCTGAACTTT TTTGCTGCAA TTGTTGAGCG TCAAAGGCTG AAACCACTAT TATCACCACT   36600
36601   ATTACTGCCC TCCTCTCTGC ATTTGAACAC CCTGCTGCAT CCTGCATCTT GCCTCTTCCT   36660
36661   TTATACTTGC TGCTTTGGAT GAGGTCCCAT GTATCATCCT CAGCCCGGGA TTTTCAGGCT   36720
36721   CCTAGAAGAC ATTTCCTCTT ACTGAGGCAT GGACACGTGC AATTGCAGCC AAAGGTGAAT   36780
36781   TGGTTGTCAG GTGTTCCTTC AACTTGGCTC CTCTCTGCCC TCTCACTGCC TCCTGCCATC   36840
36841   TAATCAGCTC TACTTATCTG CCCCTTAGAG GGACCATCTC TTCAGTTATT AGCCATTCTT   36900
36901   GTGTACACAC AACCTGCTGG TTTTCACTTC CTTGTATTTG CTCAGACAGT TTTTTCCACT   36960
36961   AAGAAGGCAG ATGCCTCAAA ACCCAGATGG ACACTGACTT TCAGAAGCTC TGCCTAAAAA   37020
37021   AAAAAAACCC ACCTACATCT CCTACTTGGC ATCTCTAAGC ACTTGTGTGT TTAGCCTGGG   37080
37081   CTGTGTGTAT TTTCACATGT TTATGTTGTT TTCATTCTTG ACTTTATAGT GATGACAATA   37140
37141   CTAATTACTA CTTATTTAAG GACTAGCATG TTCCAGGACA TGTATCTTTT TTTTTTTAAA   37200
37201   GGGCATAGGC AGAAGGAGAG GAAAAGCAGT TCAGAGTACT AAGGGGCTAT GATTGGAAGG   37260
37261   GTGTCAAGAA CTAGCTCTCT CACCCTCAAA AGGCCTCCCT GGCCCAGCCT GTCCTGCCTA   37320
37321   AATTCTCTAA TCAGAGTGCA GGTCACTGGG GAGTGAAGAT TCTCAACCTC ACTCACCTCT   37380
37381   TTCACCCCTC CACATCTGCC CACCCCATCT CCACTATTTA GTGCAAAGGC TCCTGGGAAC   37440
37441   AGCGACATTC TAAACTGTTA ACAGCTGAAG CCTTCCAAAG GATTCTGTCC CCCAGTGACA   37500
37501   GTTGGCTGAA GACTGTGAAA GAGAAAGAGC GGTCCTTCAG GGTTGGGAGA CCAAGAGGGA   37560
37561   AGGGAAATTA CTAGCCTCAG GAAGAAGCAG ACTCCCAGCC TGAGCTCCTC ACAGCCTACT   37620
```

Figure 1 - page 13

```
37621  CCTCCCCAAG CCATGCCTGC AAGCCTCCTT GAGGGTTTAT GGGGCATAGC CCTACAAGGG  37680
37681  ACCCAGAGAT GAATCAGACA TGGATCCTGC CTTTGAGGAG CTTACTGTCT ACTGGCAAAA  37740
37741  AGTGCCGAGT ACAGTTTCAA CCCAGGGCAA TTTCAAGGGT TGTGGGACTT CAGAAGAGAG  37800
37801  AAAGACGTGG GCTGGACATC AAAGAAGGCC TGCCAGAGGA GGTCGCGTTT GAGCTGGACC  37860
37861  TCGAAAGATG GCAGGGGACT TTCCACAGGC AGAGATTGGA GGTGGTGCTA GTTATGAAGC  37920
37921  CAGACACCTT CAGTTTGAGG CTGTGATCTG TGAGGACAGT GGGGAGAGGG AAAGCCAGA   37980
37981  GAAGGGTAAA AGGCTGAGGA AACCCTGGCC ACCTTCTCTA GTAAGAGGAC ACCAAGGATC  38040
38041  ACGCTTTGCC TGCTTTAACA TCTTGCCTAC CATTGCCCTG ATGAAAATAG GCCACTGTTT  38100
38101  TGAATTAGCT AAAAGTTGAG AACTCAGACT TGGATTTGAC AAGGGCCCTC TGAGGGCAGT  38160
38161  TAAACCAACT CTCAGCCCCA TGATTCTATG AGTCTGTGAT TCGCAGGTGG AGCCAATGAC  38220
38221  ACACCTTTGG GACTAGGCAA GGCCTCTTGG TCAGCGAATT CCCTCAGGGG AATAATGCTC  38280
38281  CTTCACAGGA GAATGGCAGA TGGAAAAACC CCAAAAAGTG AATATGCCCA GGACTGCTCA  38340
38341  ATTGAATTTA CAATAGTTCC AGATTATTGA CTAGCTCATG CCTGTCAGCA GAGCCAGAAT  38400
38401  GGACACATAC TTTGAAGAGT ATGATGGCAG GTAGAGGTGA AAAAAAAGAC TGAATGTGAC  38460
38461  TTTAGATGGC AAGAACATGA CAGTGAGGTA CTTGATGAGA ACCCCCCAAA AATGATCAAG  38520
38521  AAGGGGTAAC TGGGTGATAA AGGGGGAGAT TAAGAAGCCT ACACTTTATT ATACCCAGTT  38580
38581  CTTTTTTTCC CCACTGTTGC TATTTTAGAA TTGCAGCTCT ACATTTTGTG GAGGTTACAG  38640
38641  AAGGAATCTT GTGAATATTT TTTCTCTGAC AGGGAAATAA TTATGAAAAT CTTAACTTTT  38700
38701  ATAATATTTG TGCAAATTTC AAGAATAAGT TTTGTTTTAT CTTTGGTGGC ACCACATGCT  38760
38761  TTGGACTTTT GTTTTTAAAT CCCAGCATAA CCAGTATTTT CCGAGGATTC TAATCATTCC  38820
38821  CAGTGGGCTG AATTTAGCCA GCAGTAACCC TAGCCTTGCA AGACAAAGC AACCAGTGAT   38880
38881  ATTTGATAAA ATAGAAGCTG ACAGACAAAT CAGGTCTAGT CAATCAAAGG ATGACGAGCA  38940
38941  GAAGACCCAG GCCAGAGAGA GCACTAGCAC GTCTTGGATG GCCAGAAAAA GTAGGGAAGG  39000
39001  AAGGCACGCG GGGGGTCAGC CCAAATAGGG GTCAGTATGC AGGGCTCTGG CCTCCAATCC  39060
39061  TAAGACCCCT TGGGAGGGGA AAAGCATTCA TTTTCTACTT CACTTTTTAT GTACTTGCCT  39120
39121  TGGCAGAAGG AGCCTTGGTC TTGGAGGTGT AGCCCCGGCA TCCCAAATGA GATGAAGCCT  39180
39181  GCCTCTGGTC AAGTTAGGAC CAGAAAGGCT AAATTGATCT AACTTGGAAA GGAAGCTTTG  39240
39241  TGCTATCTCA GTTTTATGCT CAATGTCTGC CTTTGAGGGG CAAGAACAGC CATACAGGAG  39300
39301  AACAAAGAAT CTCAGGGTAT CAGAGAGAGG AGGCAACATA GCCAAGTCCA GTATGAGAAA  39360
39361  CCTGCCTTCT GGGGATTTCT TCATATAGCT GTTCTTTCAG CTGGTCTTTC CAGCTTCTGT  39420
39421  CTGCCCCCAG TAGGTTGCCT CAAAAGCCCA GTTTTCCTTT GATCATTCCA AGCCCCAGCG  39480
39481  AAATACCTCT TTAATGCTTA ATGTGGCAGT CACCTTTGGA TCTGACTTCC CTTCTGACAG  39540
39541  TTCACCACCC TGTGAACTGG TTCCATTGTC TTCCCTGGAA AGGTAGTTCC CTTTCTTAGC  39600
39601  CTCCTATTCA CTTCTGTTGG CCTCTTTTTC CTTCCTGCTG TTTCTCCTAA AACATTTTGC  39660
39661  TGGCCTTCAA TAATATTGGT GTCCAAATTC AGTTGGGGC CTACCACCGT TTTATGTCTC   39720
39721  TGTGGGTTAC AATTTTCTTT GAGGAATGTC CTCATTACCA TATATTTTA AACTAAATAG   39780
39781  TTTGCATGAA CAGGGATCCT CAAGCATTTG ATACAATAAG AAAGGCATAG AATGGCGGTG  39840
39841  TAATTTGGGG GCAAGCGTGT TTGCTGTAGG AGGGAAAGGC AGCGGAGAGG CTGGTTCCCA  39900
39901  GTATAGGGTT GGAGGAGGAG CTGCTGCTGG TACTGCTCAC ATGCTGCATT CAGGCTGCTG  39960
39961  GCACAGGGGG TTCTGGAGCT CCAGGCCTGG CAGGCGTGGT GGGAGGAGCA GCACCTTTGT  40020
40021  GGTCTTCTTT TTGAAACTCT CTGCCTTGAC AACTGATTGG GGAACAAGGA GTCAGTTTCA  40080
40081  CTCAATTCTC CTATAGGTGA CTCAAACCTC TATCACACCC AATCATCTGC CCCAGAGATG  40140
40141  ATCTCTCCTA TGAAAGCAGT TGAAATGCAC CAAAGTGATT TCTTGAGAGT CTTATTCCTC  40200
40201  ACTGAGAAGC TAATAGGCTG CGTGCGGCCC TCTCGTGAGT TGTAGCTTAG GTCATGAGCA  40260
40261  TAAAACCCAG TAAATTGTGT AGAAAAATGT TGAAAGACTC CACAGAGCCT AGACAAGAAG  40320
40321  TAGAGATCAT GGATCTGCCT TCTCTTTTTA AAGGCTCCTT AGGAGTCACT TCCTCCTCAA  40380
40381  AACCCTTTTA ATGGATTTCT ATGAAGAAAA TCATCTAAAT AAGAGTTTTA CTCAAACTGG  40440
40441  GGTCAGTACT TCCTGGTGGC TCAGGACTCT GAGGGGAGCT GATAGACACG CTGTGGAAGC  40500
40501  ACACTGACAA TGGTTTGGTC CTGCCTACCG GTTGCCGTTT CACTCTTCCT GTTGCTCAGA  40560
40561  TTGGCTGTGC ATTCTCTTGC TTTCAAACAA ATGTAACTGC ATGAATGAAA GCACTCCCAT  40620
40621  CCCCATTTCT GCCCAGTGAA ATCCTACCTC TCCTCTTGGC TCAGCTCAAA TGTCGCCTCC  40680
40681  TCTGTAGAAC CTTCAATGAG TGTCCAGTGG GAGGTCAGTG TGCCCTCTTC TGGACTCAAC  40740
40741  AACCATTTGG TTGGGTGCTC CCCTACACTC TAAAATGAGG GTGTTTAGCA AAGGTCTTAT  40800
```

Figure 1 - page 14

```
40801  CTCCCCTGCT GGGCTGTGAA CAAGTGAGTA GAAGGTTGCT GAGCATCGAA GCTAGGATAA  40860
40861  GCCAGAAAGG TGGCACTTGT TTTTTCAGCT GCCATTAAAT TCCTGTAAAG GAACTTCTCA  40920
40921  CTGAGGGTGC TCATTCTGTG TGTGGGGAAC TGCATGAAAA CACTCCTCAT GGCCTTTTGT  40980
40981  TTGCAAAGGC ACAGTTAGGT CTGCAAACAC AGAATTTGAG CAGCTGTGGC AAAGCAGCCC  41040
41041  TGATCACATG GCCCATCTTT TCCATTCTCC AGCTGTCCTG ACCAAAGGCC ACGCTGGAAA  41100
41101  CAGCTCTAAG AGCCACTAAG AGCTGTGGAG GCAGGAGTAG AGGAGGAAAG ACAAATGTCA  41160
41161  AAATTATTGG ATGATCCTGG GTAGCAACTG GCCAAGGGGG ATTAGAATGG GTGACAGAGC  41220
41221  CTTTCACCTT TGGGGTCAGC AGCATGTCTG ACTTCAGGAC CAGAAGGCCA AAACATCTGT  41280
41281  CAGCTGAGCA GCAGCTCCTG TGAATGAATC GCCTTTGTCT TGTTGGAGGC GGGGATGAGT  41340
41341  GTGAATTTAT TTGCTCAACA GAAAGCCATG TAAACCTGAG ATCAGATGGA AGCTCTGGTG  41400
41401  GTGGCAAGAA GCCCAGTAGC CCTTCAGACA GAAGATGCCC ATCAACAATG GAAAGGAGTA  41460
41461  CACAGGACCT CGGAAGGAAG GGTCCTCTCT CTTGGCGGAA GGCCCCTCAC CTCTTTGTGA  41520
41521  AGCCCTCTGG GGCAGAAAAA GGCCTTGCCG GTTCCAGCAA AACTTCATGG AGCATGGGGG  41580
41581  TGGCAGATGG GGTGCCTGGT CCCAGCCACT CCTCTCCCAA CTTCCCACTA GCCATGTGGG  41640
41641  CAAGCTCACA TTAGCAATGA GCTCAGGCCT GCTTTGCTCA TTTAAGGAAA AGCAGTGATC  41700
41701  CCATTATCCC AGGGGTGATT CTTTGCCCCA GACGCAGCTC CTTTTTTCTA ACTTCCTTCA  41760
41761  GCCCTGCTGG CTTCTCCTCA GCAGTAGCTA ATGTGGGATG ATGATCAGCA GCAGTTGAGC  41820
41821  TATTTTTAAG TCAACAAACT ACCAATGCTA AGAGTTCCTC AGAAAGCCAG GAAATTCGGA  41880
41881  GCCTCAGAAG CAAATGCTAA ACATGATTGA TGGGCATGGA AGGGAATGTT TTGGACTGCT  41940
41941  GTTCACAAAA GGAATCCCTT GAATTTAATC CTAAAAATGG CCAAGCTAGA AGAGTCCTTA  42000
42001  GAAACCATCT AGTCTGCTTT TTCCCTCCCT AGAAAATTTC TACAGATGAG AAAGTAAAGT  42060
42061  GGATGATGGT TTAGGGCTGA GGCACTTAGC TGATCTAGAG GTGGAAGCCA ACTCTTCCTG  42120
42121  ATTCCTATGT GAATGCTCTT TCCACAAAGA TCAGTAGAAT GTTTCTGGAT TTCTTTGTTT  42180
42181  CAATGAGCTT CGATTATCAC ACTTTATTTT TCTTAGCATG GCTCCATAA AACTAAATTA  42240
42241  TTGTACAAAA TCTAAATAGG TTAATTAAAC AAGCACCAGA CACAGAGTAA CTTAAATGAC  42300
42301  ATCAGGGTGC TAAATCTCAG TTTATAGTCA GTGGACAGAT AACTCCAAAA TATCAGCTGG  42360
42361  TGGCATATCC AAATCAGTAA GGAAGGACCA TTTGGTTTTT ATGCCACCTG AACAGTGGCG  42420
42421  GCATTCCAGC TGGTGAGTCT TCCTGGCCTC TTGATGCAGT ACTCCCCTTC AGCTGATGCT  42480
42481  TTGCTCTCTG GGGTTAATTC AATATCCAGG GGCAGGGAGC CAGACTTGGA AGGTCCTCTC  42540
42541  CCCACATCTA ACTCCTGCTT CAACACCCAG CTCCAACGTC TTCTCTGTGA AGCCTTCCTA  42600
42601  CATCTTCCCC CATTCCTCAG AGTAGCCTAA ATCCTCTCCT AATGCCCCTC TTTATAATAC  42660
42661  CCCTACAGTC ACACTGTAAG GTTACTGTGT TAGGCCCCCA TCAGGCCTAG GGTGTGTGTG  42720
42721  TGTGTGTGTG TGTGTGTGTG TGTGTGTGTG TGTGTGTGTG TGTCATGCCT ACAGTGAATC  42780
42781  TCTCCAGAAA CACCAATGAA CAGGTTTGAC TACAAGGAGA CTACAATGAG AATTTTATTG  42840
42841  CCAATATAGG AGATTTGGGA CCCACACCAG GTAGAGTTTA CTAGAAACAA GATACCCCTA  42900
42901  CTGCAGTAGG CATTGAGCAG GGAGGGAGAC AGGGGAGGGA GCAGAGCAGA GCACTGGGGG  42960
42961  TGTCTGCAGG AAAGCCTTAT TGAAATCATG GAAGCTGAGG TAGCTTATGG GAGCCTGGGT  43020
43021  CTTAGAACTG ACCCCTGGGT CATTGAAAGA GAAGCCCCTC TTGGAGGGGA ATGAGAGGCT  43080
43081  GCAGCAAGCA GCTCTGAGTC ACACAATCAG GAAGGCATTG AACGCTTGAG GCAAACAGCC  43140
43141  ATTATGACAA AGGAGAAAAT GCACTTTACT CCATGGGACT CTGTCTCCCC CGGTGGACCT  43200
43201  AGCATGCTGG GCAAAAGCAG CTATCGTTTG GCTTGAGGCT CATCTGTTAA AGAGGAGGCT  43260
43261  GGTGTAAACC TAAGCATGGG GGCATGTGGA GATGAGGGAG AGGGCTGGCC GGGCTGTTTG  43320
43321  GAGTCTGGGC CTGTCTCAGC TCTGCCACTA GTTGGTTGCA TGGCTTTGAG TAAATCTGCT  43380
43381  CCATCAGAAT AATGTGGGCA AGATAAATTC TCAAGTTCTT CCAGGTCTAA AGGTCTGGGA  43440
43441  TCCTAGGGCT GCGCGAACCT GTTCCCACCT CAAACCTGTT CATTGGTGTC TCTGGAGAGA  43500
43501  GATGGACACA AAAGTCGTCA CTTGGCCCTT TTGGAAACAG TTGAGTCAAA AAGTCTTGGC  43560
43561  CTCCTGCTCA TTTTTAACCA GGGCCTCACA GAAACAGTT CGCAATCCAA CTGGTACACT  43620
43621  GGCATGAGGT TGTAAATCCT ATCTGGGAAA GCAAACCAGA AACTTCTACC CTTTGGTGTT  43680
43681  CAAAAATACT TCATTTTTCT TAAAATTGTC TTTTTAAAAC TGTAAGGTC TGTAAACATT  43740
43741  AGTTTTAGAA CAATTGCTCC CCAATAATTT ATTTTACAAA CAGGAATATG AAAAATAAAT  43800
43801  GGTGGTAGGA GGAAGGACCC ACTAAGAACA CCATTTTTAA ATTTTGCTAA GTAAGGACAT  43860
43861  TGAGGGAAAA AACTCAAACT CTGATCTACC ATCATTGTTT AATGTTCGGC AAACATGAAG  43920
43921  CATTTTAATA CCAAAAAAAG TGAGGAGAAT AAATCTCAGC ATAAAGGAAC AACTTTTTAA  43980
```

Figure 1 - page 15

```
43981  ACTGAATTTA GCACTATGAA AAATGTACCT CATTTTCTGT AATTTTAGCG AGTTTCCCGC  44040
44041  GGATGTACAC TGGCCCCATG GATTGGCGCT GGGGATCACC AGTTTAGAGG TGCCAGTGCC  44100
44101  TTCTGACAAA GGCCCATGGA TCCATATGAC TGCCTGTCTG TTCTTTTTAG AGACGGGCCC  44160
44161  ACACTGCAGA GAAGTGATTG TGAAGGTCTC CAACCCTGTC ATGCCCCAC  CTGCCACCTT  44220
44221  GACTTGGGAG AGGGACACTC ACAAAAGCAT GTCAAATCGA CATCCATTTC TTTCTCTTTC  44280
44281  CCTCAGGTCT CAGGGAGTTT TCCTCTTCTC CTCGGACTCT TTCTCTCAAG GCCTCTTCTA  44340
44341  CAAAAACCCC TGCCCAGAGG GTTACTGCTA AAATGAAACT CCCGTGTCTG TCCCCTTCCC  44400
44401  TGGCCCCCAA CTGACTTGCC TGCCTCTGCT TGCTGCTGTC CCTGCCTATT CCCCTTCATG  44460
44461  CTGGCTCTAG AAAGATGCAA TCTTTTTCCC AGGCCCCAGC CTCTCTGGCC TCCCTGCCAT  44520
44521  CCAGCTTCTA GCCTCCCTTC TCTGGAATCT ATGGAAGAAT CATCAAGCAG CTTCTGGAAA  44580
44581  TCCAGGAGTC TGTCCTTGGT CATGGTCATC TTCAACCTGT CTGTGTTCTT GAGAACGTTC  44640
44641  ATGTGCTCCC AGAAACATTC TTTTTGTCTG CCTTTCCTGG TCTGGCCACA TTTGACTGTG  44700
44701  TCACTTCTCT CTTTTCTCAC TCTTCTCTGC CCTCCACAGA CCTCCGTGCT GCCAGGACTT  44760
44761  CCTAACGGAA GGGCTTGGCT GGCTCCCCGA AGCCATCCAG AACTGGACCC GAGGGACCCA  44820
44821  GCTCAACTTG AATGTCCTTT TATCTGCCCA GGAGATGGGA AGATGCTGAG ACCATGCTTC  44880
44881  AGTGCTGTCC CACATCTGTC TTTCTGAGTT TAGACTTGGT TTTTCCATTA TATTCCATTC  44940
44941  AACTGATTTT TCCATGATAT TCCACAATGT CTTACCTAAC TCTAGCTTTC TATACTCAAC  45000
45001  AGCAATGCCT CCTGAGAGCC TCCTGGGTGT CAAGTACTCT GTTGTGTGCT TTTGAGGACT  45060
45061  AGGGTGTTAG CAAGGCACAG TCTCTGACTT TGCAGGGCTC ACAGATTCAT GGGGAAAATT  45120
45121  GATGTTCCAG TTACAGTGAG GCAAGGCAAT CTGGCAGTAA CTCCATAGAG AGGAATGACA  45180
45181  GGCTGGGCCT AGGAATGGAG GGGAGCGGGT AATAGAGGAT CCTAAGGAAA CTGAGAGAAG  45240
45241  AGGGGCTGGA GTGCGGCTGG TCTGCGCTCC TGTGCATTGC CTTGGCTAAC ATTTTACTTG  45300
45301  TCCTTCTGAA TCACCCTGGC ATTGTCAACA AAGAATAATG TATGATCCTT CTTGGAGTAA  45360
45361  AAAGCCTTCA GCAGTGCTTC ACAAAAAATT CTATTGTATA TTTTGTGTCC TACCTCAAAT  45420
45421  TAATTAAAAA AAAAAAAAAA AAAACACGTT GTTAATTCGC TCCAAGCCCA CTCAGCTGCT  45480
45481  GAAGAATTTT GAGTATTCAG CTAGAGATCT TTGTAATGAA CAAGTAGCTC AATTATTCTG  45540
45541  GTTTCATTAT ACAATGTATC AGGCATTCTT TTTTTTTTT  TCCCCAAGGC AGAAGAATTT  45600
45601  TTCTTAGTAC AGAACAAAAT GAAAAGTCTC CCATGTCTAC CTCTTTCTAC ACAGACACAG  45660
45661  CAACCATCCT ATTTCTCAAT CTTTTCCCCA CCTTTCCCCC TTTTCTATTC CACAAAACCG  45720
45721  CCATTGTCAT CATGGCCCGT TCTCAATGAG CTGTTGGGTA CACCTCCCAG ACGGGGTGGT  45780
45781  GGCCGGGCAG AGGGGCTCCT CACTTCCCAG TAGGGGCAGC CGGGCAGAGG CGCCCCTCAC  45840
45841  CTCCCTCCCG GGGGCGGCT  GGCCAGACGG GGCGGCTGCC CGGGCGGGGG GCTGACCCCC  45900
45901  CACCTCCCTC CCGGACGGGG CGGCTGGCCG GCGGGGGGC  TGACCCCCCC ACCTCCCTCC  45960
45961  CGGACAGGGC AGCTGGCCGG GCGGGGGCT  GATCCCCCCA CCTCCCTCCC GGACGGGCG   46020
46021  GCTGCCGGGC GGAGACGCTC CTCACTTCCC AGATCCCGGCG GCTGCCGGGC GGAGGGGCTC  46080
46081  CTCACTTCTC AGACGGGGCA GCTGCCGGGC GGAGGGGCTC CTCACTTCTC AGACGGGGCG  46140
46141  GTTGCCAGGC GGAGGGTCTC CTCACTTCTC AGACGGGGCG GCCGGGCAGA GACACTCCTC  46200
46201  ACCTCCCAGA TGGGGTCGCG GCCGGGCAGA GGCGCTCCTC ACATCCCAGA CGGGGCGGCG  46260
46261  GGGCAGAGGC GCTCCCCACA TCTCAGACGA TGGGCGGCCG GCAGAGACG  CTCCTCACTT  46320
46321  CCTAGATGGG ATGGTGGCCG GGAAGAGGCG CTCGTCACTT CCTAGATGGG ATGGCAGCCG  46380
46381  GGCAGAGACG CTCCTCACTT CCAGACTGG  GCAGCCAGGC AGAGGGCTC  CTCACATCCC  46440
46441  AGACGATGGG CAGCCGGGCA GAGACGCTCC TCACTTCCTA GACAGGATGG CGGCCGGGCA  46500
46501  GAGACGCTCC TCACTTTCCA GACGGGGCAG CCAGGCAGAG GGGCTCCTCA CATCCCAGAC  46560
46561  GATGGGCGGC CAGGCAGAGA CGCTCCTCAC TTCCCAGACG GGGTGGCGGC CGGGCAGAGG  46620
46621  CTGCAGTCTT GGCACATTGG GAGGCCAAGG CAGGCGGCTG GGAGGTGGAG GTTGTAGCCA  46680
46681  GCCGAGATTA CGCCACTGCA CCCCAGCCTG GCACCATTG  AGCAGTGAGT GAACGAGACT  46740
46741  CCGTCTGCAA TCCCGGCACC TTGTGAGGCC AAGGCTGGCG GATCACTCGC GATTAGGAGC  46800
46801  TGGAGACCAG CCCGGCCAAC ACAGGGGAAC CCCGTCTCCA CCAAAAAGT  ACGAAAAACA  46860
46861  GTCAGGCGTG GCGGCGCGCG CCTGCAATCG CAGGCACTGG GCAGGCTGAG GCAGGAGAAT  46920
46921  CAGGCAGGGA GGTTGCAGTG AGCCGAGATG GCAGCAGTAC AGTCCAGCTT TGGATCGGCA  46980
46981  TCAGGGGAG  ACCATGGAAA GAGAGGGAGA GGGAGACCGT GGGGAGAGGG AGAGGGAGAG  47040
47041  CGAGAGCGTA TCAGGCATTC TTTGGCATCA AGGAATTAAA GCACATTTTC TCTGGCAAAT  47100
47101  GGCAACAGTG TCTGATTTGA AGACATACCC TACACAAGTG GTTCTTGACT AAATGTAGTT  47160
```

Figure 1 - page 16

```
47161  CCATTTAAAA ATAAGAGTTA ACCTCTTGTA GTCTGGTCTC AACTGGCTCA TTCCAGGGAG  47220
47221  TTCTTAGCTC ACACTTGCTA ATATTTTGTT TACAATTGTG CAAATTCTAC AGTTGGCAAT  47280
47281  ATTGTTTACC AGGCATTGAA CTCTTTTACT TATTAATATT TTAATAGGTT TTTGGGGAAC  47340
47341  AGGTGGTGTT TGGTTACATG AACAAGTTCT TTAGTGGTGA TTTCTGATAT TTTGGCGCAC  47400
47401  CTATCACCCA AGCAGTGTGC ACCGTACCCA ATGTGTTTTA TTTTGTCCCT CACCCCCTCC  47460
47461  CACCCTTTCC CCCAAATCCC CAAAGTCCAT TATAAGGCAC TGAACTCTTA AGCCTTGTTC  47520
47521  CTTGTTCCCA CAGCTCGGCC AATTGTGTTG GTCCTTCCCC CTGCTTTATT TAGTCACTTC  47580
47581  CTCTGGAGGC TGGCCTTTTC TACCCAAGAC ACCATGGGCA GTGGAGCACT CAATCCATAT  47640
47641  TCTCCCAGAC ATGCCCCTCA ATGCCAAGCA GAGAATCAGA GCACCTGGTG TTTGGGGACC  47700
47701  AGACCTGTGT CCACTAAAGG ACCCCAGTCA AAGGAAATGG CATCTCTTGG AAAAAAAAAA  47760
47761  AAAAGCTACT TTCTGCCCAT GAAGAAGGAC CCCGACCTTC CCCCAGTGTA AATGTATAGG  47820
47821  CAGGACCCCC ACTACCCTGT GCTCCTTTGT GCAGTTGAGG AAAAGGTGGC CCATCTGGAT  47880
47881  GGATACAAAG CTTGGCAGGA AAGCAGGGGC AGGATTTCAG CTCCCTTGGC CCCCGTGCAA  47940
47941  GTGAAGGAAG CTTTCCCCTG AGGTTTATTT GACATTGTTC TCCCCAGACA GCTGCCTTCC  48000
48001  CAATTCAAAG GCTCAAGACT GTTGAAAAGC ATATGCCAAG GGACAGACTA AACCTGTGAC  48060
48061  AGAGATGATT GCCAGTTTGC GAAAATGCTG AAAGCTTTCC ATAAATTTGG GATCCACAAG  48120
48121  GCACCTTGTC GTCACATGCT GGGTCAATCC CATTGCAGTG GGGAGTGGAG GACTGGACTG  48180
48181  GATGATGTCC AGGAGCCTAG CACTGTGTTG AAATAAATTA TTCTGCAGGC TGGTGGTGGT  48240
48241  TATAAACTCA CTACCAGCAA GGAGTTGGGG CTGAAAGGAG AAACATTATA AAACGGTTGC  48300
48301  CACTAAAGTG TAGTCTGTTC AGGGCCAATA ATTAACCCTA GTTGGAGATG ATTTCTCTCT  48360
48361  TTGACTATCA CCAGGGTTGA GAGCCGAGTG ACTCTGCCTG TCCAATTTGA TTGCTAGGGT  48420
48421  GGTCCAAAGG AGAGTTCCTT CACCTTCATC CACCTTTATT GGGTCTCTCC TCTTTCTTTT  48480
48481  ACTGCCAAAT TTCTTGAAAG AAGAGTCCAG ACTTGCTGTC TCAATAGCTT CTCTGCCTTG  48540
48541  CATCTGACTG ACTGAGTGAC TGACTGACGA GAGGTCACAG TGTGTTGGAC TGCTAAAGTA  48600
48601  GCCAGCCTTT TCTTGTTTTC CCACCCTATT TGTCAGTGTA AAGTGTTCTA AGCTGATGGC  48660
48661  TTCTCTTTCC TTTTTTTCTA CTTTCTTCCT TGGACTCCAG TGAAATGACC CTCTCCAAGT  48720
48721  TACCTCTACC CTCGTGGCTG CTTTTCTGCT TCTTCATTAG TGCCTAAGCT GAGTGTATTG  48780
48781  CTCATGGTTC TAGCCTGAGC TTTTTTCCCT GATTATCTTC TGTGTTGGAG ATTTGACCTA  48840
48841  CTCGTGGGGT TTCCATGATA ACCACTGCTG AACAGACTCC CAGAGTCATC TCAGCCAGTC  48900
48901  TCATCTATGT CCAGTCCTCA ATGCCCACAT TTCAACATGT TCAAGGCTGT CATCTTCCCT  48960
48961  CTCTACGTTG GTCTTGCTGC GGCTTCTTTA GAGAAATTAT CAAGACTTTG GAGTCATACA  49020
49021  CCTAGGTTGG AATCCTAGTT GTACACTTTT CTGTGTGGCC TTTGAAATGA AGTCCTTTTT  49080
49081  TCTCATGTTC TGTGAATGCT ACCAATGCTC ATTATACAAT AAGCACTTGT CAAATGCTGG  49140
49141  TCTCCTTCCC CATTTTTTAT TAGCATGAAC ATTTCCCCTC TCTAGTGGGC TTGGAATCAT  49200
49201  CTAGTTTTTC ATTGTAATAA TGTACGTTCT CCTCCTCTAC ACCTCCGCAA GCCCATTTCT  49260
49261  CTGGAAACAC CTCTCACGTT GGTCCTGTCC TTTCAATATT AAGGGATGTC ATCTGGGCCC  49320
49321  ATGCAACCAG TGTCTCTGCC TACCCGATCC TCTCTGCCCG CCACTACTGC CTGAAGCATG  49380
49381  TTTCAGATCA TATTCCCACC CAAAAACTGC CAGTGCCCCC ACTCTCAGTT CCATACCTTT  49440
49441  ACTTTCAAGG TTTTTAATGA TCTGCCTCAA ACCTAGTTTT CTGCCAAACT TAGGATGGCT  49500
49501  CAATCACATG GCATGCTGGG ACCTCAGTGA CAGAATCCAA TGGGATGGGG TAACCAGGGT  49560
49561  AGCCCGTGTC TATCCCAAAG CCTCCAATCT GGAGGTTGGG GCAATGCTTT AGGGCCATAA  49620
49621  TGATGCTCAA CGTGAAATGG GGCTTCACCT GTACTTGGGC ATTGGGCTCT GGTCCTCAGG  49680
49681  GCAAAGATCC TAGGCAAGAG GATCAATGAC TGGGCCCCAG CCAAGCTGCT TAAAAGCCAG  49740
49741  GGCAGCACTA GAGGACCAGT TGGAAGTCCA GAGTCTTGGG AAAAGGAGGC AAAATCTCAA  49800
49801  CCCCTATGTA TAGAGCAACA TGACGCTCGG AGGGAAGGAA GAAGGCAATG CAGTGGTCCT  49860
49861  GGGCTTCTAC GTTAATTCTG AGAGTGGCCC CGCAACTCTT CATCTTTCTC TTCCCTGGCT  49920
49921  TTAGGCATGT ATCTTGCAAC TAGCACTTGC TTAATTGATT TGACACACCT CCCTACACTT  49980
49981  ACCCCTTTCC ATACAAAGTG CCAGGTCCTC TGAAAGCTCC CTATATCACC TGGCCAATTG  50040
50041  GAATTTCAC AGCCAAGGCA GAAAACAGGT GAGGTTTGGT TGTCAATCTC CATCTTAGGC   50100
50101  ATTGAACAGG ATGTGTAGCC AGTTCATGGA AGACCTTTTT CACTCTTCTG AAGACTTAGG  50160
50161  AATAAAAAAG GGCTCTTACT GTTATCATGT GGTCAGAAGG CATTCTTTTT CCACTTTAAA  50220
50221  GAACCAAAAC TTCCTCCAGT TCAGAAACAG TAAATGAATG GTCCACCATG TGCTGCGAAC  50280
50281  TTTGCTGTTC ACCACCATGG CTGCTCCTAG CAGCATCTAT GCAAGCACCC CATGGATGCT  50340
```

Figure 1 - page 17

```
50341  ATCCAGGGTT TCTTCTTTTT ATTATTAATA GCTAACATTT ACTGAGTGCT TACTATATGC  50400
50401  CAGGCACTGT GCAAAGGGAA ACACAATGCC TCAGTCCCAG GTAGTTCCTG GGAAACTGAA  50460
50461  CAGAATCTTA AATAGAAACT CTAAGGAGTT AGGGAAGTGA GGGCTCACTG GGGCTGTGAC  50520
50521  CCCAGGGGAG ACCACACTCA AAAGATGGTT TTGCAACTCA ACCTCAGTTT CAGGCCTGCT  50580
50581  ATATCACTTC CACTCACTCA GTAGTAGGCT TGGCATTTAG TGGGGGACAG AGGCATGGTG  50640
50641  GGAAGTTGGG GGTGCTGTTC AGGCTTGGCC CTCACCAGCC TCTGCTGGGA CTGGTAGCAT  50700
50701  GAATGCTGTG TAGGATGTTG GGGAGCTGGA AGAAGACTCT TCCGCAGCCC CTCCCTCTCT  50760
50761  ATCCCATTCC CCTCTCATCT CCCCACCCTT CAAGGTTAAA TATTAAAAAT TCCCTTCACG  50820
50821  GGGTGAGCTT TCAGTCCTTG ATTCACTCCA AACAGGCTTC AAACGCAAAT AGCTGTAGAG  50880
50881  AAGATTAACA AGGTTGCCTC AAATTATTTG GCAAGGGGTG GGGAGAGGAT GCCCAGGAAC  50940
50941  CCTGGCTGGC TGGAGAGTGG GGAGAAAAGG GGGCACAGTG GGAAGCTGCA GGCAAACACC  51000
51001  TGCCATTGTA GCATTGCAGA AGGCCCCAAA GGACCCAGCC AATGTGAGAC AGGTTGGTTT  51060
51061  AAAAGCCTCC CATGGGAAGA AACCCAGAAT GATGACAAGC AGAGCCAAGT TCACGTCCCT  51120
51121  GTGGGTGAGA GTGTGGGTCT GGGAATGTGA AGCCTGGAGC AGGAGTCAGG GGCAGGGGCT  51180
51181  CTAGGAGAGC TGCTCCATGC CCAGAATTGT GCAGGGAATG GCATAAGCAG TGGCCCAGTC  51240
51241  AACTTGCTTA TCCCAGGCCC CCTTTTCCCA AATTTATGAT TTGAAAATGA ATTATTTTAA  51300
51301  AATGTCTCTG GAATCTTGAG TACAGTCTAA CAAGGCATTT GAAATGTAAA GATTTATGTA  51360
51361  TTTAGGAAAG CATGAGGTAA ATTACCTTCA TTGAAATATA TACATAGAGA GAGTACCACA  51420
51421  GGGAGTAGGA TTGTCTCAAA CAATTCCACA TGTCTGCTTC TCAGGGACCT GTACCCACCA  51480
51481  CCCTGTCCTT CCACAAAGAA TGTAACTAAC CAAAAACCCT AGTTCTGTAG CAATGACCGC  51540
51541  ATTTGAGAAC GACCCCACAC CCCGCACTTA GTTCACCATC ATTTCTCTTG GCACTGCAAG  51600
51601  AAGGAGGTCA GAATGCAGTT ATGTTGCGGG GAGGTCACTG CCACATTGCA GATCTTTTGC  51660
51661  TCATAATGAA GCTTGGCAAG TTAGGCTGGG AGAGGCAGG GCTGTCTCAT CGGTGTTGGT  51720
51721  TTAGTCGCTA TGGGTGGGGC CGGCTGGGAG GGCAAAGGGC ACAGCCATCC CCCATGCAAT  51780
51781  TCTGTAATGG ACAGTAGGAT ATGGGGGAAG GGTGTCTCAC CAGAGGAGCA AGGCAGAGCC  51840
51841  CAGATCACAG CTGTCATGCC TGAGAACAGT CTGCGTTTAA CAAGGAGCAG GCTTGTGGGG  51900
51901  CCAGAAGGTC AGATCTGGAC TCTGATTTTT AGGAAAAAGC AAGGATGGGA GAGTGAGTGG  51960
51961  GGACAGAAAC AAAGGAGGAG GCTGAGAGGA GAGTTTCCT GTAGTGGGCC ACAGGAGCAT  52020
52021  GCCAAAGGGT GAGAGGATGG AGCACTTACC AGACTGCTTA TCTGAAATGA GGAAACTCCC  52080
52081  TTAGATAAAG CAGGAACGCG GTGGTGAAAC CTGAGGTGCA AGACTCCAGG TTTCAGGAAC  52140
52141  CCCCAAAGGG TGTGGGATGG TGGAGAAGCT GTGACTCAAG TAGCAGCTGT GGAACACTAG  52200
                                                            (Fetal Tissues)I.5
52201  TGGGCAACCC AGGGGTGGAC TATGGGGGGT GGGCGGTGAG TTGCTTTGGA CGTGGGCAG  52260
52261  AGCGGTGGCA GCTTGAACAA GAATTCCTGT CTCCAGATTG GGCTGGGAGT ATGGCAGGAT  52320
52321  TGAGCACACA GGTAACTCAG CTGTCAGGAC CTGATGAGGG CCAGGGATGG TAGGGGCTGG  52380
52381  GGACAGGAGG CAAAGGGTAA GTGGTTTCAT TCATTCAAAA ATCACTGCAC AACTGCTGAG  52440
52441  CGCTACCAAC ACCAGCAGGC CAGGGATAGG AAGATGAGTA AGACATGGTC CTTACTCTTG  52500
52501  AGAGGTTTGT GATTGCTGTA GGAGATCTAG ACTGGGAAA ATAGAGACTC CAGTGCCTTA  52560
52561  AGAAATTTAG TCAAACTCAT GGTGCTTTGA AAGTATTAGA CAAAAGCAGC TCTCTATTCT  52620
52621  CATATTTTAC TCCAGTAATA CTCTTTAGCT TATGCATATC AGATTTATTT ACCCATTGAT  52680
52681  TTTTCCACTG AGGCATTGAG CTTTTGAACA TTCCACCTTC AACTCACTG TAAGATGCAC  52740
52741  ATAGACTTTA GTTGCCAATA AAATTGGCTG GCAACTTGGG ACTGCTTCAG GTCAGACACC  52800
52801  AAGGAGGTGG TACTTCTGTT CCATTTTATA GTGTTAGCCC CAGACCATTG AAGAAAACCA  52860
52861  GGACTCAGTT GAATAATTAC TTTGGGGGTC TTAACTGAAC AACTGGTTGG AGGGCATGAG  52920
52921  GGAAGGTGAG GCATTTGAG GGTAGGATGG AGACCTGGCC AGGGCAGAGG GAGGGGGAAA  52980
52981  GGTGTTTGGG CCCAGGAGAC AAAGCCTGCA TGGGAGAGGC TGCCTTCTGC ACAGCAGCGA  53040
53041  TACCAATGTC TGAGCTGTGG CTGCCCAGGA GTGCTGACGA GGCCCACACA GCTTCAGAAG  53100
53101  TGGCACTTGT AGCATGTGAG ACAGCCTGGT GTGAAGAAGC CCCAAATTCA AGTGGGCTCT  53160
53161  GTTTCCGGGC CAATTCCAAG CAGACCTGCC TGATATGCCA GAGAACACAG GTATCAAGGT  53220
53221  TCGCATTGCG TTAGTAATGC CTGTGGGAGA CAATAGGGTG AACCCGCAG CAATGTTTAG  53280
53281  CTTTCTTCTC CCTTGACTGA GGAGCCTCGG TTGTTTTTTC TTAAAGGATA TATTTTCCAC  53340
53341  TGTTTTGACT GGGCTTGTCC AGGGGTGCTG GGAAGAACAA GATAGGCAAG AAGGGAAGGA  53400
```

Figure 1 - page 18

```
53401  CTAATAAATT TTCTTGCTCA TTCCTAAAGT CCTATTTTTA GATTAGATTT TTAGATCTTG  53460
53461  AGCTCATCAC TATGTGCACT AGCTGTCATT GGATAAGTCA TGTCCAGGTG GGACACCTGG  53520
53521  TGGCGGCTCC ACTCTTGCCA ACCCTGCCCT CTATTGATGC CACCCACCTC ACAGATGAAT  53580
53581  GTGCTGGGTA GGTTCAGCCA AAAGCTCTTT CTTTTAGAAT CAGCCTCAGC AAGACTAGAG  53640
53641  TGACCTCCTG TCCCCTCTAG AGGCCATCTA GAGGTATATT CTGAATCTGC TGTGGCTCAC  53700
53701  TTCTCTCAAG ATCTCCTGGG TCAGGGGTCA ACTTCTCACC TGTACTTCAG CCAATGTATC  53760
53761  CTCCTATGCT TGGGTCCCTG CCTTTTATTT CTTTATGGGT GATTTCATC TGATTGCCTT  53820
53821  GCTGCACAGG TACAAAGCAA CAGATCTGCA GAATGAAAAC AGCTGGGGAA CCCTGAGTGG  53880
53881  GGTGAGAGTA GAATGGAGGA GGTGGTGGTA TCTTCTTAAG GGGGTACTCA TGGTGGAAGG  53940
53941  GTCTTCGTTT TTCTTGGGGA GGATTCCCTT TGTGCTGTCC AAGGAGACTT CCTTACACCA  54000
54001  TGGGCTTTGG ACATGCTTGG TAGTCAGGGC ACACTTGGCT TTGAAATGCA ACGAGCTAAG  54060
54061  TGGAATAAGC ACTTTGTACC ATACTGGCTG ATGGTACCAT ACTGTGGGTC AGATAGGAAT  54120
54121  CAACCTTCCA GGGGAAAAGA ACAAACAAAC GAAACAGACA AACAAGTGCC TGAAGACAGA  54180
54181  AATTTAATTG AGTGCTTCCT GGCTTTTATT TTAGCCCCCC TCATCTAAAG ATGTGCATCT  54240
54241  GTCCCAGATT TGAGCTATGA TGTGTGGAGA GGTAGAAGAG AGAATATTTA TATGCAAATA  54300
54301  AGAGGTGTTG ACCAGAACTC TGGGGATTTG GGTGAGGAAG GAAGCCAGGT TTTCTGTGGC  54360
54361  AGGGGTAAAA AGAGAGAGCA AGGGAGAGAA GGGGCGATCC AGCAGGAGAG AGGAGTAGAG  54420
54421  TTGTTATAGA TGACTTCTCC TGGAGAGTTG GATCAGGCCC ATTGCGGGTG AGAGGGCAAA  54480
54481  TCTTTCCCAA GAACCCAAGT GGTAGAATGG GTCTGGCCTT CCCTTTAGGT GGTTATTGGA  54540
54541  GAACTGGTGG GTATGCATGT GGAGACGCAG ATGCCTGACA AAGCTGGTGC CGTCTGGATG  54600
54601  GGGGGCAAGT AAGGTGTTTA GGAGTGAGAC TGTGGTGACT GGTACCAAAA AAAGAATGTT  54660
54661  GGGGTGATCA GATCCAACAC CAGGCCTTGG TGGTGACGAA GTCTGGCGGA GTCAAAGGAA  54720
54721  TGAGAAAACA CAGTTTGAGA GAGAAAACGG ATCAAGTGGG CTAACGCAAG TATGGAGGCT  54780
54781  GTGAAGGCCC TGAGCTCTGG AAGCCCAGAC TATTTATTGG CGATCAAACA GGTGGTGAGA  54840
54841  ATGTGGGGGT CGAAAGGGCA AGTGCATGAT CTACAGCTGT GAAAGTTTAG CATTTCCTTT  54900
54901  GAAGCATATG GAATATATTC TCCTACTTGA GATAATGGGG AGCATGTTTT TCCAGTTTAA  54960
54961  GCTAGAAGCA AGGAGCCAGC AAGTCTAGAC CCATTCCAGA GGCCACGAGG GGTTTTATGC  55020
55021  GCCGAGCCCT GGACATTATG TCAGACATGC AAACCCTGCC TCAGCTTTTT TCCCAACACT  55080
55081  CAGCTTTTTC CCAACATTTT CCCCTTCTCT TTTTTGTAAA ACCGCCACAG CTATCATTAT  55140
55141  TACTACATCA AAAGGTGGCC TCTTTTTGTT TTTAAATTAA TTGAGCAAGG CAATTGCAGG  55200
55201  CTGTGCAGCC TTTGATTGCC AGTTGGTGAT CCAACTTCAT TGTTCTTAGC CCTTATTCAA  55260
55261  AATGGAGTCG CTCTGGTTTG AATGCTTCCC ACGTATCTCC CCTTTCCCTT TTACAAGAGG  55320
55321  ACCCTTAATC CTAGGGGTTT CAGGATGAAG GTCCATGCTG AATGGGGGCA ATGATACTCC  55380
55381  TGCCTAACTA TTAGGGTCTC TTGTATTCAG GGTAGAGAGG CACTCAGTCA GAAAGCATTG  55440
55441  GTCCGTTAAG CATCTGTAGG TAAAACCCTG GCGCTCCAGC AGTTTCTCAG CTTCCTGTGC  55500
55501  GGTTTTCTTG ATCTGTCCCC ATGTTATGGG GATTGCACCC ACACGGTTCG TTCATCTCCA  55560
55561  TGAGGTAGAA CTTTCCACTG ATAATGAGAA ACAGGCCCCT TCTAATAGAA GGCACAGAGA  55620
55621  AAGCAAATGG AGGCTTCTCA AACCTTCAAT TTGCACTGTA CAGGTGGGTC CGCTAGATGC  55680
55681  TGTGGCTCAT GATAGATCTT CAGATGTTTG GTGGGCACCC ACACAGGCAC CTGATTGTCA  55740
55741  CCTGGAGAGA CACAAGCAAA TCTTCTTCCC CATATAATTA TCTTTCCTTT TTCCCAGCTC  55800
55801  TTTGTATGTG CATTCCTCCA CCATGTATCT TGTCCAGCCT TTTTATTTTC CTTTTGTCCT  55860
55861  GTTAGGTGTT GTTTCACTGC AGTTATGGGT TGATCTTTTT GTAAATTTAA AAATTTTAAT  55920
55921  GTTAATAAAG CTAAATGCAA TTACATATGC AGTGTCTTAT ATTCCTGGTC CTTCTCCAAG  55980
55981  TCGATATCCC ATATTTCTCA TCATTTGTCT ACTATTATTA CTATATTGAT CCATAGGAAT  56040
56041  AGATATTTCA GCATCCCATT GTTGCAATAA GTCTCTTCCC CATAAATTGA CAGGAATAGG  56100
56101  TGTAATAATA GACTGAATTG TCCCTTCCTG GCCATCCAGT CCTTGACATG GTAAAATCAA  56160
56161  GGAACTGTGA AAAACCTCTG AGGCGGTTCC TACGCCAATG ATACCCATGG AAGCCTTTTG  56220
56221  TTTGGGCCAG TGTCGGGTC ATTGATTTAG AGCAATAATA GAGACATCAG CTCCAGTATC  56280
56281  TACTAGTCCT TCAAAATCCT TTCCCTAAAT AGTCACTATG CAAATAGGTC TTTTGTCAGA  56340
56341  CACTTGATTA ACCCAATATA CAGCCTTTCC TGCAGGATTA GTACTACCAA AGTCGCCTGT  56400
56401  TCTTTCACTG TGCTGCTTCC TAGTTTTGTT TAGGGTAGCA GCAGCAACTG AGCAATTCTT  56460
56461  TCTCCTGGGG AGGCAGACCA CAGAGTTGAG GAACTAATAA CTAATTGAAT TTCTCTGGTA  56520
56521  TAATCAGAGT CAATTATTCC TGTATGCACA GCAACACCTT TCAAATTTAG ACTAGACCTT  56580
```

Figure 1 - page 19

```
56581  CCAAGTAATA GACCAACTGT TCCTGAGGGT AAGCGTCCTC TAACTCCCGT AGGGACCTTT  56640
56641  TTTGGCAGCT CCCCAGGAAA CAGGGAGATG GTAATTGTGC TGCAAAGGTC TATGGCAACA  56700
56701  CTGCCTGCTG TGGCAGGGGA CAATTGTTGT ACGCTTGTGA GGGCACTGGC TGTGCCGGGT  56760
56761  ATGCCTCGGT TTGTTGAGGG GCCTGAGGTG GGCCACTCTT CCCATTTCCT GAAAGAGGTT  56820
56821  GTCCATCTTT AGAACGACAC TGATTGCCC AGTGATTGCC TTTTTTACAA TGGGGGCATA  56880
56881  CACCAGGGCT TTTCTGTTGA TTGACGGTAG TAGTTCTTGC CTTTTGATTT CCTTTTCTAC  56940
56941  ATTCCTTTTT TGTGTCCAAA TTGCCGACAA TTGGAACAAG AGCCTGAGAA ATGGGGCATA  57000
57001  TTCTTTCCTA CTCTTAATCC AGCCATAGCC TGAGCTGAAA GAGTAGCCTT ATGTAAGTTA  57060
57061  CCTCCAATGC CATCGCAAGC CTTAACGTAT TCAGAGTAAT GGCTTGCTTG AATTCCTTCC  57120
57121  CTCCTTGCTG GATTATAGTA ATGGGAAATT GCCATACTTC AAGGTCTCCC TCGGCTCTAG  57180
57181  CTTTTTGAAT AGAATTTTGT ATAGCACCAC CAATTGCTCC AGGTTTTAAT GTTGCAACTA  57240
57241  CAGGAGTGGT GTTTTTCAGC TAATTCATTT TCTCGCCCAT TAATGGGAGA GAGAAGAGGT  57300
57301  GGCCATTCAC TTAATTCAGC AGGTGGAGCC AACGGGCTAG TAAAACATAC TTCTTTCAGT  57360
57361  TTCCCTTTCT TTAATTTCCT CCGGTTTCTG TTCCTCACAT TCAGAATCTG AAATTAGTTC  57420
57421  TTTACACTCG TCCTCCTCTT CCTCATCTGA ATCTACCTCA TCATCTGTTT GAAATGGCTC  57480
57481  AAAAGCTGCC TTTATTATCA CTCACATTGA CCAAAAAAAA CTGGAATTTT TGCTCCATCT  57540
57541  TTATACGCCT TTTTAAAATC TCTGCCAATT ATCTCCCATT CATCCAACTC CATAGTCCCT  57600
57601  TGTTCCAGGA ACCATGGGCA AAACTCCTTT ACCGTACTAA AGAGTGATAA CAAATTCTGA  57660
57661  GTACTAACTT TCACCCCCAC TCTTCATAAT AAATGCCTTA AGAAACTTAA ATAAGCAGAA  57720
57721  TATTTGCTTT CACTTTGTCC TGTTGTTACC CTGGTTCTTC CGAGCCCTGA GCTTTCCCAC  57780
57781  CAAGCTTCCT TTAGTCATCC TTGGGTGTCC TTTGACAATG CATCCCCTGC TTTCACATGC  57840
57841  TCTAGTGTTC CTTCACCAGG GCCTTTGTCG CCCCACGTTG GGCAGCCAGG AATGTTGGGG  57900
57901  TGATCAGATC CAACACCAGG CCTTGGGGCA ACGAAGTCTG GCAGAGTCAA AGGAAAGAGA  57960
57961  AAAGACAGTT TGAGAGAGAA GGTGGGTCCA GGTGGCCAAC GCAAGTATGG AGGCTGTGAA  58020
58021  GGCCCTGAGC TCTGGAAGCC CAGACTATTT ATTGGTGGTC AAACAAAGAA ACAGGTGGTG  58080
58081  AGAATGTGTG GGTCAAAAGG GCAAGCACAT GATCTACAGC TGTGATAGTT TAGCATTTCC  58140
58141  TTTGAAGCAT ATGGAACATA TTCTGCTACT TGAGATAATA GGGAGCATGT TCTTCCAGTT  58200
58201  TAAGCTAGAA GCAAGGAGCC AGCAAGTCTA GACTCATTCC AGAGGCCACG AGGGGTTTTA  58260
                                                                        EI.7
58261  TGCACTGAGC CCTGGACATT ATGTCAGACA TGCAAGCCCT GCCTCAGCTT TTTTTCCCAA  58320
58321  CACTCAGCTT TTTCCCAACA AGAAGATGAA GTGTTGTATC TTAGGGGCTC CATCTACAAG  58380
58381  GATGAAGTAA GACGGGAGAA AGGGGTGAAA TCAGCAAGGG TAACTATCAT CATGTGTCTG  58440
58441  GAGGTCTGCT GCTCCTTTAC TCCAGCCTCT CTGTCTCAGT TCTTCTCATT CCAGAGGTCC  58500
58501  CTGTGGACTG TGACAAGGAT TTTTCAGAAT TCAGAGAGGG AACCAACAAG GGCAAGCTT  58560
58561  GGTTTATTTC TCTTTATTTG GTTATTCTC ATTATTATTT TTCTTGCCTT TTCTACCTCT  58620
58621  AATTCCTTCT TAGCCCTTCC CTTTCTGCTT CCATTTCTAT CCCAAAATAT GAGCCACAAA  58680
58681  GAGAAATTTG GGGAATTAGA AGGAAGAGAC TTAAGGGAAA ATGTATATGT CATTGGTGTA  58740
58741  TGTGTCAGTT TTCAGTCATA ACTTGGGTTG GGGGAAGTCA GTGTACCCTT TACTCTTGCT  58800
58801  GAGGAAATTT CTTCTGAGCC TTAGCCACAT CCCACTTGCC CAGGGCATCA TTCTTTTCTT  58860
58861  TTTTTTTTCT GGCATATATC TCTACTTCAG ATTCAAACTT GGCCATTACC TCTGGCCAGC  58920
58921  CAAGCAGCTG TCCCCTGAGA GGGGGGCCAA CTCTCCTGCC CCTCACTGCC TGCCTCCCAA  58980
58981  GGCTGCCCTA GGGCTCAGCT GAAGAAGGCG GTTGTGCTTT GCTGCCCCCT GTTGCTCAAG  59040
59041  TCCTGCTTTT CCATAGGAGC TGCCGGGCTG TATGTCTGGA TGTGACTTCT CCAGGCAGGT  59100
59101  CCTCCTCTCC TGCCCGCAGT GCTCTGGCTC CTCAGGGTAG GTTTCTGTCC AGGACATGGC  59160
59161  CCCTGAAAGG GCTTGGAAAA AGCCCCCTTG CGTAGTACTG GCTGAGCTTC TACTTGCTGC  59220
59221  CCCAGGAACC TCCAGAGAGT GACCCAAACA TCTGGTATAG CCTCTAATCT TACCTAGTCA  59280
59281  GTCATGTTTC TCTTCAGGCC TCTTCTAAGA ACAGTTTCCT GGAGAAACAG AATAGAGTTG  59340
59341  TGGTCACTAC ACTGGAGTCT TCCTGGGGTA GGAGTGGGTC CTTTCTAAAG TAGAAGGGGC  59400
59401  TGTGTAGCAA GGGGGCTGTG TGAGCATTTC TAGAAATGTT GTCTGCTGAA TTTTCCACTG  59460
59461  GGAAAGAGCA AGTCCTGGCG GAGTTAGCAG CAGCTGGGCA GTAGGCAATA GATAGCATCA  59520
59521  GGGTCTCTGG ATGCTCAGTG GGGGTGGCAT CAGGGAACAC TGGTTTCCCC AGTAACGGGC  59580
59581  GCCTGGGCCT GCAGTGGCAG TCAATTCCAC AGAGGATGCC CCGGAGCTTG GCATCTCTCA  59640
```

Figure 1 - page 20

```
59641  CTGTGCTGTC TTCCCATTCC TGAGACTGGA ATATGGAGCT CATGTGGGCT GGGCAGCTTC  59700
59701  CCAGCAGTGG TTGGTCAGGA TGTGAGAGTG CTGTGGTCCA GGTACCTGTG GACAAGTGAC  59760
59761  CTGCCACACT GCAAGACCCA AAATGACACT GGACTACATT CGTTGACACA GTTACAGCTG  59820
59821  TACCAAAATT TTTTTTCCAA GGTTCAAGTT GGAACATTTG TAAGCCAAGC CCTCATGGGT  59880
59881  CCAAGCCTAT TTTCTTCACC ACACCACACT GAGTGAGGGC AGTGGCTCAT TACAGACCAC  59940
59941  AGTATCTCCC CACCTCCACC CATGTAGATG AGAACCTGGA GCCTGCCAAG GACTAGTGTC  60000
60001  CAGAATGGTG CCCAAGTCAC CTCCTGATAG GTAGGAAGTG GCCAAAATGA GGTGTAGGAC  60060
60061  CTCATGTCCT AGAGGTCAAA GCTAAGAGTC CAAGGCAAAT GGCCACAAGG CAGAAAGAGC  60120
60121  CAAACCAGAG CCCCCCTAAA ATGGGGAGAC CAGGATGGAT AGATAAGAAG AAGGGCAGGC  60180
60181  TTTGGCTGGG CGTGGTGGCT CACACCTGTA ATCCCAGCCC TTTGGGAGGC CAAGGGGGGT  60240
60241  GGATCACGAG GTCAGGAGAT CAAGACCATC CTGGCTAAGA CTGTGAAACC CCGTCTCTAC  60300
60301  TAAAAAATAC AAAAAAAATT AGCCGGGCAT GGTGGCGGGC GCCTGTAGTC CCAGCTACTC  60360
60361  TGGAGGCGGA GGCAGAGGTT GCAGTGAGCC GAGATCGTGC CACTGCACTC CAGCCTGGGC  60420
60421  GACAGAGCGA GACTCCGTCT CAAAAAAAA AAAAAAAAAA AAGAAGGGC AGGCTTTTAG  60480
60481  TTTTAGATCT AAGTCCAAAG TACAAATGTG AGCAGAGCGG GCTCTTATGG AGGGAGCCAG  60540
60541  TCACATGGGG TCTAGGATGG AGTAACAGTT CAACCCCCTT AGACCCATCC CTTCTCTCTC  60600
60601  TGTTTCTCCT TTGACTTCGA AGTTAACAAA AACATTTAAT CGCATTCTAA ATGCAAAAGC  60660
60661  CCCATGCAAA CACTTGGAAT TGGGAAAAGA GGAGAATACA ACAGTTTCTG CCCTCAAGGA  60720
60721  ACATAAAGTG AGTTCACAGC CTCTTTCTCT TTCAGCCTCC TCTTTCTCT CTCATTCCTT  60780
60781  CACCTAGCAG GTGCTAGGCA GCAACTGTAT ACCCAGACAT TATTATTTCT CTTGCCTTTT  60840
60841  CCACCTTTAA TTCCCTATTA GCCCTTTCTG CTTCCATTTC TATCCCAAAA TATAAGCCAC  60900
60901  AAAGAGAAAT TTGGGGAATT AGAAGGAAGA GACTTTAAGG GAAATGTATA TGTCATCGGT  60960
60961  GCATGTGTCA GTTTTCACTC ATAGCTTGGT TTGGGGGAAG TCAGTGTTTT TTTCCTCTTG  61020
61021  CTGAGGAAAT TTCTTCTGAG CCTTAGCCAC ATCCCACTTG CCCAGGTCTT CATTCTTTTC  61080
61081  TTTTTTTCTG GCATATATCT CTACTTCAAA TTCAAGTTGG TTGTGGGTCT TCCACCTACT  61140
61141  TTGTAGATGG AGATGTGGGG GTTGATGCCA ATCTGACAGT GACCAGCACT ACAGAGTGGA  61200
61201  ATGGGAACCT TCTCATCTTC CTGCTGGGCT CCCATCCCAG CCCCCAGGCC TCACCTTGCC  61260
61261  TCTCCTGCGC AGTGGGGTTC ATTCCAGGAT GCCCTCCCAA TAAAGCTGAG GGCATGAAGG  61320
61321  CTTCTTGAAT GGCAAGCACT TTGGAGGCTA GGAAGGGAAC AAATCTTTAA ATCACTAGGT  61380
61381  ACTCTTTTTA CTTCTCATCT TGCTTTTAAT CCAAGTCTTT GGTCTCTTAC TTGCTTGCTT  61440
61441  TCTTCTCACC CAGGACAGAG TCACAGAGAC CTTGAAGAAT GGAGGAGGTA GAAAAAGGAG  61500
61501  AAATGCAGGA AGGAGGTGTG TTATGGAGTT ATCCAGTGGA GGCTCGCATC CAGCTTTATT  61560
61561  TTGCCTCCAA AGATCTTGCA TCCTACCTGT TAAGAAGCTT GGAATGCCAC TATTCCATTA  61620
61621  AATCTTAAAG GAACTTGAGT CTTTCATTTA AAAATGTGTT CCTAAAATGT AAATGTCCCT  61680
61681  ATGTGGGACA GTATTTAGCC GACAGTAAAT TTGAGAGGAG GGTCTCAAGG GGCAGTGTCA  61740
61741  CCAGGAAAAG AGAGAAAGGC TCCTCTCCCC AAGTCAAACC TTACCTTACT TAACCGATTG  61800
61801  TATTTCCTCC CTCAGAGGAT GCCATATCTC AGTA AGGAG AGAAATA A AGGTAGAGAG  61860
61861  ACTTTTACCC AAGCACCCCC TGA CCCCAG GTGTACACAA CTGAACCTGA TGCAGTGACA  61920
61921  ATCA GTTCA CACATAAAAC ATCTGGCTAA AGGCTAAGAT CACTTCGGAT TTCCGACATA  61980
61981  CATTTTCCTA AGCAGTGCAT TTTTCTTTAA TTTTCCTTAG AAAAAGACTG TAAAGTAGCC  62040
62041  CCACAATTCC CACATCTTCA TACTCCACCC TGCATTCAAG TTTTCCTGGG ACAGGTATCT  62100
62101  ATGTGTGTGC ATGAATCTAT TTTTACGGCA TATGTCTAGG ACCCCTA G AGGAGCCAAA  62160
62161  GTTTCAGAGA GCCCAGCAAC TA GTAACTC CATGGAAGGG AGGCATGATA TTACTCTCTG  62220
62221  TTCACAGGAG CGTACGCACA GATCTTTTCT CCTCCTCATG GTCAGTTTTC TATTTGTGAT  62280
62281  TAGTAATTAG CTTCTCTTGG TACGCTACGA TCTATTACAA AAGCCAAACA TTCAGGGGGC  62340
62341  GAGCTGAAAT GACAAAATTT GGCTATAATT TATGTTGGCC CCTGACATAT ATATTTTTT  62400
                                                        (Brain)I.f
62401  AATGGTTTGG TCTCTAAGCA ACTGATCTCT TAGCAACAAG AAGCACCTTT ATAAAAGATG  62460
62461  GCACA GAAG AGTGATTGCC AGAAAAGCCA CCTGGTTCTT AAACAGC GC GCATCATTAG  62520
62521  CAAAACTCAC CATCTTCA G AGTCCAAAAA CTAGAAGTGA CCAGCAGACC CAGGTAACCT  62580
62581  TGATATTGC ACATTTTCCT GGGGAAAAAA AAAAAAAAAA AAAAACTCA TGCAACTATT  62640
62641  GAAGAGAACA AAATTCTTTG AAATATGTTC ATTTTGAGG TCTTATTAGT TGGTCTTGAC  62700
```

Figure 1 - page 21

```
62701  TAACTTTTAA TAATAGTATG TATTCTTTTA AATAACTGCT TTTTGATTTT TTTAAAAAAA  62760
62761  CGTGATATTT GTGATCAGAA AACAGTTCAC TTGAAATATT TCATTGGCAT GAGAATGGAA  62820
62821  GGAGGGGAAC AATCTATCTG TTTCAGAATT TATTTCTGTA GGTTTTCATT TGATGGGAAA  62880
62881  AAAATCCACA TCATGGCAAA AATAGGAGTA TACAGAATGT CACCCAAGTG GTGTGCACTA  62940
62941  TTAGGGAAAT ACGCGTATTT ATTTTCTAAT TTATTTTCAT ACTGCTTAAA TATTTAAAGA  63000
63001  GTAGCAAAAT AATTTTACTT TCAAACTTTA GCTTTTTAAT CCAATGTCAA TTCCAGTAGA  63060
63061  AAGTGATAGT CTTTTGTTGC AAGTGTTCAA GGACTGGTTT TTTCATTTGC TTTCATTGCC  63120
63121  GTAAGAAAAG ATTCGTTCCA AAACTAAAAA TAGGAAAAAT TACAGGCATC TGTACCTTGT  63180
63181  TTGCTTTTTT CAGGTACCCA GGGATTGAAG ACTTAAATGT CTTTCCAGAA AATTGGAATT  63240
63241  AGAAATGAGA ATTGTTACTT CATCTGTACT CCTTCAATAA AGATTGCGTA ATTATAAACC  63300
63301  CACTTGGGGC ACTCAAAGGG CATAAAAAAG GAGATATTTT ATGGGGATGA AATAAAAATC  63360
63361  CTCCTAATTG AGCTTGGAAA CAGTGTTACA CAGAGATACT GCAGATCTAA GAAAACAGAC  63420
63421  TAGAAAATTG CAGTTTCAAT AAAGACAAGT TGAAATGTG ACACATAGTT TTATTTTTA  63480
63481  TAAGAACTGC TTGTACCACT TTCTCTCTTT TTCTTTCTTT ATTTCTTTTT TCTTTCTTTC  63540
63541  TCTTTCTCTC TCTCTCTTTT TTTTTGTGCC CTTTCAGAGG TGCAAATACC TCTTTAAATT  63600
63601  GAACTGTATG CTGACATTCT CTTGGAACCA GAAAATGGGA TGCTTTGTCT GAATACAAAG  63660
63661  CTTGGTAATG GGTCAGGGCA TTCAAAACCA ACACAATCCC ACAAATTTTG GGACTTACAG  63720
63721  TTGCTCCTCT AAGCAAAGGC ACCTCAATAG CACATTATGA TTACGTTTGA TTTTAAAAGC  63780
63781  TGCTTATGAC TTGTATTTCT GTTACTGCTA CCGACTTCAG GCAGGAAGAA TTCATTTTTG  63840
63841  TGGAGACTTT GCTTGAAGTT AGAAAGTTGG GTGTTTTAGA TTGAATTGCA GAAATTTTTT  63900
63901  AAAGCAATGC ACTATGAAAT CACAGAGAAG CATATAGGTT TGTCCTTCAG AACTAAAATT  63960
63961  GTATGTACTT GCAGTGTGGT AATTACTGTA GAAATGGTTT GTGGCTTTAA AGTTAAGGAA  64020
64021  CTTGCATAAA TAATTACAAG ATGTAACTTG TGTTTGCTAT GTCTGGATAT GTTTTCAGTT  64080
64081  TTAACTGTAC TGTAGTTTCC TAAAATATGA AGGGTAGTTA ACATGAAAGC AAAGGTATGG  64140
64141  TAACATTTAT ATTGCAAGTG GCAGCTAAGT TTTTGCAGTG GTTCTTTGGG ACTTGCAAA  64200
64201  TCGAGTCACT GTGTCTTTCG AGTTCATGTG TTCTGAGTTT TATCTATACA TGAGGAAACA  64260
64261  AGGGGGTCAG TGGGCCTGTA GAGCTTGTCA TTTTGGCTGG CATAATGAGC CATCTGACGA  64320
64321  AGATGGACAA ACTCCTGCAA GATGTGAGAT AGACTATGAA ATACTCTGAT TAGACTGGCT  64380
64381  GCTATAGACT AAGCCAAATC ATTCTGCTGT GTTAGATTA GTTATTCTG AGACACGCAC  64440
64441  TTACATTCAC ACACATGCCT GCATATAAAT GGTCTCAATA TAAATCTGGA AATCAAAACA  64500
64501  AGCCTCTCTA TCAGTGAGAG CTTCCTAGGA AAAAGGATAG TTTTAATTTT GTGAAGGACA  64560
64561  GTTTCCATCA TAATCTTCAT TTAGCGTCTA AAAGTCCTAG ACAAACTTGA CGGCCCTTTT  64620
64621  CCTTCAAACC TCAGGCTGGA ATCTGGTGTG GGGCTGGCCG GGGGACACA GCAGCTAGCA  64680
64681  GGCACACTGT CAAGCAGTCC TGCTGTAGGG GCGATCTATG TTACAAATGA ATCCATTTAC  64740
64741  TTTGGACACT TTACTACCTG AACGGAAACA ATCAGGCAGG AACTTGTTCA ATAACTACAT  64800
64801  GGTTGGCCTT TCAGCAGAAT TTTTGAACTC TTATAAATAA ACCATACTTG GGATAATTTA  64860
64861  GTCTTTCTCT GGTGAGAAGG AAACAAGAAA AAAAAATGTG AGCAGTCACT CTTGAGTTAG  64920
64921  GTGCTGACG AGGACTGGGC AATTTACAAC GTGCAGTTTT GCTTAACCTT TACAGCAACT  64980
64981  GTCCAGAAGT CTCCGTGTCC CCATTCACA CATGCCTAAG CCAGATCCAG CAGTTTGCCA  65040
65041  GATGTTACCT AAACAGTAAA TGGCAAAGTT GGGATTTCAA CCCAGGACAG TCTGACTCCC  65100
65101  AAGCCTGTGC ATTTTCCTTG TGTCAGAATG GCACAAGTAG CAATTTAAAA CTGACACTAA  65160
65161  ATAATCCCTC TGGTCTTAGT AAAGCAAAAG CTCTGAGTAG GGCTGGAGGT GAAGATTTAG  65220
65221  GCATCTTTTC ACAGAAGAGA CTCCTTAACC ACTGGTTCTG TTGGGTGGAG TGACTCAGGT  65280
65281  CCTGTGTTTT CAAGGCTGCC ATTGGCTATG AGCCAGAGGT GGGTGCTCAT TTAGGCTGTG  65340
65341  GCCGTGGTGG CCACAGGCCA TGGCACCATT TCTTGCCATG ATGCACATCC CAAGTGAAGT  65400
65401  GGGGTAGGAC TCTTTGAGGT TCCCTTTCTG TGTGAACAGT TCTGAGAACA GGGCTTCCTG  65460
65461  GATGTCCCCT CCCACCCTGA CACGGGCCAC AACAGTTAGG GACTGCACAA GCAGAGTGGA  65520
65521  AGCCAAACCA CAAGCGGAGC GGAAGCCAAA TCCAGAATGG GCCAAGTGAC ATGTCACCAA  65580
65581  GTTAAGGTGA AGGAGGGAGA GCCCAGGTGT GGCTGGGGCA GGCCTGAGAG TGGGGGTGAG  65640
65641  ATGACAATAG AGAAAGCAGA GCTTTCTCCC CAGCGTTGCA GGATTTCGGT ATGCTGTCCC  65700
65701  CTCTGGCTTA TGGTGTTGCC CCTTCTTTCT TCTTCAAATA CCCCTGACAA AGGGATCAAT  65760
65761  CTTAGAGAGT TTATTAAAAA AAAATCTTCT TCTAAATAGT ATTTGGGCAG GAGATGATGT  65820
65821  ATACAGGAGC GAGGGCCAGG GAGGCTGTAG CCAGTCCTAG AATAAACACT CTGTGCATCT  65880
```

Figure 1 - page 22

```
65881  CTATTTCTTG TGATCCTTCC ATCACTCAGA CACCTGGAGC ATCGTGCCTA AAGCCAGACA  65940
65941  GTTCATGTAG GTGGGATTTA AACTCAAGTC TTTTGGCTAG AAACACTGTG GCTCTTTCAT  66000
66001  ACAACTGGGA AATATGATGG TATTTGTAGG CAGATACAGA TTCTGAGGTG GTCTGCCTTG  66060
66061  CATTTGGCAT GACCATCAAG TGAATACGAA GAGAGCTCTT CACCTGTTAC ACTTCAGTTC  66120
66121  ATCCTCAGAG GAGGGAATAA CGCTCCCAAG AGGCATAAGA GGCAACCTCC CATTTCTTTT  66180
66181  TCCATTCCCT CCCCACTCAG GGATATCTAT GGGTAATTCC TCTAGTCATG AGTCAGAGGG  66240
66241  CTGATGGGCA GCTCAGGAAG TCTGAAAAGA ATGCCCAGTA ATAGGTTCAA TTTTTGTACA  66300
66301  AAAATCGGTA ATAATCCTTG TGCAAGTAAT CTTCATGCCT CTACTTCCCT AGGGTCCTTG  66360
66361  TCTCCAAACA GACATGTTCA CCCTGCTTGA GTTCTTGCCT GGTGTGTGGT ACTATTGATG  66420
66421  TATATGGCTG GCACATTGAC ACCACACACC TGCCGTGGAC AGCACGTGCC CAGTCCCACT  66480
66481  CTCTACCTGG TGCAAAGGAA GTCTCCTTTT ATCTGGCAAT TCTGGGTAGA AGAAGAGGGC  66540
66541  CACTTATGTC TTTTGTGTGT GTGTGTGTGT GTGTGTGACA AAATTTCACT CTGTGGCCCA  66600
66601  GGCTGGAGTG CAATGGCATG ATCTTGGCTT ACTGCAACCT CCGTCTCTCG GGTTCAAGCA  66660
66661  ATTCTCCAGC CTCAGCCTCC CAAGTAGCAG GGATTACAGG CGCCTGCCAC CATGCCCGGC  66720
66721  TAATTTTTTG TATTTTTAAT AGAGATGGGG TTTTGCTATG TTGGCCAGGC TATTCTCAAA  66780
66781  TTCCTGACCT CAGGTGATCC ACCCACCTTG GCCTCCCAAA GTGCTGGGAT TACAGGCATG  66840
66841  AGCCATTGCA GCCGGCTGTC ATTTTTTAAA AAGCATAGCA TTCTTACTCT GGGAACTGAC  66900
66901  TTAGAGGTTG CTTAGTTTGG ACTTCTCGGA GGTGAGGGGC CTGAGTTGAA GTGATTTTCC  66960
66961  CAAGGGCTGT GCAGCTAGGC AAAGGTGGGA TAGAGCTCAG TTCTCTTGAC TCCCATTCCA  67020
67021  GTGCTCTTTC CTCTGTACCA TAATAGTTGC TATTCCTAAG AAGAGGGTGA GAGTAGACTA  67080
67081  TTACCCTTAT TTTACAGATA GAAAAACTAA AGGCATAGTT AGATTAGGGA TAACTGCCAC  67140
67141  TCCAAAACTA TGAAAGTTAT TAAATCTATG AGAGTGATTT AACTAACTGC TTCCCTGGAT  67200
67201  TAAAAATTTT TATTTGCCT GCTGAATATA AACATGTAAG GTTCAGTGTT AAAATGAACA  67260
67261  CATCAGAGTG TCCAAACACT ATTCTGCCTA TTGATCATAT AGTTTCTCTC CTGTATAAAA  67320
67321  AGTGAGGAAA GGGGTCGGGT GTGGTGGCTC ATGCTTGTAA TCCCAGCATT TTGGGAGGCC  67380
67381  GAGGTGGGTG GATCAGGAGG TCCAGAGTTC GAGACCAGCC TGGCCAACAT GGTGAAACCC  67440
67441  TGTCTCTACA AAAATTAGCT GGGTGTGGTA ACGTGCACCT GTAGTCCCAG CTACTCAGGA  67500
67501  GGCTGAGGCA GGAGAACTGC TTGAAACCAG AAGGGCGGAG GTTGCAGTGA GCCGAGATCA  67560
67561  TGCCACTGCA CTCTAGCCTG GGCGAAAGAG TGAAACTCCA TCTCAAAAAA AAAAGTGAGG  67620
67621  AAAGAAATGG AAAAATGGTC CCTCCCATTA TGAAGCCTGT TGTCCTAACC GAGTATGCAT  67680
67681  TTATGGAATC CCTGAAAAAG ACGAATCAGT GTATATCTGC ATATCTGTCT ATCTCAACTG  67740
67741  TCACAGCCAA ACTCCACACC AAAAATCATA ACCAGGGGCA TTGTAAGCAG TGGTCCTTGT  67800
67801  GGATTTTTCT CCTGCTGGGC CAGTTTTTTC CCCTATAATA ATTACAAACT TCATACATGA  67860
67861  GTTTGGTACT ACTCTAGAGG AGGCTCTAGC AAAACTACCC TGCTGTAGAG GAGCAATTAT  67920
67921  AGGAACTCTG CAATTCTGAT GACAGTTCTA AAAACATAAT GTGAAGGTAC GAACTCATTA  67980
67981  ATATACAGTT CTCTGTGCCA GGTTCTGTGC TAAGACCTTC ATGTAGCTTT TCTTATTTAG  68040
68041  TGTTCACTAC CTATGATGTC GATATTCTGA GCACCATTTT CCAGATGAGG AAGCTCAAAC  68100
68101  TCTTCTGCCA ATGAGGCCAA CACCATAGAG TGGTGTTTGT TTATAAAATG TATATTTTAT  68160
68161  TGCACTCAAA CGATGTACCT GGCACTGGTC TAGATGCTGG TGCTATAAAG TTAAATAAGA  68220
68221  CATGATCCTT GTCTTGAAGA AGCTCATAGC CTAATGAAGC TCATTTCCAG TTACATTTGA  68280
68281  GAACTTCTGC TCTTTGGGGC TAGTCTAATA GCACACAAGA GATTTACTCA GGAACACGTA  68340
68341  TCTTGAAGGT TGGGAAGGGT TGGAGAAGAA ATACGAGGAT AGGAAAAGAT ATGGCTGAGG  68400
68401  TTAAAACTGA AGGGAAAAAT CGAAGATGGA CAGAAAGTTG GCACTCACGG TGTGTAGAAT  68460
68461  ACAATGGGCA CAAGCATGGA TGAGAGAGTG CTGGGTTGTG CAAAAGTGTC AGCCAGCCTG  68520
68521  GTGTTTCTCT CTTGGATGAA GGAGTTCCAC ACTGAGGCAC AATATAAACA ATGAACTTGG  68580
68581  TGATATAGGA CAATAGTAGA AAATCCTAAA AACCAAGCAA AGGAGTTTGG ATGTAGTGAA  68640
68641  CAGATAACGA AGAACTGGTA CAAAATCTGC TGATGCAAAC ACTGCTGGCT TTTTAATATC  68700
68701  ACCAGATTGT GAACACCTAT TATGTAAAAA GTGCAGAGG AAAAGATTTT TGTCAAAGTA  68760
68761  ACATTGACCC TGATGGGGGG ATAATATGAA CTAGAAGATC AGTCTTTGGA AATCCTTGGA  68820
68821  CTAATCAATC AAAGAGTGGC AGTAGCCACA GAGGATACAG CCTGACCTCA GACTAATTCA  68880
68881  GAGAAAACAA TGGGCTTGAC TCAGTGAGTA GATATGGGAG AAGAGAAGAA GGAAAGAAAA  68940
68941  CCAAAAGGAT GGTGGGATCC CTAGAACTAA AGAGAAGTCT AAGGCTTAGC TACCTGGTTA  69000
69001  GGTAGAACTG TGGTGGAGCT AGTTTGTCAA CAAGGTTTAG ATCTTGTAAA TTGTCCACCC  69060
```

Figure 1 - page 23

```
69061  AAGTGAGAGT ATTCCTTGGA GATGTTAAAT ATGTCACCCA AACTATAAAT CAAGACACGT  69120
69121  TGGGTCTCAG AAAAGATGTA CTCTTCTGAG AGTACAGGAA GACAGGGGAA CGATCTGGAA  69180
69181  AACATCATTT GGATGCTAAA CTATTAGAAA TTTCAAGGTG TTATAATTTT TTATGGGTAC  69240
69241  ATTAGGGTTA ACTGGGTAGT CAGAACTTTA GGTGACTCGC AGGCCTGGTT AGAGGGGTAT  69300
69301  TGCTCCCACA GGTGCTTGAA AGAGCATCTC TAAGAATGAG AGAGGGACAG AACAGAAGAT  69360
69361  CTGGAGACCA CAGACTGTAT GACCTGGGTG ATTAAGAAGA GGGCGATAAA AAAGAATCAG  69420
69421  GACAGAGTAT GAATAAGAAG TGAACAGAGA TGTGAGAAGA GAACCAGAAA CAAACTGAGC  69480
69481  CACGTGGTTC CAAGGAGACG TTCTCTGCAA AGGCAGCAGA GAAGTAAAAA AAAAAAATGC  69540
69541  TTAGACTTGC ACATAGTTCA TCAGACAGGG TGAGAGGGAG GCCACTGATA CCCTCAGAAA  69600
69601  GCAATTTGGG AGGAACAGGA ACCTAGGAAA CCAGACTGGG TGGCAGTTGT TGTGGGGGTG  69660
69661  GAATCCCAGA GCCTAGTCAG GCCTCAAGAC CCACAGGGCC ACGTGCTGAA TGAACACAAG  69720
69721  ACAGTCGGTC TAAAGACTTG GGCCTCAGCA GAAACCCATT TTGGAATCTG TCTGCCTGTG  69780
69781  TAGCCTGGGG ATAGTCAGCT TGCGGTGGGA GGAAAGAGCA TGAACTCTAG AGTCAGACGG  69840
69841  ATGGATTTTG GTCTTTCCTC AGAAAGAAAC CAACTGTTGA GACCCTGTCA AAGAGATTTA  69900
69901  ATCTCTACTT CTTCATCTTT AAAATGGAGC TACTTCTACT TATCTCACAC AGTGGTTTCC  69960
69961  TTTTTTAATT TTAAAGACTC AAATGAGATA AGATGCCTAT AAAATATGGG GGAGGTGTTC  70020
70021  AGTAAATACC AATTTCCCTA GAACAGTGGC TGGTTATACT GTGTTACTTG GAGTATGAGA  70080
70081  TTTCTTCAGC AACTTCTAGA AGCTGTTTTT AGGGTGAAGG GGTTCCAGGT AGGGATAGGG  70140
70141  ATACTGATTG GAGGAGCTCC AGCTACCCAC ATCCCAGTTT TACCAGAGCA CCGGGATCCC  70200
70201  CCAAAAGCTT TTGCTTAAGG CGGTAGGGGA GGAAGCAGAG ACCAAACTAC TGGGACTAGT  70260
70261  AATGAATTCA GCAAGGTTTC AGTTCAGGAT ACAAGGTTAG CATACAAAAT CCAATTGTAT  70320
70321  TCTTATATAC TCTCAGCAGT CAATTGGAAC ATAAAAAATT TAAAACAATT TCAACACAGT  70380
70381  AGTACCAAAA AAAAAACCAA AGAATACTTA GGAATAAATC TAAAGAAAGA TGTCTAAGAC  70440
70441  CTCTACACCA GAAATTACAA ACATTACTG AGAGAAATTG TAAAGGACCT AAATATATGG  70500
70501  TGAGATATAT CACGTTCGTG GATAATTGGC TGTATTGATC TATAGAGCCA GTAAACTTCC  70560
70561  ATTTAAAATT TCAGCAGACT TTTTGGGGTA GAATTTCAGT GTGTGTTTGT TAGGAACCTT  70620
70621  TAAGAAGCAG TTGGCAAGAC TGCATTAAAC ATACAAGAGG TTTACAGGGG CAAATGACTG  70680
70681  GGAAAGATAA AAAGGGAGGG AGCGGGAGTA GGCCAAAAAG CTTTCAGTCC CCAGTGTAGT  70740
70741  CTGGAATCTG TGAAAGAAGA GAGGGAAGGG CGAGTTGTGT GGAAAGGGCT TCAGACAACA  70800
70801  GTATAGCTCT GAGACAGTTT CAGTCAGCAG TAGGGAACCC CCAAGCAAAG ATTGCCTGTT  70860
70861  GGAAGAGTCC TGCCTTGGCT GGAATGGGCT ACCACTAGTA CCCTTAGCAT GCTTGTCATT  70920
70921  GTTAGGAGC TACCCAGAGA AATATGGCCT TTCTGTGAAC ATGGTGGTGA ATCCATAGGG  70980
70981  TGGAACTGTC AACTATGCTC CAAATAGTAG TAGTAGTGGT AGTTGTTGTT GTTTTAAGGA  71040
71041  GATTTGAGCA GTCCACCTCC ATGGCAACCC CATAAAGTAA TTTAAAAAAA AAAGAACCAA  71100
71101  GTTGGAGAGC TCATCCTCCA ATTTACTAAT CTTGCTTTTA TATTTCAAGA CCTACTATAG  71160
71161  CTATAGTAAT CAAAATAGTT TTGTGTTGGC AAAAAATAAA CATATAGATT AATGGAACAG  71220
71221  AACAGAAAAT CCAGAAATAG ACCCATGCAT ATATTGCCAA TTTTTAATAA AAGTACTAAG  71280
71281  ACAATTCAAT TTGAGGGGGG AAAAGGGCCT TTTCAAAAAA ACGGTGCTGG ATATATCCAT  71340
71341  AAGAAAGAAA AAATAATAAC CCTATTAACC CTTACCTCAT ACCATATACA AAATTTAACT  71400
71401  CAAAATGGAT CATAGACCTA CATATAAAAC CTAAAACTAT TACACTTACA GAAGAAAAGA  71460
71461  GGAGGTGACC TTGGAGTAGA CAAAGGTCTC TCAGAACACA AAAAAGTAG GAGCCATAAA  71520
71521  GACACTTGAC AAACTTGATC AAAAATTTAA AACTTAATCC TCAATAGACA CAAAGAAAAT  71580
71581  AAAGCAGAGC ACAGACTAAG ATAAAGTATT CAAAACAACA CGTATCAGAC AACTCGAATC  71640
71641  CAGAATATAT ATATATTAAA AAAGTCAATA AGACAACCCC ATTTTTTTAA ATGGGAAAAA  71700
71701  AGATTTGGCC AGATGCTTCA TAAAAGATAT ATGAATGGCC AGTAAGTTCA TTTGAAAATG  71760
71761  CTCAAAATTA TTAATAATCA GGAAATGCA AATTAAGATC GCAATCAGAT ACCTCTAGAA  71820
71821  TGGCTAAAAT TCAAAGACTG AGAATGTGAA GCAACTGTAA CTCTCATATA CTGCTGATGG  71880
71881  GAATGCAGTG GAACCTCGGA AGATAATTTG GCAGTTTCTT AAAAAGTTAA ATATACACCT  71940
71941  GCTATACAGC CACTGTTAGA TTTTTACTCA AGAGAAGTGA AATATATGTC CACACAAAGA  72000
72001  CTTGTGCACT GACATCCATC ATAGCCTTGC TTGAAACAGC CAAAAAAAAA GGGGGGGGGG  72060
72061  GAAGGAAACG ATGGAAATGC TCCTTAAGAA GTGAATGGGT AAACTGTGGC ATAGCTATGC  72120
72121  AATTGAGTAC TGCTCAGCAA TGTTAAGGAA CAAACTATTG ATATGAACAA TAAGAATGAA  72180
72181  ACTCAAAATC AATATGCTAA GTAAAGAAG CCAGATGAAA AAGAGTACAG ACTGTTTGAT  72240
```

Figure 1 - page 24

```
72241  TATGACAATA GAATTCCAGA AAGCACGAAC TGATCAATAA TGACAGGGAG CAAATCAGTG  72300
72301  GTTATCAGGG GATGGGTGTG GAGGAAGGAT GGGTGACAAG TGGGTGATGG AAATTAAATG  72360
72361  CCACCTTGAT TTTGTAATGG TTTCACAAGT GCATGTGTAT ATGTTAGAGC TCATAAAATA  72420
72421  GTACACTTTA AATATTTGAG GTTTATTGCA TGTTACTTAT GCTTGGCGA AGTCCTTTAA  72480
72481  ATGGGATGGG GGAGGGTGGG TCTGATGGAA GGAAAGCAAC CCCACCTCTA CAGTAAAAAG  72540
72541  ATTTGACACG TGCTCTGGAG GAAACCTAGG GGAAAGTGAT ATGGTACTTT GCTTTCATAT  72600
72601  TTATCTACTT AGTATCTGCT TCTTCCCCAG GGTGGGGAGG GGCGAAGGCG GAGCAATGCC  72660
72661  TAGTGCCAAC CAGTTGTGGC GTTCAGGCTC CTTCCAGTGC TCTCGCCTGC TAAGCTGGGG  72720
72721  TGGGCACAGG GAAGACCCTT CCCCGGGGCA TGGGGAGCCG GCAGGGCTGG TTTCAATGGC  72780
72781  AATCCGCCAT AGGGTCCCGC GCTCAGAAGG GGTCCCGCTT GGAATCTAAT GAATGCTCTG  72840
72841  CAGTCACCAT ATGAAATTCT TAATCATTTT TCCTTCAAAT TCGTGTATTG TAAGTGAAGT  72900
72901  GCAATAACAC AGTGGATGCT TGAGAGCTTG GACTCTTGTC TCACCCCGGT CGCGTCTCCT  72960
72961  GCGTCTTCCT GGGACAGGTT CTGGGCCCCC ACCCGGCGAA CACCGCTGCC CTCCGCCCTG  73020
73021  GGCAGTGGCC GGCCACGGAC GTGGGGGCGG CGCAGACCTC GGCGTACAGC CAAGGGACCT  73080
73081  CGCCGCCACG CTGGGTCGCC TGTGAGGGTC GGCCTTTGGC CCGCCAGCGT CCCTGTGCTC  73140
73141  AAGCCAGCGC AACTTAACTA GCAAATAAAC CCTGCCGAGA CAGGTGGACA GAAAGACCAC  73200
73201  GGGAGAAAGG GAAAGGCTTT TTCCTGCTTT TTGAACGCGG GGCCCCGCGT TTTTATTTTG  73260
73261  CACTGGGCCG CGCAGATTCT GCGGGCGGCA CCGACCGCAG GCAGCCGGCT GGAGACCGCT  73320
73321  CGCCGCACCC CCTGCCTCGC CTAGTGCCCG AGCTGCTCCA GCTGTGAATG GGACACAATA  73380
73381  CGAGGAGCTG GTTTTGCTCC TGAAAGCGTC CAACAAAAAT CTGGCTCGAT TCGCCCTGCT  73440
73441  TGGGAGTGAC AGAGACCCAA TCTTTGTCAT GAAAAGCAGG AAACGGGAGG GCAGCTTTGC  73500
73501  TCTCCAGAGC AGGGAATGTG TCTGGGTAGA AGCAGGGAAA GTTCCTGCCC ACCTCAGATT  73560
73561  TTCTTCTGGA TGCAGACTGC CCTGTTCTTT GACTTCCTCT CCAGTGTGGA ATAAGGCTGA  73620
73621  GGGTCTCAAT TTGGTGAAAA AAGTAACCAT GACAACAGTC ACATCGTGGA GAGCATAGTA  73680
73681  AAATGTGTAA AGCTCACTGG CAATGCCTTC CCTTCCAGAA TGAAAGCTCC TCTAGTCAGA  73740
73741  CAACGACTCA ACGGCACCAA AAGAGCGGAA GGGAAGACCA GACCAGGGAA GGCTTTCCGT  73800
73801  GCCCTGCCCT GGGGCCTTCC ACAGATTAGG GGACCTCCGT GATTTGTCAG CTCTTTGCCT  73860
73861  CCAGCTTTCT CACACGGTCC GGGGCTGCTT TCGAGAGCTT ATACTAAAAG GGCAAGAGCA  73920
73921  GAGATGAGCT GTTTTTAGGA AACATGTGCT ACAAATGAAG TAAACCCATG GAATTTCAAA  73980
73981  ATAAAAATAA ACTTGGAAAG TTCCACTAAA AGGCTTAGGG CCTGATAGAA ATTGTGCAGG  74040
74041  AATCCTCGAC TCCGAGGTTT GAAGAAGGAC TGGCAGAAGC TTGTCCACCT TCGTCTAGAT  74100
74101  GAGGAGGGAG GTGCTTCTCT TCCTGCCACA GGGGAGGCTT CCCACTCAGT CCTCCTTCCA  74160
74161  TAGGCAGGAC GAAGCAATCG CATCTTTAGG GGGCACTGGT TGGAATGAGA GACAGGTGGC  74220
74221  CTGGGCTCCA AACTCTGTCA CTAATTAGCT GTGGGACCTT GGGTACATAG TTTAACCTCT  74280
74281  TAGGATGCTC CAGTGCTTGC CCTGCTCTGT CCGTGGAGAT GCAAGTGCCT TGCAAGGAGA  74340
74341  GGAATGTGTC ATGTACATAA TGTGATTTGT AGGCACACAT CCTCATGTGT TCATTTCTCT  74400
74401  TTGCTCTTCT CCCAGCCTGG CAGAGTAGGG TTGATTGGAT CTGGAAGCTT TTTGTGAGGT  74460
74461  GAGAGCAAAA TCTTTCCTCA GTTGGCTCTG GCTGCACAG CTGGGGAGAC TTTGGGAGAG  74520
74521  AACAGAAGCT TCTTTTACCT TTGTGCAAAG GAAGCCAGCC ATTTCCCTCA AGGTTGGCGG  74580
74581  AAGCTAGATT TGCTATGTTT CTGGAGCTAT CACTAGATTT ATCCAGACCA GGCATATCCT  74640
74641  CTAGCCTGTA GCCTGACTGG CTCAGTGGGC ATCCAGGGAT CCGAATGAAG CTCAAACAGC  74700
74701  TAAAAGGGC AGGCAGATAA CGACCAGAGT ATAATAAACT GTGGGGAAC GGTTGGCACT  74760
74761  GAGGAGAGCG GAGAGCCCCT GCCCTGTGGA AAGAGGGCAG TCCTTGCTTG GGGACAGCTG  74820
74821  GTTGTTGCCA CAAGGTAATG TGATTCCTCT AGAGCCAGAT CTGATTTTTT TCTTAAAAGA  74880
74881  GGCCTGTAAT CTGGACTTTA AGATATCCAA AATTTTAAAT AAAGACAACG AAAGCAAATG  74940
74941  TAAAACTCAG TATAAGCCAA AAGAAGACAG GTGAGCAGGT CGAGTGGGTG AATGATAGGA  75000
75001  AACTGCAGTC AGGACTGGGA AATCTGAGAG CAATGCACTT TGCCTGGGT TCCCACAGAG  75060
75061  AGCCCTAACA GGAGCACCCT GCCTCCCTCA GCCTGTCTTC CTCCCTCCGG GCTGAGGAGA  75120
75121  CTTTCTATCT GTCCCCATCC CTTTTGTTCA AGCCAATATT GTGGCCAATC CTTGCCTAAC  75180
75181  TTTTATGGGA TCTGGATTTT GAAACTCAAA ATATTTATTT TTTCCATCTG CTTTCTGCTT  75240
75241  CCCTTAGGCA ATGAAAAATG CTCAGCTGAC TTAATGTGGG GAGGGAGTAA AGGGCAAACA  75300
75301  GGTCAACATC TCAGAGGGAA GGGAGGACAT GGAACGCTGT CTGACCTGCC CGCAGCCAGG  75360
75361  GGAGGTGGGA TCCAGAATGG CAGGCTATAC TGGGTGGAGG AATGCCACAC ACATAGCCTT  75420
```

Figure 1 - page 25

```
75421  GGAGGCCCAA ACGGGGCAGT GTGCTTGGGA AGTTAGGCCC AGTTTGATAG AGCTGCATGG  75480
75481  AGCGCAGGGC AAGTGGCAGG GGATGAGACT GGAAAAGTGG ATGAAATAGG ATTTATGTAA  75540
75541  CATAAGAAAG TGTAATTGGC TCAAATGTCT GATTACTTAT GTGTTATTTT TGTAAAGCTG  75600
75601  GTGACCCAAC CCTACATTGG TTTTGTATAA TTTAACATCT GTGCACTTTG AAGTGACATA  75660
75661  CATTGAAGAA CCTTCAGAGT GTCAGAAACC ATGACCTGGA AGCACATCT ATCCTAATTT  75720
75721  GGGGGTGGTC TTGATCTCTA TGAAGTATCC AAACTGATAC TGATTGGACT CATTTGAGGA  75780
75781  TATCAAGTAA CATCAGACTT CACTGAGAGG TGTGCCACCG CTGTAACCAA GGGACTGCTA  75840
75841  CTACTTTCTG CCTGCACCCC ACCCCAGTTC CTATTCCCTG TTTCCCCAGC TGCATCCAAC  75900
75901  TCTTCTTGTT CCCCGGTGAT CCTTCCAACT CTTTCTCTTC ACTATATTGG GGCTGGCCCC  75960
75961  TGAAGACTCC ATTTTTTCCT TCTGCCCTGC GTTTTCAATA ATAAATTCTA TAATTTCAGT  76020
76021  GCTGGGAGCT GGTGTTAGTG TCTTCCAGGC AACTCACTGC TGTCCCTTGA CCGTCGTTAC  76080
76081  TCTTTCCTTC TAAAAGACTG AAATCTCCTG TAAGGTTCAC TTCACACTAT CCACCAATTC  76140
76141  ACCCTGTCTC CCCTACTAAC CAAAGGCTTT GGTATCTTTC TCGGGGTCTT ACCCTCCCCC  76200
76201  CCGACTCCTG CCATCATTCT AAGTAACTGA ATGTCCTTGT GGCTGATCCA ACCAATGCCC  76260
76261  TGACTACCCA GTTCATGAT GACTGCACCG TCAGTGATGT TATTTGCCCT TTCACCTCAG  76320
76321  CACACTCACA TGGACACAGC GGTGAACCTG TCATCATCAG AAACTGTGCC TCCTCTGAAA  76380
76381  TCTCATTCTC TTGCCACCAC CCTCCAGCTC CCTTGCTCAA GTCCCTTCTC TACAGCAGTT  76440
76441  CTCCAGCCTC AATGAGATTT CCAAGCCAAT GGTCCCTCCA CTTTGCCTAT GTCCATAAAT  76500
76501  CTCCTCCTAT CTTCATTTTC TTTTGTATCT AGCTCAGAGG CCATGGTTCT CCTACAGTG  76560
76561  TCCTAAAAAT ACCACTAAAT CCTTTGTTGA CCTCTCAGTT GTTCCCAGAT TTACTCATGC  76620
76621  CTGTTGCCTG AACAGATCAG AATTACTGGA GAATGTGACA CAACTGGGCA TTTTGGCATG  76680
76681  GCTCCAACTT CATGCTCTCC AAACTCAGCT GGGACCTCCA CACTGCCTAG CAGGTTTACT  76740
76741  GTGCTTTTCT AGAAGCTCCC TCCATGTTCA CAATACAAT CTCATTTCTT CCTCTCAGAG  76800
76801  TTGGAATGCT TGCAACCCCT TTATTCCCAG AGCAGCAGCC TGGGAGGATT GGATGGGTCC  76860
76861  ATTGGATTTG CTCCTGTCCT CTCCTTTCAT CACTGCCTCC AGCAAAGTAC AGTCCCTCCA  76920
76921  CAGGTGCCTG GATCTCATGC CTTCCTCCCT GGTCAGGGCT CTTGTTCTGT CAGCTATACC  76980
76981  CTCTCTTTTC CAAATCTTTG ACCTCTTCCT CACTACTGGA TTTTTCCCTT CAGCACTCAA  77040
77041  ATATATGCAA GAATCCACCC TCACAAACAA AGCCAAGCAA GTGAAAACTT CCCTAACTCC  77100
77101  ACACCTCTGT CAAGTTATCA CCCATTCTGT CTATTCTCCT TTAACAGCCA CGCTTTTTGA  77160
77161  CCATTATGCA TAGGCACTGC CTCTACTTTA TCTCCTCCTC TCCTTTCCAT TCTGGCTTCC  77220
77221  TGCTTCACCA CATTGCAGAA ACTGCTCTTG TCGTGGTCAC CAGTTTATCC AATGTCAATG  77280
77281  TTCTGCCTGC ATCTGACTTG ACCACTCAGC AGCCCTTTAT ACAGTTAACC ATATCTTCCT  77340
77341  TCTTGAAACA CTCTCTCTTC CGCTTCAGTG ATAAAATAGG GGTTTTTTGT TTGTTTTATT  77400
77401  TACACCTTAT GACAGTTCTT TCTGAGGATT TTTTTTTTGT CTGTTCCTTT TCCTACCAAA  77460
77461  TTCTAAATTC TTGAGTTCTT TGGGAGTTCA TATCACAACA TATTCTGCCT TGCAATTTCA  77520
77521  GCTTCTCTCA AGACCTTAAA TACCATCTCT ACAGTGGCCA AATTTAGGTC CCTGGTTTAA  77580
77581  TCTTTCTTGA AATCTTAACT TTTCCATTAC AGAACTGAAA TTAAGTACTT ATTTGGGTGA  77640
77641  TTATCTATAT TTTGCTTGTC TCCCCTCCTA GACTATAGGC TCCAGGAGTG CAAGCATTGT  77700
77701  CTTTTTTTTA TTCACCACTT CCATAATCCG TTGAGTCAGC TTCAATGTCA ATTCCTACCC  77760
77761  AATGGGTTCA TGCTCTGTCT GCCAAAGGCC AAAGCAAGTA TCATGAAATT TTCTAAGAGC  77820
77821  TAGGACATGT CACTGCAGCC TTTTCTCCAA ATTTAAGTGT GCAACTATAT TTTCTTTATT  77880
77881  GCAGAACAGG AAGTCAAGTA GTTTCTTTTG CCAGAAATGG GGAAATCGTA TATCAATAAC  77940
77941  CCTAGCACTG GGGGAGTGAG GAGGCCTCAA GTCTGTGAGT CCAGGCATGA CATGGCAAAC  78000
78001  TCTATAGATT TTGGAAGACT AACTGTCAGC AGTAAGGAAG AAAAATTGGT AGGAGGAGAG  78060
78061  AATAGGGGCA GGGTTATTTG TTGTGATTCT GTTTCAAGAG AGGGCTGATG AAAGCTCATG  78120
78121  GATGGCCTTG AGAATAGAGA GTGCTGAGAC CACCTCAGCT GGGGAGACCC TAACCCAGTG  78180
78181  CGCTAGAGGA ATTAAAGACA CACACACAGA AATATAGCAT GTGGAGTGGG AAATCAGGGG  78240
78241  TCTCACAGCC TTCAGAGCTG AGAGCCCTGA ACAGAGATTT ACCCACATAT TTATTGACAG  78300
78301  CAAGCCAGTG ATAAGTATTG TTTCTATAGA ATATAGATTT ACTAAAGTA TTCCTTACAG  78360
78361  AAACAAGGG ATGGGCTCTG GCTAGTTATC TGCAGCAGGA ACATGTCCTT AAGGCACAGA  78420
78421  TCGCTCATGC TATTGTTTGT GGCTTAGGAA CGCCTTTAAG TGGTTTTCTG CCCTGGGTGG  78480
78481  GCCAGGTGTT CCTTGCCCTC ATTTCAGTAA ACCCACAACC TTCAGCATGG GCATTATGGC  78540
78541  CATGACCAAC ATGTCACAAT GCTGCAGAGA TTTTGTTTAT GGCCAGTTTT GGGGCCAGTT  78600
```

Figure 1 - page 26

```
78601 TATGGCCAGA TTTGGGGGCC TGTTCCCAAC AGAGAGGAAA GGGGAAAGGA GGGACTTTCA 78660
78661 GAGATGAAAT AACAATTGAT TGGGGGAGAG ATGGTGGGCA GTGAGAAGTG GCCCAGAACC 78720
78721 TGAAGACTCT ACTGCTTCAC CCATCGGCCT CTCCAATGGG CCCTCACTTG CATGCTATTC 78780
78781 TTACTCCCTG GGAGGACCTG CCCCACACTT CTCTCCTTGG AATTCTATTC CTCCACCATG 78840
78841 ACCTCTCTGA AACTCTCCTT GACTACCCTG CGAAAGTAAC TCTTTCTGTT CTCTTTACCC 78900
78901 CCACAGCACT TGTCAAGTGG TCAGTTTTAT TTCCAGTTGT ATGCAACACG AGTGCTTATG 78960
78961 CAGTTAGCTA TATCAAGGCA TTGTGCCATC TGTAATGAAA TGGCTAAAAA ACCCATACAT 79020
79021 TTGAAGAAAC ACACTTGCTT TCTTTATTTC CTTGACTTGC AGTTAGTATT AACTGACCAA 79080
79081 AAGCATTATC TTCCTCTTTT TGCTTTTTTA TGAAGTTTTG GTAGGTCGTG TTAATAATAC 79140
79141 CCATTACTCA TTTCTCTGAT AAGATTATAG AACTGCAAGG TCTTGGATGA CATTGGCCTG 79200
79201 CTCCTTCTGT TACGGTGGG TCTTTGTTCT TAGAGCTCCC AAGATGGTGG TTGGCCACTC 79260
79261 CCAAGATGGT CGTGGGCCAC TCCCAAGATG GTGGCAAGCC TTTTGTTGTC TGACCTGGGG 79320
79321 TTCTTGGCCT CACAGATTCC AAGGAATGGA ACCTTGGGCC ATGCGGTGAG TGTTATAGCT 79380
79381 CTATTAGAAG CCGTGGGTCA TGGAAGAGAA CCGTGGAACC CAGCAACTAG TGTTCAGCTC 79440
79441 GATTAGGCTG AACCTGAGCA CTTAGCCATG CAGGAACAAT GGCGAGCCTC TAGCCCGATC 79500
79501 GGGAGTGGCG ATGGGCACCT CGCTGGATCA GAAGGTCAGT GGACACCCTG CTGGATCCGG 79560
79561 AGAGGTGGGA GTCAATGGTG GGTCTGTGAT GGTGGCATTC AGCAGTGGTG GACTGTGAAT 79620
79621 GAAAGCTCAG CTCGAGCCAG AACAAACACG GACCAGAAGA GTGTGCAGTT GCAAGATTTA 79680
79681 ATAGAGTGAA AACAGGGCTC CCATACAAGG AGAGGGACC CAAACAGGGT TGCCCACACC 79740
79741 TGGCTCGAAT GCCTGGGGTT TATAGCCTGA TCATTGTCCC TCCCTCTGTG CTCTCAGGCA 79800
79801 ATATATGATT TGACTATTTC TTTACCTCCT GCTTTTAGCC CAATTTGTAT TTTAGTGAGC 79860
79861 CCTCTTTACT ACCTGATTGG CCGGGTGTGA GCTGAGTTAC AAGCCCTGTG TTTAAAGGTA 79920
79921 GGTGCGGTCA CCTTCCCCAG CTAGGCTTAG GAATTCTTAG TCGGCCTAGG AAATCCATCT 79980
79981 AGTTCTGTCT CTCACTTCCT TTGATTTTGA AGTAAACAAT CTCTTAACTT TGGGATAGCC 80040
80041 TGAGACACCA CCTCTGACTT CTAAATGACT CAATATCCCG AAAACCCGTG GTAATCTCAG 80100
80101 TCCGTCTCAG CTGGTTCCAA TTAACCTCTT TCCAAGCTAT CTGTGTGGGC CTGCTTTAGC 80160
80161 CTTTTAAAAG GAACCAGACG TTTTTAGTCA CAATGGATGC ATATGATAGC ATGGTTACC 80220
80221 TCAGATATGC TGTGGGTTAG CTTCTATAGG CTTTCTTATA TTTAATGCTT TCCCCTGACT 80280
80281 TCACATTTAA TGCTTTTCCA AAAATTTCCC AACATCACTA AGGCTTCAGC AGCCCTTTAG 80340
80341 GACCAGTATT TCTGGGAAAA CACTCAAAAT ACATCTGAAT CTGTGTCGTA TATCATCACC 80400
80401 TAGAGCTGAC CACCATCTAG TTTCAGCAAA ATCCTAGTGA TTCCACCAGA CAAGAAAGAT 80460
80461 TGCCTCACTG GGAGACAGTT GCTGATTCCT GTTGCCCTTC ACTGGTCTAC TTTGATAATT 80520
80521 GGCATATGCC TTTCCTGCGG CATTTTATCA CATAAAGCTT TGCTGTTTTT ATCTGTGTTC 80580
80581 ATGTCTTTCT CTCTAGATGT ATCATTAAAG GCAAAAACAA TATTCATTTA GTGTTCTTCT 80640
80641 TACCTGTCCT TCTCTCCCCA ATACTGGAAT CCTAACACCA TGCATTGCAC TTTTTTGGTG 80700
80701 TTCAGGGTTC TAGGAAAGCT GGTAAATGGA TGAATCATAA ATGTAATTTG GGCAATTTT 80760
80761 TTCACAAAAT GTGTCACCTA TCTTTGTCTT TTCTCTGCCC ACTCATACTG GCTTTCTGTG 80820
80821 GCTTCTCCCC ATCTGTCTAG CATTTCTCTC TACCTCTGAA GAATATCAGT CTGGTGCAGC 80880
80881 CCTAGCACCT TCTTTGGACT CATTGTTAAA GATGTTGAGG AAGGCTAGCT CCAAGGTTTA 80940
80941 CCGTTTGCAT TTAGAGAACT GTCTTACCAT GCCTGGTTTC TTCAGCCCTG ATAAGACTAT 81000
81001 GCCATCTTCA CCCTCCCTTC CCCTGACCCT TCCTTAGCCA CCTCATCCAA CCTATGGCAA 81060
81061 CTCAACAAGA AAAGCTTACA AAGTCTTCCT TGGCAAAAGA GCTGGTTGAC TTGAGCCAAA 81120
81121 GGAAGCTAGG TGCAGTGTCC GATTCACTCC CCCAAATCCC CCTTGAAACT GGAGAATTGA 81180
81181 AAACAATCTG GTTTCTCTCT GGGTTCTTTC ATTATACCAT GTTTTCTTGC ATATAGACAG 81240
81241 AATAATGTGG TTGTTACAAT TATTTATAAA TGTAGTGTAT GCCAGGAACT GATCACTGTG 81300
81301 TGTAACGGAT ACACCATTAT TTTTCAAGGA AAAAAAATAT TTTGGGCTTT GATGATTACT 81360
81361 AGACAGATGT CCTTGGTGAT AATAATCACA GTAAGTCCCA ACTCTACCCA GTACTTCACA 81420
81421 ATTCTCTCAG TGCTTTCCTA CTTGTTGTCT CCTGTAATGA CGTATCATAT CCTGAATGGC 81480
81481 GGGAGGGCAA GGATCATTAG TCTCATTTTA CACATGCTCA TTCTGGGACT GGGAGAGAGA 81540
81541 TTTCCTGATT TGCCTAAACT GCCACAGTTT GTCAATGATG GTGGAGGGAT GGGGCAACA 81600
81601 CTGAACCTCC AGCTTCCTAA GACTTTCCCA CTTTCTCAAG CTTTTGTCGA ATGTGTCATT 81660
81661 AGTGGCATTC ACTTTGGTCA ACTTTGGTTC CTTGGGTATT GCTGGCTCCC CATTTTTTTG 81720
81721 GATTTAAACT CTTCAAATTA AATAAATCAG ATTTACATGT TAAAAGAAA AGTCTTCTCT 81780
```

Figure 1 - page 27

```
81781 AAAAGACTCC TTCATTTTTG TAAATCTTTG TAATAATTTC AACAGACCTT ACCTTAGAAT 81840
81841 TTCAGGCAAT AGGTACATAT CGTACACCTC TGTTAGTTCT TCCAGAGACT GGCGCAGGGG 81900
81901 TTGGAGATGG GAGGGAATAG ATGGGGGAAG GAATGTGGAG CAGGGGCCTG GACTCCAGTC 81960
81961 CAAGCTCTGC TGAAGGAGGG CCTTTTCCAA AGTGGATCCT CCTGAAGGCA GAGGCTCTTC 82020
82021 TAGAACACAT AAATGTGCAG CATTGGCTAG TAGGAGTCCT GCTGGAACGA GGCTGAGGCA 82080
82081 CATACAGGAT AGTTTATAGG AGAGTCAAGT CTCATGCATT AAAATTAAAC AAGCACTTGG 82140
82141 GCTTTGTTGG AATAAAGATA TGCTAGAAAT GTCACCAAGG ATATATACCA AATGCCAAAT 82200
82201 GTAGTCATAT ACAATGAAGG AGAGCAATGG TAGGAGAGGT GTCGGCAGGC TGGAGAGAAC 82260
82261 AACAAGTGCT GTGGGCTAGG AACTGTGATT TGGAAGTGTG CAACCCAAAC TAAAAGGAGA 82320
82321 GAAAATGGTT ACAGCCACTG GCAGCATCCC AGAGTCTTAC CTACTGCCTC CGGTCCTTTG 82380
82381 CAAGTAGGTA GGGTATAAAT ATAATGTTAT CTGCCCAGCA CAAAGGAGAG GGGAGAAAAG 82440
82441 AAAGCAAGAG GCAGTCAAAG GGACAGAGCC TAGTTCTGAG TCCTGTTTTA CCACTCAATC 82500
82501 CCTGGATGAC CTTGAGCAAG TTGCTTCTAT TCTGGACTTC ATTGGTAACA GCTAACTCAC 82560
82561 AGAGTCAATA TGAGGATTAA ATAAGACTAT TGGCTAAAAG GTGCTTAGAA TAGTGCCTAG 82620
82621 CACAGAGTAA GCACTTAATA AGTGTTAGCT ATTATTGTGA TAATACATGC ATAGAAGTAT 82680
82681 ATGCATGCAT GTACATTTAC CAGTATGTAC ACATTTGCAC ACACAAAATG CCCATTGTGA 82740
82741 TCTGCAAGTA GCACTAGGAT CCAAAAATTA AAAGTTATTA TGTTCCACAG GCCACCTTGA 82800
82801 AAAGTTAGGG GAAAAAAAAA ACTTGACCTT CATGTGTTGT TGCTGTTTTT AAGTGGCTCA 82860
82861 GCACTTTGAA ATAACATTTG GAGGAAAGCA TTGCAATGGA AGCAGCGCTG TGTGGGATTG 82920
82921 ATCCTGGAGA CCTGGGCTCA GGCGCTGGAG CACAATGTCC AGGAAGCCAA GGCCTGTTTG 82980
82981 GATTCCTTAC GCCATGACAT GGAGGCAAAG CTCCTCTTGG CTGCCAACCC AAGAGCCCAC 83040
83041 AGTCCTGTGA GCTTCACCCT TCCTAGGGCT GTTTGTGGTC TGGGCCCTCG AGGTTGTGGG 83100
83101 AGACCAGTTT GATTGCTAAG GGAAAATCCC AGAATGGCTC TTCTTGTCCT TACCGAATCA 83160
83161 CTACCCTTCA CCTTCCTGCG TCCTGCCCCA GCCTGGAGGG CCTACCTAGG CCTGCTATTA 83220
83221 CTTCCAACCC AGAAGTGTAG CGAATTGGGG CCATGACCAC AAGGTTTACA CTTGGTTACT 83280
83281 TGGTGGAATA TGAACTCTTG GGCAAGTTAC CTAATATTGC CAAGCCACAT CTGTAAAGTG 83340
83341 GATATGAGAA TAGAATCTAC TTCATGGGTC TGATTGTGAG GTTTAGATAT AATAAGGTGA 83400
83401 AGTTTGGCAC TCAATAAAAG GTAGCTGTGC TCATTCTTAC CAGCAGCAAC GAGGGCAGTA 83460
83461 TTGATGCTGC AGGCAGAGAG AAAGGGGGAG GCTGCTGCCT AAAGCACCCT TGCCACTCAC 83520
83521 ATGTAATTAG GTGACCATAC AATTTATTAT CCAAAAGGAG ACACTTAAGA TTGGAGGGGG 83580
83581 TGCAATTAAT AATGGTGCCA GGACAACAGG CATAAATTGG GACAGTCTTA GGCAGACTTG 83640
83641 CCCATGATTC CTTACCCACT GCCCACCCAT CATCTGACTA CACCTCTTTC TTCAAAGCAT 83700
83701 AGATCTCAGT GGGATATTTT TCTTCTTCCT GATCGCTTTG TTTTTTGAAG GGTATGATCG 83760
83761 CTTTGTTTTT GAAGGATATG ATTCTGCCAT TAACATTAGC TATCACTTAC TGAGGAGCAA 83820
83821 ACATGTGTTT GCCTTTGTGT TAGGTGTTTT ATGGAAATGA GCTCTAAAAT CCTTGCAGCA 83880
83881 ACCTTGGGAG GCAGGTGCTA CTTCCATTAC CCGGTTATAG AATGTGAGGC TTAGGGAGGT 83940
83941 TAAGTCACTT GCCCAGCCAA GGTTACAGGT CTATTAAATG GTATATTTGG TATTTGCCAC 84000
84001 TTGCCATTTT AACAGCATTT TATTGGCCTT TGCGGATCAG AATGTTTAGC GGTGACCCCA 84060
84061 GAATGACTTG TGCAGGACCC CCACTCCCAC CTCTCCCCTG CTACACTCAT GGGGTAGGTG 84120
84121 TCAGGGTGTA TATCTTCCTG TCATACATCC ACCAATTCCC CAATTCTCAG GTCATAGCAG 84180
84181 TGGGCTGAAT AACCATTGGC TGCCCTCAGA TTTCCGCAGA AATGGAAGCT TCTTAAATAT 84240
84241 AGGCTGTTAA ACCTGGTTTG AGTTTCTTTG TAAAAGGAAT CTTGTATAGT TTCCATAAGA 84300
84301 CCTAAAGATT GTACAGCTAA GCCTGCTGAA GAATTTGTCC TTATTTTTTC CATTTCAGAT 84360
84361 ATTCCCAAGG TTAGGTAGAG GGGGTGGTGT TGAAGAGCAG GCTCTCTAGA GCCAATGCTG 84420
84421 TTTATTAATA AGCTGTACAG ACACGCTTCT TCCAGGAATG TGCACTTGTG ATTCTGCTGT 84480
84481 GGTGATAAAG ATACTCTGCC TTGCCCATGA AGCATTGTT GGTGGAAAAC ATTACCTTTA 84540
84541 AATAAATGTC TGGTTCTATG TGAGCAAAGC TAGGGCTCCC ATAAAATTGG GCAATGATAC 84600
84601 TCTGAATTCA GCTGAACTGT TTGGGCAACT TTGTCACTTC TGGGGCCATC ATTTTCAGGA 84660
84661 TAGTTCCCAC AGTGTGAGAA AATGACTGCT TCCTATAGTA CTGTCAAGAG TGTGAAAAGA 84720
84721 GAGCTCTTTA GCAAACACAT TATTTATCCA TCCTTAAAAA GCTTGTCACC TCCAGGGTGC 84780
                                            (Placenta-Minor)I.2
84781 TTGTTCAGAA GTAATCTCAT TACTTAAATC ATATCCTAGC ATGTGGAAAA GCTCCCTGAG 84840
```

Figure 1 - page 28

```
84841  TTCCCCGCCT GCCCCACCTG CTGATTTCTC AGGACCGCTG ATAACAGCTT TCATGTGGAA  84900
84901  CTTGGGATTA ATATCAAGCA AGCCATGGAT TTTGTCTCGA CTGAACTTGG GCATCATGGA  84960
84961  CAGTTTCCAT TCCAGCAGTT AAGGGCTTCC TGACTTTCAA CAGTGGTGCT GATCCCAGTT  85020
85021  CTGAAGAGTG GAACATCAGA GAGCCTCCCC TCCTCAGCCA CTTGTAAGCA TAACAAACTG  85080
85081  AAAATGTAAT CTGCTTTCAA ATATTCTGTT GAGTAAAGAT TCCTTTTAAT TACTTTAACT  85140
85141  GGGTTTTTGT AGAGACAAGG GACCGTTCTC TGTTTCCCAT GTCATAAATG ACTTTAATGA  85200
85201  GAAATGGTGA ACACATCAAT TAGGGCAAGC CCACCTGCAC TGGGGCTACC CTCCCTTCAA  85260
85261  CTCCCCATAC CCTGTTGGGT AGAAACCATG TGGGAATTTA CTGATCAGCT GTTCCAGAGA  85320
85321  CCCTTAGAAC AAATAGCGTT TGCCCCCAAT TACTGAATAA TGCCTACATA ATTTGGAAAG  85380
85381  AGGGAGATTT CCTACTTTGG GTAAGAACAT TGCCTCCCTC ACCATCAGGG CCTTTGAACA  85440
85441  CACTGTTCTC TCTCCCTGGA ATAAGTCACT CCTTGGCCAT TTCTTCTCCT GGCAAACACT  85500
85501  CACTCACCCT TAAGACTCAG CTTAAGGGAG CCCATGACCC TGTTTGAGGT TCTGGAGGGT  85560
85561  TTTCTGTTAC ATCCTCCCAT AGGACCCCAC AGCTCCCTTC GATCCATCTC ATCTCATTTT  85620
85621  TCCTGTTAGC CAACTAACAG GAAATTTCAG CCACAAATGA GCACATATTA AGTAATCACT  85680
85681  GTGCATTTGA GGAATGCCAA CACCTTGAAA GGAAACCGCA AGTTGTAAAC AGAGTTTATA  85740
85741  CCTGAGGAGA CTTACTGATC ATTCAAAACA TTCAATATAT TCAAGTATAT ATTGAATTGT  85800
85801  TAGCATCAGA GACACAAACA GATATTGCAT CCATAAAAAC ATAAACAGAT AGTGGACATT  85860
85861  AATATTTTAG TTTTTGAAAT AAAAATGTGA ATGGACGACC CGAAAGGACA AACAGATGAC  85920
85921  AAACTGGATT GAGAGAGTCA ATCAAGGAAT TATCCCAGAA TGTAGCACAA AGAGAAAAGA  85980
85981  GATGAAAAAT ATGAGAAACC AGGCAAGAAA TATGAAGGAT GGATCCATGA GACTGAATGT  86040
86041  TTGTCTAATT GGTATTCTAA GAAGCAAAAA TGGCAAAAAT GGAGGGGGGT GGGGCCACAG  86100
86101  TCAAATATTA AGGAAGAACT GAAGACTGCT TGAAGTCTCA GAAGTAAAAA GTCACATACA  86160
86161  GATATCTCAC TGGGGCCAAT CCTTCAATCA ATCACTGAAG ATAGACTTAA TTTGGGAAGC  86220
86221  AGTCAAAGGT CATTTGCAAC CAAGTGTGGT AGAAAAGATG GATAATCAAA CCTAGTTCTT  86280
86281  GTCGACTATG AGACGTAAGT TAAATTAGAT GAAAATTTT AAATTATTT GCAAGGCTGA  86340
86341  TAATAGACTT CTGAAGATGC CTGGCCTCTG CTATCAGCAC CCACAGGCAG TTTAGCTAGT  86400
86401  TGAGTTTGCT CTGTTTTTCT CAAAACCTCC TTTACTTTCC TCGTATCACT GAATGGGAGG  86460
86461  TAATGAACAA ATTAGAAACT GGGGTCGACT AAGAGAGCAC TGCCTCTCCT GTATTGTCCC  86520
86521  TCATCAACTG CCTTTCTACT TATATTTCCA CAATAGATAT TATTGCTTCC TAACACAAAT  86580
86581  CTAGCCTCTT CATTTTGTT ATCCCCCAAC TGCTTTATGC ACTCCTACCT CCAGCATTGC  86640
86641  AAATACCTCT CCTCTACTTG CCATCAAAAT CTCAACCACA TTTCAAGGCC CAGAACAAGT  86700
86701  CCCATCATTC ACGTGAAGCC TCCTTTCGTC TGTATGCTAA TATCTCTTTG TACTTGTCAA  86760
86761  CAGTACCAAG CTTCTTAGTT TTCTCTCCCA ATAGTAGACT GCAGGCTTCC CTAGAGCTGA  86820
86821  GAGTGTGCCA ACATTTGCT TAATGATAAT TAGGAACTTC TCCAGGTACA TGTTACAATG  86880
86881  AAAATATCCC AGGAGGGAGA ACAAGTTGAA GGATTAGCCC CTGGATATGA ATTATTTTGA  86940
86941  TGAGGTAATA TCCTCTGACT GGGCAGAGGA TAGTAGGTGG ATAGAAAATG TGGGGAAATG  87000
87001  ACACATAAAA GGAAGTGTGG GTGGGAAGGG GCACTGGAGG CAAATGTTGA GAATCCCAAC  87060
87061  AAGTGTGTTC AGTGACCTCG TGGCTCTCAC ATGATCCCCT AATATAGCTG TGACAAGAGG  87120
87121  GATGTATTGG GAGCTACACG ACTACCCAC TCCCCAACCT GCTCCATGTT CTCAAGACAG  87180
87181  ATATAGTAAC CTTTTCAAAG GCATATAGCT CTTTAGGGAC CCCTGAGGGC ACAACTCCAG  87240
87241  TCCAAACTGT TCCTTCCAGC TACCCCAGGG ACTGTCCATT ATTATTTCTG CTCTTGCTGG  87300
87301  AGACTGAATC ATAATAAGTT TATTGAGGTT TTGCTATATG CTAGACACCT GATAAGGCCC  87360
87361  TAACAGGCTT TATCTCGTTT CTTCCTCCTA GTAACCACAT CAAGAAATAC CACTATTTCC  87420
87421  CCCATTTTTT TCTAATGAGG AAACTAAGGT AGAGATCTAG CAGTGGACAT AGTGATAGAG  87480
87481  GGTCCCCCTG GACACAGGAA TGTGAATGGT GTGGGGAGGA ATGCAGAAGC AGCTTTGAGT  87540
87541  TTCCCCAGCC AATTAGTTTC TCATTCTCTC TACCTGCAAT GCCCTTCCTC AGCTTGGTAT  87600
87601  CTTGCAGAGT AATGCTTTTC TTTCAAGACC TACTCATAAA GCCATAGGTG ACCTTCCTAG  87660
87661  GGTAGTCACT TTCTCCTCTC TTTTCATAGC TGTTTATGCC TCTGAACACT TGTGCAATCT  87720
87721  GTCTTCCCCA GATTAACTCC GTAAGAGCAA CAACCTCATT TCCCCATATT CCTACAGCCT  87780
87781  AGAGCCTAAA ACAGTGGCTA GTGGCTAGGA TATTGTAGAT TTACTCAGTG TTGGAGGTGA  87840
87841  AGACAGTGGC CTCCACAGGC GCACACTCCG TGTGCCCTCC ATGCACTGGA ACCCTCCTTG  87900
87901  GCAGAAACCT GGAGATTCCA TGAGCCTTGA TGCCCTCTTC AGGGCCACAG TGTGAGTCTG  87960
87961  TCAGTCTGAG GGCCCACAGA TGGGATATCA GGGTACCAAT TTTGCCCCTC ACTTTCCCCT  88020
```

Figure 1 - page 29

```
88021  TAAACGTTTC TCACTGATTC TGTGGACCGA AAAATGTAAC ACCCCATTAT CAACTGTAAT  88080
88081  TTGGGGTCTA GTTAAAATGA AAAATCTTCA AGAGAAATTG TATTCTCTTA TAACCTGGAA  88140
88141  ACAACTTTCT ATCAGTCAGT GAAGGTGGTT TTAATCAGGA AAGAGCCTCT GGGACATTGG  88200
88201  ACACCTGAGG CAGAAGGTTG AGAAAGGAAC TGGGCCCAGG AGTTGTTCAT TTGAGGTCTT  88260
88261  TGGATTGGGC TTTAGGGGGT CTGGGATCCC AGAATTGTAC TGAAACTTTG CATGTTGATT  88320
88321  CCCGAGTGTG TTTCTCCAGA GCAAGATTCC ACCACGTTCA CTGGATCCTT AGAATGGGTC  88380
88381  TGGGACTCTA AAAGAAATGA GAAGACTAG AGAAGTTGGC CAAAGTGGGC CACATGCACC  88440
88441  CCAGCCTCCC TGACGTCTCA GTGTATCTCT GCATACCTGG GCCTACAGGC ACCACTGGCT  88500
88501  GGCCTAAGAC AACGTGGAAG AAAAGAACCA AGGAAGGCGG CAGGGCAAAG GCACAGGGAA  88560
88561  GGGCTGGGGA GGGGCAGCTA AGACAAAGGG TAAGAATGCT GGGCAGCAGA CACAGAGATA  88620
88621  CAGAGATAAG AGGGGCCCTG TGGCTCAACC CCCTCATTTT ATAGATAAGG AAATGGACGT  88680
88681  CCAGAGAGGC TAGGTGGCCC CAGCACTCTG GGGTCAGCTA GGAGCTTCCT TGCCAGAGTG  88740
88741  TCCCTGCTCT AGGACATCTC TATGGCCTCA CAGTCTGTTC ATTAAACAAC AGATAAGCTC  88800
88801  TCAAGGAAAG GCCAGCAGTG CTGCTGCTAT CTGACTGTTT GGGTGGTAGC TATGGGCCAC  88860
88861  TGAGTTGCTG GGACTTGGCA TTTGGAATCA CTGCTAAGAT GTGCAGAAGG CAAACATCCC  88920
88921  TCTGAGGATA TGTGAATGTA TCATTCTTTG ATGACCCCAG GCCTAAAAGG CTTAAGAGGC  88980
88981  TAACCATTGG TTCACTTCAC TTCACAAACA TTTACTGAGC ACTTACTGGG TGTGAAGCAC  89040
89041  TTGTGGTAGC CCCCGGGAGC TAGATAGAAA AGCGAGGTGT GAGTCCTTGC TCTGGAGGAA  89100
89101  CTTATGTTGT GGAAATATTG ACAGACATTC CCTGTTCTG CCGTTACAAG AACTTATCAT  89160
89161  ATCCAGGTAG ATGCGCAGAA GGAAGCAAGG CCACTTGGGA CCGCAGTGTG ACAAATCTTG  89220
89221  GATGCCAAGA CTCAGGCATG GCTCTGGATC TCACCACAGA AAGAGGTTCA GGGGCCTCT  89280
89281  CTGGCTGGCG GCACCTGGGC TGCCCTAAGG ATTGTGTATC CACTTGGGGA CCTTCCGTCT  89340
89341  TTGCTACCAG AGGCAAGGAA TCCCACAACT CCATGTGCCA CAGAGACCTT AAAGCCGGAG  89400
89401  GAACGACAAA CACCACCACT GGCACTTGGC TCCGGAGGCT TCCCTTTCGC CCTCACCTCA  89460
89461  GTGTCCCGAG GCAGTTTCAG TGCTCCCCCT CAGCCCGGCC GTGGCAGGCC TGGGAAGTGA  89520
89521  ACAGGTCTCT GAGACTCGTA CTCAGCTCAT CTGGCCCCAA AGCCTGTTCT TGTGATGTGG  89580
89581  TCTCTGGGTC TTGTACTCAG CTCATCTGAC CCTAAAGCCT GCTCCTGTGC TGTTGTCACT  89640
89641  TCTGCCTTTT CCTTCCTCAG GTTAAAAGCC CAGTTTTGGC TGGAAAATTC CACTACCTTA  89700
89701  TCTACTCTGG GGCCAGGTAA CCTGTTAGGT CTTACAAAAT TGAATTGAAA AGTGAAGTCA  89760
89761  TGGGAAACCT CTTAGAAAAA TGACTGCTGT TCCTGGAACA ATCCCCAACT GGCCCTTTCT  89820
89821  GCCTCCTCCA TAAGGCGAGG TCAGACTCCT CGTGAGAAAA ACTATGGTTT GGGTGTCAGG  89880
89881  CAACCCCAAT GCAATAGGAT CTGGGGGATC AACCCCAATT CAATAGGCTC CCCAAATAGT  89940
89941  GCCCCACTT TGTCTCATGG CCTGAAATGC CTTAGATAAT CAAGAAGTCT TTTAAAACAG  90000
90001  TCATTTCTCA CTGTGTTTCA GAAAAACTTC TCTGGGAGAC TCTATCAGAT GCAGCCCACT  90060
90061  GGGAAGACAA TAGATTAGGT ATCTGAGGAA CCAGAAGCAC CATCAGACAG GCAAATAGGC  90120
90121  TAGCTGAGAT AAGGGCACTC TTGGACTACT ATTGCTTTTG ACTGCCAATG TTCCCAAGTC  90180
90181  CCAGGCTTGC TGGTAGTCAG CCAATAAGTC ATTGTGAAGA AAGGAGTGAT TCTACAAACC  90240
90241  CACATGGAGC ACCTCCTGGG GAGGTGTTGT GCTAGAAGTC ACGGAACCTC AGAGGTGAGT  90300
90301  GAGAAAGCCA CGGTCCTGCC TGATGGATGC CCAAGAGCCT TGGGTCTTCA CACACATGTG  90360
90361  AAATGTGGGT TTTAGCAGCA GGTACCTTTC ATACACCATC AATAGTCTTC CCTATGTGGG  90420
90421  TAAAACCCTA GGGGCTGAGG TCTCCCATTG GTGCCTTCAG GGCTTTTTGC TCATTCCACA  90480
90481  CAAATGGTCA GTCAGAACC ACAGCAGGGA TGGGAACTAT AGGGTGGACA AGGCATTTGC  90540
90541  CCTGAAGGTA GTCCACACCA TGTGTATCTA GCTCATTTT TCCTGTTGGT TCCTATTGTC  90600
90601  TTGCTCCTGC TCCAGAAGAA GAATGTCCCA GGGAATCACT GGAAGCTTGC TAGGAAGAAT  90660
90661  AACTGGAACC TCAAGTGTCA TGACCCCAGT GCCAGGGGAT GGAAATCATA TCACAGAATG  90720
90721  TGCACTTGGG TGAACCTTCC CTGCTTTTAA GTAACTATTG ACAAGTGACC TTCCCTGGAT  90780
90781  CTCATGTAAG TGGTTCATTT TTAAAGGAAG AGAACTGTAT TATTAGAAGA TCACAGCATT  90840
90841  TCTTTCCAGT CCTGATACTC TGTGTCTCCT TGATGTAGAA GTTCATGGGC AGCTCTACAT  90900
90901  GTCTTCCTAG AGAACTGTGA TTCTCATAAG ATGTCCTAGC TAGCAGCACC TTCAGTTTGC  90960
90961  TTGTCTTACT GCCTCCCGCG TCTAGAAAGA AAACTGAATG TCTGAATGTA GTACCCTGCT  91020
91021  CAGACAAGCT TCCTAATAAA TGTTTATTTA ATGAAACCCT CCAAGGCTCT GATTTATATA  91080
91081  GTGCCTTGGC AGTCAAAAGC AGTAGTAGTC CAAGACCCAT GTCGGAGAGA AAAAGAGGAG  91140
91141  GAGTATTTAT ACCAGGTAAG AGATGGCTCA GGCAAGGAGA AGAAGAAGCA GGCTTGTCTT  91200
```

Figure 1 - page 30

```
91201  GGGAAACCAG TGGGGCAGAA CTGGATGAGC AGGGAAACAT GGAGGAGGAA GAACTCAGCA  91260
91261  GGTAAGATGT TGTGGTAAAG CAGGAGTCAG ACTTTGAGTG GAGAGAACCA AGAAATAAGG  91320
91321  CTGGGTCAAG ATGAATTTGG GGTCGGACAT GGTGGCTCAC ACCTGTAATC CCAGCTCTTT  91380
91381  GGGAGGCCAT GGCAGGTGAA TCACCTGAGG TCAGGAGTTC GAGACCAGCT TGGCCAACAT  91440
91441  GATGATAACT CTGTCTCTAC TAAAAATACA AAAATTGGAC GGGCGTGGTA GTGGGTGCCT  91500
91501  GTAATCCCAG CTACTCGGGA GGCCGAGGCA GGAGAATCGT TGAACCTGG GAGGCGGAGG  91560
91561  TTGCAGTGAG TCAAGATCGC ATCACTGCAC TCCAGCACTC CAGCCTGGGT GACAGAGCAA  91620
91621  GACTCTGTCT AAAAAAAAAA AAAAAAGAT GAATTTGAAA GTCTTGTAGA CAACTGGAAG  91680
91681  CAAAGAAAGG TTTTTAGCAG AGGATTGACG TGATGTAAGC TGAGTCAAAA AGCAAATCTG  91740
91741  GCAGCAATGT GCAGAACAGA GTGAAAGAGA AGGTCTGAGA AGGAGGGTCT TGGAGAGTTT  91800
91801  ACAATGGGGA ATAAAAGCCG GACAAAGCTG GAGACAGTGC AAACTCAGGC AACAGGTTTG  91860
91861  TAACAAGCAC GTATGAAGGC CTGGACACTG TTCTAGAAGC GGAATACAGT TCTGAAAGAG  91920
91921  AGAGACACAG ATCCCTGTCC TTTGGGAATT CACCTTCTAG AAGGAGAGGA AACAGAGGGA  91980
91981  AGAATTTGAC TTTTCATGAA TTAATGCCTC ATTTTACTCT GTAAGAGGTG TGAGGAAATT  92040
92041  TACAAACATA CATCCACTCA GAATAATAAA AATAAGTGAT TTTACCTATT GTCTTTGACA  92100
92101  ACATCCTTTC ATTAGATAAA ATGGTGAGTT CCCTATGGCT GACATTACAA AGTCACTCAG  92160
92161  AGGTAGCTTA TGGCCTGGCA CCAAAGCATG GCTAGACAAA GGTAGTTGCA AAAAGAACAC  92220
92221  AAGTGACTAG CTCCCAGTGT GTAGCTCCGT GAAGGTTGTG ACAGTTGGTT CAGATACTAA  92280
92281  GTAATGGCGG CAAATGGGCT GGAGTCTCCA CTGGGCTCAT GGAGAGATGG TTTGTTTGGC  92340
92341  ATCATGCCTG GTCCTTTGAG AGGAGGGCTG TGCTGCAGTC CATTCCCCAC CCTCCACATT  92400
92401  CATGTCACCT GTGTTGCCCT TGAAGACACT AGAGCTTGGG ACTGCCAAGA GAGGATTGAG  92460
92461  GGTCCACCAG GAATTCTCAG TAGATTTTTC ACAACAGAGG CTTTTGAGAG CAATTAATCT  92520
92521  TAGAGAGTTT GAGGTAGGGT AATTTTTGGC AAAGAAGGAA GCCAGGAATT TGCCTTCAAC  92580
92581  TGACCACTGA GATATGCTTT GATCTTGAAT AGAGCAGAGG GTAGGGTAA GGCCCATTAT  92640
92641  AAAAATTAAC ATATAAGCCA GAAGATTAAA AAAATACAGG GACGTATCTT GAGATACAGG  92700
92701  GACACGACAT TATTAGGGAC TATGCCTAGA ACTTTGTGAC TGGATATGGT TAGGCTGGGA  92760
92761  TGGGAAGGGA TATGGTAGGA AAGTAAAGGG AAAAGGGAAG TACAAAACAC CAATATTTTG  92820
92821  AAGCTGGATG ATGGGGTAAT GATGTATAGA AAGGTTAGGA CTCGGATCAC TTGAGGTCAG  92880
92881  GAGTTCCAGA CTAGCCTGAC CAACATGGTG AAACCCATC CTCCCTACTA AAAATACAAA  92940
92941  AATTAACTGG GCATGGTGGT GCATACCTAT AATCCTAGCT ACTTGGGAAC TGAGGCAAGA  93000
93001  GAATCGCTGG AACCTGGGAG GAAGACGTTG CAGTGAGCTG AAATTGTGTC ACCACTGCAT  93060
93061  GCCAGCCTGG GCAACAGAGC AAGACTCTGT CTCAATAAAT AAATAAATAA ATAAAATAA  93120
93121  AAATAAAAAA GTAAGGACAG GGGAGAAGG TCAGGAGGAG GTTGACAGAT TGGGTTTTAG  93180
93181  ACGTAACTAT GGAGTAATGG TGAAATATCT GCATAGTGGA GTTCACTAGG CAGTCAGTGC  93240
93241  TTCAGACATG GAGAAGACAG AGGCAAGAAG GAATAGGGG GAGGTGCCTT CACAGAAGTA  93300
93301  AGAGCTTAAG AGAGGAAAAT AATGAGTTCT CAAAAGGAGA ATAAAGCAGA GAGGGCAAAC  93360
93361  GCTTTAGGCT GGAGAGATGC TCATGATCTC TCATGGGCAT GGGGGCTGAC GGAGGAATAA  93420
93421  GAACAGCTGT AGAGGAATAG AAACGATGAG AGAAGCCTGC CACAACCATC ACTGGAGAAC  93480
93481  AGATACAAGA AGGAGGAATG GCCAAATGGG TCCAACGCCA CAGAATGAGA TCAAGAACAA  93540
93541  ACATAGACAG GGAAGAGGTA CAGATCAGGC AGTAGTAAGG TCACGTGTCA GCTCTCAGAG  93600
93601  ACAGGTTTTG GTGCGATCAG GCAGAAGTCA GGAGATGAGG AAATGGATAG AGAAAAAAAT  93660
93661  GCATTTCTCC AGGAGCTGGG GTGTGAAAGA GGGATGGGCC AGGTTGCTG GAGAGAATAA  93720
93721  GAGGGAGTGC AAGCTTGGCA CCCAGCCCTC ACATCCAGGG TGGCTGGGTC TGTTTCCCTG  93780
93781  CTGGGCCAGT AGCCCCCACG CTAAAAGGAT TTAGCAGGGT CTGGTCATGC TAGGCAGAAG  93840
93841  TTCCACAAGG CCAGGGCCTG CCTCCCCTCC CTGTGGCAGG CTAGGGTTAG GGCTATAGCT  93900
93901  GTACTAGGGG ATCTGGGAGT CCTTCGTGGC ACTGTGGGAC CCTGAATGTG TTCAGACCCC  93960
93961  CAGGTCATCA GGACACCTGG GCTCTGCTGT GTCCCCAGAG GTTTTGCCC TGACTCAGGC  94020
94021  TGAGGACTTT GGGTGTAGGA CTCGCGTTTT CTTACGCAGA GGTTGGTGGG GCGTTGAATG  94080
94081  AAGTTGTTAG TAGGCTCCAC GTAGCACAGG CACACAGGCC TAGTGCATCA AGTGGCCAGA  94140
94141  GTCCCTGCTT GGTGCCAGGC CAACGTGGGA TGCTGAGCAG GCAGAGACCA CTCTGCAAAT  94200
94201  AACAATGGTG CGACCCAAGA AAATGACCCT GAGAGGGCAG TGGAGACCCA GGCATTTGAG  94260
94261  ACGGCCTGGC AAATGCATAG CACCTGAGGG CCATGTGCAT GTACATGTGT GTTTGGGGGT  94320
94321  GAGGGGAGGG TATTACTGGC CGAGGGGACA TGTAAACAAC CTCTGTGCAA GTTCTAGGAC  94380
```

Figure 1 - page 31

```
94381  CTTCCTATAT TCCTGTACCA CTATTTGAAG GCTTCTGTTT AACCTACCCA CGTGGCCCAT  94440
94441  TAGAATGTTC CACTGAACAG GAAAACCAAT GTGCATTCAG GAGAGAATCT CAAAGGACCT  94500
94501  TTCCAGCTGT GGCATTCAGA GGTCCATAAA GCTTAATCCT TTAAAAGGAA TCATTCTAAA  94560
94561  TAGCCCAGGA GTGAACATAA ATGAATGTGC AGTCCATGAA TGTGGGGACT AAATCCCATA  94620
94621  ATAGGGAGCA AAATGGCATG ATAAAGAGCA TGGGCTCTGG AGACAGACCA CCTAGGCCCC  94680
94681  AATTCCAGCT CTGTCACATA TGAGCTGGGT GCCCTAGGGC AAGCTGCTTA ACTGCCCCAG  94740
94741  GCCTCAGTTT CTCCATCTGT AAAATGGGGA TAATTAGACT TAGCTCTCAG GCTTGTCGTG  94800
94801  AAGATGAATG GCTTAATATT TCTAAAGTGC TTAGACCAAT ATCTGACACA TAGCACATGT  94860
94861  TTTCTAGGTG TTAAAAAATA TTCTTTTTGA TGGGGTTGTT TGTTTTTTTC TTGTAAATTT  94920
94921  GAGTTCATTG TAGATTCTGG ATATTAGCCC TTTGTCAGAT GAGTAGGTTG CAAAAATTTT  94980
94981  CTCCCATTTT GTAGGTTGCC TGTTCACTCT GATGGTAGTT TATTTTGCTG TGCAGAAGCT  95040
95041  CTTTAGTTTA ATTAGATCCC ATTTGTCAAT TTTGTCTTTT GTTGCCATTG CTTTTGGTGT  95100
95101  TTTAGACATG AAGTCCTTGC CCATGCAGAT GACGAGTTAG TGGGTGCAGC ACACCAGCAT  95160
95161  GGCACATGTA TACGTATGTA ACTAACCTGC ACAATGTGCA CATGTACCCT AAAACTTAAA  95220
95221  GTATAATAAT AAAATAAAA TAAACTAAAA TAAAATATAT TCTTACCCTG CTGGATTTTT  95280
95281  AAGTGATGCT CTTGTCGGGG ATCTTTATGA CATACTTTTG AGGAAGATGA GAAACGAGGC  95340
95341  TTCTTAACTC TGTTAAACAT TTTAGACACA CAAACAGTCC TCACTTTTCA TGGCAGTATG  95400
95401  GGGCTGTAAA AATGACCATG CAAGCTAAAA CCGTGCAAAG CAATCCTAAA AATCAAGAGA  95460
95461  AAAATTAAAA CTGTTCTGTG ACCTTTAAAA TTTGTTGTCA AAGCATTAGA AACTCTTACC  95520
95521  ATAGGTTATA AGTGTGTAGG GGAACAAACA AACAAAAATA GTAAATATT TTAGGACACA  95580
95581  GTAATTTGAA ACATTAGAAA CAATGCAACA TTTTAAGTGT TTTCTTTCTT TGTGAAAATA  95640
95641  AACTTACTAA CAGGTTTTTT AAAAGTGCTT GCCTTCTTCT CTTTGCATAA CTTACGATAC  95700
95701  TGAGGGAACA TCTTTTCTAT GCCAGTGAAT TGCCATAGTC CTTTATAAAT TTGCATCAGC  95760
95761  TTGCAACATC TTATCTCTTT GCTTTCAGTG TTGTGAAATA CCTCTGGAAG TTCCTATAAT  95820
95821  GTGAAGTTTT TTGCTGGGAT CACTTCCTGT GGGACATCTT CATCCTTTTT GTTGCAACCA  95880
95881  CTTTCCTCAT TTATGCTTTG AACAATGGTT TCAGGTTTCA TCAATATAAA TCGAAACTTC  95940
95941  AAGGGTCCCA ACTGTCAGAA AGTCACATAG AACTTACTCA GAATGATGTC AAATTCCACT  96000
96001  CTAGAAATTT AAAACCTCAC CCTGTTAAAA ATAGCTTGTC ATCAACAAAG GAACCAGATG  96060
96061  ATAACAGACA CAAGGCTGAC TTTTTAGTTT CGACTTATAT ATATTAAAAA AAAAACAACC  96120
96121  ACAAAACTGC TCAACATAAG CACAATGTGC TTTCAGGAGA GAATCTCAAA GGACCTTTCC  96180
96181  AGTGCATTTT CAGTGCCCTG CACCCAAGCA TTAATGATTA TTTAAATGGT AGAATAACAT  96240
96241  AAAATGATGA AACAACTGGA TAAATTCAAC TATGTTGTAA AAATTTTGTA GTTGACAGAA  96300
96301  ATCAGTCTTT GGACTTTAAG ATCTCATATA GATCAGAGGA GAAATATAAT GACATACTCC  96360
96361  TTAAGAATCT GATGAAAGTT ATGGCCTTTC TCCACTAGAA TGTGCCGATT ACAATATTTT  96420
96421  ATGCAGTGTT TCAAGGAATA CACAGAGCCC CCAATATCCA GTTAGAAGCC GTGGCTGTGA  96480
96481  ATCTAGAATT TTATTACAGG TGAAACCCAG CACAAGTCTG ATTGAGAGCC ATGCAAGTC   96540
96541  ACAGAAACTC TAGGCCCTGG CTAAGTAAAG GCAAACCTTG GAGTATGTCA TCTGCCACTG  96600
96601  AAAATGCATT TAATGATGAC TCACTCTTTC CTCACTTTAC AAGTTTGTTC AACCTACACC  96660
                      (Bone)I.6
96661  TCTTCAGCTA CAGACTACCT ACCATCCCTG AAACTCTGTT CTGAGAGTAA AGGGATTACA  96720
96721  AAACCTGGCT GAAAAGACAG ATTCAATGGC ATGTTGAAAA ACACAGCAGA ACCAGCACAT  96780
96781  CAGACTGTAA ATTGATTGTC TTGCACAGGA TGTTAGCTGC TCTTCGAATG AGGTTCCTGA  96840
96841  GTGGCACCTG AGCCTATTGC TGGTGGCATC CTATTCTGCC TGTTATCTCT TTGTTCCTCC  96900
96901  TTCCCCATTC CTTTCATTCT CTTCTCCCTT ATTCTTCCTC TGCAATTCTT TTTTTCCACA  96960
96961  CTACCGTTGG CCGGTCCCTA GGGATACTGT TTAATCTGGC CCATGGTACA AGAGATTTTA  97020
97021  GATCTTCATT GAAGTCACTA GAGATGGCCT GAGTGAGTCA CTTTGAATTC AATAGACAAA  97080
97081  CTGATGGAAG GCTCTGAGAA GACCTCAACG ATGCCCAAGA AATGTGTTCT TACTGTAGAA  97140
97141  ACTTACTATT TTGATCAAAA AAGTCATTTT GGTCAAAAAG GGGAGTGGG AGATTGCCTT  97200
97201  TTTGTTTTGA AATTGATTTG GCTTCAAGGG AAGAAGATTG CCTAAACAAA ACCTGCTGAT  97260
97261  GAAGTCACAA AATGACTCCA CCTCTGGAAT GAGCTTTATT TTCTTATAAT TTGGCAAGAA  97320
```

Figure 1 - page 32

```
           (Adipose/Breast Cancer)I.3
97321  ATTTGGCTTT CAATTGGGAA TGCACGTCAC TCTACCCACT CAAGGGCAAG ATGATAAGGT  97380
97381  TCTATCAGAC CAAGCGTCTA AAGGAACCTG AGACTCTACC AAGGTCAGAA ATGCTGCAAT  97440
97441  TCAAGCCAAA AGATCTTTCT TGGGCTTCCT TGTTTTGACT TGTAACCATA AATTAGTCTT  97500
97501  GCCTAAATGT CTGATCACAT TATAAAACAG TAAGTGAATC TGTACTGTAC AGCACCCTCT  97560

(Ovary/Breast Cancer/Endometriosis)PII
97561  GAAGCAACAG GAGCTATAGA TGAACGTTTT AGGGGATTCT GTAATTTTTC TGTCCCTTTG  97620
97621  ATTTCCACAG GACTCTAAAT TGCCCCCTCT GAGGTCAAGG AACACAAGAT GGTTTTGGAA  97680 splice acceptor site                                M  V  L  E
97681  ATGCTGAACC CGATACATTA TAACATCACG AGCATCGTGC CTGAAGCCAT GCCTGCTGCC  97740
        M  L  N     P  I  H  Y     N  I  T     S  I  V     P  E  A  M     P  A  A 97741  ACCATGCCAG TCCTGCTCCT CACTGGCCTT TTTCTCGTGG TGGGAATTA TGAGGGCACA   97800
        T  M  P     V  L  L  L     T  G  L     F  L  L     V  W  N  Y     E  G  T 97801  TCCTCAATAC CAGGTAAGTC AGTCATTTAT TTCTGTATCT AAGGAGATTA TTTACTTGGG  97860
        S  S  I     P 97861  ATTTTGGTCC ATGATGGTAA AGAAAATTTT GCAAAAGGAC AAAAAGCAAA CCTGGAAAGA  97920
97921  TCTCTGAAGA CTATGTCTGT GTTAGCAAAT GAGGACTTGG GAGAAAATTT TCAGACCAAT  97980
97981  TATCTGCACA TTTTAAATGA AAGCACTTAA AAAATATCTT AGATAAACCC TTCCACTCTG  98040
98041  TGCTGTGCTT TCGTAAAGTA GACTTGGCAC AAGTACCCTT TAAAACAAGC TCAAGATGGG  98100
98101  GTGGAGTAAA GTAAAATTCC AGGGTTTTCT GGTTAACTTT TAAAAAATAG ATTGCAATTT  98160
98161  TGCTCTGAAG GTGAAAATGT CTCTGGAACA TCTTCTTCAC TGCTTTTCTT CTCCCTTTCA  98220
98221  CTTTGTTTCC GCCATGCCCC CTCTTTGTCT TGTATTTATC CCTTCTCTTT ATTCCACTCA  98280
98281  TCATTTTCTC TTATTCTTGG GAATGTGGTG ATAGTGGTCC CCATTTTTCT CCCACTGTCT  98340
98341  GGATCCCATT CGACCCTTAT GGGGACCTGG TAGTGGGAGA AAAATGGGGA CCACTCCAGT  98400
98401  GCTCTTGAAA CATCATACCC CGGGAGAATC TTCAACAAGA TCTGTGGTTC AATCAAAAGC  98460
98461  AGAGAATAAT ATAATTATTC AGATAATCCC AATAGAAAAC CCCACCCTTC CACCCTTAAA  98520
98521  GCCGCAATGA TCAGATATCA GATTAATTCA GAATGACTTG AAATTTCAGA CTGCTTCTTT  98580
98581  AGGTTTCAGT GAAAATGCTT CATTGCAGAC ACATCTGTTC CCAATTCCAT AAGATATCCA  98640
98641  ATGAGACTTT AAGAGCATAG TTACACACTG GTAAGTGTGG TGGGCCTAGT CTCAGTGGGA  98700
98701  TCAGAAGTGG GAGCATGGGG CTAGCACAAA ATGCTCTGTG TCTGGATTCT TTTTAACATT  98760
98761  CCAGATAATT GCCTGTCTCT CTGCCTGATT CAGCCTGATA TTTTAGATTA CTTTAATGCC  98820
98821  CAGTTTAAAG GAACATTTAG TTAATTTTGT TCTCTGCTCC CTGACAGGGT CAACTCTAGA  98880
98881  GAAGGGAGGC TCAGAGCTAA GGGACAACTG TTTCATGGTC TTTAACTTGA ACTCTGTTCC  98940
98941  CCAGTGTGGC CCTTCCTCAC TGGATTTCTC CTCTCCCAAG GGGGCTTCTA GGTCAGGGTC  99000
99001  AGTGAATGGT CGGGGTGGGG TGAGTAAGTG GTGGGGGTGG AGAGCCTTTT TTTCCTCTTC  99060
99061  TTCCCTTCAT AGGCTCAGGT GCTAAATTCC AATTTGTCTG TGTTAGCAGA CAATCAGGCC  99120
99121  AGGAGAGTCC AGCATTGCCC ACGCAGCATT GCCCATCCAG TGAGCCACAG GTTCTCAAGC  99180
99181  TTTTAAGTCT ATGTAAGAAC ACCCAGCAGG TAGGAGCTTG TTAACATTTC TGTTCCTGGA  99240
99241  CCCTGCTCCT GACTTTTTGA CTCAGACTCT TCAGGCCTAG AAACATGCAT TTTTAAAAAG  99300
99301  TCCCCGCAGA TGCTTATGTT AATCAGCACT GGTGGAATTT CCTTGGACCC TTGACCAAGG  99360
99361  AGGTCAGCCT GTTAGGACAA GCCTGAGAAC CAGCAGCCCT GAAGCTCTGG ATCAGTGGGA  99420
99421  GAGTAGGCAG CACCTCACTC TGTCCACCAT TTCTGGGCCA GGGCCATCAT GCTGATCCAC  99480
99481  TGACAGTCAG ATCAAGTAGC ACAGTGATTC TCAGCACTGT CTGAGGTAGG AGCTCAGCTA  99540
99541  GTTTGGGGTT GCTATTTTTA AAAAAATCTC CCTTCCTGAT TTTTTATGAG CAGCCAAGGT  99600
99601  TGAGAGCCAC AAATATGAGC CTAACTCCTT CATTTGACAG AAGGGGAAAC TGAGACCCAG  99660
99661  GGAGTTGATC TGCCTTGCCC AGACAAAACA CTATGACAAG CATGAGAAGC CATGGAGTTC  99720
99721  AAACTTGTCG TTTTACAAGT GAATGGTTAA AGCCCAGTGA AGGGAAATGG CTTGTCATCT  99780
99781  CCCCAGCTGG ACAGAAAGTG GGAATGTAGG GGGACCACCA GGAAGTCCTA AAGCCCAGGT  99840
```

Figure 1 - page 33

```
 99841  TGATGATCAT TTTGCTAGAC AGGTAGTTTC TAGTTTCACA CTTTCCTTTT GAAAACAGAA  99900
 99901  GGTCTAGTTA GAATCCACTA GTAGCACAGA CTGTGAGATC CTATGGTTTC TGGTTGGGGG  99960
 99961  AGGGAAGATA AGAAAATTGG CCTTGTTTGG GGTGGCTTTT GCTGATCAAT ACTCCTGAGC 100020
100021  TCCTGCCAGC TCCCTTTAAT CAGTGGCTCT CTAGGTTCTT GGTTTTAGAG GTTTAGGGGA 100080
100081  AGCACAGAGT CAGGAAAGCT CAGGAACAGT GAAAGCTGGA GGGACTTATA ATGATTTAAA 100140
100141  GCCCTTAAGT GAGTTATAAT TTACAAAGCA GTTTCGTGCC CATTTTCTCT GGTGAGGTTG 100200
100201  GTGTGTTTGT GTCTGTTTTG TAGTTGGCAA AACTGAGACT CAAAGAGTCA CACAACTAGT 100260
100261  AATGATGAAA CTGGGCTCA TATCTAAGCT TCTTCTAGCC GTATTTACTG CTAAGTAAAC 100320
100321  AGGCTGCCCT GTTTTCCTGC TTAGGGGCAG GAGGATGTGT GAAAAGATTA AGAGATGTG 100380
100381  GTTTCTGCCC CGAGGGGATT ATATAAAAGT AGTAAAGACA GTCAAGGAAA CACACATAGG 100440
100441  TGGTTGACTT AGTGCCAGGT AGGGGCTATG AAAGTCCTGA GGAAAGGGTC ATTCTGCGGA 100500
100501  GAAGGGGGAG TGGCCGGGGG AGGGGGGCGG GGTTGGAAGC TTCAGTTCTG AAAAATTGCT 100560
100561  CCCAGACCAC TGATCTGGGT CAGGACTCAC AGTCACCTGG CACTGGCTGC TCTCCCTTCC 100620
100621  CCCAGGACGT ATAGCCATCC CCAGCTCTAA ACAAGGGTCC TCTCCCTCCA GATGCCATGC 100680
100681  TCTGCCCGGG GTACCACATC CCAGAGCAGG GAACTAGGGG GGAGAAAAGC ATGGCAACTG 100740
100741  ACATTCCTCT TTTTCTTAAG ATAATATTTC ACAGAAAACT GGACAGTGCG GTGACAAATT 100800
100801  TGCCATCACA ATGCAGCCTG ACAAAGCGGA TGTTACCCTT GTTCCAGAAG CTCCTCGTGT 100860
100861  GCCTTTGTAA TCACTCTCTC TCTCTCACTC CAGAGCAAAA CACTGTCTTT GATTTTGTGA 100920
100921  CAGTCACTCC CTTGCTTTTT TTTTTATCA TTTTACCACA TAATTTCACA TCCCAGAGAA 100980
100981  TACAGGTTAA TTTTGCCTTG TTTTAAAGGT TTAGCAGTC AATTCATACA TTATGTATTC 101040
101041  TTCTATCTTG CTTCTTTTGC TCAATAGTAT GTTTCTAAGA TCCATCCACA TCGTGGCATG 101100
101101  CAGGTGTAGT TCATTTTCAT TGCCATAGGG TATTGAGTTA TATAAATATC TCATGGTTTA 101160
101161  ATTGCCAGTT CCACTGTTGA GGGACACTTG AGGTGTCTTT AGTTTGGGGC TATTGTGAAC 101220
101221  AGGGCTGTTC TGAATGTATA TGTGCACACA GGTTTCTCTA TGGTGTACAT CTGTAAGGCG 101280
101281  TGGAAAGCAA CAGCTTGTTG ATTAGGACAG CTGGGGAGAG GTCCCAGCTG TTGGCTCCAA 101340
101341  GGAGGCTGTC TCTGTACAAA AATGCAGCAA AGTATTCACT GCTTCTTTTA GGGTGTGAAA 101400
101401  GAGGCTCCCA CCATCATTGC ATGCCTAGAT AAGCATTCCC AAATCTGAGA AGCAACGATC 101460
101461  AGCTTAATGT GGCTACAACC AGAATATTTC CCTAATATTT TGCCAAAGTT TCTACCTTCC 101520
101521  TCCAGCATTC TTCTCTCCAG CTGGAGGGTG GGTAGAAGGC CTAAGATATA CACGTAAATG 101580
101581  AAAAGGTCAC ACTGTGTTAA CATTCTTTTA TTTAGTAATT ATTTTTCACA TACTCTCCTC 101640
101641  TCTTGCCCCT AGACTCTGAT GGGGACATT ATACTTATAA CATCTCCAGT CCCTAATTTT 101700
101701  AGTGTCTATA CCAGTAGTAT CTATACCAGT AATTGTTTGT TGGATGAATT AAGCTGATAT 101760
101761  ACAATTGATC GCTAGGGACT CAAAACTCTG GTTCTCTTCT GGTTAGAACA CTCAGGTTCT 101820
101821  TAATCTAAGC ACAAGGTTCA ATCTCCCTTT TTCAGTAGAT ATATCTCTCC TGCGTCACAG 101880
101881  CTTACATTTG AATGGCAGGT CCCAAATATT AAGATTTTTA CATGGCGGGC TGGGTGTGGT 101940
101941  GGCACAAGCC TGTAATCCCA GCTACTCGGG AGGCTGAGGC AAAAGAATCG CTTGAACCCG 102000
102001  GGAGGTGGAG GCTGCAGTGA GCCGAGATCA TGTCCCTGCA CTACAGCCTG GGCAACAGAG 102060
102061  CGAGACTCTG TCTCAAAAAA AAGGATGGCA TTTAAAACTT CATCCTTTAT ATTAGATACA 102120
102121  CATGCCTAAT TAATTTTTAA AATTTATTCA GGAAACATTC GTTGAGCATC ACAATGTGC 102180
102181  CAAGCTATAA ATATCCAGTG AGATATTATA TTATGCATAT ATTAATTGAT TAAAAGTTAA 102240
102241  TATATCTAAT GACAGTTTAA GGAAATACAT ATTCAATCAA ATCTGCTGTG GAAATCTTTT 102300
102301  AAAGAGCTTA ATGAAATTAT TTTAATACAA AGTCAGTCAT CTACTGTATA ATGTAGTGTT 102360
102361  ACTAAAATAA TCACAAGATT AATAACCTTA GACCATATTT TGGTTCTGTA GGTATTAGCA 102420
102421  AAGATCTTTT ATTTAAAGGG AAAAAAGAGC TGACAGTCTT GCTCATATTA ACTCAGCTAT 102480
102481  TACAAAGTAA AAGACTAAAC ACTGTTTGCT GTGTTTGGGA TTAAACATCC AATTCAGATG 102540
102541  ATTCAAGCAA AAGCTTACAC TATGTATATT ATTACACAAC TTTTGCCCGT AAGGTGAGAA 102600
102601  TGCTGTTTCA CGTAGTTAGG CATGTTTTGG CTTCAGAATG ATTTCACTGA CAGAATGGAA 102660
102661  TTAAAGGAGA AGATTTAGA AAAACTGCTA CTTGTCAACT CCTGAAAACA TTCTAAAACT 102720
102721  TTTTAATCTA ACGTTTTACC AACACCAGTA AAATCAAGCT ACCAAGGTTG TTCTCTGATA 102780
102781  TAAGCAGCAC CAAATTCCCC AGTTGTTCCC TGGACGCATG TTCTTTACAA TTCTGCCATC 102840
102841  CTCTGCATAA GCAAGATTGT AAGCAGCCAC TACTCTCGGC TAAAACCAGA TCATGGGACT 102900
102901  CAAACTCCAA TCTAGAGGTT CAAAGACCCA TTGCCTGACT CCCCATCTCT TAGCTTTATT 102960
102961  TTGCCTAATG AGATTTAGCT TAAGAGCCTT TTCTTAAACG GAGTCTTTTT TGAGGGTAAC 103020
```

Figure 1 - page 34

```
103021 AAAAGAAATA GATGTTCTTG GATTGGACAT TCTCCTTGTA GATCTTGTTT CTTTCAGTTG 103080
103081 AAAGATTTCC TACAAAACTA CAGACCAGTT TTAACCCACC CATTGTGTCA ACCGGGCAC  103140
103141 TCAAACCAAA AGTTTCCAGA AAAAACTAGG CGCCAAACAG ATCTGCCAGA TTGTCACTCA 103200
103201 TCAGTGTTTC CATGTTTGCT ACCAAATGCA CCAATTGACT TGTATTAGAA ACTCACTGAT 103260
103261 ACCAGTTAAC CTGGGAAGAA ATTAGCACAC ACACCCAGT TCATTCAGAC TGAAATGATT   103320
103321 GAGACCAAAT AAAACTAGTG TGGTATGGAT ACTGAACTCC TTTTTACTCA TGGAGAAGTG 103380
103381 AAGAGCCTCA TGTTAAGCGT GAGGCTTTTG TTTTGTTTTG TTTTGTTTCA AATCACTTTA 103440
103441 TTCGTGATTC ACAGATATAC ATCACATGTA AAGAACACTT AGCTATAAAA GAACAAAAAC 103500
103501 AGGAGTAACA CAAAACAGTT GCAATTTTTG GTGTAACTAA GATGTTGCTT ATGCTCTGAC 103560
103561 ACCTGTCCTA GGTCCTGGCT ACTGCATGGG AATTGGACCC CTCATCTCCC AGGGCAGATT 103620
                    G   P   G    Y   C   M   G    I   G   P    L   I   S    H   G   R   F

103621 CCTGTGGATG GGGATCGGCA GTGCCTGCAA CTACTACAAC CGGGTGTATG GAGAATTCAT 103680
       L   W   M    G   I   G    S   A   C   N    Y   Y   N    R   V   Y    G   E   F   M

103681 GCGAGTCTGG ATCTCTGGAG AGGAAACACT CATTATCAGC AAGTGAGTCT GTTCATAATC 103740
       R   V   W    I   S   G    E   E   T   L    I   I   S    K

103741 GAAGACATAC TTTTTAAATC GAGGCTGGAG TTTTTTCCAC TTAAGACAAC TTTATTTTGA 103800
103801 ATCTTGATGT CTTTGTTTCT AACGCTATAT TTTACCACT GAAATGAAGT GAGCAATCCC   103860
103861 CAGAAATCTA ACATTGCAAA CAGAATAATT GGGTTTTGCT TGAATTGAAG CCAGCAGTAC 103920
103921 ATAAATAACT AACTCTGGAA AGTTGGGAAA TTATTTACAA TCTCTGTGAG CAGTGAATGT 103980
103981 GGAAACTTAG AAGCCAGATA ATTTGATTTT GACAAAACAT ACTTTAGGGA GAGGTGTTAT 104040
104041 CTTTTCTGCT TTCCCAAGTT TTTTGGTCTT AACCACAAAT AAACATTAAA AAGAACCAAG 104100
104101 CCAAACAAAC AAAGAAAAAA CCCACAGAAA ACAAAAATAA AACCCGAGAC ATCACTGCAC 104160
104161 TATAGTCTGG GTGACAGAGT AAGACCCTGT CTTTTAAAAA ATAAAACAAA CCTGAGGCAG 104220
104221 AGGTATCTGA TTAGCAATTT GCTAATTTAT TCTCCTGCCA AGCAACTGAG CACCTCTAAA 104280
104281 AGAGCAGATG GTAAGCCGAC CTTGGCTGAA TCCGATTAAA GTAAAGAAAA AGGAAAATAA 104340
104341 AAGAACAAGA CAGTAGAAAA AGAAGTAATT CACATGCTGC TTTCCCATTT ATGACTTTAT 104400
104401 GCGAGTATCC CGGTGGAGTG ATCTTACATA AATCAGGAAC AATATTACCC ATTTAAAAAA 104460
104461 ATAGTGTCCT CCCTCTCTGC ATTATTATAT TTTGTGGATA ACTAGCAGAT TGAATTAGCT 104520
104521 CTATGGTTAA CTAAATAGGA ATTGACTATA AGGAACTAGT TTGGTGAAAT ACTTGTTTTC 104580
104581 TTGTTTATTG ATCTTAGAAA ATGGAGAATT TCAAAGATGG CGTATTTCCC TAGACTTTCA 104640
104641 GCCAGCTTTA GTAGACTTTT AGCAAAGCTA TCTGCAAACA TTGTCTCATT AACGCATGTT 104700
104701 TATATTCGTA ATCCCTGATA GCGCTTTACC CACAAACTAA AGCTGACCAG GGTGTTTTAC 104760
104761 CAATTTGTTA GAATTATTCA TTCAGATACA AAGACTATAG CTCAAAAGTA AGTGAAGCTT 104820
104821 TTCTAAACTA CATAATTTTT TCAGGTCAAG ATTACATACA TCATCTCATA AAATACCACG 104880
104881 GTATCCTCAA AGCCCAAATA TTTGAAGCAG ATATTGAAAG AAGGGAGCAG GGGAGAAATT 104940
104941 GGTATTATTT TAATACTTCT AAATATTTCA AACTATCCAA AAAGAATTTT TTTGACCTGG 105000
105001 GATTTTTGTT TGTTTGTTTC ATTCAGTTTT GTGTTGTAGC ACTTTTAAGA GTAGCTGAGG 105060
105061 CAGACCTCAC ACAACTAAAC AGAAATGCT TCAGGTGGAA ACATCATTTC ATTGGGTTCA   105120
105121 TTGTGAAGTA CTCTAATGCA GTAGTTTCA AAGTGTGGTC CTTCAACAAG CAGCATCAAC   105180
105181 AAGCCTGGGA ACTTGTTAGC AATGCACGTT CTTGGGCCCC ACCCTGACCT ACTAAATGAG 105240
105241 ACAGTCTGGG GTAGGACCCG CGATCCGTGT TTTAACAAAG CCTGCAGGTG ATTCTGCTGC 105300
105301 ACACTTGAGT TTGAGAACCA CTGCTCTAAG AACTAGATCA TAATTACTTT TTATTTTAA   105360
105361 TTCTCCTGGT CTATTAGGCT CTAGTCAGCC AAATTTAAGT GACTATGATA CGTTCTTGAT 105420
105421 ACGTTCTCAT TTTAAAAATC AGTACTTGAG TCACTTTTAC AACTGGCTAT GGTCTCACAA 105480
105481 ATATCCTGGA AGCACTGGTG TTTGGGTTTG GGGGTAGGGA CATTTGCCGC TGCTCTTTCA 105540
105541 TTTCCCCGCA CAGCCACCTG CCTTTCAGCT CTCCCCAGCC CAGGGTCTGC CTTCCCCATC 105600
105601 ACCTCTTTCC CTCAGCAGAC AGGTGAAGTG ACCCCCAGGA TATTTATCTA GAAGGATATC 105660
105661 TACCTGCTGC CCAGGATCTA GCACAGTGCC GTGCCTCTCA CCCTAGCTGT ACCTTAGAGT 105720
105721 CACCCAGGGA GCTTTCAAA GCCCCACTGC CAGGCCACA CCCCCACTTT TAGATCAGAA    105780
105781 CCTCTGGGGG TAGGACTCAG GCATCAGTGG TGTTTAATAC TCCCCTGGGA GTTTGAGAAC 105840
```

Figure 1 - page 35

```
105841 ATTCCATCTA GAGAGAGGGT GGAGGAGGAA GCTCATGGGG CAGGAGGGCC TCTCCCCGGG 105900
105901 GTTACAGGAA GCAGCGATGC AGGACTGGTT TTGTCTTATG CTAAGGTGGT GGAGGTTTAA 105960
105961 GACTAGAACT GGAGTAAAGA ATGATAGACT TGAGAAAGGA CCACAGTACC AGGACAGAAA 106020
106021 TCATTCTGAG ATACTAGATA TTTCGATGCT AGATTCTTAA ATCTCCAGAA AAAGTCCGTG 106080
106081 AATTTCCAAA GACAATTCCT GAAGTGCTTG CTCGTTACAG TGGGGGTGGC ATCTGACCAC 106140
106141 TCCGCTAGTC TTAATTAGGA AACTGACTCC AACAACCCCG ACCGACTCAG GCGCTGGTGC 106200
106201 ACGCTGAGAC GCAGCCACAA CCCACCCACA CTACCATCAG CTCTCCCAGT TCTTTCCTTT 106260
106261 TCCTGTCCTC TCAGGCTTTT CACTTGTTGG AGTCTTTGTG TTCTCTTTAA TTGCCTCAGA 106320
106321 GCAGTTCAAT TTTGTTGTTA AAGGCTGAGC TCCCCGCGGG AATAGGACAT GTTTGTCCCC 106380
106381 ATCTCCTTTC CTTGCCTGCT CTTCAAGTCC CTTCCAGCAC TCCCCGTACC TCTTGAAAAG 106440
106441 ACCCCATTGG ACCTCAGAAA GATTTTTATT TTTATTTGAA TAGTTTGCCA GATTTTTTTT 106500
106501 TTCTTTTGAA AAGTTTGAGG TCTGTAGTCA TTACAACTGT GTAGAAATTA TGGTCCAACT 106560
106561 TTTCCAACCA GCTTCGTCCC AAAGTAGTAG GGGCTGCAGA ACTTCAGGGG AGAAGTCAGG 106620
106621 CATGTGCGCT GCTGAGATGC CGCGTGTGCC ACTGGGGGCG TGGAGGCACG GTCCATCTGG 106680
106681 TGAGCTGTAG ATGATGTGTG CACCGTTCCC CAGGCAGCTA CCCAGGCAGC TGTACTCTAA 106740
106741 ATTAATGAAG GTCTGTAGGT GCTGCGTATG ACACTATATG TCCATTATAT GTCCCTAGAT 106800
106801 TAGTTTTTGT CATGAATACA AAAAAAATTT ATGTATCACT CATAAAGGGA AATTAGCAAT 106860
106861 TAGCATGCTA ATTTGGGTTA TATTTGCATA TCTGTTAGCA ATTAACATAC TAATTAGGGT 106920
106921 TATATTTTTA CATCTGTCTT AATAATGTGC AAATTTACAC ATCATTTACA GGGGCTTCCT 106980
106981 TCATTTATTC TGTGAATATA CATTTACTGA GAATTTATTA TATACTAAGC ACTGAATGAT 107040
107041 TCTAAGTTGT AATAGTCATT ATTGGCTCTT CATCCATTAA ATATTTCTTG AAAACTTACT 107100
107101 ATGTATAGCA GCAGGTATTG TTCTAAACTC TGGGAATACA GCAGTGGACA AACCAGCCAA 107160
107161 AATTCCTTTA CCTCATGGAG CAATATGTCG TCACTAGGTC AACAATAAAC AAGTAAAATA 107220
107221 TATAGTGTAT CAGTAGAGTG ACCAATTGTT TCAGTTTGCC TGGGACCAGG GCCTTTCCCA 107280
107281 GGATGTGGGA CTTTCAGTGC TGAAACTGGC ATAGTCCCGG GCAAACCAGG ATAGTTGGTC 107340
107341 ACACTTATCA GGCAGATAGG TGTTACATAG AAAAAGAATA GGGAAGGAGG ATGGGGGAGG 107400
107401 ACCAGTTGTA GAGACGCAGG TGTGATTGTA AACAGGTGGT TCAGGCAGCC CTCACTGAGA 107460
107461 AGACAGCATT TAAATAAAGA CCTAAAGGAA ATGAGCAAGT AGCCCATGCA GAGACCTGGC 107520
107521 GGGAAAGCAT TCTAGACAGA AGGAACAGCA AGTGCCAATA TTCTAAGGCA AGAACCTGAG 107580
107581 TGGAAGAATA CAGGAGATGA GAGAAGCAAT AGGGTACCAA ATCACGTCAG GCCTTGCAGG 107640
107641 CCATTGTAAC AATTCCGGCT TTTACCCCCT GCAAGAAAGG AAGCCACTGA AGAATTTGAG 107700
107701 AGAGGACTGA CACATATGAC TCATTTATGT TTCAGCAGAA TCATTCTGGC TGCTCTGTTG 107760
107761 AGAATAGGTG CAAGAGGACA AGGGATGGGG ACAGACAGAC CAGTTAGGCA AGAGGTGATG 107820
107821 GTGGCTGGTC CAGGTGGTAG CAGTAGAGAT GATAAGAGAT GAGGGAAAAT TCTGGACATA 107880
107881 TTTTGAAGGC AAAGCCAACA GACTTGCTGA CAGATTGGAT GTAGGGTGTG AGAGAAAAA 107940
107941 AAAGAGTCAA AGTGCTGTCC AGTTTTGCAT TGAATGGGGA CATCGTGTCC TGAGATAGGT 108000
108001 GGAGCAAGTT TGGGAAGGGG AGAGATTAGG GTTCCATTCC AGACATGTTA GATTTGACAT 108060
108061 GCCCAGTTGA CATCTGAGTG GGATGATTGA GTAGAGAGAA CTGAACCTTG AGACCCTCTA 108120
108121 GTGTAAATAG GTCAGAAACT AGCAACAGAG ACTGAGAAGA GCAGCTAGAC CGAGAAGAGA 108180
108181 AAACCAGGAA AGTGTAATGT CTGAAAACCA GGTGAAAAAT CCATATCAGG GAGTAGAAAA 108240
108241 TTGTGAACCA TGTCAAATAC CACTGATGGG GCAAGGGAAT GCATGAGAT TTCAGTACTG 108300
108301 CATTTAGCAA CAGGGAGGTC ACAGGTGACC TTGACAAGAG CAGTTCAAT GGACTAGTGG 108360
108361 GGGCAAAAGT CTGACCAGAG AAGAGAATCG GGGGAGAAGA ATCAGAGGCA GCAAGTGTAG 108420
108421 ACAAGTCTTC CAAGGAGTTT GCCATAAAGA AGGCAGGAAA TGGGCCAGTA GATGAGTGAG 108480
108481 ATGTGTGGGC AAAGGAATTT TGATTTTTAA AATAGGAGAA ATTACAGCAT GTGAGTTGTA 108540
108541 GGGGGACTGG TCAGTTATGG AGGAAAATCA AATGATTGTT GATGGAAGAG AAAGAGTGTG 108600
108601 CTAGGTGAGA TGTGAAGAGG TCCCTGGGGA CAAGTGGATG GGTTGGCCTT GAATAGGGAC 108660
108661 ATGGAATTTC CATAGTAATA GGAGGGAAGG TGGAATATAT GGGCACAGGT CCGGGTCGTT 108720
108721 GGGGATTGTG GAGATTCTCT TGTAGTTGCT TCCACTTTCT TGGGAAAATT GGAAATAAAG 108780
108781 TCTTCAGCTG GGGCTGAGTA GGGAGAATAT AATAGTCATC TAGAAGAGTG AGAGAGTGAA 108840
108841 TGGGCTGGGG ACATGCAGTA GCATTGCCAG CGACACTAAG GGCCCACTTG AATTTAACCG 108900
108901 AGACCTGACA GCAGGCACGT GTGCGCTAAC GTACACACAT GCGCACACAT GTGTGCGCAT 108960
108961 GTGTGGTTTT TCTTTTTTTC CCAGCCCACT TCAACTGCCA GGTGCAAGCA CAGAATAAGC 109020
```

Figure 1 - page 36

```
109021 TAAGAGTTGG ATTTAGCTAG AGTGTGGTCT TATCAGACAA CCATGACAAA GTAAGAAGAG 109080
109081 GGTCAAGGGA GTTGAGGATT CAGGGAAGGG TATTTTAATT TTAATGATTG ACAGTAATTT 109140
109141 TTTCCCAACT TTCTGTTAAG AAAATTGTCA AATGAGTAGG AAAATTGAAA GAGCCGTCCC 109200
109201 CCTGCCACAC TTTTCCCCCT GTGACATTGA CATTTTGAAG AGACCAGGTC AGCTATAACA 109260
109261 TATCCCACAT TCTGAATTTC TCTCACTGTT TCATCAGGGT GTCATTTACT ATATTCATCT 109320
109321 ATTCTCTGTA TTTCTTATAA ACTGAAAATT GGGTCTAAAG GCTCAATTAG ATTAAGGTTG 109380
109381 CACATTTTTG CAATAACACT TCAGTAGTAC TAGGAACTTC ATATCACATC ACATCAGAAG 109440
109441 ATGAGTAACA GGTTGTCCCA CTAGCACTGA TGTTAAATTT GATCACTGGT TAGGTGGTTA 109500
109501 CAGTGAGATT CCTCTGTTAT AAAGATTGTT TATCTCTTGT AGTCACCTAG AATTTAAGCT 109560
109561 GGGTAAGTGA GGATATTAGA GAAGTGAAGG ACAGTGAAAA GGTGATAGGA TTGATGGAAC 109620
109621 AGATCTACAT GAGGCAAGTG TTTTTAAATG TTTGTTACCA GCCGGGTGCA GTGGCTCACA 109680
109681 CCTGTAATGC CAGCACTTTG GGAGGTGAAA GTGGGTGTAT TACTTGAAGT CAAGAGTTTG 109740
109741 AGACCAGCCT GGCCAACATG GTGAAACCCT GTCTCTACTA AAATGCACA AAAATTAGC 109800
109801 CGGGTGTGGT GGCGGGTGCC TGTAATCCCA GCTACTCAGG GGGCTGTGGC ACGAGAATTG 109860
109861 CTTGAACCTG GGAGGTGGAG TTTGCAATTA GCTGAGATTG CGCCACTGCA CTCCAGCCTG 109920
109921 GGCGATAGAG TGAGACTCTG TCTCAAAAAA AAAAAAAAAA AAAGAAGGCA CCAATTAGTC 109980
109981 CATTAATTGC CTCCTCATCA CTGTTGAATC TGCCCACAAG TGTGTGAATT GTTTAATCCC 110040
110041 AGAACTCAGG TGGCTTTCTT CTCATCACCT AAGAGCTTAC TCCCTGACTA CTTTTCATTT 110100
110101 TGAACAGACA ATAGGTTTGC CATCTTTGGA GATGTCTTTT ATCTTCAATC ATGCTTAATG 110160
110161 AGGGATAATA ACCCTAGTGA TCAGACACCC AACGCTGTGC ACTGTCCCTG CTGAGGCTGG 110220
110221 GGACTCAGCT GGACTCTCCT CAGTGCTAAG AAATCCTCAC TCTCCCAAAT AATCAGTATA 110280
110281 ACACTTGCCT CTGGCAGTAT TGCAGGCTGG CCCACAAGCC AGAGCCAGGC CTGTCTTGAC 110340
110341 TGCCAGGAGG AGCTCTGGGC TGGGGTCCTT AGTTCATCAC TGACCTTCTC TTCACTTTTC 110400
110401 TGATTTACTC TGGTTAGATA AATCCAGCCT ACTTTTAGTA AGTGACCTTG TTTTAAATTG 110460
110461 CTCATCTGTG GCCAGTCACA CATCCCTTGC TTTATCACAT CGGCCTGATT AGCTTTGTCC 110520
110521 CTAACAAGCC TGAGCTTTGG ATTCAAAATA GCTGAGAAGT TGGTGCCCCC TAAAGGACAC 110580
110581 AAGAATTTTA AAGGTTGGCT CTTTATTACT AATAACTAGC AAATATTTCG TTGGGTTTGT 110640
110641 TTTATGTTTG GAGTTTCTTA CTCTCTTTTT AAAACTGATT AGCAAGTTCT TAAATGAAAT 110700
110701 GGACAGGCCA ATATGATTAA TGCAGTATGC AAAAGCCCCA GGGTCAGAGC AGAAAAATAG 110760
110761 TGTTTGTCCT TTAAGTGCTT AAAATTTTTA AATATTAGTT TGTGAATAAA GAATATATAA 110820
110821 ATTACTTAAT TTCTGCTTTA ATTATAGAAT GATGGAGGGG AAGGTAAGTA AAGCTAGAGT 110880
110881 TTTCAAATAT TTTAATTAGT AAGAATTTCA TTCCTTCCTA TAGCATAATT TTTCTATATA 110940
110941 TGACAAAATT TGAAACGTCA GACAAATTCC CCAGAATACA AATGGAAGCA TCTGGATTTT 111000
111001 TATTTATTTA TTTATTTATT TTTGCTAGGG AGAGGCAAAC ATGTCCAAAA CTTAGGATTA 111060
111061 TTTGATGAAT ATTATCTGGA ATCAGATCAA GAGAATATTT AATAGTGTTT TTATTTGAAA 111120
111121 ATAGGTGGTT TTTCCTGAAA TAAATATTAA TAAGTTATTT ATACAATAAC TCTGCTTTTT 111180
111181 TTTTTTTTTT TGAGATAGGA TCTTGCTCTG TCACCTAGGT TGGAGTGCAA TGGCTTGATC 111240
111241 ATGGCTCACT GCAGCCTCAA CCTCCAGGGC TCAGCTATC CTACTGCCTC AGCCCACCAA 111300
111301 GTAGTTGGGA CTACAGGCAC ACACTACCAC ACCTTATATA TTATATATTA TTATACAATA 111360
111361 ATAATCCTGT TCTAATTTCT TGACACTACC ATTATTTCAG GGGCTTACTT TTAAAGCTTA 111420
111421 AATAGGACTA TGGAACACAT CGCAGATGTG AGAGCTGGAT TAATACTTAG CCCACAACCT 111480
111481 AATACATTGA ACCAGAGCAG CGCTTTTTTG GTCTAGAGTC CTCTGGGAAT GTATTTCAAC 111540
111541 AGGCATTAAC TGAACAACCT CATTAAGGCA AAAGTATCCT TTTAGGAGCC AAGTGTCAAC 111600
111601 TAGGAGATGG AGGAGCAAGT CTCTCCAACC TGAGAACCAA TTGCAGATAT TATAGTAACC 111660
111661 ACTTGCAATC TTTGAGGGTT ATTTGTTCTG AAAACCTCCA TAGTGGGACA ATTTGCAGCT 111720
111721 GTGAAACAAA ATTTCAGGAG ACCAGAGGAG AGGGAGGACC AAAGTTGCAA TTAATACATG 111780
111781 AAATTTTGTA TAAATATTAA GTTCACCAAG AAAGTAACAA CAACATCTAA AATCAAGATA 111840
111841 ATACCAATGA CATCTAATGC ATCTTGAATT TGCATAATTG AGCATCATGC AAATTGCCCT 111900
111901 GTCTCATGAC TCATCACATC CTGTGTCGTG GGAGAACTCT GTGACCCTGG AGACTTTGAT 111960
111961 GAGTCATGAT GGAAGGCAGA GCCCCAAAAT AGCTTCCTTT ACTACCACAG TGAACTTTGC 112020
112021 ATGCCAGTCC AGCCAGGCGC TGGCCAAGCT CAGGGCTAGA GAAAGTGCCC AAGGAGATAT 112080
112081 TTTCAAGCC CTGACTGATA CTCCACTGGA GGGGCAGGC CTGATTAGAG ACTGGAGTTG 112140
112141 GGTGGTACTA GGCAAAACTG CTGGTTCCAA AATAGGAAAA CAAGACTTTA GTAATTCCAC 112200
```

Figure 1 - page 37

```
112201 AAACTTCTGA TTCTGTGGCT CACTCTTGTA GTGGGTGGCA CTTTGTGGAG TGAGGCTGGA 112260
112261 TGATACCTGG GAGGCTGGAG GTTCTTCTGG CTCTGGTGGT ATGGAGGGTT CAGCTTCTTA 112320
112321 GCAGCCTTGC AGCTCTGACT CCAGTAGTGG GTAGTATTTT GGTGAGGTTA GAGAAGAAAG 112380
112381 AGAAGTAAGG AATGGTATAT GGGTGTGTGT GTGTGTTTTC TATCTTTGGT GATGTTGAAA 112440
112441 CAGGGAGTCA GTAGGTAGAA ATGATTCAAC TGGAGAAGGA TGTCCTCATG CTAACAGAAG 112500
112501 TGCTTATTCA ACCCGAATAC TAGAAATCAT GCACATTGCA TTTGGAGCAA CATGCATTTG 112560
112561 CTAAGAGAGC TACCTCCTAG TCAAAATGTA CCACCAGGAG TTCTCCTGAC CCTTAAAAAT 112620
112621 TGACACCAAA GTTTCCTGTC TTTTCAGGTC CTCAAGTATG TTCCACATAA TGAAGCACAA 112680
                                          S    S   S   M   F  H  I   M  K  H  N

112681 TCATTACAGC TCTCGATTCG GCAGCAAACT TGGGCTGCAG TGCATCGGTA TGCATGAGAA 112740
        H  Y  S   S   R  F   G  S  K  L    G  L   Q    C  I  G    M  H  E  K

112741 AGGCATCATA TTTAACAACA ATCCAGAGCT CTGGAAAACA ACTCGACCCT TCTTTATGAA 112800
        G  I  I    F  N  N    N  P  E  L   W  K  T    T  R  P    F  F  M  K

112801 AGGTAAGCAG GTACTTAGTT AGCTACAATC GTTTTTGTCT ATGAATGTGC CTTTTTTGAA 112860
112861 ATCATATTTT TAAAATATTT TATTTATTTA TTTATTTATT TATTTATTGA GACAGGCTCT 112920
112921 GACTCTATCA CCCAGGCTGG AGTGACCTTG GCTCACGACC TTGGCTCACT GTAACCTCCG 112980
112981 CCTCCCAGGC TCAGGCGATT CTCCCACCTC AGCCTCGCGA GTAGCTGGGA CTACAGATGT 113040
113041 GCACCACCAT GCCTGGCTAA TTTTTGTATT TTTTGTAGCG ATGGGGTTTC GCCATATTTG 113100
113101 AGACCAGGCT GGGCTCAAAC TCACGGAGTC AAACGATTGA CCTGCCTCGG CCTCCCAAAG 113160
113161 TGCTGGGATT ACAGGCATGA GCTATCATTC CTAGTCTGAA ATCATATTTT GAATTCTACT 113220
113221 GCAATAAAGG AGGAAGAGCT AACATTCATT ATGCCTTTAC TCTGTTGTAG CCATTGTTCT 113280
113281 AAACACTTGA ATGGCAGCCC CATGTGGTAA ATGTTGTTAT CTCCTACAAT TCACAGAAAA 113340
113341 TGAGGTTAAG TAACTTGCCC AAGGTCCAAA CATTAGTAAA TGATAGCCCG GAATATAGCC 113400
113401 CTGAAGCCTA TATTTCTTAA TCACCACAAA TTCTTTTCTT CTTATTGATG TGCAAAGCAA 113460
113461 TTTTATAGGC AAAAGAAGAG ATGTAGCTAT ATATTTAGAG TAATTTCAGT TAAGAATTTA 113520
113521 GCATGTCACC CATATGTTTG ATTTAAACAC GGCCAAACAA TGTGTTTGCT GAGTGCTTGA 113580
113581 CTGACAGCCC AGATGATTTA GCAGGAAGCA ATTTGTGAAT GAAATTAGAT AATTTTAGAA 113640
113641 CTGAGAGGGA CCATATCTGT CATCTAGCCT CTGATTTTAA CAGTTGAGGA AATAAAGTTC 113700
113701 CAACGAAGTT ATGATTTTCA CCCAGGCAAA ATAGGGAGTA ATGAATGAGC TGAGACCCAG 113760
113761 TTGCAAGCTT CCTTATCCAG TGGTTTTCCC CCTTAACCTC ATCATGCTGG AAATGAAACT 113820
113821 GTTGGGGAAT ACACACGACT AACCCTTGAC ATTACTATCA AGCATAAAGA AAGATAATCA 113880
113881 TACCCTGGAA ACCTTGTCAG TGGTGGATAA TCGGGCTAGA TGATTTTAGG TCTGGCCCTG 113940
113941 TCTATTCACA GCCTTCCCTC CAGCAGCCCG TGCTGTGAAC CTAGGTAGCC GCCTTCCATG 114000
114001 TGCCTGCTGA GATGGGGGGA GCTATGCCAG TACCTCTGCC CACTGGGTGT TGAGCCCAGC 114060
114061 CTTCAGAGCT GCCCTCCCTC ACCAGGACTC AGCACAACTC TTGCTGTAGA CCCCAGTGTA 114120
114121 TCACTTTCCT ATTGCTGCTG TAACAAATTG CCACAAACTA AGTGGCTTAA AAGAACACAT 114180
114181 TTATCTCACA GTTCTGTAGG TCAGAAGTCT GACATGGATC TCAATGAGCT GAAAACCAAG 114240
114241 GCATAGGCAA GGCTATGTGC CTTTCTGGGG GCTCTAGGAG AGACTCTCTT TCTTTGTCTT 114300
114301 TTCCAGCTCT AGAGGCAGC CACATTCCTT GGCTTGTGGC CCTTTCTTCC AACTTCAAAG 114360
114361 CCATCAACAG TGGGTTGAGT CCTTTGCACA TTACATCTCT CTGACCCACC TTCTGTCATC 114420
114421 CCATCTCTCT CTGGCTTTGA CCTCGGCTTG GAAAGGTTCT TTGCTTTTTT TTTTTTTTTT 114480
114481 TTTTTTTTTT CTGAGACAGA GTCTTGCTCT GTCACCCAGG CTGGAGTGCA GTGGCCCCAT 114540
114541 CTTGGCTCAC TGCAAGCTCC ACCTCCCAGG TTCACACCAT TCTCCTGTCT CAGCCTCCTG 114600
114601 AGTAGCTGGG ACTACAGGTG CCCACCACCA CGCCCAGCTA ATTTTTTGTA TTTTCAGTAG 114660
114661 AGACGGGGTT TCACCGTGTT AGCCAGGATG GTCTCGATCT CCTGACCTCA TGATTTGCCC 114720
114721 ACCTCAGCCT CCCAAAGTGC TGGGATCACA GACGTCAGCC TATAATCTTT GCCTTTAAGA 114780
114781 ACTCATGATT AGGTTTGGCC CACCCCATCT CAAGGTCCTT AACCTTAGTC ATATCTGCTA 114840
114841 AGTCCCCCTT TTCATGTAAA GTAACATGTT AGTAGGTTCT GGGGATTATG ACCCAGACAA 114900
114901 ATTTAGGATG CTATTATTCT GCCTATCACT CATGTTGGGG GAGATAAATC TCCTTATACC 114960
114961 TTATAAAACT ATGGAATGAA TTAATGGAAA ACGTATAGGA CTTAGTATTA CAGGTTGTGG 115020
```

Figure 1 - page 38

```
115021 GTTTGCGTCC CAGCACTGCC ACTTGCTACC TATCTGACCT TAGGCAAGTC ACTTCGCCTT 115080
115081 TCTGAGCTTC AGTTCCCCTA TCCACAAAAG GTGATAAATG TTATGAAACT TGCACTCTAG 115140
115141 GGCTGTTGTG AAGAACAAAT GAAATAATGC TATAAGATCC CGTAGAAATG TACATTTGAC 115200
115201 TTTTTCATTT GGCTCAGGTG TATTAGGAAT ATGTGAACTA GTATTTAGTA GTAGTTAACT 115260
115261 TTCACATACC AATATCCTCT ACCCTGACAT GCAAGAGCTA ATTAAAGAA TCTCTAAGTT 115320
115321 CATCCATTTG TTTAACACCC CACCGTTCTC ATCTTTGAAC TAGGTACCAA GATACAATGA 115380
115381 CAAACAAGAT GTGGTTCCTG CCCTCCAGGA ACTTATAATG GGGGAGAGAG GTTTGAATTA 115440
115441 GGAAGGGGCA GCCCAGCACA TCACCAAATA CTACCCTAGG TGATGGTAAT GCTGGCGGTG 115500
115501 TGCCCAGAGT GATGCCAAGT ACAGATGAAC AGGCCATCTA AGCACATTG AGGGCAGGG 115560
115561 GAGACTTTTC AGAGGAATGG ATGCTTATAA TGAGTTTTAA ATGAAGGTAG AAGCTAATTA 115620
115621 AGAAAACAAA AGACAAATAT TCTAGGAGTA AGAATAGGA TAACCAAAGG CACAGACAAA 115680
115681 TAGATAGACA TGATGCATCC AGGGCCCTGT CGGTAAGTCC TTGTGCCTGG TGCAGATACA 115740
115741 TTCAGGACG TGGCCAAGGG GAGGGCAGGG CCAGATCACC AAAGACCTCT CAGTTAAGGC 115800
115801 AAGGAATTGA GCTTATCTCA AAAACTATGG AGAATCACTA AAGATTTTAA GCAGAATAAC 115860
115861 ATAAACATAT TTGTATTTTA TAAAAATCCC TCTGGTAGCA GAGAGAATGA CTAATTGGAA 115920
115921 GGAAGCAGGA TTGTGAGCAG TGAGAACATT TAGGAGCTAC TGCAGTGATG CAGGAAGGGT 115980
115981 GGAGGGGAGG CTGTGGTTTC AAGAAATGTC AAAAGGGTAG ACCCTACAGT AGTAGAGCCT 116040
116041 ATAGTACTTG GAAATTAAGC AAAACATCTT TGTGATTTTT TTTTAGACAG CCTTCTATAG 116100
116101 GCAAGATCAG GGTTTCTACA AAAAGTGCTA CATAACTGGA CCCAAATTCA TAATCTCAGG 116160
116161 AAATAGGGGG ATAATTGCTT ATTGGAAAGT TCACTGTTGGT GTCTGACATT TCTATAATCA 116220
116221 ATGAGGGTCC TAAGCATTTT TCAGTGAATC TCCTTTTGGA GTTAGACTCC CTGTTGGTTT 116280
116281 TCCTGATATA GTGGAAAGTT TGGCACAAGT TTTAGTATCT AAATCAGTAA CATTAATGAA 116340
116341 AGTATTGACT TACTGGGTGA GTCTGTAGAG AAATAGTTAA GTGCAACTTA GGCAATGACC 116400
116401 CATCTTGGGA GGTAGGGAAG GGTGGTGGCG AGGGGTGAAG AAATAGCATG TGTTTCCCAA 116460
116461 AACTGCCGAG AAATGTGTCC ATATTGATGG TATTTGCTGA TTGTTGCCCA ATTTTCTTTT 116520
116521 CACTAGATAG AGTCAATACT TTTTAGCATA TTTTAAAAAT TAAATCATAT CTACATCATA 116580
116581 CCACTGCCTA TAAGCCATGT TATTACATTT TTGCCCATAA ATTTGGCATG TGGCTTCAAG 116640
116641 CTCTTTAAAC ACAGAGGCAA ATCATGCATC GGCCTGGGAG AAAACCACAA GTGACATTCT 116700
116701 AAGCCAACCC TTCCACACAA AGGGTTGAGT CATTTGTCCT GCTTGCTGAA GTGGCAGTCA 116760
116761 CCCAGAGAAC AACATCCTGG CCTTTCATAT CTGCCAAGTC CTTCCTATGG TCAGAAAGCC 116820
116821 TGCTCCTTCC TCAACCTTCC TTCCAAGATG TATGGAAATC TCAAAAGTCT AGGACCAGTC 116880
116881 CTCAGGCCTC CTTTCTTATT TGCAAAGTAT ACCTTTAGGC ATGGGGATTC CGCAGCTTAA 116940
116941 CCCAGTGTGT GTGTGTGTGT GTGTGTGTGT GTGTGTGTGT GTGTGAGA GAGAGAGAGA 117000
117001 GAGAGAGAGC AAGAGAGAGA GAGAGAGGAT AGTCTTCTTC TGGAGTTACG TCTACAAAGT 117060
117061 TTCCCAATAT TTTTCATCTC ATTTCAAAGA CTCTGATGTT AACAGCAAAC CTGAATAATA 117120
117121 AAAGACTTAA AAAGAGATTA CTCCTAAAAG ATGCTTAAAG AAACGTAACA CAAAGAGAGA 117180
117181 AAGGGCACT TTAAGGGTTA AACCCTCCTG TGTAGGCCAC CTACCATCAG GACCCACCAG 117240
117241 CCACTGCTCA GATATGAACA GGGCAAGAGT AAGATCAAAG CCAGTTTACT CTATTTTCAT 117300
117301 TCATTCATTC ATTCATTCAT TCCTCTATTG AAAAAATATG TATGAAGGCC CCCATGGACC 117360
117361 ATCAGCTTGA AGTGCAATGC TAATGAGTGG CTGTCACTGT CCTTAAAGAG CTCTCAGTTC 117420
117421 AGTGAGGGAA GACTGGTAAG CAAGCAAGGA ATTGCTTAGC TGTCATGCCA TTGGCTGAGT 117480
117481 AAAATAAACC TGGAAGTAGT TTGAAGAGAA ATCAAAATTA AGAGAAGGGC ACTTTGGGGG 117540
117541 ATTTTTACAA CTAGCCTTTT ACACTTAAAC AGGAAGCACC TTAGATCAAA TAGGATCCAA 117600
117601 TTTGACCAGT TTTCCAATAA TATCCTGCCA CCTGTTGAAA CGCAAAATAA ATATGACCCT 117660
117661 AGGCAAATCC AAATCATCTT TGGAGGGAAA TGTATGCAAT AAATATGAAA AAATCACTGA 117720
117721 TTTGTGATTT ATGACCACAA GTACTAAATG TTTCATTTGC AATCTCATAA ATGGCTGGCT 117780
117781 AGAGCATGAA AAAAGTTTA ATTTTTAATA GTTTGTTTAA AATAATATTT GTCCCTATCT 117840
117841 CCTTCCGTTC ATTCATTCTT AACCATAGGA TAGTACATGC TTATGTAAAA TTAGGAGACC 117900
117901 ACAGAAAAGC ATACGAAAAT ATTATGAAAA CTTCCACCCA ATTATTAAAT TAAAAATTGT 117960
117961 GGACAATTAA GCTCCAACAT AAAAAGCCAA AATGGCATGA TTGTGTGTGT GCCCTGGAGT 118020
118021 TCGTGATGGC TGATTCTCTG ATGTGTACTC TGCAGCTCTG TCAGGCCCCG GCCTTGTTCG 118080
                                             A  L    S  G  P    G  L  V  R
```

Figure 1 - page 39

```
118081 TATGGTCACA GTCTGTGCTG AATCCCTCAA AACACATCTG GACAGGTTGG AGGAGGTGAC 118140
        M  V  T     V  C  A     E  S  L  K     T  H  L     D  R  L     E  E  V  T

118141 CAATGAATCG GGCTATGTGG ACGTGTTGAC CCTTCTGCGT CGTGTCATGC TGGACACCTC 118200
        N  E  S     G  Y  V     D  V  L  T     L  L  R     V  M     L  D  T  S

118201 TAACAGGCTC TTCTTGAGGA TCCCTTTGGA CGGTACTGAA ATTTTCACTC TCACATCTTG 118260
        N  T  L     F  L  R     I  P  L  D

118261 ACCATCTGTC CTTTACTGAA CAAGGAGCTA GGAGGGATAA CAGACCAAAG GAATCACATG 118320
118321 CCATTTTCTA CATTGCTCTT GTTTAAACAT TTCTAAGTAC TCCTCGTTTT TTTCCCTAGT 118380
118381 GTTTCTGCTT TGTTCACTTA TAAAATATAA ATTTCCATAA AGTAGGGGCC AGCATCTACT 118440
118441 AGCCTTTTGT ATCTTTCCTC ATTACTCTAG GAAATAGAAT TCTACCCACA GTTGAAACTT 118500
118501 AACAAATGTG ATTAGTTCGT TTGGTTATTA ACATATCCTA CCACCAATCA ACTTTATATA 118560
118561 TTTAACCATT TCCAGTTGTT CTTTTGGGCA TGATATATAC ATACATATAT ACATACATAC 118620
118621 CCACACATAT ATACACACAC TCCTCCCTCA AAGCTACTAA ACATGAAAAC ATTGTGCCTA 118680
118681 TATGATAAAA ATGTCAATAT TGCTGGTGAT ACTGATGCTG ATGGAAATGA CGATATTAGC 118740
118741 TGCCATTAAC GTAGTATCTA ATGTGTGCCA AACAATATTA AAAATTGCTG TATATACATG 118800
118801 TTTGCCATTT ATTATTTATA ACCTTAACAA GATGTCTCAC TCATAAGACT ACTTTCCGCA 118860
118861 CTATGATACA GAAATGAATA TTAAAACATG TGCATGCTCA TGTCAAACTC ATAGAACTTG 118920
118921 ATTTTATTTT GGCAGGATTA AACCAATTTG CAACTTGAGT ACAAATGCCA ATATTTCAGC 118980
118981 TAGTTCTTGA AAAGTTGTGC CATTGTGCAA AAGTCATTGA ATTATTTGAT AACTTTTTAA 119040
119041 CCTAATGACC AAACACCTGA CAGGAATGGA ATTCACTGGA CTTGTATCTA ATTGTTTTAC 119100
119101 ACTGTTTTCT ATGGGTTACA TTTTTTATTG CCATTGTGAC CTTTATCCAC ACACTAACCT 119160
119161 GGAAAGTATA GGAATAAAAG AATTGGCATT CTTTCTGATA CACCCTTTTT GTTTTCTTCT 119220
119221 TAAAGTCATT TATATTATGT ATTACTCTTA AAGAATGTTT TAGTCTCCAT TTTAGTAGTC 119280
119281 TGTGCATAAG GTAGTAATAC ATGTACACAA AGAAAAATTC ACAAGCCCAT TCAGGTGTCT 119340
119341 TTTAGAACAT TATTTACCAC TAAATATTTA TACAGTTGAC ATAATGCTTA TTATGCCCTT 119400
119401 GAATAATAGA ATTTGTTTTG TTTTTACTTC TTATCCATAA GCATTGGCCT TACATTGCCT 119460
119461 CAAGAGGAAC AGAATTTATT ATTAAACAGG ATTCTTAAAT CCATAACTCA TATTGTGACT 119520
119521 TCATACATTT TGTAACCCTA GTAGTGAATA TACCCTAAAA ACCTATAAAT CCCCCCAAAT 119580
119581 CACTCTACTG ATGAAAAAAA AAAAACATGT GCATGCAACT CTACCACCAC CAAAAAACAA 119640
119641 ACATTAATCA TTTGAGTAGT TTGGTGGTTA CCAGAGGATG GGAAGGGTAG TGGGGAGAGA 119700
119701 AGAGATGAAG AGAAGTTGAT TAATGGGTAC AAAAATACAG GCAGATAGAA GAAACAAGAC 119760
119761 CTAGTGTTCA AAAAATCAGT GTAGTGAAGA AAATAAATAA TAATCTATGT ACAACCAAGT 119820
119821 AGCTAGTAGA GAAAATTTGA ATGTTCTCAG CATAAAGAAA AGATAAATGT TTAAGGTGAT 119880
119881 GAATATCCTC ATTACCCTGA TTTGGTTATT ACACATTATA CAAATTTATC AAAATATTAC 119940
119941 AGTTACCCCT AAATATGTAT ATCCATTATG TATCAATAGA AAATTAATCA TTTGGATTAA 120000
120001 TTCCATTCTA CTGTTGGCAT TAAGTATGTA CAACTCAATG TGACTTTTCC TGAATTAACT 120060
120061 TACACCAGTG TTCATTGATT CATACATTCA TTCATCAAAC ATTTATTGAT TGCTTATTTT 120120
120121 ATGCCAGGCA CTGTTCTAGG TTCTGGGGAC ATAACAGTAA GCAAGACAGA TAAAATTCTT 120180
120181 GCCTTCAAGG GGCTTACATT CCAGTGAGTG ATGTGGACAG GAAAAGACAT AGATATCTAA 120240
120241 TAAAATATTA GGCAATAATA AGTGCCTTGA AGGCAAAATG AAGCAGGGCA AGAGGACAGG 120300
120301 AAGTGAAGGA GGGCAACAGT GTGTGTGGGC ACAGATGTCA TGGAGAGGGT GGTTAGAAAA 120360
120361 GGCCTCTGCA GAGAAGACAT TTGACCATAG CTCGAATTTA GTGAGGCCAC AAGCCACAGG 120420
120421 CAGATATGAG GGAAGAACAC TCCAGGCGGA GGAACAATGC GTACTTTAA CACTTGCCCC 120480
120481 AACCAGCTGA ACTGGAACAC ATGCTACCTG GTATACTACA CTTGGGCACA TAGACAAGCT 120540
120541 ATAAGCCCTC CCTATTGCCC CATCTCCCCT ACTCCAGCTA CTCCATACAA GAGCTGGAGA 120600
120601 CACTTCATCT GATGGCCATT TGGATGGGAG CCCACAATCA CTTGAAGAAG TTTTAGTCAC 120660
120661 ACTTTCTCAC CTGATCTCTT TTCAGGCAGG GATGCCACTC CCAGGGTGCC TGTTCTACAG 120720
120721 ACATCACTTC TAAAGTGAAA CAGGCGTGTA TTTTAAAAGT CTAGATTTCC AGGTCCCCCT 120780
120781 CTAGCCTTGC CTCATTAGGA AGGATCATAT AAAAGGATTT GTAAATCTCT CCATTCATTT 120840
120841 TTGGATGCAG ACTATGATGC TGGCAAACCT GTGCAACCCA CAGAGTTACA TAATCCCTTT 120900
```

Figure 1 - page 40

```
120901 TCACAGGGAT CCTTGTTAAA CTCTCAATTT GCCTAAGGGA CCCAGTGCAA GAAAAGAGAA 120960
120961 AAGGACATGG TCCTGAGGTC AGACAGAAGC AGCTCCAGCC TCAGGGCCTG CCTGTCAGCC 121020
121021 ACACTGGCTG TATGGTTTTG GGCAAGCTTC CGAATTTCTA TGAATTGCAA TTTCTTCCAC 121080
121081 TGCAAAAGGA TGACACCACA ACGCCCATGG CAAGAATATG AAGATGAAAT TAAAAATCTC 121140
121141 TTTCACAAAG TGCCTAGCAT GGTGACTGGT ATTTAGCAGT TGGAAATATA TGTCTGTTCT 121200
121201 CTCTTTTGTA TATTATCTGG TATAATTTGA AAAATAAGG GTTTATTTCC TCTAGTATTC 121260
121261 AATTTAATTA AAGAGCATTT ATTAAGAGCT GATTGTATGT GAGGCTTAGG ACAAGGCATT 121320
121321 AAAGAACACA AGATGAATTC TACACTCTGG ACTAATATA AATAACTATG AAAGCTATGT 121380
121381 GATGAGTGTT ATGGGGAAA AATGAATAAA GCACCATGAG AACATGATTA GAAGCTATTA 121440
121441 AGTGTATAAT CCAGATAAAC TGTCCACTTC ATGGCTCTGC TTACCCAGCA CCAAATGAAG 121500
121501 TTAAATGTG GTTGTTAGCC ACCTAACAGG CTCTGCTTTT TACACTCCCA GGTACCAGAG 121560
121561 TGAAGGCCAT AACAGCCATA ATTACTAGTT CCATTTGTAC AGAGAAACAG GAGCTAGTTG 121620
121621 AAAGCTCAGC CCAAGGAGAA TATGTGAAAT TCTAGGCTGA AAACTTGAAA ACACAAACTT 121680
121681 GAAAACTGGC AACTCACTGG TTAAGTAGGC CAATTTGGAT GGCAAGGAGA ACAAATCAGT 121740
121741 GCTTGATTTG TCTAGTGGTA TTCACGTGGC TAAAACTCCT ACTGAAGATG GAATCTTGCT 121800
121801 GAGCTTAGAA CCCCCAGACT GTTAGGAGAA TCTGCAGGGA ATGTTTTCTG CTCAGAGCAA 121860
121861 CCTTCTTAGG CTCACATTTT GCTCAACTGC TCTTTCTTGT GTATGTGTG  TTTTTTTCC 121920
121921 TACAGAAAG  GCTATCGTGG TTAAAATCCA AGGTTATTTT GATGCATGG AAGCTCTCCT 121980
              E  S    A  I  V    V  K  I  Q    G  Y  F    D  A  W    Q  A  L  L

121981 CATCAAACCA GACATCTTCT TTAAGATTTC TTGGCTATAC AAAAAGTATG AGAAGTCTGT 122040
         I  K  P    D  I  F    F  K  I  S    W  L  Y    K  K  Y    E  K  S  V

122041 GTAAGTAATA CAACTTTGGA AGATTTATGA GTACA TTGG ATT GTTTT TTCCCTTGTG 122100
122101 TCTTTGCTGT TTTTCTTGGC CTCTCAGGTA ACTTTTCTGC TCTCTAGAGC CCACAAGGGA 122160
122161 GCTGTTGATT AAGTTGCTGA TGAAACACTT TTTACAGCAA TTTGGCTGCA TTTGGCCAGA 122220
122221 CCAGAGAGTA ATGAAGCCT TTGGCTGGGC AGCTTCTCGG CAAGGGGGCT GAGTGTGTGG 122280
122281 TCTGGGAGCT TCAGCTTGGT AACTAGGACA CTAGTGTATT TTGAGTTGAA GAGAAGGGTC 122340
122341 GACTGATCCT GTCATTAATA TCTGTCAAAA TTATCTTTGC ACAACTAAAA AACTGGAACT 122400
122401 ACAGAATCAA TTTATAGTTG TGTTGTTTTT GAATGAATTT AACATAATTC AACTTGTAAG 122460
122461 AACTGACAAT AGTCTCAATA GAATTTTTTC TTAATGAGTA CAATTAACTT CAATAAAATG 122520
122521 TGTGTGGGTT TTTGAAATTA TGTATCTTGT GTTTTGGGGG TCCTGAAATT GTCATTAAAT 122580
122581 GACTTTGTTT TGGTCTTAGA ATCATCCAGC AGAAAACTGG ACAAATGCCC AGTGGCCTAC 122640
122641 AGGCTAATCA ATGGGCTTGT AGAGTACAGG TAGCCAGTCA CTAAACACTG CTACCTCTAA 122700
122701 CCACCAGTGG AAAGCCTGTG GAATCTAGAA ACAGGAACTC CTGTTTTGTG TCCTGTTTCT 122760
122761 AATGGCCTTG GGAAGTTATT TAAATAAGA TATAACCTAT CTTCTAGAGT AGGGGCATAG 122820
122821 GTTAATGAGA TCATATAAGT AAGGCAATTA GCATAGAGCA TGGCACATAG AGGGTACTAA 122880
122881 ATATGTTAGT TTCTCCCTTT CCTGTGTTCA TATCTTCCTC AGATGTTCCT AACCATCTCA 122940
122941 AGTTCTCCAT CTCTAAATGT CCCCAAGCTT GTCTGAAGAC CTGACTTTAT TCTACCTGTG 123000
123001 GATTTTGAAA TTCGATAATA TTAGTTTCTA GAGAAGAAGC CGACTTGATG TTGTTTTGTT 123060
123061 TATTCTCTCA TGGTTGATAA GTACTAGGTG AATGTTTTAG ACACTTGGTT CTTTATACAT 123120
123121 TTCATTTCCA CCAGAGCTTA TTGTGACTTG AAAACTAATA GATAAAGAT TCATCTCTTC 123180
123181 CCTGTGATCA GAGTTGTTGG CAGTAGTGGT GGTCTGGAGA GTTCATTACA TAGTTCTCAG 123240
123241 TCATTAGTTT AGCCTTGGTC TTGGCCATTG GACCCACAGA AATTTATTGT ATGAGTCTGT 123300
123301 ATAACGGATT CTCTTAGGTT TCTGCAGTTC CCTCAAGGAG CTCTCTATGA ATTTAGAGGC 123360
123361 TGGGGCATTC CAACACCTCC CAGACCATTT GGGGCTAGTG CCCAGATGGG AATGCTATGA 123420
123421 GCATTCTCAG CCTACTAGGA AGAGGGCACC ACAGCCCAGC TGAGTGAATA TCTGTTCTTT 123480
123481 GTATATAAGA GATGCTTAGC AAACATTTGA TGAATGTGTG GATCAGTAGG GTATTTAAGT 123540
123541 GTATAGGTGA ACATGTCAAT TAGAATTTGG AAGATGGATT TATTGTACAT TTAACGTAAT 123600
123601 ACAGAACATT GTTCCCTGAG ATAAGGGAAC AATACTTA CAAAGAACAC ATACACTTAA 123660
123661 GGACAGAGAT AAGAAAAATT GAATTTAGAT TAAGGTGACT TTATTTTTCA TCCAGTCTGA 123720
123721 TCCCTTCACT TTAAAAGGAT GTAGGGCCCA GAGACTTAAA GTATCTTACA TAGAAAGAGA 123780
123781 ACAACCTGAA CTAGGACCTG ACCCCACCCC GTCCAAGTGT CTTTCAACC ACACTGCCAA 123840
```

Figure 1 - page 41

```
123841 AATGCCTATA CATATTTATG CAGCTGGTAA TTCATTCAAC ACATATTAGT GTTTACAATG 123900
123901 TGGCAGAAAC TAACAAGGCA TGAGAATAAA TATCAAGAAT GATACCTAGT CACTGGAGTT 123960
123961 TACTGTTTAG AACAGGAATC TCAAACTCAA CTGTCTTCAG GACTAGGCAA ATAAAAGCAG 124020
124021 ACTATGGGGG CCAGGTGCAA TGGCTCATGC CTGCAATCCC AGCACTTTGG GAGGCCGAGG 124080
124081 TGGGTGGATC ACCTGAGGTC AGGAGTTTGA GACCAACCTG ACCAACATGG TGAAACTCTG 124140
124141 TCTTTACTAA AAATACAAAA AATTAGCTGG GCGTGGTGGC AGGTGCCTGT AATCCCAACT 124200
124201 ACTCGGGAGG CTGAGGCAGG AGAATGGCTT GAACCCAGGA GGCAGAGGCT GCAGTGGGCT 124260
124261 GAGATCATGC CACTGCACTC CAGCCTGGGT GACAGATTGA GACTTTGTCT CAGTTAAAAG 124320
124321 AAAAAAAGAA AAAGCAGGCT ATGGGAATGT AAGACAAGGG AATGGAGGTT CCTGTGGCAA 124380
124381 ACTGAAGAGC ACCTGACAGC ACTCACAGGT TTTTTTGTTT TTGTTTTTTT AATTTAAACA 124440
124441 TTGTGCCTGC CAAATCAGAA ATTGGAAAAC ATTGTTAGAT TTAGCCTTTT GATATCAATT 124500
124501 TTTAACCCTT AACTAGAAGT CACAGGCTTG ATTTCGCTAC CAGTATCCAG AAATCTTAGC 124560
124561 TAACTCTGGC ACCTTAACAT GAAGTGTAGG GTCTATGTAA TTTAAGGGTA TTTATGAAGA 124620
124621 AATAAAATAG TAATTCACTT ACTCATAAGC ACCAATGTTT TCAATTAAAG CAGATCATTT 124680
124681 TACCTAAATA CATGGCAAAT AAATCTGTTT CGCTAGATGT CTAAACTGAG TAAAAATAGA 124740
124741 CAATATTTTG ACTTTTTTTC CAGCAAGGAT TTGAAAGATG CCATAGAAGT TCTGATAGCA 124800
                                    K  D   L  K   D  A   I  E   V  L   I  A

124801 GAAAAAAGAG GCAGGATTTC CACAGAAGAG AAACTGGAAG AATGTATGGA CTTTGCCACT 124860
       E  K  R   R  R  I   S  T  E   E  K  L   E  C  M   D  F  A   T

124861 GAGTTGATTT TAGCAGAGGT ACTGACCTGA ACTAACTGTA ATTCCATGC CACATATGTT 124920
       E  L  I   L  A  E

124921 ATGACTGTGT AGAGGTGTGT AAAGATCCCC TTTTGTAACT GTTGCATATT TCTGCTTTTA 124980
124981 AATACTTTCT CTAGCAGTTC TGTAATCCCA ATCCAAATAG CCCACACATT AGATATTTCA 125040
125041 GTAAGGCTTT TAAGATTGGA ACATTCTAGT AAGACTGACT GCTAAGATTG TGACTCTTCT 125100
125101 GTGTAACAGT ATAAAATATG AAAACAAGTT GGGGGAGGCC AAAGACACTA CATATACATA 125160
125161 GACAGTCGGC CTAATCGTTC ATCTTTCAGC TAAAGATTGT CATGTAAAAT GTCCACAGTC 125220
125221 AATCACAGAG ACATGTGGTT TCTATGATTT CATTTTGTTG AGGTTGTTGA TCCTTGAGTG 125280
125281 TCACCTCCCC TCATTTTTTG AAACTTTGAT TCACTTTTCC AAATTTTTCC CATCTTCCAA 125340
125341 TTGTTCAGAA ACGTGGTGAC CTGACAAGAG AGAATGTGAA CCAGTGCATA TTGGAAATGC 125400
                 K   R  G  D   L  T  R   E  N  V   N  Q  C   I  L  E   M

125401 TGATCGCAGC TCCTGACACC ATGTCTGTCT CTTTGTTCTT CATGCTATTT CTAATTGCAA 125460
       L  I  A   A  P  D   T  M  S   V  S  L   F  F  M   L  F  L   I  A

125461 AGCACCCTAA TGTTGAAGAG GCAATAATAA AGGAAATCCA GACTGTTATT GGTAAGAATT 125520
       K  H  P   N  V  E   E  A  I   I  K  E   I  Q  T   V  I

125521 TATCAAATAA ATAATACATT TTAAAAACAA TTTCTTCTGA ATGTCCATTT CTTATGTCCT 125580
125581 AAGAATCTGA TATCAAACAT GAAATTTTTT ATAATTTGCT CCAAACAATA AAGCAAGACA 125640
125641 TTCTGTCACA TTTGATTACA CCAGATAGAC GGAAAGATA GCTCTTTCTG TGTTCTTAAT 125700
125701 CATAAAAATG ATGCATGCTC ATTGGGAGGA ATTTAAATCA CAGAATGATG TGTAAAGCAG 125760
125761 TAAGTGACAT CCCCCAATCC TTTCCGCTCT CCTCTCCAGC CTCATCTCCC CTCTCCAGTG 125820
125821 GCAACCATTG TTAATAGTTT GCTGTGTATT TGCTAAAATC TTTTTCTATT TGCCCACAAA 125880
125881 CACATATTTA TGGTTGGATT TGTCCATTTT ACAAAAACAT GGGATCATAT ACAATGTTCT 125940
125941 GCCTACCTTG TCAGTTACAA AAGACTTTTG TGGACTCTCC CAGGGAAATT ATCGTCCCAG 126000
126001 GGAAGTGATA GTCTATCATT TATAGCACTG TTTCTGGGCT TCAAGCAGCC CCTTCACAAA 126060
126061 TGAACTTCCA GTTTGTGGCA GAAGGAAGAG GAGAGGATGA CAGCAAAGAC AGGGTAGTGA 126120
126121 TACATTTCCC TCTCCACTCC AATCCAGTGA TGCTAGCCCC TTCCTCTCCC CTGCCCTCTG 126180
126181 CAGGGGAGCT TCCAGGTCCA CACTCAGGTC TTCTCCAACT CTACCGCCTC ACTACTCTGT 126240
126241 CTCTGCTTCA ATTTCATCCT GCTCCACTCT TCTACAGAAA CAAGGCCATC TTTGAAAGAA 126300
```

Figure 1 - page 42

```
126301 ATCAAACTTG CTTTCTGGGA GAAAGCAGAA TTCCTCATTT GACACTTCCT TCACATAAGT 126360
126361 AATCTTTTAG GAACACATTT CTTACAGATG TGAAGAGAGA TCACAGAATG TGGACTTCCC 126420
126421 TCTCTTGACT TTACACAGAC CCTGCAAAAC AAGTTATTTG GTTGTAGAAG GGCATCATCT 126480
126481 TTTTCAAACC ATTGGAGTGC TCCTTGAAAT AGTTAAACGT AAGGGAAAAT TTCATCGAAG 126540
126541 GGTTAAATAT GGGAGAGAAG GGATCTGCAG ATGCCTCACA CAGGTGGGAA GTTCCAGGC 126600
126601 AAGGTAGATA GCAAGGATAC AGAATAACAT CTGGAATCCA AATTCCAGCA TGTTTTCTTG 126660
126661 AGTGCCTCCT AGCAGGTTCT CAGGTTCTGT GCCAGGTGCA GGGCTACAGC CTTGAACAAG 126720
126721 CCAACACCAC CCCTGCACTC ACGGGGCTCA TGGTCTGGTG GGAAAAAGAA AACAAGCTCA 126780
126781 ATACAGTAAA GAGAGACCGA AGGAGGGCAT TCAGAGAAAC CATAAGCCTT TAATACATAT 126840
126841 TGAATACCAT TTATTTGAGA GGTGAAATGT ACGTGTACAT GTTAATGTTC CCCTGACACT 126900
126901 TCAAAAGGCC TCTGCAAAGA TGGAAAAGCA GCAGAGCCAT TTGCAAGCGT CCATGCTCCC 126960
126961 TCCTGTGTGC CACACACAGA CTCGCTAACT ACTTCCTAGT GAGCACCTTT GGTCACCTTC 127020
127021 TCCATCATCT TCTTTTCTAC CTCCCAACCC CAGCTATACA GGCCCCATTA GACCCTTGAG 127080
127081 TGTGCCAAGG GCAGTATGTA AGAGGAAGGG CCATGAGAAG ACTCTGACCA AACTAGACCT 127140
127141 TTCCTCAGTG GCTTCGTTGT ATATGAGACA GGGCTGCCTC AGGACCCTGG GCTATTTTTC 127200
127201 ATCCTGCAAA AGTGGCATCT CTGAAGCTTT ACCATGTCTG GAATAATCT AAGTCTCTTT 127260
127261 GACCAGTGTC AGGCTAATCT GAGACAGTGA GGGTGTCCAT CTATCCCCAG CTCACCCAGG 127320
127321 GCTGATCTGA GGCACCTATT TTGTCGTGGT GGGGAGAACA TCCTTGTCAC TCTACTGCAG 127380
127381 GTCTTTCTTG ATGAGATGCA GAGGGACTAT CAGTGACATG TATGGGCAGA TGACTGCACA 127440
127441 GGTAACCAGA AGAGAAAATT TCATTGAAAT AGATCAAATC TGCCATCTCA CTTTGACTCT 127500
127501 GCAGCAGCCT GTGCATCATC TCTGGGATGG TTGTGGTGCC AGTTTGCTCG TAAGTGAAGA 127560
127561 GAGGAAATGA ATGTCCCCTA CAATTTAGAG TAGGGAACAA AAACTCAAAG ATTTCAGAAA 127620
127621 GCAGGCACAT GAGATGAATG TTTGAAGCAG ATTGGGTGTG GTCTAGATGG AACTGTATGA 127680
127681 TGTATGCCCC CTCTAAACAG GTAATTGGCC ACTCAGCGTC AGCCCATTAT TGCTATGTGG 127740
127741 GAATGTAAGT TCAGCATCAC CAAATTTTCT GGACATTCAG ACTTTTCTAT AAACTCCACC 127800
127801 AGTTTTTAAG GTAATTGGCT TCATATCTGA ATTTTTATAA AACACTCTGT GGCCCAAGCA 127860
127861 TAACATATTT GGCCCTGGTT GCTGGTGTGC ATTAGAATTA GAGCCACAAT TTTTTTCAAC 127920
127921 CAAGAGCAAA CGGTTCTGTG GAAAAAAATA GAAGCTTTAA TACCAATCAC AGATGGAAAC 127980
127981 TAACATTACC TTCTTTGTTC CTTTTATCTG TTTCCACAGG TGAGAGAGAC ATAAAGATTG 128040
                                                     G   E   R   D   I   K   I

128041 ATGATATACA AAAATTAAAA GTGATGGAAA ACTTCATTTA TGAGAGCATG CGGTACCAGC 128100
       D   D   I   Q   K   L   K   V   M   E   N   F   I   Y   E   S   M   R   Y   Q

128101 CTGTCGTGGA CTTGGTCATG CGCAAAGCCT TAGAAGATGA TGTAATCGAT GGCTACCCAG 128160
       P   V   V   D   L   V   M   R   K   A   L   E   D   D   V   I   D   G   Y   P

128161 TGAAAAAGGG GACAAACATT ATCCTGAATA TTGGAAGGAT GCACAGACTC GAGTTTTTCC 128220
       V   K   K   G   T   N   I   I   L   N   I   G   R   M   H   R   L   E   F   F

128221 CCAAACCCAA TGAATTTACT CTTGAAAATT TTGCAAAGAA TGTAAGAGCC CTTCCTTAAA 128280
       P   K   P   N   E   F   T   L   E   N   F   A   K   N

128281 ACTGAGTGTG CCACTCTTGA AAATGTCAAC TGTTAAATCC TCTCTGGTTC TTTGTGTTTG 128340
128341 CACCATAAAT ACTTCATTTT TCTTACTCAT TCCCTCTGCC ACCTCACCAG GAGCACACAC 128400
128401 GTCCCCTAGC TTGGAGCAGG GCTCCCGTAT TCATCCTCAA GCCTTCAAGG ATGTTGGGTC 128460
128461 TCCAGCTCTA AGAAGTATCT ACATGGTGGC ACAAAATAG GTCAAAATGT GAAAAAGCTG 128520
128521 GGCCCTTCAT TTGGCTAAAA TGAAGTGATT TTTGTTTAAC CCAACCACC TACTTTTCCA 128580
128581 TTTAAACTTT GTCATCATGT CATCACATTC AGCTATAGCA CCATCTGAGC AAAGGAAAGT 128640
128641 CCACTACTGC TTCAGATGAA AATCAAATGA GACCAAAAGA TTTGGTTTTT GCAAAGTGCC 128700
128701 TTTGGCTCAT CAAATGGCCC CATGAGCAGT AGGTCCCATT CTAAATAGGA CTTAATAATT 128760
128761 AGAAGAGAGA CAGTTTTTCT TTTTTTATAA TTGATGTGTA CTACAGATTC CACCTTCATT 128820
128821 ATGTCAAATT TTAGGCAATA TGTTTTTCAA TCTGAATTAC GTACGCAGTT CCCTAAGTGC 128880
```

Figure 1 - page 43

```
128881 CCTTTTTTCA ATTTGCATAT GGTGTAGAAA CATGATGCTA AATAATTCAG TACTCTAATT 128940
128941 CATTTTGTTT CTACACGGGC AATCCAGATA ATGCTATGTA AATCAGTCAA CTGATCAACA 129000
129001 AAAATTTATT GAACATCTAC TATATGCCAG GCACTAAGTC CAAATGTGGA CAAGACAGCT 129060
129061 GTGGTCCTCA TTAATTTTCT GCATAACTAC AAATAGTTAG ATGCTTGGCA CTGAATAGGC 129120
129121 CAGGAATCTA CATCCTTGCT TGCCTTTATC TCTTATATGG TGTCACACAA AATAATCTT  129180
129181 TGCCTTAGTG ACTTATAAAA CAATAGTAAA TCTGTGGCTA TTCCACAGAG CTACCTGATT 129240
129241 ATACTAACAC TTGCTGTAAT AAGATTTGGT TTGCATTGCT TTACCCCAGC ACATGAAAGG 129300
129301 CAAAACTGGG GACTCTCTGA GGTTGGGTCA GAACACAGGG GGTGAATGAA ATAGGACATA 129360
129361 GAAAGGGCTT GAGTTCCAGT TGTTCATCTG AGGGGATGGA GGGCATTGTA GCTGATAACC 129420
129421 CCAAAACAGT GTTCTGACTG ACCCATGTTT TCAGAATGAA *TCAAACAGAG ACTGAGTGAC* 129480
129481 *TCTAGCCTTT* AATATTCTGG CTAACTGTCT GATCATTTTC ATAGGTTCCT TATAGGTACT 129540
                                                                V  P  Y  R  Y

129541 TTCAGCCATT TGGCTTTGGG CCCCGTGGCT GTGCAGGAAA GTACATCGCC ATGGTGATGA 129600
        F  Q  P  F  G  F  G  P  R  G  C  A  G  K  Y  I  A  M  V  M

129601 TGAAAGCCAT CCTCGTTACA CTTCTGAGAC GATTCCACGT GAAGACATTG CAAGGACAGT 129660
        M  K  A  I  L  V  T  L  L  R  R  F  H  V  K  T  L  Q  G  Q

129661 GTGTTGAGAG CATACAGAAG ATACACGACT TGTCCTTGCA CCCAGATGAG ACTAAAAACA 129720
        C  V  E  S  I  Q  K  I  H  D  L  S  L  H  P  D  E  T  K  N

129721 TGCTGGAAAT GATCTTTACC CCAAGAAACT CAGACAGGTG TCTGGAACAC *TAGAGAAGGC* 129780
        M  L  E  M  I  F  T  P  R  N  S  D  R  C  L  E  H

129781 TGGTCAGTAC CGACTCTGGA GCATTTCTCA TCAGTAGTTC ACATACAAAT CATCCATCCT 129840
129841 TGCCAATAGT GTCATCCTCA CAGTGAACAC TCAGTGGCCC ATGGCATTTT ATAGGCATAC 129900
129901 CTCCTATGGG TTGTCACCAA GCTAGGTGCT ATTGGTCATC TGCTCCTGTT CACACCAGAG 129960
129961 AACCAGGCTA CAAGAGAAAA AGCAGAGGCC AAGAGTTTGA GGGAGAAATA GTCGGTGAAG 130020
130021 AAACCGTATC CATAAAGACC CGATTCCACC AAATGTGCTT TGAGAAGGAT AGGCCTTCAT 130080
130081 TAACAAAATG TATGTCTGGT TCCCCAGTAG AGCTCTACTG CCTCAACCCA AGGGGATTTT 130140
130141 TATGTCTGGG GCAGAAACAC TCAAGTTGAT TAGAAAGACC AGGCCAATGT CAGGGTACCT 130200
130201 GGGGCCAAAC CCACCTGCTA GTGTGAATTA AAGTACTTTA ATTTTGTTTT CTGTGGAGGT 130260
130261 GGAAAAGCAA CATTCATAGT CTTTGGAGAA ATGCTTAGAA ATTCAGCATT TGACCCTTGC 130320
130321 TGTGAATTAA GCCCAATTAA TTCCTGTTTG TCTACATATG ATCTGTCTGT GGCAAAAGTT 130380
130381 TAATCAGAGG AAATTCTTTC CCAGTCTGTC GATTTATGCC TCAGCCACTT GCCTGTGCTA 130440
130441 CAATTCATTG TGTTACCTGT AGATTCAGGT AATACAAACT ATATATAATC ATCAAGTAAT 130500
130501 ACAAACTAAT TTAGTAATAG CCTGGGTTAA GTATTATTAG GGCCCTGTGT CTGCTGTAGA 130560
130561 AAAAAAAATT CACATGATGC ACTTCAAATT CAAATAAAAA TCCTTTTGGC ATGTTCCCAT 130620
130621 TTTTGCTTAG CTCAATTAGT GTGGCTAACC AAGAGATAAC TGTAAATGTG ACATTGATTT 130680
130681 GCTCTTACTA CAGCTTCAGT GATTGGGGGA GGAAAAGTCC CAACCCAATG GGCTCAAACT 130740
130741 TCTAAGGGGT ACTCCTCTCA TCCCCTTATC CTTCTCCCTC GACATTTTCT CCCTCTTTCT 130800
130801 TCCCATGACC CCAAAGCCAA GGGCAACAGA TCAGTAAAGA ACGTGGTCAG AGTAGAACCC 130860
130861 CTGAAGTATT TTTTAATCCT ACCTCAAAAT TTAACAGTTA CCTGAGAGAT TTAACATTAT 130920
130921 CTAGTTCATT GAATCATTGT ATGTGGTCAT GGATAAATTG CACACCTTGG AATTCGCTTT 130980
130981 CTAAAGGAAA TCAAATGAAT GGAGGAACTT TCCAAACACC ACTTTACTTG TGTTATATAG 131040
131041 CCAATATAAC TATCTCTACT GAATGTCATT GAAAAACTAA AAAATTAAAC TTATTTACAA 131100
131101 ATAGGTAAAT ATTTGTCATT GAATCCATTG CCATCCCATT TGACTGTTCT TTTCATCCTA 131160
131161 CTGTCTAGTA ATAAGCTGAG TATAAGATGA CAGTGTAATC TCCCTGAAAG CAGGAGCTAC 131220
131221 TTTCTTTCTT TTGTAATCTA TTTCCATCCC CATTTCCCTG TCCTGTCTCC CTGTATTCAC 131280
131281 TCCCAAGCTC AGTTCTGAAT AGACATTCCT GCTCAGAGAT ACTCCCAACT GATGCAGAAA 131340
131341 CCAAATAAAG AGGTAGGTAT TCCAAGAATT CAAGAATGGA CATTAGTAAA GAATAAAACA 131400
131401 TTTATTTGAG CTTGGAATTA TTTGGATCAT CTATATGGCC TAAAAATATA TGGACTATGC 131460
```

Figure 1 - page 44

```
131461 CTGTGTACCT GAATACGTAT GTAGTCAGGT CAAGACAATC ATCCAAATAA CTTAGACCCC 131520
131521 TAAAAGCAAG GCCAGGATTT GCAATTTAAT GTGTCCCAAT TAATTCACTT GAAAATTAGT 131580
131581 AACACTCTGT TTACGTTGCC TCTGGCTGGA GCTGCATGGT GGAAGAAGCC CAACTTTGGA 131640
131641 TCCATGTACT TCACCCATCC AATACTCTTG GGACATTTAT GTGTATTTTA TCTGTATATA 131700
131701 TGAAGCCAAT GTCTATGTCT ACACAGTCAA AGTGAAATGC ATGTTTGATA TAGCTGTACA 131760
131761 TAGATATCTA TTTTGCAGGT ACAAAAATAT CCTGGGGGAA AACTGGGAGT GGAAGGGTGG 131820
131821 GGGGTGGGAG TGAGGACAT GGGGGAGGGA CAGGAAGAGG AGAAGTGTTG GTTTGAACGA 131880
131881 TCCAAGCAAA CTCTCCCAGA ATCAAATTAC CTGGGTAGTT GTTCAACTTT TCACTCTGCT 131940
131941 TAGCCTGTAT AGACAAACCC CATATATTTG TAGAGGCTTG GCCTTGGAAT TCTGGAATAC 132000
132001 CATTGGCTTT TCAGTAGGCT GATGAACACA TTTTGAAAAT TCTATTATCT TCAGAATTTT 132060
132061 GCCCCATTGT TAAGTGCTTA ACCGTCACTC TTGAATGTGC AATGTGCTGT GGATTCCATT 132120
132121 TTCATCAGTT CTGAAAGAAC TGCAATGTGT AAATTATCAG TGAAATGCAT GCATATAAGG 132180
132181 GCTCTATCAT TATCAAATTG TAAGGACAAT TGTACCCTTC TATATCTTTG GGCATGCTAG 132240
132241 ACACCCCCAT GCCTTCATTG AGATCCCATT TTCCCCCTCT CAAGTGGAAA ATAATCACAT 132300
132301 CCAGCAAGCT CTCTCATTAT TGAGAAATAC CATTTGGAAA TTGCCACTTT TTATTCCTAA 132360
132361 GCAGCACCTT TCACTGTTCA TGATGCTAAT GTTCCACAAA AGCATGTGCC ATTGGCCCAC 132420
132421 TGAAGGATAG AGGGACCCTT TTCAATCTAT ATCAGCTGGG CTCTGGGACT GAATCTCTCA 132480
132481 CCTATTCTTG CAGAAAGACA TACTAATTAA ACCTTGTCAA AGTAGTAAGT CAAATGGAGC 132540
132541 GTATGATGCT TTCAGTTGCT CTTAGCTCAA AGAACAAAGT CAAGGGATTA ACCCTTCAGG 132600
132601 GATCAATCCT GTCAGGGCTT ACCTGTTTCA ACTTCCTCAT TTCCTTTCTG CAGCTTTTAG 132660
132661 CAGGTATTGG CCTATTCTAG GAAGTCAATG GCCATAACCC TGTTTCTACC AGGTCAACAA 132720
132721 GACAATGGAA TGTATTTAGA CAGGGCAACC CCCATTCATC AAGTCCAGCC CATTAAGTAT 132780
132781 ACCCTGCTCT CTCCCATCAA GAAAACATTT CGAAGTGCAA AACAAATGAG AGTCATAAGA 132840
132841 AAATGATAAT TATCATAAGA ATAACTTTGA ATCCACTGTG ATTTATAACC AAAAGCAAAT 132900
132901 GTTTCACAAA CCTCAGTATT TTAATTTGTT AGCAAAACAT TCTTGCAAA GAAGGTCTTA 132960
132961 ATTACAAGGC ATGGCAGCTG AGTGCCTGTA GTCCAGGTAA TTTTTAAAGT TCCTTTCAGC 133020
133021 TCTGCGACTC CATGAATAGG GAGGCAGTGG AGCCCTGCCT TTTTGTAAGA ATATGCTTTG 133080
133081 GACAAGCTGT TTCATCTCTC CATATCA
```

Figure 2 - page 1

```
        1   2   3    4   5   6   7    8   9  10   11  12  13   14  15  16 17   18  19  20
1       ATGGTTTTGG  AAATGCTGAA  CCCGATACAT  TATAACATCA  CXAGCATCGT  GCCTGAAGCC   60
        M   V   L    E   M   L   N    P   I   H    Y   N   I    T   S   I   V    P   E   A 21  22  23   24  25  26  27   28  29  30   31  32  33   34  35  36 37   38  39  40
61      ATGCCTGCTG  CCACCATGCC  AGTCCTGCTC  CTCACTGGCC  TTTTTCTCXT  GGTGXGGAAT  120
        M   P   A    A   T   M   P    V   L   L    L   T   G    L   F   L   L    V   X   N 41  42  43   44  45 46  47    48  49 50    51  52  53   54  55 56  57   58  59 60
121     TATGAGGGCA  CATCCTCAAT  ACCAGGTCCT  GGCTACTGCA  TGGGAATTGG  ACCCCTCATC  180
        Y   E   G    T   S   S   I    P   G   P    G   Y   C    M   G   I    G   P   L   I 61 62  63   64  65  66  67   68  69  70   71  72 73    74  75  76  77   78 79  80
181     TCCCAXGGCA  GATTCCTGTG  GATGGGGATC  GGCAGTGCCT  GCAACTACTA  CAACCGGGTX  240
        S   H   G    R   F   L   W    M   G   I    G   S   A    C   N   Y   Y    N   R   V 81  82  83   84  85  86  87   88  89  90   91  92  93   94   95 96  97   98  99 100
241     TATGGAGAAT  TCATGCGAGT  CTGGATCTCT  GGAGAGGAAA  CACTCATTAT  CAGCAAGTCC  300
        Y   G   E    F   M   R   V    W   I   S    G   E   E    T   L   I    S   K   S 101 102 103 104 105 106 107 108 109 110 111 112 113  114 115 116 117 118 119 120
301     TCAAGTATGT  TCCACATAAT  GAAGCACAAT  CATTACAGCT  CTCGATTCGG  CAGCAAACTT  360
        S   S   M    F   H   I   M    K   H   N    H   Y   S    R   F   G    S   K   L 121 122 123 124 125 126 127  128 129 130 131 132 133  134 135 136 137 138 139 140
361     GGGCTGCAGT  GCATCGGTAT  GCATGAGAAA  GGCATCATAT  TTAACAACAA  TCCAGAGCTC  420
        G   L   Q    C   I   G   M    H   E   K    G   I   I    F   N   N   N    P   E   L 141 142 143 144 145 146 147  148 149 150 151 152 153  154 155 156 157 158 159 160
421     TGGAAAACAA  CTCGACCCTT  CTTTATGAAA  GCTCTGTCAG  GCCCCGGCCT  TGTTCGTATG  480
        W   K   T    T   R   P   F    F   M   K    A   L   S    G   P   G   L    V   R   M 161 162 163 164 165 166 167  168 169 170 171 172 173  174 175 176 177 178 179 180
481     GTCACAGTCT  GTGCTGAATC  CCTCAAAACA  CATCTGGACA  GGTTGGAGGA  GGTGACCAAT  540
        V   T   V    C   A   E   S    L   K   T    H   L   D    R   L   E    E   V   T   N 181 182 183  184 185 186 187 188 189 190 191 192 193 194 195 196 197  198 199 200
541     GAATCGGGCT  ATGTGGACGT  GTTGACCCTT  CTGCGTCGTG  TCATGCTGGA  CACCTCTAAC  600
        E   S   G    Y   V   D   V    L   T   L    L   R   R    V   M   L    D   T   S   N 201 202 203 204 205 206 207 208 209 210  211 212 213 214 215 216 217  218 219 220
601     AXGCTCTTCT  TGAGGATCCC  TTTGGACGAA  AGXGCTATCG  TGGTTAAAAT  CCAAGGTTAT  660
        X   L   F    L   R   I   P    L   D   E    S   A   I    V   V   K   I    Q   G   Y 221 222 223 224 225 226 227  228 229 230 231 232 233  234 235 236 237  238 239 240
661     TTTGATGCAT  GGCAAGCTCT  CCTCATCAAA  CCAGACATCT  TCTTTAAGAT  TCTTGGCTA   720
        F   D   A    W   Q   A   L    L   I   K    P   D   I    F   F   K    I   S   W   L 241 242 243 244 245 246 247  248 249 250 251 252 253  254 255 256 257 258 259 260
721     TACAAAAAGT  ATGAGAAGTC  TGTCAAGGAT  TTGAAAGATG  CCATAGAAGT  TCTGATAGCA  780
        Y   K   K    Y   E   K   S    V   K   D    L   K   D    A   I   E    V   L   I   A 261 262 263 264 265 266 267  268 269 270 271 272 273  274 275 276 277 278 279 280
781     GAAAAAAGAX  GCAGGATTTC  CACAGAAGAG  AAACTGGAAG  AATGTATGGA  CTTTGCCACT  840
        E   K   R    X   R   I   S    T   E   E    K   L   E    E   C   M    D   F   A   T
```

Figure 2 - page 2

```
         281 282 283 284 285 286 287 288 289 290 291 292 293  294 295 296 297 298 299 300
841      GAGTTGATTT TAGCAGAGAA ACGTGGTGAC CTGACAAGAG AGAATGTGAA CCAGTGCATA                    900
          E  L  I   L  A  E  K  R  G  D   L  T  R    E  N  V   N  Q  C  I 301 302 303  304 305 306 307 308 309 310 311 312 313  314 315 316 317 318 319 320
901      TTGGAAATGC TGATCGCAGC TCCTGACACC ATGTCTGTCT CTTTGTTCTT CATGCTATTT                    960
          L  E  M    L  I  A  A  P  D  T   M  S  V   S  L  F   F  M  L  F 321 322 323 324 325 326 327  328 329 330 331 332 333 334 335 336 337 338 339 340
961      CTGATTGCAA AGCACCCTAA TGTTGAAGAG GCAATAATAA AGGAAATCCA GACTGTTATT                   1020
          L  I  A   K  H  P   N  V  E  E  A  I  I   K  E  I  Q  T  V  I 341 342 343 344 345 346 347 348 349 350 351 352 353  354 355 356 357 358 359 360
1021     GGTGAGAGAG ACATAAAGAT TGATGATATA CAAAAATTAA AAGTGATGGA AAACTTCATT                   1080
          G  E  R   D  I  K  I  D  D  I   Q  K  L   K  V  M  E  N  F  I 361 362 363 364 365 366 367  368 369 370 371 372 373 374 375 376 377  378 379 380
1081     TATGAGAGCA GCGGTACCA GCCTGTCGTG GACTTGGTCA TGCGCAAAGC CTTAGAAGAT                    1140
          Y  E  S    R  Y  Q  P  V  V  D  L  V  M  R  K  A   L  E  D 381 382 383  384 385 386 387 388 389 390  391 392 393 394 395 396 397 398 399 400
1141     GATGTAATCG ATGGCTACCC AGTGAAAAAG GGGACAAACA TTATCCTGAA TATTGGAAGG                   1200
          D  V  I    D  G  Y  P  V  K  K   G  T  N   I  I  L  N  I  G  R 401 402 403 404 405 406 407 408 409 410  411 412 413  414 415 416 417 418 419 420
1201     ATGCACAGAC TCGAGTTTTT CCCCAAACCC AATGAATTTA CTCTTGAAAA TTTTGCAAAG                   1260
          M  H  R  L  E  F  F  P  K  P   N  E  F   T  L  E  N  F  A  K 421 422 423  424 425 426 427 428 429 430 431 432 433 434  435 436 437 438 439 440
1261     AATGTTCCTT ATAGGTACTT TCAGCCATTT GGCTTTGGGC CCGTGGCTG TGCAGGAAAG                    1320
          N  V  P    Y  R  Y  F  Q  P  F  G  F  G   P  R  G  C  A  G  K 441 442 443 444 445 446 447  448 449 450  451 452 453 454 455 456 457 458 459 460
1321     TACATCGCCA TGGTGATGAT GAAAGCCATC CTCGTTACAC TTCTGAGACG ATTCACGTG                    1380
          Y  I  A  M  V  M  M   K  A  I   L  V  T  L  L  R  R  F  H  V 461 462 463 464 465 466 467 468 469 470  471 472 473 474 475 476 477 478 479 480
1381     AAGACATTGC AAGGACAGTG TGTTGAGAGC ATACAGAAGA TACACGACTT GTCCTTGCAC                   1440
          K  T  L  Q  G  Q  C  V  E  S   I  Q  K  I  H  D  L  S  L  H 481 482 483 484 485 486 487 488 489 490  491 492 493  494 495 496 497 498 499 500
1441     CCAGATGAGA CTAAAAACAT GCTGGAAATG ATCTTTACCC AAGAAACTC AGACAGGTGT                    1500
          P  D  E  T  K  N  M  L  E  M   I  F  T   P  R  N  S  D  R  C 501 502 503
1501     CTGGAACACT AG
          L  E  H
```

CYP19A1 POLYMORPHISMS

CROSS-REFERENCE TO RELATED APPLICATIONS

This application is a continuation-in-part of U.S. patent application Ser. No. 11/203,569, filed Aug. 12, 2005 now abandoned.

STATEMENT AS TO FEDERALLY SPONSORED RESEARCH

Funding for the work described herein was provided in part by the federal government under grant nos. GM61388, and GM35720, awarded by the National Institutes of Health. The federal government has certain rights in the invention.

TECHNICAL FIELD

This document relates to aromatase (CYP19A1) nucleic acid and amino acid sequence variants.

BACKGROUND

CYP19A1 is an enzyme that catalyzes the formation of aromatic C18 estrogens from C19 androgen. In humans, a number of tissues have the capacity to express aromatase, including the ovaries and testes, the placenta and fetal liver, adipose tissue, chondrocytes and osteoblasts of bone, the vasculature smooth muscle, and numerous sites in the brain, including several areas of the hypothalamus, limbic system, and cerebral cortex.

SUMMARY

This document provides methods and materials related to aromatase (CYP19A1) nucleic acid and amino acid sequence variants. For example, this document provides nucleic acid sequence variants that occur in both coding and non-coding regions of CYP19A1 nucleic acids. This document also provides CYP19A1 enzymes having one or more amino acid sequence variants. Such nucleic acid sequence variants and CYP19A1 enzymes can be used to identify, for example, humans having a particular genotype. For example, the nucleic acid sequence variants and CYP19A1 enzymes provided herein can be used to identify potential relationships among a group of humans.

This document is based, in part, on the discovery of sequence variants that occur in both coding and non-coding regions of CYP19A1 nucleic acids. Certain CYP19A1 nucleotide sequence variants may encode CYP19A1 enzymes that are associated with individual differences in enzymatic activity. Other CYP19A1 sequence variants in non-coding regions of the CYP19A1 nucleic acid may alter regulation of transcription and/or splicing of the CYP19A1 nucleic acid. Discovery of these sequence variants allows individual differences in enzyme activity in humans to be assessed such that particular treatment regimens can be tailored to an individual based on the presence or absence of one or more sequence variants. Identification of CYP19A1 sequence variants also may allow predisposition to certain clinical conditions to be assessed in individuals.

In one aspect, this document features an isolated nucleic acid molecule that includes a CYP19A1 nucleic acid sequence, wherein the nucleic acid molecule is at least ten nucleotides in length, and wherein the CYP19A1 nucleic acid sequence includes, or consists essentially of, a nucleotide sequence variant at a position selected from the group consisting of:

a) position 42, 109, 186, 602, 633, 963, or 1091 relative to the adenine in the CYP19A1 translation initiation codon within SEQ ID NO:1;

b) position −566, −554, −316, −278, −245, −35, or −2 relative to the intron/exon splice junction of exon I.1 within SEQ ID NO:1;

c) position −639, −632, −429, −149, −125, −124, −38, or −21 relative to the intron/exon splice junction of exon 2a within SEQ ID NO:1;

d) position −563, −562, or −241 relative to the intron/exon splice junction of exon I.4 within SEQ ID NO:1;

e) position −638 or −80 relative to the intron/exon splice junction of exon I.5 within SEQ ID NO:1;

f) position −651, −550, −543, −495, −439, −428, −408, −194, or −26 relative to the intron/exon splice junction of exon I.7 within SEQ ID NO:1;

g) position 25 relative to the intron/exon splice junction of intron I.7 within SEQ ID NO:1;

h) position −739, −725, −690, −425, −391, −108, −66, or −35 relative to the intron/exon splice junction of exon I.f within SEQ ID NO:1;

i) position −827, −757, −555, −217, or −125 relative to the intron/exon splice junction of exon I.2 within SEQ ID NO:1;

j) position −362, −301, or −273 relative to the intron/exon splicejunction of exon I.6 within SEQ ID NO:1;

k) position 53, 61, or 353 relative to the intron/exon splice junction of intron I.6 within SEQ ID NO:1;

l) position −83 relative to the intron/exon splice junction of exon PII within SEQ ID NO:1;

m) position −27 relative to the intron/exon splice junction of intron 2 within SEQ ID NO:1;

n) position 48 relative to the intron/exon splice junction of intron 3 within SEQ ID NO:1;

o) position 8 relative to the intron/exon splice junction of intron 4 within SEQ ID NO:1;

p) position 44 relative to the intron/exon splice junction of intron 6 within SEQ ID NO:1; and q) position 29 to the intron/exon splice junction of intron 8 within SEQ ID NO:1.

In certain embodiments, the nucleotide sequence variant is a nucleotide substitution. In certain embodiments, the nucleotide sequence variant is a guanine substitution for cytosine at position 42 relative to the adenine in the CYP19A1 translation initiation codon, a cytosine substitution for thymine at position 109 relative to the adenine in the CYP19A1 translation initiation codon, a thymine substitution for cytosine at position 186 relative to the adenine in the CYP19A1 translation initiation codon, a thymine substitution for cytosine at position 602 relative to the adenine in the CYP19A1 translation initiation codon, a cytosine substitution for thymine at position 633 relative to the adenine in the CYP19A1 translation initiation codon, a guanine substitution for cytosine at position 963 relative to the adenine in the CYP19A1 translation initiation codon, or a cytosine substitution for thymine at position 1091 relative to the adenine in the CYP19A1 translation initiation codon.

In certain embodiments, the nucleotide sequence variant is a thymine substitution for cytosine at position −566 relative to the intron/exon splice junction of exon I.1, a cytosine substitution for thymine at position −554 relative to the intron/exon splice junction of exon I.1, a cytosine substitution for thymine at position −316 relative to the intron/exon splice junction of exon I.1, a thymine substitution for cytosine at position −278 relative to the intron/exon splice junction of exon I.1, a thymine substitution for guanine at position −245 relative to the intron/exon splice junction of exon I.1, an adenine substitution for guanine at position −35 relative to the intron/exon splice junction of exon I.1, or an adenine substitution for guanine at position −2 relative to the intron/exon splice junction of exon I.1.

In certain embodiments, the nucleotide sequence variant is an adenine substitution for guanine at position −639 relative to the intron/exon splice junction of exon 2a within SEQ ID NO:1, a thymine substitution for cytosine at position −632 relative to the intron/exon splice junction of exon 2a within SEQ ID NO:1, a cytosine substitution for thymine at position −429 relative to the intron/exon splice junction of exon 2a within SEQ ID NO:1, a guanine substitution for cytosine at position −149 relative to the intron/exon splice junction of exon 2a within SEQ ID NO:1, a thymine substitution for cytosine at position −125 relative to the intron/exon splice junction of exon 2a within SEQ ID NO:1, an adenine substitution for guanine at position −124 relative to the intron/exon splice junction of exon 2a within SEQ ID NO:1, a guanine substitution for adenine at position −38 relative to the intron/exon splice junction of exon 2a within SEQ ID NO:1, or an adenine substitution for cytosine at position −21 relative to the intron/exon splice junction of exon 2a within SEQ ID NO:1.

In certain embodiments, the nucleotide sequence variant is an adenine substitution for guanine at position −563 relative to the intron/exon splice junction of exon I.4 within SEQ ID NO:1, an adenine substitution for cytosine at position −562 relative to the intron/exon splice junction of exon I.4 within SEQ ID NO:1, or a thymine substitution for guanine at position −241 relative to the intron/exon splice junction of exon I.4 within SEQ ID NO:1. In certain embodiments, the nucleotide sequence variant is a thymine substitution for cytosine at position −638 relative to the intron/exon splice junction of exon I.5 within SEQ ID NO:1 or a thymine substitution for adenine at position −80 relative to the intron/exon splice junction of exon I.5 within SEQ ID NO:1.

In certain embodiments, the nucleotide sequence variant is a thymine substitution for cytosine at position −651 relative to the intron/exon splice junction of exon I.7 within SEQ ID NO:1, an adenine substitution for guanine at position −550 relative to the intron/exon splice junction of exon I.7 within SEQ ID NO:1, an adenine substitution for guanine at position −543 relative to the intron/exon splice junction of exon I.7 within SEQ ID NO:1, an adenine substitution for guanine at position −495 relative to the intron/exon splice junction of exon I.7 within SEQ ID NO:1, a cytosine substitution for adenine at position −439 relative to the intron/exon splice junction of exon I.7 within SEQ ID NO:1, an adenine substitution for guanine at position −428 relative to the intron/exon splice junction of exon I.7 within SEQ ID NO:1, an adenine substitution for guanine at position −408 relative to the intron/exon splice junction of exon I.7 within SEQ ID NO:1, a thymine substitution for guanine at position −194 relative to the intron/exon splice junction of exon I.7 within SEQ ID NO:1, or a thymine substitution for cytosine at position −26 relative to the intron/exon splice junction of exon I.7 within SEQ ID NO:1.

In certain embodiments, the nucleotide sequence variant is an adenine substitution for guanine at position 25 relative to the intron/exon splice junction of intron I.7 within SEQ ID NO:1.

In certain embodiments, the nucleotide sequence variant is an adenine substitution for cytosine at position −739 relative to the intron/exon splice junction of exon I.f within SEQ ID NO:1, an adenine substitution for guanine at position −725 relative to the intron/exon splice junction of exon I.f within SEQ ID NO:1, a cytosine substitution for adenine at position −690 relative to the intron/exon splice junction of exon I.f within SEQ ID NO:1, a thymine substitution for cytosine at position −425 relative to the intron/exon splice junction of exon I.f within SEQ ID NO:1, a guanine substitution for thymine at position −391 relative to the intron/exon splice junction of exon I.f within SEQ ID NO:1, a thymine or adenine substitution for cytosine at position −108 relative to the intron/exon splice junction of exon I.f within SEQ ID NO:1, a thymine substitution for cytosine at position −66 relative to the intron/exon splice junction of exon I.f within SEQ ID NO:1, or a guanine substitution for adenine at position −35 relative to the intron/exon splice junction of exon I.f within SEQ ID NO:1.

In certain embodiments, the nucleotide sequence variant is a guanine substitution for adenine at position −827 relative to the intron/exon splice junction of exon I.2 within SEQ ID NO:1, an adenine substitution for guanine at position −757 relative to the intron/exon splice junction of exon I.2 within SEQ ID NO:1, an adenine substitution for thymine at position −555 relative to the intron/exon splice junction of exon I.2 within SEQ ID NO:1, an adenine substitution for guanine at position −217 relative to the intron/exon splice junction of exon I.2 within SEQ ID NO:1, or a thymine substitution for cytosine at position −125 relative to the intron/exon splice junction of exon I.2 within SEQ ID NO:1.

In certain embodiments, the nucleotide sequence variant is a thymine substitution for cytosine at position −362 relative to the intron/exon splicejunction of exon I.6 within SEQ ID NO:1, a guanine substitution for thymine at position −301 relative to the intron/exon splicejunction of exon I.6 within SEQ ID NO:1, or an adenine substitution for thymine at position −273 relative to the intron/exon splicejunction of exon I.6 within SEQ ID NO:1.

In certain embodiments, the nucleotide sequence variant is an adenine substitution for cytosine at position −83 relative to the intron/exon splice junction of exon PII within SEQ ID NO:1.

In certain embodiments, the nucleotide sequence variant is a cytosine substitution for thymine at position −27 relative to the intron/exon splice junction of intron 2 within SEQ ID NO:1.

In certain embodiments, the nucleotide sequence variant is an adenine substitution for guanine at position 48 relative to the intron/exon splice junction of intron 3 within SEQ ID NO:1.

In certain embodiments, the nucleotide sequence variant is an adenine substitution for guanine at position 8 relative to the intron/exon splice junction of intron 4 within SEQ ID NO:1.

In certain embodiments, the nucleotide sequence variant is a cytosine substitution for guanine at position 44 relative to the intron/exon splice junction of intron 6 within SEQ ID NO:1.

In certain embodiments, the nucleotide sequence variant is a thymine substitution for cytosine at position 29 to the intron/exon splice junction of intron 8 within SEQ ID NO:1.

In another aspect, this document features an isolated nucleic acid molecule that includes, or consists essentially of, a CYP19A1 nucleic acid sequence, wherein the nucleic acid molecule is at least ten nucleotides in length, and wherein the CYP19A1 nucleic acid sequence includes two or more nucleotide sequence variants at positions selected from the group consisting of:

a) position 42, 109, 186, 602, 633, 963, or 1091 relative to the adenine in the CYP19A1 translation initiation codon within SEQ ID NO:1;

b) position −566, −554, −316, −278, −245, −35, or −2 relative to the intron/exon splice junction of exon I.1 within SEQ ID NO:1;

c) position −639, −632, −429, −149, −125, −124, −38, or −21 relative to the intron/exon splice junction of exon 2a within SEQ ID NO:1;

d) position −563, −562, or −241 relative to the intron/exon splice junction of exon I.4 within SEQ ID NO:1;

e) position −638 or −80 relative to the intron/exon splice junction of exon I.5 within SEQ ID NO:1;

f) position −651, −550, −543, −495, −439, −428, −408, −194, or −26 relative to the intron/exon splice junction of exon I.7 within SEQ ID NO:1;

g) position 25 relative to the intron/exon splice junction of intron I.7 within SEQ ID NO:1;

h) position −739, −725, −690, −425, −391, −108, −66, or −35 relative to the intron/exon splice junction of exon I.f within SEQ ID NO:1;

i) position −827, −757, −555, −217, or −125 relative to the intron/exon splice junction of exon I.2 within SEQ ID NO:1;

j) position −362, −301, or −273 relative to the intron/exon splicejunction of exon I.6 within SEQ ID NO:1;

k) position 53, 61, or 353 relative to the intron/exon splice junction of intron I.6 within SEQ ID NO:1;

l) position −83 relative to the intron/exon splice junction of exon PII within SEQ ID NO:1;

m) position −27 relative to the intron/exon splice junction of intron 2 within SEQ ID NO:1;

n) position 48 relative to the intron/exon splice junction of intron 3 within SEQ ID NO:1;

o) position 8 relative to the intron/exon splice junction of intron 4 within SEQ ID NO:1;

p) position 44 relative to the intron/exon splice junction of intron 6 within SEQ ID NO:1; and q) position 29 to the intron/exon splice junction of intron 8 within SEQ ID NO:1.

In another aspect, this document features an isolated nucleic acid molecule that includes, or consists essentially of, a CYP19A1 nucleic acid sequence, wherein the nucleic acid molecule is at least ten nucleotides in length, wherein the nucleic acid molecule includes a linkage disequilibrium tag-SNP, and wherein the CYP19A1 nucleic acid sequence includes a nucleotide sequence variant at a position selected from the group consisting of: position −725 relative to the intron/exon splice junction of exon I.f within SEQ ID NO:1; position 602 relative to the adenine in the CYP19A1 translation initiation codon within SEQ ID NO:1; position −125 relative to the intron/exon splice junction of exon 2a within SEQ ID NO:1; position −21 relative to the intron/exon splice junction of exon 2a within SEQ ID NO:1; position −83 relative to the intron/exon splice junction of exon PII within SEQ ID NO:1; and position −278 relative to the intron/exon splice junction of exon I.1 within SEQ ID NO:1.

In another aspect, this document features an isolated nucleic acid encoding a CYP19A1 polypeptide, wherein the polypeptide includes, or consists essentially of, a CYP19A1 amino acid sequence variant relative to the amino acid sequence of SEQ ID NO:3, and wherein the amino acid sequence variant is at a residue selected from the group consisting of 201 and 364.

In certain embodiments, the amino acid sequence variant is a methionine at residue 201 or a threonine at residue 364.

In another aspect, this document features an isolated CYP19A1 polypeptide, wherein the polypeptide includes a CYP19A1 amino acid sequence variant relative to the amino acid sequence of SEQ ID NO:3, wherein the amino acid sequence variant is at a residue selected from the group consisting of 201 and 364.

In certain embodiments, the amino acid sequence variant is a methionine at residue 201 or a threonine at residue 364.

In another aspect, this document features an isolated nucleic acid that includes, or consists essentially of, a variant CYP19A1 nucleic acid sequence, wherein the variant CYP19A1 nucleic acid sequence is selected from the group consisting of:

a) at least a ten-nucleotide sequence of SEQ ID NO:1, wherein the sequence includes nucleotide position 42 relative to the adenine in the CYP19A1 translation initiation codon of SEQ ID NO:1, with the proviso that the nucleotide at position 42 is guanine;

b) at least a ten-nucleotide sequence of SEQ ID NO:1, wherein the sequence includes nucleotide position 109 relative to the adenine in the CYP19A1 translation initiation codon of SEQ ID NO:1, with the proviso that the nucleotide at position 109 is cytosine;

c) at least a ten-nucleotide sequence of SEQ ID NO:1, wherein the sequence includes nucleotide position 186 relative to the adenine in the CYP19A1 translation initiation codon of SEQ ID NO:1, with the proviso that the nucleotide at position 186 is thymine;

d) at least a ten-nucleotide sequence of SEQ ID NO:1, wherein the sequence includes nucleotide position 602 relative to the adenine in the CYP19A1 translation initiation codon of SEQ ID NO:1, with the proviso that the nucleotide at position 602 is thymine;

e) at least a ten-nucleotide sequence of SEQ ID NO:1, wherein the sequence includes nucleotide position 633 relative to the adenine in the CYP19A1 translation initiation codon of SEQ ID NO:1, with the proviso that the nucleotide at position 633 is cytosine;

f) at least a ten-nucleotide sequence of SEQ ID NO:1, wherein the sequence includes nucleotide position 963 relative to the adenine in the CYP19A1 translation initiation codon of SEQ ID NO:1, with the proviso that the nucleotide at position 963 is guanine;

g) at least a ten-nucleotide sequence of SEQ ID NO:1, wherein the sequence includes nucleotide position 1091 relative to the adenine in the CYP19A1 translation initiation codon of SEQ ID NO:1, with the proviso that the nucleotide at position 1091 is cytosine;

h) at least a ten-nucleotide sequence of SEQ ID NO:1, wherein the sequence includes nucleotide position −566 relative to the intron/exon splice junction of exon I.1 of SEQ ID NO:1, with the proviso that the nucleotide at position −566 is thymine;

i) at least a ten-nucleotide sequence of SEQ ID NO:1, wherein the sequence includes nucleotide position −554 relative to the intron/exon splice junction of exon I.1 of SEQ ID NO:1, with the proviso that the nucleotide at position −554 is cytosine;

j) at least a ten-nucleotide sequence of SEQ ID NO:1, wherein the sequence includes nucleotide position −316 relative to the intron/exon splice junction of exon I.1 of SEQ ID NO:1, with the proviso that the nucleotide at position −316 is cytosine;

k) at least a ten-nucleotide sequence of SEQ ID NO:1, wherein the sequence includes nucleotide position −278 relative to the intron/exon splice junction of exon I.1 of SEQ ID NO:1, with the proviso that the nucleotide at position −278 is thymine;

l) at least a ten-nucleotide sequence of SEQ ID NO:1, wherein the sequence includes nucleotide position −245 relative to the intron/exon splice junction of exon I.1 of SEQ ID NO:1, with the proviso that the nucleotide at position −245 is thymine;

m) at least a ten-nucleotide sequence of SEQ ID NO:1, wherein the sequence includes nucleotide position −35 relative to the intron/exon splice junction of exon I.1 of SEQ ID NO:1, with the proviso that the nucleotide at position −35 is adenine;

n) at least a ten-nucleotide sequence of SEQ ID NO:1, wherein the sequence includes nucleotide position −2 relative to the intron/exon splice junction of exon I.1 of SEQ ID NO:1, with the proviso that the nucleotide at position −2 is adenine;

o) at least a ten-nucleotide sequence of SEQ ID NO:1, wherein the sequence includes nucleotide position −639 relative to the intron/exon splice junction of exon 2a of SEQ ID NO:1, with the proviso that the nucleotide at position −639 is adenine;

p) at least a ten-nucleotide sequence of SEQ ID NO:1, wherein the sequence includes nucleotide position −632 relative to the intron/exon splice junction of exon 2a of SEQ ID NO:1, with the proviso that the nucleotide at position −632 is thymine;

q) at least a ten-nucleotide sequence of SEQ ID NO:1, wherein the sequence includes nucleotide position −429 relative to the intron/exon splice junction of exon 2a of SEQ ID NO:1, with the proviso that the nucleotide at position −429 is cytosine;

r) at least a ten-nucleotide sequence of SEQ ID NO:1, wherein the sequence includes nucleotide position −149 relative to the intron/exon splice junction of exon 2a of SEQ ID NO:1, with the proviso that the nucleotide at position −149 is guanine;

s) at least a ten-nucleotide sequence of SEQ ID NO:1, wherein the sequence includes nucleotide position −125 relative to the intron/exon splice junction of exon 2a of SEQ ID NO:1, with the proviso that the nucleotide at position −125 is thymine;

t) at least a ten-nucleotide sequence of SEQ ID NO:1, wherein the sequence includes nucleotide position −124 relative to the intron/exon splice junction of exon 2a of SEQ ID NO:1, with the proviso that the nucleotide at position −124 is adenine;

u) at least a ten-nucleotide sequence of SEQ ID NO:1, wherein the sequence includes nucleotide position −38 relative to the intron/exon splice junction of exon 2a of SEQ ID NO:1, with the proviso that the nucleotide at position −38 is guanine;

v) at least a ten-nucleotide sequence of SEQ ID NO:1, wherein the sequence includes nucleotide position −21 relative to the intron/exon splice junction of exon 2a of SEQ ID NO:1, with the proviso that the nucleotide at position −21 is adenine;

w) at least a ten-nucleotide sequence of SEQ ID NO:1, wherein the sequence includes nucleotide position −563 relative to the intron/exon splice junction of exon I.4 of SEQ ID NO:1, with the proviso that the nucleotide at position −563 is adenine;

x) at least a ten-nucleotide sequence of SEQ ID NO:1, wherein the sequence includes nucleotide position −562 relative to the intron/exon splice junction of exon I.4 of SEQ ID NO:1, with the proviso that the nucleotide at position −562 is adenine;

y) at least a ten-nucleotide sequence of SEQ ID NO:1, wherein the sequence includes nucleotide position −241 relative to the intron/exon splice junction of exon I.4 of SEQ ID NO:1, with the proviso that the nucleotide at position −241 is thymine;

z) at least a ten-nucleotide sequence of SEQ ID NO:1, wherein the sequence includes nucleotide position −638 relative to the intron/exon splice junction of exon I.5 of SEQ ID NO:1, with the proviso that the nucleotide at position −638 is thymine;

aa) at least a ten-nucleotide sequence of SEQ ID NO:1, wherein the sequence includes nucleotide position −80 relative to the intron/exon splice junction of exon I.5 of SEQ ID NO:1, with the proviso that the nucleotide at position −80 is thymine;

bb) at least a ten-nucleotide sequence of SEQ ID NO:1, wherein the sequence includes nucleotide position −651 relative to the intron/exon splice junction of exon I.7 of SEQ ID NO:1, with the proviso that the nucleotide at position −651 is thymine;

cc) at least a ten-nucleotide sequence of SEQ ID NO:1, wherein the sequence includes nucleotide position −550 relative to the intron/exon splice junction of exon I.7 of SEQ ID NO:1, with the proviso that the nucleotide at position −550 is adenine;

dd) at least a ten-nucleotide sequence of SEQ ID NO:1, wherein the sequence includes nucleotide position −543 relative to the intron/exon splice junction of exon I.7 of SEQ ID NO:1, with the proviso that the nucleotide at position −543 is adenine;

ee) at least a ten-nucleotide sequence of SEQ ID NO:1, wherein the sequence includes nucleotide position −495 relative to the intron/exon splice junction of exon I.7 of SEQ ID NO:1, with the proviso that the nucleotide at position −495 is adenine;

ff) at least a ten-nucleotide sequence of SEQ ID NO:1, wherein the sequence includes nucleotide position −439 relative to the intron/exon splice junction of exon I.7 of SEQ ID NO:1, with the proviso that the nucleotide at position −439 is cytosine;

gg) at least a ten-nucleotide sequence of SEQ ID NO:1, wherein the sequence includes nucleotide position −428 relative to the intron/exon splice junction of exon I.7 of SEQ ID NO:1, with the proviso that the nucleotide at position −428 is adenine;

hh) at least a ten-nucleotide sequence of SEQ ID NO:1, wherein the sequence includes nucleotide position −408 relative to the intron/exon splice junction of exon I.7 of SEQ ID NO:1, with the proviso that the nucleotide at position −408 is adenine;

ii) at least a ten-nucleotide sequence of SEQ ID NO:1, wherein the sequence includes nucleotide position 194 relative to the intron/exon splice junction of exon I.7 of SEQ ID NO:1, with the proviso that the nucleotide at position 194 is thymine;

jj) at least a ten-nucleotide sequence of SEQ ID NO:1, wherein the sequence includes nucleotide position −26 relative to the intron/exon splice junction of exon I.7 of SEQ ID NO:1, with the proviso that the nucleotide at position −26 is thymine;

kk) at least a ten-nucleotide sequence of SEQ ID NO:1, wherein the sequence includes nucleotide position 25 relative to the intron/exon splice junction of intron I.7 of SEQ ID NO:1, with the proviso that the nucleotide at position 25 is adenine;

ll) at least a ten-nucleotide sequence of SEQ ID NO:1, wherein the sequence includes nucleotide position −739 relative to the intron/exon splice junction of exon I.f of SEQ ID NO:1, with the proviso that the nucleotide at position −739 is adenine;

mm) at least a ten-nucleotide sequence of SEQ ID NO:1, wherein the sequence includes nucleotide position −725 relative to the intron/exon splice junction of exon I.f of SEQ ID NO:1, with the proviso that the nucleotide at position −725 is adenine;

nn) at least a ten-nucleotide sequence of SEQ ID NO:1, wherein the sequence includes nucleotide position −690 relative to the intron/exon splice junction of exon I.f of SEQ ID NO:1, with the proviso that the nucleotide at position −690 is cytosine;

oo) at least a ten-nucleotide sequence of SEQ ID NO:1, wherein the sequence includes nucleotide position −425 relative to the intron/exon splice junction of exon I.f of SEQ ID NO:1, with the proviso that the nucleotide at position −425 is thymine;

pp) at least a ten-nucleotide sequence of SEQ ID NO:1, wherein the sequence includes nucleotide position −391 relative to the intron/exon splice junction of exon I.f of SEQ ID NO:1, with the proviso that the nucleotide at position −391 is guanine;

qq) at least a ten-nucleotide sequence of SEQ ID NO:1, wherein the sequence includes nucleotide position −108 relative to the intron/exon splice junction of exon I.f of SEQ ID NO:1, with the proviso that the nucleotide at position −108 is adenine;

rr) at least a ten-nucleotide sequence of SEQ ID NO:1, wherein the sequence includes nucleotide position −108 relative to the intron/exon splice junction of exon I.f of SEQ ID NO:1, with the proviso that the nucleotide at position −108 is thymine;

ss) at least a ten-nucleotide sequence of SEQ ID NO:1, wherein the sequence includes nucleotide position −66 relative to the intron/exon splice junction of exon I.f of SEQ ID NO:1, with the proviso that the nucleotide at position −66 is thymine;

uu) at least a ten-nucleotide sequence of SEQ ID NO:1, wherein the sequence includes nucleotide position −35 relative to the intron/exon splice junction of exon I.f of SEQ ID NO:1, with the proviso that the nucleotide at position −35 is guanine;

vv) at least a ten-nucleotide sequence of SEQ ID NO:1, wherein the sequence includes nucleotide position −827 relative to the intron/exon splice junction of exon I.2 of SEQ ID NO:1, with the proviso that the nucleotide at position −827 is guanine;

ww) at least a ten-nucleotide sequence of SEQ ID NO:1, wherein the sequence includes nucleotide position −757 relative to the intron/exon splice junction of exon I.2 of SEQ ID NO:1, with the proviso that the nucleotide at position −757 is adenine;

xx) at least a ten-nucleotide sequence of SEQ ID NO:1, wherein the sequence includes nucleotide position −555 relative to the intron/exon splice junction of exon I.2 of SEQ ID NO:1, with the proviso that the nucleotide at position −555 is adenine;

yy) at least a ten-nucleotide sequence of SEQ ID NO:1, wherein the sequence includes nucleotide position −217 relative to the intron/exon splice junction of exon I.2 of SEQ ID NO:1, with the proviso that the nucleotide at position −217 is adenine;

zz) at least a ten-nucleotide sequence of SEQ ID NO:1, wherein the sequence includes nucleotide position −125 relative to the intron/exon splice junction of exon I.2 of SEQ ID NO:1, with the proviso that the nucleotide at position −125 is thymine;

aaa) at least a ten-nucleotide sequence of SEQ ID NO:1, wherein the sequence includes nucleotide position −362 relative to the intron/exon splice junction of exon I.6 of SEQ ID NO:1, with the proviso that the nucleotide at position −362 is thymine;

bbb) at least a ten-nucleotide sequence of SEQ ID NO:1, wherein the sequence includes nucleotide position −301 relative to the intron/exon splice junction of exon I.6 of SEQ ID NO:1, with the proviso that the nucleotide at position −301 is guanine;

ccc) at least a ten-nucleotide sequence of SEQ ID NO:1, wherein the sequence includes nucleotide position −273 relative to the intron/exon splice junction of exon I.6 of SEQ ID NO:1, with the proviso that the nucleotide at position −273 is adenine;

ddd) at least a ten-nucleotide sequence of SEQ ID NO:1, wherein the sequence includes nucleotide position −83 relative to the intron/exon splice junction of exon PII of SEQ ID NO:1, with the proviso that the nucleotide at position −83 is adenine;

eee) at least a ten-nucleotide sequence of SEQ ID NO:1, wherein the sequence includes nucleotide position −27 relative to the intron/exon splice junction of intron 2 of SEQ ID NO:1, with the proviso that the nucleotide at position −27 is cytosine;

fff) at least a ten-nucleotide sequence of SEQ ID NO:1, wherein the sequence includes nucleotide position 48 relative to the intron/exon splice junction of intron 3 of SEQ ID NO:1, with the proviso that the nucleotide at position 48 is adenine;

ggg) at least a ten-nucleotide sequence of SEQ ID NO:1, wherein the sequence includes nucleotide position 8 relative to the intron/exon splice junction of intron 4 of SEQ ID NO:1, with the proviso that the nucleotide at position 8 is adenine;

hhh) at least a ten-nucleotide sequence of SEQ ID NO:1, wherein the sequence includes nucleotide position 44 relative to the intron/exon splice junction of intron 6 of SEQ ID NO:1, with the proviso that the nucleotide at position 44 is cytosine;

iii) at least a ten-nucleotide sequence of SEQ ID NO:1, wherein the sequence includes nucleotide position 29 relative to the intron/exon splice junction of intron 8 of SEQ ID NO:1, with the proviso that the nucleotide at position 29 is thymine; and jjj) the complement of any one of a) through iii).

In certain embodiments, the CYP19A1 nucleotide sequences can include one or more of the variants described herein in combination with one or more previously-described variant(s).

In another aspect, this document features a method for predicting the therapeutic efficacy of a compound in a subject, wherein the compound inhibits aromatase activity, the method includes:

a) estimating the level of aromatase activity in the subject d by determining whether the subject contains a variant CYP19A1 nucleic acid, wherein the variant CYP19A1 nucleic acid includes a non-synonymous single nucleotide polymorphism; and b) correlating the level of aromatase activity with the ability of the compound to inhibit aromatase activity, wherein the compound is predicted to be therapeutically effective if the level of aromatase activity is reduced in the subject, and wherein the compound is predicted not to be therapeutically effective if the level of aromatase activity is increased in the subject.

In another aspect, this document features a method for estimating the dose of a compound for administration to a subject, wherein the compound inhibits aromatase activity, the method includes determining the level of aromatase activity in a biological sample from the subject, wherein the dose is estimated to be higher if the level of aromatase activity is increased in the biological sample as compared to a control level of aromatase activity, and wherein the dose is estimated to be lower if the level of aromatase activity is decreased in the biological sample as compared to the control level of aromatase activity.

In certain embodiments, the aromatase activity is CYP19A1 activity.

In certain embodiments, the determining of the level of aromatase activity includes determining whether the subject contains a variant CYP19A1 nucleic acid.

In certain embodiments, the variant CYP19A1 nucleic acid includes a non-synonymous single nucleotide polymorphism.

In still another aspect, this document features a method for determining if a subject is predisposed to a disease. The method can include: a) obtaining a biological sample from the mammal, and b) detecting the presence or absence of a CYP19A1 nucleotide sequence variant in the sample, wherein predisposition to the disease is determined based on the presence or absence of the variant. The method can further include detecting the presence or absence of a plurality of the CYP19A1 nucleotide sequence variants in the sample to obtain a variant profile of the subject, and predisposition to the disease is determined based on the variant profile.

This document also features a method for assisting a medical or research professional. The method can include: a) obtaining a biological sample from a subject, and b) detecting the presence or absence of a plurality of CYP19A1 nucleotide sequence variants in the sample to obtain a variant profile of the subject. The method can further include communicating the profile to the medical or research professional.

In another aspect, this document features a method for determining the aromatase status of an individual, wherein the method includes determining whether the subject contains a variant CYP19A1 nucleic acid.

In yet another aspect, this document features a method for predicting the therapeutic efficacy of a compound in a subject, wherein the compound is an aromatase inhibitor, e.g., a nonsteroidal agent, e.g., anastrozole and letrozole, or a steroid agent, e.g., exemestane. The method can include: a) determining the aromatase status of the subject; and b) correlating the aromatase status with the ability of the compound to inhibit aromatase activity. Determination of the aromatase status can include determining whether the subject has a variant CYP19A1 nucleic acid. The variant CYP19A1 nucleic acid can contain a single nucleotide polymorphism. Alternatively, determination of the aromatase status can include measuring aromatase activity (e.g., CYP19A1 activity) in a biological sample from the subject. The subject can suffer from or have a predisposition to an aromatase-mediated or estrogen-dependent disease, e.g., an estrogen-responsive cancer (e.g., breast cancer), endometrial cancer, and endometriosis.

This document also features a method for predicting the therapeutic efficacy of a compound in a subject, wherein the compound is an aromatase inhibitor, e.g., a nonsteroidal agent, e.g., anastrozole and letrozole, or a steroid agent, e.g., exemestane. The method can include: a) estimating the level of aromatase activity in the subject; and b) correlating the level of aromatase activity with the ability of the compound (e.g., aromatase inhibitor) to inhibit aromatase activity. The aromatase can be CYP19A 1. The aromatase activity can be estimated in vitro in a biological sample from the subject. Alternatively, the level of aromatase activity in the subject can be estimated by determining whether the subject has a variant CYP19A1 nucleic acid. The variant CYP19A1 nucleic acid can contain a non-synonymous single nucleotide polymorphism. The subject can suffer from or have a predisposition to an aromatase-mediated or estrogen-dependent disease, e.g., an estrogen-responsive cancer (e.g., breast cancer), endometrial cancer, or endometriosis.

In yet another aspect, this document features a method for estimating the dose of a compound for administration to a subject, wherein the compound is an aromatase inhibitor, e.g., a nonsteroidal agent, e.g., anastrozole and letrozole, or a steroid agent, e.g., exemestane. The method can include determining the level of aromatase activity in a biological sample from the subject. The dose can be estimated to be higher if the level of aromatase activity is increased in the biological sample as compared to a control level of aromatase activity, and estimated to be lower if the level of aromatase activity is decreased in the biological sample as compared to the control level of aromatase activity. The aromatase activity can be CYP19A1 activity. Determination of the level of aromatase activity can include determining whether the subject has a variant CYP19A1 nucleic acid. The variant CYP19A1 nucleic acid can contain a non-synonymous single nucleotide polymorphism. The subject can suffer from or have a predisposition to an aromatase-mediated or estrogen-dependent disease, e.g., an estrogen-responsive cancer (e.g., breast cancer), endometrial cancer, and endometriosis.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description and drawings, and from the claims.

DESCRIPTION OF DRAWINGS

FIG. 1 is a depiction of the nucleotide sequence of the reference CYP19A1 (SEQ ID NO:1). Coding sequences are depicted in bold type. Introns are in regular type. A promoter (PII) and splice site are in italics. Positions of single nucleotide polymorphisms (SNPs) are shaded. Start and stop codons are double-underlined. Primers within coding sequences are underlined. The corresponding amino acid sequences of translated coding sequences are provided below the nucleotide sequence (SEQ ID NOs:4-12, respectively).

FIG. 2 is a depiction of a cDNA sequence (SEQ ID NO:2) containing the open reading frame of the reference CYP19A1. FIG. 2 also shows the reference amino acid sequence (SEQ ID NO:3) of the encoded CYP19A1. Positions of SNPs are shaded, as are the positions of amino acid changes that result from the SNPs. Start and stop codons are double-underlined.

DETAILED DESCRIPTION

Figure 3:
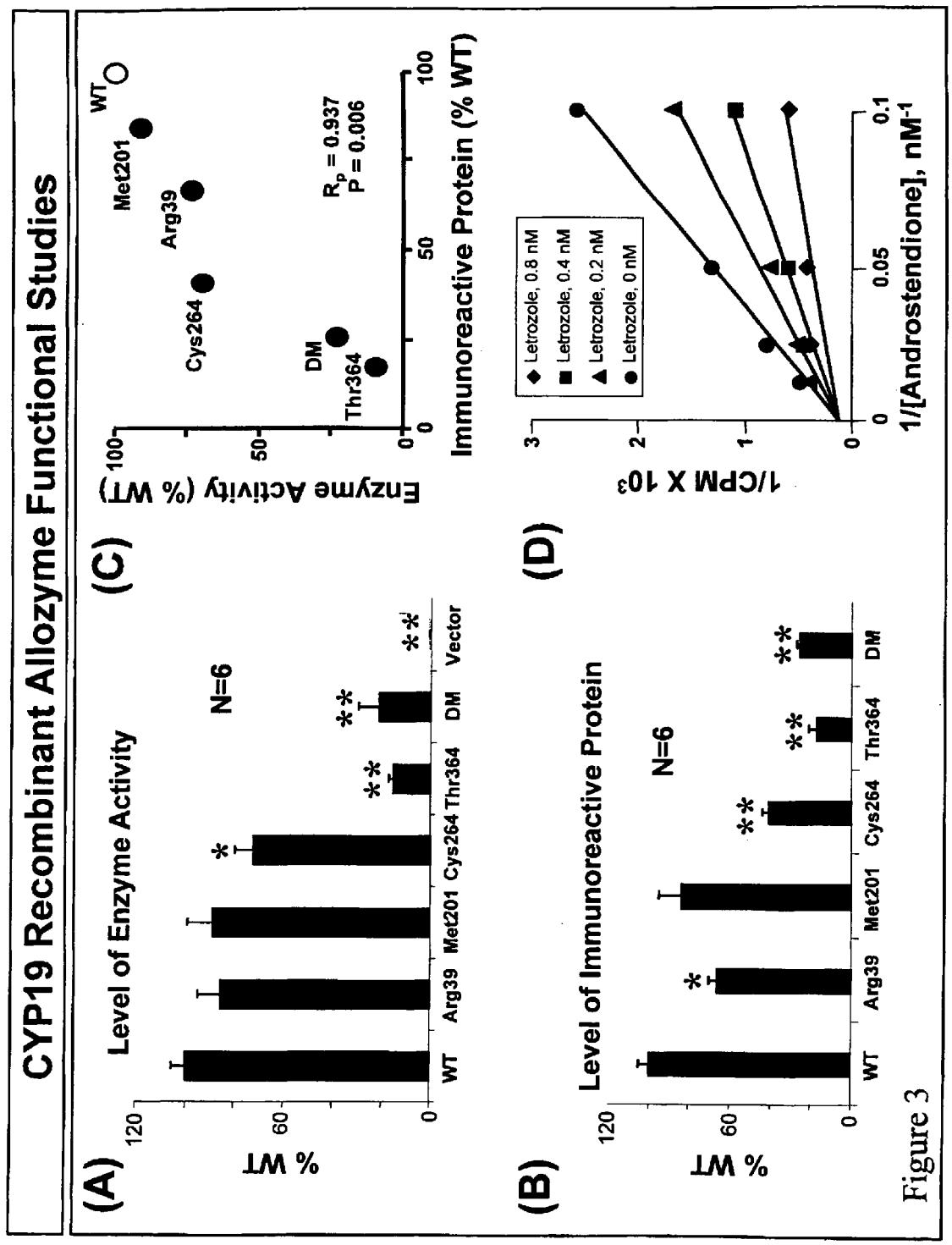
FIGS. 3A to 3D depict the characterization of CYP19A1 recombinant allozyme enzyme activity, immunoreactive protein levels, and inhibitor kinetics. (3A) Average levels of enzyme activity are shown for each of the recombinant allozymes, assayed with 20 nM androstenedione as substrate. All values have been corrected for transfection efficiency. Each bar represents the average of 6 independent transfections (mean ±SEM). *=$P<0.05$ and **=$P<0.001$ when compared to the wild type allozyme. The Arg39, Met201 and Cys264 variants also differed significantly from the Thr362 and DM allozymes (P<0.05). (3B) Average levels of immunoreactive protein on the basis of Western blot analysis. Each bar represents the average of 6 independent transfections (mean ±SEM). *=P<0.05 and **=P<0.001 when compared to the wild type allozyme. In addition, the Met201 variant differed significantly (P<0.05) from the Cys264, Thr364 and DM allozymes while the Arg39 allozyme differed significantly (P<0.05) only from the Thr362 and the DM variants. (3C) Correlation of levels of CYP19A1 enzyme activity and immunoreactive protein for recombinant allozymes. The correlation was still significant (Rp=0.92, P<0.03) even if the double mutant (DM) data were not included in the analysis. (3D) Letrozole inhibitor kinetics performed with wild type CYP19A1. The double inverse plots show the effect of various concentrations of letrozole on CYP19A1 enzyme activity.

This document features CYP19A1 nucleotide and amino acid sequence variants. CYP19A1 is an enzyme that synthesizes estrogens by converting C19 androgens (e.g., androstenedione and testosterone) to aromatic C18 estrogenic steroids (e.g., estrone and 17-estradiol). Known substrates of CYP191A include testosterone, androstenedione, and 16α hydroxy androstenedione. CYP19A1 also is known as aromatase, aromatase cytochrome P450, and estrogen synthetase, and its gene symbols include ARO, ARO1, CPV1, CYAR, CYP19, and P-450AROM. The aromatase gene is located as a single copy on chromosome 15q21.2 and has a highly complex gene structure. See generally Simpson, E. R., et al., *Endocr. Rev.* (1994) 15(3):342-55; Simpson, E. R., et al., *Annu. Rev. Physiol.* (2002) 64:93-127; Bulun, S. E., et al., *J. Steroid Biochem. Molec. Biol.* (2003) 86(3-5):219-224; Sebastian, S. and S. E. Bulun, *J. Clin. Endocrinol. Metab.* (2001) 86(10): p. 4600-4602.

Increased levels of aromatase may be involved in mediating certain disorders, e.g., breast cancer, endometrial cancer, and endometriosis, and it may be expressed at higher levels in breast cancer cells and/or surrounding adipose stromal cells than in non-cancerous breast cells. Aromatase inhibitors (e.g., anastrozole and letrozole and exemestane) have been found to be valuable in treating these estrogen-dependent and aromatase-mediated diseases including breast cancer. Aromatase inhibitors are increasingly being used to treat postmenopausal women with estrogen-responsive breast cancer. Thus, detecting CYP19A1 nucleic acid and amino acid sequence variants can facilitate the prediction of therapeutic efficacy and/or the effective dose of such agents on an individual basis.

In addition, genetically-based variations in CYP19A1 activity that lead to altered levels of CYP19A1 or altered CYP19A1 activity may be important in certain clinical disorders, e.g., aromatase-mediated diseases. For example, placental aromatase deficiency can result in maternal virilization and pseudohermaphroditism of female fetus. Aromatase gene deficiency in females can result in clitoromegaly and posterior labioscotal fusion at birth, absence of growth spur and breast development, primary amenorrhea, virilization and multicystic ovaries in adult. Aromatase gene deficiency in males can result in extremely tall height with osteoporosis, macroorchidism and infertility in adult while overexpression of aromatase in males can result in estrogen excess, gynecomastia, premature growth spurt, early fusion of epiphyses, and decreased adult height. As such, detecting CYP19A1 nucleic acid and amino acid sequence variants may also indicate predisposition to such disorders.

Nucleic Acid Molecules

This document features isolated nucleic acids that include a CYP19A1 nucleic acid sequence. The CYP19A1 nucleic acid sequence includes a nucleotide sequence variant and nucleotides flanking the sequence variant. As used herein, "isolated nucleic acid" refers to a nucleic acid that is separated from other nucleic acid molecules that are present in a mammalian genome, including nucleic acids that normally flank one or both sides of the nucleic acid in a mammalian genome (e.g., nucleic acids that encode non-CYP19A1 proteins). The term "isolated" as used herein with respect to nucleic acids also includes any non-naturally-occurring nucleic acid sequence since such non-naturally-occurring sequences are not found in nature and do not have immediately contiguous sequences in a naturally-occurring genome.

An isolated nucleic acid can be, for example, a DNA molecule, provided one of the nucleic acid sequences normally found immediately flanking that DNA molecule in a naturally-occurring genome is removed or absent. Thus, an isolated nucleic acid includes, without limitation, a DNA molecule that exists as a separate molecule (e.g., a chemically synthesized nucleic acid, or a cDNA or genomic DNA fragment produced by PCR or restriction endonuclease treatment) independent of other sequences as well as DNA that is incorporated into a vector, an autonomously replicating plasmid, a virus (e.g., a retrovirus, lentivirus, adenovirus, or herpes virus), or into the genomic DNA of a prokaryote or eukaryote. In addition, an isolated nucleic acid can include an engineered nucleic acid such as a recombinant DNA molecule that is part of a hybrid or fusion nucleic acid. A nucleic acid existing among hundreds to millions of other nucleic acids within, for example, cDNA libraries or genomic libraries, or gel slices containing a genomic DNA restriction digest, is not to be considered an isolated nucleic acid.

Nucleic acids provided herein can be at least about 8 nucleotides in length. For example, the nucleic acid can be about 8, 9, 10-20 (e.g., 11, 12, 13, 14, 15, 16, 17, 18, 19, or 20 nucleotides in length), 20-50, 50-100 or greater than 100 nucleotides in length (e.g., greater than 150, 200, 250, 300, 350, 400, 450, 500, 750, 1000, 1500, or 2000 nucleotides in length). Nucleic acids provided herein can be in a sense or antisense orientation, can be complementary to the CYP19A1 reference sequence, and can be DNA, RNA, or nucleic acid analogs. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine or 5-bromo-2'-doxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, Summerton and Weller, *Antisense Nucleic Acid Drug Dev.* (1997) 7(3):187-195; and Hyrup et al. (1996) *Bioorgan. Med. Chem.* 4(1):5-23. In addition, the deoxyphosphate backbone can be replaced with, for example, a phosphorothioate or phosphorodithioate backbone, a phosphoroamidite, or an alkyl phosphotriester backbone.

As used herein, "nucleotide sequence variant" refers to any alteration in a CYP19A1 reference sequence, and includes variations that occur in coding and non-coding regions, including exons, introns, and untranslated sequences. Nucleotides are referred to herein by the standard one-letter designation (A, C, G, or T). Variations include single nucleotide substitutions, deletions of one or more nucleotides, and insertions of one or more nucleotides. The reference CYP19A1 nucleic acid sequence is provided in FIG. 1 (SEQ ID NO:1) and in GenBank (Accession No. NT_010194.16, the reverse complement of nucleotides 22290228-22423334). A reference CYP19A1 cDNA including the CYP19A1 ORF is provided in FIG. 2 (SEQ ID NO:2) and in GenBank (Accession No. NM_000103.2). The corresponding reference CYP19A1 amino acid sequence also is provided in FIG. 2 (SEQ ID NO:3).

The CYP19A1 gene spans 123 kb and includes a 30 kb coding region with 9 translated exons, including exons 2 to 10, and a 93 kb regulatory region containing 10 tissue-specific exon 1s and promoters that are alternatively spliced to a common splice acceptor site 5' of exon 2 in various cell types. With respect to the reference sequence shown in FIG. 1, the translation initiation codon begins at nucleotide 97669 of SEQ ID NO:1. Exon I.1 (placenta major) contains nucleotides 1984 to 2086 of SEQ ID NO:1. Intron I.1 contains nucleotides 2087 to 16656 of SEQ ID NO:1. Exon 2a (placenta minor) contains nucleotides 16657 to 16765 of SEQ ID NO:1. Intron 2a contains nucleotides 16766 to 21825 of SEQ ID NO:1. Exon I.4 (skin/adipose) contains nucleotides 21826 to 22148 of SEQ ID NO:1. Intron I.4 contains nucleotides 22149 to 52242 of SEQ ID NO:1. Exon I.5 (fetal tissue) contains nucleotides 52243 to 52331 of SEQ ID NO:1. Intron I.5 contains nucleotides 52332 to 58318 of SEQ ID NO:1. Exon I.7 contains nucleotides 58319 to 58419 of SEQ ID NO:1. Intron I.7 contains nucleotides 58420 to 62438 of SEQ ID NO:1. Exon I.f (brain) contains nucleotides 62439 to 62573 of SEQ ID NO:1. Intron I.f contains nucleotides 62574 to 84791 of SEQ ID NO:1. Exon I.2 (placenta minor) contains nucleotides 84792 to 85063 of SEQ ID NO:1. Intron I.2 contains nucleotides 85064 to 96671 of SEQ ID NO:1. Exon I.6 (bone) contains nucleotides 96672 to 96827 of SEQ ID NO:1. Intron I.6 contains nucleotides 96828 to 97325 of SEQ ID NO:1. Exon I.3 (adipose/breast) contains nucleotides 97326 to 97529 of SEQ ID NO:1. Intron I.3 contains nucleotides 97530 to 97551 of SEQ ID NO:1. Exon PII (ovary/breast cancer/endometriosis; splice junction GenBank Accession No. S52794)) contains nucleotides 97552 to 97676 of SEQ ID NO:1 (italicized, this sequence includes the splice acceptor site "AG" at nucleotides 97629-97630). Exon 2 contains nucleotides 97677 to 97813 of SEQ ID NO:1. Intron 2 contains nucleotides 97814 to 103571 of SEQ ID NO:1. Exon 3 contains nucleotides 103572 to 103722 of SEQ ID NO:1. Intron 3 contains nucleotides 103723 to 112647 of SEQ ID NO:1. Exon 4 contains nucleotides 112648 to 112802 of SEQ ID NO:1. Intron 4 contains nucleotides 112803 to 118055 of SEQ ID NO:1. Exon 5 contains nucleotides 118056 to 118232 of SEQ ID NO:1. Intron 5 contains nucleotides 118233 to 121925 of SEQ ID NO:1. Exon 6 contains nucleotides 121926 to 122040 of SEQ ID NO:1. Intron 6 contains nucleotides 122041 to 124763 of SEQ ID NO:1. Exon 7 contains nucleotides 124764 to 124878 of SEQ ID NO:1. Intron 7 contains nucleotides 124879 to 125348 of SEQ ID NO:1. Exon 8 contains nucleotides 125349 to 125511 of SEQ ID NO:1. Intron 8 contains nucleotides 125512 to 1280119 of SEQ ID NO:1. Exon 9 contains nucleotides 128020 to 128261 of SEQ ID NO:1. Intron 9 contains nucleotides 128262 to 129524 of SEQ ID NO:1 (italicized font indicates a first forward primer; underlining indicates a second forward primer). Exon 10 contains nucleotides 129525 to 131109 of SEQ ID NO:1.

As used herein, "untranslated sequence" includes 5' and 3' flanking regions that are outside of the messenger RNA (mRNA) as well as 5' and 3' untranslated regions (5'-UTR or 3'-UTR) that are part of the mRNA, but are not translated. Positions of nucleotide sequence variants in 5' untranslated sequences are designated as "–X" relative to the "A" in the translation initiation codon; positions of nucleotide sequence variants in the coding sequence and 3' untranslated sequence are designated as "+X" or "X" relative to the "A" in the translation initiation codon. Nucleotide sequence variants that occur in introns are designated as "+X" or "X" relative to the "G" in the splice donor site (GT) or as "–X" relative to the "G" in the splice acceptor site (AG).

In some embodiments, a CYP19A1 nucleotide sequence variant encodes a CYP19A1 polypeptide having an altered amino acid sequence. The term "polypeptide" refers to a chain of at least four amino acid residues (e.g., 4-8, 9-12, 13-15, 16-18, 19-21, 22-50, 51-75, 76-100, 101-125 residues, or a full-length CYP19A1 polypeptide). CYP19A1 polypeptides may or may not have CYP19A1 catalytic activity, or may have altered activity relative to the reference CYP19A1 polypeptide. Polypeptides that do not have activity or have altered activity can be useful for diagnostic purposes (e.g., for producing antibodies having specific binding affinity for variant CYP19A1 polypeptides).

Corresponding CYP19A1 polypeptides, irrespective of length, that differ in amino acid sequence are herein referred to as allozymes. For example, a CYP19A1 nucleic acid sequence that includes a thymine at position 602 relative to the adenine in the translation initiation codon (i.e., nucleotide 118206 of SEQ ID NO:1 or nucleotide 602 of SEQ ID NO:2) encodes a CYP19A1 polypeptide having a methionine at amino acid residue 201. This polypeptide (Thr(201)Met) would be considered an allozyme with respect to the reference CYP19A1 polypeptide that contains a threonine at amino acid residue 201. As another example, a CYP19A1 nucleic acid sequence that includes a cytosine at position 1091 relative to the adenine in the translation initiation codon (i.e., nucleotide 128089 of SEQ ID NO:1 or nucleotide 1091 of SEQ ID NO:2) encodes a CYP19A1 polypeptide having a threonine at amino acid residue 364. This polypeptide (Met (364)Thr) would be considered an allozyme with respect to the reference CYP19A1 polypeptide that contains a methionine at amino acid residue 364. Further examples of allozymes include: a CYP19A1 nucleic acid sequence that includes a cytosine at position 115 relative to the adenine in the translation initiation codon (i.e., nucleotide 97783 of SEQ ID NO:1 or nucleotide 115 of SEQ ID NO:2) encodes a CYP19A1 polypeptide (Trp39Arg) having an arginine at amino acid residue 39 instead of a tryptophan; and a CYP19A1 nucleic acid sequence that includes a thymine at position 790 relative to the adenine in the translation initiation codon (i.e., nucleotide 124810 of SEQ ID NO:1 or nucleotide 790 of SEQ ID NO:2) encodes a CYP19A1 polypeptide (Arg264Cys) having a cysteine at amino acid residue 264.

CYP19A1 allozymes as described above are encoded by a series of CYP19A1 alleles. These alleles represent nucleic acid sequences containing sequence variants, typically multiple sequence variants, within coding and non-coding sequences. Representative examples of single nucleotide variants are described herein. Table 2 sets out a series of CYP19A1 alleles that encode CYP19A1. Some alleles are commonly observed, i.e., have allele frequencies >1%, such as the allele having a thymine at nucleotide 790 in place of a cytosine. The relatively large number of alleles and allozymes for CYP19A1 indicates the potential complexity of CYP19A1 pharmacogenetics. Such complexity emphasizes the need for determining single nucleotide variants, (i.e., single nucleotide polymorphisms, SNPs) as well as complete CYP19A1 haplotypes (i.e., the set of alleles on one chromosome or a part of a chromosome) of patients.

Certain CYP19A1 nucleotide sequence variants do not alter the amino acid sequence. Such variants, however, could alter regulation of transcription as well as mRNA stability. CYP19A1 variants can occur in intron sequences, for example, within introns 1.7, 2, 3, 4, 5, 6, 7, or 8. For example, a CYP19A1 nucleic acid sequence can have a variant that is an adenine substitution for guanine at position 25 relative to the intron/exon splice junction of intron I.7 within SEQ ID NO:1, a cytosine substitution for guanine at position 54 relative to the intron/exon splice junction of intron I.7, a guanine substitution for adenine at position −59 relative to the intron/exon splice junction of intron 2 within SEQ ID NO:1, a cytosine substitution for thymine at position −27 relative to the intron/exon splice junction of intron 2 within SEQ ID NO:1, an adenine substitution for guanine at position 48 relative to the intron/exon splice junction of intron 3 within SEQ ID NO:1, adenine substitution for guanine at position 8 relative to the intron/exon splice junction of intron 4 within SEQ ID NO:1, a deletion of a TCT trinucleotide at position 27 relative to the intron/exon splice junction of intron 4 within SEQ ID NO:1, an insertion of a $(TTTA)_n$ (n=7, 8, 10, 11, 12, or 13) tract at position 77 relative to the intron/exon splice junction of intron 4 within SEQ ID NO:1, a guaniane substitution for thymine at position −16 relative to the intron/exon splice junction of intron 5 within SEQ ID NO:1, a thymine substitution for adenine at position 36 relative to the intron/exon splice junction of intron 6 within SEQ ID NO:1, a cytosine substitution for guanine at position 44 relative to the intron/exon splice junction of intron 6 within SEQ ID NO:1, a guanine substitution for thymine at position −106 relative to the intron/exon splice junction of intron 6 within SEQ ID NO:1, a thymine substitution for cystine at position 26 relative to the intron/exon splice junction of intron 7 within SEQ ID NO:1, a guanine substitution for adenine at position −79 relative to the intron/exon splice junction of intron 7 within SEQ ID NO:1, or a thymine substitution for cytosine at position 29 to the intron/exon splice junction of intron 8 within SEQ ID NO:1.

CYP19A1 nucleotide sequence variants that do not change the amino acid sequence also can be within an exon, in the 5' flanking region, or in 5' or 3' untranslated regions. For example, a CYP19A1 nucleic acid sequence can have a variant within an exon that is an adenine substitution for guanine at position −35 relative to the intron/exon splice junction of exon I.1, an adenine substitution for guanine at position −2 relative to the intron/exon splice junction of exon I.1, a guanine substitution for adenine at position −38 relative to the intron/exon splice junction of exon 2a within SEQ ID NO:1, an adenine substitution for cytosine at position −21 relative to the intron/exon splice junction of exon 2a within SEQ ID NO:1, a thymine substitution for guanine at position −241 relative to the intron/exon splice junction of exon I.4 within SEQ ID NO:1, a thymine substitution for adenine at position −80 relative to the intron/exon splice junction of exon I.5 within SEQ ID NO:1, a thymine substitution for cytosine at position −26 relative to the intron/exon splice junction of exon I.7 within SEQ ID NO:1, a thymine or adenine substitution for cytosine at position −108 relative to the intron/exon splice junction of exon I.f within SEQ ID NO:1, a thymine substitution for cytosine at position −66 relative to the intron/exon splice junction of exon I.f within SEQ ID NO:1, a guanine substitution for adenine at position −35 relative to the intron/exon splice junction of exon I.f within SEQ ID NO:1, a cytosine substitution for guanine at position −224 relative to the intron/exon splice junction of exon I.2, an adenine substitution for guanine at position −217 relative to the intron/exon splice junction of exon I.2 within SEQ ID NO:1, a thymine substitution for cytosine at position −125 relative to the intron/exon splice junction of exon I.2 within SEQ ID NO:1, an adenine substitution for guanine at position −77 relative to the intron/exon splice junction of exon I.6, an adenine substitution for cytosine at position −83 relative to the intron/exon splice junction of exon PII within SEQ ID NO:1, a guanine substitution for cytosine at position 42 relative to the adenine in the CYP19A1 translation initiation codon, a cytosine substitution for thymine at position 109 relative to the adenine in the CYP19A 1 translation initiation codon, a thymine substitution for cytosine at position 186 relative to the adenine in the CYP19A1 translation initiation codon, a thymine substitution for cytosine at position 602 relative to the adenine in the CYP19A 1 translation initiation codon, a cytosine substitution for thymine at position 633 relative to the adenine in the CYP19A1 translation initiation codon, a guanine substitution for cytosine at position 963 relative to the adenine in the CYP19A1 translation initiation codon, or a cytosine substitution for thymine at position 1091 relative to the adenine in the CYP19A1 translation initiation codon.

For example, a CYP19A1 nucleic acid sequence can have a variant within the 5' FR that is an adenine substitution for guanine at position −588 relative to the intron/exon splice junction of exon I.1, a thymine substitution for cytosine at position −566 relative to the intron/exon splice junction of exon I.1, a cytosine substitution for thymine at position −554 relative to the intron/exon splice junction of exon I.1, a cytosine substitution for thymine at position −316 relative to the intron/exon splice junction of exon I.1, a thymine substitution for cytosine at position −278 relative to the intron/exon splice junction of exon I.1, a thymine substitution for guanine at position −245 relative to the intron/exon splice junction of exon I.1, a thymine substitution for cytosine at position −144 relative to the intron/exon splice junction of exon I.1, an adenine substitution for guanine at position −639 relative to the intron/exon splice junction of exon 2a within SEQ ID NO:1, a thymine substitution for cytosine at position −632 relative to the intron/exon splice junction of exon 2a within SEQ ID NO:1, a thymine substitution for cytosine at position −468 relative to the intron/exon splice junction of exon 2a, a cytosine substitution for thymine at position −429 relative to the intron/exon splice junction of exon 2a within SEQ ID NO:1, a guanine substitution for cytosine at position −149 relative to the intron/exon splice junction of exon 2a within SEQ ID NO:1, a thymine substitution for cytosine at position −125 relative to the intron/exon splice junction of exon 2a within SEQ ID NO:1, an adenine substitution for guanine at position −124 relative to the intron/exon splice junction of exon 2a within SEQ ID NO:1, an adenine substitution for guanine at position −563 relative to the intron/exon splice junction of exon I.4 within SEQ ID NO:1, an adenine substitution for cytosine at position −562 relative to the intron/exon splice junction of exon I.4 within SEQ ID NO:1, a thymine substitution for cytosine at position −638 relative to the intron/exon splice junction of exon I.5 within SEQ ID NO:1, a guanine substitution for cytosine at position −628 relative to the intron/exon splice junction of exon I.5, a cytosine substitution for thymine at position −334 relative to the intron/exon splice junction of exon I.5, a cytosine substitution for guanine at position −317 relative to the intron/exon splice junction of exon I.5, a thymine substitution for cytosine at position −128 relative to the intron/exon splice junction of exon I.5, a thymine substitution for cytosine at position −651 relative to the intron/exon splice junction of exon I.7 within SEQ ID NO:1, an adenine substitution for guanine at position −550 relative to the intron/exon splice junction of exon I.7 within SEQ ID NO:1, an adenine substitution for guanine at position −543 relative to the intron/exon splice junction of exon I.7 within SEQ ID NO:1, an adenine substitution for guanine at position −495 relative to the intron/exon splice junction of exon I.7 within SEQ ID NO:1, a cytosine substitution for adenine at position −439 relative to the intron/exon splice junction of exon I.7 within SEQ ID NO:1, an adenine substitution for guanine at position −428 relative to the intron/exon splice junction of exon I.7 within SEQ ID NO:1, an adenine substitution for guanine at position −408 relative to the intron/exon splice junction of exon I.7 within SEQ ID NO:1, a thymine substitution for guanine at position −194 relative to the intron/exon splice junction of exon I.7 within SEQ ID NO:1, an adenine substitution for cytosine at position −739 relative to the intron/exon splice junction of exon I.f within SEQ ID NO:1, an adenine substitution for guanine at position −725 relative to the intron/exon splice junction of exon I.f within SEQ ID NO:1, a cytosine substitution for adenine at position −690 relative to the intron/exon splice junction of exon I.f within SEQ ID NO:1, a thymine substitution for cytosine at position −649 relative to the intron/exon splice junction of exon I.f, a thymine substitution for cytosine at position −425 relative to the intron/exon splice junction of exon I.f within SEQ ID NO:1, a guanine substitution for thymine at position −391 relative to the intron/exon splice junction of exon I.f within SEQ ID NO:1, a guanine substitution for adenine at position −827 relative to the intron/exon splice junction of exon I.2 within SEQ ID NO:1, an adenine substitution for guanine at position −757 relative to the intron/exon splice junction of exon I.2 within SEQ ID NO:1, a cytyosine substitution for thymine at position −596 relative to the intron/exon splice junction of exon I.2, an adenine substitution for thymine at position −555 relative to the intron/exon splice junction of exon I.2 within SEQ ID NO:1, a thymine substitution for cytosine at position −362 relative to the intron/exon splicejunction of exon I.6 within SEQ ID NO:1, a guanine substitution for thymine at position −301 relative to the intron/exon splicejunction of exon I.6 within SEQ ID NO:1, or an adenine substitution for thymine at position −273 relative to the intron/exon splicejunction of exon I.6 within SEQ ID NO:1, or a cytosine substitution for adenine at position −196 relative to the intron/exon splice junction of exon I.6.

For example, a CYP19A1 nucleic acid sequence can have a variant within the 3' UTR can be at, for example, For example, a CYP19A1 nucleic acid sequence can have a variant within the 3' UTR that is a thymine substitution for cytosine at position 1531 relative to the intron/exon splicejunction of the 3'UTR within SEQ ID NO:1, or a thymine substitution for guanine at position 1673 relative to the intron/exon splicejunction of the 3'UTR within SEQ ID NO:1.

In some embodiments, nucleic acid molecules provided herein can have at least 97% (e.g., 97.5%, 98%, 98.5%, 99.0%, 99.5%, 99.6%, 99.7%, 99.8%, 99.9%, or 100%) sequence identity with a region of SEQ ID NO:1 or SEQ ID NO:2 that includes one or more variants described herein. The region of SEQ ID NO:1 or 2 is at least ten nucleotides in length (e.g., 10, 15, 20, 50, 60, 70, 75, 100, 150, 200, 250, 300, 350, 400, 450, 500, or more than 500 nucleotides in length). For example, a nucleic acid molecule can have at least 99% identity with nucleotides 1400 to 1500, 1400 to 1750, 1500 to 1600, 1500 to 2000, 1700 to 1800, 1800 to 1900, 1900 to 2100, 16000 to 16200, 16200 to 16400, 16600 to 16650, 16680 to 16800, 21000 to 22000, 21500 to 21600, 21800 to 22000, 51600 to 51800, 51950 to 52050, 52200 to 52300, 57700 to 57800, 57700 to 58000, 58200 to 58500, 61800 to 62000, 62100 to 62200, 62400 to 62600, 84200 to 84400, 84450 to 84550, 84780 to 84960, 96500 to 96600, 96800 to 96900, 97700 to 97800, 103500 to 103550, 103500 to 103600, 103600 to 103700, 103700 to 103800, 112800 to 112900, 112810 to 112840, 118200 to 118300, 121900 to 122000, 122000 to 122100, 124600 to 124700, 124800 to 124900, or 124900 to 125000, 125200 to 125300, 125400 to 125500, 128000 to 1281000, 129700 to 129800, 129900 to 130000 of SEQ ID NO:1, where the nucleotide sequence of SEQ ID NO:1 includes one or more of the variants described herein. Thus, the nucleotide sequence of SEQ ID NO:1 can have, for example, a thymine at position 1521 (position −566 relative to exon I.1), a cytosine at position 1533 (position −554 relative to exon I.1), a guanine at position 16617 (position −149 relative to exon 2a), or any other variant listed in Table 2 (which provides the positions of the variants relative to the listed downstream (i.e., 3') exon), and combinations thereof. Similarly, a nucleic acid molecule can have at least 99% identity with, for example, nucleotides 1 to 100, 60 to 180, 180 to 280, 600 to 700, 780 to 900, or 1080 to 1200 of SEQ ID NO:2, where the nucleotide sequence of SEQ ID NO:2 includes one or more of the variants described herein. For example, the nucleotide sequence of SEQ ID NO:2 can have a cytosine at position 1091, or any change within an exon listed in Table 2, and combinations thereof.

Percent sequence identity is calculated by determining the number of matched positions in aligned nucleic acid sequences, dividing the number of matched positions by the total number of aligned nucleotides, and multiplying by 100. A matched position refers to a position in which identical nucleotides occur at the same position in aligned nucleic acid sequences. Percent sequence identity also can be determined for any amino acid sequence. To determine percent sequence identity, a target nucleic acid or amino acid sequence is compared to the identified nucleic acid or amino acid sequence using the BLAST 2 Sequences (Bl2seq) program from the stand-alone version of BLASTZ containing BLASTN version 2.0.14 and BLASTP version 2.0.14. This stand-alone version of BLASTZ can be obtained from Fish & Richardson's web site (World Wide Web at "fr" dot "com" slash "blast") or the U.S. government's National Center for Biotechnology Information web site (World Wide Web at "ncbi" dot "nlm" dot "nih" dot "gov"). Instructions explaining how to use the Bl2seq program can be found in the readme file accompanying BLASTZ.

Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: −i is set to a file containing the first nucleic acid sequence to be compared (e.g., C:\seq1.txt); −j is set to a file containing the second nucleic acid sequence to be compared (e.g., C:\seq2.txt); −p is set to blastn; −o is set to any desired file name (e.g., C:\output.txt); −q is set to −1; −r is set to 2; and all other options are left at their default setting. The following command will generate an output file containing a comparison between two sequences: C:\Bl2seq −i c:\seq1.txt −j c:\seq2.txt −p blastn −o c:\output.txt −q −1 −r 2. If the target sequence shares homology with any portion of the identified sequence, then the designated output file will present those regions of homology as aligned sequences. If the target sequence does not share homology with any portion of the identified sequence, then the designated output file will not present aligned sequences.

Once aligned, a length is determined by counting the number of consecutive nucleotides from the target sequence presented in alignment with sequence from the identified sequence starting with any matched position and ending with any other matched position. A matched position is any position where an identical nucleotide is presented in both the target and identified sequence. Gaps presented in the target sequence are not counted since gaps are not nucleotides. Likewise, gaps presented in the identified sequence are not counted since target sequence nucleotides are counted, not nucleotides from the identified sequence.

The percent identity over a particular length is determined by counting the number of matched positions over that length and dividing that number by the length followed by multiplying the resulting value by 100. For example, if (1) an 800 nucleotide target sequence is compared to the sequence set forth in SEQ ID NO:2, (2) the Bl2seq program presents 750 nucleotides from the target sequence aligned with a region of the sequence set forth in SEQ ID NO:2 where the first and last nucleotides of that 750 nucleotide region are matches, and (3) the number of matches over those 750 aligned nucleotides is 725, then the 800 nucleotide target sequence contains a length of 750 and a percent identity over that length of 96.7 (i.e., 725 750×100=96.7).

It will be appreciated that different regions within a single nucleic acid target sequence that aligns with an identified sequence can each have their own percent identity. It is noted that the percent identity value is rounded to the nearest tenth. For example, 78.11, 78.12, 78.13, and 78.14 are rounded down to 78.1, while 78.15, 78.16, 78.17, 78.18, and 78.19 are rounded up to 78.2. It also is noted that the length value will always be an integer.

Isolated nucleic acid molecules provided herein can be produced by standard techniques, including, without limitation, common molecular cloning and chemical nucleic acid synthesis techniques. For example, polymerase chain reaction (PCR) techniques can be used to obtain an isolated nucleic acid containing a CYP19A1 nucleotide sequence variant. PCR refers to a procedure or technique in which target nucleic acids are enzymatically amplified. Sequence information from the ends of the region of interest or beyond typically is employed to design oligonucleotide primers that are identical in sequence to opposite strands of the template to be amplified. PCR can be used to amplify specific sequences from DNA as well as RNA, including sequences from total genomic DNA or total cellular RNA. Primers are typically 14 to 40 nucleotides in length, but can range from 10 nucleotides to hundreds of nucleotides in length. General PCR techniques are described, for example in *PCR Primer: A Laboratory Manual*, ed. by Dieffenbach and Dveksler, Cold Spring Harbor Laboratory Press, 1995. When using RNA as a source of template, reverse transcriptase can be used to synthesize complementary DNA (cDNA) strands. Ligase chain reaction, strand displacement amplification, self-sustained sequence replication, or nucleic acid sequence-based amplification also can be used to obtain isolated nucleic acids. See, for example, Lewis *Genetic Engineering News* (1992) 12(9): 1; Guatelli et al., *Proc. Natl. Acad. Sci. USA* (1990) 87:1874-1878; and Weiss, *Science* (1991) 254:1292.

Isolated nucleic acids provided herein also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector.

Isolated nucleic acids provided herein also can be obtained by mutagenesis. For example, the reference sequences depicted in FIG. 1 or 2 can be mutated using standard techniques including oligonucleotide-directed mutagenesis and site-directed mutagenesis through PCR. See, *Short Protocols in Molecular Biology*, Chapter 8 (1992) Green Publishing Associates and John Wiley & Sons, edited by Ausubel et al. Examples of positions that can be modified include those described herein.

CYP19A1 Polypeptides

Isolated CYP19A1 polypeptides provided herein include an amino acid sequence variant relative to the reference CYP19A1 (FIG. 2; SEQ ID NO:3). The term "isolated" with respect to a CYP19A1 polypeptide refers to a polypeptide that has been separated from cellular components by which it is naturally accompanied. Typically, the polypeptide is isolated when it is at least 60% (e.g., 70%, 80%, 90%, 95%, or 99%), by weight, free from proteins and naturally-occurring organic molecules with which it is naturally associated. In general, an isolated polypeptide will yield a single major band on a non-reducing polyacrylamide gel.

CYP19A1 polypeptides provided herein include variants at one or more amino acid residues (e.g., residue 39, 201, 264, or 364). In particular, a methionine residue can be substituted for the threonine at position 201, or a threonine can be substituted for the methionine at position 364. In some embodiments, activity of CYP19A1 polypeptides is altered relative to the reference CYP19A1. Certain CYP19A1 allozymes can have reduced activity, while other allozymes can have activity that is comparable to the reference CYP19A1. Other allozymes can have increased activity relative to the reference CYP19 μl. Activity of CYP19A1 polypeptides can be assessed in vitro. For example, the activity of CYP19A1 polypeptides can be assessed by determining the amount of $^3H_2O$ released from the substrate [1β$^3$H]androst-4-ene-3,17-dione (NEN Life Sciences Products, Boston, Mass.) as described, e.g., Hahn et al., *J. Biol. Chem.* (1984) 259:1689-1694 and Brueggemeier et al., *J. Steroid Biochem. Mol. Biol.* (2001) 79:75-84. For example, the reactions are carried out for 20 minutes at 37° C. in 0.05M Tris HCl, pH 7.4, under air. Each reaction mixture contains either 20 or 100 nM [1β$^3$H] androst-4-ene-3,17-dione (25.3 Ci/mmol), 30 to 60 ng of microsomal protein and an NADPH regeneration system (1.5 mM glucose-6-phosphate, 1 unit of glucose-6-phosphate dehydrogenase and 3.5 mM NADPH) in a final volume of 100 μl. After incubation, 6 volumes of chloroform are added to the reaction mixture, and the mixture is vortexed for 30 seconds to terminate the reaction and partition the remaining substrate into the organic phase. After centrifugation at 14,000×g for 10 minutes, radioactivity remaining in the aqueous phase is determined by liquid scintillation counting.

Other biochemical properties of allozymes, such as apparent $K_m$ and $K_i$ values, also can be altered relative to the reference CYP19A1. Apparent $K_m$ values can be calculated, for example, using the method of Wilkinson with a computer program written by Cleland. Wilkinson, *Biochem. J.* (1961) 80:324-332; and Cleland, *Nature* (1963) 198:463-365. Apparent $K_m$ values also can be determined by nonlinear least squares regression analysis with the GraphPad Prism program (GraphPad Software, San Diego, Calif.). Apparent $K_m$ values can be determined using the radiochemical assay and described above for measuring alloxyme activity. Ki values can be determined for each allozyme in the presence of an aromatase inhibitor, such as letrozole or exemestane.

Isolated polypeptides provided herein can be obtained by, for example, extraction from a natural source (e.g., brain or adipose tissue), chemical synthesis, or by recombinant production in a host cell. To recombinantly produce CYP19A1 polypeptides, a nucleic acid encoding a CYP19A1 nucleotide sequence variant can be ligated into an expression vector and used to transform a prokaryotic (e.g., bacteria) or eukaryotic (e.g., insect, yeast, or mammal) host cell. In general, nucleic acid constructs include a regulatory sequence operably linked to a CYP19A1 nucleic acid sequence. Regulatory sequences (e.g., promoters, enhancers, polyadenylation signals, or terminators) do not typically encode a gene product, but instead affect the expression of the nucleic acid sequence. In addition, a construct can include a tag sequence designed to facilitate subsequent manipulations of the expressed nucleic acid sequence (e.g., purification, localization). Tag sequences, such as green fluorescent protein (GFP), glutathione S-transferase (GST), six histidine ($His_6$), c-myc, hemagglutinin, or FLAG™ tag (KODAK™) sequences are typically expressed as a fusion with the expressed nucleic acid sequence. Such tags can be inserted anywhere within the polypeptide including at either the carboxyl or amino termini. The type and combination of regulatory and tag sequences can vary with each particular host, cloning or expression system, and desired outcome. A variety of cloning and expression vectors containing combinations of regulatory and tag sequences are commercially available. Suitable cloning vectors include, without limitation, pUC18, pUC19, and pBR322 and derivatives thereof (NEW ENGLAND BIOLABS®, Beverly, Mass.), and pGEN (PROMEGA™, Madison, Wis.). Additionally, representative prokaryotic expression vectors include pBAD (NVITROGEN™, Carlsbad, Calif.), the pTYB family of vectors (NEW ENGLAND BIOLABS®), and pGEMEX vectors (PROMEGA™); representative mammalian expression vectors include pTet-On/pTet-Off (CLONTECH™, Palo Alto, Calif.), pIND, pVAX1, pCR3.1, pcDNA3.1, pcDNA4, or pUni (INVITROGEN™), and pCI or pSI (PROMEGA™); representative insect expression vectors include pBacPAK8 or pBacPAK9 (CLONTECH™), and p2Bac (INVITROGEN™); and representative yeast expression vectors include MATCHMAKER (CLONTECH™) and pPICZ A, B, and C (INVITROGEN™).

In bacterial systems, a strain of *Escherichia coli* can be used to express CYP19A1 variant polypeptides. For example, BL-21 cells can be transformed with a pGEX vector containing a CYP19A1 nucleic acid sequence. The transformed bacteria can be grown exponentially and then stimulated with isopropylthiogalactopyranoside (IPTG) prior to harvesting. In general, the CYP19A1-GST fusion proteins produced from the pGEX expression vector are soluble and can be purified easily from lysed cells by adsorption to glutathione-agarose beads followed by elution in the presence of free glutathione. The pGEX vectors are designed to include thrombin or factor Xa protease cleavage sites so that the expressed CYP19A1 polypeptide can be released from the GST moiety.

In eukaryotic host cells, a number of viral-based expression systems can be utilized to express CYP19A1 variant polypeptides. A nucleic acid encoding a polypeptide provided herein can be cloned into, for example, a baculoviral vector such as pBlueBac (INVITROGEN™) and then used to co-transfect insect cells such as *Spodoptera frugiperda* (Sf9) cells with wild type DNA from *Autographa californica* multinuclear polyhedrosis virus (AcMNPV). Recombinant viruses producing polypeptides provided herein can be identified by standard methodology. Alternatively, a nucleic acid encoding a polypeptide provided herein can be introduced into a SV40, retroviral, or vaccinia based viral vector and used to infect suitable host cells.

Eukaryotic cell lines that stably express CYP19A1 variant polypeptides can be produced using expression vectors with the appropriate control elements and a selectable marker. For example, the eukaryotic expression vector pCR3.1 (INVITROGEN™) and p91023(B) (see Wong et al., *Science* (1985) 228:810-815) or modified derivatives thereof are suitable for expression of CYP19A1 variant polypeptides in, for example, Chinese hamster ovary (CHO) cells, COS-1 cells, human embryonic kidney 293 cells, NIH3T3 cells, BHK21 cells, MDCK cells, and human vascular endothelial cells (HU-VEC). Following introduction of the expression vector by electroporation, lipofection, calcium phosphate or calcium chloride co-precipitation, DEAE dextran, or other suitable transfection method, stable cell lines are selected, e.g., by antibiotic resistance to G418, kanamycin, or hygromycin. Alternatively, amplified sequences can be ligated into a eukaryotic expression vector such as pcDNA3 (INVITROGEN™) and then transcribed and translated in vitro using wheat germ extract or rabbit reticulocyte lysate.

CYP19A1 variant polypeptides can be purified by known chromatographic methods including ion exchange and gel filtration chromatography. See, for example, Caine et al., *Protein Expr. Purif.* (1996) 8(2):159-166. CYP19A1 polypeptides can be "engineered" to contain a tag sequence describe herein that allows the polypeptide to be purified (e.g., captured onto an affinity matrix). Immunoaffinity chromatography also can be used to purify CYP19A1 polypeptides.

Non-Human Mammals

This document features non-human mammals that include CYP19A1 nucleic acids provided herein, as well as progeny and cells of such non-human mammals. Non-human mammals include, for example, rodents such as rats, guinea pigs, and mice, and farm animals such as pigs, sheep, goats, horses, and cattle. Non-human mammals provided herein can express a CYP19A1 variant nucleic acid in addition to an endogenous CYP19A1 (e.g., a transgenic non-human that includes a CYP19A1 nucleic acid randomly integrated into the genome of the non-human mammal). Alternatively, an endogenous CYP19A1 nucleic acid can be replaced with a CYP19A1 variant nucleic acid provided herein by homologous recombination. See, Shastry, *Mol. Cell Biochem.* (1998) 181(1-2): 163-179, for a review of gene targeting technology.

In one embodiment, non-human mammals are produced that lack an endogenous CYP19A1 nucleic acid (i.e., a knockout), and then a CYP19A1 variant nucleic acid provided herein is introduced into the knockout non-human mammal. Nucleic acid constructs used for producing knockout non-human mammals can include a nucleic acid sequence encoding a selectable marker, which is generally used to interrupt the targeted exon site by homologous recombination. Typically, the selectable marker is flanked by sequences homologous to the sequences flanking the desired insertion site. It is not necessary for the flanking sequences to be immediately adjacent to the desired insertion site. Suitable markers for positive drug selection include, for example, the aminoglycoside 3N phosphotransferase gene that imparts resistance to geneticin (G418, an aminoglycoside antibiotic), and other antibiotic resistance markers, such as the hygromycin-B-phosphotransferase gene that imparts hygromycin resistance. Other selection systems include negative-selection markers such as the thymidine kinase (TK) gene from herpes simplex virus. Constructs utilizing both positive and negative drug selection also can be used. For example, a construct can contain the aminoglycoside phosphotransferase gene and the TK gene. In this system, cells are selected that are resistant to G418 and sensitive to gancyclovir.

To create non-human mammals having a particular gene inactivated in all cells, it is necessary to introduce a knockout construct into the germ cells (sperm or eggs, i.e., the "germ line") of the desired species. Genes or other DNA sequences can be introduced into the pronuclei of fertilized eggs by microinjection. Following pronuclear fusion, the developing embryo may carry the introduced gene in all its somatic and germ cells because the zygote is the mitotic progenitor of all cells in the embryo. Since targeted insertion of a knockout construct is a relatively rare event, it is desirable to generate and screen a large number of animals when employing such an approach. Because of this, it can be advantageous to work with the large cell populations and selection criteria that are characteristic of cultured cell systems. However, for production of knockout animals from an initial population of cultured cells, it is necessary that a cultured cell containing the desired knockout construct be capable of generating a whole animal. This is generally accomplished by placing the cell into a developing embryo environment of some sort.

Cells capable of giving rise to at least several differentiated cell types are "pluripotent." Pluripotent cells capable of giving rise to all cell types of an embryo, including germ cells, are hereinafter termed "totipotent" cells. Totipotent murine cell lines (embryonic stem, or "ES" cells) have been isolated by culture of cells derived from very young embryos (blastocysts). Such cells are capable, upon incorporation into an embryo, of differentiating into all cell types, including germ cells, and can be employed to generate animals lacking an endogenous CYP19A1 nucleic acid. That is, cultured ES cells can be transformed with a knockout construct and cells selected in which the CYP19A1 gene is inactivated.

Nucleic acid constructs can be introduced into ES cells, for example, by electroporation or other standard technique. Selected cells can be screened for gene targeting events. For example, the polymerase chain reaction (PCR) can be used to confirm the presence of the transgene.

The ES cells further can be characterized to determine the number of targeting events. For example, genomic DNA can be harvested from ES cells and used for Southern analysis. See, for example, Section 9.37-9.52 of Sambrook et al., *Molecular Cloning, A Laboratory Manual* (1989) second edition, Cold Spring Harbor Press, Plainview; NY.

To generate a knockout animal, ES cells having at least one inactivated CYP19A1 allele are incorporated into a developing embryo. This can be accomplished through injection into the blastocyst cavity of a murine blastocyst-stage embryo, by injection into a morula-stage embryo, by co-culture of ES cells with a morula-stage embryo, or through fusion of the ES cell with an enucleated zygote. The resulting embryo is raised to sexual maturity and bred in order to obtain animals, whose cells (including germ cells) carry the inactivated CYP19A1 allele. If the original ES cell was heterozygous for the inactivated CYP19A1 allele, several of these animals can be bred with each other in order to generate animals homozygous for the inactivated allele.

Alternatively, direct microinjection of DNA into eggs can be used to avoid the manipulations required to turn a cultured cell into an animal. Fertilized eggs are totipotent, i.e., capable of developing into an adult without further substantive manipulation other than implantation into a surrogate mother. To enhance the probability of homologous recombination when eggs are directly injected with knockout constructs, it is useful to incorporate at least about 8 kb of homologous DNA into the targeting construct. In addition, it is also useful to prepare the knockout constructs from isogenic DNA.

Embryos derived from microinjected eggs can be screened for homologous recombination events in several ways. For example, if the CYP19A1 gene is interrupted by a coding region that produces a detectable (e.g., fluorescent) gene product, then the injected eggs are cultured to the blastocyst stage and analyzed for presence of the indicator polypeptide. Embryos with fluorescing cells, for example, are then implanted into a surrogate mother and allowed to develop to term. Alternatively, injected eggs are allowed to develop and DNA from the resulting pups analyzed by PCR or RT-PCR for evidence of homologous recombination.

Nuclear transplantation also can be used to generate non-human mammals provided herein. For example, fetal fibroblasts can be genetically modified such that they contain an inactivated endogenous CYP19A1 gene and express a CYP19A1 nucleic acid provided herein, and then fused with enucleated oocytes. After activation of the oocytes, the eggs are cultured to the blastocyst stage, and implanted into a recipient. See, Cibelli et al., *Science* (1998) 280:1256-1258. Adult somatic cells, including, for example, cumulus cells and mammary cells, can be used to produce animals such as mice and sheep, respectively. See, for example, Wakayama et al., *Nature* (1998) 394(6691):369-374; and Wilmut et al., *Nature* (1997) 385(6619):810-813. Nuclei can be removed from genetically modified adult somatic cells, and transplanted into enucleated oocytes. After activation, the eggs can be cultured to the 2-8 cell stage, or to the blastocyst stage, and implanted into a suitable recipient (Wakayama et al. (1998), supra.)

Non-human mammals provided herein such as mice can be used, for example, to screen toxicity of compounds that are substrates for CYP19A1, drugs that alter CYP19A1 activity, or for carcinogenesis. For example, CYP19A1 activity or toxicity can be assessed in a first group of such non-human mammals in the presence of a compound, and compared with CYP19A1 activity or toxicity in a corresponding control group in the absence of the compound. As used herein, suitable compounds include biological macromolecules such as an oligonucleotide (RNA or DNA), or a polypeptide of any length, a chemical compound, a mixture of chemical compounds, or an extract isolated from bacterial, plant, fungal, or animal matter. The concentration of compound to be tested depends on the type of compound and in vitro test data.

Non-human mammals can be exposed to test compounds by any route of administration, including enterally (e.g., orally) and parenterally (e.g., subcutaneously, intravascularly, intramuscularly, or intranasally). Suitable formulations for oral administration can include tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulfate). Tablets can be coated by methods known in the art. Preparations for oral administration can also be formulated to give controlled release of the compound.

Compounds can be prepared for parenteral administration in liquid form (e.g., solutions, solvents, suspensions, and emulsions) including sterile aqueous or non-aqueous carriers. Aqueous carriers include, without limitation, water, alcohol, saline, and buffered solutions. Examples of non-aqueous carriers include, without limitation, propylene glycol, polyethylene glycol, vegetable oils, and injectable organic esters. Preservatives and other additives such as, for example, antimicrobials, anti-oxidants, chelating agents, inert gases, and the like may also be present. Pharmaceutically acceptable carriers for intravenous administration include solutions containing pharmaceutically acceptable salts or sugars. Intranasal preparations can be presented in a liquid form (e.g., nasal drops or aerosols) or as a dry product (e.g., a powder). Both liquid and dry nasal preparations can be administered using a suitable inhalation device. Nebulised aqueous suspensions or solutions can also be prepared with or without a suitable pH and/or tonicity adjustment.

Detecting CYP19A1 Sequence Variants

CYP19A1 nucleotide sequence variants can be detected, for example, by sequencing exons, introns, 5' untranslated sequences, or 3' untranslated sequences, by performing allele-specific hybridization, allele-specific restriction digests, mutation specific polymerase chain reactions (MSPCR), by single-stranded conformational polymorphism (SSCP) detection (Schafer et al., *Nat. Biotechnol.* (1995) 15:33-39), denaturing high performance liquid chromatography (DHPLC, Underhill et al., *Genome Res.* (1997) 7:996-1005), infrared matrix-assisted laser desorption/ionization (IR-MALDI) mass spectrometry (WO 99/57318), and combinations of such methods.

Genomic DNA generally is used in the analysis of CYP19A1 nucleotide sequence variants, although mRNA also can be used. Genomic DNA is typically extracted from a biological sample such as a peripheral blood sample, but can be extracted from other biological samples, including tissues (e.g., mucosal scrapings of the lining of the mouth or from renal or hepatic tissue). Routine methods can be used to extract genomic DNA from a blood or tissue sample, including, for example, phenol extraction. Alternatively, genomic DNA can be extracted with kits such as the QIA$_{AMP}$™ Tissue Kit (QIAGEN®, Chatsworth, Calif.), WIZARD® Genomic DNA purification kit (PROMEGA™) and the A.S.A.P.™ Genomic DNA isolation kit (BOEHRINGER MANNHEIM™, Indianapolis, Ind.).

Typically, an amplification step is performed before proceeding with the detection method. For example, exons or introns of the CYP19A1 gene can be amplified then directly sequenced. Dye primer sequencing can be used to increase the accuracy of detecting heterozygous samples.

Allele specific hybridization also can be used to detect sequence variants, including complete haplotypes of a subject (e.g., a mammal such as a human). See, Stoneking et al., *Am. J. Hum. Genet.* (1991) 48:370-382; and Prince et al., *Genome Res.* (2001) 11(1):152-162. In practice, samples of DNA or RNA from one or more mammals can be amplified using pairs of primers and the resulting amplification products can be immobilized on a substrate (e.g., in discrete regions). Hybridization conditions are selected such that a nucleic acid probe can specifically bind to the sequence of interest, e.g., the variant nucleic acid sequence. Such hybridizations typically are performed under high stringency as some sequence variants include only a single nucleotide difference. High stringency conditions can include the use of low ionic strength solutions and high temperatures for washing. For example, nucleic acid molecules can be hybridized at 42° C. in 2×SSC (0.3M NaCl/0.03 M sodium citrate) with 0.1% sodium dodecyl sulfate (SDS) and washed in 0.1×SSC (0.015M NaCl/ 0.0015 M sodium citrate), 0.1% SDS at 65° C. Hybridization conditions can be adjusted to account for unique features of the nucleic acid molecule, including length and sequence composition. Probes can be labeled (e.g., fluorescently) to facilitate detection. In some embodiments, one of the primers used in the amplification reaction is biotinylated (e.g., 5' end of reverse primer) and the resulting biotinylated amplification product is immobilized on an avidin or streptavidin coated substrate.

Allele-specific restriction digests can be performed in the following manner. For nucleotide sequence variants that introduce a restriction site, restriction digest with the particular restriction enzyme can differentiate the alleles. For CYP19A1 sequence variants that do not alter a common restriction site, mutagenic primers can be designed that introduce a restriction site when the variant allele is present or when the wild type allele is present. A portion of CYP19A1 nucleic acid can be amplified using the mutagenic primer and a wild type primer, followed by digest with the appropriate restriction endonuclease.

Certain variants, such as insertions or deletions of one or more nucleotides, change the size of the DNA fragment encompassing the variant. The insertion or deletion of nucleotides can be assessed by amplifying the region encompassing the variant and determining the size of the amplified products in comparison with size standards. For example, a region of CYP19A1 can be amplified using a primer set from either side of the variant. One of the primers is typically labeled, for example, with a fluorescent moiety, to facilitate sizing. The amplified products can be electrophoresed through acrylamide gels with a set of size standards that are labeled with a fluorescent moiety that differs from the primer.

PCR conditions and primers can be developed that amplify a product only when the variant allele is present or only when the wild type allele is present (MSPCR or allele-specific PCR). For example, patient DNA and a control can be amplified separately using either a wild type primer or a primer specific for the variant allele. Each set of reactions is then examined for the presence of amplification products using standard methods to visualize the DNA. For example, the reactions can be electrophoresed through an agarose gel and the DNA visualized by staining with ethidium bromide or other DNA intercalating dye. In DNA samples from heterozygous patients, reaction products would be detected with each set of primers. Patient samples containing solely the wild type allele would have amplification products only in the reaction using the wild type primer. Similarly, patient samples containing solely the variant allele would have amplification products only in the reaction using the variant primer. Allele-specific PCR also can be performed using allele-specific primers that introduce priming sites for two universal energy-transfer-labeled primers (e.g., one primer labeled with a green dye such as fluoroscein and one primer labeled with a red dye such as sulforhodamine). Amplification products can be analyzed for green and red fluorescence in a plate reader. See, Myakishev et al., *Genome* (2001) 11(1):163-169.

Mismatch cleavage methods also can be used to detect differing sequences by PCR amplification, followed by hybridization with the wild type sequence and cleavage at points of mismatch. Chemical reagents, such as carbodiimide or hydroxylamine and osmium tetroxide can be used to modify mismatched nucleotides to facilitate cleavage.

Alternatively, CYP19A1 variants can be detected by antibodies that have specific binding affinity for variant CYP19A1 polypeptides. Variant CYP19A1 polypeptides can be produced in various ways, including recombinantly, as discussed above. Host animals such as rabbits, chickens, mice, guinea pigs, and rats can be immunized by injection of a CYP19A1 variant polypeptide. Various adjuvants that can be used to increase the immunological response depend on the host species and include Freund's adjuvant (complete and incomplete), mineral gels such as aluminum hydroxide, surface active substances such as lysolecithin, pluronic polyols, polyanions, peptides, oil emulsions, keyhole limpet hemocyanin, and dinitrophenol. Polyclonal antibodies are heterogeneous populations of antibody molecules that are contained in the sera of the immunized animals. Monoclonal antibodies, which are homogeneous populations of antibodies to a particular antigen, can be prepared using a CYP19A1 variant polypeptide and standard hybridoma technology. In particular, monoclonal antibodies can be obtained by any technique that provides for the production of antibody molecules by continuous cell lines in culture such as described by Kohler et al., Nature (1975) 256:495, the human B-cell hybridoma technique (Kosbor et al., Immunology Today (1983) 4:72; Cole et al., Proc. Natl. Acad. Sci USA (1983) 80:2026), and the EBV-hybridoma technique (Cole et al., Monoclonal Antibodies and Cancer Therapy (1983) Alan R. Liss, Inc., pp. 77-96. Such antibodies can be of any immunoglobulin class including IgG, IgM, IgE, IgA, IgD and any subclass thereof. The hybridoma producing the monoclonal antibodies provided herein can be cultivated in vitro and in vivo.

Antibody fragments that have specific binding affinity for a CYP19A1 variant polypeptide can be generated by known techniques. For example, such fragments include but are not limited to F(ab')2 fragments that can be produced by pepsin digestion of the antibody molecule, and Fab fragments that can be generated by reducing the disulfide bridges of F(ab')2 fragments. Alternatively, Fab expression libraries can be constructed. See, for example, Huse et al., Science, 246:1275 (1989). Once produced, antibodies or fragments thereof are tested for recognition of CYP19A1 variant polypeptides by standard immunoassay methods including ELISA techniques, radioimmunoassays and Western blotting. See, Short Protocols in Molecular Biology, Chapter 11 (1992) Green Publishing Associates and John Wiley & Sons, edited by Ausubel et al.

Methods

As a result of the present document, it is possible to determine aromatase status of a subject (e.g., a mammal such as a human). "Aromatase status" refers to the ability of a subject to catalyze the formation of aromatic C18 estrogens from C19 androgen. Aromatase status of a subject can be determined by measuring the level of aromatase (e.g., CYP19A1) activity in the subject using, for example, the methods described herein. Alternatively, aromatase status can be evaluated by determining whether an aromatase nucleic acid sequence (e.g., a CYP19A1 nucleic acid sequence) of a subject contains one or more variants (e.g., one or more variants that are correlated with increased or decreased aromatase activity). A variant that results in decreased or increased CYP19A1 activity, for example, can be the to result in "reduced" or "enhanced" aromatase status, respectively.

In some embodiments, the variant profile of a subject can be used to determine the aromatase status of the subject. "Variant profile" refers to the presence or absence of a plurality (e.g., two or more) of CYP19A1 nucleotide sequence variants or CYP19A1 amino acid sequence variants. For example, a variant profile can include the complete CYP19A1 haplotype of the subject (e.g., see Tables 3-6 and 8) or can include the presence or absence of a set of particular non-synonymous cSNPs (e.g., single nucleotide substitutions that alter the amino acid sequence of a CYP19A1 polypeptide). In one embodiment, determining the variant profile includes detecting the presence or absence of two or more non-synonymous SNPs (e.g., 2, 3, or 4 non-synonymous SNPs), including those described herein. There may be ethnic-specific pharmacogenetic variation, as certain of the nucleotide and amino acid sequence variants described herein were detected solely in African-American, Caucasian-American, Han Chinese-American, or Mexican-American subjects. In addition, determining the variant profile can include detecting the presence or absence of any type of CYP19A1 SNP together with any other CYP19A1 SNP (e.g., a polymorphism pair or a group of polymorphism pairs). Further, determining the variant profile can include detecting the presence or absence of any CYP19A1 SNP together with any SNP from another aromatase.

Aromatase activity (e.g., CYP19A1 activity) can be measured using, for example, in vitro methods such as those described herein. As used herein, the term "reduced aromatase status" refers to a decrease (e.g., a 5%, 10%, 15%, 20%, 25%, 30%, 40%, 50%, 60%, 70%, 75%, 80%, 90%, 95%, or 100% decrease) in aromatase activity (e.g., CYP19A1 activity) of a subject, as compared to a control level of aromatase activity. Similarly, the term "enhanced aromatase status" refers to an increase (e.g., a 5%, 10%, 15%, 20%, 25%, 30%, 40%, 50%, 60%, 70%, 75%, 80%, 90%, 95%, 100%, or more than 100% increase) in aromatase activity of a subject, as compared to a control level of aromatase activity. A control level of aromatase activity can be, for example, an average level of aromatase activity in a population of individuals. In one embodiment, the population includes individuals that do not contain particular CYP19A1 nucleotide sequence variants or particular CYP19A1 amino acid sequence variants (e.g., particular variants that affect aromatase status). Alternatively, a control level of aromatase activity can refer to the level of aromatase activity in a control subject (e.g., a subject that does not contain a CYP19A1 nucleic acid containing a variant).

In some embodiments, evaluation of aromatase status can be used in diagnostic assays to determine whether a particular therapeutic agent may be useful in an individual, or to determine an appropriate dose of the agent to administer to the individual. For example, an individual having enhanced aromatase status may catalyzes the formation of aromatic C18 estrogens from C19 androgen more than an individual having normal or reduced aromatase status. Thus, an individual with enhanced aromatase status may require higher doses of drugs, such as aromatase inhibitors, or alternate therapies altogether.

In further embodiments, aromatase status can be linked to predisposition to a particular condition, e.g., breast cancer, endometrial cancer, and endometriosis. Additional risk factors for a particular condition, including, for example, family history and other genetic factors can be considered when determining risk. Predisposition to such diseases can be determined based on the presence or absence of a single CYP19A1 sequence variant or based on a variant profile.

Articles of Manufacture

Articles of manufacture provided herein can include populations of isolated CYP19A1 nucleic acid molecules or CYP19A1 polypeptides immobilized on a substrate. Suitable substrates provide a base for the immobilization of the nucleic acids or polypeptides, and in some embodiments, allow immobilization of nucleic acids or polypeptides into discrete regions. In embodiments in which the substrate includes a plurality of discrete regions, different populations of isolated nucleic acids or polypeptides can be immobilized in each discrete region. Thus, each discrete region of the substrate can include a different CYP19A1 nucleic acid or CYP19A1 polypeptide sequence variant. Such articles of manufacture can include two or more sequence variants of CYP19A1, or can include all of the sequence variants known for CYP19A1. For example, the article of manufacture can include two or more of the sequence variants identified herein and one or more other CYP19A1 sequence variants, such as nucleic acid variants that occur in the promoter region of the CYP19A1 gene. Furthermore, nucleic acid molecules containing sequence variants for other aromatases can be included on the substrate.

Suitable substrates can be of any shape or form and can be constructed from, for example, glass, silicon, metal, plastic, cellulose, or a composite. For example, a suitable substrate can include a multiwell plate or membrane, a glass slide, a chip, or polystyrene or magnetic beads. Nucleic acid molecules or polypeptides can be synthesized in situ, immobilized directly on the substrate, or immobilized via a linker, including by covalent, ionic, or physical linkage. Linkers for immobilizing nucleic acids and polypeptides, including reversible or cleavable linkers, are known in the art. See, for example, U.S. Pat. No. 5,451,683 and WO98/20019. Immobilized nucleic acid molecules are typically about 20 nucleotides in length, but can vary from about 10 nucleotides to about 1000 nucleotides in length.

In practice, a sample of DNA or RNA from a subject can be amplified, the amplification product hybridized to an article of manufacture containing populations of isolated nucleic acid molecules in discrete regions, and hybridization can be detected. Typically, the amplified product is labeled to facilitate detection of hybridization. See, for example, Hacia et al., *Nature Genet.* (1996) 14:441-447; and U.S. Pat. Nos. 5,770,722 and 5,733,729.

The invention will be further described in the following examples, which do not limit the scope of the invention described in the claims.

EXAMPLES

Example 1

Methods and Materials

PCR Amplification and DNA Sequencing: DNA samples from 60 African-American, 60 Caucasian-American, 60 Han Chinese-American, and 60 Mexican-American subjects were obtained from the Coriell Institute Cell Repository (Camden, N.J.). These samples had been anonymized, and written informed consent had been obtained from all donors for the use of their DNA for this purpose. All experiments were reviewed and approved by the Mayo Clinic Institutional Review Board. Twenty-eight PCR reactions were performed with each DNA sample to amplify all CYP19A1 exons and splice junctions as well as a portion of the 5'-flanking region of the gene. The amplicons were then sequenced using dye-primer sequencing chemistry to facilitate the identification of heterozygous bases (Chadwick et al. *Biotechniques* (1996) 20:676-683). To make that possible, universal M13 sequencing tags were added to the 5'-ends of each forward and reverse primer. All forward primers contained the M13 forward sequence (5'-TGTAAAACGACGGCCAGT-3'; SEQ ID NO:5), and all reverse primers contained the M13 reverse sequence (5'-CAGGAAACAGCTATGACC-3'; SEQ ID NO:6). The sequences and locations of each primer within the gene are listed in Tables 1A and 1B. "F" represents forward; "R," reverse; and "UTR," untranslated region. The locations of primers within the gene were chosen to avoid repetitive sequence. The primer set used to amplify exon 10 for the Han Chinese American samples differed from that used for the other DNA samples in order to avoid PCR-induced artifacts. The area from (−643) to (−137) bp upstream of exon I.7 was amplified using a 1:10,000 dilution of the reaction mixture obtained after 30 cycles of the exon I.7 "long PCR reaction". This was done to avoid nonspecific amplification products.

Amplifications were performed with AMPLITAQ GOLD® DNA polymerase (PERKIN ELMER®, Foster City, Calif.) using a "hot start" to help ensure amplification specificity. Amplicons were sequenced in the Mayo Molecular Biology Core Facility with an ABI 377 DNA sequencer using BIGDYE™ (PERKIN ELMER®) dye-primer sequencing chemistry. Both DNA strands were sequenced in all cases. To exclude PCR-induced artifacts, independent amplification followed by DNA sequencing was performed for all samples in which a SNP was only observed once among the samples resequenced. DNA sequence chromatograms were analyzed using the PolyPhred 3.0 (Nickerson et al. *Nucl. Acids Res.* (1997) 25:2745-2751) and Consed 8.0 (Gordon et al. *Genome Res.* (1998) 8:195-202) programs developed by the University of Washington (Seattle, Wash.). The University of Wisconsin GCG software package, Version 10, was also used to analyze nucleotide sequence. GenBank accession numbers for the CYP19A1 reference sequences were NT_010194.16 and NM_000103.2.

CYP19 Genescan Analysis: A (TTTA)n repeat at position 77 in intron 4 was analyzed by using Genescan to detect polymorphism length. In this case, the reverse primer was labeled with a fluorescence tag, [(3',6'-dipivaloyfluoresceinyl)-6-carboxamidohexyl]-1-O-(2-cyanoethyl)-(N,N-diisopropyl)-phosphoramidite (6-FAM) (Glen Research, Sterling, Va.). An internal size standard (500-TAMPA; Perkin Elmer, Foster City, Calif.) was used to determine repeat length. These chromatogram traces were analyzed using GeneScan Analysis V3 (Perkin Elmer).

TABLE 1A

CYP19A1 Resequencing Primers

| Forward or Reverse | Region amplified by Primer | M13 Tag Sequence | Primer Sequence |
|---|---|---|---|
| F | Exon 1.1 | TGTAAAACGACGGCCAGT | GACTGATCATCTCTCAGCAATACCCAC (SEQ ID NO:13) |
| R | Exon 1.1 | CAGGAAACAGCTATGACC | CAGATTATAGAGTCCCGCCTTGGG (SEQ ID NO:14) |
| F | Exon 1.1 | TGTAAAACGACGGCCAGT | CTCTGGCCTTCTTTGCCCTCCTT (SEQ ID NO:15) |
| R | Exon 1.1 | CAGGAAACAGCTATGACC | CCAACACTATCTACCTGGAAAGAGT (SEQ ID NO:16) |
| F | Exon 2a | TGTAAAACGACGGCCAGT | GTCTGTTATGTTGTCACACAGG (SEQ ID NO:17) |
| R | Exon 2a | CAGGAAACAGCTATGACC | CAATCAAGCAGCACTTGGAATG (SEQ ID NO:18) |
| F | Exon 2a | TGTAAAACGACGGCCAGT | GGTGTCTTCTGACTGGCCTTCAT (SEQ ID NO:19) |

TABLE 1A-continued

CYP19A1 Resequencing Primers

| Forward or Reverse | Region amplified by Primer | M13 Tag Sequence | Primer Sequence |
|---|---|---|---|
| R | Exon 2a | CAGGAAACAGCTATGACC | GACACTCAGAGCCCTGGAAAGAA (SEQ ID NO:20) |
| F | Exon 1.4 | TGTAAAACGACGGCCAGT | GCTTAGGCTAAGCTGAATATATTT (SEQ ID NO:21) |
| R | Exon 1.4 | CAGGAAACAGCTATGACC | CATTATGAATCGAGCTGACATTCT (SEQ ID NO:22) |
| F | Exon 1.4 | TGTAAAACGACGGCCAGT | GGTAATGAGAGAAGATTCTGTTC (SEQ ID NO:23) |
| R | Exon 1.4 | CAGGAAACAGCTATGACC | CAAAGCACAGAACAGTCTCTTGT (SEQ ID NO:24) |
| F | Exon 1.5 | TGTAAAACGACGGCCAGT | CTAGTTCTGTAGCAATGACCGCA (SEQ ID NO:25) |
| R | Exon 1.5 | CAGGAAACAGCTATGACC | CTGTGGCCCACTACAGAGAAA (SEQ ID NO:26) |
| F | Exon 1.5 | TGTAAAACGACGGCCAGT | GCAAGGATGGGAGAGTGAGT (SEQ ID NO:27) |
| R | Exon 1.5 | CAGGAAACAGCTATGACC | GAATGAATGAAACCACTTACCCT (SEQ ID NO:28) |
| F | Exon 1.7 | TGTAAAACGACGGCCAGT | CCACTCTTCATAATAAATGCCTTAAGA (SEQ ID NO:29) |
| R | Exon 1.7 | CAGGAAACAGCTATGACC | CCTATTATCTCAAGTAGCAGAATATGT (SEQ ID NO:30) |
| F | Exon 1.7 | TGTAAAACGACGGCCAGT | CTACAGCTGTGATAGTTTAGCAT (SEQ ID NO:31) |
| R | Exon 1.7 | CAGGAAACAGCTATGACC | CCTTGTCACAGTCCACAGGGA (SEQ ID NO:32) |
| F | Exon 1.f | TGTAAAACGACGGCCAGT | AGTCAAACCTTACCTTACTTAACCG (SEQ ID NO:33) |
| R | Exon 1.f | CAGGAAACAGCTATGACC | GCGTACGCTCCTGTGAACAGA (SEQ ID NO:34) |
| F | Exon 1.f | TGTAAAACGACGGCCAGT | CTACGAGGAGCCAAAGTTTCA (SEQ ID NO:35) |
| R | Exon 1.f | CAGGAAACAGCTATGACC | CCCAGGAAAATGTGCAAATATC (SEQ ID NO:36) |
| F | Exon 1.2 | TGTAAAACGACGGCCAGT | CATTGGCTGCCCTCAGATTTC (SEQ ID NO:37) |
| R | Exon 1.2 | CAGGAAACAGCTATGACC | CACTCTTGACAGTACTATAGG (SEQ ID NO:38) |
| F | Exon 1.2 | TGTAAAACGACGGCCAGT | TCAGGATAGTTCCCACAGTG (SEQ ID NO:39) |
| R | Exon 1.2 | CAGGAAACAGCTATGACC | CTCAACAGAATATTTGAAAGCAGATT (SEQ ID NO:40) |

TABLE 1B

CYP19A1 Resequencing Primers

| Forward or Reverse | Region amplified by Primer | M13 Tag Sequence | Primer Sequence |
|---|---|---|---|
| F | Exon 1.6 | TGTAAAACGACGGCCAGT | TCACATAGAACTTACTCAGAATGATG (SEQ ID NO:41) |
| R | Exon 1.6 | CAGGAAACAGCTATGACC | CTCTGTGTATTCCTTGAAACACTG (SEQ ID NO:42) |
| F | Exon 1.6 | TGTAAAACGACGGCCAGT | GCCTTTCTCCACTAGAATGTGCCGAT (SEQ ID NO:43) |
| R | Exon 1.6 | CAGGAAACAGCTATGACC | GGTGCCACTCAGGAACCTCAT (SEQ ID NO:44) |
| F | 5'FR | TGTAAAACGACGGCCAGT | GTCTTGCACAGGATGTTAGCTGCT (SEQ ID NO:45) |
| R | 5'FR | CAGGAAACAGCTATGACC | GAGTCATTTTGTGACTTCATCAGCAGGT (SEQ ID NO:46) |
| F | 5'FR | TGTAAAACGACGGCCAGT | CAAGGGAAGAAGATTGCCTAAACA (SEQ ID NO:47) |
| R | 5'FR | CAGGAAACAGCTATGACC | CCATCTTGTGTTCCTTGACCTCAGA (SEQ ID NO:48) |
| F | Exon 2 | TGTAAAACGACGGCCAGT | CTGAAGCAACAGGAGCTATAGATGA (SEQ ID NO:49) |
| R | Exon 2 | CAGGAAACAGCTATGACC | CCATCATGGACCAAAATCCCAAGT (SEQ ID NO:50) |
| F | Exon 3 | TGTAAAACGACGGCCAGT | GTGATTCACAGATATACATCACAT (SEQ ID NO:51) |
| R | Exon 3 | CAGGAAACAGCTATGACC | CCAATTATTCTGTTTGCAATGTTAGA (SEQ ID NO:52) |
| F | Exon 4 | TGTAAAACGACGGCCAGT | GGAGCAACATGCATTTGCTAAGA (SEQ ID NO:53) |
| R | Exon 4 | CAGGAAACAGCTATGACC | GGTGATAGAGGTCAGAGCCTGTCTCA (SEQ ID NO:54) |
| F | Exon 5 | TGTAAAACGACGGCCAGT | GGCATGATTGTGTGTGTGCCCTGGA (SEQ ID NO:55) |
| R | Exon 5 | CAGGAAACAGCTATGACC | GGCATGTGATTCCTTTGGTCTGTTA (SEQ ID NO:56) |
| F | Exon 6 | TGTAAAACGACGGCCAGT | GTTAGGAGAATCTGCAGGGAATGA (SEQ ID NO:57) |
| R | Exon 6 | CAGGAAACAGCTATGACC | CTTGCCGAGAAGCTGCCCAGCCA (SEQ ID NO:58) |
| F | Exon 7 | TGTAAAACGACGGCCAGT | CATGAAGTGTAGGGTCTATGTAAT (SEQ ID NO:59) |
| R | Exon 7 | CAGGAAACAGCTATGACC | GATCTTTACACACCTCTACACAGT (SEQ ID NO:60) |
| F | Exon 8 | TGTAAAACGACGGCCAGT | GACATGTGGTTTCTATGATTTCAT (SEQ ID NO:61) |
| R | Exon 8 | CAGGAAACAGCTATGACC | GATTAAGAACACAGAAAGAGCTATCT (SEQ ID NO:62) |
| F | Exon 9 | TGTAAAACGACGGCCAGT | CTAACATTACCTTCTTTGTTCCT (SEQ ID NO:63) |
| R | Exon 9 | CAGGAAACAGCTATGACC | GGTGAGGTGGCAGAGGGAATGAGTA (SEQ ID NO:64) |
| F | Exon 10* | TGTAAAACGACGGCCAGT | CAGAATGAATCAAACAGAGACTGA (SEQ ID NO:65) |
| R | Exon 10* | CAGGAAACAGCTATGACC | GCCATGGGCCACTGAGTGTTCA (SEQ ID NO:66) |
| F | Exon 10** | TGTAAAACGACGGCCAGT | CAAACAGAGACTGAGTGACTCAGC (SEQ ID NO:67) |
| R | Exon 10** | CAGGAAACAGCTATGACC | GGATGGATTTGTATGTGAACTAC (SEQ ID NO:68) |
| F | 3'UTR | TGTAAAACGACGGCCAGT | CTCAGACAGGTGTCTGGAACACTA (SEQ ID NO:69) |
| R | 3'UTR | CAGGAAACAGCTATGACC | CTGGTCTTTCTAATCAACTTGAGT (SEQ ID NO:70) |

The * means that these primers were used for the exon 10 amplification of the Caucasian-American population, African-American population, and Mexican-American population. The ** means that these primers were used for the exon 10 amplification of the Han Chinese-American Population.

Recombinant CYP19A1 Expression Constructs and Allozyme Expression: A CYP19A1 cDNA sequence for the non-synonymous cSNP that was observed during the resequencing experiments was created using the QUICKCHANGE® Site-Directed Mutagenesis kit (STRATAGENE®, La Jolla, Calif.), using the wild type CYP19A1 cDNA open reading frame (ORF) in the pUni/V5-His-TOPO (pUni) vector (INVITROGEN™) as template. Specifically, the full-length wild type ORF (GenBank accession number NM_001785) was amplified using human brain MARATHON-READY™ cDNA (CLONTECH™) as template. The resultant CYP19A1 cDNA was subcloned into pUni, a vector that is only 2.3 kilobases in length, so it is well suited for performing "circular PCR" during site-directed mutagenesis. Site-directed mutagenesis was performed using internal primers that contained the variant nucleotide sequences. The CYP19A1 cDNA insert in pUni were excised and re-ligated into the eukaryotic expression vector pCR3.1 (INVITROGEN™). The sequence of the insert in pCR3.1 was confirmed by completely sequencing both strands.

To make it possible to correct for transfection efficiency, an expression construct was designed and contained a green fluorescent protein (GFP) and human NADPH-b5 reductase (DIA1) fusion protein that would be targeted to the endoplasmic reticulum because of the DIA1 portion of the construct. The DIA1 cDNA was amplified using a human liver Marathon-Ready cDNA library (BD Biosciences Clonetech, Palto Alto, Calif.) as template, and was cloned into the GFP fusion TOPO TA expression vector (Invitrogen, Carlsbad, Calif.).

Expression constructs for the wild type and variant CYP19A1 sequences were transfected into COS-1 cells using the TRANSFAST™ reagent (PROMEGA™), with a 1:1 charge ratio. Specifically, 7 μg of aromatase expression construct DNA was cotransfected with 7 μg of DIA1-GFP expression construct DNA. After 48 hours, the COS-1 cells were harvested in 0.25 M sucrose and were homogenized for 20 seconds with a POLYTRON® homogenizer (Brinkmann Instruments, Westbury, N.Y.). The homogenates were centrifuged at 500×g for 5 minutes and at 6,500×g for 10 minutes. The supernatant was then transferred to a new tube and was centrifuged at 11,600×g for 15 minutes. The supernatant from that step was centrifuged at 132,000×g for 45 minutes and the pellet was resuspended in 0.05 M potassium phosphate buffer (pH 7.4), followed by storage at −70° C.

To correct for variation in transfection efficiency, green fluorescence was measured in the microsomal fraction with a SPECTRAmax GEMINI™ XS dual-scanning microplate spectrofluorometer (Molecular Devices Corporation, Sunnyvale, Calif.) using excitation and emission wavelengths of 395 nm and 507 nm, respectively. Levels of immunoreactive protein and enzyme activity for these transfections were then corrected on the basis of the GFP values. The resultant supernatant preparations were used for enzyme assays and substrate kinetic studies.

CYP19A1 Western Blot Analysis: A mouse anti-human aromatase monoclonal antibody directed against human aromatase amino acids 376-390 was purchased from Serotec (Raleigh, N.C.). Aliquots of COS-1 cell microsomal fractions transfected with CYP19A1 allozyme cDNA expression constructs were loaded onto 12.5% acrylamide SDS-PAGE gels on the basis of GFP values to correct for transfection efficiency. After electrophoresis, proteins were transferred to PDVF membranes and were detected using the ECL™ Western Blotting System (Amersham Pharmacia, Piscataway, N.J.). An AMBIS Radioanalytic Imaging System, Quant Probe Version 4.31 (Ambis, Inc., San Diego, Calif.) was used to quantitate levels of immunoreactive protein relative to that for the WT allozyme.

Immunofluorescence Microscopy: Fluorescein isothiocyanate (FITC)-conjugated goat anti-mouse immunoglobulin and tetramethylrhodamine isothiocyanate (TRITC)-conjugated goat anti-rabbit immunoglobulin were purchased from Southern Biotech (Birmingham, Ala.). COS-1 cells were subcultured to 50-70% confluence on coverslips, were transfected with expression constructs and were then cultured for an additional 48 hours. The cells were washed with phosphatebuffered saline (PBS), fixed with 3% paraformaldehyde for 12 minutes at room temperature and were washed and incubated at room temperature for 5 minutes with buffer containing 0.5% Triton X-100. The coverslips were then incubated with the primary antibodies (rabbit polyclonal anti-human antibody against calnexin, an endoplasmic reticulum marker, and mouse monoclonal antihuman aromatase antibody) followed by FITC-conjugated goat anti-mouse or TRITC-conjugated goat anti-rabbit IgG antibody. The COS-1 cells were then viewed by fluorescence microscopy using a Nikon 80i fluorescence microscope with 488 or 570 nm filters for excitation of the green or red fluorochrome, respectively.

Data Analysis: Statistical comparison of the data was performed by ANOVA using the StatView program, version 4.5 (Abacus Concepts, Inc., Berkeley, Calif.). Linkage analysis was performed after all DNA samples had been genotyped at each of the polymorphic sites observed, using the EH program developed by Terwilliger and Ott, *Handbook of Human Genetic Linkage* (1994) The Johns Hopkins University Press, Baltimore, pp. 188-193. D' values, a quantitative method for reporting linkage data that is independent of allele frequency (Hartl and Clark *Principles of Population Genetics*, $3^{rd}$ edition (1997) Sinauer Associates, Inc., (Sunderland, Mass.), pp. 96-106; and Hedrick *Genetics of Populations*, $2^{nd}$ edition (2000) Jones and Bartlett (Sudbury, Mass.), pp. 396-405), were calculated. The genotype data also were used to assign inferred haplotypes using a program based on the E-M algorithm (Long et al. *Am. J. Hum. Genet.* (1995) 56:799-810; and Excoffier and Slatkin *Mol. Biol. Evol.* (1995) 12:921-927). Unambiguous haplotype assignment was possible on the basis of genotype for samples that contained no more than one heterozygous polymorphism.

CYP19A1 Enzyme Activity: Aromatase catalyzes the formation of aromatic C18 estrogens from C19 androgen. The amount of $^3H_2O$ released from the substrate [1β$^3$H]androst-4-ene-3,17-dione was used to assay the activity of the T115C, C602T, C790T, T1091C, and DM (a T155C and C790T double mutant) polymorphisms, and wild type CYP19A1. The reactions were carried out for 20 minutes at 37° C. in 0.05M Tris HCl, pH 7.4, under air. Each reaction mixture contained either 20 or 100 nM [1β$_3$H]androst-4-ene-3,17-dione (25.3 Ci/mmol), 30 to 60 ng of microsomal protein and an NADPH regeneration system (1.5 mM glucose-6-phosphate, 1 unit of glucose-6-phosphate dehydrogenase and 3.5 mM NADPH) in a final volume of 100 μl. After incubation, 6 volumes of chloroform were added to the reaction mixture, and the mixture was vortexed for 30 seconds to terminate the reaction and partition the remaining substrate into the organic phase. After centrifugation at 14,000×g for 10 minutes, radioactivity remaining in the aqueous phase was determined by liquid scintillation counting.

Estimating Apparent $K_m$ Values: To estimate apparent $K_m$ values of CYP19A1, the T115C, C602T, C790T, T1091C, and DM polymorphisms, and wild type CYP19A1, assays were performed as described above for calculating enzyme activity. Triplicate assays were performed for each variant allozyme in the presence of eight concentrations of [1β$^3$H] androst-4-ene-3,17-dione that vaired from 0.3 to 40 nM. For the T1091C variant, the [1β$^3$H]androst-4-ene-3,17-dione concentration ranged from 1.25 to 160 nM. COS-1 cells were transfected with an expression construct containing a sequence encoding the wild type CYP19A1 or an allozyme variant. Microsomal fractions were prepared. Transfection efficiency was corrected for by Co-transfection of a fusion construct containing green fluorescent protein (GFP) and human NADPH-b5 reductase, and normalizing the amount of microsomal fraction to use in assays based on the levels of the fusion construct. Blanks for each substrate concentration can be included by assaying COS-1 cell cytosol after transfection with empty pCR3.1 vector. Apparent $K_m$ values were calculated with the method of Wilkinson (*Biochem. J.* (1961) 80:324-332) using a computer program written by Cleland (*Nature* (1963) 198:463-465). Points that deviated from linearity on double inverse plots, i.e., those showing substrate inhibition, were not used to perform these calculations.

Calculating $K_i$ Values: $K_i$ values for the T115C, C602T, C790T, T1091C, and DM polymorphisms, and wild type CYP19A1 were determined by performing the assay described above for calculating enzyme activity but including the aromatase inhibitors letrozole and exemestane. Triplicate assays were performed using six concentrations of 1β³H] androst-4-ene-3,17-dione that varied from 1.25 to 320 nM, in the presence of one of three concentrations of letrozole (0.2, 0.4, or 0.8 nM) or exemestane (1.25, 2.5, or 5 nM). In the case of the T1091C variant, the letrozole concentrations were 0.1, 0.2, or 0.4 nM but the exemestane concentrations were as with the other allozymes. For the determination of $K_i$ values, Lineweaver-Burke double inverse plots were performed at each concentration of inhibitor. Slopes were calculated for the double inverse plots, and secondary plots of slope against inhibitor concentration were determined. Intercepts on the inhibitor concentration axis were used to determine $K_i$ values. Pearson product moment correlation coefficients were calculated using Excel™ and group means were compared by the use of ANOVA with the Prism program.

Example 2

CYP19A1 Polymorphisms

Twenty-eight separate PCR amplifications were performed for each of the 60 DNA samples studied. All exons, including at least 500 bp of each of the 5'-untranslated exons, all exon-intron splice junctions, and a portion of the 3'-untranslated region (3'-UTR) were sequenced. All PCR amplicons were sequenced on both strands, making it possible to verify the presence of polymorphisms using data from the complimentary strand. A total of 88 polymorphisms were observed (Table 2), resulting in 44 haplotypes. SNPs within the ORF are numbered by location in the cDNA, with the "A" of the ATG being (+1). Introns are numbered with a positive number indicating the number of nucleotides away from the intron/exon splice junction in the 3' direction, and a negative number in the 5' direction. For each 5'UTR alternatively spliced exon, the exons are numbered with the "G" of the GT splice site as (+1) and the nucleotide directly 5 prime as (−1), i.e., there is no zero.

Variant allele frequencies ranged from 0.8% to 94.1%, with differences between the African-American, Caucasian-American, Han Chinese-American, and Mexican-American subjects, as shown in Table 2. Seventy-three polymorphisms were observed in the DNA samples from African-American subjects, while 42 were found in the samples from Caucasian-American subjects, 34 were found in the samples from Han Chinese-American subjects, and 46 were found in the samples from Mexican-American subjects. Eighty-eight polymorphisms were observed, including 85 SNPs, 2 insertion-deletion events and a polymorphic TTTA repeat. There were large ethnic variations in both allele frequencies and types, with 69 polymorphisms in African-American DNA, 37 in DNA samples from Caucasian-American subjects, 30 in Han Chinese American subjects, and 44 in DNA from Mexican-American subjects. Thirty-two polymorphisms were observed only in AA subjects, 6 in Han Chinese American subjects, 6 in Mexican-American subjects and 5 in Caucasian-American subjects. Of the polymorphisms identified in the course of these studies, 62 had not been reported previously, 31 of which were "common", with allele frequencies of greater than 1% in at least one ethnic group. All polymorphisms were in Hardy-Weinberg equilibrium except for one polymorphism in CA subjects which was located (−41) bp upstream of exon I.1. Ten of the SNPs were within the coding-region (cSNPs), and 4 of those cSNPs—located in exons 2, 5, 7, and 9—were nonsynonymous and resulted in the amino acid alterations Trp39Arg, Thr201Met, Arg264Cys, and Met364Thr (these variants may also be referred to by the designation of the non-wild type amino acid residue three-letter abbreviation and the amino acid residue number; e.g, "Trp39Arg" can be referred to as "Arg39"). The Trp39Arg polymorphism had a frequency of 6.7% in Han Chinese-American subjects but was not observed in DNA from Caucasian-American, African-American, or Mexican-American subjects. The Thr201Met polymorphism had frequencies of 5% in African Americans, 5% in Caucasian Americans, and 0.8% in Mexican Americans, but was not observed in Han Chinese Americans. The Arg264Cys polymorphism had frequencies of 22.5% in African Americans, 2.5% in Caucasian Americans, 11.7% in Han Chinese Americans, and 5% in Mexican Americans. The Met364Thr polymorphism had a frequency of 0.8% in Han Chinese Americans, but was not observed in African Americans, Caucasian Americans, or Mexican Americans. Homozygous samples were only observed for Arg264Cys in both African-American and Han Chinese-American subjects. To exclude artifacts introduced by PCR-dependent misincorporation, independent amplifications were performed and the amplicons were sequenced in all cases in which a polymorphism was observed only once among the DNA samples studied.

"Nucleotide diversity", a quantitative measure of genetic variation, adjusted for the number of alleles studied, was also determined. Two standard measures of nucleotide diversity are π, average heterozygosity per site, and θ, a population mutation measure that is theoretically equal to the neutral mutation parameter (Tajima et al. *Genetics* (1989) 123:585-595; Fullerton et al. *Am. J. Hum. Genet.* (2000) 67:881-900). The π values (π×10⁴) were 9.95±5.04 for the Caucasian Americans; 8.16±4.20 for the African Americans; 8.75±4.47 for the Han Chinese Americans; and 7.87±4.05 for the Mexican Americans. The θ values (θ×10⁴) were 11.5±3.00 for the Caucasian Americans; 6.22±1.77 for the African Americans; 5.01±1.47 for the Han Chinese Americans; and 7.33±2.01 for the Mexican Americans. In addition, values for Tajima's D, a test of the "neutral" mutation hypothesis (Tajima et al. supra), were estimated for each population. The Tajima's D values were −0.43 for the Caucasian Americans; 0.95 for the African Americans; 2.22 for the Han Chinese Americans; and 0.23 for the Mexican Americans. Only the value for Tajima's D in Han Chinese-American subjects differed significantly for values for the other ethnic groups.

TABLE 2

CYPI9A1 Polymorphisms

| Location | Nucleotide | Sequence Change | Amino Acid Change | Frequency of Variant Allele ||||
|---|---|---|---|---|---|---|---|
| | | | | African-American | Caucasian | Han Chinese American | Mexican-American |
| 5FR Exon 1.1 | -588 | G → A | | 0.408 | 0.142 | 0.150 | 0.175 |
| 5'FR Exon 1.1 | -566 | C → T | | 0.000 | 0.000 | 0.006 | 0.000 |
| 5'FR Exon 1.1 | -554 | T → C | | 0.008 | 0.000 | 0.000 | 0.000 |
| 5'FR Exon 1.1 | -316 | T → C | | 0.008 | 0.000 | 0.000 | 0.000 |
| 5'FR Exon 1.1 | -278 | C → T | | 0.000 | 0.000 | 0.283 | 0.416 |
| 5'FR Exon 1.1 | -245 | G → T | | 0.000 | 0.008 | 0.000 | 0.000 |
| 5FR Exon 1.1 | -144 | C → T | | 0.250 | 0.158 | 0.150 | 0.158 |
| Exon 1.1 | -35 | G → A | | 0.008 | 0.000 | 0.000 | 0.008 |
| Exon 1.1 | -2 | G → A | | 0.008 | 0.000 | 0.000 | 0.000 |
| 5'FR Exon 2a | -639 | G → A | | 0.000 | 0.008 | 0.000 | 0.000 |
| 5'FR Exon 2a | -632 | C → T | | 0.042 | 0.000 | 0.000 | 0.000 |
| 5'FR Exon 2a | -468 | C → T | | 0.185 | 0.175 | 0.000 | 0.300 |
| 5'FR Exon 2a | -429 | T → C | | 0.000 | 0.042 | 0.000 | 0.000 |
| 5'FR Exon 2a | -149 | C → G | | 0.008 | 0.000 | 0.000 | 0.000 |
| 5'FR Exon 2a | -125 | C → T | | 0.150 | 0.000 | 0.000 | 0.025 |
| 5'FR Exon 2a | -124 | G → A | | 0.008 | 0.000 | 0.000 | 0.000 |
| Exon 2a | -38 | A → G | | 0.000 | 0.000 | 0.000 | 0.008 |
| Exon 2a | -21 | C → A | | 0.092 | 0.008 | 0.000 | 0.000 |
| 5'FR Exon 1.4 | -563 | G → A | | 0.042 | 0.000 | 0.000 | 0.000 |
| 5'FR Exon 1.4 | -562 | C → A | | 0.042 | 0.000 | 0.000 | 0.000 |

TABLE 2-continued

CYP19A1 Polymorphisms

| | | | | | | | | | | | |
|---|---|---|---|---|---|---|---|---|---|---|---|
| Exon 1.4 | -241 | G → T | | | | 0.000 | | 0.000 | | 0.008 | | 0.000 |
| 5'FR Exon 1.5 | -638 | C → T | | | | 0.000 | | 0.000 | | 0.000 | | 0.008 |
| 5'FR Exon 1.5 | -628 | C → G | | | | 0.469 | | 0.867 | | 0.683 | | 0.874 |
| 5'FR Exon 1.5 | -334 | T → C | | | | 0.339 | | 0.050 | | 0.167 | | 0.126 |
| 5'FR Exon 1.5 | -317 | G → C | | | | 0.075 | | 0.092 | | 0.000 | | 0.025 |
| 5'FR Exon 1.5 | -128 | C → T | | | | 0.016 | | 0.000 | | 0.000 | | 0.000 |
| Exon 1.5 | -80 | A → T | | | | 0.025 | | 0.000 | | 0.000 | | 0.000 |
| 5'FR Exon 1.7 | -651 | C → T | | | | 0.025 | | 0.000 | | 0.000 | | 0.000 |
| 5'FR Exon 1.7 | -550 | G → A | | | | 0.008 | | 0.000 | | 0.000 | | 0.000 |
| 5'FR Exon 1.7 | -543 | G → A | | | | 0.042 | | 0.000 | | 0.000 | | 0.000 |
| 5'FR Exon 1.7 | -495 | G → A | | | | 0.033 | | 0.000 | | 0.000 | | 0.000 |
| 5'FR Exon 1.7 | -439 | A → C | | | | 0.000 | | 0.008 | | 0.000 | | 0.008 |
| 5'FR Exon 1.7 | -428 | G → A | | | | 0.000 | | 0.008 | | 0.000 | | 0.000 |
| 5'FR Exon 1.7 | -408 | G → A | | | | 0.017 | | 0.000 | | 0.000 | | 0.000 |
| 5'FR Exon 1.7 | -194 | G → T | | | | 0.008 | | 0.000 | | 0.000 | | 0.000 |
| Exon 1.7 | -26 | C → T | | | | 0.017 | | 0.000 | | 0.000 | | 0.000 |
| Intron 1.7 | 25 | G → A | | | | 0.033 | | 0.000 | | 0.000 | | 0.000 |
| Intron 1.7 | 54 | G → C | | | | 0.361 | | 0.058 | | 0.000 | | 0.000 |
| 5'FR Exon 1.f | -739 | C → A | | | | 0.042 | | 0.000 | | 0.000 | | 0.000 |
| 5'FR Exon 1.f | -725 | G → A | | | | 0.150 | | 0.092 | | 0.000 | | 0.025 |
| 5'FR Exon 1.f | -690 | A → C | | | | 0.150 | | 0.092 | | 0.000 | | 0.025 |
| 5'FR Exon 1.f | -649 | C → T | | | | 0.442 | | 0.942 | | 0.317 | | 0.941 |
| 5'FR Exon 1.f | -425 | C → T | | | | 0.000 | | 0.000 | | 0.000 | | 0.008 |
| 5'FR Exon 1.f | -391 | T → G | | | | 0.008 | | 0.000 | | 0.000 | | 0.000 |

TABLE 2-continued

CYPI9A1 Polymorphisms

| | | | | | | | |
|---|---|---|---|---|---|---|---|
| Exon 1.f | -108 | C → T or A | | 0.008 (T) | 0.000 | 0.000 | 0.008 (A) |
| Exon 1.f | -66 | C → T | | 0.033 | 0.000 | 0.000 | 0.000 |
| Exon 1.f | -35 | A → G | | 0.008 | 0.000 | 0.000 | 0.000 |
| 5'FR Exon 1.2 | -827 | A → G | | 0.008 | 0.000 | 0.000 | 0.008 |
| 5'FR Exon 1.2 | -757 | G → A | | 0.017 | 0.000 | 0.000 | 0.000 |
| 5'FR Exon 1.2 | -596 | T → C | | 0.392 | 0.125 | 0.225 | 0.108 |
| 5'FR Exon 1.2 | -555 | T → A | | 0.017 | 0.000 | 0.000 | 0.000 |
| Exon 1.2 | -224 | G → C | | 0.125 | 0.450 | 0.437 | 0.267 |
| Exon 1.2 | -217 | G → A | | 0.000 | 0.000 | 0.000 | 0.008 |
| Exon 1.2 | -125 | C → T | | 0.016 | 0.000 | 0.000 | 0.000 |
| 5'FR Exon 1.6 | -362 | C → T | | 0.000 | 0.000 | 0.000 | 0.008 |
| 5'FR Exon 1.6 | -301 | T → G | | 0.008 | 0.000 | 0.000 | 0.000 |
| 5'FR Exon 1.6 | -273 | T → A | | 0.000 | 0.008 | 0.000 | 0.000 |
| 5'FR Exon 1.6 | -196 | A → C | | 0.300 | 0.608 | 0.442 | 0.517 |
| Exon 1.6 | -77 | G → A | | 0.492 | 0.117 | 0.425 | 0.267 |
| Intron 1.6 | 53 | C → A | | 0.000 | 0.000 | 0.017 | 0.000 |
| Intron 1.6 | 61 | C → T | | 0.030 | 0.025 | 0.000 | 0.033 |
| Intron 1.6 | 353 | GT I → D | | 0.000 | 0.000 | 0.017 | 0.000 |
| Exon PII | -83 | C → A | | 0.067 | 0.008 | 0.008 | 0.025 |
| Exon 2 | 42 | C → G | | 0.033 | 0.000 | 0.000 | 0.000 |
| Exon 2 | 109 | T → C | | 0.033 | 0.000 | 0.000 | 0.000 |
| Exon 2 | 115 | T → C | Trp (39) Arg | 0.000 | 0.000 | 0.067 | 0.000 |
| Intron 2 | -59 | A → G | | 0.175 | 0.542 | 0.450 | 0.283 |
| Intron 2 | -27 | T → C | | 0.100 | 0.000 | 0.000 | 0.000 |
| Exon 3 | 186 | C → T | | 0.067 | 0.008 | 0.008 | 0.033 |
| Exon 3 | 240 | A → G | | 0.167 | 0.542 | 0.467 | 0.283 |
| Exon 3 | 48 | G → A | | 0.008 | 0.000 | 0.000 | 0.000 |
| Intron 4 | 8 | G → A | | 0.008 | 0.000 | 0.008 | 0.000 |
| Intron 4 | 27 | TCT I → D | | 0.308 | 0.333 | 0.333 | 0.417 |

TABLE 2-continued

CYPI9A1 Polymorphisms

| Location | Position | Change | AA Change | | | | |
|---|---|---|---|---|---|---|---|
| Intron 4 | 77 | (TTTA)ₙ | | | | | |
| | | n = 7 | | 0.833 | 0.475 | 0.533 | 0.658 |
| | | n = 8 | | 0.025 | 0.125 | 0.008 | 0.092 |
| | | n = 10 | | 0.008 | 0.008 | 0.017 | 0.017 |
| | | n = 11 | | 0.125 | 0.342 | 0.350 | 0.200 |
| | | n = 12 | | 0.000 | 0.033 | 0.092 | 0.033 |
| | | n = 13 | | 0.008 | 0.008 | 0.000 | 0.000 |
| Exon 5 | 602 | C → T | Thr (201) Met | 0.050 | 0.050 | 0.000 | 0.008 |
| Intron 5 | -16 | T → G | | 0.200 | 0.542 | 0.508 | 0.317 |
| Exon 6 | 633 | T → C | | 0.000 | 0.000 | 0.000 | 0.008 |
| Intron 6 | 36 | A → T | | 0.200 | 0.542 | 0.508 | 0.317 |
| Intron 6 | 44 | G → C | | 0.008 | 0.000 | 0.000 | 0.008 |
| Intron 6 | -106 | T → G | | 0.192 | 0.542 | 0.542 | 0.308 |
| Exon 7 | 790 | C → T | Arg (264) Cys | 0.225 | 0.025 | 0.117 | 0.05 |
| Intron 7 | 26 | C → T | | 0.033 | 0.100 | 0.000 | 0.225 |
| Intron 7 | -79 | A → G | | 0.183 | 0.542 | 0.508 | 0.317 |
| Exon 8 | 963 | C → G | | 0.017 | 0.000 | 0.000 | 0.000 |
| Intron 8 | 29 | C → T | | 0.008 | 0.000 | 0.000 | 0.000 |
| Exon 9 | 1091 | T → C | Met(364) Thr | 0.000 | 0.000 | 0.008 | 0.000 |
| 3UTR | 1531 | C → T | | 0.192 | 0.558 | 0.517 | 0.317 |
| 3UTR | 1673 | G → T | | 0.308 | 0.292 | 0.333 | 0.533 |

The shaded areas represent previosly reported SNPs.

I/D refers to an insertion/deletion even in which a C is deleted in the most common (wild type) sequence.

Example 3

Linkage Disequilibrium Analysis and Haplotype Analysis

Linkage disequilibrium analysis was performed after all of the DNA samples had been genotyped at each of the polymorphic sites. Pairwise combinations of these polymorphisms were tested for linkage disequilibrium using the EH program developed by Terwilliger and Ott, *Handbook of Human Genetic Linkage* (1994) The Johns Hopkins University Press, Baltimore, pp. 188-193. The output of this program was used to calculate D' values, a method for reporting linkage data that is independent of allele frequency. Pairwise combinations with a statistically significant linkage disequilibrium (P value <0.001) were identified (data not shown).

The genotype data also were used for haplotype analysis (Tables 3-6). Only haplotypes with frequencies greater than or equal to 1.0% are shown in the tables. Haplotypes can be determined unequivocally only if not more than one polymorphism in an allele is heterozygous, but it is possible to "infer" haplotypes computationally (Schaid et al. *Am. J. Hum. Genet.* (2002) 70:425-434). Ethnic-group-specific haplotype analysis for CYP19A1 demonstrated 12 unequivocal haplotypes and 32 inferred haplotypes—with striking variations among the four ethnic groups in haplotype frequencies. "Inferred" haplotypes with frequencies >2% are also listed. The variant nucleotide is shaded. All others are wild type. As shown in the tables, 16.8% unequivocal haplotypes were identified by these studies for Caucasian-American subjects. 12.8% for African-American subjects, 59.6% for Han Chinese-American subjects, and 46.9% for Mexican-American subjects. The unequivocal haplotypes included 1 that were ethnic-specific for Caucasian-American subjects, 2 that were ethnic-specific for African-American subjects, 4 that were ethnic-specific for Han Chinese-American subjects, and 4 that were common to all four ethnic groups.

Tables 3-6

Human CYP19A1 Haplotype Analysis

TABLE 3

Haplotypes for Caucasian American Population (CYP19A1)

| Frequency | Observed or Inferred | 5'FR of Exon 1.1 | 5'FR of Exon 1.1 | 5'FR of Exon 1.1 | 5'FR of Exon 1.1 | 5'FR of Exon 1.1 | 5'FR of Exon 1.1 | 5'FR of Exon 1.1 | Exon 1.1 | Exon 1.1 | 5'FR of Exon 2a | 5'FR of Exon 2a |
|---|---|---|---|---|---|---|---|---|---|---|---|---|
| 1.0% | i | A | C | T | T | C | G | T | G | G | G | C |
| 3.3% | i | A | C | T | T | C | G | T | G | G | G | C |
| 3.2% | i | A | C | T | T | C | G | T | G | G | G | C |
| 1.0% | i | A | C | T | T | C | G | T | G | G | G | C |
| 1.5% | i | A | C | T | T | C | G | T | G | G | G | C |
| 2.5% | o | G | C | T | T | C | G | C | G | G | G | C |
| 6.7% | i | G | C | T | T | C | G | C | G | G | G | C |
| 2.6% | o | G | C | T | T | C | G | C | G | G | G | C |
| 6.7% | i | G | C | T | T | C | G | C | G | G | G | C |
| 1.5% | i | G | C | T | T | C | G | C | G | G | G | C |
| 1.8% | i | G | C | T | T | C | G | C | G | G | G | C |
| 11.7% | o | G | C | T | T | C | G | C | G | G | G | C |
| 3.3% | i | G | C | T | T | C | G | C | G | G | G | C |

| Frequency | Observed or Inferred | 5'FR of Exon 2a | 5'FR of Exon 2a | 5'FR of Exon 2a | 5'FR of Exon 2a | 5'FR of Exon 2a | Exon 2a | Exon 2a | 5'FR of Exon 1.4 | 5'FR of Exon 1.4 | Exon 1.4 | 5'FR of Exon 1.5 |
|---|---|---|---|---|---|---|---|---|---|---|---|---|
| 1.0% | i | C | T | C | C | G | A | C | G | C | G | C |
| 3.3% | i | C | T | C | C | G | A | C | G | C | G | C |
| 3.2% | i | C | T | C | C | G | A | C | G | C | G | C |
| 1.0% | i | C | T | C | C | G | A | C | G | C | G | C |
| 1.5% | i | C | T | C | C | G | A | C | G | C | G | C |
| 2.5% | o | C | C | C | C | G | A | C | G | C | G | C |
| 6.7% | i | C | T | C | C | G | A | C | G | C | G | C |
| 2.6% | o | C | T | C | C | G | A | C | G | C | G | C |
| 6.7% | i | C | T | C | C | G | A | C | G | C | G | C |
| 1.5% | i | C | T | C | C | G | A | C | G | C | G | C |
| 1.8% | i | C | T | C | C | G | A | C | G | C | G | C |
| 11.7% | o | T | T | C | C | G | A | C | G | C | G | C |
| 3.3% | i | T | T | C | C | G | A | C | G | C | G | C |

TABLE 3-continued

Haplotypes for Caucasian American Population (CYP19A1)

| Frequency | Observed or Inferred | 5'FR of Exon 1.5 | 5'FR of Exon 1.5 | 5'FR of Exon 1.5 | 5'FR of Exon 1.5 | Exon 1.5 | 5'FR of Exon 1.7 | 5'FR of Exon 1.7 | 5'FR of Exon 1.7 | 5'FR of Exon 1.7 | 5'FR of Exon 1.7 | 5'FR of Exon 1.7 |
|---|---|---|---|---|---|---|---|---|---|---|---|---|
| 1.0% | i | G | T | G | C | A | C | G | G | G | A | G |
| 3.3% | i | G | T | G | C | A | C | G | G | G | A | G |
| 3.2% | i | G | T | G | C | A | C | G | G | G | A | G |
| 1.0% | i | G | T | G | C | A | C | G | G | G | A | G |
| 1.5% | i | G | T | G | C | A | C | G | G | G | A | G |
| 2.5% | o | G | T | G | C | A | C | G | G | G | A | G |
| 6.7% | i | G | T | C | C | A | C | G | G | G | A | G |
| 2.6% | o | G | T | G | C | A | C | G | G | G | A | G |
| 6.7% | i | G | T | G | C | A | C | G | G | G | A | G |
| 1.5% | i | G | T | G | C | A | C | G | G | G | A | G |
| 1.8% | i | G | T | G | C | A | C | G | G | G | A | G |
| 11.7% | o | G | T | G | C | A | C | G | G | G | A | G |
| 3.3% | i | G | T | G | C | A | C | G | G | G | A | G |

| Frequency | Observed or Inferred | 5'FR of Exon 1.7 | 5'FR of Exon 1.7 | Exon 1.7 | Intron 1.7 | Intron 1.7 | 5'FR of Exon 1.f | 5'FR of Exon 1.f | 5'FR of Exon 1.f | 5'FR of Exon 1.f | 5'FR of Exon 1.f | 5'FR of Exon 1.f |
|---|---|---|---|---|---|---|---|---|---|---|---|---|
| 1.0% | i | G | G | C | G | G | C | G | A | C | C | T |
| 3.3% | i | G | G | C | G | G | C | G | A | C | C | T |
| 3.2% | i | G | G | C | G | G | C | G | A | C | C | T |
| 1.0% | i | G | G | C | G | G | C | G | A | C | C | T |
| 1.5% | i | G | G | C | G | G | C | G | A | C | C | T |
| 2.5% | o | G | G | C | G | G | C | G | A | C | C | T |
| 6.7% | i | G | G | C | G | G | C | A | C | C | C | T |
| 2.6% | o | G | G | C | G | G | C | G | A | C | C | T |
| 6.7% | i | G | G | C | G | G | C | G | A | C | C | T |
| 1.5% | i | G | G | C | G | G | C | G | A | C | C | T |
| 1.8% | i | G | G | C | G | G | C | G | A | C | C | T |
| 11.7% | o | G | G | C | G | G | C | G | A | C | C | T |
| 3.3% | i | G | G | C | G | G | C | G | A | C | C | T |

TABLE 3-continued

Haplotypes for Caucasian American Population (CYP19A1)

| Frequency | Observed or Inferred | Exon 1.f | Exon 1.f | Exon 1.f | 5′FR of Exon 1.2 | 5′FR of Exon 1.2 | 5′FR of Exon 1.2 | 5′FR of Exon 1.2 | Exon 1.2 | Exon 1.2 | Exon 1.2 | 5′FR of Exon 1.6 |
|---|---|---|---|---|---|---|---|---|---|---|---|---|
| 1.0% | i | C | C | A | A | G | T | T | C | G | C | C |
| 3.3% | i | C | C | A | A | G | T | T | G | G | C | C |
| 3.2% | i | C | C | A | A | G | T | T | G | G | C | C |
| 1.0% | i | C | C | A | A | G | T | T | G | G | C | C |
| 1.5% | i | C | C | A | A | G | T | T | G | G | C | C |
| 2.5% | o | C | C | A | A | G | T | T | C | G | C | C |
| 6.7% | i | C | C | A | A | G | C | T | G | G | C | C |
| 2.6% | o | C | C | A | A | G | T | T | C | G | C | C |
| 6.7% | i | C | C | A | A | G | T | T | G | G | C | C |
| 1.5% | i | C | C | A | A | G | T | T | G | G | C | C |
| 1.8% | i | C | C | A | A | G | T | T | G | G | C | C |
| 11.7% | o | C | C | A | A | A | T | T | C | G | C | C |
| 3.3% | i | C | C | A | A | G | T | T | G | G | C | C |

| Frequency | Observed or Inferred | 5′FR of Exon 1.6 | 5′FR of Exon 1.6 | 5′FR of Exon 1.6 | Exon 1.6 | Intron 1.6 | Intron 1.6 | Intron 1.6 | Exon PII | Exon 2 | Exon 2 | Exon 2 |
|---|---|---|---|---|---|---|---|---|---|---|---|---|
| 1.0% | i | T | T | C | A | C | C | i | C | C | T | T |
| 3.3% | i | T | T | A | G | C | C | i | C | C | T | T |
| 3.2% | i | T | T | A | G | C | C | i | C | C | T | T |
| 1.0% | i | T | T | C | A | C | C | i | C | C | T | T |
| 1.5% | i | T | T | C | G | C | C | i | C | C | T | T |
| 2.5% | o | T | T | C | A | C | C | i | C | C | T | T |
| 6.7% | i | T | T | A | G | C | C | i | C | C | T | T |
| 2.6% | o | T | T | C | A | C | C | i | C | C | T | T |
| 6.7% | i | T | T | A | G | C | C | i | C | C | T | T |
| 1.5% | i | T | T | C | A | C | C | i | C | C | T | T |
| 1.8% | i | T | T | C | G | C | C | i | C | C | T | T |
| 11.7% | o | T | T | C | A | C | C | i | C | C | T | G |
| 3.3% | i | T | T | C | G | C | C | i | C | C | T | T |

TABLE 3-continued

Haplotypes for Caucasian American Population (CYP19A1)

| Frequency | Observed or Inferred | Intron 2 | Intron 2 | Exon 3 | Exon 3 | Intron 3 | Intron 4 | Intron 4 | Exon 5 | Intron 5 | Exon 6 |
|---|---|---|---|---|---|---|---|---|---|---|---|
| 1.0% | i | G | T | C | G | G | G | i | T | C | G | T |
| 3.3% | i | A | T | C | A | G | G | d | A | C | T | T |
| 3.2% | i | G | T | C | G | G | G | i | T | T | G | T |
| 1.0% | i | G | T | C | G | G | G | i | T | C | G | T |
| 1.5% | i | A | T | C | A | G | G | i | A | C | T | T |
| 2.5% | o | G | T | C | G | G | G | i | T | C | G | T |
| 6.7% | i | A | T | C | A | G | G | d | A | C | T | T |
| 2.6% | o | G | T | C | G | G | G | i | T | C | G | T |
| 6.7% | i | A | T | C | A | G | G | d | A | C | T | T |
| 1.5% | i | G | T | C | G | G | G | i | T | C | G | T |
| 1.8% | i | A | T | C | A | G | G | i | A | C | T | T |
| 11.7% | o | G | T | C | G | G | G | i | T | C | G | T |
| 3.3% | i | A | T | C | A | G | G | i | A | C | T | T |

| Frequency | Observed or Inferred | Intron 6 | Intron 6 | Intron 6 | Exon 7 | Intron 7 | Intron 7 | Exon 8 | Intron 8 | Exon 9 | 3'UTR | 3'UTR |
|---|---|---|---|---|---|---|---|---|---|---|---|---|
| 1.0% | i | T | G | G | C | C | G | C | C | T | T | G |
| 3.3% | i | A | G | T | C | C | A | C | C | T | C | G |
| 3.2% | i | T | G | G | C | C | G | C | C | T | T | G |
| 1.0% | i | T | G | G | C | C | G | C | C | T | T | G |
| 1.5% | i | A | G | T | C | T | A | C | C | T | C | T |
| 2.5% | o | T | G | G | C | C | G | C | C | T | T | G |
| 6.7% | i | A | G | T | C | C | A | C | C | T | C | T |
| 2.6% | o | T | G | G | C | C | G | C | C | T | T | G |
| 6.7% | i | A | G | T | C | C | A | C | C | T | C | G |
| 1.5% | i | T | G | G | C | C | G | C | C | T | T | G |
| 1.8% | i | A | G | T | C | T | A | C | C | T | C | T |
| 11.7% | o | T | G | G | C | C | G | C | C | T | T | G |
| 3.3% | i | A | G | T | C | T | A | C | C | T | C | T |

In the intron 4 column, "i" indicates an insertion and "d" indicates a deletion.

TABLE 4

Haplotypes for African American Population (CYP19A1)

| Frequency | Observed or Inferred | 5'FR of Exon 1.1 | 5'FR of Exon 1.1 | 5'FR of Exon 1.1 | 5'FR of Exon 1.1 | 5'FR of Exon 1.1 | 5'FR of Exon 1.1 | Exon 1.1 | Exon 1.1 | 5'FR of Exon 2a | 5'FR of Exon 2a | 5'FR of Exon 2a | 5'FR of Exon 2a | 5'FR of Exon 2a | 5'FR of Exon 2a | 5'FR of Exon 2a | Exon 2a | Exon 2a | 5'FR of Exon 1.4 | 5'FR of Exon 1.4 | Exon 1.4 | 5'FR of Exon 1.5 |
|---|---|---|---|---|---|---|---|---|---|---|---|---|---|---|---|---|---|---|---|---|---|---|
| 1.7% | i | A | C | T | T | C | G | C | G | G | C | C | T | C | T | G | A | C | G | C | G | C |
| 6.7% | i | A | C | T | T | C | G | C | G | G | C | C | T | C | T | G | A | C | G | C | G | C |
| 2.5% | i | A | C | T | T | C | G | C | G | G | C | C | T | C | T | G | A | C | G | C | G | C |
| 3.6% | o | A | C | T | T | C | G | T | G | G | C | C | T | C | C | G | A | C | G | C | G | C |
| 1.7% | i | A | C | T | T | C | G | T | G | G | C | C | T | C | C | G | A | C | G | C | G | C |
| 1.4% | i | A | C | T | T | C | G | T | G | G | C | C | T | C | C | G | A | C | G | C | G | C |
| 1.7% | i | G | C | T | T | C | G | C | G | G | C | C | T | C | C | G | A | A | G | C | G | C |
| 1.7% | i | G | C | T | T | C | G | C | G | G | C | C | T | C | C | G | A | A | G | C | G | C |
| 1.7% | i | G | C | T | T | C | G | C | G | G | C | C | T | C | C | G | A | C | G | C | G | C |
| 7.2% | i | G | C | T | T | C | G | C | G | G | C | C | T | C | C | G | A | C | G | C | G | C |
| 3.0% | o | G | C | T | T | C | G | C | G | G | C | C | T | C | C | G | A | C | G | C | G | C |
| 2.5% | i | G | C | T | T | C | G | C | G | G | C | C | T | C | C | G | A | C | G | C | G | C |
| 1.7% | o | G | C | T | T | C | G | C | G | G | C | C | T | C | C | G | A | C | G | C | G | C |
| 1.4% | i | G | C | T | T | C | G | C | G | G | C | C | T | C | C | G | A | C | G | C | G | C |
| 4.2% | i | G | C | T | T | C | G | C | G | G | C | C | T | C | C | G | A | C | G | C | G | C |
| 2.5% | i | G | C | T | T | C | G | C | G | G | C | C | T | C | C | G | A | C | G | C | G | C |
| 4.5% | o | G | C | T | T | C | G | C | G | G | C | T | T | C | C | G | A | C | G | C | G | C |
| 1.7% | i | G | C | T | T | C | G | C | G | G | C | T | T | C | C | G | A | C | G | C | G | C |
| 3.9% | i | G | C | T | T | C | G | C | G | G | C | T | T | C | C | G | A | C | G | C | G | C |

TABLE 4-continued

Haplotypes for African American Population (CYP19A1)

| Frequency | Observed or Inferred | 5'FR of Exon 1.5 | 5'FR of Exon 1.5 | 5'FR of Exon 1.5 | 5'FR of Exon 1.5 | Exon 1.5 | 5'FR of Exon 1.7 | 5'FR of Exon 1.7 | 5'FR of Exon 1.7 | 5'FR of Exon 1.7 | 5'FR of Exon 1.7 | 5'FR of Exon 1.7 |
|---|---|---|---|---|---|---|---|---|---|---|---|---|
| 1.7% | i | G | T | G | C | A | C | G | G | G | A | G |
| 6.7% | i | G | T | G | C | A | C | G | G | G | A | G |
| 2.5% | i | G | T | G | C | A | C | G | G | G | A | G |
| 3.6% | o | C | C | G | C | A | C | G | G | G | A | G |
| 1.7% | i | C | T | C | C | A | C | G | G | G | A | G |
| 1.4% | i | G | T | G | C | A | C | G | G | G | A | G |
| 1.7% | i | C | C | G | C | A | C | G | G | G | A | G |
| 1.7% | i | C | C | G | C | A | C | G | G | G | A | G |
| 1.7% | i | C | C | G | C | A | C | G | G | G | A | G |
| 7.2% | i | C | C | G | C | A | C | G | G | G | A | G |
| 3.0% | o | C | C | G | C | A | C | G | G | G | A | G |
| 2.5% | i | C | T | C | C | A | C | G | G | G | A | G |
| 1.7% | o | G | T | G | C | A | C | G | G | G | A | G |
| 1.4% | i | G | T | G | C | A | C | G | G | G | A | G |
| 4.2% | i | G | T | G | C | A | C | G | G | G | A | G |
| 2.5% | i | G | T | G | C | A | C | G | G | G | A | G |
| 4.5% | o | C | C | G | C | A | C | G | G | G | A | G |
| 1.7% | i | G | T | G | C | A | C | G | G | G | A | G |
| 3.9% | i | G | T | G | C | A | C | G | G | G | A | G |

| Frequency | Observed or Inferred | 5'FR of Exon 1.7 | 5'FR of Exon 1.7 | Exon 1.7 | Intron 1.7 | Intron 1.7 | 5'FR of Exon 1.f | 5'FR of Exon 1.f | 5'FR of Exon 1.f | 5'FR of Exon 1.f | 5'FR of Exon 1.f | 5'FR of Exon 1.f |
|---|---|---|---|---|---|---|---|---|---|---|---|---|
| 1.7% | i | G | G | C | G | G | C | G | A | C | C | T |
| 6.7% | i | G | G | C | G | G | C | G | A | C | C | T |
| 2.5% | i | G | G | C | G | G | C | G | A | C | C | T |
| 3.6% | o | G | G | C | G | C | C | G | A | T | C | T |
| 1.7% | i | A | G | C | G | G | C | A | C | C | C | T |
| 1.4% | i | G | G | C | G | G | C | G | A | C | C | T |
| 1.7% | i | G | G | C | G | C | C | G | A | T | C | T |
| 1.7% | i | G | G | C | G | G | A | A | C | C | C | T |
| 1.7% | i | G | G | C | G | C | C | G | A | T | C | T |
| 7.2% | i | G | G | C | G | C | C | G | A | T | C | T |
| 3.0% | o | G | G | C | G | C | C | G | A | T | C | T |
| 2.5% | i | G | G | C | G | G | C | A | C | C | C | T |
| 1.7% | o | G | G | C | G | G | C | G | A | C | C | T |
| 1.4% | i | G | G | C | G | G | C | G | A | C | C | T |
| 4.2% | i | G | G | C | G | G | C | G | A | C | C | T |
| 2.5% | i | G | G | C | G | G | C | G | A | C | C | T |
| 4.5% | o | G | G | C | G | C | C | G | A | T | C | T |
| 1.7% | i | G | G | C | G | G | C | G | A | C | C | T |
| 3.9% | i | G | G | C | G | G | C | G | A | C | C | T |

TABLE 4-continued

Haplotypes for African American Population (CYP19A1)

| Frequency | Observed or Inferred | Exon 1.f | Exon 1.f | Exon 1.f | 5'FR of Exon 1.2 | 5'FR of Exon 1.2 | 5'FR of Exon 1.2 | 5'FR of Exon 1.2 | Exon 1.2 | Exon 1.2 | Exon 1.2 | 5'FR of Exon 1.6 | 5'FR of Exon 1.6 | 5'FR of Exon 1.6 | 5'FR of Exon 1.6 | Exon 1.6 | Intron 1.6 | Intron 1.6 | Intron 1.6 | Exon PII | Exon 2 | Exon 2 | Exon 2 |
|---|---|---|---|---|---|---|---|---|---|---|---|---|---|---|---|---|---|---|---|---|---|---|---|
| 1.7% | i | C | C | A | A | G | T | T | G | G | C | C | T | T | A | G | C | C | i | C | C | T | T |
| 6.7% | i | C | C | A | A | G | T | T | G | G | C | C | T | T | A | G | C | C | i | C | C | T | T |
| 2.5% | i | C | C | A | A | G | T | T | G | G | C | C | T | T | C | G | C | C | i | A | C | T | T |
| 3.6% | o | C | C | A | A | G | C | T | G | G | C | C | T | T | A | G | C | C | i | C | C | T | T |
| 1.7% | i | C | C | A | A | G | C | A | G | G | C | C | T | T | C | G | C | C | i | C | G | C | T |
| 1.4% | i | C | C | A | A | G | T | T | G | G | C | C | T | T | A | G | C | C | i | C | C | T | T |
| 1.7% | i | C | C | A | A | G | T | T | G | G | C | C | T | T | A | G | C | C | i | C | C | T | T |
| 1.7% | i | C | C | A | A | G | T | T | G | G | C | C | T | T | A | G | C | C | i | C | C | T | T |
| 1.7% | i | C | C | A | A | G | C | T | G | G | C | C | T | T | A | G | C | C | i | C | C | T | T |
| 7.2% | i | C | C | A | A | G | C | T | G | G | C | C | T | T | A | G | C | C | i | C | C | T | T |
| 3.0% | o | C | C | A | A | G | C | T | G | G | C | C | T | T | A | G | C | C | i | C | C | T | T |
| 2.5% | i | C | C | A | A | G | C | T | G | G | C | C | T | T | A | G | C | C | i | C | C | T | T |
| 1.7% | o | C | C | A | A | G | T | T | C | G | C | C | T | T | C | A | C | C | i | C | C | T | T |
| 1.4% | i | C | C | A | A | G | T | T | G | G | C | C | T | T | A | G | C | C | i | C | C | T | T |
| 4.2% | i | C | C | A | A | G | T | T | G | G | C | C | T | T | A | G | C | C | i | C | C | T | T |
| 2.5% | i | C | C | A | A | G | T | T | G | G | C | C | T | T | A | G | T | i | C | C | T | T |
| 4.5% | o | C | C | A | A | G | C | T | G | G | C | C | T | T | A | G | C | C | i | C | C | T | T |
| 1.7% | i | C | C | A | A | G | T | T | C | G | C | C | T | T | C | A | C | C | i | C | C | T | T |
| 3.9% | i | C | C | A | A | G | T | T | G | G | C | C | T | T | A | G | C | C | i | C | C | T | T |

TABLE 4-continued

Haplotypes for African American Population (CYP19A1)

| Frequency | Observed or Inferred | Intron 2 | Intron 2 | Exon 3 | Exon 3 | Intron 3 | Intron 4 | Intron 4 | Intron 4 | Exon 5 | Intron 5 | Exon 6 |
|---|---|---|---|---|---|---|---|---|---|---|---|---|
| 1.7% | i | A | T | C | A | G | G | i | A | C | T | T |
| 6.7% | i | A | T | C | A | G | G | i | A | C | T | T |
| 2.5% | i | A | T | T | A | G | G | d | A | C | T | T |
| 3.6% | o | A | T | C | A | G | G | i | A | C | T | T |
| 1.7% | i | A | C | C | A | G | G | i | A | C | T | T |
| 1.4% | i | A | T | C | A | G | G | d | A | C | T | T |
| 1.7% | i | G | T | C | G | G | G | i | T | T | G | T |
| 1.7% | i | A | T | C | A | G | G | d | A | C | T | T |
| 1.7% | i | A | T | C | A | G | G | d | A | C | T | T |
| 7.2% | i | A | T | C | A | G | G | i | A | C | T | T |
| 3.0% | o | A | T | C | A | G | G | i | A | C | T | T |
| 2.5% | i | A | T | C | A | G | G | d | A | C | T | T |
| 1.7% | o | G | T | C | G | G | G | i | T | C | G | T |
| 1.4% | i | A | T | C | A | G | G | d | A | C | T | T |
| 4.2% | i | A | T | C | A | G | G | i | A | C | T | T |
| 2.5% | i | A | T | C | A | G | G | d | A | C | T | T |
| 4.5% | o | A | T | C | A | G | G | i | A | C | T | T |
| 1.7% | i | G | T | C | G | G | G | i | T | C | G | T |
| 3.9% | i | A | T | C | A | G | G | d | A | C | T | T |

| Frequency | Observed or Inferred | Intron 6 | Intron 6 | Intron 6 | Exon 7 | Intron 7 | Intron 7 | Exon 8 | Intron 8 | Exon 9 | 3′UTR | 3′UTR |
|---|---|---|---|---|---|---|---|---|---|---|---|---|
| 1.7% | i | A | G | G | C | C | G | C | C | T | C | G |
| 6.7% | i | A | G | T | T | C | A | C | C | T | C | G |
| 2.5% | i | A | G | T | C | C | A | C | C | T | C | G |
| 3.6% | o | A | G | T | C | C | A | C | C | T | C | G |
| 1.7% | i | A | G | T | C | C | A | G | C | T | C | G |
| 1.4% | i | A | G | T | C | C | A | C | C | T | C | T |
| 1.7% | i | T | G | G | C | C | G | C | C | T | T | G |
| 1.7% | i | A | G | T | C | C | A | C | C | T | C | T |
| 1.7% | i | A | G | T | C | C | A | C | C | T | C | T |
| 7.2% | i | A | G | T | C | C | A | C | C | T | C | G |
| 3.0% | o | A | G | T | T | C | A | C | C | T | C | G |
| 2.5% | i | A | G | T | C | C | A | C | C | T | C | T |
| 1.7% | o | T | G | G | C | C | G | C | C | T | T | G |
| 1.4% | i | A | G | T | C | C | A | C | C | T | C | T |
| 4.2% | i | A | G | T | C | C | A | C | C | T | T | G |
| 2.5% | i | A | G | T | C | C | A | C | C | T | C | G |
| 4.5% | o | A | G | T | T | C | A | C | C | T | C | G |
| 1.7% | i | T | G | G | C | C | G | C | C | T | T | G |
| 3.9% | i | A | G | T | C | C | A | C | C | T | C | T |

TABLE 5

Haplotypes for Han Chinese Population (CYP19A1)

| Frequency | Observed or Inferred | 5'FR of Exon 1.1 | 5'FR of Exon 1.1 | 5'FR of Exon 1.1 | 5'FR of Exon 1.1 | 5'FR of Exon 1.1 | 5'FR of Exon 1.1 | 5'FR of Exon 1.1 | Exon 1.1 | Exon 1.1 | 5'FR of Exon 2a | 5'FR of Exon 2a |
|---|---|---|---|---|---|---|---|---|---|---|---|---|
| 1.7% | i | A | C | T | T | C | G | T | G | G | G | C |
| 2.3% | i | A | C | T | T | C | G | T | G | G | G | C |
| 5.8% | o | A | C | T | T | C | G | T | G | G | G | C |
| 1.2% | i | A | C | T | T | T | G | T | G | G | G | C |
| 4.9% | i | G | C | T | T | C | G | C | G | G | G | C |
| 1.7% | o | G | C | T | T | C | G | C | G | G | G | C |
| 3.6% | i | G | C | T | T | C | G | C | G | G | G | C |
| 1.7% | i | G | C | T | T | C | G | C | G | G | G | C |
| 27.0% | o | G | C | T | T | C | G | C | G | G | G | C |
| 3.3% | o | G | C | T | T | C | G | C | G | G | G | C |
| 6.8% | o | G | C | T | T | C | G | C | G | G | G | C |
| 1.7% | i | G | C | T | T | T | G | C | G | G | G | C |
| 2.6% | i | G | C | T | T | T | G | C | G | G | G | C |
| 15.0% | o | G | C | T | T | T | G | C | G | G | G | C |
| 1.7% | i | G | C | T | T | T | G | C | G | G | G | C |

| Frequency | Observed or Inferred | 5'FR of Exon 2a | 5'FR of Exon 2a | 5'FR of Exon 2a | 5'FR of Exon 2a | 5'FR of Exon 2a | Exon 2a | Exon 2a | 5'FR of Exon 1.4 | 5'FR of Exon 1.4 | Exon 1.4 | 5'FR of Exon 1.5 |
|---|---|---|---|---|---|---|---|---|---|---|---|---|
| 1.7% | i | C | T | C | C | G | A | C | G | C | G | C |
| 2.3% | i | C | T | C | C | G | A | C | G | C | G | C |
| 5.8% | o | C | T | C | C | G | A | C | G | C | G | C |
| 1.2% | i | C | T | C | C | G | A | C | G | C | G | C |
| 4.9% | i | C | T | C | C | G | A | C | G | C | G | C |
| 1.7% | o | C | T | C | C | G | A | C | G | C | G | C |
| 3.6% | i | C | T | C | C | G | A | C | G | C | G | C |
| 1.7% | i | C | T | C | C | G | A | C | G | C | G | C |
| 27.0% | o | C | T | C | C | G | A | C | G | C | G | C |
| 3.3% | o | C | T | C | C | G | A | C | G | C | G | C |
| 6.8% | o | C | T | C | C | G | A | C | G | C | G | C |
| 1.7% | i | C | T | C | C | G | A | C | G | C | G | C |
| 2.6% | i | C | T | C | C | G | A | C | G | C | G | C |
| 15.0% | o | C | T | C | C | G | A | C | G | C | G | C |
| 1.7% | i | C | T | C | C | G | A | C | G | C | G | C |

| Frequency | Observed or Inferred | 5'FR of Exon 1.5 | 5'FR of Exon 1.5 | 5'FR of Exon 1.5 | 5'FR of Exon 1.5 | Exon 1.5 | 5'FR of Exon 1.7 | 5'FR of Exon 1.7 | 5'FR of Exon 1.7 | 5'FR of Exon 1.7 | 5'FR of Exon 1.7 | 5'FR of Exon 1.7 |
|---|---|---|---|---|---|---|---|---|---|---|---|---|
| 1.7% | i | C | C | G | C | A | C | G | G | G | A | G |
| 2.3% | i | C | C | G | C | A | C | G | G | G | A | G |
| 5.8% | o | C | T | G | C | A | C | G | G | G | A | G |
| 1.2% | i | G | T | G | C | A | C | G | G | G | A | G |
| 4.9% | i | C | C | G | C | A | C | G | G | G | A | G |
| 1.7% | o | C | C | G | C | A | C | G | G | G | A | G |
| 3.6% | i | C | T | G | C | A | C | G | G | G | A | G |
| 1.7% | i | G | T | G | C | A | C | G | G | G | A | G |
| 27.0% | o | G | T | G | C | A | C | G | G | G | A | G |
| 3.3% | o | G | T | G | C | A | C | G | G | G | A | G |
| 6.8% | o | G | T | G | C | A | C | G | G | G | A | G |
| 1.7% | i | C | T | G | C | A | C | G | G | G | A | G |
| 2.6% | i | G | T | G | C | A | C | G | G | G | A | G |
| 15.0% | o | G | T | G | C | A | C | G | G | G | A | G |
| 1.7% | i | G | T | G | C | A | C | G | G | G | A | G |

TABLE 5-continued

Haplotypes for Han Chinese Population (CYP19A1)

| Frequency | Observed or Inferred | 5'FR of Exon 1.7 | 5'FR of Exon 1.7 | Exon 1.7 | Intron 1.7 | Intron 1.7 | 5'FR of Exon 1.f | 5'FR of Exon 1.f | 5'FR of Exon 1.f | 5'FR of Exon 1.f | 5'FR of Exon 1.f | 5'FR of Exon 1.f |
|---|---|---|---|---|---|---|---|---|---|---|---|---|
| 1.7% | i | G | G | C | G | C | C | G | A | T | C | T |
| 2.3% | i | G | G | C | G | C | C | G | A | T | C | T |
| 5.8% | o | G | G | C | G | C | C | G | A | T | C | T |
| 1.2% | i | G | G | C | G | G | C | G | A | C | C | T |
| 4.9% | i | G | G | C | G | C | C | G | A | T | C | T |
| 1.7% | o | G | G | C | G | C | C | G | A | T | C | T |
| 3.6% | i | G | G | C | G | C | C | G | A | T | C | T |
| 1.7% | i | G | G | C | G | G | C | G | A | C | C | T |
| 27.0% | o | G | G | C | G | G | C | G | A | C | C | T |
| 3.3% | o | G | G | C | G | G | C | G | A | C | C | T |
| 6.8% | o | G | G | C | G | G | C | G | A | C | C | T |
| 1.7% | i | G | G | C | G | C | C | G | A | T | C | T |
| 2.6% | i | G | G | C | G | G | C | G | A | C | C | T |
| 15.0% | o | G | G | C | G | G | C | G | A | C | C | T |
| 1.7% | i | G | G | C | G | G | C | G | A | C | C | T |

| Frequency | Observed or Inferred | Exon 1.f | Exon 1.f | Exon 1.f | 5'FR of Exon 1.2 | 5'FR of Exon 1.2 | 5'FR of Exon 1.2 | 5'FR of Exon 1.2 | Exon 1.2 | Exon 1.2 | Exon 1.2 | 5'FR of Exon 1.6 |
|---|---|---|---|---|---|---|---|---|---|---|---|---|
| 1.7% | i | C | C | A | A | G | C | T | G | G | C | C |
| 2.3% | i | C | C | A | A | G | C | T | G | G | C | C |
| 5.8% | o | C | C | A | A | G | T | T | C | G | C | C |
| 1.2% | i | C | C | A | A | G | T | T | G | G | C | C |
| 4.9% | i | C | C | A | A | G | C | T | G | G | C | C |
| 1.7% | o | C | C | A | A | G | C | T | G | G | C | C |
| 3.6% | i | C | C | A | A | G | C | T | G | G | C | C |
| 1.7% | i | C | C | A | A | G | T | T | C | G | C | C |
| 27.0% | o | C | C | A | A | G | T | T | C | G | C | C |
| 3.3% | o | C | C | A | A | G | T | T | G | G | C | C |
| 6.8% | o | C | C | A | A | G | T | T | G | G | C | C |
| 1.7% | i | C | C | A | A | G | T | T | C | G | C | C |
| 2.6% | i | C | C | A | A | G | T | T | C | G | C | C |
| 15.0% | o | C | C | A | A | G | T | T | G | G | C | C |
| 1.7% | i | C | C | A | A | G | T | T | G | G | C | C |

| Frequency | Observed or Inferred | 5'FR of Exon 1.6 | 5'FR of Exon 1.6 | 5'FR of Exon 1.6 | Exon 1.6 | Intron 1.6 | Intron 1.6 | Intron 1.6 | Exon PII | Exon 2 | Exon 2 | Exon 2 |
|---|---|---|---|---|---|---|---|---|---|---|---|---|
| 1.7% | i | T | T | A | G | C | C | i | C | C | T | T |
| 2.3% | i | T | T | A | G | C | C | i | C | C | T | T |
| 5.8% | o | T | T | C | A | C | C | i | C | C | T | T |
| 1.2% | i | T | T | A | G | C | C | i | C | C | T | T |
| 4.9% | i | T | T | A | G | C | C | i | C | C | T | T |
| 1.7% | o | T | T | A | G | C | C | i | C | C | T | T |
| 3.6% | i | T | T | A | G | C | C | i | C | C | T | T |
| 1.7% | i | T | T | C | A | A | C | i | C | C | T | T |
| 27.0% | o | T | T | C | A | C | C | i | C | C | T | T |
| 3.3% | o | T | T | A | G | C | C | i | C | C | T | C |
| 6.8% | o | T | T | A | G | C | C | i | C | C | T | T |
| 1.7% | i | T | T | C | A | C | C | i | C | C | T | T |
| 2.6% | i | T | T | C | A | C | C | i | C | C | T | T |
| 15.0% | o | T | T | A | G | C | C | i | C | C | T | T |
| 1.7% | i | T | T | A | G | C | C | i | C | C | T | T |

TABLE 5-continued

Haplotypes for Han Chinese Population (CYP19A1)

| Frequency | Observed or Inferred | Intron 2 | Intron 2 | Exon 3 | Exon 3 | Intron 3 | Intron 4 | Intron 4 | Intron 4 | Exon 5 | Intron 5 | Exon 6 |
|---|---|---|---|---|---|---|---|---|---|---|---|---|
| 1.7% | i | A | T | C | A | G | G | i | A | C | T | T |
| 2.3% | i | A | T | C | A | G | G | i | A | C | T | T |
| 5.8% | o | G | T | C | G | G | G | i | T | C | G | T |
| 1.2% | i | A | T | C | A | G | G | d | A | C | T | T |
| 4.9% | i | A | T | C | A | G | G | i | A | C | T | T |
| 1.7% | o | A | T | C | A | G | G | i | A | C | T | T |
| 3.6% | i | A | T | C | A | G | G | i | A | C | G | T |
| 1.7% | i | G | T | C | G | G | G | i | T | C | G | T |
| 27.0% | o | G | T | C | G | G | G | i | T | C | G | T |
| 3.3% | o | A | T | C | A | G | G | d | A | C | T | T |
| 6.8% | o | A | T | C | A | G | G | d | A | C | T | T |
| 1.7% | i | G | T | C | G | G | G | i | T | C | G | T |
| 2.6% | i | G | T | C | G | G | G | i | T | C | G | T |
| 15.0% | o | A | T | C | A | G | G | d | A | C | T | T |
| 1.7% | i | A | T | C | A | G | G | d | A | C | T | T |

| Frequency | Observed or Inferred | Intron 6 | Intron 6 | Intron 6 | Exon 7 | Intron 7 | Intron 7 | Exon 8 | Intron 8 | Exon 9 | 3'UTR | 3'UTR |
|---|---|---|---|---|---|---|---|---|---|---|---|---|
| 1.7% | i | A | G | G | C | C | A | C | C | T | C | G |
| 2.3% | i | A | G | T | T | C | A | C | C | T | C | G |
| 5.8% | o | T | G | G | C | C | G | C | C | T | T | G |
| 1.2% | i | A | G | T | C | C | A | C | C | T | C | T |
| 4.9% | i | A | G | T | T | C | A | C | C | T | C | G |
| 1.7% | o | A | G | T | T | C | A | C | C | T | T | G |
| 3.6% | i | T | G | G | C | C | G | C | C | T | T | G |
| 1.7% | i | T | G | G | C | C | G | C | C | T | T | G |
| 27.0% | o | T | G | G | C | C | G | C | C | T | T | G |
| 3.3% | o | A | G | T | C | C | A | C | C | T | C | T |
| 6.8% | o | A | G | T | C | C | A | C | C | T | C | T |
| 1.7% | i | T | G | G | C | C | G | C | C | T | T | G |
| 2.6% | i | T | G | G | C | C | G | C | C | T | T | G |
| 15.0% | o | A | G | T | C | C | A | C | C | T | C | T |
| 1.7% | i | A | G | T | C | C | A | C | C | T | T | G |

TABLE 6

Haplotypes for Mexican American Population (CYP19A1)

| Frequency | Observed or Inferred | 5'FR of Exon 1.1 | 5'FR of Exon 1.1 | 5'FR of Exon 1.1 | 5'FR of Exon 1.1 | 5'FR of Exon 1.1 | 5'FR of Exon 1.1 | 5'FR of Exon 1.1 | Exon 1.1 | Exon 1.1 | 5'FR of Exon 2a | 5'FR of Exon 2a |
|---|---|---|---|---|---|---|---|---|---|---|---|---|
| 1.7% | i | A | C | T | T | C | G | T | G | G | G | C |
| 1.7% | i | A | C | T | T | C | G | T | G | G | G | C |
| 1.7% | i | A | C | T | T | C | G | T | G | G | G | C |
| 1.7% | i | A | C | T | T | C | G | T | G | G | G | C |
| 2.5% | i | G | C | T | T | C | G | C | G | G | G | C |
| 13.8% | o | G | C | T | T | C | G | C | G | G | G | C |
| 19.5% | o | G | C | T | T | C | G | C | G | G | G | C |
| 1.5% | i | G | C | T | T | C | G | C | G | G | G | C |
| 6.9% | i | G | C | T | T | C | G | C | G | G | G | C |
| 7.0% | o | G | C | T | T | C | G | C | G | G | G | C |
| 3.8% | i | G | C | T | T | C | G | C | G | G | G | C |
| 2.5% | i | G | C | T | T | C | G | C | G | G | G | C |
| 6.6% | o | G | C | T | T | C | G | C | G | G | G | C |
| 2.4% | i | G | C | T | T | T | G | C | G | G | G | C |

TABLE 6-continued

Haplotypes for Mexican American Population (CYP19A1)

| Frequency | Observed or Inferred | 5'FR of Exon 2a | 5'FR of Exon 2a | 5'FR of Exon 2a | 5'FR of Exon 2a | 5'FR of Exon 2a | Exon 2a | Exon 2a | 5'FR of Exon 1.4 | 5'FR of Exon 1.4 | Exon 1.4 | 5'FR of Exon 1.5 |
|---|---|---|---|---|---|---|---|---|---|---|---|---|
| 1.7% | i | C | T | C | C | G | A | C | G | C | G | C |
| 1.7% | i | C | T | C | C | G | A | C | G | C | G | C |
| 1.7% | i | C | T | C | C | G | A | C | G | C | G | C |
| 1.7% | i | C | T | C | C | G | A | C | G | C | G | C |
| 2.5% | i | C | T | C | C | G | A | C | G | C | G | C |
| 13.8% | o | C | T | C | C | G | A | C | G | C | G | C |
| 19.5% | o | C | T | C | C | G | A | C | G | C | G | C |
| 1.5% | i | C | T | C | C | G | A | C | G | C | G | C |
| 6.9% | i | C | T | C | C | G | A | C | G | C | G | C |
| 7.0% | o | T | T | C | C | G | A | C | G | C | G | C |
| 3.8% | i | T | T | C | C | G | A | C | G | C | G | C |
| 2.5% | i | T | T | C | C | G | A | C | G | C | G | C |
| 6.6% | o | T | T | C | C | G | A | C | G | C | G | C |
| 2.4% | i | T | T | C | C | G | A | C | G | C | G | C |

| Frequency | Observed or Inferred | 5'FR of Exon 1.5 | 5'FR of Exon 1.5 | 5'FR of Exon 1.5 | 5'FR of Exon 1.5 | Exon 1.5 | 5'FR of Exon 1.7 | 5'FR of Exon 1.7 | 5'FR of Exon 1.7 | 5'FR of Exon 1.7 | 5'FR of Exon 1.7 | 5'FR of Exon 1.7 |
|---|---|---|---|---|---|---|---|---|---|---|---|---|
| 1.7% | i | C | C | G | C | A | C | G | G | G | A | G |
| 1.7% | i | C | C | G | C | A | C | G | G | G | A | G |
| 1.7% | i | G | T | G | C | A | C | G | G | G | A | G |
| 1.7% | i | G | T | G | C | A | C | G | G | G | A | G |
| 2.5% | i | C | C | G | C | A | C | G | G | G | A | G |
| 13.8% | o | G | T | G | C | A | C | G | G | G | A | G |
| 19.5% | o | G | T | G | C | A | C | G | G | G | A | G |
| 1.5% | i | G | T | G | C | A | C | G | G | G | A | G |
| 6.9% | i | G | T | G | C | A | C | G | G | G | A | G |
| 7.0% | o | G | T | G | C | A | C | G | G | G | A | G |
| 3.8% | i | G | T | G | C | A | C | G | G | G | A | G |
| 2.5% | i | G | T | G | C | A | C | G | G | G | A | G |
| 6.6% | o | G | T | G | C | A | C | G | G | G | A | G |
| 2.4% | i | G | T | G | C | A | C | G | G | G | A | G |

| Frequency | Observed or Inferred | 5'FR of Exon 1.7 | 5'FR of Exon 1.7 | Exon 1.7 | Intron 1.7 | Intron 1.7 | 5'FR of Exon 1.f | 5'FR of Exon 1.f | 5'FR of Exon 1.f | 5'FR of Exon 1.f | 5'FR of Exon 1.f | 5'FR of Exon 1.f |
|---|---|---|---|---|---|---|---|---|---|---|---|---|
| 1.7% | i | G | G | C | G | C | C | G | A | T | C | T |
| 1.7% | i | G | G | C | G | C | C | G | A | T | C | T |
| 1.7% | i | G | G | C | G | G | C | G | A | C | C | T |
| 1.7% | i | G | G | C | G | G | C | G | A | C | C | T |
| 2.5% | i | G | G | C | G | C | C | G | A | T | C | T |
| 13.8% | o | G | G | C | G | G | C | G | A | C | C | T |
| 19.5% | o | G | G | C | G | G | C | G | A | C | C | T |
| 1.5% | i | G | G | C | G | G | C | G | A | C | C | T |
| 6.9% | i | G | G | C | G | G | C | G | A | C | C | T |
| 7.0% | o | G | G | C | G | G | C | G | A | C | C | T |
| 3.8% | i | G | G | C | G | G | C | G | A | C | C | T |
| 2.5% | i | G | G | C | G | G | C | G | A | C | C | T |
| 6.6% | o | G | G | C | G | G | C | G | A | C | C | T |
| 2.4% | i | G | G | C | G | G | C | G | A | C | C | T |

| Frequency | Observed or Inferred | Exon 1.f | Exon 1.f | Exon 1.f | 5'FR of Exon 1.2 | 5'FR of Exon 1.2 | 5'FR of Exon 1.2 | 5'FR of Exon 1.2 | Exon 1.2 | Exon 1.2 | Exon 1.2 | 5'FR of Exon 1.6 |
|---|---|---|---|---|---|---|---|---|---|---|---|---|
| 1.7% | i | C | C | A | A | G | C | T | G | G | C | C |
| 1.7% | i | C | C | A | A | G | C | T | G | G | C | C |
| 1.7% | i | C | C | A | A | G | T | T | G | G | C | C |
| 1.7% | i | C | C | A | A | G | T | T | G | G | C | C |
| 2.5% | i | C | C | A | A | G | C | T | G | G | C | C |
| 13.8% | o | C | C | A | A | G | T | T | C | G | C | C |
| 19.5% | o | C | C | A | A | G | T | T | G | G | C | C |
| 1.5% | i | C | C | A | A | G | T | T | G | G | C | C |
| 6.9% | i | C | C | A | A | G | T | T | G | G | C | C |
| 7.0% | o | C | C | A | A | G | T | T | C | G | C | C |
| 3.8% | i | C | C | A | A | G | T | T | G | G | C | C |
| 2.5% | i | C | C | A | A | G | T | T | G | G | C | C |
| 6.6% | o | C | C | A | A | G | T | T | G | G | C | C |
| 2.4% | i | C | C | A | A | G | T | T | G | G | C | C |

TABLE 6-continued

Haplotypes for Mexican American Population (CYP19A1)

| Frequency | Observed or Inferred | 5'FR of Exon 1.6 | 5'FR of Exon 1.6 | 5'FR of Exon 1.6 | Exon 1.6 | Intron 1.6 | Intron 1.6 | Intron 1.6 | Exon PII | Exon 2 | Exon 2 | Exon 2 |
|---|---|---|---|---|---|---|---|---|---|---|---|---|
| 1.7% | i | T | T | A | G | C | C | i | C | C | T | T |
| 1.7% | i | T | T | A | G | C | C | i | C | C | T | T |
| 1.7% | i | T | T | A | G | C | C | i | C | C | T | T |
| 1.7% | i | T | T | C | G | C | C | i | C | C | T | T |
| 2.5% | i | T | T | A | G | C | C | i | C | C | T | T |
| 13.8% | o | T | T | C | A | C | C | i | C | C | T | T |
| 19.5% | o | T | T | A | G | C | C | i | C | C | T | T |
| 1.5% | i | T | T | A | G | C | T | i | C | C | T | T |
| 6.9% | i | T | T | C | G | C | C | i | C | C | T | T |
| 7.0% | o | T | T | C | A | C | C | i | C | C | T | T |
| 3.8% | i | T | T | A | G | C | C | i | C | C | T | T |
| 2.5% | i | T | T | C | G | C | C | i | C | C | T | T |
| 6.6% | o | T | T | C | G | C | C | i | C | C | T | T |
| 2.4% | i | T | T | C | G | C | C | i | C | C | T | T |

| Frequency | Observed or Inferred | Intron 2 | Intron 2 | Exon 3 | Exon 3 | Intron 3 | Intron 4 | Intron 4 | Intron 4 | Exon 5 | Intron 5 | Exon 6 |
|---|---|---|---|---|---|---|---|---|---|---|---|---|
| 1.7% | i | A | T | C | A | G | G | i | A | C | G | T |
| 1.7% | i | A | T | C | A | G | G | i | A | C | T | T |
| 1.7% | i | A | T | C | A | G | G | d | A | C | T | T |
| 1.7% | i | A | T | C | A | G | G | i | A | C | T | T |
| 2.5% | i | A | T | C | A | G | G | i | A | C | T | T |
| 13.8% | o | G | T | C | G | G | G | i | T | C | G | T |
| 19.5% | o | A | T | C | A | G | G | d | A | C | T | T |
| 1.5% | i | A | T | C | A | G | G | d | A | C | T | T |
| 6.9% | i | A | T | C | A | G | G | i | A | C | T | T |
| 7.0% | o | G | T | C | G | G | G | i | T | C | G | T |
| 3.8% | i | A | T | C | A | G | G | d | A | C | T | T |
| 2.5% | i | A | T | C | A | G | G | i | A | C | T | T |
| 6.6% | o | A | T | C | A | G | G | i | A | C | T | T |
| 2.4% | i | A | T | C | A | G | G | i | A | C | T | T |

| Frequency | Observed or Inferred | Intron 6 | Intron 6 | Intron 6 | Exon 7 | Intron 7 | Intron 7 | Exon 8 | Intron 8 | Exon 9 | 3'UTR | 3'UTR |
|---|---|---|---|---|---|---|---|---|---|---|---|---|
| 1.7% | i | T | G | G | C | C | G | C | C | T | T | G |
| 1.7% | i | A | G | T | T | C | A | C | C | T | C | G |
| 1.7% | i | A | G | T | C | C | A | C | C | T | C | G |
| 1.7% | i | A | G | T | C | T | A | C | C | T | C | T |
| 2.5% | i | A | G | T | T | C | A | C | C | T | C | G |
| 13.8% | o | T | G | G | C | C | G | C | C | T | T | G |
| 19.5% | o | A | G | T | C | C | A | C | C | T | C | T |
| 1.5% | i | A | G | T | C | C | A | C | C | T | C | G |
| 6.9% | i | A | G | T | C | T | A | C | C | T | C | T |
| 7.0% | o | T | G | G | C | C | G | C | C | T | T | G |
| 3.8% | i | A | G | T | C | C | A | C | C | T | C | T |
| 2.5% | i | A | G | T | C | C | A | C | C | T | C | T |
| 6.6% | o | A | G | T | C | T | A | C | C | T | C | T |
| 2.4% | i | A | G | T | C | T | A | C | C | T | C | T |

Example 4

Tag SNPs for CYP19A1

Haplotypes defined by common single nucleotide polymorphisms (SNPs) have important implications for mapping of disease genes and human traits. Often only a small subset of the SNPs is sufficient to capture the full haplotype information. Such subsets of markers are called tagged SNPs (tSNPs). Tagged SNPs were identified as described (Schaid et al. *Am. J. Hum. Genet.* (2002) 70:425-434; Hartle et al. *Organization of Genetic Variation* Chapter 3, pages 95-107, in: Principles of Population Genetics 3rd Ed., Sinaeur Associates, Inc., 2000) and analyzed for linkage disequilibrium (Carlson et al. *Am. J. Hum. Genet.* (2004) 74:106-120). Table 7 shows the linkage disequilibrium tag-SNPs for CYP19A1. Table 8 shows haplotype tag SNPs for CYP19A1.

TABLE 7

Linkage Disequilibrium tag-SNPs for CYP19A1

| Caucasian American Population | African American Population | Han Chinese Population | Mexican American Population |
|---|---|---|---|
| 5'FR Exon I.1 (−588) | 5'FR Exon I.1 (−588) | 5'FR Exon I.1 (−588) | 5'FR Exon I.1 (−588) |
| 5'FR Exon 2a (−468) | 5'FR Exon I.1 (−144) | 5'FR Exon I.1 (−278) | 5'FR Exon 2a (−468) |
| 5'FR Exon I.5 (−628) | 5'FR Exon 2a (−468) | 5'FR Exon I.5 (−628) | 5'FR Exon I.5 (−628) |
| Intron I.7 (54) | 5'FR Exon 2a (−125) | 5'FR Exon I.5 (−334) | 5'FR Exon I.5 (−334) |
| 5'FR Exon I.f (−725) | Exon 2a (−21) | 5'FR Exon I.2 (−596) | 5'FR Exon I.2 (−596) |
| 5'FR Exon I.2 (−596) | 5'FR Exon I.5 (−628) | Exon 2 (115) | 5'FR Exon I.6 (−196) |
| 5'FR Exon I.6 (−196) | 5'FR Exon I.5 (−334) | Intron 2 (−59) | Intron 4 (27) |
| Exon 3 (240) | 5'FR Exon I.5 (−317) | Intron 4 (27) | Intron 4 (77) |
| Intron 4 (27) | Intron I.7 (54) | Intron 5 (−16) | Intron 6 (−106) |
| Exon 5 (602) | 5'FR Exon I.f (−725) | Exon 7 (790) | Exon 7 (790) |
| Intron 7 (26) | 5'FR Exon I.f (−649) | 3'UTR (1531) | Intron 7 (26) |
| 3'UTR (1673) | 5'FR Exon I.2 (−596) | | 3'UTR (1673) |
| | Exon I.2 (−224) | | |
| | 5'FR Exon I.6 (−196) | | |
| | Exon I.6 (−77) | | |
| | Exon PII (−83) | | |
| | Intron 2 (−59) | | |

Table 8

CYP19A1 Haplotype Tag SNPs

TABLE 8

Haplotype-tag SNPs for CYP19A1

| Caucasian American Population | African American Population | Han Chinese Population | Mexican American Population |
|---|---|---|---|
| 5'FR Exon I.1 (−144) | 5'FR Exon I.1 (−588) | 5'FR Exon I.1 (−278) | 5'FR Exon I.1 (−278) |
| 5'FR Exon 2a (−468) | 5'FR Exon 2a (−468) | 5'FR Exon I.1 (−144) | 5'FR Exon I.1 (−144) |
| 5'FR Exon 2a (−429) | Exon 2a (−21) | 5'FR Exon I.5 (−334) | 5'FR Exon 2a (−468) |
| 5'FR Exon I.5 (−628) | 5'FR Exon I.f (−725) | 5'FR Exon I.f (−649) | 5'FR Exon I.f (−649) |
| 5'FR Exon I.2 (−596) | 5'FR Exon I.f (−649) | Exon I.2 (−224) | 5'FR Exon I.6 (−196) |
| Exon I.2 (−224) | 5'FR Exon I.2 (−596) | 5'FR Exon I.6 (−196) | Intron 4 (77) |
| 5'FR Exon I.6 (−196) | 5'FR Exon I.6 (−196) | Exon 2 (115) | Exon 7 (790) |
| Exon I.6 (−77) | Intron 4 (77) | Intron 6 (36) | Intron 7 (26) |
| Intron 2 (−59) | Intron 6 (−106) | Intron 6 (−106) | 3'UTR (1531) |
| Intron 4 (77) | Exon 7 (790) | 3'UTR (1531) | 3'UTR (1673) |
| 3'UTR (1531) | 3'UTR (1673) | | |
| 3'UTR (1673) | | | |

Example 5

Activity of CYP19A1 Allozymes

Enzymatic Activity: The properties of the four CYP19A1 non-synonymous cSNPs observed during the gene resequencing experiments were studied by expressing each variant allozyme in COS-1 cells. Enzyme activity and immunoreactive protein levels were then determined using microsomes isolated from these cells. Experiments were performed as described in Example 1. Because one of the DNA samples that had been resequenced contained two non-synonymous cSNPs, resulting in both Trp39Arg and Arg264Cys alterations in encoded amino acids, an expression construct was created and designated as a "double mutant" (DM) construct. This construct contained both cSNPs even though it was not possible to determine unequivocally that a single allele that included both polymorphisms was present in this subject. Finally, to make it possible to correct for transfection efficiency, an expression vector for a GFP and DIA1 fusion protein that would be targeted to the endoplasmic reticulum was also created and co-transfected with the CYP19A1 allozyme constructs. Six independent transfections were performed for each allozyme. The resulting activities were adjusted to a percentage of the wild type CYP19A1 enzyme activity and are shown in Table 9. As shown graphically in FIG. 3A, the Cys264, Thr364 and DM allozymes had 72%, 15% and 21% of the wild type enzyme activity, respectively—all of which differed significantly from the wild type value. Values for neither the Arg39 nor Met201 allozymes differed significantly from that for wild type. Very similar results were obtained when a 5-fold higher substrate concentration, 100 nM androstenedione rather than 20 nM, was used to perform the assays.

Substrate Kinetic Studies: One possible explanation for the decreased levels of enzyme activity observed with several of the variant allozymes would involve an alteration in substrate kinetics. Therefore, apparent $K_m$ values were determined for the wild type and variant allozymes with androstenedione as the substrate. An elevated $K_m$ value when compared with that for the wild type allozyme was observed only with the Thr364 variant (Table 9). However, even though the increase in apparent $K_m$ for this allozyme might have contributed to the observed decrease in activity observed—the major mechanism involved a decrease in protein level—as described subsequently and as demonstrated by the lack of a significant increase in activity when the substrate concentration was increased 5-fold from 20 to 100 nM.

TABLE 9

Enzymatic Activity and $K_m$ of Recombinant Human CYP19A1 Allozymes

| Polymorphism | Amino Acid Change | % WT activity | Apparent $K_m$ |
|---|---|---|---|
| T115C | 39Arg | 85.4 ± 9.5 | 6.0 ± 2.0 |
| C602T | 201Met | 88.6 ± 10 | 7.1 ± 1.9 |
| C790T | 264Cys | 72 ± 7.6 | 5.9 ± 2.6 |
| T1091C | 364Thr | 15.2 ± 1.8 | 26.0 ± 10** |
| DM (T115C + C790T) | 39Arg + 264Cys | ~21 | 7.3 ± 1.9 |
| wild type | none | 100 | 6.7 ± 2.0 |

**indicates $P < 0.001$ when compared to the values for all other allozymes.

Example 6

Inhibitor Kinetics

Alterations in the amino acid sequences of the variant allozymes might influence the response to two aromatase inhibitors, letrozole and exemestane. These two drugs are representatives of nonsteroidal and steroidal aromatase inhibitors, respectively. Experiments were performed as described in Example 1. $IC_{50}$ values for the wild type allozyme were found to be 0.6 and 4.5 nM for these two inhibitors, respectively. $K_i$ values for letrozole and exemestane were then determined with the recombinant variant CYP19A1 allozymes. The results are shown in Table 10. $K_i$ values were similar for all of the allozymes studied—with only the value for letrozole for the DM allozyme being significantly different from that for the wild type enzyme. An example of the data used to calculate the $K_i$ value for letrozole with wild type aromatase is shown in FIG. 3D.

TABLE 10

Inhibitor Kinetics of Recombinant CYP19A1 Allozymes

| Polymorphism | Amino Acid Change | $K_1$ (nM) in Presence of Letrozole | $K_1$ (nM) in Presence of Exemestane |
|---|---|---|---|
| T115C | 39Arg | 0.18 ± 0.06 | 0.94 ± 0.59 |
| C602T | 201Met | 0.22 ± 0.06 | 1.16 ± 0.09 |
| C790T | 264Cys | 0.21 ± 0.08 | 1.04 ± 0.33 |
| T1091C | 364Thr | 0.29 ± 0.09 | 2.86 ± 1.29 |
| DM (T115C + C790T) | 39Arg + 264Cys | 0.46 ± 0.12* | 1.09 ± 0.10 |
| wild type | none | 0.21 ± 0.05 | 1.05 ± 0.41 |

*indicates $P < 0.05$ when compared with wild type, Arg39, Cys264, or Met201 allozymes.

Example 7

CYP19A1 Allozyme Protein Levels

It has been previously reported that a common mechanism for the functional effects of nonsynonymous cSNPs is an alteration in protein quantity (Weinshilboum et al. *Clin. Pharmocol. Ther.* (2004) 75:253-258). Therefore, quantitative Western blot analysis was performed using monoclonal antibody against a polypeptide corresponding to CYP19A1 amino acids 376 to 390, an area that did not include any of the amino acids altered by the four nonsynonymous cSNPs. As shown in FIG. 3B, levels of recombinant protein corresponded to levels of enzyme activity for the variant allozymes. When level of enzyme activity was plotted against level of immunoreactive protein for the wild type enzyme and all 5 of the variant allozymes, including the "DM" construct, a significant correlation was observed, Rp=0.937, P=0.006 (FIG. 3C). This observation suggests that a major mechanism by which these genetic polymorphisms influence aromatase activity, at least after the transient transfection of mammalian cells, is through a reduction in the quantity of enzyme protein. To exclude the possibility that a defect in the expression vector introduced during site-directed mutagenesis might have caused the decreased levels of immunoreactive protein, in vitro translation studies were performed with all expression constructs using a RRL. Similar quantities of recombinant protein were produced for all of the allozymes studied (data not shown).

Example 8

Subcellular Localization of CYP19A1 Allozymes

Aromatase, like other eukaryotic cytochrome P450 enzymes, is localized to the endoplasmic reticulum (Nelson et al. *Pharmacogenetics* (1996) 6:1-42). Therefore, another mechanism that might explain decreased levels of the variant allozymes in microsomes could involve changes in subcellular localization. Amino acids 20-39 in CYP19A1 are hydrophobic and represent a putative transmembrane domain that is located in the endoplasmic reticulum (Haugen et al. *Biochem. Biophys. Res. Comm.* (1977) 77:967-973). Because of the possibility that the change from Trp to the more hydrophilic Arg at amino acid 39 might alter the subcellular localization of the Trp39Arg allozyme, subcellular localization was studied using fluorescence microscopy. Two other allozymes—those with the lowest levels of microsomal activity and protein—Thr364 and the DM allozyme, were also studied. With calnexin as an endoplasmic reticulum marker, immunofluorescent studies were performed using COS-1 cells transiently transfected with constructs encoding the wild type or the three variant allozymes. All of the allozymes colocalized with calnexin (data not shown), indicating that they were localized to the endoplasmic reticulum. Therefore, the decreased levels of immunoreactive protein observed for these allozymes could not be explained by alterations in their subcellular localization.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. An isolated nucleic acid molecule consisting of:
   (a) 15 to 100 contiguous nucleotides of SEQ ID NO:1, wherein said nucleic acid molecule comprises nucleotide 128089 of SEQ ID NO:1, with the proviso that the nucleotide at position 128089 is cytosine; and
   (b) the complement of (a).

2. The isolated nucleic acid of molecule of claim 1, wherein said isolated nucleic acid molecule is from 20 to 50 nucleotides in length.

3. A vector comprising the isolated nucleic acid molecule of claim 1.

4. The vector of claim 3, wherein said isolated nucleic acid molecule is from 20 to 50 nucleotides in length.

5. An isolated nucleic acid molecule consisting of:
   (a) fifteen to 100 contiguous nucleotides of SEQ ID NO:1, wherein said nucleic acid molecule includes nucleotide 128089 of SEQ ID NO:1, with the proviso that the nucleotide at position 128089 is cytosine; or
   (b) the complement of a),
and with respect to (a) or (b), a label.

6. The isolated nucleic acid molecule of claim 5, wherein said label is a fluorescent moiety.

7. The isolated nucleic acid molecule of claim 5, wherein said label is biotin.

* * * * *

SEQUENCE LISTING

<160> NUMBER OF SEQ ID NOS: 74

<210> SEQ ID NO 1
<211> LENGTH: 133107
<212> TYPE: DNA
<213> ORGANISM: Homo sapiens
<220> FEATURE:
<221> NAME/KEY: CDS
<222> LOCATION: (97669)..(97812)
<220> FEATURE:
<221> NAME/KEY: CDS
<222> LOCATION: (103571)..(103723)
<220> FEATURE:
<221> NAME/KEY: CDS
<222> LOCATION: (112649)..(112801)
<220> FEATURE:
<221> NAME/KEY: CDS
<222> LOCATION: (118055)..(118231)
<220> FEATURE:
<221> NAME/KEY: CDS
<222> LOCATION: (121925)..(122041)
<220> FEATURE:
<221> NAME/KEY: CDS
<222> LOCATION: (124765)..(124878)
<220> FEATURE:
<221> NAME/KEY: CDS
<222> LOCATION: (125349)..(125510)
<220> FEATURE:
<221> NAME/KEY: CDS
<222> LOCATION: (128019)..(128261)
<220> FEATURE:
<221> NAME/KEY: CDS
<222> LOCATION: (129525)..(129770)

<400> SEQUENCE: 1

| | | | | | |
|---|---|---|---|---|---|
| aacgtagaca | gcaatcttca | agccccatgt | taagaacctc | gggtttgaca | ttgtttaaga | 60 |
| aaaaaaaaaa | atcactctgt | ttggatgtct | cccatttggg | agacccaacc | agaaggcagg | 120 |
| attgctgttt | ccatagccca | ataactcaag | gaagaggtgc | ctccccgcca | atgagccagc | 180 |
| tggagcagtt | atagagaaag | gacttcctct | atcagagacc | acactgtttc | agcacctgag | 240 |
| ggagaccagt | aaaatgatca | gagagcaagc | tccttttgac | ttaatggtag | gagctctgta | 300 |
| accatctact | ccccaaagat | tcacattctg | atgtggtttg | gatctgtgtc | cccacccaaa | 360 |
| tctcatgttg | aattgcgatt | cccagtattg | gtggtggagc | ccagtgggag | gtgactggat | 420 |
| catgggagtg | gtccttcatg | aatggtttag | caccatcccc | tcagtgctgt | tctcatgata | 480 |
| gtgagttatc | atgagatctg | gttgtttaaa | agtgtgtagc | atctctcctg | gcccctcttc | 540 |
| ctcctgctcc | caccatgtga | gatgttcctg | ctcctgcttt | gccttcctcc | atgagtaaaa | 600 |
| gctccctgag | gcctccccag | atgcaggtgc | tgccatgctt | cctgttcagc | ctgtggaacc | 660 |
| atgagccaat | taaacttctt | ttcttgtaag | ttacccagtc | tcgggctttt | ctttatagca | 720 |
| aggcaagaat | ggactaatac | acataccaat | tcttgcaggt | aggatttttt | ggcacaggag | 780 |
| agaaagctga | gtagtatcag | acttcttgcc | ccctactctc | cagggtgagc | cagggtagag | 840 |
| cctctgagaa | tgcacaagga | aactgaagtg | acatctcaat | cagaaattct | gagtcaaagt | 900 |
| ttagattcct | gagttttaat | aggaacattg | accaacttca | gtattcttag | aagagcatac | 960 |
| aggataagaa | gaaattagga | aagcatgaag | gtccaagtgt | ttcataaagt | accccccactg | 1020 |
| tggggatatg | atgactggga | ggggatggca | gtgatgtaaa | aagctttgtc | catttcctcc | 1080 |
| caactcaaac | gttctgtgac | ctacttgaag | aactgtcatg | tatccttatc | tcttttcatc | 1140 |
| caggtatcag | gtttagggcc | aatggggagg | agccactgag | agggagggtt | gacactcagc | 1200 |

```
atcattcaga tcttcattta attcagtaaa cacttaactg agcacttcct gtgcctggta   1260
tgataatggg cattggagat acggaagtaa aaaagacagg cagattaccc tgtgagcagc   1320
tggaacaccg tggagccttc tgggcttctc tttatcctaa cattcattgc agttactgtt   1380
gactgatcat ctctcagcaa tacccaccat taaccatgga atagaagcct cctgaggcta   1440
ggggccatgt cacccccaac acatagcaca gttcctgatt tggaattcac tattacccgt   1500
tgaataaatg agtgaatgaa cgaatgaata aatgaaaagc tgtatagtga aggcacttct   1560
atgtagaaca atgtggtgtg tggtgggggg tgtgatctta tgattacatg tatatagatt   1620
tttgtccatg gttcttgtcc ataactccca tgacacttgc tgaggtcttt tgctataatg   1680
tagaggtgct ttaggcctca ggaaacagaa tatttctctg gccttctttg ccctcctttc   1740
atccacccaa ggcgggactc tataatctga ttgtgggtca taagaccctc attcagagg   1800
aggtcatgcc ccatacccctg gaggaaggaa tgctgcacaa agagaggaag aagaatctgg   1860
acagacagac cttgctgaga ttagatcata ccctttttgt ccaatcacat tttgttcaat   1920
cacatgcttc agtcatggac aacaaatgaa atctccataa aaggcccaaa ggacagggtt   1980
cagggagttt ctggagggct gaacacgtgg aggcaaacag gaaggtgaag aagaacttat   2040
cctatcagga cggaaggtcc tgtgctcggg atcttccaga cgtcgcgtat gtatctctta   2100
atctgactga gccctcaacc tgtgggatca gacactcttt ccaggtagat agtgttggaa   2160
ctgagttgga ggacacccag ctggtgcccg ctgcttggtg tgtgggggaa aatcccctac   2220
atttggtcgc agaagtcttc tgtgttgatg actgttgtcg tggtgtgaga gcagagggaa   2280
aacactgctt gagtgttttt ctgaaatagg agggcctaag aactatactg ttctatgcca   2340
cagaactggc cccctacttt ccttgaaagg ctggctatcc aatggtgagg agaggaagtg   2400
gtagcctgaa ccagcctccc catttcccca cctcccaccc cagttcagag cccagatcca   2460
gtagacagag cagagatgag gcctgcttgg agccaggcag gctctattag acaacttcag   2520
gccaagaagc tgcccctctt gggatgcagg actcaaaagg cttgtagcat ggccaccccg   2580
tgggctgggt tggtggaaag cctgggatat tgctctgggg caagaggggc agaaggaagc   2640
gcaaatgaaa agccagactc ctttcctacc agactccact gtcagatccc tctccaactc   2700
ttcctgtgtg ggatgatggc attttttcaca gaagaagggg gacatgttga tatggcctac   2760
aaggtagaca tcttcactca tctctcaccc taaagtggct gtgcccaagc agctgccatg   2820
ctctgccctc tttcctcttc tcctctatct tctctctcca accctctttc caccgcagtg   2880
ccacacagtg acctatctcc atcactggcc tatttcagtg ttgcccactt taaggcctaa   2940
ctccgagtac ccttcctcat ctagccttga cttcctaggc cagtcccaag cactgtgagc   3000
tctacaagct gcaggggctc tgtggttatg cacctgggct ttggaatcag acctgacctt   3060
gaaactgttt tttaactgca tgactttaga tatgctactc aagttcttta aagagactgt   3120
aattgtatct atttcatagg gttgtgaagc tttaataaga aaatacttgt aaagcacttg   3180
tataataaat gttcaacacg ggttggtatt gttggatatg ggccatatga actggctgag   3240
acttacactg tgtgtgcctt gtgctgttag ttgacacttt agttcttctg tgccttgtgc   3300
tgttaatcga catcttagtt cttccacatc ctatttcttc agttgggtta caatattctt   3360
aaggcaggga cctatcttaa ctgtcctctc acagcaggga cttgtgccaa gtaggaatat   3420
ttgattaatg gattcattag ctaatcacac tttgtagatg cttttgagg aacagaactt   3480
ttgaatgcac gataaacttg ggttctcgtc tgaataccat ggctttgagg ttggttatat   3540
ggagcctttc agtgtgaatc cctaagcctc ttgagatttc ttgagaggca gatatgcctg   3600
```

```
catagcctgc cctgcctgat acttcacaga atgggctgct acttttttact tattattaaa   3660 aaaaaaaaaa agctatcaat ctggcctgtt ttgttgacac aggaggctca ggatataatg    3720
cggacacagg gagatatctc aattcccttt ttttggagac caaagcagcc aagaacattg   3780
tgtgctatct ttacaatgag aagtagtttt tccattaaaa ggcagatgct tcatttccaa   3840
aagttaaata gaatggtcct taaaaatgat tccagctggt taactttagg gctctggaga   3900
ataaaatcaa attcaagaat ataccccaac tttagttcca cagcatttct tcctgattgt   3960
gaagtaaata atttcctgg cctggcactt gggtattctt gtcttcagtg atgagattga    4020
cagctacact gtgacttttg atggttttac tgccccacca cccttccacc acactggtga   4080
ttagggagag agccacccta aaagttgtca ccacatgcat cttccactca gcctcttatg   4140
gttttaactc cccattccta ctgttaaacc ccaagaaact tcacaccatc caaccaaagt   4200
cagcaattct ccctttttc tttcttttat tctttcatgt attcatttac tcagcaaatg    4260
gtaattgggt gcctactatc tgccaggaac tgtgccagga gccaggaata gcatggagag   4320
caaagccagg catcattcct gaagcctgga gtggggagac agatttacca aacaatatta   4380
gacatgaggg tgcaattcta aatgcggcca cgagacaaat gctctggaag aaaggaatgc   4440
agttccttga gatcatatca ctgaagagcc tgtcctagag ttggatgtgt ggttcaggga   4500
aggcttccct gagaaaagga tgcttgtgtt ggcacctgaa gctgagttgt aaactaggcg   4560 aagataggg tgaggagaat tgcagagagg aggaacaaca cgttcaaggc cctatggcag    4620
gagatggcat ggcttatttg aggaaccgta agaagccaat gcggtgccac atggagcgtc   4680
aggagcaagg aggagggagt gaaatgaggc tgtaaccaag gcagggacca gactctgtgg   4740
gtgggacctt ccttgtaggg ctgaggcctt tactgtaaaa gcaatgggaa acaaatgagg   4800
agttttacgt gtgtgtggga tggggaggag tcggtagatg gatgacagat tttcatttta   4860
aaagattacc ttttactgcc aagacttgca gtggcttctg tcactatgga aaccatgtat   4920
gatctctgac ctccaccagg gccaacttca gcctttaaaa ccacctggaa ataaggaagt   4980
gctgagttct agaaaatgta actttctctt tcatctgtat gtaaaaaggt agttgaaaaa   5040
cagaaccgtg actaaattta gatcatttag ccaatcttga tactagtagg ggttttttgta  5100 taaaacacag tgtgttgtta gcattttctt ggaagttagc ctttggtgct tccaggtaag   5160
agcaccaaat ctgcttatct ctagggttgg gaataagaat agatgatatt gcttccgttg   5220
tgagattttg gtccaagtcg ggctggtaac aacagatttc cgcctatcgt agtagcagtg   5280
tcttagacct ttgagttgcc cactcattgt ttgacgtgga gctgtctgtg gttgtgaagg   5340
tgatgccatt tcaaatcccc acttcccatt gtttttctctc cttctttgca acaaacatgc   5400
cctcccaccc caccccactc cacctttcta gtgtagtgta cccaattgtc acagatcaga   5460
ttctctggaa acaagtgctg agatggaatt tggagtacaa aatggttatt agggatcagc   5520
acctatgaag gaaagaagga gaagcaggat tgggcagagg gagaaatcca gcacagtcca   5580
accctgcaaa gcctcagcca acccactggg aagctctgga ttgtgtattg ctcatcagag   5640
tgtcctgtgt caggccagag tgactgggct tttacctacc tcactcagtc acaggacaga   5700
tgtgggatgc cctgggaagg tatgacctgg ggccaggtgg ctctctgcag ctgaagcatg   5760
ctttaatctt aatctctgca gccaggcagt cagtcctttc ttgaaggggg accctcaggt   5820
ccccacatct ccacatctac cacatcaacc acctgaatct gccattccaa cattagtagg   5880 cttttaaattg taaccgtgac aggctgtaga aagaaatctt ttcctttttc acctggagtg   5940
```

```
atggcctttc aataaatgaa aaagtgattg ttttcagaaa caatgaaaat gtaaaggaag    6000
ctctaagagt ggattctgtg caatcatgag aatggctcat gaatttgaaa ctgcaaaatc    6060
cacagaagta agttaatact gcaaagctcc acttatggaa ctcgagccac tgttttttgaa   6120 agataaaaca aagccttaca tgtgtagagc acttcagttt tcaaagtgct ttctcatgtc    6180
atttgagttc cataataagc ctgtgaacgg ggcagggcag gttttataag catttcacag    6240
atgaggaagt cagggctcag gaggtttaag tgatctgccc aaggtcacat tgttgaaacc    6300
tcatcaacgt tcacccatgc cctgtttatc aaaagtagga aatttttggc ccccatcttg    6360
ggccactgag gaatgctcaa aatgatggac aggaagtgaa acaatagagc agggaaatga    6420
ttcaaagtga tggagtggaa aacagctcag actggcactt ggctccaagg cttaaaaaca    6480
aacctggagc agacactgaa tgctagaatg tgtaagctag tcaggaaaga aagccaagcc    6540
tggtctagca gattaaggag gattttaaga gatcaatgat gtaagaacat gatttcctaa    6600
aaaccatgta ggggaactgt catctctgca gtgaataggt gcatataggt cctaaaaaaa    6660
aagtgaattt ggggcctgat agcctaagac cttcattcc tgggttgcaa aggcagagta    6720
acaagctaga atagatatgc ctcacctctc cagagagact ggttgggagt gaccaaaagg    6780
gattcctgcc aatattaagc ctggagaaga tgacacccca tctgctgagc ctggagactc    6840
aagccaggga ccagaggagt ggccccggct aagagaagct tacctttttat tgccaagact    6900 tgcactggct tctgtcacta tggaaaccac gtatgatctc tgacctccac cagggccaac    6960
ttcagccttt aaaaccacct ttccaaatga aacaagaaag tgctgagttc tagaaaatgt    7020 gacttttttag gtcaaactgt ggaccctaaa catgtgctac tttcttaaag ctgtatgagt    7080
aaacacatgg tctccaaacc accccgatt ctgtaatcat aagagggcac cagtatctgg     7140
gcatcagtga gtatcctggc agatggatct ggctggatga ggtaagggag ttgtacaggt    7200
gtgctgagtc tatctctact cctgagcctg ggagatgtga aaaacagga aatgagagt      7260 ctccccgcca gtgacttgat aggggattga gaaccaccat ttttgtccct tctgagaagg    7320
cacctcagct gctggccctg agcccagaga gcagacaaaa gaaaacatta cccttatact    7380
tagggggcac agcaatgctc ttagaagagg ctcacatgaa accaagccac tagggaacag    7440
taatacattt aaaatattaa cgttaggaca taaacattcc agtagagcac aaaaagactt    7500
tctggaacca aatgacaaga tctgcagaca aattcagtag ctgaaggaaa gaaaagtagt    7560
agttaatagg aagtaaattt cccaagttaa gaaagggcct gagtctgcct attggaaggt    7620
tttggcaagt tatgggcaag acaaatgatt cataggttga gaaattccag aagtctaagg    7680
atgaaaagaa aatcttacag tcttccagaa agaaagtaca agtgacttat aggggaagaa    7740
ggatcatggg ggcatcaact ttctcttcta tgacacctga agtagggatg attgaggcca    7800
atcgtgtgaa gattactgag agaaaaacac tgcacaccaa gaatcctgta gcaagacccc    7860
actcctctgt cagggtcaag gaaacatagt tgagaatatg caaggaaaag acctgtcacc    7920
catatcttcc accagataaa agggtgttaa gatctaacca aacaatagat gaatcagctt    7980
aaaggctaca ggatgaaaag aggaggaaaa gggagaaaaa aattagtggt gagcaaggag    8040
ccttacaaca catcgtcagt taaattcaga cagataataa tagacagttc aggaatgtgt    8100
aatataattg ctgaaaatag aagagacata tttcaaggga aatgttaaca atagcctgga    8160
acaaaaagtt ctaaggagaa agaggggaa gtgaagtttc cacaggtctc acattggtgt     8220
gtgagagtgg gaagtgaaag cgtcctaaag gcctcatgct gggggaggag gaacagcagg    8280
agaggagaga atctggggaa atagttggac tcttatgttg gtataatgga ataaaagaat    8340
```

```
gagtttgact accagtgaca aaaaggagaa ggacctggta gaatgaaaaa ctagactaga    8400
gctcccaaat taagaagaga aagaaaataa ttgaacagaa acttgataac taattaatat    8460
aaagaacatc aagggggctt aaataagtaa taaatattaa gtaaaataga agcaataaaa    8520
ttcaatgtat tattaaatgt gaatagaatt attcttaaaa gagactatta gatttggtaa    8580
aataaaaagc agacagttat atgctttctt gtatatatat atgtatgtgt gtgtgtgtat    8640
gtgtgtatat atatatatat acacacacat acaagaaata aacacattta acaaatgtga    8700
taaaaattga gaataaaaag tcaagaaaaa ataccaggca aatgcaaata acaaagcagg    8760
aaagaattac tctgttaata cccagcaaaa tgaaatgtaa agagcactga ataagataga    8820
gttgctatgt aatgataata atttgcaaaa agtcactaac cagtatgtgt taaaaatcaa    8880
atgtgaaaaa tagtaaagcc atgtgtgatt tcagtaccct tcttctttac agagagcaag    8940
aagtcgcgcc ccctgaact cgcccccatt ctatccagtc ctaccacata aataaccatt    9000
ctgggtcata caaatacata tgctcttgca aagatgcaaa aaaagatgct aactatactt    9060
atctccttct gggtcagtat ttacaggttt gcccccattc cttatttcca tgaggagaga    9120
tttccctaaa atgccccttg tcctctttcc gcttctcctt ttcttctccc cagagaggag    9180
gaatgtcttg gctgactcat cttcttcacc tctcctcttt cctttttcgta gccagcctta    9240 tcagcaagct ctcattctag tctactctca cgtggctcca gctctccagg ggcagcctct    9300
ctgcaggaag gcctcgggtg ttcagtgctg cctgtgatga gtgggtctgt ctttctcatt    9360
tggaaaaaat gttgctgaac atttaatgtt accatttcca atgtcagctt tatccctaat    9420
aaagctgacg ttttgatctc catctgcctt gctctcatcc taccacccga ttggtttaga    9480
attgtggtgg agaaaacagg aactcaattc tgggggtctc cttacaactc caaaacaacc    9540
ttattcttcc caaagtcaac cagccatctt taatgtggct atactcctca tctgcgcttc    9600
ctcatccctc attcattcgc cacgtcacgg ccatgtagct tcttctccca ccaaacattg    9660
aacccatcct gccaaggtcg ctgatgactt atttgcaaaa tacaatgaaa acttttcagt    9720
ctaaaggtca atcttacttg aagtctctgc aactttcaaa gctcttcatc acttcctcct    9780
ccttgacatt ccttcctctc tgagcttcca tgacactact ttctcttggt tttcctccta    9840
cttctccgac tgttccttct cagcctcctt gaactgttct tcaacttctg tgcacccaac    9900
tgctagtgtt ctccagggtt gtgccctaca tcctcactct gttgactctt ccttggtgat    9960
tttatccact gccgaggcct ctgaccacca catacccaaa ccctgcctgt tgcccagggc    10020
tctctttgga gctctagact caaagggcca agtaccagtg gtgtaactcc atgtacgaca    10080
gaagaaggta ccatatcatt ttatttttta tcactttatt aatgatagca agattttttc    10140
atattttact gatcagttgt gcatgtttac aggtgtatgt gtataaatcc tttcctcact    10200
tgacatttct tatgccccct ctcctcctcc tttcctttct gtcctgcacc ttagtttggg    10260
tccacaacac acctcaacga tgtcgctgtg ccacttctcc aagtgcacct tctactccca    10320
gtctgctagt ttgtgagccc agactcgatt cttcggtcca tgtgatatgt tcatacacag    10380
ggctctccac aaccccaccc ctgcctactc tctctctgcc ctgtttctca ccattccgcc    10440
cttgtgcctc acgttccttc ttccagcttc cgggaggtgc ctgctccctc cctgctcctt    10500
gccactatca tgctcatttc tctgcctgtt ttcctcttct ccccttctct gactggctga    10560
ctttattctt taaaacacac atctgatgtc ccttctgggg agccccag ccccacatcc    10620 cagggagggc tagctgctcc gactgtgtgc tcccactgta attgtattta cccatcctgg    10680
```

```
tgtatatctg gtcatttcac aatggcctgt cgctccctgt ctgtctccct gttaggctgt    10740
gaactccttg ggaatactcc tgtatcttgc tcatctaata ctcccagaac ctcatgcata    10800
cctggcatgt agtagatgtt caatacattt ttgaatgagt gaaagtgtga tagagggcag    10860
tgcccttaca atttctttct gagatcttgc ttcctgacca caggattcac tcgctgaaga    10920
ggagtgatca gtttcatacc agcagcaccc tctgcccact gacagatggt tctccactgg    10980
gaaactttct tcatccccgg tggtatttga agggagttct ctatacatgt ttaccttgta    11040
aaatttccct ccatcagtgg ccctggcctt gctggccttc ccattatacc tcttgggggg    11100
cactactaat acccatgtct tctgctgttt ctcaaaaggc ccctagcctt actatccaaa    11160
tagacactga aaaggggtgg aaatcctggg ggcagtcagc tctcagaggg tgcctttta    11220 gtgtctcctg cccctctggt ttgccattgc ctggctcctg ctgagtctgg agtgggccc    11280 tatgtgtgaa gcagtagcct cctgttagag tgctccagac catctcagtg tgaaccaagg    11340
gctgttgtgg ccaagagctc ggcatcccag agtcagtgac gagaagggag gaggcaggcc    11400
agggcaagaa catggctcag acttgtgtgg gagtgtatta gtcggggttt ttcagagaag    11460
cagaaccaat aggttgtata cagaaagaga tttattataa ggaattggct catgcaatta    11520
tgtaggctga caaatcccaa agtctgcagg gtaagttggc aagctggaga cctacgagag    11580
tgtaggcctg gtctgaggac cagcaagctc acaacccagg aagagccaat gtttcagttt    11640
gtatctgaag gcaggaagaa gccagcatcc tagcttgaag ccagtcaggc agcagcaatt    11700
ctcttacttg tgggacagta aacttttgc tctattcagg ccttcagctg attttttgag    11760
gccacttgca ttggtgaggg caatctgctt tactccaact cattccattt agatgtgaat    11820
cacatccaga acaccctcc ccaacacacc cagaaaaatg tttgaccaaa tatctgggca    11880
ccctatgacc cagtcaagtt gacacataaa attaaccatc acagggagca ataggggat    11940 cagatgactc tcaactccag ctgttggaag tcacacttaa cgtacacaca catgtacaca    12000
cacacacaca cacacacaca cacacacaca caccctgcc ctgtaactca ggattcccag    12060
tgagggtggt tccacccatt agagctatct ttggaaattt gtggaggcat ttgttactat    12120
cacagtttgt tacgacggtg aatgtgggat gccattgaca tttagtggat gggtagggg    12180 ggatgtcaga tgctctgcag tggtcaggac catccacatc acaagtgact gtccctcatc    12240
actttcaaat gtcctgctca atgtttatgt ccatgaaaac ttgtttatac ataggtggat    12300
ctagcatcca accccatttt atatataaac acacaggatt tattttttgc agttttaaaa    12360
tacactgaat ttttcaggaa tgcagcatag agtgaagatg gtacatattt gttcaggact    12420
ttatgaagat tgttcaccat tttggaaaat catgttacaa atggcaatgg taatcacagt    12480
gtttgagcca tactaaaaac acatgtgact ctgtgtgcat ttaaatctat tgcattcatg    12540
gcgactctac acataggtgc agacatctaa ctacttagta ggatttccag tgtagtcatg    12600
tacaagattt tttagatact gaaatactta ttttctata aaattgcttt tctttctttc    12660
ttgattataa cccagtgagt gtattccatt ttttttttat attatgaatt ttgggaggaa    12720
attttatgtg taggtagata tattatctat gggtttcatt tgagcataac aaaaggagag    12780
ttacaagtta tgtgttgttg gtttgttttc atttgtttgt tttttctgag acggagtctt    12840
gtgttataag aagggacact gagtctgatg tggcagagag ccactatttc aactgaacta    12900
gtgcctgtga agaacacgca tctgtctgtt gggctgagcc tggccccaag ggacctgtgg    12960
accctggatc ctgaagacac tggatccttg agaatcgctt gaaccccgga ggcagaggtt    13020
gcagtgagct gagatcatgc cactatatga cagagcaaga ttctgcctca aggaaaaaaa    13080
```

```
aaaaaaaaga acaatgtcaa atgaattagt gaatggatgg atgagtgaat gcatgcatgc   13140
atgatttggg gggtgagaac attagatggc tctactcatt taatcccagt gtctgtggaa   13200
atcaaacaca ggagactgct ttgtgttttc taccagccag ctcaccaact gagcccctaa   13260
tggtgccttg gctttactca ggagtttaat tagccctggc gcttgattct gaaagaaatg   13320
gagagcagtg atgaacacaa acaggagaga tctgggcagt aacaagcctg gcatatggca   13380
ccatggatca cccattggcc ttagggctgg actaagtcct aggtgacttt acttctaaat   13440
gttactcatg tttattcttt caagatgcta gataattaag acctgactac ccgaaaccaa   13500
aaatacgagc tgcttttgga tgattagtgg tgcatgcaga gtcattggaa atgtagtggg   13560
agtagggaaa acagttctgg gtttggattc aaaagactga gcttgacccc agactttccc   13620
cacaactacc tgtatggtca tgggcaagct agttcatatt tccaggttta aaagcctatg   13680
gttcaatgaa atgcagtaaa caacgattca gaggaattac acagtgatgt gtttatagta   13740
gatacaccac gaagttaaaa acacttgtac tttcaggtct ctcattgccc tggccccttc   13800
caaagccctg tgtctcattt tgttagatgg tatcattatc ctaaacctgg gtctcatatt   13860
aaggtttctt ccaggttcaa aattctatgt tactggccaa tgaatttaaa aaagaacatt   13920
ttctgttata caactccatt ctattccata acttgtaatt ttttagtttc aaggacacca   13980
ctatgtcata tacacattgt tctttctttt aggtacttag catgattttg gacaaatctg   14040
ataaagaaaa ttgaaagtct agatccctgg gatttactac tataatgctt aaagttgagc   14100
cacattctca actttatcgt agttgaaaat tctacagcaa gaattcttta actgtaagat   14160
ctgtgttggg ttactgtgag tttcatttca gtctcatttt cattgttctg gagttctgga   14220
catctgaggc agcccatgca attttcttcc tttcttttc tagaagagct tcgcctctgg   14280
ccacttggaa gctgggcctt gggaggtcca ggggtaaact gtgcattaag ctgacagtgc   14340
tcagtaagaa aaatctttac tctgtggcaa tctggtttgg acacctaccc taatcaaact   14400
gggaacattt ggggaggact caggaattat cttaattata gacacctctg acttataatg   14460
attcaactta tgattttca gttttataat ggtgtgaagt tcactttcag tagaaactgt   14520
acttcaagta cccatacaac cattctgttt ctcactttca gtacaatatt caataaataa   14580
caagagctat tcaacacttt attataaaat gggctttgat tttgcctaat tgtacgctaa   14640
tgtaagtgtt ctgagcacat ttaaggtagg ctgggctaag ctatgatatt tggtaggtta   14700
ggtggactca atgccctttt tttttttttt tttttttttt ttttgagacg gagtctcact   14760
ctgtcaccag gctggagtgc agtggcgcca tcttggctca ctgcaacctc tgactcctgg   14820
gttcaagcga ttctcttgcc tcagtctccc aagtagctgg gattacaggc atgtgccacc   14880
acgcccagct aattttttgta ttttagtag agacggggtt tcaccgtgtt agccaggatg   14940
gtcttgatct actgacctcg tgatccgccc acctcggcct cccaaagtgc tgggattaca   15000
ggcatgagcc atggcgcctg gcctgcactt tcaactttc aatatttcca gcgtacaatg   15060
ggcatataga gatgtagcac catggtaagt tgaggagcat ctgtacttgt tggataagta   15120
tgaagctcaa tcctcatggt tagtgtcata ctctgctagc ccaagaggct agagcagaaa   15180
aagtgggtgg caggggaggc gaatatctat gggctgcaag tccttacaat gggatctttc   15240
ttcccagact cctcagtcct caccactcct acaccctgcc agtgaagaac acccacagga   15300
catctgtctt cagcttgcca ttcagatcca ctataagggc ttcaccctgt agcaacttgg   15360
cttggacact gaccctaggc aaacagggaa tgttttttga gatagggtct cttgcttctt   15420
```

```
gcccaagctg gcctcagcct cctgggctca agcaatcttc tggcctccca agcagctggg    15480
actacaggca cataaccgtg tgccctaaac ttggaaattt tacctggttc aggaattctc    15540
ttaattattt tgttttctt gtaactggta ttttgttccc tttgtgagga ggggaaagga    15600
agtattttct ttatttatcc tgctttctca ttttcaccaa aaatgaggtt acagatctac    15660
ttctgacttt aatttgtaac acccccaga attttgttat tgttttgcct ctgacttttg    15720
ttttcccaac ataaaatcac ttccacctca gaattataac ccctagggtc cctagaactg    15780
ataataaaaa ttctagatca gtggacaact taaaggattt cctgttaaca tttactctac    15840
ctgtctaaaa tttgcatctt ccattgcttt ttctcaattt taatttctat gtgtttgttt    15900
gctagttgga tttaagtaga catttcgttt ttaaccagtt ttaaagttgc cttttatttt    15960
tggctaataa ttatgtttta gtttatatta ttttattgcc atttcattct caaccagcca    16020
ggagctggcc tggattagaa gaactggttc taacctcatt ggtctgttat gttgtcacac    16080
agggtacatt acttaattca tcagagtggg gctcaatcag tgtgatggcc cctctcttta    16140
caatgttctg gtagcctata aatcggcttt gttttattca ctcttatttc tatgttagca    16200
tctttggaaa aattcctaaa cttatttggg aacaaattgt tattatatga ggctaatggt    16260
acctagaaat aactagaata attcccaaga agttatgcct ttataaaata ttcatctttg    16320
gcaatgacca gaaatgtcta cctttacata aattagtgtg tccactcttt ttggggctgg    16380
tggggtgtct tctgactggc cttcatgtgt gggaatagcc ccattccaag tgctgcttga    16440
ttgtaaaatt ggaccaagcc tgtcatcaca ctgcccagtc tttgggtagg gggagctgag    16500
agattctgtg aatattgtca gaagggacat gttttttggat agggagggaa aaaaagcaag    16560
atccccaggt cccctgattt taaccatgac gtagaaaact ccacacagac cctcctccct    16620
tccgccctgg cacagagtcc cgttgtcctt tcataggcgg tgtcagaaac cctgtggtga    16680
aattcagcct gtggattcca gaaatttgga gtgttcttgg ggggaaaaat ccgcacacac    16740
aaagcaacat ttggaaatcc ctgtggtgag ttgggaggtg gggaggggat gcagtatggg    16800
aaggctggaa gggaaagcgc cggtgtacat ccctcccctct tctttccagg gctctgagtg    16860
tcagggctga gatgaagatg acaccctggc agaggaggag gcagggtgct gggggcaggg    16920
catggacatt gaggtctgtg ctgagcttta cagtttgcaa gcactttcat gttatcttgt    16980
gggggtagat cagtgactcc atagccattt tataggcata gacactgaat ttcacagtgg    17040
ttaaataaat ttcccaagac cacatggttg gaaaaaaaaa aaaagtagaa gacacatcca    17100
aatccaaaaa ttttgtgctg gaaggttttc atgccataaa acagttccat ctccgtttat    17160
cattgatccc acaagttcta ctatttactt tactttcttc ggaagcttag ttgatttttt    17220
ccttctatag gacatctgca cttaaattct ttaggaagta ttatgcctga gtgtggctac    17280
tccctacctg agagcagctt cctataagaa ggagcttctc agcaggcaag gagagagagg    17340
gctggagaaa ggccaggcat ggtgagcaat tgtgggccac ccaagggcct ggactctcag    17400
ggtggtgata acatagtggt aggggtttgg ggagaggccc agagacagtg gccctggagg    17460
ccactgcaag ggaaaacagg aagaaggcag taggtcaagt tccttcttta aaccaagcca    17520
actaaggctt gtccagggcc cttcctgtag ctccagcatt catttggtgc agaagaaaac    17580
actgaattcc ttgagccat tattgaggct tgaaagtttg gaagctctgt gttagcagca    17640
ttttagggac agttcagcca gaagtggatg tgttccctac agacatgaaa ttctagcaac    17700
tgcattgttt cctaatggga tcacaggtta tggactcatg gagctgaaaa agtctccaca    17760
atgggagaga aactgagagg tgctgaatcc agctggtgag acccagcaca gtagaggctg    17820
```

-continued

```
gcccaatgcc acccagtgag ttagtgttcc ctcaagattg ttacagttaa atgcacttgc    17880
aaaatcctag tggggaagcg ggggtggggg tgatgcaagg atggaaaaca ttttgtcaag    17940
catcagatta tgacaaggc tcttcctaaa agtaagaat gtgatgactg aaagggcct      18000 aggatatatt ttatatattg gaggtggtac tggcatttga gtatttctag tttgctttta   18060
ttatctggat gatgaacagt aacaacagca gaagcagcaa taaactctta cataaaattt   18120
atctctaaat gccaaagcag tttgtttctc taaatatagt gtacaaaaag agaggtattt   18180
acataaagtg actcgctatt aatttattaa ttgtcacttg cacttcccaa tcaggtaagg   18240
attgcacagt tcaggcgaaa gcctccactg gctgcttgtt ctctgctcag ctcttgggca   18300
cagacacctg ccctgccttg tgatgaggaa gccttcctct gacaagggca gagatctcca   18360
tactcaccaa cagctccttt ccatgcacag ggaagcagcc aggggctcgc aggttttcac   18420
tcagcctatt tcaagcccag cctaagcagc cctttgtct gtggagccag gtccgaccca    18480
tggcccgtgg cgggaaggcc acaccagatg ctgatgtggg acgggagctg tagctccatc   18540
ttctcattct cttgcagaag gggatgagtg tggtgctccc tgacttagca gcttctctca   18600
ggaattttat ttattatgtt tttttttttt tcccctaaac agcatttctc tccgtttagt   18660
taacaggatg ttgatgggtt tctcttcctt tggggtcct tccctttcga tgagggccca    18720
ggccttcccc cttcccagca tagtccagcc tgcctggata ctctttcatg ggcctctggg   18780
gccagaggac aagtccctag tgctgtccat ctgctctgtg catgtctgtt caattcagta   18840
gatgttcact gaagagccac tctggaggga tgcagattag gcctggagaa tgtagcaatg   18900
gaaatgtttg atatctgact tcatggagcc tgtagatgag tgagggacat aagtgggacc   18960
ttaaaaaatc atctacaaga cagagagaga tatgatcaag ttagaaggtc ttttcttaaa   19020
gatcccagag ataatctacc cctagatgtg cagacgaaat tagggccaga ggggtggat   19080 gaactggttt gaggactcta aggatggcgt aagtgatttc gaatcgaaag atggggaagg   19140
agctcctgga gaaggtggcc actgggcagg gcatcatgag ggaaattgga ttgtggcaga   19200
gggagcaggg tgagcacagg ctgggaagga aagtgtggtg ggctccccca acagtaggca   19260
gtcatggggg atctaggggc atggtgggtg gatgggagg ggtgctcaca gggtccatca    19320
gtgatgattg tgaagggcct gaattatgtg tgcaatggag aggcactggt gggtcacaga   19380
tgacttctat gtggggcttg gccagcagtg tgcagggtgg ttgggaagtt caaaggctgt   19440
agcttgggtg tgggcaagag acagcaaggc cctggatgaa gtaagcaggc tggagtgggg   19500
agacaggaat gggttgaagg cacagggtgg agagaaccca cccattgggt tccagctgca   19560
ctgtccagta caggccgtga gccacaggtg gctgtcgagc actggagtgt ggctggtctg   19620
aattgagatg tgctgtaagg ataaaacaca caccagattt tgaaagcttg atgtgaagaa   19680
tgtacaattc tcaatcattt ttaaaatatt gattacatga tgaaataatt tcatttagaa   19740
tatgctgggt tgaattaaat atattaagat taatttcacc tgtttctctt tttaatatgt   19800
gtgttacaca atttaagatt acttacatgg ctcacattct atctccattg gacagcactg   19860
ggttagaggg gaagaggata aggcagagct ttggggacag gaaggaacag ggctgagagg   19920
aggacctgag aagtgggtt aaggaaaaag gagagatcat acagatttgg tgtcttccca    19980
gattgagaca gcttttgggc ctcttgggc cacaaggagc ttcagaaatt gccagtgtct    20040
ttacatggag tacctgaaat gtccatctgg tctcctcact cacctggcac ctaaccatgt   20100
gctgttttgt acttgactgt tgcttacctg tgtctctaag tccttgcctc agccagataa   20160
```

```
aaagccttct cagggcaatg ccattgtatc ctgtctgttc tctccagtgc ttacttcacc    20220
cagggctggg ggtagcaggt gctccctgga acttggcaaa catcctcata ttgggaggag    20280
cttggctggt tttccttgat ctccctcttc ccagtgtgtg gctcttgaca actgattgga    20340
ccccagactt aaggtaagac tatacaatgt gatgctcaca gtatgcacat gatgcagctg    20400
tgagcaggga tgggagccga ggatggtgcc tgagcacaga ggggaagagc attggatggg    20460
gagatttgag ttggaaggtc agatcctcaa aggtctactc attggagtct ccacatctgt    20520
gaaaggaggg gatgatatct atctcctagt gttgtagaaa gtaagagtta atatacgtga    20580
acaaatgatg gctggcattc aagtgtcgct ctgtgaccct cagaaggtgt tcacatccat    20640
gagctcatct gaacttcaca gcagggcagg cattattata atttccattg cagacaaga    20700 aacctgaggt tcagagaata caaatgacct gatagagatc acctgactat taaggtagag    20760
ctggatctgg agcccagcct gacgtctgcc actgtcttt gctgtccact taaaagagca    20820
gcttgcacac gtgcagggct acataggtt caaaggcctt tcatgcccat taactgctta    20880
ttcttcctag aaggatgcat aagcccaaag ttttgctata tatgaagaca tgattttcat    20940
gagattcctg cagccaatga agaaacaagc cttcagtaat catgtggatc catggtttag    21000
ttgtccctta tgggtgacag gtgatgggtt atgaggatta gataagagct gtttgtaaga    21060
atgtctacaa ggtgcagtga caggctctgg tcagatattt tgatcatgct acagtgcatg    21120
aaattgttca taagaattgt atgtgcatct gtatctaaca ggatctgctt atatcttcag    21180
aaaactttgt cataaattta aattacttaa agtgtctgat cttcagatac tttaagtagt    21240
gcatttgaga atgggaatgt tgattacagt gcgtataggg aaatagatga atattccatt    21300
aataactatt aaaatctgct aaagcttagg ctaagctgaa tatatttagt tgtaataaaa    21360
ttgggtgaac acattccaac ttcagcctga ttaagggaaa gggtgtaggg gtgagacact    21420
taggcggagc ttgaaaagga atggtgagag tttggccaat gggaaggaag gctgtgccag    21480
acaggaatag tgtgggctga cgacaactga gggcaaagtg cttgtcccct catagttgcg    21540
caatgaatgc agaggggctg aggttcatct gtcgtcttca gctctgcagg ctacatctca    21600
gggtgtttcc tgtgaaagtt ccagaagaaa gctgtatggt cagcttgggg aaatatgtgg    21660
ttcatgctgg aatgctggac ataccacatt attggaaaga tgcacattga atgaccgaca    21720
aaatgaaact caactttcca aatgctggta atgagagaag attctgttct aatgaccagt    21780
tgtttcctga aagaatgtca gctcgattca taatgaatgc attctaacca tgacagccac    21840
agtcaggaca caaaaaacaa agtgtccttg atcccaggaa acagccctct ggaatctgtg    21900
aaatctagaa actagattgg gaaaactctg acacccctgc cccatgacca accaagacta    21960
agagtcccag gaagattgag gtcacagaag gcagaggcct gccccctctc caggagatcc    22020
ctgacccatg tggggtcatg ggcggggcat gagtgatgtg atgggaaact ggctcctggc    22080
tccaagtaga acgtgaccaa ctggagcctg acaggaggtc cctggcactg gtcagcccat    22140
caaaccaggt aagtccttgg agtctgagta gggacaagag actgttctgt gctttggcag    22200
ggatcaggaa gatgttagaa tgtggttgtt ggaacttatc tttggagctg aacaaacatg    22260
gctttgcatc tccactttgc tatcaactga gtggctttaa ttaagtggct tcatttctta    22320
gatcctcagt ttcttcatat tcacctgtaa atttttttt ttacattttt agactgttga    22380
gggcagtaaa ttagatcatg tacataaagc accgagcact gtgctagaca cattggtact    22440
tactacacag tgggatagca ccccagctgt gacagccttg tgaggggagc tacacaggag    22500
gcccagggag agtgctctga gttaaggata ggtccagatc ctacacttct agcaacaccc    22560
```

```
aaagccccct cttgaacatg ttggggtgtg atggggggtgg ggagatacag tcgtgttccc   22620
tggctgtgtc aaagtgtgaa atctttatac tccgtctgcc ccagattctc tcaaagagca   22680
cagaattgaa ggatagcact ggaccaagtg tcaggagaat tgagatgggc tctgccactc   22740
cctggctggg tgaccttgga caagtccttc aacctattga ggtctgggct tcttcatttg   22800
tacattggaa caagattatc tgctctgtca caggatgaac tccagcctca ttagcctggc   22860
attcaagaac cttccatcat attccctcac cacagctccc atgagtcctc ttcatgccca   22920
catggttctg ccatatcaaa ctcttctggg cctttctttc accccctagac agaatgttct   22980 tgcattctgt gtgggggtga atgttcttgc ccaaatctct gtgtatctaa agcccatata   23040
cctttgcatc ccctgcagca tcttgcacag gggcttgcat aaagcagatc attgttttct   23100
cagttaggat taggtttggg gcaggaaaac aaaaataata tttatttagc aagttagaag   23160
tgatttttct cttgccgggc gcagtggctc acgcctgtaa tcccagcact ttgggaggcc   23220
aaggcaggcc gatcacgagg tcaggagatc aagaccatcc tggctaacat ggtgaaaccc   23280
tgtctctact aaaaatacaa aaaaaataat aattagccag gcatggtggt ggaggcctgt   23340
agtcccagct actcgggagg ctgagacagg agaatggcgt gaacctggga ggcagagctt   23400
gcagtgagct gagaatgtgc tattgcactc tagcctgggc gatagagtga gactctgtca   23460
aaaaaaaaaa aaaaagaag tgattttttcc cttatgccaa agaatcctaa aaggaggt   23520 agcccaggac tgggaaggtg gctccttgtg ttggggaccc atgctcccctc tgtcttgcca   23580 caccagcact cttggcaccc tacctcatag tcccatatgg ctgcctgggt ttcagacatc   23640
ttattctcat ttagccagca aaggatgaaa agggcaaagc atgcattctc ttccttaagg   23700
gaggcttcct aaatgctgca catgcacactt ttgcttatag ctttttggct agaacttagt   23760
cacatggtca tatccagctg caagagaggc tggggaatat agttttttaac tgcacatatt   23820 gccattcctt ctttctttct tttctttctt cctttttttt tttttaagag acagaggtct   23880
ccccatgttg cccaggctgc tctccaactc ctgggctcaa gcaatgcacc cacttcggcc   23940
ttccaaagag ttgggattac aggggtgagc caccatacct ggccatattg ccatttctaa   24000
taaaattgat aggggagact gggagaacag atattcacaa cccatacagt gcctctgcca   24060
cagctactga aagaaccaaa aatataaaaa ctcactaaga agtttaaagc cctatctaat   24120
atatgagatt attattacaa aacacttaac tcatttttaga taagttaatt gtcctgactt   24180
ttaggttgaa aacagcccaa ttttttcttca cctctagtgg aaatatgatg acatgttttt   24240
tcttttttat tttttgtaga gacaggatct cgctatgttg cccaggctgg tcttgaactc   24300
ctggctcaag caatcctcct gtctcaaact cccaaagtgc tgggattaga gacatgagcc   24360
aacatgccca gccaacatat ttttttcata gaataataac tcagagttgt aagtgaagat   24420
aaattattag tccttcccct taccttacca cattttacta ctgaggaaac tgaactccag   24480
tgaggctaag tgatgtgccc atgatggcac agctgaatgg cgaaggaacc agaactggga   24540
cttgagttcc tggactccat caggggcttttt tccttgatga gcagcccatt caggttctgc   24600
taactgtcac tcggaagcct tgaattctgt gcatctccta accctgcgtg agagccctgc   24660
tctgccagca cccctggagg cagatccagg tcaccgtgtt gtcagccaca ttcttgccag   24720
cacgtagttc aagtttccat ctgaagagag ggaaacatga agaaatagag gagcgtgcta   24780
ttaaaataac gaggccttttt tgctaagagc aaacaatcac ttcctttcct tggcacccag   24840
aatctgcagg gccctgaatt aggcactgaa gggagatcca gggaagcatg aggaatagtc   24900
```

```
actgcccttg agggcctgga tgtataggtt cattctactt ttcattcatt tattcaagaa    24960
ttatttcttg agcctctacc aacagcagac actgagcctg cactgggtt tagagcaaga    25020
accatataac tgggtataca acagtaaact gtgcagatat ggttcttgct ctaaaattgc    25080
ttgtagtcta gtgaaggaca gaggcaagta aacaagcaac tacaaaatga aatgaagatt    25140
gcagtgatgg ggaggggagg gggtactctg ggtgtagact ggggtagggt gggcaaggct    25200
gagtgggtga gatatcatta cagtggaaac ccgaagactg agtatgtgtg agctaagcat    25260
gcaccatgag gggtctggca gttgggacgg aagtgtactc cccatggaga gaatgtgcag    25320
aagcacgcat aaccttctga ccggactgca gcaggcctgg gtgacggtgg tggtgaaggt    25380
ggggagtgtt gagaaacaca accagcaagg taggcagggg cccgtaagtg aaggactttg    25440
aaaggcctgt tggagagttt ctgtgttatc tcaaggccag tgagataaag ggcttgaagc    25500
agcagatttg tatgttagag tcctctggcc tcggggtaga gagtggatga aagcaagcag    25560
gatcggattc agagaggtca attaggagct gttgccaggg acagtggctt gaaccaggaa    25620
acagcccaga gaggtgcaga gaggttgagg aatttgagac atctttaaga ggtacaacca    25680
acaggtttgg agactgggtc ggaagtagga aatgaggaaa atggaggaaa ccaacactta    25740
tgaagaaaca aagacagagg ctgacaaaca aaagcaatag ccattctcca ggaagaaaat    25800
ggtggcatga ccatgtgttt tgagcaagga aaaattgcaa tgggctagag agattttgaa    25860
ggacttttcta gaagagttag aattggagct gggtctccga catgggtagg attttggtgg    25920
gtagagagga cattccaggc taaacaatga tgcaagttag agttctaagg cagaacagtg    25980
tgtgatttgt ttagcatgat ttggtcatgg ttttcttggg agagtcccaa agaactgatt    26040
ctccaggggg tgttactaaa actcttattg aaaggaggga ctacagagat gaatctcatc    26100
actctcccag aatggcacag agcttttcat ggaccccgg gccacctatg taggaacctc    26160
aggggggtctg tggaccacta aaagcccaac atgcctgaga ctccacagat actggcttcc    26220
accatgataa aggcaaaaag tccctctttc ccaaaatcaa tacttttatt ctcataggcc    26280
tcctgctgtg gtctagtccc catgttgaaa gctgctgtcc cagggtgttg cttcactact    26340
tctaggctcc tgcagagtcc tgcctcatag gccgcactgg tgagtgaggc cagcaaaccc    26400
atcagggaga ctacatgaat ccaaggccgt ggaagactta ggtttggata ttccctctgc    26460
tccctcctgg ctgtgtgacc ctagaataat tactcaccct ctcaaaaccg agactcagag    26520
acgttgggta attattctag ggtcacacag cgaggaagga ggagagggag tatccaaacc    26580
taagtctgtc tgacagcaaa gcctgttctc tccatctctc caggttccta agccaggtga    26640
gcgttgaacc tttcttgaat caaggttcca attccaaggt aggaaagcac agtcagtcag    26700
ggaaatattt acactgagac cacgcacccc agcccttttcc caacctgctc ttgtgtgatc    26760
cttttgaggt tttttgtttg ttttgagata gagtctcact ctgtcgccca ggctggactg    26820
cagtggtatg atctcagctc actgcaacct ccgcctccca ggttcaagtg attctcctgc    26880
ctcagcctcc tgagtagctg ggattataga tgcccgccac catgcccagc taattttttgt    26940
attttttagta gagatgggat ttcaccatgt tggccaggct ggtcttgaac tcctgacctc    27000
aagtgatccc cccacctcag cctcccaaag tgctgggatt acaggcatga gccactgtgc    27060
ctggccttaa gttttttata gatgggaaaa ccgaggtcca aacgtgagca agggctctgc    27120
atgctacctc tctatttttct cagccccttc tgcaggctcc atgccataag aacatggctc    27180
ctaaggttca ggcctatggc cccagtttag gtggtgcctc tgctctgctc cccaccaccc    27240
cagcctccta tttgaaggcc aagactactc agctttgatt caggttgaat gagtcatcaa    27300
```

```
gggtaaaaca aagaagagaa taaaacaaag aagagaaggc ctattccctt gcagatgaaa   27360
tcaatccact caccttttga catctttttg ttctagaatg atgacagtat gcaatgactc   27420
agaatcatca cactcacaga gactactttg tattttttct tgcaaatgaa gagacaatat   27480
gcccaaaaaa tgagctgaaa atggctcatg aagggaggga agatgacctc cagcacacca   27540
gggcagagtg ggggccacat gaaggtgcaa gagtgggagg gaaccacaac gccttggcag   27600
agaggagagc aagtggggggc caagccacaa agctcttcaa ggccagtcaa cagtgaaacc   27660
tgaaggagtc ccatccatcc ccaagtctgc ttgagttaaa gccctgcacc ctcacaagca   27720
gctggaggga ggggaggaaa gatattttca aaagagccat catatatggg gtgtgggaaa   27780
gaaaaacttg ctgcgtctaa caccagagag cctctccaag ccaagccatc tgcctcaggg   27840
caaaggaggg aatggaagcg ggagagaagg gtttggagcc agctctcagc aacatgtttc   27900
tatctggaga aatgagctga gaagatctga atcttctcca gcctgttctg caaatgtggg   27960
ataatcggcc cctggcccaa aggctggtgc tcacagcgtg gctccggcat tacccaggac   28020
tttggttctt ggtgatggga aagaggacaa atttggaagc cagagaagct agggctggat   28080
ggtctggagg aaaacctcca cttctctcag actgtttttt ctgaggaaac agatgattgc   28140
aacctcagag gttgggagga tgaaatgatg taatgcatct ggagctgctc tgtaaactgt   28200
aaaatgctat gcaaacggtg cttgttaatg tgtttacata tatgggtgag ttaacatagt   28260
ctgacagact ggacgccaaa ctcagagtcc aaggcaatgg ggcattatat tctgtgcctt   28320
agcatctgga aaacatgatg aaattggaaa tgcatttatt gaaaatgaaa agttttctac   28380
agagcttcct gtccttttcca atgaattcca ggcttcccat ggtgcttgca gggctctgcc   28440
ggaagctgct gggaaagctg acttccattc tggttgctat gaactccatt tttggttctg   28500
ttctgtgacc atcttcattt cagtcacttg caccattata aggattgaaa agactcttgg   28560
cagaaaagca gttttttgtt tcatagcatt agggtttgat atataatatt ttttttgaac   28620
agaaaaattt cacataagag ttcataaagg gtggtatttt agagctgaag gggcttagaa   28680
gactgtctag ttcaaccctg agattttttt caggtgagga actgaggccc aggcagaaag   28740
actggttttc tccagccctc acacatgtca gtgagccagg gttaaaatcc ccagaggtct   28800
gactcctatt catgtgctac ttcccttacc ccagggtcaa aagctcagat gctttcagag   28860
tccagataag tgaggaggag ggcattggcg ggtaggaagg tagggagttg tgggacattc   28920
agttttgttt acatttatcc tgttagaggt ttaacgagct acttgaatct taaatttatg   28980
tcagtcatca aatctgggaa gttttcagcc attgttttttt caaatatttt gttctataac   29040
aatctctttc tccttgcctt taaggattcc aatgacatga acattagacc atttggtatt   29100
gtcccacaga tcctcgaggc tttattcatt attttttcaaa acttttctta tctttcacat   29160
tggataattt ctgatgatct accttctagt ctactgacat tacctctgtc atttgcattc   29220
tgctattggg cccatccagt gaatttattt cagatattgt gtttctcagt tctaatatat   29280
tgccatttgg ttcttctttt atataaatttc tattgcttga ctgagaattt ctatttttcc   29340
attcattgta agagcattca cctttatgtc acgcaggatg attataatag atgcttcgga   29400
gttttttttt tccagttcca acattgtctt atcttttccc ttgagaactg gtcatgtttt   29460
cctggtcctt atcactttgg gtagttttaa attgtttcct ggacatttca tatagtatac   29520
tatgagactc tgggtcctgt taaaatcata aagcatgttg agtttgtttt tgttttagca   29580
ggtaatcaac cccgttaagt tcaacagcaa gctctgtctc atcttgtgta ggcagtggtc   29640
```

```
tcaacgtcag ctcagttttc aaagcctttg ttaatgctgt tgtgttcca cacatgcaca   29700 tcttggaggt gaggtcagga cttgtgctgg ctcctacatg gaatcccttt ctcccctct   29760 ttcctctgca agagttccgt cttgccggaa aaggaccagc tccttttcct ggtcctctgg   29820
ctagaaggat ggatttctct cagagctgga gccgctgatg atgtcacaaa gtttcatgcc   29880
acttggccag accttagagc aaagtgcaag gggaaaaaag tgaggactcc cctgatactt   29940
ttgacataac agggacccct tttctgaatt tctgtaccca aagggacagg ttttctcttg   30000
agattttagt gctcaagctg ctgccaaggt gatggcgata cagtttgggg gctgcatctg   30060
actgtgtgtc caagctgaga gagaaaaaaa gacaaagatt ttccccacac ttttgtctt   30120 gcagaggccc cttttccaga ttatctatcc agaaagatgg gccatttctt ggggttgttg   30180
ctgtctatga ctgctgggag gtctcatgat tcagctcacc cttgggccaa agccaggaga   30240
aaacaaattc caggaaattc accatcacca tattggtcat tcagcaaatt ttgacttctt   30300
ttcgcaatct agctgctttt agaggacttt tcagagacct cagttaattg ttttttttgt   30360
attttgttaa gagtgtttgg ttgtaatcag tgagggagat agtgtgcaat gcatgccttc   30420
catttggttg gaactagaag ttgagcaaca cagttggaat tcatcttttt tggttagtgc   30480
ttccccagga ctttcacgga cagaatccca aaatagaacc tgtatttggg aatcctatat   30540
tccctggcct ggtggtggca ggtcccagga gtctatggct ccaagttttc taccttattt   30600
gggtagacac ttaaaacaat gctcattcaa caaagacgta gtgggtgccc accatatgct   30660
atatcctgga gacacaaaaa tgactaagac atagtgccca ccctcaagta gctcatgggc   30720
gagtggaata aagggatttt cagtaaaaat ttaagatcca agcttgaaag cttctttccc   30780
aagcatcttt gtggatctga gaaccacaac acccttgtcag agagcaattt ctagcctgat   30840
tctggagctt tgcccttcta gaaacttcta tcattgtttc tctcctctga gcggaaccaa   30900
cagtaaagca ctatatatta aaaaacagta tataaaattc tccttttgtt ttgtgaactc   30960
tacaaatgcc tagattacct gttttttaaca gtcttcttgc ctactaaaca tagacttaga   31020
gaacacagtc tgtttggggg ctccagaact caaaagggaa gtgaagacaa tggagagtgt   31080
tcagatagca cttttagtag atagaatctg atatttaaaa ataaagagtg ggggagttgg   31140
gggccatctg ccaaggagat aatccttcat aaagcagatt aaccatatct ttgtcttagt   31200
tcaaatcact ataacaaatt accatagacc gggtagctta accaacaaac atttatttct   31260
cattgttctg gaggctagaa atctgagatc agggtgctag cagagacagg ttctggcaag   31320
ggtctttgcc aacttttgct gtattctcac atagcagaaa gagagctaaa aagccgtctg   31380
gtacctcttc ttacagaggc accaatccaa ttcatgtggg ctccaccctc atgacctaat   31440
cacctcaaaa ggtcccacca cataatacca tcacactggg gattcaattt caacatgtga   31500
attttggggg aacacaaaca ctcagtccat aacactcccc cagcccacct ctgctgcctt   31560
ttctctttga aagcacttac cttctctttc tgcattgatg taatgccaga ggattggatc   31620
tgggaaagga agtaaatgtg ggagggaaga atcagggttc agccatttag cgagcacaag   31680
taggtgccgt gtgtcagcaa gggtaccctg tgcatgagtt attttaccac ccttacagca   31740
atccagcagg cctgtgtgat aagtgttgtg tttcctgtgt ggtagacgag gagaccgaga   31800
ctcagaagtg acgtgatttt tctcaaggta ttagctggca aattgtagac tagaatccag   31860
gtctcctgag tgtgggttct gtttatctag tttacctact gcgccggcct ctaagacttt   31920
ggggtctgaa tatgtacctc ttcataccac tagagcccca gcagtcttct aagtgacatg   31980
tgagccatac tggggaggag tttggggaaa ggagacctta ccactgacag cagagtctgg   32040
```

```
gggctcacaa gagaggaaga tgcccactgg gaagccagat ctcaggttct tcagacctat  32100
acctccctgg gatataattc aatcaagtgc ttattcccct cttaaaaaa aactaaaatg   32160
atgcagaaac taactatgaa acaaaggaag aaaaaacaag agaaggcagg gattatttcc  32220
caggacattt tcctctgacc aggagggtaa gttggggaca gaggaccgac ttggtgggga  32280
tcagaggcag cccaagggag aagagtcatt ccttctactc tcccacctgt cctcattgct  32340
ggctctgacc cagatgagag ctgggggcgt tgacatggga agcttctctc cttcctgagt  32400
ggtcagtgag gggcagcttc tcctcctact ccaggagggt tgcgggaacc tgcatgttgc  32460
atcccagagc agccagagct tcttcttgcc agtctcctac cttcccttc tggctccttt   32520
actcccacct cctcatgccc tctttctcat ttaatagcag ggagaaagga aatgaaactt  32580
gatggagcct gactgtgcca ggcactgtgc caagaacttt gtgttcattt gtttctagaa  32640
gagggcttgg tatactgtag atgctcaata aacgttaact cttagcttta gtgtctccgg  32700
tccttcactt cagtgatctc taggcacagt tgatggctca gtttcacaac tgctgcagag  32760
aggatgaaag aacaatgtca agtggttggg tgggggaaaa tgaaactggc attagggcta  32820
atcacataca tttctcaggg tgctcctctt ttgaggccct atttccatga gaaggaaatt  32880
gaggcaaacc cagaagttga cagcttagct gggaaccaaa gatgatgata tacgggagcc  32940
catggaatct catagctcga gcagcacttt tggcaccaac ctgcacccaa agagcatctt  33000
taaaagttgt cacatacttg ctccgggcag ctctttcaca ccactaccat gctctgtgcc  33060
agacatgact aattttttaa atctctgaca ctcttaatta gtcatgagct aattctgtaa  33120
gaatgttaga gtaagcacac taaaattata ttcttctgca aagagaaaga agattacctg  33180
agaccacttg tcccccctca aagaagcaag gtctcagcca aaatctttga agccttgtga  33240
catcaataga ttttctaggg tggcatcatg tcctttgat ttttctgtat atagtagttc   33300
aaaatgccacc ttctcctctc ctttccattg ccactgccct ggctaggtcc tcatcagtgc 33360
catcaactct caccaggctc cctgccacca atccaaacaa aaccaaacac tactaatcat  33420
ggatcttcat ggcacgtttg ctttcgttgg ctccaaaagc ctccagtggc tttccattgc  33480
agattggaaa ggtctagact cagcgatcaa aacttccacc actgattgct tttccaaaca  33540
tctcccctac ttcctgttgt gaataccacc tggtttactt attatctctg gcttgccatt  33600
atctggttta cttattatca tcaatatgtc tagaccctc tgatcttccc aactttaccc   33660
gtgcctttc agttctcttc ttctcattcc tcaccactga tggacagtca tccttccttc  33720
caagaagggc ttaagtctgg ttgcctggac tctagataat ttccctcctc cttagcaatt  33780
ccaccttga ttgtctggac tccttgtgcc atgtacaatt atcctgtatt gttaattgtc   33840
tttctatgtc tgtaacttgc ttctgtgtta tagacatcat catggcacag tgccgtgctt  33900
tttcacagaa taggtactta atattctatt atttaattta ctagaacttt gcaatttcat  33960
aaagataact ttgtcattaa aaatgttcc agtgggatt tagggccctt gagatggtgc    34020
aagaaaagga gataaagggt ttttttaag ctatttgttc tttctgtgca aattacataa   34080
cttccaatta tttccaacgt taaagaaata gtccctctga atcctttatg atttaaacat  34140
taaaatgatt cactagtttt tagaaaaaaa acaaaaaaca aaaaacaaa aactgctgtc   34200
acccttccaa aaatgtaaaa aagaagaaag aaaacccaaa tattggctct tttggaggaa  34260
aaataaactg gctgtgcttt tatttctcca atattctgaa agaactggga atgcaccaca  34320
aaatggcagt gcttgtgtgt acccgagtgt gtacacctca cctctgtctt gagtccactc  34380
```

```
tccctaccaa gcttttcttg ggtagaagtc atggagccat atccagcacc agtcacctga    34440
gcactcctct cataaaggag actttgggtt taatccctgc caggggatt caagtgctgc    34500
tctcctaagg aggagagcag gttttctttg cttgactata tttcaacacc tctgacagaa    34560
tgactccagc cagccagggt gcttttttgc ttcccagctt ctcatagcgc cccagatgta    34620
gcatcctttc ggtcctcaac atttacttcc ctctttactc actgtattag ttttctgttg    34680
ctatgtaatt accaaagctt attaatttaa agcaatacaa ggtggcgcgc agtggctcat    34740
gcttgtaacc ccaacacttt gggagaccaa ggagggcgga tcacctgagg tcaggagttc    34800
gagaccagcc tggccaacat agtgaaaccc cgtttctact aaaaatacaa aaattagccc    34860
agtgtggtga tgcatgcctg tagttccagc tactcaggag gctgaggcag gagaattgct    34920
tgaacccagg aggcagaggt tgcagtaagc caagattgca ccattgcact ccatcctggg    34980
cgacagagtg agactctgtc tcaaaacaaa caaacgaaaa cacacacaca aatttattat    35040
ctcatggtac cagctggctc ctctgctcag ggtctcacta ggcccaaagc ccttttcatc    35100
ctgtgtccct gtctatcact gccatcatcc cacatccctg tctctgtggc atcttgtgct    35160
tcacagctca aggtcatatt atctgcattt agttttgaga caatcataac gttatgacca    35220
cttctccat tcttctctgc tagctgagtt tctccaaggc ctaagacata ggccacaccc    35280
tcacaattct atactcaggc actttctaaa atcacacatt ccttaatgca gtgaagaatt    35340
gatgctcatg agtgacatcc tacattgaaa ggaagagacg tggccgggcg cgatggatca    35400
cgcctgtgat cccagcactt tgggaggcca aggtgggcgg ataacttgag gtcaggagtt    35460
tgagactagc ctggccaata tggtgaaacc ctgtctctac taaaaataca aaaattagct    35520
gggcgtggtg gcaggcgcct gtaatgccag ctgctcggga ggctgaggca ggagaatcgc    35580
ttgaacctgg aaggcggagg ttccagtaag ccaagatcgt gccactgcac tccagcctgg    35640
gtgacaagag tgaaaccctg tctcaaaaaa aaaaaaaaa aaaaaaaaaa ggaagagaca    35700
caattacctg agggatgaat ggcaaatgtt ctatttagaa acgcattttt aaagctcacc    35760
ttgtagggtt tcttgtcatg catcatttaa aaaaataaat taaaaaccctt gaatattagg    35820
ctgaggattt tctcttgaaa gagacaaaga gacatggtca agtcactggg aatttcatga    35880
cttaggagga ttctctcaga agactttcta agaataactt caataatctc caataatctg    35940
caacctactt ttctttcatt gaaacaaaca aagttagcta tggaattaat atttggaaaa    36000
tgaagaaagc ttaaaggaaa taaacatttc ccataatctt accatccact gaaaaccatg    36060
gttaacttga catgggagtg ggcttgggtt ggaaaaaaat agggagagag ttttatctct    36120
ggaaagcatt gctggctccc ttccacactt tacagcatgt attagcttag tgacactgta    36180
gggagaagca caagccatgt aaagaggact taatttgtca agatttactg actagctaag    36240
ggctaaaaag agatgagtgg ggtggaagca atggtttcca caacacccc aagataaggg    36300
gtatcacttg tgcaaattta gcaccaggga gtggggccag cccagaactt caactcaaca    36360
tttgtcaagc cctcagtata ccttccaacc cagaaaaaca ataaaaatgt taattttga    36420
aatcactagc aaaatactaa atacaaggtc aatattttaa accaaagtgc cctgagagca    36480
ccgttgtttc taatgacttc ctcctccctg atcgtctatt tttctccctg gtcttatctt    36540
tctgaacttt tttgctgcaa ttgttgagcg tcaaaggctg aaaccactat tatcaccact    36600
attactgccc tcctctctgc atttgaacac cctgctgcat cctgcatctt gcctcttcct    36660
ttatacttgc tgctttggat gaggtccat gtatcatcct cagcccggga ttttcaggct    36720
cctagaagac atttcctctt actgaggcat ggacacgtgc aattgcagcc aaaggtgaat    36780
```

```
tggttgtcag gtgttccttc aacttggctc ctctctgccc tctcactgcc tcctgccatc   36840
taatcagctc tacttatctg ccccttagag ggaccatctc ttcagttatt agccattctt   36900
gtgtacacac aacctgctgg ttttcacttc cttgtatttg ctcagacagt tttttccact   36960
aagaaggcag atgcctcaaa acccagatgg acactgactt tcagaagctc tgcctaaaaa   37020
aaaaaaaccc acctacatct cctacttggc atctctaagc acttgtgtgt ttagcctggg   37080
ctgtgtgtat tttcacatgt ttatgttgtt ttcattcttg actttatagt gatgacaata   37140
ctaattacta cttatttaag gactagcatg ttccaggaca tgtatctttt ttttttaaa   37200
gggcataggc agaaggagag gaaaagcagt tcagagtact aaggggctat gattggaagg   37260
gtgtcaagaa ctagctctct caccctcaaa aggcctccct ggcccagcct gtcctgccta   37320
aattctctaa tcagagtgca ggtcactggg gagtgaagat tctcaacctc actcacctct   37380
ttcacccctc cacatctgcc caccccatct ccactattta gtgcaaaggc tcctgggaac   37440
agcgacattc taaactgtta acagctgaag ccttccaaag gattctgtcc cccagtgaca   37500
gttggctgaa gactgtgaaa gagaaagagc ggtccttcag ggttgggaga ccaagaggga   37560
agggaaatta ctagcctcag gaagaagcag actcccagcc tgagctcctc acagcctact   37620
cctccccaag ccatgcctgc aagcctcctt gagggtttat ggggcatagc cctacaaggg   37680
acccagagat gaatcagaca tggatcctgc ctttgaggag cttactgtct actggcaaaa   37740
agtgccgagt acagtttcaa cccagggcaa tttcaagggt tgtgggactt cagaagagag   37800
aaagacgtgg gctggacatc aaagaaggcc tgccagagga ggtcgcgttt gagctggacc   37860
tcgaaagatg gcaggggact ttccacaggc agagattgga ggtggtgcta gttatgaagc   37920
cagacacctt cagtttgagg ctgtgatctg tgaggacagt ggggagaggg gaaagccaga   37980
gaagggtaaa aggctgagga aaccctggcc accttctcta gtaagaggac accaaggatc   38040
acgctttgcc tgctttaaca tcttgcctac cattgccctg atgaaaatag gccactgttt   38100
tgaattagct aaaagttgag aactcagact tggatttgac aagggccctc tgagggcagt   38160
taaaccaact ctcagcccca tgattctatg agtctgtgat tcgcaggtgg agccaatgac   38220
acacctttgg gactaggcaa ggcctcttgg tcagcgaatt ccctcagggg aataatgctc   38280
cttcacagga gaatggcaga tggaaaaacc ccaaaaagtg aatatgccca ggactgctca   38340
attgaattta caatagttcc agattattga ctagctcatg cctgtcagca gagccagaat   38400
ggacacatac tttgaagagt atgatggcag gtagaggtga aaaaaaagac tgaatgtgac   38460
tttagatggc aagaacatga cagtgaggta cttgatgaga acccccaaa aatgatcaag   38520
aaggggtaac tgggtgataa aggggagat taagaagcct acactttatt atacccagtt   38580
cttttttttcc ccactgttgc tattttagaa ttgcagctct acattttgtg gaggttacag   38640
aaggaatctt gtgaatattt tttctctgac agggaaataa ttatgaaaat cttaactttt   38700
ataatatttg tgcaaatttc aagaataagt tttgttttat ctttggtggc accacatgct   38760
ttggactttt gttttaaat cccagcataa ccagtatttt ccgaggattc taatcattcc   38820
cagtgggctg aatttagcca gcagtaaccc tagccttgca aagacaaagc aaccagtgat   38880
atttgataaa atagaagctg acagacaaat caggtctagt caatcaaagg atgacgagca   38940
gaagacccag gccagagaga gcactagcac gtcttggatg gccagaaaaa gtagggaagg   39000
aaggcacgcg gggggtcagc ccaaataggg gtcagtatgc agggctctgg cctccaatcc   39060
taagacccct tgggagggga aaagcattca ttttctactt cacttttttat gtacttgcct   39120
```

```
tggcagaagg agccttggtc ttggaggtgt agccccggca tcccaaatga gatgaagcct     39180
gcctctggtc aagttaggac cagaaaggct aaattgatct aacttggaaa ggaagctttg     39240
tgctatctca gttttatgct caatgtctgc ctttgagggg caagaacagc catacaggag     39300
aacaaagaat ctcagggtat cagagagagg aggcaacata gccaagtcca gtatgagaaa     39360
cctgccttct ggggatttct tcatatagct gttctttcag ctggtctttc cagcttctgt     39420
ctgcccccag taggttgcct caaaagccca gttttccttt gatcattcca gccccagcg     39480 aaatacctct ttaatgctta atgtggcagt cacctttgga tctgacttcc cttctgacag     39540
ttcaccaccc tgtgaactgg ttccattgtc ttccctggaa aggtagttcc ctttcttagc     39600
ctcctattca cttctgttgg cctctttttc cttcctgctg tttctcctaa aacattttgc     39660
tggccttcaa taatattggt gtccaaattc agtttgggc ctaccaccgt tttatgtctc     39720
tgtgggttac aattttcttt gaggaatgtc ctcattacca tatatttta aactaaatag     39780 tttgcatgaa cagggatcct caagcatttg atacaataag aaaggcatag aatggcggtg     39840
taatttgggg gcaagcgtgt ttgctgtagg agggaaaggc agcggagagg ctggttccca     39900
gtatagggtt ggaggaggag ctgctgctgg tactgctcac atgctgcatt caggctgctg     39960
gcacaggggg ttctggagct ccaggcctgg caggcgtggt gggaggagca gcacctttgt     40020
ggtcttcttt ttgaaactct ctgccttgac aactgattgg ggaacaagga gtcagtttca     40080
ctcaattctc ctataggtga ctcaaacctc tatcacaccc aatcatctgc cccagagatg     40140
atctctccta tgaaagcagt tgaaatgcac caaagtgatt tcttgagagt cttattcctc     40200
actgagaagc taataggctg cgtgcggccc tctcgtgagt tgtagcttag gtcatgagca     40260
taaaacccag taaattgtgt agaaaaatgt tgaaagactc cacagagcct agacaagaag     40320
tagagatcat ggatctgcct tctctttta aaggctcctt aggagtcact tcctcctcaa     40380
aaccctttta atggatttct atgaagaaaa tcatctaaat aagagttta ctcaaactgg     40440 ggtcagtact tcctggtggc tcaggactct gagggagct gatagacacg ctgtggaagc     40500
acactgacaa tggtttggtc ctgcctaccg gttgccgttt cactcttcct gttgctcaga     40560
ttggctgtgc attctcttgc tttcaaacaa atgtaactgc atgaatgaaa gcactcccat     40620
ccccatttct gcccagtgaa atcctacctc tcctcttggc tcagctcaaa tgtcgcctcc     40680
tctgtagaac cttcaatgag tgtccagtgg gaggtcagtg tgccctcttc tggactcaac     40740
aaccatttgg ttgggtgctc ccctacactc taaaatgagg gtgtttagca aaggtcttat     40800
ctcccctgct gggctgtgaa caagtgagta gaaggttgct gagcatcgaa gctaggataa     40860
gccagaaagg tggcacttgt ttttcagct gccattaaat tcctgtaaag gaacttctca     40920
ctgagggtgc tcattctgtg tgtggggaac tgcatgaaaa cactcctcat ggccttttgt     40980
ttgcaaaggc acagttaggt ctgcaaacac agaatttgag cagctgtggc aaagcagccc     41040
tgatcacatg gcccatcttt tccattctcc agctgtcctg accaaaggcc acgctggaaa     41100
cagctctaag agccactaag agctgtggag gcaggagtag aggaggaaag acaaatgtca     41160
aaattattgg atgatcctgg gtagcaactg gccaaggggg attagaatgg gtgacagagc     41220
ctttcacctt tggggtcagc agcatgtctg acttcaggac cagaaggcca aacatctgt     41280 cagctgagca gcagctcctg tgaatgaatc gcctttgtct tgttggaggc ggggatgagt     41340
gtgaatttat ttgctcaaca gaaagccatg taaacctgag atcagatgga agctctggtg     41400
gtggcaagaa gcccagtagc ccttcagaca gaagatgccc atcaacaatg gaaaggagta     41460
cacaggacct cggaaggaag ggtcctctct cttggcggaa ggcccctcac ctctttgtga     41520
```

```
agccctctgg ggcagaaaaa ggccttgccg gttccagcaa aacttcatgg agcatggggg   41580
tggcagatgg ggtgcctggt cccagccact cctctcccaa cttcccacta gccatgtggg   41640
caagctcaca ttagcaatga gctcaggcct gctttgctca tttaaggaaa agcagtgatc   41700
ccattatccc aggggtgatt ctttgcccca gacgcagctc cttttttcta acttccttca   41760
gccctgctgg cttctcctca gcagtagcta atgtgggatg atgatcagca gcagttgagc   41820 tattttaag tcaacaaact accaatgcta agagttcctc agaaagccag gaaattcgga   41880
gcctcagaag caaatgctaa acatgattga tgggcatgga agggaatgtt ttggactgct   41940
gttcacaaaa ggaatccctt gaatttaatc ctaaaaatgg ccaagctaga agagtcctta   42000
gaaaccatct agtctgcttt ttccctccct agaaaatttc tacagatgag aaagtaaagt   42060
ggatgatggt ttagggctga ggcacttagc tgatctagag gtggaagcca actcttcctg   42120
attcctatgt gaatgctctt tccacaaaga tcagtagaat gtttctggat ttctttgttt   42180
caatgagctt cgattatcac actttatttt tcttagcatg ggctccataa aactaaatta   42240
ttgtacaaaa tctaaataag ttaattaaac aagcaccaga cacagagtaa cttaaatgac   42300
atcagggtgc taaatctcag tttatagtca gtggacagat aactctgaaa tatcagctgg   42360
tggcatatcc aaatcagtaa ggaaggacca tttggttttt atgccacctg aacagtggcg   42420
gcattccagc tggtgagtct tcctggcctc ttgatgcagt actcccctc agctgatgct   42480 ttgctctctg gggttaattc aatatccagg ggcaggagc cagacttgga aggtcctctc   42540
cccacatcta actcctgctt caacacccag ctccaacgtc ttctctgtga agccttccta   42600
catcttcccc cattcctcag agtagcctaa atcctctcct aatgcccctc tttataatac   42660
ccctacagtc acactgtaag gttactgtgt taggcccca tcaggcctag ggtgtgtgtg   42720
tgtgtgtgtg tgtgtgtgtg tgtgtgtgtg tgtgtgtgtg tgtcatgcct acagtgaatc   42780
tctccagaaa caccaatgaa caggtttgac tacaaggaga ctacaatgag aatttttattg   42840 ccaatatagg agatttggga cccacaccag gtagagttta ctagaaacaa gataccccta   42900
ctgcagtagg cattgagcag ggagggagac aggggaggga gcagagcaga gcactggggg   42960
tgtctgcagg aaagccttat tgaaatcatg gaagctgagg tagcttatgg gagcctgggt   43020
cttagaactg accctggt cattgaaaga gaagcccctc ttggagggga atgagaggct   43080
gcagcaagca gctctgagtc acacaatcag gaaggcattg aacgcttgag gcaaacagcc   43140
attatgacaa aggagaaaat gcactttact ccatgggact ctgtctcccc cggtggacct   43200
agcatgctgg gcaaaagcag ctatcgtttg gcttgaggct catctgttaa agaggaggct   43260
ggtgtaaacc taagcatggg ggcatgtgga gatgagggag agggctggcc gggctgtttg   43320
gagtctgggc ctgtctcagc tctgccacta gttggttgca tggctttgag taaatctgct   43380
ccatcagaat aatgtgggca agataaattc tcaagttctt ccaggtctaa aggtctggga   43440
tcctagggct gcgcgaacct gttcccacct caaacctgtt cattggtgtc tctggagaga   43500
gatggacaca aaagtcgtca cttggcccctt ttggaaacag ttgagtcaaa aagtcttggc   43560
ctcctgctca ttttttaacca gggcctcaca gaaaacagtt cgcaatccaa ctggtacact   43620
ggcatgaggt tgtaaatcct atctgggaaa gcaaaccaga aacttctacc ctttggtgtt   43680
caaaaatact tcattttct taaaattgtc ttttaaaac tgtaaggtc tgtaaacatt   43740 agttttagaa caattgctcc ccaataattt atttacaaa caggaatatg aaaaataaat   43800
ggtggtagga ggaaggaccc actaagaaca ccattttaa attttgctaa gtaaggacat   43860
```

```
tgagggaaaa aactcaaact ctgatctacc atcattgttt aatgttcggc aaacatgaag    43920
cattttaata ccaaaaaaag tgaggagaat aaatctcagc ataaaggaac aactttttaa    43980
actgaattta gcactatgaa aaatgtacct cattttctgt aattttagcg agtttcccgc    44040
ggatgtacac tggcccatg gattggcgct ggggatcacc agtttagagg tgccagtgcc     44100
ttctgacaaa ggcccatgga tccatatgac tgcctgtctg ttcttttag agacgggccc     44160 acactgcaga gaagtgattg tgaaggtctc caaccctgtc atgccccac ctgccacctt     44220 gacttgggag agggacactc acaaaagcat gtcaaatcga catccatttc tttctctttc    44280
cctcaggtct cagggagttt tcctcttctc ctcggactct ttctctcaag gcctcttcta    44340
caaaaacccc tgcccagagg gttactgcta aaatgaaact cccgtgtctg tccccttccc    44400
tggcccccaa ctgacttgcc tgcctctgct tgctgctgtc cctgcctatt cccctttcatg   44460 ctggctctag aaagatgcaa tcttttttccc aggccccagc ctctctggcc tccctgccat   44520
ccagcttcta gcctcccttc tctggaatct atggaagaat catcaagcag cttctggaaa    44580
tccaggagtc tgtccttggt catggtcatc ttcaacctgt ctgtgttctt gagaacgttc    44640
atgtgctccc agaaacattc ttttgtctg cctttcctgg tctggccaca tttgactgtg     44700
tcacttctct cttttctcac tcttctctgc cctccacaga cctccgtgct gccaggactt    44760
cctaacggaa gggcttggct ggctccccga agccatccag aactggaccc gagggaccca   44820
gctcaacttg aatgtccttt tatctgccca ggagatggga agatgctgag accatgcttc   44880
agtgctgtcc cacatctgtc tttctgagtt tagacttggt ttttccatta tattccattc    44940
aactgatttt tccatgatat tccacaatgt cttacctaac tctagctttc tatactcaac    45000
agcaatgcct cctgagagcc tcctgggtgt caagtactct gttgtgtgct tttgaggact    45060
agggtgttag caaggcacag tctctgactt tgcagggctc acagattcat ggggaaaatt    45120
gatgttccag ttacagtgag gcaaggcaat ctggcagtaa ctccatagag aggaatgaca    45180
ggctgggcct aggaatggag gggagcgggt aatagaggat cctaaggaaa ctgagagaag    45240
aggggctgga gtgcggctgg tctgcgctcc tgtgcattgc cttggctaac attttacttg    45300
tccttctgaa tcaccctggc attgtcaaca aagaataatg tatgatcctt cttggagtaa    45360 aaagcttca gcagtgcttc acaaaaaatt ctattgtata ttttgtgtcc tacctcaaat     45420
taattaaaaa aaaaaaaaaa aaaacacgtt gttaattcgc tccaagccca ctcagctgct    45480
gaagaatttt gagtattcag ctagagatct ttgtaatgaa caagtagctc aattattctg    45540
gtttcattat acaatgtatc aggcattctt ttttttttt tccccaaggc agaagaattt     45600
ttcttagtac agaacaaaat gaaaagtctc ccatgtctac ctctttctac acagacacag    45660
caaccatcct atttctcaat cttttcccca cctttccccc ttttctattc cacaaaaccg    45720
ccattgtcat catggcccgt tctcaatgag ctgttgggta cacctcccag acggggtggt    45780
ggccgggcag aggggctcct cacttcccag taggggcagc cgggcagagg cgcccctcac    45840
ctccctcccg gggcggct ggccagacgg ggcggctggc cgggcggggg gctgaccccc       45900 cacctcccctc ccgacgggg cggctggccg gcggggggc tgacccccc acctccctcc       45960 cggacagggc agctggccgg gcggggggct gatccccca cctccctccc ggacggggcg      46020
gctgccgggc ggagacgctc ctcacttccc agatggggcg gctgccgggc ggaggggctc    46080
ctcacttctc agacggggca gctgccgggc ggaggggctc ctcacttctc agacggggcg    46140
gttgccaggc ggagggtctc ctcacttctc agacggggcg gccgggcaga gacactcctc    46200
acctcccaga tggggtcgcg gccgggcaga ggcgctcctc acatcccaga cggggcggcg   46260
```

```
gggcagaggc gctccccaca tctcagacga tgggcggccg ggcagagacg ctcctcactt    46320
cctagatggg atggtggccg ggaagaggcg ctcgtcactt cctagatggg atggcagccg    46380
ggcagagacg ctcctcactt tccagactgg gcagccaggc agaggggctc ctcacatccc    46440
agacgatggg cagccgggca gagacgctcc tcacttccta gacaggatgg cggccgggca    46500
gagacgctcc tcactttcca gacggggcag ccaggcagag gggctcctca catcccagac    46560
gatgggcggc caggcagaga cgctcctcac ttcccagacg gggtggcggc cgggcagagg    46620
ctgcagtctt ggcacattgg gaggccaagg caggcggctg ggaggtggag gttgtagcca    46680
gccgagatta cgccactgca ccccagcctg gcaccattg agcagtgagt gaacgagact     46740
ccgtctgcaa tcccggcacc ttgtgaggcc aaggctggcg gatcactcgc gattaggagc    46800
tggagaccag cccggccaac acagggaac cccgtctcca ccaaaaagt acgaaaaaca      46860 gtcaggcgtg gcggcgcgcg cctgcaatcg caggcactgg gcaggctgag gcaggagaat    46920
caggcaggga ggttgcagtg agccgagatg gcagcagtac agtccagctt tggatcggca    46980
tcagagggag accatggaaa gagagggaga gggagaccgt ggggagaggg agagggagag    47040
cgagagcgta tcaggcattc tttggcatca aggaattaaa gcacattttc tctggcaaat    47100
ggcaacagtg tctgatttga agacataccc tacacaagtg gttcttgact aaatgtagtt    47160
ccatttaaaa ataagagtta acctcttgta gtctggtctc aactggctca ttccagggag    47220
ttcttagctc acacttgcta atattttgtt tacaattgtg caaattctac agttggcaat    47280
attgtttacc aggcattgaa ctcttttact tattaatatt ttaataggtt tttggggaac    47340
aggtggtgtt tggttacatg aacaagttct ttagtggtga tttctgatat tttggcgcac    47400
ctatcaccca agcagtgtgc accgtaccca atgtgttta ttttgtccct caccccctcc    47460
caccctttcc cccaaatccc caaagtccat tataaggcac tgaactctta agccttgttc    47520
cttgttccca cagctcggcc aattgtgttg gtccttcccc ctgctttatt tagtcacttc    47580
ctctggaggc tggccttttc tacccaagac accatgggca gtggagcact caatccatat    47640
tctcccagac atgcccctca atgccaagca gagaatcaga gcacctggtg tttggggacc    47700
agacctgtgt ccactaaagg accccagtca aggaaatgg catctcttgg aaaaaaaaaa    47760
aaaagctact ttctgcccat gaagaaggac cccgaccttc ccccagtgta aatgtatagg    47820
caggaccccc actaccctgt gctcctttgt gcagttgagg aaaaggtggc ccatctggat    47880
ggatacaaag cttggcagga aagcaggggc aggatttcag ctcccttggc ccccgtgcaa    47940
gtgaaggaag cttcccctg aggtttattt gacattgttc tccccagaca gctgccttcc     48000
caattcaaag gctcaagact gttgaaaagc atatgccaag ggacagacta aacctgtgac    48060
agagatgatt gccagtttgc gaaaatgctg aaagctttcc ataaatttgg gatccacaag    48120
gcaccttgtc gtcacatgct gggtcaatcc cattgcagtg gggagtggag gactggactg    48180
gatgatgtcc aggagcctag cactgtgttg aaataaatta ttctgcaggc tggtggtggt    48240
tataaactca ctaccagcaa ggagttgggg ctgaaaggag aaacattata aaacggttgc    48300
cactaaagtg tagtctgttc agggccaata attaacccta gttggagatg atttctctct    48360
ttgactatca ccagggttga gagccgagtg actctgcctg tccaatttga ttgctagggt    48420
ggtccaaagg agagttcctt caccttcatc cacctttatt gggtctctcc tctttctttt    48480
actgccaaat ttcttgaaag aagagtccag acttgctgtc tcaatagctt ctctgccttg    48540
catctgactg actgagtgac tgactgacga gaggtcacag tgtgttggac tgctaaagta    48600
```

-continued

```
gccagcctttt tcttgttttc ccaccctatt tgtcagtgta aagtgttcta agctgatggc   48660
ttctctttcc tttttttcta ctttcttcct tggactccag tgaaatgacc ctctccaagt   48720
tacctctacc ctcgtggctg cttttctgct tcttcattag tgcctaagct gagtgtattg   48780
ctcatggttc tagcctgagc ttttttccct gattatcttc tgtgttggag atttgaccta   48840
ctcgtggggt ttccatgata accactctgc aacagactcc cagagtcatc tcagccagtc   48900
tcatctatgt ccagtcctca atgcccacat ttcaacatgt tcaaggctgt catcttccct   48960
ctctacgttg gtcttgctgc ggcttcttta gagaaattat caagactttg gagtcataca   49020
cctaggttgg aatcctagtt gtacactttt ctgtgtggcc tttgaaatga agtccttttt   49080
tctcatgttc tgtgaatgct accaatgctc attatacaat aagcacttgt caaatgctgg   49140
tctccttccc cattttttat tagcatgaac atttcccctc tctagtgggc ttggaatcat   49200
ctagttttc attgtaataa tgtacgttct cctcctctac acctccgcaa gcccatttct   49260
ctggaaacac ctctcacgtt ggtcctgtcc tttcaatatt aagggatgtc atctgggccc   49320
atgcaaccag tgtctctgcc tacccgatcc tctctgcccg ccactactgc ctgaagcatg   49380
tttcagatca tattcccacc caaaaactgc cagtgccccc actctcagtt ccataccttt   49440
actttcaagg tttttaatga tctgcctcaa acctagtttt ctgccaaact taggatggct   49500
caatcacatg gcatgctggg acctcagtga cagaatccaa tgggatgggg taaccagggt   49560
agcccgtgtc tatcccaaag cctccaatct ggaggttggg gcaatgcttt agggccataa   49620
tgatgctcaa cgtgaaatgg ggcttcacct gtacttgggc attgggctct ggtcctcagg   49680
gcaaagatcc taggcaagag gatcaatgac tgggccccag ccaagctgct taaaagccag   49740
ggcagcacta gaggaccagt tggaagtcca gagtcttggg aaaaggaggc aaaatctcaa   49800
cccctatgta tagagcaaca tgacgctcgg agggaaggaa gaaggcaatg cagtggtcct   49860
gggcttctac gttaattctg agagtggccc cgcaactctt catctttctc ttccctggct   49920
ttaggcatgt atcttgcaac tagcacttgc ttaattgatt tgacacacct ccctacactt   49980
acccctttcc atacaaagtg ccaggtcctc tgaaagctcc ctatatcacc tggccaattg   50040
gaattttcac agccaaggca gaaaacaggt gaggtttggt tgtcaatctc catcttaggc   50100
attgaacagg atgtgtagcc agttcatgga agacctttt cactcttctg aagacttagg   50160
aataaaaaag ggctcttact gttatcatgt ggtcagaagg cattctttt ccactttaaa   50220
gaaccaaaac ttcctccagt tcagaaacag taaatgaatg gtccaccatg tgctgcgaac   50280
tttgctgttc accaccatgg ctgctcctag cagcatctat gcaagcaccc catggatgct   50340
atccagggtt tcttcttttt attattaata gctaacattt actgagtgct tactatatgc   50400
caggcactgt gcaaagggaa acacaatgcc tcagtcccag gtagttcctg ggaaactgaa   50460
cagaatctta aatagaaact ctaaggagtt agggaagtga gggctcactg gggctgtgac   50520
cccaggggag accacactca aaagatggtt ttgcaactca acctcagttt caggcctgct   50580
atatcacttc cactcactca gtagtaggct tggcatttag tgggggacag aggcatggtg   50640
ggaagttggg ggtgctgttc aggcttggcc ctcaccagcc tctgctggga ctggtagcat   50700
gaatgctgtg taggatgttg gggagctgga agaagactct tccgcagccc ctccctctct   50760
atcccattcc cctctcatct ccccacccctt caaggttaaa tattaaaaat tcccttcacg   50820
gggtgagctt tcagtccttg attcactcca aacaggcttc aaacgcaaat agctgtagag   50880
aagattaaca aggttgcctc aaattatttg gcaggggtg gggagaggat gcccaggaac   50940
cctggctggc tggagagtgg ggagaaaagg gggcacagtg ggaagctgca ggcaaacacc   51000
```

```
tgccattgta gcattgcaga aggcccaaa ggacccagcc aatgtgagac aggttggttt    51060
aaaagcctcc catgggaaga aacccagaat gatgacaagc agagccaagt tcacgtccct    51120
gtgggtgaga gtgtgggtct gggaatgtga agcctggagc aggagtcagg ggcaggggct    51180
ctaggagagc tgctccatgc ccagaattgt gcagggaatg gcataagcag tggcccagtc    51240
aacttgctta tcccaggccc cctttttccca aatttatgat ttgaaaatga attattttaa    51300
aatgtctctg gaatcttgag tacagtctaa caaggcattt gaaatgtaaa gatttatgta    51360
tttaggaaag catgaggtaa attaccttca ttgaaatata tacatagaga gagtaccaca    51420
gggagtagga ttgtctcaaa caattccaca tgtctgcttc tcagggacct gtacccacca    51480
ccctgtcctt ccacaaagaa tgtaactaac caaaaaccct agttctgtag caatgaccgc    51540
atttgagaac gaccccacac cccgcactta gttcaccatc atttctcttg gcactgcaag    51600
aaggaggtca gaatgcagtt atgttgcggg gaggtcactg ccacattgca gatcttttgc    51660
tcataatgaa gcttggcaag ttaggctggg agacggcagg gctgtctcat cggtgttggt    51720
ttagtcgcta tgggtggggc cggctgggag ggcaaagggc acagccatcc cccatgcaat    51780
tctgtaatgg acagtaggat atggggggaag ggtgtctcac cagaggagca aggcagagcc    51840
cagatcacag ctgtcatgcc tgagaacagt ctgcgtttaa caaggagcag gcttgtgggg    51900
ccagaaggtc agatctggac tctgattttt aggaaaaagc aaggatggga gagtgagtgg    51960
ggacaagaac aaaggaggag gctgagagga gagtttctct gtagtgggcc acaggagcat    52020
gccaaagggt gagaggatgg agcacttacc agactgctta tctgaaatga ggaaactccc    52080
ttagataaag caggaacgcg gtggtgaaac ctgaggtgca agactccagg tttcaggaac    52140
cccccaaaggg tgtgggatgg tggagaagct gtgactcaag tagcagctgt ggaacactag    52200
tggccaaccc aggggtggac tatgggggt gggcggtgag ttgctttgga cagtgggcag    52260
agcggtggca gcttgaacaa gaattcctgt ctccagattg ggctgggagt atggcaggat    52320
tgagcacaca ggtaactcag ctgtcaggac ctgatgaggg ccagggatgg tagggggctgg    52380
ggacaggagg caaagggtaa gtggttttcat tcattcaaaa atcactgcac aactgctgag    52440
cgctaccaac accagcaggc cagggatagg aagatgagta agacatggtc cttactcttg    52500
agaggtttgt gattgctgta ggagatctag actggggaaa atagagactc cagtgcctta    52560
agaaatttag tcaaactcat ggtgctttga agtattaga caaaagcagc tctctattct    52620
catattttac tccagtaata ctcttttagct tatgcatatc agatttattt acccattgat    52680
tttttccactg aggcattgag cttttgaaca ttccaccttc aactcagctg taagatgcac    52740
atagacttta gttgccaata aaattggctg gcaacctggg actgcttcag gtcagacacc    52800
aaggaggtgg tacttctgtt ccattttata gtgttagccc cagaccattg aagaaaacca    52860
ggactcagtt gaataattac tttgggggtc ttaactgaac aactggttgg agggcatgag    52920
ggaaggtgag ggcatttgag ggtaggatgg agacctggcc agggcagagg gaggggaaa    52980
ggtgtttggg cccaggagac aaagcctgca tgggagaggc tgccttctgc acagcagcga    53040
taccaatgtc tgagctgtgg ctgcccagga gtgctgacga ggcccacaca gcttcagaag    53100
tggcacttgt agcatgtgag acagcctggt gtgaagaagc cccaaattca agtgggctct    53160
gtttccgggc caattccaag cagacctgcc tgatatgcca gagaacacag gtatcaaggt    53220
tcgcattgcg ttagtaatgc ctgtgggaga caatagggtg aaccccgcag caatgtttag    53280
ctttcttctc ccttgactga ggagcctcgg ttgtttttc ttaaaggata tattttccac    53340
```

```
tgttttgact gggcttgtcc aggggtgctg ggaagaacaa gataggcaag aaggaagga    53400 ctaataaatt ttcttgctca ttcctaaagt cctattttta gattagattt ttagatcttg   53460
agctcatcac tatgtgcact agctgtcatt ggataagtca tgtccaggtg ggacacctgg   53520
tggcggctcc actcttgcca accctgccct ctattgatgc cacccacctc acagatgaat   53580
gtgctgggta ggttcagcca aaagctcttt cttttagaat cagcctcagc aagactagag   53640
tgacctcctg tcccctctag aggccatcta gaggtatatt ctgaatctgc tgtggctcac   53700
ttctctcaag atctcctggg tcaggggtca acttctcacc tgtacttcag ccaatgtatc   53760
ctcctatgct tgggtccctg ccttttattt ctttatgggt gattttcatc tgattgcctt   53820
gctgcacagg tacaaagcaa cagatctgca gaatgaaaac agctggggaa ccctgagtgg   53880
ggtgagagta gaatggagga ggtggtggta tcttcttaag ggggtactca tggtggaagg   53940
gtcttcgttt ttcttgggga ggattcccctt tgtgctgtcc aaggagactt ccttacacca   54000
tgggctttgg acatgcttgg tagtcagggc acacttggct ttgaaatgca acgagctaag   54060
tggaataagc actttgtacc atactggctg atggtaccat actgtgggtc agataggaat   54120
caaccttcca ggggaaaaga acaaacaaac gaaacagaca aacaagtgcc tgaagacaga   54180
aatttaattg agtgcttcct ggcttttatt ttagccccccc tcatctaaag atgtgcatct   54240
gtcccagatt tgagctatga tgtgtggaga ggtagaagag agaatattta tatgcaaata   54300
agaggtgttg accagaactc tggggatttg ggtgaggaag gaagccaggt tttctgtggc   54360
aggggtaaaa agagagagca agggagagaa ggggcgatcc agcaggagag aggagtagag   54420
ttgttataga tgacttctcc tggagagttg gatcaggccc attgcgggtg agagggcaaa   54480
tctttcccaa gaacccaagt ggtagaatgg gtctggcctt cccttttaggt ggttattgga   54540 gaactggtgg gtatgcatgt ggagacgcag atgcctgaca aagctggtgc cgtctggatg   54600
gggggcaagt aaggtgttta ggagtgagac tgtggtgact ggtaccaaaa aaagaatgtt   54660
ggggtgatca gatccaacac caggccttgg tggtgacgaa gtctggcgga gtcaaaggaa   54720
tgagaaaaca cagtttgaga gagaaaacgg atcaagtggg ctaacgcaag tatggaggct   54780
gtgaaggccc tgagctctgg aagcccagac tatttattgg cgatcaaaca ggtggtgaga   54840
atgtgggggt cgaaagggca agtgcatgat ctacagctgt gaaagtttag catttccttt   54900
gaagcatatg gaatatattc tcctacttga gataatgggg agcatgtttt tccagtttaa   54960
gctagaagca aggagccagc aagtctagac ccattccaga ggccacgagg ggttttatgc   55020
gccgagccct ggacattatg tcagacatgc aaaccctgcc tcagcttttt tcccaacact   55080 cagcttttc ccaacatttt ccccttctct tttttgtaaa accgccacag ctatcattat   55140
tactagcata aaaggtggcc tctttttgtt tttaaattaa ttgagcaagg caattgcagg   55200
ctgtgcagcc tttgattgcc agttggtgat ccaacttcat tgttcttagc ccttattcaa   55260
aatggagtcg ctctggtttg aatgcttccc acgtatctcc cctttccctt ttacaagagg   55320
acccttaatc ctaggggttt caggatgaag gtccatgctg aatgggggca atgatactcc   55380
tgcctaacta ttagggtctc ttgtattcag ggtagagagg cactcagtca gaaagcattg   55440
gtccgttaag catctgtagg taaaaccctg gcgctccagc agtttctcag cttcctgtgc   55500
ggttttcttg atctgtcccc atgttatggg gattgcaccc acgggttcg ttcatctcca   55560 tgaggtagaa ctttccactg ataatgagaa acaggcccct tctaatagaa ggcacagaga   55620
aagcaaatgg aggcttctca aaccttcaat ttgcactgta caggtgggtc cgctagatgc   55680
tgtggctcat gatagatctt cagatgtttg gtgggcaccc acacaggcac ctgattgtca   55740
```

```
cctggagaga cacaagcaaa tcttcttccc catataatta tctttccttt ttcccagctc   55800
tttgtatgtg cattcctcca ccatgtatct tgtccagcct ttttattttc cttttgtcct   55860
gttaggtgtt gtttcactgc agttatgggt tgatctttt gtaaatttaa aaattttaat   55920
gttaataaag ctaaatgcaa ttacatatgc agtgtcttat attcctggtc cttctccaag   55980
tcgatatccc atatttctca tcatttgtct actattatta ctatattgat ccataggaat   56040
agatatttca gcatcccatt gttgcaataa gtctcttccc cataaattga caggaatagg   56100
tgtaataata gactgaattg tcccttcctg gccatccagt ccttgacatg gtaaaatcaa   56160
ggaactgtga aaaacctctg aggcggttcc tacgccaatg atacccatgg aagcctttg   56220 tttgggccag tgtcgggtc attgatttag agcaataata gagacatcag ctccagtatc   56280
tactagtcct tcaaaatcct ttccctaaat agtcactatg caaataggtc ttttgtcaga   56340
cacttgatta acccaatata cagcctttcc tgcaggatta gtactaccaa agtcgcctgt   56400
tctttcactg tgctgcttcc tagttttgtt tagggtagca gcagcaactg agcaattctt   56460
tctcctgggg aggcagacca cagagttgag gaactaataa ctaattgaat ttctctggta   56520
taatcagagt caattattcc tgtatgcaca gcaacacctt tcaaatttag actagacctt   56580
ccaagtaata gaccaactgt tcctgagggt aagcgtcctc taactcccgt agggaccttt   56640
tttggcagct ccccaggaaa cagggagatg gtaattgtgc tgcaaaggtc tatggcaaca   56700
ctgcctgctg tggcagggga caattgttgt acgcttgtga gggcactggc tgtgccgggt   56760
atgcctcggt ttgttgaggg gcctgaggtg ggccactctt cccatttcct gaaagaggtt   56820
gtccatcttt agaacgacac tgatttgccc agtgattgcc ttttttacaa tgggggcata   56880
caccagggct tttctgttga ttgacggtag tagttcttgc cttttgattt ccttttctac   56940
attccttttt tgtgtccaaa ttgccgacaa ttggaacaag agcctgagaa atggggcata   57000
ttctttccta ctcttaatcc agccatagcc tgagctgaaa gagtagcctt atgtaagtta   57060
cctccaatgc catcgcaagc cttaacgtat tcagagtaat ggcttgcttg aattccttcc   57120
ctccttgctg gattatagta atgggaaatt gccatacttc aaggtctccc tcggctctag   57180 cttttgaat agaattttgt atagcaccac caattgctcc aggttttaat gttgcaacta   57240
caggagtggt gttttcagc taattcattt tctcgcccat taatgggaga gagaagaggt   57300
ggccattcac ttaattcagc aggtggagcc aacgggctag taaaacatac ttctttcagt   57360
ttccctttct ttaatttcct ccggttctg ttcctcacat tcagaatctg aaattagttc   57420
tttacactcg tcctcctctt cctcatctga atctacctca tcatctgttt gaaatggctc   57480
aaaagctgcc tttattatca ctcacattga ccaaaaaaaa ctggaatttt tgctccatct   57540
ttatacgcct ttttaaaatc tctgccaatt atctcccatt catccaactc catagtccct   57600
tgttccagga accatgggca aaactccttt accgtactaa agagtgataa caaattctga   57660
gtactaactt tcacccccac tcttcataat aaatgcctta agaaacttaa ataagcagaa   57720
tatttgcttt cactttgtcc tgttgttacc ctggttcttc cgagccctca gctttcccac   57780
caagcttcct ttagtcatcc ttgggtgtcc tttgacaatg catcccctgc tttcacatgc   57840
tctagtgttc cttcaccagg gcctttgtcg ccccacgttg ggcagccagg aatgttgggg   57900
tgatcagatc caacaccagg ccttggggca acgaagtctg gcagagtcaa aggaaagaga   57960
aaagacagtt tgagagagaa agtgggtcca ggtggccaac gcaagtatgg aggctgtgaa   58020
ggccctgagc tctggaagcc cagactattt attggtggtc aaacaaagaa acaggtggtg   58080
```

```
agaatgtgtg ggtcaaaagg gcaagcacat gatctacagc tgtgatagtt tagcatttcc   58140
tttgaagcat atggaacata ttctgctact tgagataata gggagcatgt tcttccagtt   58200
taagctagaa gcaaggagcc agcaagtcta gactcattcc agaggccacg agggqtttta   58260 tgcactgagc cctggacatt atgtcagaca tgcaagccct gcctcagctt ttttcccaa    58320 cactcagctt tttcccaaca agaagatgaa gtgttgtatc ttaggggctc catctacaag   58380
gatgaagtaa gaccggagaa agggggtgaaa tcagcaaggg taactatcat catgtgtctg  58440
gaggtctgct gctcctttac tccagcctct ctgtctcagt tcttctcatt ccagaggtcc   58500
ctgtggactg tgacaaggat ttttcagaat tcagagaggg aaccaacaag gggcaagctt   58560
ggtttatttc tctttatttg gtttattctc attattattt ttcttgcctt ttctacctct   58620
aattccttct tagcccttcc ctttctgctt ccatttctat cccaaaatat gagccacaaa   58680
gagaaatttg gggaattaga aggaagagac ttaagggaaa atgtatatgt cattggtgta   58740
tgtgtcagtt ttcagtcata acttgggttg ggggaagtca gtgtacccctt tactcttgct  58800 gaggaaattt cttctgagcc ttagccacat cccacttgcc cagggcatca ttcttttctt   58860
ttttttttct ggcatatatc tctacttcag attcaaactt ggccattacc tctggccagc   58920
caagcagctg tcccctgaga gggggggccaa ctctcctgcc cctcactgcc tgcctcccaa   58980
ggctgcccta gggctcagct gaagaaggcg ttgtgctttt gctgccccct gttgctcaag   59040
tcctgctttt ccataggagc tgccgggctg tatgtctgga tgtgacttct ccaggcaggt   59100
cctcctctcc tgcccgcagt gctctggctc ctcagggtag gtttctgtcc aggacatggc   59160
ccctgaaagg gcttggaaaa agcccccttg cgtagtactg gctgagcttc tacttgctgc   59220
cccaggaacc tccagagagt gacccaaaca tctggtatag cctctaatct tacctagtca   59280
gtcatgtttc tcttcaggcc tcttctaaga acagtttcct ggagaaacag aatagagttg   59340
tggtcactac actggagtct tcctggggta ggagtgggtc ctttctaaag tagaaggggc   59400
tgtgtagcaa gggggctgtg tgagcatttc tagaaatgtt gtctgctgaa ttttccactg   59460
ggaaagagca agtcctggcg gagttagcag cagctgggca gtaggcaata gatagcatca   59520
gggtctctgg atgctcagtg ggggtggcat cagggaacac tggtttcccc agtaacgggc   59580
gcctgggcct gcagtggcag tcaattccac agaggatgcc ccggagcttg gcatctctca   59640
ctgtgctgtc ttcccattcc tgagactgga atatggagct catgtgggct gggcagcttc   59700
ccagcagtgg ttggtcagga tgtgagagtg ctgtggtcca ggtacctgtg gacaagtgac   59760
ctgccacact gcaagaccca aaatgacact ggactacatt cgttgacaca gttacagctg   59820
taccaaaatt ttttttccaa ggttcaagtt ggaacatttg taagccaagc cctcatgggt   59880
ccaagcctat tttcttcacc acaccacact gagtgagggc agtggctcat tacagaccac   59940
agtatctccc cacctccacc catgtagatg agaacctgga gcctgccaag gactagtgtc   60000
cagaatggtc cccaagtcac ctcctgatag gtaggaagtg gccaaaatga ggtgtaggac   60060
ctcatgtcct agaggtcaaa gctaagagtc caaggcaaat ggccacaagg cagaaagagc   60120
caaaccagag cccccctaaa atggggagac caggatggat agataagaag aagggcaggc   60180
tttggctggg cgtggtggct cacacctgta atcccagccc tttgggaggc caaggggggt   60240
ggatcacgag gtcaggagat caagaccatc ctggctaaga ctgtgaaacc ccgtctctac   60300
taaaaaatac aaaaaaaatt agccgggcat ggtggcgggc gcctgtagtc ccagctactc   60360
tggaggcgga ggcagaggtt gcagtgagcc gagatcgtgc cactgcactc cagcctgggc   60420
gacagagcga gactccgtct caaaaaaaaa aaaaaaaaa aaagaagggc aggcttttag   60480
```

```
ttttagatct aagtccaaag tacaaatgtg agcagagcgg gctcttatgg agggagccag    60540
tcacatgggg tctaggatgg agtaacagtt caaccccctt agacccatcc cttctctctc    60600
tgtttctcct ttgacttcga agttaacaaa acatttaatt cgcattctaa atgcaaaagc    60660
cccatgcaaa cacttggaat tgggaaaaga ggagaataca acagtttctg ccctcaagga    60720
acataaagtg agttcacagc ctctttctct ttcagcctcc tcttttctct ctcattcctt    60780
cacctagcag gtgctaggca gcaactgtat acccagacat tattatttct cttgccttttt   60840 ccacctttaa ttccctatta gcccttctg cttccattc tatcccaaaa tataagccac      60900
aaagagaaat ttggggaatt agaaggaaga gactttaagg gaaatgtata tgtcatcggt    60960
gcatgtgtca gttttcactc atagcttggt ttgggggaag tcagtgtttt tttcctcttg    61020
ctgaggaaat ttcttctgag ccttagccac atcccacttg cccaggtctt cattcttttc    61080 ttttttttctg gcatatatct ctacttcaaa ttcaagttgg ttgtgggtct tccacctact   61140
ttgtagatgg agatgtgggg gttgatgcca atctgacagt gaccagcact acagagtgga    61200
atgggaacct tctcatcttc ctgctgggct cccatcccag cccccaggcc tcaccttgcc    61260
tctcctgcgc agtggggttc attccaggat gccctcccaa taaagctgag gcatgaagg     61320 cttcttgaat ggcaagcact ttggaggcta ggaagggaac aaatctttaa atcactaggt    61380 actctttttta cttctcatct tgcttttaat ccaagtctttt ggtctcttac ttgcttgctt  61440
tcttctcacc caggacagag tcacagagac cttgaagaat ggaggaggta gaaaaaggag    61500 aaaatgcagga aggaggtgtg ttatggagtt atccagtgga ggctcgcatc cagctttatt   61560
ttgcctccaa agatcttgca tcctacctgt taagaagctt ggaatgccac tattccatta   61620
aatcttaaag gaacttgagt ctttcattta aaaatgtgtt cctaaaatgt aaatgtccct   61680
atgtgggaca gtatttagcc gacagtaaat ttgagaggag ggtctcaagg ggcagtgtca   61740
ccaggaaaag agagaaaggc tcctctcccc aagtcaaacc ttaccttact taaccgattg    61800
tatttcctcc ctcagaggat gccatatctc agtacaggag agaaaataga aggtagagag    61860
acttttaccc aagcaccccc tgaacccccag gtgtacacaa ctgaacctga tgcagtgaca   61920
atcacgttca cacataaaac atctggctaa aggctaagat cacttcggat ttccgacata    61980
cattttccta agcagtgcat ttttctttaa ttttccttag aaaaagactg taaagtagcc    62040
ccacaattcc cacatcttca tactccaccc tgcattcaag ttttcctggg acaggtatct    62100
atgtgtgtgc atgaatctat ttttacggca tatgtctagg acccctacg aggagccaaa    62160 gtttcagaga gcccagcaac tatgtaactc catggaaggg aggcatgata ttactctctg    62220
ttcacaggag cgtacgcaca gatctttct cctcctcatg gtcagttttc tatttgtgat     62280
tagtaattag cttctcttgg tacgctacga tctattacaa aagccaaaca ttcaggggc     62340 gagctgaaat gacaaaattt ggctataatt tatgttggcc cctgacatat atatttttt     62400 aatggtttgg tctctaagca actgatctct tagcaacaag aagcacctttt ataaaagatg   62460 gcacacgaag agtgattgcc agaaaagcca cctggttctt aaacagccgc gcatcattag    62520
caaaactcac catcttcaag agtccaaaaa ctagaagtga ccagcagacc caggtaacct    62580
tgatatttgc acatttttcct ggggaaaaaa aaaaaaaaaa aaaaaactca tgcaactatt   62640
gaagagaaca aaattctttg aaatatgttc atttttgagg tcttattagt tggtcttgac    62700
taacttttaa taatagtatg tattcttta ataactgct tttgattttt tttaaaaaaa      62760
cgtgatattt gtgatcagaa aacagttcac ttgaaatatt tcattggcat gagaatggaa    62820
```

```
ggaggggaac aatctatctg tttcagaatt tatttctgta ggttttcatt tgatgggaaa   62880
aaaatccaca tcatggcaaa aataggagta tacagaatgt cacccaagtg gtgtgcacta   62940
ttagggaaat acgcgtattt attttctaat ttattttcat actgcttaaa tatttaaaga   63000
gtagcaaaat aattttactt tcaaacttta gcttttaat ccaatgtcaa ttccagtaga    63060
aagtgatagt cttttgttgc aagtgttcaa ggactggttt tttcatttgc tttcattgcc   63120
gtaagaaaag attcgttcca aaactaaaaa taggaaaaat tacaggcatc tgtaccttgt   63180
ttgctttttt caggtaccca gggattgaag acttaaatgt cttttccagaa aattggaatt   63240
agaaatgaga attgttactt catctgtact ccttcaataa agattgcgta attataaacc   63300
cacttggggc actcaaaggg cataaaaaag gagatatttt atggggatga aataaaaatc   63360
ctcctaattg agcttggaaa cagtgttaca cagagatact gcagatctaa gaaaacagac   63420
tagaaaattg cagtttcaat aaagacaagt tgaaatagtg acacatagtt ttatttttta   63480
taagaactgc ttgtaccact ttctctcttt ttcttttctt attttctttt tctttctttc   63540
tctttctctc tctctctttt tttttgtgcc ctttcagagg tgcaaatacc tctttaaatt   63600
gaactgtatg ctgacattct cttggaacca gaaaatggga tgctttgtct gaatacaaag   63660
cttggtaatg ggtcagggca ttcaaaacca acacaatccc acaaattttg ggacttacag   63720
ttgctcctct aagcaaaggc acctcaatag cacattatga ttcgtttga ttttaaaagc     63780
tgcttatgac ttgtatttct gttactgcta ccgacttcag gcaggaagaa ttcattttg     63840
tggagacttt gcttgaagtt agaaagttgg gtgttttaga ttgaattgca gaaatttttt   63900
aaagcaatgc actatgaaat cacagagaag catataggtt tgtccttcag aactaaaatt   63960
gtatgtactt gcagtgtggt aattactgta gaaatggttt gtggctttaa agttaaggaa   64020
cttgcataaa taattacaag atgtaacttg tgtttgctat gtctggatat gttttcagtt   64080
ttaactgtac tgtagtttcc taaaatatga agggtagtta acatgaaagc aaaggtatgg   64140
taacatttat attgcaagtg gcagctaagt ttttgcagtg gttctttggg actttgcaaa   64200
tcgagtcact gtgtctttcg agttcatgtg ttctgagttt tatctataca tgaggaaaca   64260
aggggggtcag tgggcctgta gagcttgtca ttttggctgg cataatgagc catctgacga   64320
agatggacaa actcctgcaa gatgtgagat agactatgaa atactctgat tagactggct   64380
gctatagact aagccaaatc attctgctgt gttaggatta gttatttctg agacacgcac   64440
ttacattcac acacatgcct gcatataaat ggtctcaata taaatctgga aatcaaaaca   64500
agcctctcta tcagtgagag cttcctagga aaaggatag ttttaatttt gtgaaggaca    64560
gtttccatca taatcttcat ttagcgtcta aaagtcctag acaaacttga cggcccttt    64620
ccttcaaacc tcaggctgga atctggtgtg gggctggccg ggggacaca gcagctagca    64680
ggcacactgt caagcagtcc tgctgtaggg gcgatctatg ttacaaatga atccatttac   64740
tttggacact ttactacctg aacggaaaca atcaggcagg aacttgttca ataactacat   64800
ggttggcctt tcagcagaat ttttgaactc ttataaataa accatacttg ggataattta   64860
gtctttctct ggtgagaagg aaacaagaaa aaaaatgtg agcagtcact cttgagttag    64920
gtgcttgacg aggactgggc aatttacaac gtgcagtttt gcttaacctt tacagcaact   64980
gtccagaagt ctccgtgtcc ccatttcaca catgcctaag ccagatccag cagttttgcca   65040
gatgttacct aaacagtaaa tggcaaagtt gggatttcaa cccaggacag tctgactccc   65100
aagcctgtgc attttccttg tgtcagaatg gcacaagtag caatttaaaa ctgacactaa   65160
ataatccctc tggtcttagt aaagcaaaag ctctgagtag ggctggaggt gaagatttag   65220
```

```
gcatctttc acagaagaga ctccttaacc actggttctg ttgggtggag tgactcaggt   65280
cctgtgtttt caaggctgcc attggctatg agccagaggt gggtgctcat ttaggctgtg   65340
gccgtggtgg ccacaggcca tggcaccatt tcttgccatg atgcacatcc caagtgaagt   65400
ggggtaggac tctttgaggt tcccttctg tgtgaacagt tctgagaaca gggcttcctg    65460
gatgtcccct cccaccctga cacgggccac aacagttagg gactgcacaa gcagagtgga   65520
agccaaacca caagcggagc ggaagccaaa tccagaatgg gccaagtgac atgtcaccaa   65580
gttaaggtga aggagggaga gcccaggtgt ggctggggca ggcctgagag tgggggtgag   65640
atgacaatag agaaagcaga gctttctccc cagcgttgca ggatttcggt atgctgtccc   65700
ctctggctta tggtgttgcc ccttctttct tcttcaaata cccctgacaa agggatcaat   65760
cttagagagt ttattaaaaa aaaatcttct tctaaatagt atttgggcag agatgatgt    65820 atacaggagc gagggccagg gaggctgtag ccagtcctag aataaacact ctgtgcatct   65880
ctatttcttg tgatccttcc atcactcaga cacctggagc atcgtgccta aagccagaca   65940
gttcatgtag gtgggattta aactcaagtc ttttggctag aaacactgtg gctctttcat   66000
acaactggga aatatgatgg tatttgtagg cagatacaga ttctgaggtg gtctgccttg   66060
catttggcat gaccatcaag tgaatacgaa gagagctctt cacctgttac acttcagttc   66120
atcctcagag gagggaataa cgctcccaag aggcataaga ggcaacctcc catttctttt   66180
tccattccct ccccactcag ggatatctat gggtaattcc tctagtcatg agtcagaggg   66240
ctgatgggca gctcaggaag tctgaaaaga atgcccagta ataggttcaa ttttgtaca    66300 aaaatcggta ataatccttg tgcaagtaat cttcatgcct ctacttccct agggtccttg   66360
tctccaaaca gacatgttca ccctgcttga gttcttgcct ggtgtgtggt actattgatg   66420
tatatggctg gcacattgac accacacacc tgccgtggac agcacgtgcc cagtcccact   66480
ctctacctgg tgcaaaggaa gtctccttt atctggcaat tctgggtaga agaagagggc   66540
cacttatgtc ttttgtgtgt gtgtgtgtgt gtgtgtgaca aaatttcact ctgtggccca   66600
ggctggagtg caatggcatg atcttggctt actgcaacct ccgtctctcg ggttcaagca   66660
attctccagc ctcagcctcc caagtagcag ggattacagg cgcctgccac catgcccggc   66720
taattttttg tattttaat agagatgggg ttttgctatg ttggccaggc tattctcaaa    66780
ttcctgacct caggtgatcc acccaccttg gcctcccaaa gtgctgggat tacaggcatg   66840
agccattgca gccggctgtc attttttaaa aagcatagca ttcttactct gggaactgac   66900
ttagaggttg cttagtttgg acttctcgga ggtgagggc ctgagttgaa gtgattttcc    66960
caagggctgt gcagctaggc aaaggtggga tagagctcag ttctcttgac tcccattcca   67020
gtgctctttc ctctgtacca taatagttgc tattcctaag aagagggtga gagtagacta   67080
ttacccttat tttacagata gaaaaactaa aggcatagtt agattaggga taactgccac   67140
tccaaaacta tgaaagttat taaatctatg agagtgattt aactaactgc ttccctggat   67200
taaaaatttt tattttgcct gctgaatata aacatgtaag gttcagtgtt aaaatgaaca   67260
catcagagtg tccaaacact attctgccta ttgatcatat agtttctctc ctgtataaaa   67320
agtgaggaag ggggtcgggt gtggtggctc atgcttgtaa tcccagcatt tgggaggcc    67380 gaggtgggtg gatcaggagg tccagagttc gagaccagcc tggccaacat ggtgaaaccc   67440
tgtctctaca aaaattagct gggtgtggta acgtgcacct gtagtcccag ctactcagga   67500
ggctgaggca ggagaactgc ttgaaaccag aagggcggag gttgcagtga gccgagatca   67560
```

```
tgccactgca ctctagcctg ggcgaaagag tgaaactcca tctcaaaaaa aaaagtgagg   67620
aaagaaatgg aaaaatggtc cctcccatta tgaagcctgt tgtcctaacc gagtatgcat   67680
ttatggaatc cctgaaaaag acgaatcagt gtatatctgc atatctgtct atctcaactg   67740
tcacagccaa actccacacc aaaaatcata accaggggca ttgtaagcag tggtccttgt   67800
ggattttcct cctgctgggc cagttttttc ccctataata attacaaact tcatacatga   67860
gtttggtact actctagagg aggctctagc aaaactaccc tgctgtagag gagcaattat   67920
aggaactctg caattctgat gacagttcta aaaacataat gtgaaggtac gaactcatta   67980
atatacagtt ctctgtgcca ggttctgtgc taagaccttc atgtagcttt tcttatttag   68040
tgttcactac ctatgatgtc gatattctga gcaccatttt ccagatgagg aagctcaaac   68100
tcttctgcca atgaggccaa caccatagag tggtgtttgt ttataaaatg tatatttat    68160 tgcactcaaa cgatgtacct ggcactggtc tagatgctgg tgctataaag ttaaataaga   68220
catgatcctt gtcttgaaga agctcatagc ctaatgaagc tcatttccag ttacatttga   68280
gaacttctgc tctttggggc tagtctaata gcacacaaga gatttactca ggaacacgta   68340
tcttgaaggt tgggaagggt tggagaagaa atacgaggat aggaaaagat atggctgagg   68400
ttaaaactga agggaaaaat cgaagatgga cagaaagttg gcactcacgg tgtgtagaat   68460
acaatgggca caagcatgga tgagagagtg ctggggttgtg caaaagtgtc agccagcctg   68520
gtgtttctct cttggatgaa ggagttccac actgaggcac aatataaaca atgaacttgg   68580
tgatatagga caatagtaga aaatcctaaa aaccaagcaa aggagtttgg atgtagtgaa   68640
cagataacga agaactggta caaaatctgc tgatgcaaac actgctggct ttttaatatc   68700
accagattgt gaacacctat tatgtaaaaa gtgccagagg aaaagatttt tgtcaaagta   68760
acattgaccc tgatgggggg ataatatgaa ctagaagatc agtctttgga aatccttgga   68820
ctaatcaatc aaagagtggc agtagccaca gaggatacag cctgacctca gactaattca   68880
gagaaaacaa tgggcttgac tcagtgagta gatatgggag aagagaagaa ggaaagaaaa   68940
ccaaaaggat ggtgggatcc ctagaactaa agagaagtct aaggcttagc tacctggtta   69000
ggtagaactg tggtggagct agtttgtcaa caaggtttag atcttgtaaa ttgtccaccc   69060
aagtgagagt attccttgga gatgttaaat atgtcaccca aactataaat caagacacgt   69120
tgggtctcag aaaagatgta ctcttctgag agtacaggaa gacagggggaa cgatctggaa   69180 aacatcattt ggatgctaaa ctattagaaa tttcaaggtg ttataatttt ttatgggtac   69240
attagggtta actgggtagt cagaacttta ggtgactcgc aggcctggtt agaggggtat   69300
tgctcccaca ggtgcttgaa agagcatctc taagaatgag agagggacag aacagaagat   69360
ctggagacca cagactgtat gacctgggtg attaagaaga gggcgataaa aaagaatcag   69420
gacagagtat gaataagaag tgaacagaga tgtgagaaga gaaccagaaa caaactgagc   69480
cacgtggttc caaggagacg ttctctgcaa aggcagcaga gaagtaaaaa aaaaaaatgc   69540
ttagacttgc acatagttca tcagacaggg tgagagggag gccactgata ccctcagaaa   69600
gcaatttggg aggaacagga acctaggaaa ccagactggg tggcagttgt tgtgggggtg   69660
gaatcccaga gcctagtcag gcctcaagac ccacagggcc acgtgctgaa tgaacacaag   69720
acagtcggtc taaagacttg ggcctcagca gaaacccatt ttggaatctg tctgcctgtg   69780
tagcctgggg atagtcagct tgcggtggga ggaaagagca tgaactctag agtcagacgg   69840
atggattttg gtcttcctc agaaagaaac caactgttga gaccctgtca aagagattta   69900
atctctactt cttcatcttt aaaatggagc tacttctact tatctcacac agtggtttcc   69960
```

```
tttttttaatt ttaaagactc aaatgagata agatgcctat aaaatatggg ggaggtgttc    70020
agtaaatacc aatttcccta gaacagtggc tggttatact gtgttacttg gagtatgaga    70080
tttcttcagc aacttctaga agctgttttt agggtgaagg ggttccaggt agggataggg    70140
atactgattg gaggagctcc agctacccac atcccagttt taccagagca ccgggatccc    70200
ccaaaagctt ttgcttaagg cggtagggga ggaagcagag accaaactac tgggactagt    70260
aatgaattca gcaaggtttc agttcaggat acaaggttag catacaaaat ccaattgtat    70320
tcttatatac tctcagcagt caattggaac ataaaaaatt taaaacaatt tcaacacagt    70380
agtaccaaaa aaaaaaccaa agaatactta ggaataaatc taaagaaaga tgtctaagac    70440
ctctacacca gaaattacaa aacattactg agagaaattg taaaggacct aaatatatgg    70500
tgagatatat cacgttcgtg gataattggc tgtattgatc tatagagcca gtaaacttcc    70560
atttaaaatt tcagcagact ttttgggggta gaatttcagt gtgtgtttgt taggaacctt    70620
taagaagcag ttggcaagac tgcattaaac atacaagagg tttacagggg caaatgactg    70680
ggaaagataa aaagggaggg agcgggagta ggccaaaaag cttttcagtcc ccagtgtagt    70740 ctggaatctg tgaaagaaga gagggaaggg cgagttgtgt ggaaagggct tcagacaaca    70800
gtatagctct gagacagttt cagtcagcag tagggaaccc ccaagcaaag attgcctgtt    70860
ggaagagtcc tgccttggct ggaatgggct accactagta cccttagcat gcttgtcatt    70920
gtttaggagc tacccagaga aatatggcct ttctgtgaac atggtggtga atccatagg    70980 tggaactgtc aactatgctc caaatagtag tagtagtggg agttgttgtt gttttaagga    71040
gatttgagca gtccacctcc atggcaaccc cataaagtaa tttaaaaaaaa aaagaaccaa    71100 gttggagagc tcatcctcca atttactaat cttgcttttta tatttcaaga cctactatag    71160
ctatagtaat caaaatagtt ttgtgttggc aaaaaataaa catatagatt aatggaacag    71220
aacagaaaat ccagaaatag acccatgcat atattgccaa ttttttaataa aagtactaag    71280 acaattcaat ttgaggggggg aaaagggcct tttcaaaaaa acggtgctgg atatatccat    71340
aagaaagaaa aaataataac cctattaacc cttacctcat accatataca aaatttaact    71400
caaaatggat catagaccta catataaaac ctaaaactat tacacttaca gaagaaaaga    71460
ggaggtgacc ttggagtaga caaaggtctc tcagaacaca aaaaaagtag gagccataaa    71520
gacacttgac aaacttgatc aaaaatttaa aacttaatcc tcaatagaca caaagaaaat    71580
aaagcagagc acagactaag ataaagtatt caaaacaaca cgtatcagac aactcgaatc    71640
cagaatatat atatattaaa aaagtcaata agacaacccc atttttttaa atgggaaaaa    71700
agatttggcc agatgcttca taaaagatat atgaatggcc agtaagttca tttgaaaatg    71760
ctcaaaatta ttaataatca ggaaaatgca aattaagatc gcaatcagat acctctagaa    71820
tggctaaaat tcaaagactg agaatgtgaa gcaactgtaa ctctcatata ctgctgatgg    71880
gaatgcagtg gaacctcgga agataaatttg gcagtttctt aaaaagttaa atatacacct    71940
gctatacagc cactgttaga ttttttactca agagaagtga aatatatgtc cacacaaaga    72000
cttgtgcact gacatccatc atagccttgc ttgaaacagc caaaaaaaaa gggggggggg    72060
gaaggaaacg atggaaatgc tccttaagaa gtgaatgggt aaactgtggc atagctatgc    72120
aattgagtac tgctcagcaa tgttaaggaa caaactattg atatgaacaa taagaatgaa    72180
actcaaaatc aatatgctaa gtaaaagaag ccagatgaaa aagagtacag actgtttgat    72240
tatgacaata gaattccaga aagcacgaac tgatcaataa tgacagggag caaatcagtg    72300
```

```
gttatcaggg gatgggtgtg gaggaaggat gggtgacaag tgggtgatgg aaattaaatg   72360
ccaccttgat tttgtaatgg tttcacaagt gcatgtgtat atgttagagc tcataaaata   72420
gtacacttta aatatttgag gtttattgca tgttacttat gctttggcga agtcctttaa   72480
atgggatggg ggagggtggg tctgatggaa ggaaagcaac cccacctcta cagtaaaaag   72540
atttgacacg tgctctggag gaaacctagg gaaagtgat atggtacttt gctttcatat    72600
ttatctactt agtatctgct tcttccccag ggtggggagg ggcgaaggcg gagcaatgcc   72660
tagtgccaac cagttgtggc gttcaggctc cttccagtgc tctcgcctgc taagctgggg   72720
tgggcacagg gaagacccttt ccccggggca tggggagccg gcagggctgg tttcaatggc   72780
aatccgccat agggtcccgc gctcagaagg ggtcccgctt ggaatctaat gaatgctctg   72840
cagtcaccat atgaaattct taatcatttt tccttcaaat tcgtgtattg taagtgaagt   72900
gcaataacac agtggatgct tgagagcttg gactcttgtc tcaccccggt cgcgtctcct   72960
gcgtcttcct gggacaggtt ctgggccccc accggcgaa caccgctgcc ctccgccctg    73020
ggcagtggcc ggccacggac gtgggggcgg cgcagacctc ggcgtacagc caagggacct   73080
cgccgccacg ctgggtcgcc tgtgagggtc ggcctttggc ccgccagcgt ccctgtgctc   73140
aagccagcgc aacttaacta gcaaataaac cctgccgaga caggtggaca gaaagaccac   73200
gggagaaagg gaaaggcttt ttcctgcttt ttgaacgcgg ggccccgcgt ttttattttg   73260
cactgggccg cgcagattct gcgggcggca ccgaccgcag gcagccggct ggagaccgct   73320
cgccgcaccc cctgcctcgc ctagtgcccg agctgctcca gctgtgaatg ggacacaata   73380
cgaggagctg gttttgctcc tgaaagcgtc caacaaaaat ctggctcgat tcgccctgct   73440
tgggagtgac agagacccaa tctttgtcat gaaaagcagg aaacgggagg gcagctttgc   73500
tctccagagc agggaatgtg tctgggtaga agcagggaaa gttcctgccc acctcagatt   73560
ttcttctgga tgcagactgc cctgttcttt gacttcctct ccagtgtgga ataaggctga   73620
gggtctcaat ttggtgaaaa agtaaccat gacaacagtc acatcgtgga gagcatagta    73680
aaatgtgtaa agctcactgg caatgccttc ccttccagaa tgaaagctcc tctagtcaga   73740
caacgactca acggcaccaa aagagcggaa gggaagacca gaccagggaa ggcttttccgt  73800 gccctgccct ggggccttcc acagattagg ggacctccgt gatttgtcag ctctttgcct   73860
ccagctttct cacacggtcc ggggctgctt tcgagagctt atactaaaag ggcaagagca   73920
gagatgagct gtttttagga aacatgtgct acaaatgaag taaacccatg gaatttcaaa   73980
ataaaaataa acttggaaag ttccactaaa aggcttaggg cctgatagaa attgtgcagg   74040
aatcctcgac tccgaggttt gaagaaggac tggcagaagc ttgtccacct tcgtctagat   74100
gaggagggag gtgcttctct tcctgccaca ggggaggctt cccactcagt cctccttcca   74160
taggcaggac gaagcaatcg catctttagg gggcactggt tggaatgaga gacaggtggc   74220
ctgggctcca aactctgtca ctaattagct gtgggacctt gggtacatag tttaacctct   74280
taggatgctc cagtgcttgc cctgctctgt ccgtggagat gcaagtgcct tgcaaggaga   74340
ggaatgtgtc atgtacataa tgtgatttgt aggcacacat cctcatgtgt tcatttctct   74400
ttgctcttct cccagcctgg cagagtaggg ttgattggat ctggaagctt tttgtgaggt   74460
gagagcaaaa tctttcctca gttggctctg ggctgcacag ctggggagac tttgggagag   74520
aacagaagct tctttttacct ttgtgcaaag gaagccagcc atttccctca aggttggcgg  74580
aagctagatt tgctatgttt ctggagctat cactagattt atccagacca ggcatatcct   74640
ctagcctgta gcctgactgg ctcagtgggc atccagggat ccgaatgaag ctcaaacagc   74700
```

```
taaaaagggc aggcagataa cgaccagagt ataataaact gtgggggaac ggttggcact    74760
gaggagagcg gagagcccct gccctgtgga aagagggcag tccttgcttg gggacagctg    74820
gttgttgcca caaggtaatg tgattcctct agagccagat ctgattttt tcttaaaaga    74880 ggcctgtaat ctggactttta agatatccaa aattttaaat aaagacaacg aaagcaaatg    74940
taaaactcag tataagccaa aagaagacag gtgagcaggt cgagtgggtg aatgatagga    75000
aactgcagtc aggactggga aatctgagag caatgcactt ttgcctgggt tcccacagag    75060
agccctaaca ggagcaccct gcctccctca gcctgtcttc ctccctccgg gctgaggaga    75120
ctttctatct gtccccatcc cttttgttca agccaatatt gtggccaatc cttgcctaac    75180
ttttatggga tctggatttt gaaactcaaa atatttattt tttccatctg ctttctgctt    75240
cccttaggca atgaaaaatg ctcagctgac ttaatgtggg gagggagtaa agggcaaaca    75300
ggtcaacatc tcagagggaa gggaggacat ggaacgctgt ctgacctgcc cgcagccagg    75360
ggaggtggga tccagaatgg caggctatac tgggtggagg aatgccacac acatagcctt    75420
ggaggcccaa acggggcagt gtgcttggga agttaggccc agtttgatag agctgcatgg    75480
agcgcagggc aagtggcagg ggatgagact ggaaaagtgg atgaaatagg atttatgtaa    75540
cataagaaag tgtaattggc tcaaatgtct gattacttat gtgttatttt tgtaaagctg    75600
gtgacccaac cctacattgg ttttgtataa tttaacatct gtgcactttg aagtgacata    75660
cattgaagaa ccttcagagt gtcagaaacc atgacctgga aagcacatct atcctaatttt   75720 gggggtggtc ttgatctcta tgaagtatcc aaactgatac tgattggact catttgagga    75780
tatcaagtaa catcagactt cactgagagg tgtgccaccg ctgtaaccaa gggactgcta    75840
ctactttctg cctgcacccc accccagttc ctattccctg tttccccagc tgcatccaac    75900
tcttcttgtt ccccggtgat ccttccaact cttctctttc actatattgg ggctggcccc    75960
tgaagactcc atttttttcct tctgccctgc gttttcaata ataaattcta aatttcagt    76020 gctgggagct ggtgttagtg tcttccaggc aactcactgc tgtcccttga ccgtcgttac    76080
tctttccttc taaaagactg aaatctcctg taaggttcac ttcacactat ccaccaattc    76140
accctgtctc ccctactaac caaaggcttt ggtatctttc tcggggtctt accctccccc    76200
ccgactcctg ccatcattct aagtaactga atgtccttgt ggctgatcca accaatgccc    76260
tgactaccca gttccatgat gactgcaccg tcagtgatgt tatttgccct ttcacctcag    76320
cacactcaca tggacacagc ggtgaacctg tcatcatcag aaactgtgcc tcctctgaaa    76380
tctcattctc ttgccaccac cctccagctc ccttgctcaa gtcccttctc tacagcagtt    76440
ctccagcctc aatgagattt ccaagccaat ggtccctcca ctttgcctat gtccataaat    76500
ctcctcctat cttcattttc ttttgtatct agctcagagg ccatggttct tcctacagtg    76560
tcctaaaaat accactaaat cctttgttga cctctcagtt gttcccagat ttactcatgc    76620
ctgttgcctg aacagatcag aattactgga gaatgtgaca caactgggca ttttggcatg    76680
gctccaactt catgctctcc aaaactcagct gggacctcca cactgcctag caggtttact    76740
gtgcttttct agaagctccc tccatgttca caatcacaat ctcatttctt cctctcagag    76800
ttggaatgct tgcaacccct ttattcccag agcagcagcc tgggaggatt ggatgggtcc    76860
attggatttg ctcctgtcct ctcctttcat cactgcctcc agcaaagtac agtccctcca    76920
caggtgcctg gatctcatgc cttcctcct ggtcagggct cttgttctgt cagctatacc     76980
ctctcttttc caaatctttg acctcttcct cactactgga ttttcccctt cagcactcaa    77040
```

```
atatatgcaa gaatccaccc tcacaaacaa agccaagcaa gtgaaaactt ccctaactcc    77100
acacctctgt caagttatca cccattctgt ctattctcct ttaacagcca cgcttttga     77160
ccattatgca taggcactgc ctctacttta tctcctcctc tcctttccat tctggcttcc    77220
tgcttcacca cattgcagaa actgctcttg tcgtggtcac cagtttatcc aatgtcaatg    77280
ttctgcctgc atctgacttg accactcagc agcccttat  acagttaacc atatcttcct    77340
tcttgaaaca ctctctcttc cgcttcagtg ataaaatagg ggttttttgt ttgttttatt    77400
tacaccttat gacagttctt tctgaggatt ttttttttgt ctgttccttt tcctaccaaa    77460
ttctaaattc ttgagttctt tgggagttca tatcacaaca tattctgcct tgcaatttca    77520
gcttctctca agaccttaaa taccatctct acagtggcca aatttaggtc cctggtttaa    77580
tctttcttga aatcttaact tttccattac agaactgaaa ttaagtactt atttgggtga    77640
ttatctatat tttgcttgtc tcccctccta gactataggc tccaggagtg caagcattgt    77700
cttttttta  ttcaccactt ccataatccg ttgagtcagc ttcaatgtca attcctaccc    77760
aatgggttca tgctctgtct gccaaaggcc aaagcaagta tcatgaaatt ttctaagagc    77820
taggacatgt cactgcagcc ttttctccaa atttaagtgt gcaactatat tttcttatt    77880
gcagaacagg aagtcaagta gtttcttttg ccagaaatgg ggaaatcgta tatcaataac    77940
cctagcactg ggggagtgag gaggcctcaa gtctgtgagt ccaggcatga catggcaaac    78000
tctatagatt ttggaagact aactgtcagc agtaaggaag aaaaattggt aggaggagag    78060
aatagggca  gggttatttg ttgtgattct gtttcaagag agggctgatg aaagctcatg    78120
gatggccttg agaatagaga gtgctgagac cacctcagct ggggagaccc taacccagtg    78180
cgctagagga attaaagaca cacacacaga aatatagcat gtggagtggg aaatcagggg    78240
tctcacagcc ttcagagctg agagccctga acagagattt acccacatat ttattgacag    78300
caagccagtg ataagtattg tttctataga atatagattt actaaaagta ttccttacag    78360
aaacaaaggg atgggctctg gctagttatc tgcagcagga acatgtcctt aaggcacaga    78420
tcgctcatgc tattgtttgt ggcttaggaa cgcctttaag tggttttctg ccctgggtgg    78480
gccaggtgtt ccttgccctc atttcagtaa acccacaacc ttcagcatgg gcattatggc    78540
catgaccaac atgtcacaat gctgcagaga ttttgtttat ggccagtttt ggggccagtt    78600
tatgccaga  tttgggggcc tgttcccaac agagaggaaa ggggaaagga gggactttca    78660
gagatgaaat aacaattgat tgggggagag atggtgggca gtgagaagtg gcccagaacc    78720
tgaagactct actgcttcac ccatcggcct ctccaatggg ccctcacttg catgctattc    78780
ttactccctg ggaggacctg ccccacactt ctctccttgg aattctattc ctccaccatg    78840
acctctctga aactctcctt gactaccctg cgaaagtaac tctttctgtt ctctttaccc    78900
ccacagcact tgtcaagtgg tcagttttat ttccagttgt atgcaacacg agtgcttatg    78960
cagttagcta tatcaaggca ttgtgccatc tgtaatgaaa tggctaaaaa acccatacat    79020
ttgaagaaac acacttgctt tctttatttc cttgacttgc agttagtatt aactgaccaa    79080
aagcattatc ttcctctttt tgcttttta  tgaagttttg gtaggtcgtg ttaataatac    79140
ccattactca tttctctgat aagattatag aactgcaagg tcttggatga cattggcctg    79200
ctccttctgt tacgggtggg tctttgttct tagagctccc aagatggtgg ttggccactc    79260
ccaagatggt cgtgggccac tcccaagatg gtggcaagcc ttttgttgtc tgacctgggg    79320
ttcttggcct cacagattcc aaggaatgga accttgggcc atgcgtgag  tgttatagct    79380
ctattagaag ccgtgggtca tggaagagaa ccgtggaacc cagcaactag tgttcagctc    79440
```

```
gattaggctg aacctgagca cttagccatg caggaacaat ggcgagcctc tagcccgatc   79500
gggagtggcg atgggcacct cgctggatca gaaggtcagt ggacaccctg ctggatccgg   79560
agaggtggga gtcaatggtg ggtctgtgat ggtggcattc agcagtggtg gactgtgaat   79620
gaaagctcag ctcgagccag aacaaacacg gaccagaaga gtgtgcagtt gcaagattta   79680
atagagtgaa aacagggctc ccatacaagg agagaggacc caaacagggt tgcccacacc   79740
tggctcgaat gcctggggtt tatagcctga tcattgtccc tccctctgtg ctctcaggca   79800
atatatgatt tgactatttc tttacctcct gcttttagcc caatttgtat tttagtgagc   79860 cctcttact acctgattgg ccgggtgtga gctgagttac aagccctgtg tttaaaggta   79920
ggtgcggtca ccttccccag ctaggcttag gaattcttag tcggcctagg aaatccatct   79980
agttctgtct ctcacttcct ttgattttga agtaaacaat ctcttaactt tgggatagcc   80040
tgagacacca cctctgactt ctaaatgact caatatcccg aaaacccgtg gtaatctcag   80100
tccgtctcag ctggttccaa ttaacctctt tccaagctat ctgtgtgggc ctgctttagc   80160
cttttaaaag gaaccagacg ttttagtca caatggatgc atatgatagc atggtttacc   80220
tcagatatgc tgtgggttag cttctatagg ctttcttata tttaatgctt tcccctgact   80280
tcacatttaa tgcttttcca aaaatttccc aacatcacta aggcttcagc agccctttag   80340
gaccagtatt tctgggaaaa cactcaaaat acatctgaat ctgtgtcgta tatcatcacc   80400
tagagcatgc caccatctag tttcagcaaa atcctagtga ttccaccaga caagaaagat   80460
tgcctcactg ggagacagtt gctgattcct gttgccttc actggtctac tttgataatt   80520
ggcatatgcc tttcctgcgg catttatca cataaagctt tgctgttttt atctgtgttc   80580
atgtctttct ctctagatgt atcattaaag gcaaaaacaa tattcattta gtgttcttct   80640
tacctgtcct tctctcccca atactggaat cctaacacca tgcattgcac ttttttggtg   80700
ttcagggttc taggaaagct ggtaaatgga tgaatcataa atgtaatttg gggcaatttt   80760
ttcacaaaat gtgtcaccta tctttgtctt ttctctgccc actcatactg gctttctgtg   80820
gcttctcccc atctgtctag catttctctc tacctctgaa gaatatcagt ctggtgcagc   80880
cctagcacct tctttggact cattgttaaa gatgttgagg aaggctagct ccaaggttta   80940
ccgtttgcat ttagagaact gtcttaccat gcctggtttc ttcagccctg ataagactat   81000
gccatcttca ccctcccttc ccctgaccct tccttagcca cctcatccaa cctatggcaa   81060
ctcaacaaga aaagcttaca aagtcttcct tggcaaaaga gctggttgac ttgagccaaa   81120
ggaagctagg tgcagtgtcc gattcactcc cccaaatccc ccttgaaact ggagaattga   81180
aaacaatctg gtttctctct gggttctttc attataccat gttttcttgc atatagacag   81240
aataatgtgg ttgttacaat tatttataaa tgtagtgtat gccaggaact gatcactgtg   81300
tgtaacggat acaccattat ttttcaagga aaaaaatat tttgggcttt gatgattact   81360
agacagatgt ccttggtgat aataatcaca gtaagtccca actctaccca gtacttcaca   81420
attctctcag tgctttccta cttgttgtct cctgtaatga cgtatcatat cctgaatggc   81480
gggagggcaa ggatcattag tctcattta cacatgctca ttctgggact gggagagaga   81540
tttcctgatt tgcctaaact gccacagttt gtcaatgatg gtggagggat ggggcaaca   81600 ctgaacctcc agcttcctaa gactttccca cttttctcaag cttttgtcga atgtgtcatt   81660
agtggcattc actttggtca actttggttc cttgggtatt gctggctccc cattttttg   81720 gatttaaact cttcaaatta aataaatcag atttacatgt taaaaagaaa agtcttctct   81780
```

```
aaaagactcc ttcattttg taaatctttg taataatttc aacagacctt accttagaat   81840
ttcaggcaat aggtacatat cgtacacctc tgttagttct tccagagact ggcgcagggg   81900
ttggagatgg gagggaatag atggggggaag gaatgtggag cagggccctg gactccagtc   81960
caagctctgc tgaaggaggg ccttttccaa agtggatcct cctgaaggca gaggctcttc   82020
tagaacacat aaatgtgcag cattggctag taggagtcct gctggaacga ggctgaggca   82080
catacaggat agtttatagg agagtcaagt ctcatgcatt aaaattaaac aagcacttgg   82140
gctttgttgg aataaagata tgctagaaat gtcaccaagg atatatacca aatgccaaat   82200
gtagtcatat acaatgaagg agagcaatgg taggagaggt gtcggcaggc tggagagaac   82260
aacaagtgct gtgggctagg aactgtgatt tggaagtgtg caacccaaac taaaaggaga   82320
gaaaatggtt acagccactg gcagcatccc agagtcttac ctactgcctc cggtcctttg   82380
caagtaggta gggtataaat ataatgttat ctgcccagca caaaggagag gggagaaaag   82440
aaagcaagag gcagtcaaag ggacagagcc tagttctgag tcctgttta ccactcaatc    82500
cctggatgac cttgagcaag ttgcttctat tctggacttc attggtaaca gctaactcac   82560
agagtcaata tgaggattaa ataagactat tggctaaaag gtgcttagaa tagtgcctag   82620
cacagagtaa gcacttaata agtgttagct attattgtga taatacatgc atagaagtat   82680
atgcatgcat gtacatttac cagtatgtac acatttgcac acacaaaatg cccattgtga   82740
tctgcaagta gcactaggat ccaaaaatta aaagttatta tgttccacag gccaccttga   82800
aaagttaggg gaaaaaaaaa acttgacctt catgtgttgt tgctgttttt aagtggctca   82860
gcactttgaa ataacatttg gaggaaagca ttgcaatgga agcagcgctg tgtgggattg   82920
atcctggaga cctgggctca ggcgctggag cacaatgtcc aggaagccaa ggcctgtttg   82980
gattccttac gccatgacat ggaggcaaag ctcctcttgg ctgccaaccc aagagcccac   83040
agtcctgtga gcttcaccct tcctagggct gtttgtggtc tgggccctcg aggttgtggg   83100
agaccagttt gattgctaag ggaaaatccc agaatggctc ttcttgtcct taccgaatca   83160
ctacccttca ccttcctgcg tcctgcccca gcctggaggg cctacctagg cctgctatta   83220
cttccaaccc agaagtgtag cgaattgggg ccatgaccac aaggtttaca cttggttact   83280
tggtggaata tgaactcttg ggcaagttac ctaatattgc caagccacat ctgtaaagtg   83340
gatatgagaa tagaatctac ttcatgggtc tgattgtgag gtttagatat aataaggtga   83400
agtttggcac tcaataaaag gtagctgtgc tcattcttac cagcagcaac gagggcagta   83460
ttgatgctgc aggcagagag aaaggggggag gctgctgcct aaagcaccct tgccactcac   83520
atgtaattag gtgaccatac aatttattat ccaaaaggag acacttaaga ttggagggggg  83580
tgcaattaat aatggtgcca ggacaacagg cataaattgg gacagtctta ggcagacttg   83640
cccatgattc cttacccact gcccacccat catctgacta cacctctttc ttcaaagcat   83700
agatctcagt gggatatttt tcttcttcct gatcgctttg tttttgaag ggtatgatcg    83760
ctttgttttt gaaggatatg attctgccat taacattagc tatcacttac tgaggagcaa   83820
acatgtgttt gcctttgtgt taggtgtttt atggaaatga gctctaaaat ccttgcagca   83880
accttgggag gcaggtgcta cttccattac ccggttatag aatgtgaggc ttagggaggt   83940
taagtcactt gcccagccaa ggttacaggt ctattaaatg gtatatttgg tatttgccac   84000
ttgccatttt aacagcattt tattggcctt tgcggatcag aatgtttagc ggtgaccccca  84060
gaatgacttg tgcaggaccc ccactcccac ctctcccctg ctacactcat ggggtaggtg   84120
tcagggtgta tatcttcctg tcatacatcc accaattccc caattctcag gtcatagcag   84180
```

```
tgggctgaat aaccattggc tgccctcaga tttccgcaga aatggaagct tcttaaatat    84240
aggctgttaa acctggtttg agtttctttg taaaaggaat cttgtatagt ttccataaga    84300
cctaaagatt gtacagctaa gcctgctgaa gaatttgtcc ttattttttc catttcagat    84360
attcccaagg ttaggtagag ggggtggtgt tgaagagcag gctctctaga gccaatgctg    84420
tttattaata agctgtacag acacgcttct tccaggaatg tgcactttg attctgctgt     84480
ggtgataaag atactctgcc ttgcccatta agcatttgtt ggtggaaaac attacctta     84540
aataaatgtc tggttctatg tgagcaaagc tagggctccc ataaaattgg gcaatgatac    84600
tctgaattca gctgaactgt ttgggcaact ttgtcacttc tggggccatc attttcagga    84660
tagttcccac agtgtgagaa aatgactgct cctatagta ctgtcaagag tgtgaaaaga     84720
gagctcttta gcaaacacat tatttatcca tccttaaaaa gcttgtcacc tccagggtgc    84780
ttgttcagaa gtaatctcat tacttaaatc atatcctagc atgtggaaaa gctccctgag   84840
ttccccgcct gccccacctg ctgatttctc aggaccgctg ataacagctt tcatgtggaa    84900
cttgggatta atatcaagca agccatggat tttgtctcca ctgaacttgg gcatcatgga    84960
cagtttccat tccagcagtt aagggcttcc tgactttcaa cagtggtgct gatcccagtt    85020
ctgaagagtg gaacatcaga gagcctcccc tcctcagcca cttgtaagca taacaaactg    85080
aaaatgtaat ctgctttcaa atattctgtt gagtaaagat tcctttaat tactttaact     85140
gggttttgt agagacaagg gaccgttctc tgtttcccat gtcataaatg actttaatga    85200
gaaatggtga acacatcaat tagggcaagc ccacctgcac tggggctacc ctcccttcaa    85260
ctccccatac cctgttgggt agaaaccatg tgggaattta ctgatcagct gttccagaga    85320
cccttagaac aaatagcgtt tgcccccaat tactgaataa tgcctacata atttggaaag    85380
agggagattt cctactttgg gtaagaacat tgcctccctc accatcaggg cctttgaaca    85440
cactgttctc tctccctgga ataagtcact ccttggccat tcttctcct ggcaaacact     85500
cactcaccct taagactcag cttaagggag cccatgaccc tgtttgaggt tctggagggt    85560
tttctgttac atcctcccat aggaccccac agctcccttc gatccatctc atctcatttt    85620
tcctgttagc caactaacag gaaatttcag ccacaaatga gcacatatta agtaatcact    85680
gtgcatttga ggaatgccaa caccttgaaa ggaaaccgca agttgtaaac agagtttata   85740
cctgaggaga cttactgatc attcaaaaca ttcaatatat tcaagtatat attgaattgt    85800
tagcatcaga gacacaaaca gatattgcat ccataaaaac ataaacagat agtggacatt    85860
aatattttag tttttgaaat aaaaatgtga atggacgacc cgaaaggaca aacagatgac    85920
aaactggatt gagagagtca atcaaggaat tatcccagaa tgtagcacaa agagaaaaga   85980
gatgaaaaat atgagaaacc aggcaagaaa tatgaaggat ggatccatga gactgaatgt    86040
ttgtctaatt ggtattctaa gaagcaaaaa tggcaaaaat ggagggggt ggggccacag     86100
tcaaatatta aggaagaact gaagactgct tgaagtctca gaagtaaaaa gtcacataca    86160
gatatctcac tggggccaat ccttcaatca atcactgaag atagacttaa tttgggaagc    86220
agtcaaaggt catttgcaac caagtgtggt agaaaagatg gataatcaaa cctagttctt    86280
gtcgactatg agacgtaagt taaattagat gaaaaatttt aaaattattt gcaaggctga   86340
taatagactt ctgaagatgc ctggcctctg ctatcagcac ccacaggcag tttagctagt    86400
tgagtttgct ctgttttct caaaacctcc tttactttcc tcgtatcact gaatgggagg     86460
taatgaacaa attagaaact ggggtcgact aagagagcac tgcctctcct gtattgtccc    86520
```

```
tcatcaactg cctttctact tatatttcca caatagatat tattgcttcc taacacaaat   86580
ctagcctctt cattttttgtt atcccccaac tgctttatgc actcctacct ccagcattgc   86640
aaatacctct cctctacttg ccatcaaaat ctcaaccaca tttcaaggcc cagaacaagt   86700
cccatcattc acgtgaagcc tcctttcgtc tgtatgctaa tatctctttg tacttgtcaa   86760
cagtaccaag cttcttagtt ttctctccca atagtagact gcaggcttcc ctagagctga   86820
gagtgtgcca aacatttgct taatgataat taggaacttc tccaggtaca tgttacaatg   86880
aaaatatccc aggagggaga acaagttgaa ggattagccc ctggatatga attattttga   86940
tgaggtaata tcctctgact gggcagagga tagtaggtgg atagaaaatg tggggaaatg   87000
acacataaaa ggaagtgtgg gtgggaaggg gcactggagg caaatgttga gaatcccaac   87060
aagtgtgttc agtgacctcg tggctctcac atgatcccct aatatagctg tgacaagagg   87120
gatgtattgg gagctacacg actaccccac tccccaacct gctccatgtt ctcaagacag   87180
atatagtaac cttttcaaag gcatatagct ctttagggac ccctgagggc acaactccag   87240
tccaaactgt tccttccagc taccccaggg actgtccatt attatttctg ctcttgctgg   87300
agactgaatc ataataagtt tattgaggtt ttgctatatg ctagacacct gataaggccc   87360
taacaggctt tatctcgttt cttcctccta gtaaccacat caagaaatac cactatttcc   87420
cccatttttt tctaatgagg aaactaaggt agagatctag cagtggacat agtgatagag   87480 ggtcccctg gacacaggaa tgtgaatggt gtggggagga atgcagaagc agctttgagt   87540
ttccccagcc aattagtttc tcattctctc tacctgcaat gcccttcctc agcttggtat   87600
cttgcagagt aatgcttttc tttcaagacc tactcataaa gccataggtg accttcctag   87660
ggtagtcact ttctcctctc ttttcatagc tgtttatgcc tctgaacact tgtgcaatct   87720
gtcttcccca gattaactcc gtaagagcaa caacctcatt tccccatatt cctacagcct   87780
agagcctaaa acagtggcta gtggctagga tattgtagat ttactcagtg ttggaggtga   87840
agacagtggc ctccacaggc gcacactccg tgtgccctcc atgcactgga accctccttg   87900
gcagaaacct ggagattcca tgagccttga tgccctcttc agggccacag tgtgagtctg   87960
tcagtctgag ggcccacaga tgggatatca gggtaccaat tttgcccctc acttccccct   88020
taaacgtttc tcactgattc tgtggaccga aaaatgtaac accccattat caactgtaat   88080
ttggggtcta gttaaaatga aaaatcttca agagaaattg tattctctta taacctggaa   88140
acaactttct atcagtcagt gaaggtggtt ttaatcagga aagagcctct gggacattgg   88200
acacctgagg cagaaggttg agaaaggaac tgggcccagg agttgttcat ttgaggtctt   88260
tggattgggc tttaggggt ctgggatccc agaattgtac tgaaactttg catgttgatt   88320
cccgagtgtg tttctccaga gcaagattcc accacgttca ctggatcctt agaatgggtc   88380
tgggactcta aaagaaatga gaagagctag agaagttggc caaagtgggc cacatgcacc   88440
ccagcctccc tgacgtctca gtgtatctct gcatacctgg gcctacaggc accactggct   88500
ggcctaagac aacgtggaag aaaagaacca aggaaggcgg cagggcaaag gcacagggaa   88560
gggctgggga gggcagcta agacaaaggg taagaatgct gggcagcaga cacagagata   88620
cagagataag aggggccctg tggctcaacc ccctcatttt atagataagg aaatggacgt   88680
ccagagaggc taggtggccc cagcactctg gggtcagcta ggagcttcct tgccagagtg   88740
tccctgctct aggacatctc tatggcctca cagtctgttc attaaacaac agataagctc   88800
tcaaggaaag gccagcagtg ctgctgctat ctgactgttt gggtggtagc tatgggccac   88860
tgagttgctg ggacttggca tttggaatca ctgctaagat gtgcagaagg caaacatccc   88920
```

```
tctgaggata tgtgaatgta tcattctttg atgacccccag gcctaaaagg cttaagaggc   88980
taaccattgg ttcacttcac ttcacaaaca tttactgagc acttactggg tgtgaagcac   89040
ttgtggtagc ccccgggagc tagatagaaa agcgaggtgt gagtccttgc tctggaggaa   89100
cttatgttgt ggaaatattg acagacattc cctgtttctg ccgttacaag aacttatcat   89160
atccaggtag atgcgcagaa ggaagcaagg ccacttggga ccgcagtgtg acaaatcttg   89220
gatgccaaga ctcaggcatg gctctggatc tcaccacaga aagaggttca gggggcctct   89280
ctggctggcg gcacctgggc tgccctaagg attgtgtatc cacttgggga ccttccgtct   89340
ttgctaccag aggcaaggaa tcccacaact ccatgtgcca cagagacctt aaagccggag   89400
gaacgacaaa caccaccact ggcacttggc tccggaggct tccctttcgc cctcacctca   89460
gtgtcccgag gcagtttcag tgctccccct cagcccgggc gtggcaggcc tgggaagtga   89520
acaggtctct gagactcgta ctcagctcat ctggccccaa agcctgttct tgtgatgtgg   89580
tctctgggtc ttgtactcag ctcatctgac cctaaagcct gctcctgtgc tgttgtcact   89640
tctgcctttt ccttcctcag gttaaaagcc cagttttggc tggaaaattc cactaccttta   89700
tctactctgg ggccaggtaa cctgttaggt cttacaaaat tgaattgaaa agtgaagtca   89760
tgggaaacct cttagaaaaa tgactgctgt tcctggaaca atccccaact ggccctttct   89820
gcctcctcca taaggcgagg tcagactcct cgtgagaaaa actatggttt gggtgtcagg   89880
caacccccaat gcaataggat ctggggatc aacccccaatt caataggctc cccaaatagt   89940
gccccacttt tgtctcatgg cctgaaatgc cttagataat caagaagtct tttaaaacag   90000
tcatttctca ctgtgttcca gaaaaacttc tctgggagac tctatcagat gcagcccact   90060
gggaagacaa tagattaggt atctgaggaa ccagaagcac catcagacag gcaaataggc   90120
tagctgagat aagggcactc ttggactact attgcttttg actgccaatg ttcccaagtc   90180
ccaggcttgc tggtagtcag ccaataagtc attgtgaaga aaggagtgat tctacaaacc   90240
cacatggagc acctcctggg gaggtgttgt gctagaagtc acggaacctc agaggtgagt   90300
gagaaagcca cggtcctgcc tgatggatgc ccaagagcct tgggtcttca cacacatgtg   90360
aaatgtgggt tttagcagca ggtaccttc atacaccatc aatagtcttc cctatgtggg   90420
taaaacccta ggggctgagg tctcccattg gtgccttcag ggcttttttgc tcattccaca   90480
caaatggtca gtcagagacc acagcaggga tgggaactat agggtggaca aggcatttgc   90540
cctgaaggta gtccacacca tgtgtatcta gctgcatttt tcctgttggt tcctattgtc   90600
ttgctcctgc tccagaagaa gaatgtccca gggaatcact ggaagcttgc taggaagaat   90660
aactggaacc tcaagtgtca tgaccccagt gccaggggat ggaaatcata tcacagaatg   90720
tgcacttggg tgaaccttcc ctgcttttaa gtaactattg acaagtgacc ttccctggat   90780
ctcatgtaag tggttcattt ttaaaggaag agaactgtat tattagaaga tcacagcatt   90840
tctttccagt cctgatactc tgtgtctcct tgatgtagaa gttcatgggc agctctacat   90900
gtcttcctag agaactgtga ttctcataag atgtcctagc tagcagcacc ttcagtttgc   90960
ttgtcttact gcctcccgcg tctagaaaga aaactgaatg tctgaatgta gtaccctgct   91020
cagacaagct tcctaataaa tgtttattta atgaaaccct ccaaggctct gatttatata   91080
gtgccttggc agtcaaaagc agtagtagtc caagacccat gtcggagaga aaagaggag   91140
gagtatttat accaggtaag agatggctca ggcaaggaga agaagaagca ggcttgtctt   91200
gggaaaccag tggggcagaa ctggatgagc agggaaacat ggaggaggaa gaactcagca   91260
```

```
ggtaagatgt tgtggtaaag caggagtcag actttgagtg gagagaacca agaaataagg    91320
ctgggtcaag atgaatttgg ggtcggacat ggtggctcac acctgtaatc ccagctcttt    91380
gggaggccat ggcaggtgaa tcacctgagg tcaggagttc gagaccagct tggccaacat    91440
gatgataact ctgtctctac taaaaataca aaaattggac gggcgtggta gtgggtgcct    91500
gtaatcccag ctactcggga ggccgaggca ggagaatcgt ttgaacctgg gaggcggagg    91560
ttgcagtgag tcaagatcgc atcactgcac tccagcactc cagcctggt gacagagcaa     91620
gactctgtct aaaaaaaaaa aaaaaagat gaatttgaaa gtcttgtaga caactggaag     91680
caaagaaagg tttttagcag aggattgacg tgatgtaagc tgagtcaaaa agcaaatctg    91740
gcagcaatgt gcagaacaga gtgaaagaga aggtctgaga aggagggtct tggagagttt    91800
acaatgggga ataaaagccg gacaaagctg agacagtgc aaactcaggc aacaggtttg      91860
taacaagcac gtatgaaggc ctggacactg ttctagaagc ggaatacagt tctgaaagag    91920
agagacacag atccctgtcc tttgggaatt caccttctag aaggagagga aacagaggga    91980
agaatttgac ttttcatgaa ttaatgcctc attttactct gtaagaggtg tgaggaaatt    92040
tacaaacata catccactca gaataataaa aataagtgat tttacctatt gtctttgaca    92100
acatcctttc attagataaa atggtgagtt ccctatggct gacattacaa agtcactcag    92160
aggtagctta tggcctggca ccaaagcatg gctagacaaa ggtagttgca aaagaacac     92220
aagtgactag ctcccagtgt gtagctccgt gaaggttgtg acagttggtt cagatactaa    92280
gtaatggcgg caaatgggct ggagtctcca ctgggctcat ggagagatgg tttgtttggc    92340
atcatgcctg gtcctttgag aggagggctg tgctgcagtc cattccccac cctccacatt    92400
catgtcacct gtgttgccct tgaagacact agagcttggg actgccaaga gaggattgag    92460
ggtccaccag gaattctcag tagatttttc acaacagagg cttttgagag caattaatct    92520
tagagagttt gaggtagggt aattttttggc aaagaaggaa gccaggaatt tgccttcaac   92580
tgaccactga gatatgcttt gatcttgaat agagcagagg gtagggttaa ggcccattat    92640
aaaaattaac atataagcca gaagattaaa aaaatacagg gacgtatctt gagatacagg    92700
gacacgacat tattagggac tatgcctaga actttgtgac tggatatggt taggctggga    92760
tgggaaggga tatggtagga aagtaaaggg aaaaggaag tacaaaacac caatattttg      92820
aagctggatg atgggggtaat gatgtataag aaggttagga ctcggatcac ttgaggtcag    92880
gagttccaga ctagcctgac caacatggtg aaaccctatc ctccctacta aaaatacaaa    92940
aattaactgg gcatggtggt gcatacctat aatcctagct acttgggaac tgaggcaaga    93000
gaatcgctgg aacctgggag gaagacgttg cagtgagctg aaattgtgtc accactgcat    93060
gccagcctgg gcaacagagc aagactctgt ctcaataaat aaataaataa ataaaaataa    93120
aaataaaaaa gtaaggacag ggggagaagg tcaggaggag gttgacagat tgggttttag    93180
acgtaactat ggagtaatgg tgaaatatct gcatagtgga gttcactagg cagtcagtgc    93240
ttcagacatg gagaagacag aggcaagaag ggaatagggg gaggtgcctt cacagaagta    93300
agagcttaag agaggaaaat aatgagttct caaaaggaga ataaagcaga gagggcaaac    93360
gcttttaggct ggagagatgc tcatgatctc tcatgggcat gggggctgac ggaggaataa   93420
gaacagctgt agaggaatag aaacgatgag agaagcctgc cacaaccatc actggagaac    93480
agatacaaga aggaggaatg gccaaatggg tccaacgcca cagaatgaga tcaagaacaa    93540
acatagacag ggaagaggta cagatcaggc agtagtaagg tcacgtgtca gctctcagag    93600
acaggttttg gtgcgatcag gcagaagtca ggagatgagg aaatggatag agaaaaaaat    93660
```

```
gcatttctcc aggagctggg gtgtgaaaga gggatgggcc aggtttgctg gagagaataa   93720
gagggagtgc aagcttggca cccagccctc acatccaggg tggctgggtc tgtttccctg   93780
ctgggccagt agccccacg ctaaaaggat ttagcagggt ctggtcatgc taggcagaag    93840
ttccacaagg ccagggcctg cctcccctcc ctgtggcagg ctaggttag ggctatagct    93900 gtactagggg atctgggagt ccttcgtggc actgtgggac cctgaatgtg ttcagacccc   93960
caggtcatca ggacacctgg gctctgctgt gtccccagag gttttttgccc tgactcaggc  94020 tgaggacttt gggtgtagga ctcgcgtttt cttacgcaga ggttggtggg gcgttgaatg   94080
aagttgttag taggctccac gtagcacagg cacacaggcc tagtgcatca agtggccaga   94140
gtccctgctt ggtgccaggc aacgtggga tgctgagcag gcagagacca ctctgcaaat    94200
aacaatggtg cgacccaaga aaatgaccct gagagggcag tggagaccca ggcatttgag   94260
acggcctggc aaatgcatag cacctgaggg ccatgtgcat gtacatgtgt gtttgggggt   94320
gaggggaggg tattactggc cgaggggaca tgtaaacaac ctctgtgcaa gttctaggac   94380
cttcctatat tcctgtacca ctatttgaag gcttctgttt aacctaccca cgtggcccat   94440
tagaatgttc cactgaacag gaaaaccaat gtgcattcag gagagaatct caaaggacct   94500
ttccagctgt ggcattcaga ggtccataaa gcttaatcct ttaaaaggaa tcattctaaa   94560
tagcccagga gtgaacataa atgaatgaaa agtccatgaa tgtggggact aaatcccata   94620
atagggagca aaatggcatg ataaagagca tgggctctgg agacagacca cctaggcccc   94680
aattccagct ctgtcacata tgagctgggt gccctagggc aagctgctta actgcccag    94740 gcctcagttt ctccatctgt aaaatgggga taattagact tagctctcag gcttgtcgtg   94800
aagatgaatg gcttaatatt tctaaagtgc ttagaccaat atctgacaca tagcacatgt   94860
tttctaggtg ttaaaaaata ttcttttga tggggttgtt tgttttttc ttgtaaattt     94920 gagttcattg tagattctgg atattagccc tttgtcagat gagtaggttg caaaaatttt   94980
ctcccatttt gtaggttgcc tgttcactct gatggtagtt tattttgctg tgcagaagct   95040 ctttagtttta attagatccc atttgtcaat tttgtctttt gttgccattg cttttggtgt  95100
tttagacatg aagtccttgc ccatgcagat gacgagttag tgggtgcagc acaccagcat   95160
ggcacatgta tacgtatgta actaacctgc acaatgtgca catgtaccct aaaacttaaa   95220
gtataataat aaaaataaaa taaactaaaa taaaatatat tcttaccctg ctggattttt   95280
aagtgatgct cttgtcgggg atctttatga catacttttg aggaagatga gaacgaggc    95340 ttcttaactc tgttaaacat tttagacaca caaacagtcc tcacttttca tggcagtatg   95400
gggctgtaaa aatgaccatg caagctaaaa ccgtgcaaag caatcctaaa aatcaagaga   95460
aaaattaaaa ctgttctgtg acctttaaaa tttgttgtca aagcattaga aactcttacc   95520
ataggttata agtgtgtagg ggaacaaaca aacaaaaata gtaaatatt ttaggacaca    95580 gtaatttgaa acattagaaa caatgcaaca ttttaagtgt tttctttctt tgtgaaaata   95640
aacttactaa caggttttt aaaagtgctt gccttcttct ctttgcataa cttacgatac    95700
tgagggaaca tcttttctat gccagtgaat tgccatagtc ctttataaat ttgcatcagc   95760
ttgcaacatc ttatctcttt gctttcagtg ttgtgaaata cctctggaag ttcctataat   95820
gtgaagtttt ttgctgggat cacttcctgt gggacatctt catcctttt gttgcaacca    95880 ctttcctcat ttatgctttg aacaatggtt tcaggtttca tcaatataaa tcgaaacttc   95940
aagggtccca actgtcagaa agtcacatag aacttactca gaatgatgtc aaattccact   96000
```

-continued

```
ctagaaattt aaaacctcac cctgttaaaa atagcttgtc atcaacaaag gaaccagatg    96060
ataacagaca caaggctgac ttttttagttt cgacttatat atattaaaaa aaaaacaacc   96120
acaaaactgc tcaacataag cacaatgtgc tttcaggaga gaatctcaaa ggaccttttcc  96180 agtgcatttt cagtgccctg cacccaagca ttaatgatta tttaaatggt agaataacat   96240
aaaatgatga aacaactgga taaattcaac tatgttgtaa aaattttgta gttgacagaa   96300
atcagtcttt ggactttaag atctcatata gatcagagga gaaatataat gacatactcc   96360
ttaagaatct gatgaaagtt atggcctttc tccactagaa tgtgccgatt acaatatttt   96420
atgcagtgtt tcaaggaata cacagagccc ccaatatcca gttagaagcc ctggctgtga   96480
atctagaatt ttattacagg tgaaacccag cacaagtctg attgagagcc attgcaagtc   96540
acagaaactc taggccctgt ctaagtaaag gcaaaccttg gagtatgtca tctgccactg   96600
aaaatgcatt taatgatgac tcactctttc ctcactatac aagtttgttc aacctacacc   96660
tcttcagcta cagactacct accatccctg aaactctgtt ctgagagtaa agggattaca   96720
aaacctggct gaaaagacag attcaatggc atgttgaaaa acacagcaga accagcacat   96780
cagactgtaa attgattgtc ttgcacagga tgttagctgc tcttcgaatg aggttcctga   96840
gtggcacctg agcctattgc tggtggcatc ctattctgcc tgttctctct tcttcctcc    96900 ttccccattc ctttcattct cttctccctt attcttcctc tgcaattctt tttttccaca   96960
ctaccgttgg ccggtcccta gggatactgt ttaatctggc ccatggtaca agagatttta   97020
gatcttcatt gaagtcacta gagatggcct gagtgagtca ctttgaattc aatagacaaa   97080
ctgatggaag gctctgagaa gacctcaacg atgcccaaga aatgtgttct tactgtagaa   97140
acttactatt tgatcaaaaa aagtcatttt ggtcaaaaag gggagttggg agattgcctt   97200
tttgttttga aattgatttg gcttcaaggg aagaagattg cctaaacaaa acctgctgat   97260
gaagtcacaa aatgactcca cctctggaat gagctttatt ttcttataat ttggcaagaa   97320
atttggcttt caattgggaa tgcacgtcac tctacccact caagggcaag atgataaggt   97380
tctatcagac caagcgtcta aaggaacctg agactctacc aaggtcagaa atgctgcaat   97440
tcaagccaaa agatctttct tgggcttcct tgttttgact tgtaaccata aattagtctt   97500
gcctaaatgt ctgatcacat tataaaacag taagtgaatc tgtactgtac agcaccctct   97560
gaagcaacag gagctataga tgaaccttttt aggggattct gtaatttttc tgtccctttg   97620
atttccacag gactctaaat tgccccctct gaggtcaagg aacacaag atg gtt ttg    97677
                                                     Met Val Leu
                                                      1 gaa atg ctg aac ccg ata cat tat aac atc acc agc atc gtg cct gaa    97725
Glu Met Leu Asn Pro Ile His Tyr Asn Ile Thr Ser Ile Val Pro Glu
  5                  10                  15 gcc atg cct gct gcc acc atg cca gtc ctg ctc ctc act ggc ctt ttt    97773
Ala Met Pro Ala Ala Thr Met Pro Val Leu Leu Leu Thr Gly Leu Phe
 20                  25                  30                  35 ctc ttg gtg tgg aat tat gag ggc aca tcc tca ata cca gtaagtcag      97822
Leu Leu Val Trp Asn Tyr Glu Gly Thr Ser Ser Ile Pro
                 40                  45 tcatttattt ctgtatctaa ggagattatt tacttgggat tttggtccat gatggtaaag  97882
aaaattttgc aaaaggacaa aaagcaaacc tggaaagatc tctgaagact atgtctgtgt  97942
tagcaaatga ggacttggga gaaaattttc agaccaatta tctgcacatt ttaaatgaaa  98002
gcacttaaaa aatatcttag ataaacccctt ccactctgtg ctgtgctttc gtaaagtaga  98062
cttggcacaa gtacccttta aaacaagctc aagatggggt ggagtaaagt aaaattccag  98122
```

```
ggttttctgg ttaactttta aaaaatagat tgcaattttg ctctgaaggt gaaaatgtct  98182
ctggaacatc ttcttcactg cttttcttct ccctttcact ttgtttccgc catgcccct   98242
ctttgtcttg tatttatccc ttctcttгат tccactcatc attttctctt attcttggga  98302
atgtggtgat agtggtcccc atttttctcc cactgtctgg atcccattcg acccttatgg  98362
gagcctggta gtgggagaaa aatggggacc actccagtgc tcttggaaca tcataccccg  98422
ggagaatctt caacaagatc tgtggttcaa tcaaaagcag agaataatat aattattcag  98482
ataatcccaa tagaaaaccc cacccttcca cccttaaagc cgcaatgatc agatatcaga  98542
ttaattcaga atgacttgaa atttcagact gcttctttag gtttcagtga aaatgcttca  98602
ttgcagacac atctgttccc aattccataa gatatccaat gagactttaa gagcatagtt  98662
acacactggt aagtgtggtg ggcctagtct cagtgggatc agaagtggga gcatggggct  98722
agcacaaaat gctctgtgtc tggattcttt ttaacattcc agataattgc ctgtctctct  98782
gcctgattca gcctgatatt ttagattact ttaatgccca gtttaaagga acatttagtt  98842
aattttgttc tctgctccct gacagggtca actctagaga agggaggctc agagctaagg  98902
gacaactgtt tcatggtctt taacttgaac tctgttcccc agtgtggccc ttcctcactg  98962
gatttctcct ctcccaaggg ggcttctagg tcagggtcag tgaatggtcg gggtggggtg  99022
agtaagtggt gggggtggag agcctttttt tcctcttctt cccttcatag gctcaggtgc  99082
taaattccaa tttgtctgtg ttagcagaca atcaggccag gagagtccag cattgcccac  99142
gcagcattgc ccatccagtg agccacaggt tctcaagctt ttaagtctat gtaagaacac  99202
ccagcaggta ggagcttgtt aacatttctg ttcctggacc ctgctcctga ctttttgact  99262
cagactcttc aggcctagaa acatgcattt ttaaaaagtc cccgcagatg cttatgttaa  99322
tcagcactgg tggaatttcc ttggaccctt gaccaaggag gtcagcctgt taggacaagc  99382
ctgagaacca gcagccctga agctctggat cagtgggaga gtaggcagca cctcactctg  99442
tccaccattt ctgggccagg gccatcatgc tgatccactg acagtcagat caagtagcac  99502
agtgattctc agcactgtct gaggtaggag ctcagctagt ttgggggttgc tatttttaaa  99562
aaaatctccc ttcctgattt tttatgagca gccaaggttg agagccacaa atatgagcct  99622
aactccttca tttgacagaa ggggaaactg agacccaggg agttgatctg ccttgcccag  99682
acaaaacact atgacaagca tgagaagcca tggagttcaa acttgtcgtt ttacaagtga  99742
atggttaaag cccagtgaag ggaaatggct tgtcatctcc ccagctggac agaaagtggg  99802
aatgtagggg gaccaccagg aagtcctaaa gcccaggttg atgatcattt tgctagacag  99862
gtagtttcta gtttcacact ttccttttga aaacagaagg tctagttaga atccactagt  99922
agcacagact gtgagatcct atggtttctg gttgggggag ggaagataag aaaattggcc  99982
ttgtttgggg tggcttttgc tgatcaatac tcctgagctc ctgccagctc cctttaatca  100042
gtggctctct aggttcttgg ttttagaggt ttaggggaag cacagagtca ggaaagctca  100102
ggaacagtga aagctggagg gacttataat gatttaaagc ccttaagtga gttataattt  100162
acaaagcagt ttcgtgccca ttttctctgg tgaggttggt gtgtttgtgt ctgttttgta  100222
gttggcaaaa ctgagactca aagagtcaca caactagtaa tgatgaaact ggggctcata  100282
tctaagcttc ttctagccgt atttactgct aagtaaacag gctgccctgt tttcctgctt  100342
aggggcagga ggatgtgtga aaagattaaa gagatgtggt ttctgccccg aggggattat  100402
ataaaagtag taaagacagt caaggaaaca cacataggtg gttgacttag tgccaggtag  100462
```

```
gggctatgaa agtcctgagg aaagggtcat tctgcggaga aggggagtg gccggggag    100522
gggggcgggg ttggaagctt cagttctgaa aaattgctcc cagaccactg atctgggtca  100582
ggactcacag tcacctggca ctggctgctc tcccttcccc caggacgtat agccatcccc  100642
agctctaaac aagggtcctc tccctccaga tgccatgctc tgcccggggt accacatccc  100702
agagcaggga actagggggg agaaaagcat ggcaactgac attcctcttt ttcttaagat  100762
aatatttcac agaaaactgg acagtgcggt gacaaatttg ccatcacaat gcagcctgac  100822
aaagcggatg ttaccttgt tccagaagct cctcgtgtgc ctttgtaatc actctctctc   100882
tctcactcca gagcaaaaca ctgtctttga ttttgtgaca gtcactccct tgcttttttt   100942
ttttatcatt ttaccacata atttcacatc ccagagaata caggttaatt ttgccttgtt   101002
ttaaaggttt tagcagtcaa ttcatacatt atgtattctt ctatcttgct tcttttgctc   101062
aatagtatgt ttctaagatc catccacatc gtggcatgca ggtgtagttc attttcattg   101122
ccatagggta ttgagttata taaatatctc atggtttaat tgccagttcc actgttgagg   101182
gacacttgag gtgtctttag tttggggcta ttgtgaacag ggctgttctg aatgtatatg   101242
tgcacacagg tttctctatg gtgtacatct gtaaggcgtg gaaagcaaca gcttgttgat   101302
taggacagct ggggagaggt cccagctgtt ggctccaagg aggctgtctc tgtacaaaaa   101362
tgcagcaaag tattcactgc ttcttttagg gtgtgaaaga ggctcccacc atcattgcat   101422
gcctagataa gcattcccaa atctgagaag caacgatcag cttaatgtgg ctacaaccag   101482
aatatttccc taatattttg ccaaagtttc taccttcctc cagcattctt ctctccagct   101542
ggagggtggg tagaaggcct aagatataca cgtaaatgaa aaggtcacac tgtgttaaca   101602
ttcttttatt tagtaattat ttttcacata ctctcctctc ttgcccctag actctgatgg   101662
ggaccattat acttataaca tctccagtcc ctaattttag tgtctatacc agtagtatct   101722
ataccagtaa ttgtttgttg gatgaattaa gctgatatac aattgatcgc tagggactca   101782
aaactctggt tctcttctgg ttagaacact caggttctta atctaagcac aaggttcaat   101842
ctcccttttt cagtagatat atctctcctg cgtcacagct tacatttgaa tggcaggtcc    101902
caaatattaa gatttttaca tggcgggctg ggtgtggtgg cacaagcctg taatcccagc    101962
tactcgggag gctgaggcaa agaatcgct tgaacccggg aggtggaggc tgcagtgagc     102022
cgagatcatg tccctgcact acagcctggg caacagagcg agactctgtc tcaaaaaaaa    102082
ggatggcatt taaaacttca tccttatat tagatacaca tgcctaatta attttttaaa    102142
tttattcagg aaacattcgt tgagcatcta caatgtgcca agctataaat atccagtgag    102202
atattatatt atgcatatat taattgatta aaagttaata tatctaatga cagtttaagg    102262
aaatacatat tcaatcaaat ctgctgtgga aatcttttaa agagcttaat gaaattattt    102322
taatacaaag tcagtcatct actgtataat gtagtgttac taaaataatc acaagattaa    102382
taaccttaga ccatattttg gttctgtagg tattagcaaa gatctttat ttaaaggaa      102442
aaaagagctg acagtcttgc tcatattaac tcagctatta caaagtaaaa gactaaacac    102502
tgtttgctgt gtttgggatt aaacatccaa ttcagatgat tcaagcaaaa gcttacacta    102562
tgtatattat tacacaactt tgcccgtaa ggtgagaatg ctgtttcacg tagttaggca     102622
tgttttggct tcagaatgat ttcactgaca gaatggaatt aaaggagaaa gatttagaaa    102682
aactgctact tgtcaactcc tgaaaacatt ctaaaacttt ttaatctaac gttttaccaa    102742
caccagtaaa atcaagctac caaggttgtt ctctgatata agcagcacca aattcccag     102802
ttgttccctg gacgcatgtt ctttacaatt ctgccatcct ctgcataagc aagattgtaa    102862
```

```
gcagccacta ctctcggcta aaaccagatc atgggactca aactccaatc tagaggttca    102922
aagacccatt gcctgactcc ccatctctta gctttatttt gcctaatgag atttagctta    102982
agagcctttt cttaaacgga gtcttttttg agggtaacaa aagaaataga tgttcttgga    103042
ttggacattc tccttgtaga tcttgtttct ttcagttgaa agatttccta caaaactaca    103102
gaccagtttt aacccaccca ttgtgtcaac cggggcactc aaaccaaaag tttccagaaa    103162
aaactaggcg ccaaacagat ctgccagatt gtcactcatc agtgtttcca tgtttgctac    103222
caaatgcacc aattgacttg tattagaaac tcactgatac cagttaacct gggaagaaat    103282
tagcacacac accccagttc attcagactg aaatgattga gaccaaataa aactagtgtg    103342
gtatggatac tgaactcctt tttactcatg gagaagtgaa gagcctcatg ttaagcgtga    103402
ggcttttgtt ttgttttgtt ttgtttcaaa tcactttatt cgtgattcac agatatacat    103462
cacatgtaaa gaaacttag ctataaaaga acaaaaacag gagtaacaca aaacagttgc    103522 aattttttggt gtaactaaga tgttgcttat gctctgacac ctgtcctca ggt cct ggc    103579
                                                       Gly Pro Gly
                                                                50 tac tgc atg gga att gga ccc ctc atc tcc cac ggc aga ttc ctg tgg      103627
Tyr Cys Met Gly Ile Gly Pro Leu Ile Ser His Gly Arg Phe Leu Trp
         55                  60                  65 atg ggg atc ggc agt gcc tgc aac tac tac aac cgg gta tat gga gaa      103675
Met Gly Ile Gly Ser Ala Cys Asn Tyr Tyr Asn Arg Val Tyr Gly Glu
     70                  75                  80 ttc atg cga gtc tgg atc tct gga gag gaa aca ctc att atc agc aag      103723
Phe Met Arg Val Trp Ile Ser Gly Glu Glu Thr Leu Ile Ile Ser Lys
 85                  90                  95 tgagtctgtt cataatcgaa gacatacttt ttaaatcgag gctggagttt tttccactta    103783
agacaacttt attttgaatc ttgatgtctt tgtttctaac gctatatttt taccactgaa    103843
atgaagtgag caatccccag aaatctaaca ttgcaaacag aataattggg ttttgcttga    103903
attgaagcca gcagtacata aataactaac tctggaaagt tgggaaatta tttacaatct    103963
ctgtgagcag tgaatgtgga aacttagaag ccagataatt tgattttgac aaaacatact    104023
ttagggagag gtgttatctt ttctgctttc ccaagttttt tggtcttaac cacaaataaa    104083
cattaaaaag aaccaagcca acaaacaaa gaaaaaccc acagaaaaca aaaataaaac     104143
ccgagacatc actgcactat agtctgggtg acagagtaag accctgtctt ttaaaaaata    104203
aaacaaacct gaggcagagg tatctgatta gcaatttgct aatttattct cctgccaagc    104263
aactgagcac ctctaaaaga gcagatggta agccgacctt ggctgaatcc gattaaagta    104323
aagaaaaagg aaaataaaag aacaagacag tagaaaaaga agtaattcac atgctgcttt    104383
cccatttatg actttatgcg agtatcccgg tggagtgatc ttacataaat caggaacaat    104443 attaccatt taaaaaaata gtgtcctccc tctctgcatt attatatttt gtggataact    104503
agcagattga attagctcta tggttaacta aataggaatt gactataagg aactagtttg    104563
gtgaaatact tgttttcttg tttattgatc ttagaaaatg gagaatttca agatggcgt    104623 atttccctag actttcagcc agctttagta gacttttagc aaagctatct gcaaacattg    104683
tctcattaac gcatgtttat attcgtaatc cctgatagcg ctttaccac aaactaaagc    104743 tgaccagggt gttttaccaa tttgttagaa ttattcattc agatacaaag actatagctc    104803
aaaagtaagt gaagctttc taaactacat aatttttttca ggtcaagatt acatacatca    104863
tctcataaaa taccacggta tcctcaaagc ccaaatattt gaagcagata ttgaaagaag    104923
```

```
ggagcagggg agaaattggt attattttaa tacttctaaa tatttcaaac tatccaaaaa   104983
gaatttttt gacctgggat ttttgtttgt ttgtttcatt cagttttgtg ttgtagcact   105043
tttaagagta gctgaggcag acctcacaca actaaacaga aatggcttca ggtgaaaca   105103
tcatttcatt gggttcattg tgaagtactc taatgcagta gttttcaaag tgtggtcctt   105163
caacaagcag catcaacaag cctgggaact tgttagcaat gcacgttctt gggcccacc   105223
ctgacctact aaatgagaca gtctggggta ggacccgcga tccgtgtttt aacaaagcct   105283
gcaggtgatt ctgctgcaca cttgagtttg agaaccactg ctctaagaac tagatcataa   105343
ttactttttt attttaattc tcctggtcta ttaggctcta gtcagccaaa tttaagtgac   105403
tatgatacgt tcttgatacg ttctcatttt aaaaatcagt acttgagtca cttttacaac   105463
tggctatggt ctcacaaata tcctggaagc actggtgttt gggtttgggg gtagggacat   105523
ttgccgctgc tctttcattt ccccgcacag ccacctgcct ttcagctctc cccagcccag   105583
ggtctgcctt ccccatcacc tctttccctc agcagacagg tgaagtgacc cccaggatat   105643
ttatctagaa ggatatctac ctgctgccca ggatctagca cagtgccgtg cctctcaccc   105703
tagctgtacc ttagagtcac ccaggggagct tttcaaagcc ccactgccca ggccacaccc   105763
ccactttag atcagaacct ctgggggtag gactcaggca tcagtggtgt ttaatactcc   105823
cctgggagtt tgagaacatt ccatctagag agagggtgga ggaggaagct catggggcag   105883
gagggcctct ccccggggtt acaggaagca gcgatgcagg actggttttg tcttatgcta   105943
aggtggtgga ggtttaagac tagaactgga gtaaagaatg atagacttga gaaaggacca   106003
cagtaccagg acagaaatca ttctgagata ctagatattt cgatgctaga ttcttaaatc   106063
tccagaaaaa gtccgtgaat ttccaaagac aattcctgaa gtgcttgctc gttacagtgg   106123
gggtggcatc tgaccactcc gctagtctta attaggaaac tgactccaac aaccccgacc   106183
gactcaggcg ctggtgcacg ctgagacgca gccacaaccc acccacacta ccatcagctc   106243
tcccagttct ttccttttcc tgtcctctca ggcttttcac ttgttggagt ctttgtgttc   106303
tctttaattg cctcagagca gttcaatttt gttgttaaag gctgagctcc ccgcgggaat   106363
aggacatgtt tgtccccatc tcctttcctt gcctgctctt caagtcccctt ccagcactcc   106423
ccgtacctct tgaaaagacc ccattggacc tcagaaagat ttttattttt atttgaatag   106483
tttgccagat ttttttttc ttttgaaaag tttgaggtct gtagtcatta caactgtgta   106543
gaaattatgg tccaactttt ccaaccagct tcgtcccaaa gtagtagggg ctgcagaact   106603
tcagggagga agtcaggcat gtgcgctgct gagatgccgc gtgtgccact gggggcgtgg   106663
aggcacggtc catctggtga gctgtagatg atgtgtgcac cgttccccag gcagctaccc   106723
aggcagctgt actctaaatt aatgaaggtc tgtaggtgct gcgtatgaca ctatatgtcc   106783
attatatgtc cctagattag ttttttgtcat gaatacaaaa aaaatttatg tatcactcat   106843
aaagggaaat tagcaattag catgctaatt tgggttatat ttgcatatct gttagcaatt   106903
aacatactaa ttagggttat atttttacat ctgtcttaat aatgtgcaaa tttacacatc   106963
atttacaggg gcttccttca tttattctgt gaatatacat ttactgagaa tttattatat   107023
actaagcact gaatgattct aagttgtaat agtcattatt ggctcttcat ccattaaata   107083
tttcttgaaa acttactatg tatagcagca ggtattgttc taaactctgg gaatacagca   107143
gtggacaaac cagccaaaat tcctttacct catggagcaa tatgtcgtca ctaggtcaac   107203
aataaacaag taaatatat agtgtatcag tagagtgacc aattgtttca gtttgcctgg   107263
gaccagggcc tttcccagga tgtgggactt tcagtgctga aactggcata gtcccgggca   107323
```

```
aaccaggata gttggtcaca cttatcaggc agataggtgt tacatagaaa aagaataggg   107383
aaggaggatg ggggaggacc agttgtagag acgcaggtgt gattgtaaac aggtggttca   107443
ggcagccctc actgagaaga cagcatttaa ataaagacct aaaggaaatg agcaagtagc   107503
ccatgcagag acctggcggg aaagcattct agacagaagg aacagcaagt gccaatattc   107563
taaggcaaga acctgagtgg aagaatacag gagatgagag aagcaatagg gtaccaaatc   107623
acgtcaggcc ttgcaggcca ttgtaacaat tccggctttt accccctgca agaaaggaag   107683
ccactgaaga atttgagaga ggactgacac atatgactca tttatgtttc agcagaatca   107743
ttctggctgc tctgttgaga ataggtgcaa gaggacaagg gatggggaca gacagaccag   107803
ttaggcaaga ggtgatggtg gctggtccag gtggtagcag tagagatgat aagagatgag   107863
ggaaaattct ggacatattt tgaaggcaaa gccaacagac ttgctgacag attggatgta   107923
gggtgtgaga gaaaaaaaaa gagtcaaagt gctgtccagt tttgcattga atggggacat   107983
cgtgtcctga gataggtgga gcaagtttgg gaaggggaga gattagggtt ccattccaga   108043
catgttagat ttgacatgcc cagttgacat ctgagtggga tgattgagta gagagaactg   108103
aaccttgaga ccctctagtg taaataggtc agaaactagc aacagagact gagaagagca   108163
gctagaccga gaagagaaaa ccaggaaagt gtaatgtctg aaaaccaggt gaaaaatcca   108223
tatcagggag tagaaaattg tgaaccatgt caaataccac tgatgggggca agggaatgca   108283 tggagatttc agtactgcat ttagcaacag ggaggtcaca ggtgaccttg acaagagcag   108343
tttcaatgga ctagtggggg caaaagtctg accagaaag agaatcgggg gagaagaatc   108403
agaggcagca agtgtagaca agtcttccaa ggagtttgcc ataaagaagg caggaaatgg   108463
gccagtagat gagtgagatg tgtgggcaaa ggaattttga ttttaaaat aggagaaatt   108523 acagcatgtg agttgtaggg ggactggtca gttatggagg aaaatcaaat gattgttgat   108583
ggaagagaaa gagtgtgcta ggtgagatgt gaagaggtcc ctggggacaa gtggatgggt   108643
tggccttgaa tagggacatg gaatttccat agtaatagga gggaaggtgg aatatatggg   108703
cacaggtccg ggtcgttggg gattgtggag attctcttgt agttgcttcc actttcttgg   108763
gaaaattgga ataaagtct tcagctgggg ctgagtaggg agaatataat agtcatctag   108823
aagagtgaga gagtgaatgg gctggggaca tgcagtagca ttgccagcga cactaagggc   108883
ccacttgaat ttaaccgaga cctgacagca ggcacgtgtg cgctaacgta cacacatgcg   108943
cacacatgtg tgcgcatgtg tggttttct ttttttccca gcccacttca actgccaggt   109003
gcaagcacag aataagctaa gagttggatt tagctagagt gtggtcttat cagacaacca   109063
tgacaaagta agaagagggt caagggagtt gaggattcag ggaagggtat tttaattta   109123 atgattgaca gtaatttttt cccaactttc tgttaagaaa attgtcaaat gagtaggaaa   109183
attgaaagag ccgtcccccct gccacacttt tccccctgtg acattgacat tttgaagaga   109243
ccaggtcagc tataacatat cccacattct gaatttctct cactgtttca tcagggtgtc   109303
atttactata ttcatctatt ctctgtattt cttataaact gaaaattggg tctaaaggct   109363
caattagatt aaggttgcac atttttgcaa taacacttca gtagtactag gaacttcata   109423
tcacatcaca tcagaagatg agtaacaggt tgtcccacta gcactgatgt taaatttgat   109483
cactggttag gtggttacag tgagattcct ctgttataaa gattgtttat ctcttgtagt   109543 caccctagaat ttaagctggg taagtgagga tattagagaa gtgaaggaca gtgaaaggt   109603 gataggattg atggaacaga tctacatgag gcaagtgttt ttaaatgttt gttaccagcc   109663
```

```
gggtgcagtg gctcacacct gtaatgccag cactttggga ggtgaaagtg ggtgtattac   109723
ttgaagtcaa gagtttgaga ccagcctggc caacatggtg aaaccctgtc tctactaaaa   109783
atgcacaaaa aattagccgg gtgtggtggc gggtgcctgt aatcccagct actcaggggg   109843
ctgtggcacg agaattgctt gaacctggga ggtggagttt gcaattagct gagattgcgc   109903
cactgcactc cagcctgggc gatagagtga gactctgtct caaaaaaaaa aaaaaaaaa    109963 gaaggcacca attagtccat taattgcctc ctcatcactg ttgaatctgc ccacaagtgt   110023
gtgaattgtt taatcccaga actcaggtgg cttctttctc atcacctaag agcttactcc   110083
ctgactactt ttcattttga acagacaata ggtttgccat ctttggagat gtcttttatc   110143
ttcaatcatg cttaatgagg gataataacc ctagtgatca gacacccaac gctgtgcact   110203
gtccctgctg aggctgggga ctcagctgga ctctcctcag tgctaagaaa tcctcactct   110263
cccaaataat cagtataaca cttgcctctg gcagtattgc aggctggccc acaagccaga   110323
gccaggcctg tcttgactgc caggaggagc tctgggctgg ggtccttagt tcatcactga   110383
ccttctcttc acttttctga tttactctgg ttagataaat ccagcctact tttagtaagt   110443
gaccttgttt taaattgctc atctgtggcc agtcacacat cccttgcttt atcacatcgg   110503
cctgattagc tttgtcccta acaagcctga gctttggatt caaaatagct gagaagttgg   110563
tgccccctaa aggacacaag aattttaaag gttggctctt tattactaat aactagcaaa   110623
tatttcgttg ggtttgtttt atgtttggag tttcttactc tcttttttaaa actgattagc   110683 aagttcttaa atgaaatgga caggccaata tgattaatgc agtatgcaaa agccccaggg   110743
tcagagcaga aaaatagtgt ttgtccttta agtgcttaaa attttttaaat attagtttgt   110803 gaataaagaa tatataaatt acttaatttc tgctttaatt atagaatgat ggaggggaag   110863
gtaagtaaag ctagagtttt caaatatttt aattagtaag aatttcattc cttcctatag   110923
cataattttt ctatatatga caaaatttga aacgtcagac aaattcccca gaatacaaat   110983
ggaagcatct ggatttttat ttatttattt atttattttt gctagggaga ggcaaacatg   111043
tccaaaactt aggattattt gatgaatatt atctggaatc agatcaagag aatatttaat   111103 agtgtttta tttgaaaata ggtggttttt cctgaaataa atattaataa gttatttata   111163
caataactct gcttttttt ttttttttga gataggatct tgctctgtca cctaggttgg   111223
agtgcaatgg cttgatcatg gctcactgca gcctcaacct ccagggctcg agctatccta   111283
ctgcctcagc ccaccaagta gttgggacta caggcacaca ctaccacacc ttatatatta   111343
tatattatta tacaataata atcctgttct aatttcttga cactaccatt atttcagggg   111403
cttactttta aagcttaaat aggactatgg aacacatcgc agatgtgaga gctggattaa   111463
tacttagccc acaacctaat acattgaacc agagcagcgc ttttttggtc tagagtcctc   111523
tgggaatgta tttcaacagg cattaactga acaacctcat taaggcaaaa gtatccttt   111583 aggagccaag tgtcaactag gagatggagg agcaagtctc tccaacctga gaccaattg   111643 cagatattat agtaaccact tgcaatcttt gagggttatt tgttctgaaa acctccatag   111703
tgggagaatt tgcagctgtg aaacaaaatt tcaggagacc agaggagagg gaggaccaaa   111763
gttgcaatta atacatgaaa ttttgtataa atattaagtt caccaagaaa gtaacaacaa   111823
catctaaaat caagataata ccaatgacat ctaatgcatc ttgaatttgc ataattgagc   111883
atcatgcaaa ttgccctgtc tcatgactca tcacatcctg tgtcgtggga gaactctgtg   111943
accctggaga ctttgatgag tcatgatgga aggcagagcc ccaaaatagc ttccttact    112003 accacagtga acttgcatg ccagtccagc caggcgctgg ccaagctcag ggctagaaga   112063
```

-continued

```
agtgcccaag gagatatttt tcaagccctg actgatactc cactggaggg ggcaggcctg    112123
attagagact ggagttgggt ggtactaggc aaaactgctg gttccaaaat aggaaaacaa    112183
gactttagta attccacaaa cttctgattc tgtggctcac tcttgtagtg ggtggcactt    112243
tgtggagtga ggctggatga tacctgggag gctggaggtt cttctggctc tggtggtatg    112303
gagggttcag cttcttagca gccttgcagc tctgactcca gtagtgggta gtattttggt    112363
gaggttagag aagaaagaga agtaaggaat ggtatatggg tgtgtgtgtg tgttttctat    112423
ctttggtgat gttgaaacag ggagtcagta ggtagaaatg attcaactgg agaaggatgt    112483
cctcatgcta acagaagtgc ttattcaacc cgaatactag aaatcatgca cattgcattt    112543
ggagcaacat gcatttgcta agagagctac ctcctagtca aatgtacca ccaggagttc     112603 tcctgacccct aaaaattga caccaaagtt tcctgtcttt tcagg tcc tca agt atg   112660
                                                Ser Ser Ser Met
                                                            100
```

```
ttc cac ata atg aag cac aat cat tac agc tct cga ttc ggc agc aaa    112708
Phe His Ile Met Lys His Asn His Tyr Ser Ser Arg Phe Gly Ser Lys
    105                 110                 115 ctt ggg ctg cag tgc atc ggt atg cat gag aaa ggc atc ata ttt aac    112756
Leu Gly Leu Gln Cys Ile Gly Met His Glu Lys Gly Ile Ile Phe Asn
120                 125                 130                 135 aac aat cca gag ctc tgg aaa aca act cga ccc ttc ttt atg aaa        112801
Asn Asn Pro Glu Leu Trp Lys Thr Thr Arg Pro Phe Phe Met Lys
                140                 145                 150
```

```
ggtaagcagg tacttagtta gctacaatct ttttgtcta tgaatgtgcc ttttttgaaa    112861
tcatattttt aaaatatttt atttatttat ttatttattt atttattgag acaggctctg    112921
actctatcac ccaggcagga gtgaccttgg ctcacgacct tggctcactg taacctccgc    112981
ctcccaggct caggcgattc tcccacctca gcctcgcgag tagctgggac tacagatgtg    113041
caccaccatg cctggctaat ttttgtattt tttgtagcga tggggtttcg ccatatttga    113101
gaccaggctg ggctcaaact cacggagtca acgattgac ctgcctcggc ctcccaaagt     113161
gctgggatta caggcatgag ctatcattcc tagtctgaaa tcatattttg aattctactg    113221
caataaagga ggaagagcta acattcatta tgcctttact ctgttgtagc cattgttcta    113281
aacacttgaa tggcagcccc atgtggtaaa tgttgttatc tcctacaatt cacagaaaat    113341
gaggttaagt aacttgccca aggtccaaac attagtaaat gatagcccgg aatatagccc    113401
tgaagcctat atttcttaat caccacaaat tcttttcttc ttattgatgt gcaaagcaat    113461
tttataggca aagaagagaa tgtagctata tatttagagt aatttcagtt aagaatttag    113521
catgtcaccc atatgtttga tttaaacacg gccaaacaat gtgtttgctg agtgcttgac    113581
tgacagccca gatgatttag caggaagcaa tttgtgaatg aaattagata attttagaac    113641
tgagagggac catatctgtc atctagcctc tgattttaac agttgaggaa ataaagttcc    113701
aacgaagtta tgattttcac ccaggcaaaa tagggagtaa tgaatgagct gagacccagt    113761
tgcaagcttc cttatccagt ggttttcccc cttaacctca tcatgctgga atgaaactg     113821 ttggggaata cacacgacta acccttgaca ttactatcaa gcataaagaa agataatcat    113881
accctggaaa ccttgtcagt ggtggaatct ggggctagat gatttaggt ctggcccctg     113941 ctattcacag ccttccctcc agcagcccgt gctgtgaacc taggtagccg ccttccatgt    114001
gcctgctgag atgggggag ctatgccagt acctctgccc actgggtgtt gagcccagcc    114061
ttcagagctg ccctccctca ccaggactca gcacaactct gctgtagac cccagtgtat    114121
```

```
cactttccta ttgctgctgt aacaaattgc cacaaactaa gtggcttaaa agaacacatt    114181
tatctcacag ttctgtaggt cagaagtctg acatggatct caatgagctg aaaaccaagg    114241
cataggcaag gctatgtgcc tttctggggg ctctaggaga gactctcttt ctttgtcttt    114301
tccagctcta gaggccagcc acattccttg gcttgtggcc ctttcttcca acttcaaagc    114361
catcaacagt gggttgagtc ctttgcacat tacatctctc tgacccacct tctgtcatcc    114421
catctctctc tggctttgac ctcggcttgg aaaggttctt tgcttttttt tttttttttt    114481 ttttttttc tgagacagag tcttgctctg tcacccaggc tggagtgcag tggccccatc    114541
ttggctcact gcaagctcca cctcccaggt tcacaccatt ctcctgtctc agcctcctga    114601
gtagctggga ctacaggtgc ccaccaccac gcccagctaa ttttttgtat tttcagtaga    114661
gacgggtttt caccgtgtta gccaggatgg tctcgatctc ctgacctcat gatttgccca    114721
cctcagcctc ccaaagtgct gggatcacag acgtcagcct ataatctttg cctttaagaa    114781
ctcatgatta ggtttggccc accccatctc aaggtcctta accttagtca tatctgctaa    114841
gtcccccttt tcatgtaaag taacatgtta gtaggttctg gggattatga cccagacaaa    114901
tttaggatgc tattattctg cctatcactc atgttggggg agataaatct ccttataccct    114961 tataaaacta tggaatgaat taatggaaaa cgtataggac ttagtattac aggttgtggg    115021
tttgcgtccc agcactgcca cttgctacct atctgacctt aggcaagtca cttcgccttt    115081
ctgagcttca gttcccctat ccacaaaagg tgataaatgt tatgaaactt gcactctagg    115141
gctgttgtga agaacaaatg aaataatgct ataagatccc gtagaaatgt acatttgact    115201
ttttcatttg gctcaggtgt attaggaata tgtgaactag tatttagtag tagttaactt    115261
tcacatacca atatcctcta ccctgacatg caagagctaa ttaaaagaat ctctaagttc    115321
atccatttgt ttaacacccc accgttctca tctttgaact aggtaccaag atacaatgac    115381
aaacaagatg tggttcctgc cctccaggaa cttataatgg gggagagagg tttgaattag    115441
gaaggggcag cccagcacat caccaaatac taccctaggt gatggtaatg ctggcggtgt    115501
gcccagagtg atgccaagta cagatgaaca ggccatctaa agcacattga ggggcagggg    115561
agacttttca gaggaatgga tgcttataat gagttttaaa tgaaggtaga agctaattaa    115621
gaaaacaaaa gacaaatatt ctaggagtaa agaataggat aaccaaaggc acagacaaat    115681
agatagacat gatgcatcca gggccctgtc ggtaagtcct tgtgcctggt gcagatacat    115741
tcagggacgt ggccaagggg agggcagggc cagatcacca aagacctctc agttaaggca    115801
aggaattgag cttatctcaa aaactatgga gaatcactaa agattttaag cagaataaca    115861
taaacatatt tgtattttat aaaaatccct ctggtagcag agagaatgac taattggaag    115921
gaagcaggat tgtgagcagt gagaacattt aggagctact gcagtgatgc aggaagggtg    115981
gaggggaggc tgtggtttca agaaatgtca aagggtaga ccctacagta gtagagccta    116041
tagtacttgg aaattaagca aaacatcttt gtgattttt tttagacagc cttctatagg    116101
caagatcagg gtttctacaa aaagtgctac ataactggac ccaaattcat aatctcagga    116161 aatagggga taattgctta ttggaaagtt cactgtggtg tctgacattt ctataatcaa    116221
tgagggtcct aagcattttt cagtgaatct ccttttggag ttagactccc tgttggtttt    116281
cctgatatag tggaaagttt ggcacaagtt ttagtatcta aatcagtaac attaatgaaa    116341
gtattgactt actgggtgag tctgtagaga aatagttaag tgcaacttag gcaatgaccc    116401
atcttgggag gtagggaagg gtggtggcga ggggtgaaga aatagcatgt gtttcccaaa    116461
actgccgaga aatgtgtcca tattgatggt atttgctgat tgttgcccaa ttttcttttc    116521
```

```
actagataga gtcaatactt tttagcatat tttaaaaatt aaatcatatc tacatcatac  116581
cactgcctat aagccatgtt attacatttt tgcccataaa tttggcatgt ggcttcaagc  116641 tcttaaaca cagaggcaaa tcatgcatcg gcctgggaga aaaccacaag tgacattcta  116701
agccaaccct tccacacaaa gggttgagtc atttgtcctg cttgctgaag tggcagtcac  116761
ccagagaaca acatcctggc ctttcatatc tgccaagtcc ttcctatggt cagaaagcct  116821
gctccttcct caaccttcct tccaagatgt atggaaatct caaaagtcta ggaccagtcc  116881
tcaggcctcc tttcttattt gcaaagtata cctttaggca tggggattcc gcagcttaac  116941
ccagtgtgtg tgtgtgtgtg tgtgtgtgtg tgtgtgtgtg tgtgagagag agagagagag  117001
agagagagca agagagagag agagaggata gtcttcttct ggagttacgt ctacaaagtt  117061
tcccaatatt tttcatctca tttcaaagac tctgatgtta acagcaaacc tgaataataa  117121
aagacttaaa aagagattac tcctaaaaga tgcttaaaga aacgtaacac aaagagagaa  117181
aggggcactt taagggttaa accctcctgt gtaggccacc taccatcagg acccaccagc  117241
cactgctcag atatgaacag ggcaagagta agatcaaagc cagtttactc tattttcatt  117301
cattcattca ttcattcatt cctctattga aaaaatatgt atgaaggccc ccatggacca  117361
tcagcttgaa gtgcaatgct aatgagtggc tgtcactgtc cttaaagagc tctcagttca  117421
gtgagggaag actggtaagc aagcaaggaa ttgcttagct gtcatgccat ggctgagta  117481 aaataaacct ggaagtagtt tgaagagaaa tcaaaattaa gagaagggca ctttggggga  117541 ttttttacaac tagcctttta cacttaaaca ggaagcacct tagatcaaat aggatccaat  117601
ttgaccagtt ttccaataat atcctgccac ctgttgaaac gcaaaataaa tatgacccta  117661
ggcaaatcca aatcatcttt ggagggaaat gtatgcaata aatatgaaaa aatcactgat  117721
ttgtgattta tgaccacaag tactaaatgt ttcatttgca atctcataaa tggctggcta  117781
gagcatgaaa aaaagtttaa ttttttaatag tttgtttaaa ataatatttg tccctatctc  117841
cttccgttca ttcattctta accataggat agtacatgct tatgtaaaat taggagacca  117901
cagaaaagca tacgaaaata ttatgaaaac ttccacccaa ttattaaatt aaaaattgtg  117961
gacaattaag ctccaacata aaaagccaaa atggcatgat tgtgtgtgtg ccctggagtt  118021
cgtgatggct gattctctga tgtgtactct gca gct ctg tca ggc ccc ggc ctt  118075
                                   Ala Leu Ser Gly Pro Gly Leu
                                                       155 gtt cgt atg gtc aca gtc tgt gct gaa tcc ctc aaa aca cat ctg gac   118123
Val Arg Met Val Thr Val Cys Ala Glu Ser Leu Lys Thr His Leu Asp
        160                 165                 170 agg ttg gag gag gtg acc aat gaa tcg ggc tat gtg gac gtg ttg acc   118171
Arg Leu Glu Glu Val Thr Asn Glu Ser Gly Tyr Val Asp Val Leu Thr
    175                 180                 185 ctt ctg cgt cgt gtc atg ctg gac acc tct aac acg ctc ttc ttg agg   118219
Leu Leu Arg Arg Val Met Leu Asp Thr Ser Asn Thr Leu Phe Leu Arg
190                 195                 200                 205 atc cct ttg gac ggtactgaaa tttttcactct cacatcttga ccatctgtcc     118271
Ile Pro Leu Asp tttactgaac aaggagctag gagggataac agaccaaagg aatcacatgc cattttctac  118331
attgctcttg tttaaacatt tctaagtact cctcgttttt ttccctagtg tttctgcttt  118391
gttcacttat aaaatataaa tttccataaa gtaggggcca gcatctacta gcctttgta  118451 tctttcctca ttactctagg aaatagaatt ctacccacag ttgaaactta acaaatgtga  118511
ttagttcgtt tggttattaa catatcctac caccaatcaa ctttatatat ttaaccattt  118571
```

```
ccagttgttc ttttgggcat gatatataca tacatatata catacatacc cacacatata   118631
tacacacact cctccctcaa agctactaaa catgaaaaca ttgtgcctat atgataaaaa   118691
tgtcaatatt gctggtgata ctgatgctga tggaaatgac gatattagct gccattaacg   118751
tagtatctaa tgtgtgccaa acaatattaa aaattgctgt atatacatgt ttgccattta   118811
ttatttataa ccttaacaag atgtctcact cataagacta ctttccgcac tatgatacag   118871
aaatgaatat taaaacatgt gcatgctcat gtcaaactca tagaacttga ttttattttg   118931
gcaggattaa accaatttgc aacttgagta caaatgccaa tatttcagct agttcttgaa   118991
aagttgtgcc attgtgcaaa agtcattgaa ttatttgata acttttttaac ctaatgacca   119051
aacacctgac aggaatggaa ttcactggac ttgtatctaa ttgttttaca ctgttttcta   119111
tgggttacat ttttttattgc cattgtgacc tttatccaca cactaacctg gaaagtatag   119171
gaataaaaga attggcattc tttctgatac accctttttg ttttcttctt aaagtcattt   119231
atattatgta ttactcttaa agaatgtttt agtctccatt ttagtagtct gtgcataagg   119291
tagtaataca tgtacacaaa gaaaaattca caagcccatt caggtgtctt ttagaacatt   119351
atttaccact aaatatttat acagttgaca taatgcttat tatgcccttg aataatagaa   119411
tttgttttgt ttttacttct tatccataag cattggcctt acattgcctc aagaggaaca   119471
gaatttatta ttaaacagga ttcttaaatc cataactcat attgtgactt catacatttt   119531
gtaaccctag tagtgaatat accctaaaaa cctataaatc cccccaaatc actctactga   119591
tgaaaaaaaa aaaacatgtg catgcaactc taccaccacc aaaaaacaaa cattaatcat   119651
ttgagtagtt tggtggttac cagaggatgg gaagggtagt ggggagagaa gagatgaaga   119711
gaagttgatt aatgggtaca aaaatacagg cagatagaag aaacaagacc tagtgttcaa   119771
aaaatcagtg tagtgaagaa aataaataat aatctatgta caaccaagta gctagtagag   119831
aaaatttgaa tgttctcagc ataaagaaaa gataaatgtt taaggtgatg aatatcctca   119891
ttaccctgat ttggttatta cacattatac aaatttatca aaatattaca gttaccccta   119951
aatatgtata tccattatgt atcaatagaa aattaatcat ttggattaat tccattctac   120011
tgttggcatt aagtatgtac aactcaatgt gacttttcct gaattaactt acaccagtgt   120071
tcattgattc atacattcat tcatcaaaca tttattgatt gcttatttta tgccaggcac   120131
tgttctaggt tctggggaca taacagtaag caagacagat aaaattcttg ccttcaaggg   120191
gcttacattc cagtgagtga tgtggacagg aaaagacata gatatctaat aaaatattag   120251
gcaataataa gtgccttgaa ggcaaaatga agcagggcaa gaggacagga agtgaaggag   120311
ggcaacagtg tgtgtgggca cagatgtcat ggagagggtg gttagaaaag gcctctgcag   120371
agaagacatt tgaccatagc tcgaatttag tgaggccaca agccacaggc agatatgagg   120431
gaagaacact ccaggcggag gaacaatgcg tacttttaac acttgcccca accagctgaa   120491
ctggaacaca tgctacctgg tatactacac ttgggcacat agacaagcta taagccctcc   120551
ctattgccgc atctccccta ctccagctac tccatacaag agctggagac acttcatctg   120611
atggccattt ggatgggagc ccacaatcac ttgaagaagt tttagtcaca ctttctcacc   120671
tgatctcttt tcaggcaggg atgccactcc caggtgcct gttctacaga catcacttct   120731
aaagtgaaac aggcgtgtat tttaaaagtc tagatttcca ggtcccctc tagccttgcc   120791
tcattaggaa ggatcatata aaaggatttg taaatctctc cattcatttt tggatgcaga   120851
ctatgatgct ggcaaacctg tgcaacccac agagttacat aatccctttt cacagggatc   120911
```

```
cttgttaaac tctcaatttg cctaagggac ccagtgcaag aaaagagaaa aggacatggt    120971
cctgaggtca gacagaagca gctccagcct cagggcctgc ctgtcagcca cactggcgtg   121031
atggttttgg gcaagcttcc gaatttctat gaattgcaat ttcttccact gcaaaaggat   121091
gacaccacaa cgcccatggc aagaatatga agatgaaatt aaaaatctct ttcacaaagt   121151
gcctagcatg gtgactggta tttagcagtt ggaaatatat gtctgttctc tcttttgtat   121211
attatctggt ataatttgaa aaaataaggg tttatttcct ctagtattca atttaattaa   121271
agagcattta ttaagagctg attgtatgtg aggcttagga caaggcatta agaacacaa    121331
gatgaattct acactctgga ctgaatataa ataactatga agctatgtg atgagtgtta    121391
tgggggaaaa atgaataaag caccatgaga acatgattag aagctattaa gtgtataatc   121451
cagataaact gtccacttca tggctctgct tacccagcac caaatgaagt taaaatgtgg   121511
ttgttagcca cctaacaggc tctgcttttt acactcccag gtaccagagt gaaggccata   121571
acagccataa ttactagttc catttgtaca gagaaacagg agctagttga aagctcagcc   121631
caaggagaat atgtgaaatt ctaggctgaa aacttgaaaa cacaaacttg aaaactggca   121691
actcactggt taagtaggcc aatttggatg gcaaggagaa caaatcagtg cttgatttgt   121751
ctagtggtat tcacgtggct aaaactccta ctgaagatgg aatcttgctg agcttagaac   121811
ccccagactg ttaggagaat ctgcagggaa tgttttctgc tcagagcaac cttcttaggc   121871
tcacattttg ctcaactgct ctttcttgtg tatgtgtgtt tttttttcct aca gaa       121927
                                                           Glu
                                                           210 agt gct atc gtg gtt aaa atc caa ggt tat ttt gat gca tgg caa gct      121975
Ser Ala Ile Val Val Lys Ile Gln Gly Tyr Phe Asp Ala Trp Gln Ala
            215                 220                 225 ctc ctc atc aaa cca gac atc ttc ttt aag att tct tgg cta tac aaa      122023
Leu Leu Ile Lys Pro Asp Ile Phe Phe Lys Ile Ser Trp Leu Tyr Lys
            230                 235                 240 aag tat gag aag tct gtg taagtaatac aactttggaa gatttatgag              122071
Lys Tyr Glu Lys Ser Val
            245 tacaattgga ttggtttttt tcccttgtgt ctttgctgtt tttcttggcc tctcaggtaa   122131
cttttctgct ctctagagcc cacaagggag ctgttgatta agttgctgat gaaacacttt   122191
ttacagcaat ttggctgcat ttggccagac cagagagtaa atgaagcctt tggctgggca   122251
gcttctcggc aagggggctg agtgtgtggt ctgggagctt cagcttggta actaggacac   122311
tagtgtattt tgagttgaag agaagggtcg actgatcctg tcattaatat ctgtcaaaat   122371
tatctttgca caactaaaaa actggaacta cagaatcaat ttatagttgt gttgttttg    122431
aatgaattta acataattca acttgtaaga actgacaata gtctcaatag aattttttct   122491
taatgagtac aattaacttc aataaaatgt gtgtgggttt ttgaaattat gtatcttgtg   122551
ttttgggggt cctgaaattg tcattaaatg actttgtttt ggtcttagaa tcatccagca   122611
gaaaactgga caaatgccca gtggcctaca ggctaatcaa tgggcttgta gagtacaggt   122671
agccagtcac taaacactgc tacctctaac caccagtgga aagcctgtgg aatctagaaa   122731
caggaactcc tgttttgtgt cctgtttcta atggccttgg gaagttattt aaaataagat   122791
ataacctatc ttctagagta ggggcatagg ttaatgagat catataagta aggcaattag   122851
catagagcat ggcacataga gggtactaaa tatgttagtt tctccctttc ctgtgttcat   122911
atcttcctca gatgttccta accatctcaa gttctccatc tctaaatgtc cccaagcttg   122971
tctgaagacc tgactttatt ctacctgtgg attttgaaat tcgataatat tagtttctag   123031
```

```
agaagaagcc gacttgatgt tgttttgttt attctctcat ggttgataag tactaggtga   123091
atgttttaga cacttggttc tttatacatt tcatttccac cagagcttat tgtgacttga   123151
aaactaatag ataaaagatt catctcttcc ctgtgatcag agttgttggc agtagtggtg   123211
gtctggagag ttcattacat agttctcagt cattagttta gccttggtct tggccattgg   123271
acccacagaa atttattgta tgagtctgta taacggattc tcttaggttt ctgcagttcc   123331
ctcaaggagc tctctatgaa tttagaggct ggggcattcc aacacctccc agaccatttg   123391
gggctagtgc ccagatggga atgctatgag cattctcagc ctactaggaa gagggcacca   123451
cagcccagct gagtgaatat ctgttctttg tatataagag atgcttagca aacatttgat   123511
gaatgtgtgg atcagtaggg tatttaagtg tataggtgaa catgtcaatt agaatttgga   123571
agatggattt attgtacatt taacgtaata cagaacattg ttccctgaga taagggaaca   123631
atacacttac aaagaacaca tacacttaag gacagagata agaaaaattg aatttagatt   123691
aaggtgactt tattttttcat ccagtctgat cccttcactt taaaaggatg tagggcccag   123751
agacttaaag tatcttacat agaaagagaa caacctgaac taggacctga ccccaccccg   123811
tccaagtgtt ctttcaacca cactgccaaa atgcctatac atatttatgc agctggtaat   123871
tcattcaaca catattagtg tttacaatgt ggcagaaact aacaaggcat gagaataaat   123931
atcaagaatg atacctagtc actggagttt actgtttaga acaggaatct caaactcaac   123991
tgtcttcagg actaggcaaa taaaagcaga ctatgggggc caggtgcaat ggctcatgcc   124051
tgcaatccca gcactttggg aggccgaggt gggtggatca cctgaggtca ggagtttgag   124111
accaacctga ccaacatggt gaaactctgt ctttactaaa aatacaaaaa attagctggg   124171
cgtggtggca ggtgcctgta atcccaacta ctcgggaggc tgaggcagga gaatggcttg   124231
aacccaggag gcagaggctg cagtgggctg agatcatgcc actgcactcc agcctgggtg   124291
acagattgag actttgtctc agttaaaaga aaaaagaaa aagcaggcta tgggaatgta   124351
agacaaggga atggaggttc ctgtggcaaa ctgaagagca cctgacagca ctcacaggtt   124411 ttttttgtttt tgtttttta atttaaacat tgtgcctgcc aaatcagaaa ttggaaaaca   124471
ttgttagatt tagccttttg atatcaattt ttaacccttta actagaagtc acaggcttga   124531
tttcgctacc agtatccaga aatcttagct aactctggca ccttaacatg aagtgtaggg   124591
tctatgtaat ttaagggtat ttatgaagaa ataaaatagt aattcactta ctcataagca   124651
ccaatgtttt caattaaagc agatcatttt acctaaatac atggcaaata aatctgtttc   124711
gctagatgtc taaactgagt aaaaatagac aatatttga cttttttttcc agc aag      124767
                                                                    Lys gat ttg aaa gat gcc ata gaa gtt ctg ata gca gaa aaa aga cgc agg     124815
Asp Leu Lys Asp Ala Ile Glu Val Leu Ile Ala Glu Lys Arg Arg Arg
250             255                 260                 265 att tcc aca gaa gag aaa ctg gaa gaa tgt atg gac ttt gcc act gag     124863
Ile Ser Thr Glu Glu Lys Leu Glu Glu Cys Met Asp Phe Ala Thr Glu
            270                 275                 280 ttg att tta gca gag gtactgacct gaactaactg taattcccat gccacatatg     124918
Leu Ile Leu Ala Glu
            285 ttatgactgt gtagaggtgt gtaaagatcc cctttttgtaa ctgttgcata tttctgcttt  124978 taaatacttt ctctagcagt tctgtaatcc caatccaaat agcccacaca ttagatattt   125038 cagtaaggct tttaagattg gaacattcta gtaagactga ctgctaagat tgtgactctt   125098 ctgtgtaaca gtataaaata tgaaaacaag ttgggggagg ccaaagacac tacatataca   125158
```

```
tagacagtcg gcctaatcgt tcatctttca gctaaagatt gtcatgtaaa atgtccacag  125218
tcaatcacag agacatgtgg tttctatgat ttcattttgt tgaggttgtt gatccttgag  125278
tgtcacctcc cctcattttt tgaaactttg attcactttt ccaaattttt cccatcttcc  125338
aattgttcag aaa cgt ggt gac ctg aca aga gag aat gtg aac cag tgc    125387
           Lys Arg Gly Asp Leu Thr Arg Glu Asn Val Asn Gln Cys
                290                 295 ata ttg gaa atg ctg atc gca gct cct gac acc atg tct gtc tct ttg   125435
Ile Leu Glu Met Leu Ile Ala Ala Pro Asp Thr Met Ser Val Ser Leu
300             305                 310                 315 ttc ttc atg cta ttt ctc att gca aag cac cct aat gtt gaa gag gca   125483
Phe Phe Met Leu Phe Leu Ile Ala Lys His Pro Asn Val Glu Glu Ala
                320                 325                 330 ata ata aag gaa atc cag act gtt att ggtaagaatt tatcaaataa          125530
Ile Ile Lys Glu Ile Gln Thr Val Ile
                335                 340 ataatacatc ttaaaaacaa tttcttctga atgtccattt cttatgtcct aagaatctga  125590
tatcaaacat gaaattttt ataatttgct ccaaacaata aagcaagaca ttctgtcaca   125650
tttgattaca ccagatagac ggaaaagata gctctttctg tgttcttaat cataaaaatg  125710
atgcatgctc attgggagga atttaaatca cagaatgatg tgtaaagcag taagtgacat  125770
cccccaatcc tttccgctct cctctccagc ctcatctccc ctctcagtg gcaaccattg   125830 ttaatagttt gctgtgtatt tgctaaaatc tttttctatt tgcccacaaa cacatattta  125890
tggttggatt tgtccatttt acaaaaacat gggatcatat acaatgttct gcctaccttg  125950
tcagttacaa aagacttttg tggactctcc cagggaaatt atcgtcccag ggaagtgata  126010
gtctatcatt tatagcactg tttctgggct tcaagcagcc ccttcacaaa tgaacttcca  126070
gtttgtggca aaggaagag gagaggatga cagcaaagac agggtagtga tacatttccc   126130
tctccactcc aatccagtga tgctagcccc ttcctctccc ctgccctctg caggggagct  126190
tccaggtcca cactcaggtc ttctccaact ctaccgcctc actactctgt ctctgcttca  126250
atttcatcct gctccactct tctacagaaa caaggccatc tttgaaagaa atcaaacttg  126310
ctttctggga gaaagcagaa ttcctcattt gacacttcct tcacataagt aatctttttag 126370 gaacacattt cttacagatg tgaagagaga tcacagaatg tggacttccc tctcttgact  126430
ttacacagac cctgcaaaac aagttatttg gttgtagaag gcatcatct ttttcaaacc   126490 attggagtgc tccttgaaat agttaaacgt aagggaaaat ttcatcgaag ggttaaatat  126550
gggagagaag ggatctgcag atgcctcaca caggtgggaa gtttccaggc aaggtagata  126610
gcaaggatac agaataacat ctggaatcca aattccagca tgttttcttg agtgcctcct  126670
agcaggttct caggttctgt gccaggtgca gggctacagc cttgaacaag ccaacaccac  126730
ccctgcactc acggggctca tggtctggtg ggaaaaagaa aacaagctca atacagtaaa  126790
gagagaccga aggagggcat tcagagaaac cataagcctt taatacatat tgaataccat  126850
ttatttgaga ggtgaaatgt acgtgtacat gttaatgttc ccctgacact tcaaaaggcc  126910
tctgcaaaga tggaaaagca gcagagccat ttgcaagcgt ccatgctccc tcctgtgtgc  126970
cacacacaga ctcgctaact acttcctagt gagcacttt ggtcaccttc tccatcatct   127030
tcttttctac ctcccaaccc cagctataca ggccccatta gacccttgag tgtgccaagg  127090
gcagtatgta agaggaaggg ccatgagaag actctgacca aactagacct ttcctcagtg  127150
gcttcgttgt atatgagaca gggctgcctc aggaccctgg gctattttc atcctgcaaa   127210
```

```
agtggcatct ctgaagcttt accatgtctg ggaataatct aagtctcttt gaccagtgtc    127270
aggctaatct gagacagtga gggtgtccat ctatccccag ctcacccagg gctgatctga    127330
ggcacctatt ttgtcgtggt ggggagaaca tccttgtcac tctactgcag gtctttcttg    127390
atgagatgca gagggactat cagtgacatg tatgggcaga tgactgcaca ggtaaccaga    127450
agagaaaatt tcattgaaat agatcaaatc tgccatctca ctttgactct gcagcagcct    127510
gtgcatcatc tctgggatgg ttgtggtgcc agtttgctcg taagtgaaga gaggaaatga    127570
atgtccccta caatttagag tagggaacaa aaactcaaag atttcagaaa gcaggcacat    127630
gagatgaatg tttgaagcag attgggtgtg gtctagatgg aactgtatga tgtatgcccc    127690
ctctaaacag gtaattggcc actcagcgtc agcccattat tgctatgtgg gaatgtaagt    127750
tcagcatcac caaattttct ggacattcag acttttctat aaactccacc agttttaag    127810 gtaattggct tcatatctga attttttataa aacactctgt ggcccaagca taacatattt    127870
ggccctggtt gctggtgtgc attagaatta gagccacaat ttttttcaac caagagcaaa    127930
cggttctgtg gaaaaaaata gaagctttaa taccaatcac agatggaaac taacattacc    127990
ttctttgttc cttttatctg tttccaca ggt gag aga gac ata aag att gat      128042
                                Gly Glu Arg Asp Ile Lys Ile Asp
                                                        345 gat ata caa aaa tta aaa gtg atg gaa aac ttc att tat gag agc atg      128090
Asp Ile Gln Lys Leu Lys Val Met Glu Asn Phe Ile Tyr Glu Ser Met
    350                 355                 360 cgg tac cag cct gtc gtg gac ttg gtc atg cgc aaa gcc tta gaa gat      128138
Arg Tyr Gln Pro Val Val Asp Leu Val Met Arg Lys Ala Leu Glu Asp
365                 370                 375                 380 gat gta atc gat ggc tac cca gtg aaa aag ggg aca aac att atc ctg      128186
Asp Val Ile Asp Gly Tyr Pro Val Lys Lys Gly Thr Asn Ile Ile Leu
                385                 390                 395 aat att gga agg atg cac aga ctc gag ttt ttc ccc aaa ccc aat gaa      128234
Asn Ile Gly Arg Met His Arg Leu Glu Phe Phe Pro Lys Pro Asn Glu
            400                 405                 410 ttt act ctt gaa aat ttt gca aag aat gtaagagccc ttccttaaaa            128281
Phe Thr Leu Glu Asn Phe Ala Lys Asn
        415                 420 ctgagtgtgc cactcttgaa aatgtcaact gttaaatcct ctctggttct ttgtgtttgc    128341
accataaata cttcattttt cttactcatt ccctctgcca cctcaccagg agcacacacg    128401 tccccctagct tggagcaggg ctcccgtatt catcctcaag ccttcaagga tgttgggtct   128461
ccagctctaa gaagtatcta catggtggcc acaaaatagg tcaaaatgtg aaaaagctgg    128521
gcccttcatt tggctaaaat gaagtgattt ttgtttaacc caaccaacct acttttccat    128581
ttaaactttg tcatcatgtc atcacattca gctatagcac catctgagca aaggaaagtc    128641
cactactgct tcagatgaaa atcaaatgag accaaaagat ttggttttg caaagtgcct     128701 ttggctcatc aaatggcccc atgagcagta ggtcccattc taaataggac ttaataatta    128761
gaagagagac agttttttctt tttttataat tgatgtgtac tacagattcc accttcatta   128821
tgtcaaattt taggcaatat gttttttcaat ctgaattacg tacgcagttc cctaagtgcc   128881
cttttttcaa tttgcatatg gtgtagaaac atgatgctaa ataattcagt actctaattc    128941
attttgtttc tacacgggca atccagataa tgctatgtaa atcagtcaac tgatcaacaa    129001
aaatttattg aacatctact atatgccagg cactaagtcc aaatgtggac aagacagctg    129061
tggtcctcat taatttttctg cataactaca aatagttaga tgcttggcac tgaataggcc    129121
aggaatctac atccttgctt gcctttatct cttatatggt gtcacacaaa aataatcttt    129181
```

```
gccttagtga cttataaaac aatagtaaat ctgtggctat tccacagagc tacctgatta 129241 tactaacact tgctgtaata agatttggtt tgcattgctt taccccagca catgaaaggc 129301 aaaactgggg actctctgag gttgggtcag aacacagggg gtgaatgaaa taggacatag 129361 aaagggcttg agttccagtt gttcatctga ggggatggag ggcattgtag ctgataaccc 129421 caaaacagtg ttctgactga cccatgtttt cagaatgaat caaacagaga ctgagtgact 129481 ctagccttta atattctggc taactgtctg atcattttca tag gtt cct tat agg       129536
                                              Val Pro Tyr Arg
                                                          425 tac ttt cag cca ttt ggc ttt ggg ccc cgt ggc tgt gca gga aag tac       129584
Tyr Phe Gln Pro Phe Gly Phe Gly Pro Arg Gly Cys Ala Gly Lys Tyr
            430                 435                 440 atc gcc atg gtg atg atg aaa gcc atc ctc gtt aca ctt ctg aga cga       129632
Ile Ala Met Val Met Met Lys Ala Ile Leu Val Thr Leu Leu Arg Arg
                445                 450                 455 ttc cac gtg aag aca ttg caa gga cag tgt gtt gag agc ata cag aag       129680
Phe His Val Lys Thr Leu Gln Gly Gln Cys Val Glu Ser Ile Gln Lys
            460                 465                 470 ata cac gac ttg tcc ttg cac cca gat gag act aaa aac atg ctg gaa       129728
Ile His Asp Leu Ser Leu His Pro Asp Glu Thr Lys Asn Met Leu Glu
    475                 480                 485 atg atc ttt acc cca aga aac tca gac agg tgt ctg gaa cac                129770
Met Ile Phe Thr Pro Arg Asn Ser Asp Arg Cys Leu Glu His
490                 495                 500 tagagaaggc tggtcagtac ccactctgga gcatttctca tcagtagttc acatacaaat 129830
catccatcct tgccaatagt gtcatcctca cagtgaacac tcagtggccc atggcatttt 129890
ataggcatac ctcctatggg ttgtcaccaa gctaggtgct atttgtcatc tgctcctgtt 129950
cacaccagag aaccaggcta caagagaaaa agcagaggcc aagagtttga gggagaaata 130010
gtcggtgaag aaaccgtatc cataaagacc cgattccacc aaatgtgctt tgagaaggat 130070
aggccttcat taacaaaatg tatgtctggt tccccagtag agctctactg cctcaaccca 130130
aggggatttt tatgtctggg gcagaaacac tcaagttgat tagaaagacc aggccaatgt 130190
cagggtacct ggggccaaac ccacctgcta gtgtgaatta aagtacttta attttgtttt 130250
ctgtggaggt ggaaaagcaa cattcatagt ctttggagaa atgcttagaa attcagcatt 130310
tgacccttgc tgtgaattaa gcccaattaa ttcctgtttg tctacatatg atctgtctgt 130370
ggcaaaagtt taatcagagg aaattctttc ccagtctgtc gatttatgcc tcagccactt 130430
gcctgtgcta caattcattg tgttacctgt agattcaggt aatacaaact atatataatc 130490
atcaagtaat acaaactaat ttagtaatag cctgggttaa gtattattag ggccctgtgt 130550
ctgctgtaga aaaaaaatt cacatgatgc acttcaaatt caaataaaaa tccttttggc 130610
atgttcccat ttttgcttag ctcaattagt gtggctaacc aagagataac tgtaaatgtg 130670
acattgattt gctcttacta cagcttcagt gattggggga ggaaaagtcc caacccaatg 130730
ggctcaaact tctaaggggt actcctctca tccccttatc cttctccctc gacatttcct 130790
ccctctttct tcccatgacc ccaaagccaa gggcaacaga tcagtaaaga acgtggtcag 130850
agtgaacccc ctgaagtatt ttttaatcct acctcaaaat ttaacagtta cctgagagat 130910
ttaacattat ctagttcatt gaatcattgt atgtggtcat ggataaattg cacaccttgg 130970
aattcgcttt ctaaaggaaa tcaaatgaat ggaggaactt tccaaacacc actttacttg 131030
tgttatatag ccaatataac tatctctact gaatgtcatt gaaaaactaa aaaattaaac 131090
```

```
ttatttacaa ataggtaaat atttgtcatt gaatccattg ccatcccatt tgactgttct  131150
tttcatccta ctgtctagta ataagctgag tataagatga cagtgtaatc tccctgaaag  131210
caggagctac tttctttctt ttgtaatcta tttccatccc catttccctg tcctgtctcc  131270
ctgtattcac tcccaagctc agttctgaat agacattcct gctcagagat actcccaact  131330
gatgcagaaa ccaaataaag aggtaggtat tccaagaatt caagaatgga cattagtaaa  131390
gaataaaaca tttatttgag cttggaatta tttggatcat ctatatggcc taaaaatata  131450
tggactatgc ctgtgtacct gaatacgtat gtagtcaggt caagacaatc atccaaataa  131510
cttagacccc taaaagcaag gccaggattt gcaatttaat gtgtcccaat taattcactt  131570
gaaaattagt aacactctgt ttacgttgcc tctggctgga gctgcatggt ggaagaagcc  131630
caactttgga tccatgtact tcacccatcc aatactcttg gacatttat gtgtatttta  131690
tctgtatata tgaagccaat gtctatgtct acacagtcaa agtgaaatgc atgtttgata  131750
tagctgtaca tagatatcta ttttgcaggt acaaaaatat cctgggggaa aactgggagt  131810
ggaagggtgg ggggtgggag tgagggacat gggggaggga caggaagagg agaagtgttg  131870
gtttgaacga tccaagcaaa ctctcccaga atcaaattac ctgggtagtt gttcaacttt  131930
tcactctgct tagcctgtat agacaaaccc catatatttg tagaggcttg gccttggaat  131990
tctggaatac cattggcttt tcagtaggct gatgaacaca ttttgaaaat tctattatct  132050
tcagaatttt gccccattgt taagtgctta accgtcactc ttgaatgtgc aatgtgctgt  132110
ggattccatt ttcatcagtt ctgaaagaac tgcaatgtgt aaattatcag tgaaatgcat  132170
gcatataagg gctctatcat tatcaaattg taaggacaat tgtacccttc tatatctttg  132230
ggcatgctag acaccccat gccttcattg agatcccatt ttccccctct caagtggaaa  132290
ataatcacat ccagcaagct ctctcattat tgagaaatac catttggaaa ttgccacttt  132350
ttattcctaa gcagcacctt tcactgttca tgatgctaat gttccacaaa agcatgtgcc  132410
attggcccac tgaaggatag agggacccctt ttcaatctat atcagctggg ctctgggact  132470
gaatctctca cctattcttg cagaaagaca tactaattaa accttgtcaa agtagtaagt  132530
caaatggagc gtatgatgct ttcagttgct cttagctcaa agaacaaagt caagggatta  132590
acccttcagg gatcaatcct gtcagggctt acctgtttca acttcctcat ttcctttctg  132650
cagcttttag caggtattgg cctattctag gaagtcaatg gccataaccc tgtttctacc  132710
aggtcaacaa gacaatggaa tgtatttaga cagggcaacc cccattcatc aagtccagcc  132770
cattaagtat accctgctct ctcccatcaa gaaaacattt cgaagtgcaa aacaaatgag  132830
agtcataaga aaatgataat tatcataaga ataactttga atccactgtg atttataacc  132890
aaaagcaaat gtttcacaaa cctcagtatt ttaatttgtt agcaaaacat ttcttgcaaa  132950
gaaggtctta attacaaggc atggcagctg agtgcctgta gtccaggtaa ttttttaaagt 133010
tcctttcagc tctgcgactc catgaatagg gaggcagtgg agccctgcct ttttgtaaga  133070
atatgctttg acaagctgt ttcatctctc catatca                            133107
```

```
<210> SEQ ID NO 2
<211> LENGTH: 1512
<212> TYPE: DNA
<213> ORGANISM: Homo sapiens
<220> FEATURE:
<221> NAME/KEY: CDS
<222> LOCATION: (1)..(1509)

<400> SEQUENCE: 2
```

```
atg gtt ttg gaa atg ctg aac ccg ata cat tat aac atc acc agc atc       48
Met Val Leu Glu Met Leu Asn Pro Ile His Tyr Asn Ile Thr Ser Ile
1               5                   10                  15 gtg cct gaa gcc atg cct gct gcc acc atg cca gtc ctg ctc ctc act       96
Val Pro Glu Ala Met Pro Ala Ala Thr Met Pro Val Leu Leu Leu Thr
                20                  25                  30 ggc ctt ttt ctc ttg gtg tgg aat tat gag ggc aca tcc tca ata cca      144
Gly Leu Phe Leu Leu Val Trp Asn Tyr Glu Gly Thr Ser Ser Ile Pro
            35                  40                  45 ggt cct ggc tac tgc atg gga att gga ccc ctc atc tcc cac ggc aga      192
Gly Pro Gly Tyr Cys Met Gly Ile Gly Pro Leu Ile Ser His Gly Arg
        50                  55                  60 ttc ctg tgg atg ggg atc ggc agt gcc tgc aac tac tac aac cgg gta      240
Phe Leu Trp Met Gly Ile Gly Ser Ala Cys Asn Tyr Tyr Asn Arg Val
65                  70                  75                  80 tat gga gaa ttc atg cga gtc tgg atc tct gga gag gaa aca ctc att      288
Tyr Gly Glu Phe Met Arg Val Trp Ile Ser Gly Glu Glu Thr Leu Ile
                85                  90                  95 atc agc aag tcc tca agt atg ttc cac ata atg aag cac aat cat tac      336
Ile Ser Lys Ser Ser Ser Met Phe His Ile Met Lys His Asn His Tyr
            100                 105                 110 agc tct cga ttc ggc agc aaa ctt ggg ctg cag tgc atc ggt atg cat      384
Ser Ser Arg Phe Gly Ser Lys Leu Gly Leu Gln Cys Ile Gly Met His
        115                 120                 125 gag aaa ggc atc ata ttt aac aac aat cca gag ctc tgg aaa aca act      432
Glu Lys Gly Ile Ile Phe Asn Asn Asn Pro Glu Leu Trp Lys Thr Thr
    130                 135                 140 cga ccc ttc ttt atg aaa gct ctg tca ggc ccc ggc ctt gtt cgt atg      480
Arg Pro Phe Phe Met Lys Ala Leu Ser Gly Pro Gly Leu Val Arg Met
145                 150                 155                 160 gtc aca gtc tgt gct gaa tcc ctc aaa aca cat ctg gac agg ttg gag      528
Val Thr Val Cys Ala Glu Ser Leu Lys Thr His Leu Asp Arg Leu Glu
                165                 170                 175 gag gtg acc aat gaa tcg ggc tat gtg gac gtg ttg acc ctt ctg cgt      576
Glu Val Thr Asn Glu Ser Gly Tyr Val Asp Val Leu Thr Leu Leu Arg
            180                 185                 190 cgt gtc atg ctg gac acc tct aac acg ctc ttc ttg agg atc cct ttg      624
Arg Val Met Leu Asp Thr Ser Asn Thr Leu Phe Leu Arg Ile Pro Leu
        195                 200                 205 gac gaa agt gct atc gtg gtt aaa atc caa ggt tat ttt gat gca tgg      672
Asp Glu Ser Ala Ile Val Val Lys Ile Gln Gly Tyr Phe Asp Ala Trp
    210                 215                 220 caa gct ctc ctc atc aaa cca gac atc ttc ttt aag att tct tgg cta      720
Gln Ala Leu Leu Ile Lys Pro Asp Ile Phe Phe Lys Ile Ser Trp Leu
225                 230                 235                 240 tac aaa aag tat gag aag tct gtc aag gat ttg aaa gat gcc ata gaa      768
Tyr Lys Lys Tyr Glu Lys Ser Val Lys Asp Leu Lys Asp Ala Ile Glu
                245                 250                 255 gtt ctg ata gca gaa aaa aga cgc agg att tcc aca gaa gag aaa ctg      816
Val Leu Ile Ala Glu Lys Arg Arg Arg Ile Ser Thr Glu Glu Lys Leu
            260                 265                 270 gaa gaa tgt atg gac ttt gcc act gag ttg att tta gca gag aaa cgt      864
Glu Glu Cys Met Asp Phe Ala Thr Glu Leu Ile Leu Ala Glu Lys Arg
        275                 280                 285 ggt gac ctg aca aga gag aat gtg aac cag tgc ata ttg gaa atg ctg      912
Gly Asp Leu Thr Arg Glu Asn Val Asn Gln Cys Ile Leu Glu Met Leu
    290                 295                 300 atc gca gct cct gac acc atg tct gtc tct ttg ttc ttc atg cta ttt      960
Ile Ala Ala Pro Asp Thr Met Ser Val Ser Leu Phe Phe Met Leu Phe
305                 310                 315                 320
```

```
ctc att gca aag cac cct aat gtt gaa gag gca ata ata aag gaa atc    1008
Leu Ile Ala Lys His Pro Asn Val Glu Glu Ala Ile Ile Lys Glu Ile
            325                 330                 335 cag act gtt att ggt gag aga gac ata aag att gat gat ata caa aaa    1056
Gln Thr Val Ile Gly Glu Arg Asp Ile Lys Ile Asp Asp Ile Gln Lys
        340                 345                 350 tta aaa gtg atg gaa aac ttc att tat gag agc atg cgg tac cag cct    1104
Leu Lys Val Met Glu Asn Phe Ile Tyr Glu Ser Met Arg Tyr Gln Pro
355                 360                 365 gtc gtg gac ttg gtc atg cgc aaa gcc tta gaa gat gat gta atc gat    1152
Val Val Asp Leu Val Met Arg Lys Ala Leu Glu Asp Asp Val Ile Asp
    370                 375                 380 ggc tac cca gtg aaa aag ggg aca aac att atc ctg aat att gga agg    1200
Gly Tyr Pro Val Lys Lys Gly Thr Asn Ile Ile Leu Asn Ile Gly Arg
385                 390                 395                 400 atg cac aga ctc gag ttt ttc ccc aaa ccc aat gaa ttt act ctt gaa    1248
Met His Arg Leu Glu Phe Phe Pro Lys Pro Asn Glu Phe Thr Leu Glu
                405                 410                 415 aat ttt gca aag aat gtt cct tat agg tac ttt cag cca ttt ggc ttt    1296
Asn Phe Ala Lys Asn Val Pro Tyr Arg Tyr Phe Gln Pro Phe Gly Phe
            420                 425                 430 ggg ccc cgt ggc tgt gca gga aag tac atc gcc atg gtg atg atg aaa    1344
Gly Pro Arg Gly Cys Ala Gly Lys Tyr Ile Ala Met Val Met Met Lys
        435                 440                 445 gcc atc ctc gtt aca ctt ctg aga cga ttc cac gtg aag aca ttg caa    1392
Ala Ile Leu Val Thr Leu Leu Arg Arg Phe His Val Lys Thr Leu Gln
    450                 455                 460 gga cag tgt gtt gag agc ata cag aag ata cac gac ttg tcc ttg cac    1440
Gly Gln Cys Val Glu Ser Ile Gln Lys Ile His Asp Leu Ser Leu His
465                 470                 475                 480 cca gat gag act aaa aac atg ctg gaa atg atc ttt acc cca aga aac    1488
Pro Asp Glu Thr Lys Asn Met Leu Glu Met Ile Phe Thr Pro Arg Asn
                485                 490                 495 tca gac agg tgt ctg gaa cac tag                                    1512
Ser Asp Arg Cys Leu Glu His
            500

<210> SEQ ID NO 3
<211> LENGTH: 503
<212> TYPE: PRT
<213> ORGANISM: Homo sapiens

<400> SEQUENCE: 3

Met Val Leu Glu Met Leu Asn Pro Ile His Tyr Asn Ile Thr Ser Ile
1               5                   10                  15

Val Pro Glu Ala Met Pro Ala Ala Thr Met Pro Val Leu Leu Leu Thr
            20                  25                  30

Gly Leu Phe Leu Leu Val Trp Asn Tyr Glu Gly Thr Ser Ser Ile Pro
        35                  40                  45

Gly Pro Gly Tyr Cys Met Gly Ile Gly Pro Leu Ile Ser His Gly Arg
    50                  55                  60

Phe Leu Trp Met Gly Ile Gly Ser Ala Cys Asn Tyr Tyr Asn Arg Val
65                  70                  75                  80

Tyr Gly Glu Phe Met Arg Val Trp Ile Ser Gly Glu Glu Thr Leu Ile
                85                  90                  95

Ile Ser Lys Ser Ser Ser Met Phe His Ile Met Lys His Asn His Tyr
            100                 105                 110

Ser Ser Arg Phe Gly Ser Lys Leu Gly Leu Gln Cys Ile Gly Met His
```

```
                115                 120                 125
Glu Lys Gly Ile Ile Phe Asn Asn Pro Glu Leu Trp Lys Thr Thr
    130                 135                 140
Arg Pro Phe Phe Met Lys Ala Leu Ser Gly Pro Gly Leu Val Arg Met
145                 150                 155                 160
Val Thr Val Cys Ala Glu Ser Leu Lys Thr His Leu Asp Arg Leu Glu
                165                 170                 175
Glu Val Thr Asn Glu Ser Gly Tyr Val Asp Val Leu Thr Leu Leu Arg
                180                 185                 190
Arg Val Met Leu Asp Thr Ser Asn Thr Leu Phe Leu Arg Ile Pro Leu
            195                 200                 205
Asp Glu Ser Ala Ile Val Val Lys Ile Gln Gly Tyr Phe Asp Ala Trp
        210                 215                 220
Gln Ala Leu Leu Ile Lys Pro Asp Ile Phe Phe Lys Ile Ser Trp Leu
225                 230                 235                 240
Tyr Lys Lys Tyr Glu Lys Ser Val Lys Asp Leu Lys Asp Ala Ile Glu
                245                 250                 255
Val Leu Ile Ala Glu Lys Arg Arg Arg Ile Ser Thr Glu Glu Lys Leu
                260                 265                 270
Glu Glu Cys Met Asp Phe Ala Thr Glu Leu Ile Leu Ala Glu Lys Arg
            275                 280                 285
Gly Asp Leu Thr Arg Glu Asn Val Asn Gln Cys Ile Leu Glu Met Leu
        290                 295                 300
Ile Ala Ala Pro Asp Thr Met Ser Val Ser Leu Phe Phe Met Leu Phe
305                 310                 315                 320
Leu Ile Ala Lys His Pro Asn Val Glu Glu Ala Ile Ile Lys Glu Ile
                325                 330                 335
Gln Thr Val Ile Gly Glu Arg Asp Ile Lys Ile Asp Asp Ile Gln Lys
                340                 345                 350
Leu Lys Val Met Glu Asn Phe Ile Tyr Glu Ser Met Arg Tyr Gln Pro
            355                 360                 365
Val Val Asp Leu Val Met Arg Lys Ala Leu Glu Asp Asp Val Ile Asp
        370                 375                 380
Gly Tyr Pro Val Lys Lys Gly Thr Asn Ile Ile Leu Asn Ile Gly Arg
385                 390                 395                 400
Met His Arg Leu Glu Phe Pro Lys Pro Asn Glu Phe Thr Leu Glu
                405                 410                 415
Asn Phe Ala Lys Asn Val Pro Tyr Arg Tyr Phe Gln Pro Phe Gly Phe
                420                 425                 430
Gly Pro Arg Gly Cys Ala Gly Lys Tyr Ile Ala Met Val Met Met Lys
            435                 440                 445
Ala Ile Leu Val Thr Leu Leu Arg Arg Phe His Val Lys Thr Leu Gln
        450                 455                 460
Gly Gln Cys Val Glu Ser Ile Gln Lys Ile His Asp Leu Ser Leu His
465                 470                 475                 480
Pro Asp Glu Thr Lys Asn Met Leu Glu Met Ile Phe Thr Pro Arg Asn
                485                 490                 495
Ser Asp Arg Cys Leu Glu His
                500

<210> SEQ ID NO 4
<211> LENGTH: 48
<212> TYPE: PRT
<213> ORGANISM: Homo sapiens
```

```
<400> SEQUENCE: 4

Met Val Leu Glu Met Leu Asn Pro Ile His Tyr Asn Ile Thr Ser Ile
1               5                   10                  15

Val Pro Glu Ala Met Pro Ala Ala Thr Met Pro Val Leu Leu Leu Thr
            20                  25                  30

Gly Leu Phe Leu Leu Val Trp Asn Tyr Glu Gly Thr Ser Ser Ile Pro
        35                  40                  45

<210> SEQ ID NO 5
<211> LENGTH: 51
<212> TYPE: PRT
<213> ORGANISM: Homo sapiens

<400> SEQUENCE: 5

Gly Pro Gly Tyr Cys Met Gly Ile Gly Pro Leu Ile Ser His Gly Arg
1               5                   10                  15

Phe Leu Trp Met Gly Ile Gly Ser Ala Cys Asn Tyr Tyr Asn Arg Val
            20                  25                  30

Tyr Gly Glu Phe Met Arg Val Trp Ile Ser Gly Glu Glu Thr Leu Ile
        35                  40                  45

Ile Ser Lys
    50

<210> SEQ ID NO 6
<211> LENGTH: 51
<212> TYPE: PRT
<213> ORGANISM: Homo sapiens

<400> SEQUENCE: 6

Ser Ser Ser Met Phe His Ile Met Lys His Asn His Tyr Ser Ser Arg
1               5                   10                  15

Phe Gly Ser Lys Leu Gly Leu Gln Cys Ile Gly Met His Glu Lys Gly
            20                  25                  30

Ile Ile Phe Asn Asn Asn Pro Glu Leu Trp Lys Thr Thr Arg Pro Phe
        35                  40                  45

Phe Met Lys
    50

<210> SEQ ID NO 7
<211> LENGTH: 59
<212> TYPE: PRT
<213> ORGANISM: Homo sapiens

<400> SEQUENCE: 7

Ala Leu Ser Gly Pro Gly Leu Val Arg Met Val Thr Val Cys Ala Glu
1               5                   10                  15

Ser Leu Lys Thr His Leu Asp Arg Leu Glu Glu Val Thr Asn Glu Ser
            20                  25                  30

Gly Tyr Val Asp Val Leu Thr Leu Leu Arg Arg Val Met Leu Asp Thr
        35                  40                  45

Ser Asn Thr Leu Phe Leu Arg Ile Pro Leu Asp
    50                  55

<210> SEQ ID NO 8
<211> LENGTH: 39
<212> TYPE: PRT
<213> ORGANISM: Homo sapiens

<400> SEQUENCE: 8
```

```
Glu Ser Ala Ile Val Val Lys Ile Gln Gly Tyr Phe Asp Ala Trp Gln
1               5                   10                  15

Ala Leu Leu Ile Lys Pro Asp Ile Phe Phe Lys Ile Ser Trp Leu Tyr
            20                  25                  30

Lys Lys Tyr Glu Lys Ser Val
        35
```

<210> SEQ ID NO 9
<211> LENGTH: 38
<212> TYPE: PRT
<213> ORGANISM: Homo sapiens

<400> SEQUENCE: 9

```
Lys Asp Leu Lys Asp Ala Ile Glu Val Leu Ile Ala Glu Lys Arg Arg
1               5                   10                  15

Arg Ile Ser Thr Glu Glu Lys Leu Glu Glu Cys Met Asp Phe Ala Thr
            20                  25                  30

Glu Leu Ile Leu Ala Glu
        35
```

<210> SEQ ID NO 10
<211> LENGTH: 54
<212> TYPE: PRT
<213> ORGANISM: Homo sapiens

<400> SEQUENCE: 10

```
Lys Arg Gly Asp Leu Thr Arg Glu Asn Val Asn Gln Cys Ile Leu Glu
1               5                   10                  15

Met Leu Ile Ala Ala Pro Asp Thr Met Ser Val Ser Leu Phe Phe Met
            20                  25                  30

Leu Phe Leu Ile Ala Lys His Pro Asn Val Glu Glu Ala Ile Ile Lys
        35                  40                  45

Glu Ile Gln Thr Val Ile
    50
```

<210> SEQ ID NO 11
<211> LENGTH: 81
<212> TYPE: PRT
<213> ORGANISM: Homo sapiens

<400> SEQUENCE: 11

```
Gly Glu Arg Asp Ile Lys Ile Asp Ile Gln Lys Leu Lys Val Met
1               5                   10                  15

Glu Asn Phe Ile Tyr Glu Ser Met Arg Tyr Gln Pro Val Val Asp Leu
            20                  25                  30

Val Met Arg Lys Ala Leu Glu Asp Asp Val Ile Asp Gly Tyr Pro Val
        35                  40                  45

Lys Lys Gly Thr Asn Ile Ile Leu Asn Ile Gly Arg Met His Arg Leu
        50                  55                  60

Glu Phe Phe Pro Lys Pro Asn Glu Phe Thr Leu Glu Asn Phe Ala Lys
65                  70                  75                  80

Asn
```

<210> SEQ ID NO 12
<211> LENGTH: 82
<212> TYPE: PRT
<213> ORGANISM: Homo sapiens

<400> SEQUENCE: 12

-continued

```
Val Pro Tyr Arg Tyr Phe Gln Pro Phe Gly Pro Arg Gly Cys
1               5                   10                  15

Ala Gly Lys Tyr Ile Ala Met Val Met Met Lys Ala Ile Leu Val Thr
            20                  25                  30

Leu Leu Arg Arg Phe His Val Lys Thr Leu Gln Gly Gln Cys Val Glu
            35                  40                  45

Ser Ile Gln Lys Ile His Asp Leu Ser Leu His Pro Asp Glu Thr Lys
    50                  55                  60

Asn Met Leu Glu Met Ile Phe Thr Pro Arg Asn Ser Asp Arg Cys Leu
65              70                  75                  80

Glu His

<210> SEQ ID NO 13
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gactgatcat ctctcagcaa tacccac                                        27

<210> SEQ ID NO 14
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
cagattatag agtcccgcct tggg                                           24

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ctctggcctt ctttgccctc ctt                                            23

<210> SEQ ID NO 16
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ccaacactat ctacctggaa agagt                                          25

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 17
gtctgttatg ttgtcacaca gg                                          22

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
caatcaagca gcacttggaa tg                                          22

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ggtgtcttct gactggcctt cat                                         23

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gacactcaga gccctggaaa gaa                                         23

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
gcttaggcta agctgaatat attt                                        24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cattatgaat cgagctgaca ttct                                        24

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
```
ggtaatgaga gaagattctg ttc                    23

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
caaagcacag aacagtctct tgt                    23

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ctagttctgt agcaatgacc gca                    23

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ctgtggccca ctacagagaa a                      21

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gcaaggatgg gagagtgagt                        20

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gaatgaatga aaccacttac cct                    23

<210> SEQ ID NO 29
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29

```
ccactcttca taataaatgc cttaaga                                        27
```

<210> SEQ ID NO 30
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30

```
cctattatct caagtagcag aatatgt                                        27
```

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31

```
ctacagctgt gatagtttag cat                                            23
```

<210> SEQ ID NO 32
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32

```
ccttgtcaca gtccacaggg a                                              21
```

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33

```
agtcaaacct taccttactt aaccg                                          25
```

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34

```
gcgtacgctc ctgtgaacag a                                              21
```

<210> SEQ ID NO 35
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35

```
ctacgaggag ccaaagtttc a                                              21
```

```
<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
cccaggaaaa tgtgcaaata tc                                              22

<210> SEQ ID NO 37
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
cattggctgc cctcagattt c                                               21

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
cactcttgac agtactatag g                                               21

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
tcaggatagt tcccacagtg                                                 20

<210> SEQ ID NO 40
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ctcaacagaa tatttgaaag cagatt                                          26

<210> SEQ ID NO 41
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
tcacatagaa cttactcaga atgatg                                          26
```

```
<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ctctgtgtat tccttgaaac actg                                           24

<210> SEQ ID NO 43
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
gcctttctcc actagaatgt gccgat                                         26

<210> SEQ ID NO 44
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
ggtgccactc aggaacctca t                                              21

<210> SEQ ID NO 45
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
gtcttgcaca ggatgttagc tgct                                           24

<210> SEQ ID NO 46
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gagtcatttt gtgacttcat cagcaggt                                       28

<210> SEQ ID NO 47
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
caagggaaga agattgccta aaca                                           24
```

```
<210> SEQ ID NO 48
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
ccatcttgtg ttccttgacc tcaga                                       25

<210> SEQ ID NO 49
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ctgaagcaac aggagctata gatga                                       25

<210> SEQ ID NO 50
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
ccatcatgga ccaaaatccc aagt                                        24

<210> SEQ ID NO 51
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
gtgattcaca gatatacatc acat                                        24

<210> SEQ ID NO 52
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ccaattattc tgtttgcaat gttaga                                      26

<210> SEQ ID NO 53
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ggagcaacat gcatttgcta aga                                         23

<210> SEQ ID NO 54
```

```
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ggtgatagag gtcagagcct gtctca                                          26

<210> SEQ ID NO 55
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ggcatgattg tgtgtgtgcc ctgga                                           25

<210> SEQ ID NO 56
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
ggcatgtgat tcctttggtc tgtta                                           25

<210> SEQ ID NO 57
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
gttaggagaa tctgcaggga atga                                            24

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
cttgccgaga agctgcccag cca                                             23

<210> SEQ ID NO 59
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
catgaagtgt agggtctatg taat                                            24

<210> SEQ ID NO 60
<211> LENGTH: 24
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gatctttaca cacctctaca cagt                                             24

<210> SEQ ID NO 61
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gacatgtggt ttctatgatt tcat                                             24

<210> SEQ ID NO 62
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
gattaagaac acagaaagag ctatct                                           26

<210> SEQ ID NO 63
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
ctaacattac cttctttgtt cct                                              23

<210> SEQ ID NO 64
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
ggtgaggtgg cagagggaat gagta                                            25

<210> SEQ ID NO 65
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
cagaatgaat caaacagaga ctga                                             24

<210> SEQ ID NO 66
<211> LENGTH: 22
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 66
gccatgggcc actgagtgtt ca                                              22

<210> SEQ ID NO 67
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
caaacagaga ctgagtgact ctagc                                           25

<210> SEQ ID NO 68
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
ggatggattt gtatgtgaac tac                                             23

<210> SEQ ID NO 69
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
ctcagacagg tgtctggaac acta                                            24

<210> SEQ ID NO 70
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
ctggtctttc taatcaactt gagt                                            24

<210> SEQ ID NO 71
<211> LENGTH: 52
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: This sequence may encompass 7, 8 or 10-13 TTTA
      repeating units

<400> SEQUENCE: 71
tttatttatt tatttattta tttatttatt tatttattta tttatttatt ta             52

<210> SEQ ID NO 72
```

-continued

```
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 72

His His His His His His
  1               5

<210> SEQ ID NO 73
<211> LENGTH: 18
<212> TYPE: DNA
<213> ORGANISM: Artificial Sequence
<220> FEATURE:
<223> OTHER INFORMATION: Description of Artificial Sequence: Synthetic
      M13 tag sequence

<400> SEQUENCE: 73
tgtaaaacga cggccagt                                                  18

<210> SEQ ID NO 74
<211> LENGTH: 18
<212> TYPE: DNA
<213> ORGANISM: Artificial Sequence
<220> FEATURE:
<223> OTHER INFORMATION: Description of Artificial Sequence: Synthetic
      M13 tag sequence

<400> SEQUENCE: 74
caggaaacag ctatgacc                                                  18
```